(12) United States Patent
Carpenter et al.

(10) Patent No.: US 11,339,383 B2
(45) Date of Patent: *May 24, 2022

(54) G PROTEINS

(71) Applicant: HEPTARES THERAPEUTICS LIMITED, Cambridge (GB)

(72) Inventors: Byron Carpenter, Swindon (GB); Andrew Leslie, Swindon (GB); Rony Nehmé, Swindon (GB); Christopher Gordon Tate, Swindon (GB); Antony Warne, Swindon (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/835,431

(22) Filed: Mar. 31, 2020

(65) Prior Publication Data

US 2020/0231949 A1 Jul. 23, 2020

Related U.S. Application Data

(63) Continuation of application No. 15/549,246, filed as application No. PCT/GB2017/050221 on Jan. 27, 2017, now Pat. No. 10,738,287.

(30) Foreign Application Priority Data

Jan. 29, 2016 (GB) ..................... 1601690

(51) Int. Cl.
*C12N 9/14* (2006.01)
*C07K 14/47* (2006.01)

(52) U.S. Cl.
CPC ............ *C12N 9/14* (2013.01); *C07K 14/4722* (2013.01); *C12Y 306/05001* (2013.01)

(58) Field of Classification Search
CPC ... C12N 9/14; C12Y 306/05001; A61P 35/00; C07K 14/4722
See application file for complete search history.

(56) References Cited

U.S. PATENT DOCUMENTS

| | | | |
|---|---|---|---|
| 6,034,071 A | 3/2000 | Iyengar | |
| 6,383,761 B2 | 5/2002 | Conklin | |
| 7,294,472 B2 * | 11/2007 | Gilchrist | A61P 25/28 435/7.1 |
| 8,546,536 B2 | 10/2013 | Lowery | |
| 10,738,287 B2 * | 8/2020 | Carpenter | C12N 9/14 |
| 2002/0197706 A1 | 12/2002 | Nadkarni | |
| 2005/0136512 A1 | 6/2005 | Yao | |

FOREIGN PATENT DOCUMENTS

| | | |
|---|---|---|
| CN | 1287169 A | 3/2001 |
| EP | 0184187 | 6/1986 |
| EP | 0239400 | 9/1987 |
| GB | 2188638 A | 10/1987 |
| WO | WO 95/32425 | 11/1995 |
| WO | WO 98/16557 | 4/1998 |
| WO | WO 2002/068600 | 9/2002 |
| WO | WO 2004/092199 | 10/2004 |
| WO | WO 2008/068534 | 6/2008 |
| WO | WO 2008/114020 | 9/2008 |
| WO | WO 2009/071914 | 6/2009 |
| WO | WO 2009/081136 | 7/2009 |
| WO | WO 2010/149964 | 12/2010 |
| WO | WO 2012/007593 | 1/2012 |
| WO | WO 2014/122183 | 8/2014 |
| WO | 2015/121092 | 8/2015 |

OTHER PUBLICATIONS

Aris et al., Structural requirements for the stabilization of metarhodopsin II by the C terminus of the a-subunit of transducin. The J. Biol. Chem., 2001, vol. 276(4): 2333-2339 (Year: 2001).*

Bubis et al., Chemical modification of transducin with idoacetic acid: transducin-a carboxymethylated Cys347 allows transducin binding to light-activated rhodopsin but prevents its release in the presence of GTP. Arch. Biochem. Biophys., 2001, vol. 395(2): 146-157. (Year: 2001).*

Abdulaev et al. Heterotrimeric G-protein alpha-subunit adopts a "preactivated" conformation when associated with betagamma-subunits. J Biol Chem, Nov. 11, 2005;280(45):38071-80.

Abdulaev et al. The receptor-bound "empty pocket" state of the heterotrimeric G-protein alpha-subunit is conformationally dynamic. Biochemistry, Oct. 31, 2006;45(43):12986-97.

Accelrys. QUANTA (© 2001, 2002).

Alexander et al. Energetic analysis of the rhodopsin-G-protein complex links the α5 helix to GDP release. Nat Struct Mol Biol. Jan. 2014;21(1):56-63.

Alexander et al. The Concise Guide to Pharmacology 2015/16: G protein-coupled receptors. Br J Pharmacol. Dec. 2015;172(24):5744-869.

Anantharaman et al. Comparative genomics uncovers novel structural and functional features of the heterotrimeric GTPase signaling system. Gene. Apr. 15, 2011;475(2):63-78.

Balbes et al. A Perspective of Modern Methods in Computer-Aided Drug Design. Chapter 7, Reviews in Computational Chemistry, vol. 5. Ed. Lipkowitz & Boyd. John Wiley & Sons, Inc., Hoboken, New Jersey. 1994.

(Continued)

*Primary Examiner* — Ganapathirama Raghu
(74) *Attorney, Agent, or Firm* — Mueting Raasch Group

(57) ABSTRACT

The invention provides a mutant of a parent heterotrimeric G protein alpha (Gα) subunit, which mutant (i) lacks at least one helix of the helical domain of the parent Gα subunit; (ii) is capable of binding to a GPCR in the absence of a heterotrimeric G protein beta (Gβ) subunit and a heterotrimeric G protein gamma (Gγ) subunit; and (iii) has an amino acid sequence that contains one or more mutations compared to the amino acid sequence of the parent heterotrimeric Gα subunit, which mutations are selected from a deletion, a substitution and an insertion.

22 Claims, 66 Drawing Sheets

Figure 2:
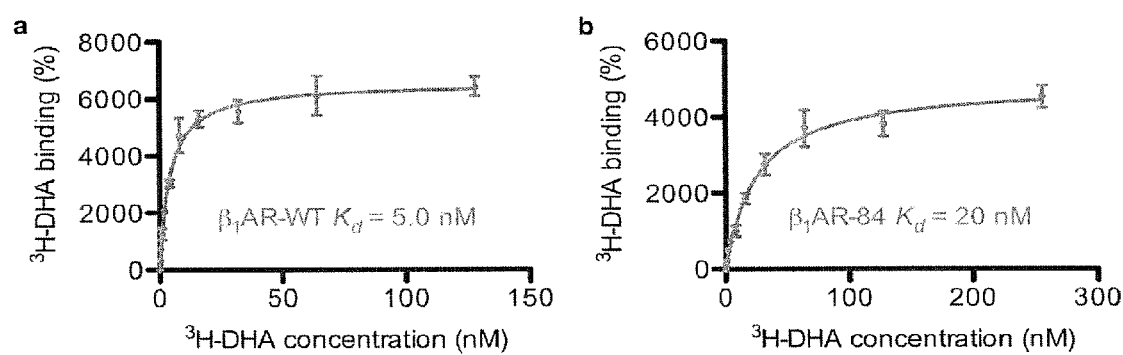

Specification includes a Sequence Listing.

(56) References Cited

OTHER PUBLICATIONS

Ballesteros & Weinstein. Integrated methods for the construction of three-dimensional models and computational probing of structure-function relations in G protein-coupled receptors. Methods Neurosci. 1995;25:366-428.

Baltoumas et al., Interactions of the A-Subunits of Heterotrimeric G-Proteins with GPCRs, Effectors and RGS Proteins: A Critical Review and Analysis of Interacting Surfaces, Conformational Shifts, Structural Diversity and Electrostatic Potentials, *J. Struct. Biol.*, 2013, vol. 182, 2013.

Banères et al. Molecular characterization of a purified 5-HT4 receptor: a structural basis for drug efficacy. J Biol Chem. May 27, 2005;280(21):20253-60.

Barren et al. Mechanisms of dominant negative G-protein alpha subunits. J Neurosci Res. Dec. 2007;85(16):3505-14.

Barren et al. Mutation R238E in transducin-alpha yields a GTPase and effector-deficient, but not dominant-negative, G-protein alpha-subunit. Mol Vis. May 12, 2006;12:492-8.

Berlot. A highly effective dominant negative alpha s construct containing mutations that affect distinct functions inhibits multiple Gs-coupled receptor ignalling pathways. J Biol Chem. Jun. 7, 2002;277(23):21080-5.

Bockaert et al. GPCR-GIP networks: a first step in the discovery of new therapeutic drugs? Curr Opin Drug Discov Devel. Sep. 2004;7(5):649-57.

Borle. An overview of techniques for the measurement of calcium distribution, calcium fluxes, and cytosolic free calcium in mammalian cells. Environ Health Perspect. Mar. 1990;84:45-56.

Bornancin et al. The transitory complex between photoexcited rhodopsin and transducin. Reciprocal interaction between the retinal site in rhodopsin and the nucleotide site in transducin. Eur J Biochem. Oct. 1, 1989;184(3):687-98.

Brenner & Lerner. Encoded combinatorial chemistry. Proc Natl Acad Sci U S A. Jun. 15, 1992;89(12):5381-3.

Bubis et al. Chemical modification of transducin with iodoacetic acid: transducin-alpha carboxymethylated at Cys(347) allows transducin binding to Light-activated rhodopsin but prevents its release in the presence of GTP. Arch Biochem Biophys. Nov. 15, 2001;395(2):146-57.

Cabrera-Vera et al. Insights into G protein structure, function, and regulation. Endocr Rev. Dec. 2003;24(6):765-81.

Carpenter & Tate. Engineering a minimal G protein to facilitate crystallisation of G protein-coupled receptors in their active conformation. Protein Eng Des Sel. Dec. 2016;29(12):583-594.

Carpenter et al. Structure of the adenosine A(2A) receptor bound to an engineered G protein. Nature. Aug. 4, 2016;536(7614):104-7.

Carson. RIBBONS 2.0. J Appl Cryst. Oct. 1991;24(5):958-61.

CGN Server—Common Galpha Numbering system. http://mrc-lmb.cam.ac.uk/CGN.2015.

Chabre & Deterre. Molecular mechanism of visual transduction. Eur J Biochem. Feb. 1, 1989;179(2):255-66.

Chan et al. Molecular chaperoning function of Ric-8 is to fold nascent heterotrimeric G protein α subunits. Proc Natl Acad Sci U S A. Mar. 5, 2013;110(10):3794-9.

Chan et al. Purification of heterotrimeric G protein alpha subunits by GST-Ric-8 association: primary characterization of purified G alpha(olf). J Biol Chem, Jan. 28, 2011;286(4):2625-35.

Chen et al. Adenosine receptors as drug targets—what are the challenges? Nat Rev Drug Discov. Apr. 2013;12(4):265-86.

Choe et al. Crystal structure of metarhodopsin II. Nature. Mar. 31, 2011;471(7340):651-5.

Chung et al. Conformational changes in the G protein Gs induced by the β2 adrenergic receptor. Nature. Sep. 28, 2011;477(7366):611-5.

Clawges et al. Human 5-HT1 receptor subtypes exhibit distinct G protein coupling behaviors in membranes from Sf9 cells. Biochemistry, Oct. 21, 1997;36(42):12930-8.

Cleator et al. A dominant negative Galphas mutant that prevents thyroid-stimulating hormone receptor activation of cAMP production and inositol 1,4,5-trisphosphate turnover: competition by different G proteins for activation by a common receptor. J Biol Chem. Aug. 27, 2004;279(35):36601-7.

Cleator et al. The N54 mutant of Galphas has a conditional dominant negative phenotype which suppresses hormone-stimulated but not basal cAMP levels. FEBS Lett. Jan. 25, 1999;443(2):205-8.

Cohen et al. Molecular modeling software and methods for medicinal chemistry. J Med Chem. Mar. 1990;33(3):883-94.

Coleman & Sprang. Crystal structures of the G protein Gi alpha 1 complexed with GDP and Mg2+: a crystallographic titration experiment. Biochemistry. Oct. 13, 1998;37(41):14376-85.

Congreve et al. Discovery of 1,2,4-triazine derivatives as adenosine A(2A) antagonists using structure based drug design. J Med Chem. Mar. 8, 2012;55(5):1898-903.

Conklin et al. Carboxyl-terminal mutations of Gq alpha and Gs alpha that alter the fidelity of receptor activation. Mol Pharmacol. Oct. 1996;50(4):885-90.

Conklin et al. Substitution of three amino acids switches receptor specificity of Gq alpha to that of Gi alpha. Nature. May 20, 1993;363(6426):274-6.

Cornell et al. A Second Generation Force Field for the Simulation of Proteins, Nucleic Acids, and Organic Molecules. J Am Chem Soc. May 1, 1995;117(19):5179-97.

De Lean et al. A ternary complex model explains the agonist-specific binding properties of the adenylate cyclase-coupled beta-adrenergic receptor. J Biol Chem. Aug. 10, 1980;255(15):7108-17.

Dohlman & Jones. Signal activation and inactivation by the Gα helical domain: a long-neglected partner in G protein signaling. Sci Signal. May 29, 2012;5(226):re2.

Doré et al. Structure of the adenosine A(2A) receptor in complex with ZM241385 and the xanthines XAC and caffeine. Structure. Sep. 7, 2011;19(9):1283-93.

Dror et al. Signal Transduction. Structural basis for nucleotide exchange in heterotrimeric G proteins. Science. Jun. 19, 2015;348(6241):1361-5.

Dupriez et al. Aequorin-based functional assays for G-protein-coupled receptors, ion channels, and tyrosine kinase receptors. Receptors Channels. 2002;8(5-6):319-30.

Eglen. Functional G protein-coupled receptor assays for primary and secondary screening. Comb Chem High Throughput Screen. Jun. 2005;8(4):311-8.

Emsley et al. Features and development of Coot. Acta Crystallogr D Biol Crystallogr. Apr. 2010;66(Pt4):486-501.

Evans & Murshudov. How good are my data and what is the resolution? Acta Crystallogr D Biol Crystallogr. Jul. 2013;69(Pt 7):1204-14.

Feig & Cooper. Inhibition of NIH 3T3 cell proliferation by a mutant ras protein with preferential affinity for GDP. Mol Cell Biol, Aug. 1988;8(8):3235-43.

Feig. Tools of the trade: use of dominant-inhibitory mutants of Ras-family GTPases. Nat Cell Biol. Jun. 1999;1(2):E25-7.

Fenalti et al. Molecular control of delta-opioid receptor signalling. Nature. Feb. 13, 2014;506(7487):191-6.

Ferguson et al. The influence of bound GDP on the kinetics of guanine nucleotide binding to G proteins. J Biol Chem. Jun. 5, 1986;261(16):7393-9.

Fishman et al. Pharmacological and therapeutic effects of A3 adenosine receptor agonists. Drug Discov Today. Apr. 2012;17(7-8):359-66.

Flock et al. Universal allosteric mechanism for Gα activation by GPCRs. Nature. Aug. 13, 2015;524(7564):173-179.

Foord et al. International Union of Pharmacology. XLVI. G protein-coupled receptor list. Pharmacol Rev. Jun. 2005;57(2):279-88.

Fredholm et al. International Union of Basic and Clinical Pharmacology. LXXXI. Nomenclature and classification of adenosine receptors—an update. Pharmacol Rev. Mar. 2011;63(1):1-34.

Fredholm et al. International Union of Pharmacology. XXV. Nomenclature and classification of adenosine receptors. Pharmacol Rev. Dec. 2001;53(4):527-52.

Fredriksson et al. The G-protein-coupled receptors in the human genome form five main families. Phylogenetic analysis, paralogon groups, and fingerprints. Mol Pharmacol. Jun. 2003;63(6):1256-72.

(56) References Cited

OTHER PUBLICATIONS

Freson et al., Genetic Variation of the Extra-large Stimulatory G Protein A-Subunit Leads to Gs Hyperfunction in Platelets and is a Risk factor for Bleeding, *Thromb Haemost*, 2001, vol. 86, 733-738 (2001).
Frishman & Argos. Knowledge-based protein secondary structure assignment. Proteins. Dec. 1995;23(4):566-79.
Fung & Nash. Characterization of transducin from bovine retinal rod outer segments. II. Evidence for distinct binding sites and conformational changes revealed by limited proteolysis with trypsin. J Biol Chem. Sep. 10, 1983;258(17):10503-10.
Fung et al. Flow of information in the light-triggered cyclic nucleotide cascade of vision. Proc Natl Acad Sci U S A. Jan. 1981;78(1):152-6.
Fung. Characterization of transducin from bovine retinal rod outer segments. I. Separation and reconstitution of the subunits. J Biol Chem. Sep. 10, 1983;258(17):10495-502.
González & Maher. Cellular fluorescent indicators and voltage/ion probe reader (VIPR) tools for ion channel and receptor drug discovery. Receptors Channels. 2002;8(5-6):283-95.
Green et al. Beta 1- and beta 2-adrenergic receptors display subtype-selective coupling to Gs. Mol Pharmacol. May 1992;41(5):889-93.
Grishina & Berlot. A surface-exposed region of G(salpha) in which substitutions decrease receptor-mediated activation and increase receptor affinity. Mol Pharmacol. Jun. 2000;57(6):1081-92.
Guida. Software for structure-based drug design. Curr Opin Struct Biol. Oct. 1994;4(5):777-81.
Hall & Self. The effect of Mg2+ on the guanine nucleotide exchange rate of p21N-ras. J Biol Chem. Aug. 25, 1986;261(24):10963-5.
Hamm et al. Site of G protein binding to rhodopsin mapped with synthetic peptides from the alpha subunit. Science. Aug. 12, 1988;241(4867):832-5.
Hansson et al. PCR-mediated deletion of plasmid DNA. Anal Biochem. Apr. 15, 2008;375(2):373-5.
Hanzal-Bayer et al. The complex of Arl2-GTP and PDE delta: from structure to function. EMBO J. May 1, 2002;21(9):2095-106.
Heinig & Frishman. STRIDE: a web server for secondary structure assignment from known atomic coordinates of proteins. Nucleic Acids Res. Jul. 1, 2004;32(Web Server issue):W500-2.
Herrmann et al. Rhodopsin-transducin coupling: role of the Galpha C-terminus in nucleotide exchange catalysis. Vision Res. Dec. 2006;46(27):4582-93.
Herrmann et al. Sequence of interactions in receptor-G protein coupling. J Biol Chem. Jun. 4, 2004;279(23):24283-90.
Herrmann et al. Signal transfer from GPCRs to G proteins: role of the G alpha N-terminal region in rhodopsin-transducin coupling. J Biol Chem. Oct. 6, 2006;281(40):30234-41.
Higashijima et al. Effects of Mg2+ and the beta gamma-subunit complex on the interactions of guanine nucleotides with G proteins. J Biol Chem. Jan. 15, 1987;262(2):762-6.
Hildebrandt et al. A mutation in the putative Mg(2+)-binding site of Gs alpha prevents its activation by receptors. Mol Cell Biol. Oct. 1991;11(10):4830-8.
Hino et al. G-protein-coupled receptor inactivation by an allosteric inverse-agonist antibody. Nature. Jan. 29, 2012;482(7384):237-40.
Holm & Rosenström. Dali server: conservation mapping in 3D. Nucleic Acids Res. Jul. 2010;38(Web Server issue):W545-9.
Hou et al. Selective role of G protein gamma subunits in receptor interaction. J Biol Chem. Dec. 15, 2000;275(50):38961-4.
Huang et al. Pivotal role of extended linker 2 in the activation of Gα by G protein-coupled receptor. J Biol Chem. Jan. 2, 2015;290(1):272-83.
Hubbell et al. Rhodopsin structure, dynamics, and activation: a perspective from crystallography, site-directed spin labeling, sulfhydryl reactivity, and disulfide cross-linking. Adv Protein Chem. 2003;63:243-90.
Hudson et al. High-content screening of known G protein-coupled receptors by arresting translocation. Methods Enzymol. 2006;414:63-78.

Iiri et al. A Gsalpha mutant designed to inhibit receptor signaling through Gs. Proc Natl Acad Sci U S A. Jan. 19, 1999;96(2):499-504.
Iiri et al. Rapid GDP release from Gs alpha in patients with gain and loss of endocrine function. Nature. Sep. 8, 1994;371(6493):164-8.
International Union of Basic and Clinical Pharmacology (IUPHAR) and British Pharmacological Society (BPS). Guide to Pharmacology: G protein-coupled receptors. http://www.guidetopharmacology.org/GRAC/ReceptorFamiliesForward?type=GPCR. Wayback machine version dated Jan. 22, 2016.
InterPro. Guanine nucleotide binding protein (G-protein), alpha subunit (IPR001019). http://www.ebi.ac.uk/interpro/entry/IPR001019. Wayback machine version dated Jan. 10, 2016.
Jaakola et al. The 2.6 angstrom crystal structure of a human A2A adenosine receptor bound to an antagonist. Science. Nov. 21, 2008;322(5905):1211-7.
Jameson et al. Real-time detection of basal and stimulated G protein GTPase activity using fluorescent GTP analogues. J Biol Chem. Mar. 4, 2005;280(9):7712-9.
Johnston et al. Structure of Galpha(i1) bound to a GDP-selective peptide provides insight into guanine nucleotide exchange. Structure. Jul. 2005;13(7): 1069-80.
Jones et al. Improved methods for building protein models in electron density maps and the location of errors in these models. Acta Crystallogr A. Mar. 1, 1991;47 ( Pt 2): 110-9.
Jones et al. The crystal structure of a self-activating G protein alpha subunit reveals its distinct mechanism of signal initiation. Sci Signal. Feb. 8, 2011;4(159):ra8.
Kapoor et al. Structural evidence for a sequential release mechanism for activation of heterotrimeric G proteins. J Mol Biol. Nov. 6, 2009;393(4):882-97.
Kawate & Gouaux. Fluorescence-detection size-exclusion chromatography for precrystallization screening of integral membrane proteins. Structure. Apr. 2006;14(4):673-81.
Kaya et al. A conserved phenylalanine as a relay between the α5 helix and the GDP binding region of heterotrimeric Gi protein α subunit. J Biol Chem. Aug. 29, 2014;289(35):24475-87.
Kenakin. Protean agonists. Keys to receptor active states? Ann N Y Acad Sci. May 30, 1997;812:116-25.
Kent et al. Development of a generic dual-reporter gene assay for screening G-protein-coupled receptors. J Biomol Screen. Aug. 2005;10(5):437-46.
Kerr et al. Encoded combinatorial peptide libraries containing non-natural amino acids. J Am Chem Soc. Mar. 1993;115(6):2529-31.
Kimple et al. Structural determinants for GoLoco-induced inhibition of nucleotide release by Galpha subunits. Nature. Apr. 25, 2002;416(6883):878-81.
Kleuss & Krause. Galpha(s) is palmitoylated at the N-terminal glycine. EMBO J. Feb. 17, 2003;22(4):826-32.
Kobilka & Deupi. Conformational complexity of G-protein-coupled receptors. Trends Pharmacol Sci. Aug. 2007;28(8):397-406.
Köhler & Milstein. Continuous cultures of fused cells secreting antibody of predefined specificity. Nature. Aug. 7, 1975;256(5517):495-7.
Krumm et al. Structural prerequisites for G-protein activation by the neurotensin receptor. Nat Commun. Jul. 24, 2015;6:7895.
Kruse et al. Activation and allosteric modulation of a muscarinic acetylcholine receptor. Nature. Dec. 5, 2013;504(7478):101-6.
Kühn. Interactions of Rod Cell Proteins with the Disk Membrane: Influence of Light, Ionic Strength, and Nucleotides. Curr Top Membr Transp. 1981;15:171-201.
Kull et al. Adenosine A(2A) receptors are colocalized with and activate g(olf) in rat striatum. Mol Pharmacol. Oct. 2000;58(4):771-7.
Kyte & Doolittle. A simple method for displaying the hydropathic character of a protein. J Mol Biol. May 5, 1982;157(1):105-32.
Lambright et al. Structural determinants for activation of the alpha-subunit of a heterotrimeric G protein. Nature. Jun. 23, 1994;369(6482):621-8.
Lebon et al. Agonist-bound adenosine A2A receptor structures reveal common features of GPCR activation. Nature. May 18, 2011;474(7352):521-5.

(56) References Cited

OTHER PUBLICATIONS

Lebon et al. Agonist-bound structures of G protein-coupled receptors. Curr Opin Struct Biol. Aug. 2012;22(4):482-90.
Lebon et al. Molecular Determinants of CGS21680 Binding to the Human Adenosine A2A Receptor. Mol Pharmacol. Jun. 2015;87(6):907-15.
Lebon et al. Thermostabilisation of an agonist-bound conformation of the human adenosine A(2A) receptor. J Mol Biol. Jun. 10, 2011;409(3):298-310.
Leff. The two-state model of receptor activation. Trends Pharmacol Sci. Mar. 1995;16(3):89-97.
Leroy et al. G protein-coupled receptor-mediated ERK1/2 phosphorylation: towards a generic sensor of GPCR activation. J Recept Signal Transduct Res. 2007;27(1):83-97.
Leslie. The integration of macromolecular diffraction data. Acta Crystallogr D Biol Crystallogr. Jan. 2006;62(Pt 1):48-57.
Levin Am, Clinical Implications of Genetic Defects in G Proteins: Organic Mutations in G-as as the molecular basis for the McGune-Albright Syndrome, Arch. Med. Res., 1999, vol. 30, 522-531 (1999).
Li & Cerione. Communication between switch II and switch III of the transducin alpha subunit is essential for target activation, J Biol Chem. Aug. 29, 1997;272(35):21673-6.
Liu & Wu. Analysis of the coupling of G12/13 to G protein-coupled receptors using a luciferase reporter assay. Methods Mol Biol. 2004;237:145-9.
Liu et al. Structural basis for allosteric regulation of GPCRs by sodium ions. Science. Jul. 13, 2012;337(6091):232-6.
Maclean et al. Encoded combinatorial chemistry: synthesis and screening of a library of highly functionalized pyrrolidines. Proc Natl Acad Sci U S A. Apr. 1, 1997;94(7):2805-10.
Magnani et al. A mutagenesis and screening strategy to generate optimally thermostabilized membrane proteins for structural studies. Nat Protoc. Aug. 2016;11(8):1554-71.
Majumdar et al. Perturbing the linker regions of the alpha-subunit of transducin: a new class of constitutively active GTP-binding proteins. J Biol Chem. Sep. 17, 2004;279(38):40137-45.
Manglik et al. Structural Insights into the Dynamic Process of β2-Adrenergic Receptor Signaling. Cell. May 21, 2015;161(5):1101-11.
Markby et al. Separate GTP binding and GTPase activating domains of a G alpha subunit. Science. Dec. 17, 1993;262(5141):1895-901.
McCoy et al. Phaser crystallographic software. J Appl Crystallogr. Aug. 1, 2007;40(Pt 4):658-674.
McIntire et al. The G protein beta subunit is a determinant in the coupling of Gs to the beta 1-adrenergic and A2a adenosine receptors. J Biol Chem. May 11, 2001;276(19):15801-9.
McPherson. Crystallization of Biological Macromolecules. Cold Spring Harbor Laboratory Press, New York. 1998. ISBN: 0-87969-617-6.
Miller-Gallacher et al. The 2.1 Å resolution structure of cyanopindolol-bound β1-adrenoceptor identifies an intramembrane Na+ ion that stabilises the ligand-free receptor. PLoS One. Mar. 24, 2014;9(3):e92727.
Milligan & White. Protein-protein interactions at G-protein-coupled receptors. Trends Pharmacol Sci. Oct. 2001;22(10):513-8.
Milligan. Signal Transduction: A Practical Approach. $2^{nd}$ ed (1999). Oxford University Press, Oxford, UK.
Moran et al. Radio Frequency Tag Encoded Combinatorial Library Method for the Discovery of Tripeptide-Substituted Cinnamic Acid Inhibitors of the Protein Tyrosine Phosphatase PTP1B. J Am Chem Soc. Nov. 1995;117(43):10787-8.
Müller & Jacobson. Recent developments in adenosine receptor ligands and their potential as novel drugs. Biochim Biophys Acta. May 2011;1808(5):1290-308.
Muradov & Artemyev. Coupling between the N- and C-terminal domains influences transducin-alpha intrinsic GDP/GTP exchange. Biochemistry. Apr. 11, 2000;39(14):3937-42.
Murphree et al. Human A(2A) adenosine receptors: high-affinity agonist binding to receptor-G protein complexes containing Gbeta(4). Mol Pharmacol. Feb. 2002;61(2):455-62.

Murshudov et al. REFMAC5 for the refinement of macromolecular crystal structures. Acta Crystallogr D Biol Crystallogr. Apr. 2011;67(Pt 4):355-67.
Natochin et al. Dominant negative mutants of transducin-alpha that block activated receptor. Biochemistry. May 23, 2006;45(20):6488-94.
Natochin et al. Probing the mechanism of rhodopsin-catalyzed transducin activation. J Neurochem. Apr. 2001;77(1):202-10.
Navia & Murcko. Use of structural information in drug design. Curr Opin Struct Biol. Apr. 1992;2(2):202-10.
Nehmé et al. Mini-G proteins: Novel tools for studying GPCRs in their active conformation. PLoS One. Apr. 20, 2017;12(4):e0175642.
Neubig et al. International Union of Pharmacology Committee on Receptor Nomenclature and Drug Classification. XXXVIII. Update on terms and symbols in quantitative pharmacology. Pharmacol Rev. Dec. 2003;55(4):597-606.
Neves et al. G protein pathways. Science. May 31, 2002;296(5573):1636-9.
Newman-Tancredi et al. Agonist and inverse agonist efficacy at human recombinant serotonin 5-HT1A receptors as a function of receptor:G-protein stoichiometry. Neuropharmacology. Apr.-May 1997;36(4-5):451-9.
Nicolaou et al. Radiofrequency Encoded Combinatorial Chemistry. Angew Chem Int Ed Engl. Nov. 3, 1995;34(20):2289-91.
Nishimura et al. Structural basis for the specific inhibition of heterotrimeric Gq protein by a small molecule. Proc Natl Acad Sci U S A. Aug. 3, 2010;107(31):13666-71.
Noel et al. The 2.2 A crystal structure of transducin-alpha complexed with GTP gamma S. Nature. Dec. 16, 1993;366(6456):654-63.
Ohlmeyer et al. Complex synthetic chemical libraries indexed with molecular tags. Proc Natl Acad Sci U S A. Dec. 1, 1993;90(23):10922-6.
Oldham et al. Mechanism of the receptor-catalyzed activation of heterotrimeric G proteins. Nat Struct Mol Biol. Sep. 2006;13(9):772-7.
Overington et al. How many drug targets are there? Nat Rev Drug Discov. Dec. 2006;5(12):993-6.
Pardon et al. A general protocol for the generation of Nanobodies for structural biology. Nat Protoc. Mar. 2014;9(3):674-93.
Park et al. Crystal structure of the ligand-free G-protein-coupled receptor opsin. Nature. Jul. 10, 2008;454(7201):183-7.
Pereira & Cerione. A switch 3 point mutation in the alpha subunit of transducin yields a unique dominant-negative inhibitor. J Biol Chem. Oct. 21, 2005;280(42):35696-703.
Phillips et al. Rhodopsin/transducin interactions. II. Influence of the transducin-beta gamma subunit complex on the coupling of the transducin-alpha subunit to rhodopsin. J Biol Chem. Aug. 25, 1992;267(24):17040-6.
Pina et al,. A Three Base Pair Deletion of Encoding the Amino Acid (Lysine-270) in the A-Cone Transducin Gene. Mol. Vision, 2004, vol. 10, 265-271 (2004).
Plant et al. Phospholipid/alkanethiol bilayers for cell-surface receptor studies by surface plasmon resonance. Anal Biochem. Apr. 10, 1995;226(2):342-8.
Posner et al. The A326S mutant of Gialpha1 as an approximation of the receptor-bound state. J Biol Chem. Aug. 21, 1998;273(34):21752-8.
Preininger et al. Helix dipole movement and conformational variability contribute to allosteric GDP release in Galphai subunits. Biochemistry. Mar. 31, 2009;48(12):2630-42.
Ramachandran & Cerione. A dominant-negative Galpha mutant that traps a stable rhodopsin-Galpha-GTP-betagamma complex. J Biol Chem. Apr. 8, 2011;286(14):12702-11.
Rasmussen et al. Crystal structure of the β2 adrenergic receptor-Gs protein complex. Nature. Jul. 19, 2011;477(7366):549-55.
Rasmussen et al. Structure of a nanobody-stabilized active state of the β(2) adrenoceptor. Nature. Jan. 13, 2011;469(7329):175-80.
Richardson & Robishaw. The alpha2A-adrenergic receptor discriminates between Gi heterotrimers of different betagamma subunit composition in Sf9 insect cell membranes. J Biol Chem. May 7, 1999;274(19):13525-33.

(56) References Cited

OTHER PUBLICATIONS

Ring et al. Adrenaline-activated structure of β2-adrenoceptor stabilized by an engineered nanobody. Nature. Oct. 24, 2013;502(7472):575-579.
Roberts & Strange. Mechanisms of inverse agonist action at D2 dopamine receptors. Br J Pharmacol. May 2005;145(1):34-42.
Rodgers et al. Development of displacement binding and GTPgammaS scintillation proximity assays for the identification of antagonists of the mu-opioid receptor. Assay Drug Dev Technol. Oct. 2003;1(5):627-36.
Rosenbaum et al. Structure and function of an irreversible agonist-β(2) adrenoceptor complex. Nature. Jan. 13, 2011;469(7329):236-40.
Rosenbaum et al. The structure and function of G-protein-coupled receptors. Nature. May 21, 2009;459(7245):356-63.
Rusinova et al. Specificity of Gbetagamma signaling to Kir3 channels depends on the helical domain of pertussis toxin-sensitive Galpha subunits. J Biol Chem. Nov. 23, 2007;282(47):34019-30.
Sambrook & Russell. Molecular Cloning: A Laboratory Manual. 3rd ed. 2001. Cold Spring Harbor Laboratory Press, New York.
Savinainen et al. Identification of WIN55212-3 as a competitive neutral antagonist of the human cannabinoid CB2 receptor. Br J Pharmacol. Jul. 2005;145(5):636-45.
Scheerer et al. Crystal structure of opsin in its G-protein-interacting conformation. Nature. Sep. 25, 2008;455(7212):497-502.
Sebestyén et al. Efficiency and limitations of the 'portioning-mixing' peptide synthesis. Peptides 1992. Proceedings of the $22^{nd}$ European Peptide Symposium, Sep. 13-19, 1992 Interlaken, Switzerland. pp. 63-64.
Semack et al. Structural Elements in the Gαs and Gαq C Termini That Mediate Selective G Protein-coupled Receptor (GPCR) Signaling. J Biol Chem. Aug. 19, 2016;291(34):17929-40.
Serrano-Vega & Tate. Transferability of thermostabilizing mutations between beta-adrenergic receptors. Mol Membr Biol. Dec. 2009;26(8):385-96.
Serrano-Vega et al. Conformational thermostabilization of the beta1-adrenergic receptor in a detergent-resistant form. Proc Natl Acad Sci U S A. Jan. 22, 2008;105(3):877-82.
Shibata et al. Thermostabilization of the neurotensin receptor NTS1. J Mol Biol. Jul. 10, 2009;390(2):262-77.
Simonds et al. G-protein beta gamma dimers. Membrane targeting requires subunit coexpression and intact gamma C-A-A-X domain. J Biol Chem. Mar. 25, 1991;266(9):5363-6.
Singh et al. A constitutively active Ga subunit provides insights into the mechanism of G protein activation. Biochemistry. Apr. 17, 2012;51(15):3232-40.
Singh et al., A Constitutively Active Ga Subunit Provides Insights into the Mechanism of G Protein Activation, ACB Biochemistry, 2012, vol. 51, 3232-3240 (2012).
Skerra. 'Anticalins': a new class of engineered ligand-binding proteins with antibody-like properties. J Biotechnol. Jun. 2001;74(4):257-75.
Skiba et al. Mapping of effector binding sites of transducin alpha-subunit using G alpha t/G alpha il chimeras. J Biol Chem. Jan. 5, 1996;271(1):413-24.
Slepak et al. Functional analysis of a dominant negative mutant of G alpha i2. J Biol Chem. Feb. 24, 1995;270(8):4037-41.
Sounier et al. Propagation of conformational changes during mu-opioid receptor activation. Nature. Aug. 20, 2015;524(7565):375-8.
Spiegel et al. The G protein connection: molecular basis of membrane association. Trends Biochem Sci. Sep. 1991;16(9):338-41.
Sprang. G protein mechanisms: insights from structural analysis. Annu Rev Biochem. 1997;66:639-78.
Standfuss et al. The structural basis of agonist-induced activation in constitutively active rhodopsin. Nature. Mar. 31, 2011;471(7340):656-60.
Sun et al. Probing Gαi 1 protein activation at single-amino acid resolution. Nat Struct Mol Biol. Sep. 2015;22(9):686-694.
Sunahara et al. Crystal structure of the adenylyl cyclase activator Gsalpha. Science. Dec. 12, 1997;278(5345):1943-7.
Syrovatkina et al. Regulation, Signaling, and Physiological Functions of G-Proteins. J Mol Biol. Sep. 25, 2016;428(19):3850-68.
Tate & Schertler. Engineering G protein-coupled receptors to facilitate their structure determination. Curr Opin Struct Biol. Aug. 2009;19(4):386-95.
Tate. A crystal clear solution for determining G-protein-coupled receptor structures. Trends Biochem Sci. Sep. 2012;37(9):343-52.
Tate. Practical considerations of membrane protein instability during purification and crystallisation. Methods Mol Biol. 2010;601:187-203.
Tesmer et al. Crystal structure of the catalytic domains of adenylyl cyclase in a complex with Gsalpha.GTPgammaS. Science. Dec. 12, 1997;278(5345):1907-16.
Tesmer et al. Snapshot of activated G proteins at the membrane: the Galphaq-GRK2-Gbetagamma complex. Science. Dec. 9, 2005;310(5754):1686-90.
Thomas & Tate. Quality control in eukaryotic membrane protein overproduction. J Mol Biol. Dec. 12, 2014;426(24):4139-54.
Thompson et al. CLUSTAL W: improving the sensitivity of progressive multiple sequence alignment through sequence weighting, position-specific gap penalties and weight matrix choice. Nucleic Acids Res. Nov. 11, 1994;22(22):4673-80.
Traut. Physiological concentrations of purines and pyrimidines. Mol Cell Biochem. Nov. 9, 1994;140(1):1-22.
Umezawa & Nishio. CH/pi interactions as demonstrated in the crystal structure of guanine-nucleotide binding proteins, Src homology-2 domains and human growth hormone in complex with their specific ligands. Bioorg Med Chem. Apr. 1998;6(4):493-504.
Urano et al. Heterotrimeric G protein signalling in the plant kingdom. Open Biol. Mar. 27, 2013;3(3):120186.
Van Eps et al. Interaction of a G protein with an activated receptor opens the interdomain interface in the alpha subunit. Proc Natl Acad Sci U S A. Jun. 7, 2011;108(23):9420-4.
Venkatakrishnan et al. Diverse activation pathways in class A GPCRs converge near the G-protein-coupling region. Nature. Aug. 25, 2016;536(7617):484-7.
Venkatakrishnan et al. Molecular signatures of G-protein-coupled receptors. Nature. Feb. 14, 2013;494(7436):185-94.
Vetter & Wittinghofer. The guanine nucleotide-binding switch in three dimensions. Science. Nov. 9, 2001;294(5545):1299-304.
Vuong et al. Millisecond activation of transducin in the cyclic nucleotide cascade of vision. Nature. Oct. 18-24, 1984;311(5987):659-61.
Wang et al. Structural basis for molecular recognition at serotonin receptors. Science. May 3, 2013;340(6132):610-4.
Warne et al. Expression and purification of truncated, non-glycosylated turkey beta-adrenergic receptors for crystallization. Biochim Biophys Acta. Feb. 17, 2003;1610(1):133-40.
Warne et al. Structure of a beta1-adrenergic G-protein-coupled receptor. Nature. Jul. 24, 2008;454(7203):486-91.
Warne et al. The structural basis for agonist and partial agonist action on a β(1)-adrenergic receptor. Nature. Jan. 13, 2011;469(7329):241-4.
Warner et al. A novel mutation in the switch 3 region of Gsalpha in a patient with Albright hereditary osteodystrophy impairs GDP binding and receptor activation. J Biol Chem. Sep. 11, 1998;273(37):23976-83.
Weber et al. A 1536-well cAMP assay for Gs- and Gi-coupled receptors using enzyme fragmentation complementation. Assay Drug Dev Technol. Feb. 2004;2(1):39-49.
Weichert et al. Covalent agonists for studying G protein-coupled receptor activation. Proc Natl Acad Sci U S A. Jul. 22, 2014;111(29):10744-8.
Weiss et al. Receptor activation of G proteins. FASEB J. Oct. 1988;2(13):2841-8.
Weng et al., Structural Basis for the Function of Heterotrimeric G-Proteins, Sem. Neurosci. 1998, vol. 9, 175-188 (1998).
Westfield et al. Structural flexibility of the G alpha s alpha-helical domain in the beta2-adrenoceptor Gs complex. Proc Natl Acad Sci U S A. Sep. 20, 2011;108(38):16086-91.
Whisstock et al, Prediction of Protein Function from Protein Sequence, Q. Rev. Biophysics, 2003, vol. 36 (3), 307-340 (2003).

(56) References Cited

OTHER PUBLICATIONS

White et al. Structure of the agonist-bound neurotensin receptor. Nature. Oct. 25, 2012;490(7421):508-13.

Wittinghofer & Vetter. Structure-function relationships of the G domain, a canonical switch motif. Annu Rev Biochem. 2011;80:943-71.

Wu et al. Dominant-negative inhibition of pheromone receptor signaling by a single point mutation in the G protein alpha subunit. J Biol Chem. Aug. 20, 2004;279(34):35287-97.

Xu et al. Structure of an agonist-bound human A2A adenosine receptor. Science. Apr. 15, 2011;332(6027):322-7.

Yu & Simon. Interaction of the xanthine nucleotide binding Goalpha mutant with G protein-coupled receptors. J Biol Chem, Nov. 13, 1998;273(46):30183-8.

Yu et al. Characterization of a Goalpha mutant that binds xanthine nucleotides. J Biol Chem. Jul. 18, 1997;272(29):18015-9.

Yu et al. Inhibition of subsets of G protein-coupled receptors by empty mutants of G protein alpha subunits in g(o), G(11), and G(16). J Biol Chem. Jan. 7, 2000;275(1):71-6.

Zhang et al. Agonist-bound structure of the human P2Y12 receptor. Nature. May 1, 2014;509(7498):119-22.

Zhang et al. High-resolution crystal structure of human protease-activated receptor 1. Nature. Dec. 20, 2012;492(7429):387-92.

Zhang et al. The importance of ligands for G protein-coupled receptor stability. Trends Biochem Sci. Feb. 2015;40(2):79-87.

Zurita & Birnbaumer. The same mutation in Gsalpha and transducin alpha reveals behavioral differences between these highly homologous G protein alpha-subunits. Proc Natl Acad Sci U S A. Feb. 19, 2008;105(7):2363-8.

Hsu et al., "Molecular Cloning of a Novel Splice Variant of the α Subunit of the Mammalian $G_0$ Protein*", *The Journal of Biological Chemistry*, vol. 265, No. 19, Issue of July 5, pp. 11220-11226, 1990.

\* cited by examiner

Figure 1

```
Human G alpha s    1  MGCLGNSKTEDQRNEEKAQREANKKIEKQLQKDKQVYRATHRLLLLGAGESGKSTIVKQM  60
Mini Gs v2         1                    MIEKQLQKDKQVYRATHRLLLLGA  GKSTIVKQM
                                         **********************  *********
                         8901234567890123456789012345678901   1234567       123
                         RN2       3         4         5   B1              R1

Human G alpha s   61  RILHVNGFNGEGGEEDPQAARSNSDGEKATKVQDIKNNLKEAIETIVAAMSNLVPPVELA  120
Mini Gs v2        37  RILHGGSGGGGG---------------------------------------------
                      ****  ***  *
                         4567
                         1

Human G alpha s  121  NPENQFRVDYILSVMNVPDFDFPPEFYEHAKALWEDEGVRACYERSNEYQLIDCAQYFLD  180
Mini Gs v2        49  ---------------------------------------------------------

Human G alpha s  181  KIDVIKQADYVPSDQDLLRCRVLTSGIFETKFQVDKVNFHMFDVGGQRDERRKWIQCFND  240
Mini Gs v2        49  ------------------------TSGIFETKFQVDKVNFHMFDVGGQRDERRKWIQCFND
                                              ************************************
                                              12345678  12345678  1234567890
                                               S2    |   S3    |   R2      | |

Human G alpha s  241  VTAIIFVVASSGYNMVIREDNQTNRLQEALNLFKSIWNNRWLRTISVILFLNKQDLLAEK  300
Mini Gs v2        86  VTAIIFVV  S  Y           RLQEALN FKSIWNNRWLRTISVILFLNKQDLLAEK
                      ********  *  *           *********************************
                         1234567              1234567890123456789  1234567 1234567
                         S4    |              S3              |   S5    | S6

Human G alpha s  301  VLAGKSKIEDYFPEFARYTTPEDATPEPGEDPRVTRAKYFIRDEFLRISTASGDGRHYCY  360
Mini Gs v2       136  VLAGKSKIEDYFPEFARYTTPEDATPEPGEDPRVTRAKYFIRDEFLRISTASGDGRHYCY
                      ************************************************************
                         8901234567         12345678901234567890123456       12
                         1       |          H4       |       2       |      S6

Human G alpha s  361  PHFTCAVDTENIRRVFNDCRDIIQRMHLRQYELL  394
Mini Gs v2       196  PHFTCAVDTEN  R FNDCRDIIQRMHLRQYELL  229
                      ***********  * *******************
                         345    12345678901234567890123456
                         H5    |         1        2    2
```

Figure 8

Mini Gs₃₉₃ gene sequence

CCATGGGTCACCACCATCATCACCATGAAAATCTTTATTTCCAGGGTATCGAGAAGCAGCTGCAGAAG
GACAAGCAGGTCTACCGGGCCACGCACCGCCTGCTGCTGCTGGGTGCTGATAATTCTGGTAAAAGCAC
CATTGTGAAGCAGATGAGGATCCTGCATGGTGGGAGTGGCGGGAGCGGAGGTACTTCTGGAATCTTTG
AGACCAAGTTCCAGGTGGACAAAGTCAACTTCCACATGTTTGACGTGGGTGGCCAGCGCGATGAACGC
CGCAAGTGGATCCAGTGCTTCAACGATGTGACTGCCATCATCTTCGTGGTGGACAGCAGCGATTACAA
CCGCCTGCAGGAGGCTCTGAACGACTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAG
GACTACTTTCCAGAATTTGCTCGCTACACTACTCCTGAGGATGCTACTCCCGAGCCCGGAGAGGACCC
ACGCGTGACCCGGGCCAAGTACTTCATTCGAGATGAGTTTCTGAGGATCAGCACTGCCAGTGGAGATG
GGCGTCACTACTGCTACCCTCATTTCACCTGCGCTGTGGACACTGAGAACGCCCGCCGTATCTTCAAC
GACTGCCGTGACATCATTCAGCGCATGCACCTTCGTCAGTACGAGCTGCTCTAATAGCTCGAG

Mini Gs₃₉₃ protein sequence

MGHHHHHHENLYFQGIEKQLQKDKQVYRATHRLLLLGADNSGKSTIVKQMRILHGGSGGSGGTSGIFE
TKFQVDKVNFHMFDVGGQRDERRKWIQCFNDVTAIIFVVDSSDYNRLQEALNDFKSIWNNRWLRTISV
ILFLNKQDLLAEKVLAGKSKIEDYFPEFARYTTPEDATPEPGEDPRVTRAKYFIRDEFLRISTASGDG
RHYCYPHFTCAVDTENARRIFNDCRDIIQRMHLRQYELL

Figure 19

```
                    10         20         30         40         50
sp|P04896   MGCLGNSKTEDQRNEEKAQREANKKIEKQLQKDKQVYRATHRLLLLGAGE
Mini Gs C   ------------------------GIEKQLQKDKQVYRATHRLLLLGADN
Mini Gs D   ------------------------GIEKQLQKDKQVYRATHRLLLLGADN
                                    **********************.:
            89012345678901234567890123456789012         1234567
            HN2            3         4         5 |     S1      |

60         70         80         90        100
sp|P04896   SGKSTIVKQMRILHVNGFNGEGGEEDPQAARSNSDGEKATKVQDIKNNLK
Mini Gs C   SGKSTIVKQMRIYHGGSGGSGG---------------------------
Mini Gs D   SGKSTIVKQMRIYHGGSGGSGG---------------------------
            ************ *    .  ...*
              1234567
              H1    |

110        120        130        140        150
sp|P04896   EAIETIVAAMSNLVPPVELANPENQFRVDYILSVMNVPDFDFPPEFYEHA
Mini Gs C   -------------------------------------------------
Mini Gs D   -------------------------------------------------

160        170        180        190        200
sp|P04896   KALWEDEGVRACYERSNEYQLIDCAQYFLDKIDVIKQDDYVPSDQDLLRC
Mini Gs C   -------------------------------------------------
Mini Gs D   -------------------------------------------------
            89012 123456789012    1234567890123          123456
            HC1 |  HD         |   HE        1 |          HF    |

210        220        230        240        250
sp|P04896   RVLTSGIFETKFQVDKVNFHMFDVGGQRDERRKWIQCFNDVTAIIFVVAS
Mini Gs C   ---TSGIFETKFQVDKVNFHMFDVGGQRDERRKWIQCFNDVTAIIFVVDS
Mini Gs D   ---TSGIFETKFQVDKVNFHMFDVGGQRDERRKWIQCFNDVTAIIFVVDS
               *********************************************  *
               12345678   12345678   1234567890       1234567
               S2     |   S3     |   H2        |      S4     |

260        270        280        290        300
sp|P04896   SSYNMVIREDNQTNRLQEALNLFKSIWNNRWLRTISVILFLNKQDLLAEK
Mini Gs C   SDY----------NRLQEALNDFKSIWNNRWLRTISVILFLNKQDLLAEK
Mini Gs D   SDY----------NRLQEALNDFKSIWNNRWLRTISVILFLNKQDLLAEK
            *.*          ******* ****************************
                        123456789012345678    1234567 1234567
                        H3            1   |   S5    |  HG 310        320        330        340        350
sp|P04896   VLAGKSKIEDYFPEFARYTTPEDATPEPGEDPRVTRAKYFIRDEFLRIST
Mini Gs C   VLAGKSKIEDYFPEFARYTTPEDATPEPGEDPRVTRAKYFIRDEFLRIST
Mini Gs D   VLAGKSKIEDYFPEFARYTTPEDATPEPGEDPRVTRAKYFIRDEFLRIST
            *************************************************
            8901234567         12345678901234567890123456789
            HG 1     |         H4           1            2   |

360        370        380        390 394
sp|P04896   ASGDGRHYCYPHFTCAVDTENIRRVFNDCRDIIQRMHLRQYELL
Mini Gs C   ASGDGRHYCYPHFTCAVDTENARRIFNDCRDIIQRMHLRQYELL
Mini Gs D   ASGDGRHYCYPHFTCAVDTENARRIFNDCRDIIQRMHLRQYELL
            ********************  *:********************
               12345   12345678901234567890123456
               S6      H5          1         2    2
```

Figure 20

Figure 21

```
                          .                          1.50         .
adrb2_human     1 MGQPGNGSAFLLAPNRSHAPDHDVTQQRDEVWVVGMGIVMSLIVLAIVFGNVLVITAIAK  60
AA2AR_human     1                               MPIMGSSVYITVELAIAVLAILGNVLVCWAVWL  33
AA2AR_human A   1                               MPIMGSSVYITVELAIAVLAILGNVLVCWAVWL  33
AA2AR_human B   1                               MPIMGSSVYITVELAIAVLAILGNVLVCWAVWL  33

.        2.50         .          .          .
adrb2_human    61 FERLQTVTNYFITSLACADLVMGLAVVPFGAAHILMKMWTFGNFWCEFWTSIDVLCVTAS 120
AA2AR_human    34 NSNLQNVTNYFVVSLAAADIAVGVLAIPFAITISTGF--CAACHGCLFIACFVLVLTQSS  91
AA2AR chain A  34 NSNLQNVTNYFVVSLAAADIAVGVLAIPFAITISTGF--CAACHGCLFIACFVLVLTQSS  91
AA2AR chain B  34 NSNLQNVTNYFVVSLAAADIAVGVLAIPFAITISTGF--CAACHGCLFIACFVLVLTQSS  91

.        3.50         .          .        4.50          .
adrb2_human   121 IETLCVIAVDRYFAITSPFKYQSLLTKNKARVIILMVWIVSGLTSFLPIQMHWYRATHQE 180
AA2AR_human    92 IFSLLAIAIDRYIAIRIPLRYNGLVTGTRAKGIIAICWVLSFAIGLTPMLGWNNCGQPKE 151
AA2AR chain A  92 IFSLLAIAIDRYIAIRIPLRYNGLVTGTRAKGIIAICWVLSFAIGLTPMLGWNNCGQPKE 151
AA2AR chain B  92 IFSLLAIAIDRYIAIRIPLRYNGLVTGTRAKGIIAICWVLSFAIGLTPMLGWNNCGQPKE 151

.         5.50          .
adrb2_human   181 AIN-------CYANETCCDFFTNQAYAIASSIVSFYVPLVIMVFVYSRVFQEAKRQLQKI 233
AA2AR_human   152 GKNHSQGCGEGQVACLFEDVVPMNYMVYFNFFACVLVPLLLMLGVYLRIFLAARRQLKQM 211
AA2AR chain A 152 GKAHSQGCGEGQVACLFEDVVPMNYMVYFNFFACVLVPLLLMLGVYLRIFLAARRQLKQM 211
AA2AR chain B 152 GKAHSQGCGEGQVACLFEDVVPMNYMVYFNFFACVLVPLLLMLGVYLRIFLAARRQLKQM 211

.          .                         .      6.50  .
adrb2_human   234 DKSEGRFHVQNLSQVEQDGRTGHGLRRSSKFCLKEHKALKTLGIIMGTFTLCWLPFFIVN 293
AA2AR_human   212 ESQPLPGERARS------------------TLQKEVHAAKSLAIIVGLFALCWLPLHIIN 253
AA2AR chain A 212 ESQPLPGERARS------------------TLQKEVHAAKSLAIIVGLFALCWLPLHIIN 253
AA2AR chain B 212 ESQPLPGERARS------------------TLQKEVHAAKSLAIIVGLFALCWLPLHIIN 253

.         .                          7.50.   .
adrb2_human   294 IVHVIQDNLI--RKEVYILLNWIGYVNSGFNPLIYCRSPDFRIAFQELLCLRRSSLKAYG 351
AA2AR_human   254 CFTFFCPDCSHAPLWLMYLAIVLSHTNSVVNPFIYAYRIREFRQTFRKIIRSHVLRQQEP 313
AA2AR chain A 254 CFTFFCPDCSHAPLWLMYLAIVLSHTNSVVNPFIYAYRIREFRQTFRKIIRSHVLENLYF 313
AA2AR chain B 254 CFTFFCPDCSHAPLWLMYLAIVLSHTNSVVNPFIYAYRIREFRQTFRKIIRSHVLENLYF 313 adrb2_human   352 NGYSSNGNTGEQSGYHVEQEKENKLLCEDLPGTEDFVGHQGTVPSDNIDSQGRNCSTNDS 411
AA2AR_human   314 FKAAGTSARVLAAHGSDGEQVSLRLNGHPPGVWANGSAPHPERRPNGYALGLVSGGSAQE 373
AA2AR chain A 314 QGHHHHHHHHHH 325
AA2AR chain B 314 QGHHHHHHHHHH 325 adrb2_human   412 LL 413
AA2AR_human   374 SQGNTGLPDVELLSHELKGVCPEPPGLDDPLAQDGAGVS 412
``` a

C

Figure 25 b

| Domain | Gα SSE | Length of consensus SSE | Start in human reference | End in human reference | Alternative Name |
|---|---|---|---|---|---|
| G | HN | 53 | 1 | 53 | |
| G | hns1 | 3 | 54 | 56 | |
| G | S1 | 7 | 57 | 63 | |
| G | s1h1 | 6 | 64 | 69 | P-loop |
| G | H1 | 12 | 70 | 81 | |
| G | h1ha | 20 | 82 | 101 | L1 |
| H | HA | 29 | 102 | 130 | |
| H | ha-hb | 9 | 131 | 139 | |
| H | HB | 14 | 140 | 153 | |
| H | hbhc | 15 | 154 | 168 | |
| H | HC | 12 | 169 | 180 | |
| H | hchd | 1 | 181 | 181 | |
| H | HD | 12 | 182 | 193 | |
| H | hdhe | 5 | 194 | 198 | |
| H | HE | 13 | 199 | 211 | |
| H | hehf | 7 | 212 | 218 | |
| H | HF | 6 | 219 | 224 | |
| G | hfs2 | 7 | 225 | 231 | L2/SwI |
| G | S2 | 8 | 232 | 239 | |
| G | s2s3 | 2 | 240 | 241 | |
| G | S3 | 8 | 242 | 249 | |
| G | s3h2 | 3 | 250 | 252 | SwII |
| G | H2 | 10 | 253 | 262 | |
| G | h2s4 | 5 | 263 | 267 | |
| G | S4 | 7 | 268 | 274 | |
| G | s4h3 | 15 | 275 | 289 | SwIII |
| G | H3 | 18 | 290 | 307 | |
| G | h3s5 | 3 | 308 | 310 | |
| G | S5 | 7 | 311 | 317 | |
| G | s5hg | 1 | 318 | 318 | |
| G | HG | 17 | 319 | 335 | |
| G | hgh4 | 10 | 336 | 345 | |
| G | H4 | 27 | 346 | 372 | |
| G | h4s6 | 20 | 373 | 392 | |
| G | S6 | 5 | 393 | 397 | |
| G | s6-h5 | 5 | 398 | 402 | TCAT |
| G | H5 | 26 | 403 | 428 | |

Figure 26 - 1

MINI-G_s CONSTRUCTS

Key

Bold: start and stop codons
Underlined: histidine tag
Italic: TEV protease site
Grey: mutations
Grey & bold: linker
*: deletion For each mini-G_s construct both the DNA (top) and amino acid sequence (bottom) are given.

MINI-G_s55

SEQ ID NO 1:

MGHHHHHHHHHH*ENLYFQS*GCLGNSKTEDQRNEEKAQREANKKIEKQLQKDKQVYRATHRLLLLGAGESGKSTIV
KQMRILHVNGGG*DQDLLRCRVLTSGIFETKFQVDKVNFHMFDVGGQRDERRKWIQCFNDVTAIIFVVASSSYNM
VIREDNQTNRLQEALNLFKSIWNNRWLRTISVILFLNKQDLLAEKVLAGKSKIEDYFPEFARYTTPEDATPEPGE
DPRVTRAKYFIRDEFLRISTASGDGRHYCYPHFTCAVDTENIRRVFNDCRDIIQRMHLRQYELL

SEQ ID NO 46:

ATGGGTCACCACCATCATCACCATCATCACCACCAT*GAAAATCTTTATTTCCAGTCT*GGCTGCCTCGGGAACAGT
AAGACCGAGGACCAGCGCAACGAGGAGAAGGCGCAGCGTGAGGCCAACAAAAAGATCGAGAAGCAGCTGCAGAAG
GACAAGCAGGTCTACCGGGCCACGCACCGCCTGCTGCTGCTGGGTGCTGGAGAATCTGGTAAAAGCACCATTGTG
AAGCAGATGAGGATCCTGCATGTTAATGGCGGAGGT*GATCAGGACCTGCTTCGCTGCCGTGTCCTGACTTCTGG
AATCTTTGAGACCAAGTTCCAGGTCGACAAAGTCAACTTCCACATGTTTGACGTGGGTGGCCAGCGCGATGAACG
CCGCAAGTGGATCCAGTGCTTCAACGATGTGACTGCCATCATCTTCGTGGTGGCCAGCAGCAGCTACAACATGGT
CATCCGGGAGGACAACCAGACCAACCGCCTGCAGGAGGCTCTGAACCTCTTCAAGAGCATCTGGAACAACAGATG
GCTGCGCACCATCTCTGTGATCCTGTTCCTCAACAAGCAAGATCTGCTCGCTGAGAAAGTCCTTGCTGGGAAATC
GAAGATTGAGGACTACTTTCCAGAATTTGCTCGCTACACTACTCCTGAGGATGCTACTCCCGAGCCCGGAGAGGA
CCCACGCGTGACCCGGGCCAAGTACTTCATTCGAGATGAGTTTCTGAGGATCAGCACTGCCAGTGGAGATGGGCG
TCACTACTGCTACCCTCATTTCACCTGCGCTGTGGACACTGAGAACATCCGCCGTGTGTTCAACGACTGCCGTGA
CATCATTCAGCGCATGCACCTTCGTCAGTACGAGCTGCTCTAA

MINI-G_s77

SEQ ID NO 2:

MGHHHHHHH*ANKKIEKQLQKDKQVYRATHRLLLLGAGESGKSTIVKQMRILHVNGGG*DQDALRSRVLTSGIFET
KFQVDKVNFHMFDVGGQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

Figure 26 - 2

SEQ ID NO 47:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT\*GATCAGGACGGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

MINI-G$_s$81

SEQ ID NO 3:

MGHHHHHH*ANKKIEKQLQKDKQVYRATHRLLLLGAGESGKSTIVKQMRILHVNGGG*DQDALRSRVLTSGIFET
KFQVDKVNFHMFDVGGQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 48:

ATGGGTCACCACCATCATCACCAT*GCCAACAAAAAGATCGAGAAGCAGCTGCAGAAGGACAAGCAGGTCTACCG
GGCCACGATCCGCCTGCTGCTGCTGGGTGCTGGAGAATCTGGTAAAAGCACCATTGTGAAGCAGATGAGGATCCT
GCATGTTAATGGCGGAGGT\*GATCAGGACGGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

MINI-G$_s$84

SEQ ID NO 4:

MGHHHHHH*ANKKIEKQLQKDKQVYRATIRLLLLGAGESGKSTIVKQMRILHVNGGG*DQDALRSRVLTSGIFET
KFQVDKVNFHMFDVGGQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 49:

ATGGGTCACCACCATCATCACCAT*GCCAACAAAAAGATCGAGAAGCAGCTGCAGAAGGACAAGCAGGTCTACCG
GGCCACGATCCGCCTGCTGCTGCTGGGTGCTGGAGAATCTGGTAAAAGCACCATTGTGAAGCAGATGAGGATCCT
GCATGTTAATGGCGGAGGT\*GATCAGGACGGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT

Figure 26 - 3

```
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA
```

Mini-G$_s$186

SEQ ID NO 5:

MGHHHHHH\*ANKKIEKQLQKDKQVYRATHRLLLLGLGESGKSTIVKQMRILHVNGGG\*DQDALRSRVLTSGIFET
KFQVDKVNFHMFDVGGQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 50:

ATGGGTCACCACCATCATCACCAT\*GCCAACAAAAAGATCGAGAAGCAGCTGCAGAAGGACAAGCAGGTCTACCG
GGCCACGCACCGCCTGCTGCTGGGTCTGGGAGAATCTGGTAAAAGCACCATTGTGAAGCAGATGAGGATCCT
GCATGTTAATGGCGGAGGT\*GATCAGGACGCGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

Mini-G$_s$130

SEQ ID NO 6:

MGHHHHHH\*ANKKIEKQLQKDKQVYRATHRLLLLGAESGKSTIVKQMRILHVNGGG\*DQDALRSRVLTSGIFET
KFQVDKVNFHMFDVGGQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 51:

ATGGGTCACCACCATCATCACCAT\*GCCAACAAAAAGATCGAGAAGCAGCTGCAGAAGGACAAGCAGGTCTACCG
GGCCACGCACCGCCTGCTGCTGGGTGCTGAGGAATCTGGTAAAAGCACCATTGTGAAGCAGATGAGGATCCT
GCATGTTAATGGCGGAGGT\*GATCAGGACGCGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC

Figure 26 - 4

ACCTTCGTCAGTACGAGCTGCTCTAA

MINI-G$_s$116

SEQ ID NO 7:

MGHHHHHH*ANKKIEKQLQKDKQVYRATHRLLLLGAGNSGKSTIVKQMRILHVNGGG\*DQDALRSRVLTSGIFET
KFQVDKVNFHMFDVGGQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 52:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAAATCTGGTAAAAGCACCATTGTGAAGCAGATGAGGATCCT
GCATGTTAATGGCGGAGGT\*GATCAGGACGCGCTTCGCTCGCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

MINI-G$_s$134

SEQ ID NO 8:

MGHHHHHH*ANKKIEKQLQKDKQVYRATHRLLLLGAGESGKSTIVKQMRILHVNGGG\*DQDALRSAVLTSGIFET
KFQVDKVNFHMFDVGGQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 53:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT\*GATCAGGACGCGCTTCGCTCGGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

MINI-G$_s$111

SEQ ID NO 9:

Figure 26 - 5

MGHHHHHH*ANKKIEKQLQKDKQVYRATHRLLLLGAGESGKSTIVKQMRILHVNGGG\*DQDALRSRVLTSGIFET
KFQVDKVNFHMFDVGSQRDERRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 54:

ATGGGT<u>CACCACCATCATCACCAT</u>\*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT\*GATCAGGAC░░░CTTCGC░░░CGTGTCCTGACTTCTGGAATCTTTGAGACCAAGT
TCCAGGTCGACAAAGTCAACTTCCACATGTTTGACGTGGGT░░░CAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

<u>Mini-G<sub>s</sub>98</u>

SEQ ID NO 10:

MGHHHHHH*ANKKIEKQLQKDKQVYRATHRLLLLGAGESGKSTIVKQMRILHVNGGG\*DQDALRSRVLTSGIFET
KFQVDKVNFHMFDVGGGG\*RRKWIQCFNDVTAIIFVVASSSYNMVIREDNQTNRLQEALNLFKSIWNNRWLRTIS
VILFLNKQDLLAEKVLAGKSKIEDYFPEFARYTTPEDATPEPGEDPRVTRAKYFIRDEFLRISTASGDGRHYCYP
HFTCAVDTENIRRVFNDCRDIIQRMHLRQYELL

SEQ ID NO 55:

ATGGGT<u>CACCACCATCATCACCAT</u>\*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT\*GATCAGGAC░░░CTTCGC░░░CGTGTCCTGACTTCTGGAATCTTTGAGACCAAGT
TCCAGGTCGACAAAGTCAACTTCCACATGTTTGACGTGGGTGGCGGAGGG\*CGCCGCAAGTGGATCCAGTGCTTC
AACGATGTGACTGCCATCATCTTCGTGGTGGCCAGCAGCAGCTACAACATGGTCATCCGGGAGGACAACCAGACC
AACCGCCTGCAGGAGGCTCTGAACCTCTTCAAGAGCATCTGGAACAACAGATGGCTGCGCACCATCTCTGTGATC
CTGTTCCTCAACAAGCAAGATCTGCTCGCTGAGAAAGTCCTTGCTGGGAAATCGAAGATTGAGGACTACTTTCCA
GAATTTGCTCGCTACACTACTCCTGAGGATGCTACTCCCGAGCCCGGAGAGGACCCACGCGTGACCCGGGCCAAG
TACTTCATTCGAGATGAGTTTCTGAGGATCAGCACTGCCAGTGGAGATGGGCGTCACTACTGCTACCCTCATTTC
ACCTGCGCTGTGGACACTGAGAACATCCGCCGTGTGTTCAACGACTGCCGTGACATCATTCAGCGCATGCACCTT
CGTCAGTACGAGCTGCTCTAA

<u>Mini-G<sub>s</sub>175</u>

<u>SEQ ID NO 11:</u>

MGHHHHHH*ANKKIEKQLQKDKQVYRATHRLLLLGAGESGKSTIVKQMRILHVNGGG\*DQDALRSRVLTSGIFET
KFQVDKVNFHMFDVGGQRDSRRKWIQCFNDVTAIIFVVASSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 56:

Figure 26 - 6

ATGGGTCACCACCATCATCACCAT*GCCAACAAAAAGATCGAGAAGCAGCTGCAGAAGGACAAGCAGGTCTACCG
GGCCACGCACCGCCTGCTGCTGGGTGCTGGAGAATCTGGTAAAAGCACCATTGTGAAGCAGATGAGGATCCT
GCATGTTAATGGCGGAGGT*GATCAGGACGGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

<u>Mini-G$_s$92</u>

SEQ ID NO 12:

MGHHHHHH*ANKKIEKQLQKDKQVYRATHRLLLLGAGESGKSTIVKQMRILHVNGGG*DQD*LR*RVLTSGIFET
KFQVDKVNFHMFDVGGQRDERRKWIQCFNDVTAIIFVV*SSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 57:

ATGGGTCACCACCATCATCACCAT*GCCAACAAAAAGATCGAGAAGCAGCTGCAGAAGGACAAGCAGGTCTACCG
GGCCACGCACCGCCTGCTGCTGGGTGCTGGAGAATCTGGTAAAAGCACCATTGTGAAGCAGATGAGGATCCT
GCATGTTAATGGCGGAGGT*GATCAGGACGGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGACAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

<u>Mini-G$_s$104</u>

SEQ ID NO 13:

MGHHHHHH*ANKKIEKQLQKDKQVYRATHRLLLLGAGESGKSTIVKQMRILHVNGGG*DQD*LR*RVLTSGIFET
KFQVDKVNFHMFDVGGQRDERRKWIQCFNDVTAIIFVV*SSSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 58:

ATGGGTCACCACCATCATCACCAT*GCCAACAAAAAGATCGAGAAGCAGCTGCAGAAGGACAAGCAGGTCTACCG
GGCCACGCACCGCCTGCTGCTGGGTGCTGGAGAATCTGGTAAAAGCACCATTGTGAAGCAGATGAGGATCCT
GCATGTTAATGGCGGAGGT*GATCAGGACGGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGACAGCAGCAGCTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT

Figure 26 - 7

```
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA
```

MINI-G<sub>s</sub>117

SEQ ID NO 14:

MGHHHHHH*ANKKIEKQLQKDKQVYRATHRLLLLGAGESGKSTIVKQMRILHVNGGG*DQDALRSRVLTSGIFET
KFQVDKVNFHMFDVGGQRDERRKWIQCFNDVTAIIFVVASSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 59:

```
ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT*GATCAGGACGACCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAACTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA
```

MINI-G<sub>s</sub>118

SEQ ID NO 15:

MGHHHHHH*ANKKIEKQLQKDKQVYRATHRLLLLGAGESGKSTIVKQMRILHVNGGG*DQDALRSRVLTSGIFET
KFQVDKVNFHMFDVGGQRDERRKWIQCFNDVTAIIFVVASSYNMVIREDNQTNRLQEALNLFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 60:

Figure 26 - 8

ATGGGT<u>CACCACCATCATCACCAT</u>\*GCCAACAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT\*GATCAGGACGCGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGTACAACATGGTCATCCGGGAGGACAACC
AGACCAACCGCCTGCAGGAGGCTCTGAACCTCTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA

<u>Mini-G$_s$105</u>

SEQ ID NO 16:

<u>M</u>GHHHHHH\*ANKKIEKQLQKDKQVYRATHRLLLLGAGESGKSTIVKQMRILHVNGGG\*DQDALRSRVLTSGIFET
KFQVDKVNFHMFDVGGQRDERRKWIQCFNDVTAIIFVVASSSYN\*RLQEALNLFKSIWNNRWLRTISVILFLNKQ
DLLAEKVLAGKSKIEDYFPEFARYTTPEDATPEPGEDPRVTRAKYFIRDEFLRISTASGDGRHYCYPHFTCAVDT
ENIRRVFNDCRDIIQRMHLRQYELL

SEQ ID NO 61:

ATGGGT<u>CACCACCATCATCACCAT</u>\*GCCAACAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT\*GATCAGGACGCGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAAC\*CGCCTGCAGGAGGCTCTGAAC
CTCTTCAAGAGCATCTGGAACAACAGATGGCTGCGCACCATCTCTGTGATCCTGTTCCTCAACAAGCAAGATCTG
CTCGCTGAGAAAGTCCTTGCTGGGAAATCGAAGATTGAGGACTACTTTCCAGAATTTGCTCGCTACACTACTCCT
GAGGATGCTACTCCCGAGCCCGGAGAGGACCCACGCGTGACCCGGGCCAAGTACTTCATTCGAGATGAGTTTCTG
AGGATCAGCACTGCCAGTGGAGATGGGCGTCACTACTGCTACCCTCATTTCACCTGCGCTGTGGACACTGAGAAC
ATCCGCCGTGTGTTCAACGACTGCCGTGACATCATTCAGCGCATGCACCTTCGTCAGTACGAGCTGCTCTAA

<u>Mini-G$_s$94</u>

SEQ ID NO 17:

<u>M</u>GHHHHHH\*ANKKIEKQLQKDKQVYRATHRLLLLGAGESGKSTIVKQMRILHVNGGG\*DQDALRSRVLTSGIFET
KFQVDKVNFHMFDVGGQRDERRKWIQCFNDVTAIIFVVASSSYNMVIREDNQTNRLQEALNQFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 62:

ATGGGT<u>CACCACCATCATCACCAT</u>\*GCCAACAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT\*GATCAGGACGCGCTTCGCTCCCGTGTCCTGACTTCTGGAATCTTTGAGACCAAGT
TCCAGGTCGACAAAGTCAACTTCCACATGTTTGACGTGGGTGGCCAGCGCGATGAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACCAGTTCAAGAGCATCTGGAACAACAGATGGCTGCGCACCATCTCTG

Figure 26 - 9

```
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA
```

MINI-G$_s$113

SEQ ID NO 18:

MGHHHHHH*ANKKIEKQLQKDKQVYRATHRLLLLGAGESGKSTIVKQMRILHVNGGG*DQDALRSRVLTSGIFET
KFQVDKVNFHMFDVGGQRDERRKWIQCFNDVTAIIFVVASSSYNMVIREDNQTNRLQEALNEFKSIWNNRWLRTI
SVILFLNKQDLLAEKVLAGKSKIEDYFPEFARYTTPEDATPEPGEDPRVTRAKYFIRDEFLRISTASGDGRHYCY
PHFTCAVDTENIRRVFNDCRDIIQRMHLRQYELL

SEQ ID NO 63:

```
ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGTTAATGGCGGAGGT*GATCAGGACGCGCTTCGCTCCCGTGTCCTGACTTCTGGAATCTTTGAGACCAAGT
TCCAGGTCGACAAAGTCAACTTCCACATGTTTGACGTGGGTGGCCAGCGCGATAACGCCGCAAGTGGATCCAGT
GCTTCAACGATGTGACTGCCATCATCTTCGTGGTGGCCAGCAGCAGCTACAACATGGTCATCCGGGAGGACAACC
AGACCAACCGCCTGCAGGAGGCTCTGAACGAGTTCAAGAGCATCTGGAACAACAGATGGCTGCGCACCATCTCTG
TGATCCTGTTCCTCAACAAGCAAGATCTGCTCGCTGAGAAAGTCCTTGCTGGGAAATCGAAGATTGAGGACTACT
TTCCAGAATTTGCTCGCTACACTACTCCTGAGGATGCTACTCCCGAGCCCGGAGAGGACCCACGCGTGACCCGGG
CCAAGTACTTCATTCGAGATGAGTTTCTGAGGATCAGCACTGCCAGTGGAGATGGGCGTCACTACTGCTACCCTC
ATTTCACCTGCGCTGTGGACACTGAGAACATCCGCCGTGTGTTCAACGACTGCCGTGACATCATTCAGCGCATGC
ACCTTCGTCAGTACGAGCTGCTCTAA
```

MINI-G$_s$161

SEQ ID NO 19:

MGHHHHHH*ANKKIEKQLQKDKQVYRATHRLLLLGAGESGKSTIVKQMRILHGGGGG*ETKFQVDKVNFHMFDVG
GQRDERRKWIQCFNDVTAIIFVVASSSYNMVIREDNQTNRLQEALNLFKSIWNNRWLRTISVILFLNKQDLLAEK
VLAGKSKIEDYFPEFARYTTPEDATPEPGEDPRVTRAKYFIRDEFLRISTASGDGRHYCYPHFTCAVDTENIRRV
FNDCRDIIQRMHLRQYELL

SEQ ID NO 64:

```
ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGGGGGAGGTGGAGGC*GAGACCAAGTTCCAGGTGGACAAAGTCAACTTCCACATGTTTGACGTGGGTGGCC
AGCGCGATAACGCCGCAAGTGGATCCAGTGCTTCAACGATGTGACTGCCATCATCTTCGTGGTGGCCAGCAGCA
GCTACAACATGGTCATCCGGGAGGACAACCAGACCAACCGCCTGCAGGAGGCTCTGAACCTCTTCAAGAGCATCT
GGAACAACAGATGGCTGCGCACCATCTCTGTGATCCTGTTCCTCAACAAGCAAGATCTGCTCGCTGAGAAAGTCC
TTGCTGGGAAATCGAAGATTGAGGACTACTTTCCAGAATTTGCTCGCTACACTACTCCTGAGGATGCTACTCCCG
AGCCCGGAGAGGACCCACGCGTGACCCGGGCCAAGTACTTCATTCGAGATGAGTTTCTGAGGATCAGCACTGCCA
GTGGAGATGGGCGTCACTACTGCTACCCTCATTTCACCTGCGCTGTGGACACTGAGAACATCCGCCGTGTGTTCA
ACGACTGCCGTGACATCATTCAGCGCATGCACCTTCGTCAGTACGAGCTGCTCTAA
```

Figure 26 - 10

MINI-G₅162

SEQ ID NO 20:

MGHHHHHH*ANKKIEKQLQKDKQVYRATHRLLLLGAGESGKSTIVKQMRILHGGGGG*ETKFQVDKVNFHMFDVG
GQRDERRKWIQCFNDVTAIIFVVSSSYNMVIREDNQTNRLQEALNLFKSIWNNRWLRTISVILFLNKQDLLAEK
VLAGKSKIEDYFPEFARYTTPEDATPEPGEDPRVTRAKYFIRDEFLRISTASGDGRHYCYPHFTCAVDTENIRRV
FNDCRDIIQRMHLRQYELL

SEQ ID NO 65:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGGGGAGGTGGAGGC*GAGACCAAGTTCCAGGTGGACAAAGTCAACTTCCACATGTTTGACGTGGGTGGCC
AGCGCGATGAACGCCGCAAGTGGATCCAGTGCTTCAACGATGTGACTGCCATCATCTTCGTGGTGGACAGCAGCA
GCTACAACATGGTCATCCGGGAGGACAACCAGACCAACCGCCTGCAGGAGGCTCTGAACCTCTTCAAGAGCATCT
GGAACAACAGATGGCTGCGCACCATCTCTGTGATCCTGTTCCTCAACAAGCAAGATCTGCTCGCTGAGAAAGTCC
TTGCTGGGAAATCGAAGATTGAGGACTACTTTCCAGAATTTGCTCGCTACACTACTCCTGAGGATGCTACTCCCG
AGCCCGGAGAGGACCCACGCGTGACCCGGGCCAAGTACTTCATTCGAGATGAGTTTCTGAGGATCAGCACTGCCA
GTGGAGATGGGCGTCACTACTGCTACCCTCATTTCACCTGCGCTGTGGACACTGAGAACATCCGCCGTGTGTTCA
ACGACTGCCGTGACATCATTCAGCGCATGCACCTTCGTCAGTACGAGCTGCTCTAA

MINI-G₅164

SEQ ID NO 21:

MGHHHHHH*ANKKIEKQLQKDKQVYRATHRLLLLGAGESGKSTIVKQMRILHGGGGG*ETKFQVDKVNFHMFDVG
GQRDERRKWIQCFNDVTAIIFVVSSSYN*RLQEALNLFKSIWNNRWLRTISVILFLNKQDLLAEKVLAGKSKIE
DYFPEFARYTTPEDATPEPGEDPRVTRAKYFIRDEFLRISTASGDGRHYCYPHFTCAVDTENIRRVFNDCRDIIQ
RMHLRQYELL

SEQ ID NO 66:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGGGGAGGTGGAGGC*GAGACCAAGTTCCAGGTGGACAAAGTCAACTTCCACATGTTTGACGTGGGTGGCC
AGCGCGATGAACGCCGCAAGTGGATCCAGTGCTTCAACGATGTGACTGCCATCATCTTCGTGGTGGACAGCAGCA
GCTACAAC*CGCCTGCAGGAGGCTCTGAACCTCTTCAAGAGCATCTGGAACAACAGATGGCTGCGCACCATCTCT
GTGATCCTGTTCCTCAACAAGCAAGATCTGCTCGCTGAGAAAGTCCTTGCTGGGAAATCGAAGATTGAGGACTAC
TTTCCAGAATTTGCTCGCTACACTACTCCTGAGGATGCTACTCCCGAGCCCGGAGAGGACCCACGCGTGACCCGG
GCCAAGTACTTCATTCGAGATGAGTTTCTGAGGATCAGCACTGCCAGTGGAGATGGGCGTCACTACTGCTACCCT
CATTTCACCTGCGCTGTGGACACTGAGAACATCCGCCGTGTGTTCAACGACTGCCGTGACATCATTCAGCGCATG
CACCTTCGTCAGTACGAGCTGCTCTAA

MINI-G₅165

SEQ ID NO 22:

MGHHHHHH*ANKKIEKQLQKDKQVYRATHRLLLLGAGESGKSTIVKQMRILHGGGGG*ETKFQVDKVNFHMFDVG
GQRDERRKWIQCFNDVTAIIFVVSSSYN*RLQEALNLFKSIWNNRWLRTISVILFLNKQDLLAEKVLAGKSKIE

Figure 26 - 11

DYFPEFARYTTPEDATPEPGEDPRVTRAKYFIRDEFLRISTASGDGRHYCYPHFTCAVDTENIRRVFNDCRDIIQ
RMHLRQYELL

SEQ ID NO 67:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGGGGGAGGTGGAGGC\*GAGACCAAGTTCCAGGTGGACAAAGTCAACTTCCACATGTTTGACGTGGGTGGCC
AGCGCGATGAACGCCGCAAGTGGATCCAGTGCTTCAACGATGTGACTGCCATCATCTTCGTGGTGACAGCAGCG
ATTACAAC*CGCCTGCAGGAGGCTCTGAACCTCTTCAAGAGCATCTGGAACAACAGATGGCTGCGCACCATCTCT
GTGATCCTGTTCCTCAACAAGCAAGATCTGCTCGCTGAGAAAGTCCTTGCTGGGAAATCGAAGATTGAGGACTAC
TTTCCAGAATTTGCTCGCTACACTACTCCTGAGGATGCTACTCCCGAGCCCGGAGAGGACCCACGCGTGACCCGG
GCCAAGTACTTCATTCGAGATGAGTTTCTGAGGATCAGCACTGCCAGTGGAGATGGGCGTCACTACTGCTACCCT
CATTTCACCTGCGCTGTGGACACTGAGAACATCCGCCGTGTGTTCAACGACTGCCGTGACATCATTCAGCGCATG
CACCTTCGTCAGTACGAGCTGCTCTAA

MINI-G$_s$169

SEQ ID NO 23:

MGHHHHHH*ANKKIEKQLQKDKQVYRATHRLLLLGAGESGKSTIVKQMRILHGGGGG\*ETKFQVDKVNFHMFDVG
GQRDERRKWIQCFNDVTAIIFVVSSDYN*RLQEALNDFKSIWNNRWLRTISVILFLNKQDLLAEKVLAGKSKIE
DYFPEFARYTTPEDATPEPGEDPRVTRAKYFIRDEFLRISTASGDGRHYCYPHFTCAVDTENIRRVFNDCRDIIQ
RMHLRQYELL

SEQ ID NO 68:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGGAGAATCTGGTAAAAGCACCATTGTGAAGCAGATGAGGATCCT
GCATGGGGGAGGTGGAGGC\*GAGACCAAGTTCCAGGTGGACAAAGTCAACTTCCACATGTTTGACGTGGGTGGCC
AGCGCGATGAACGCCGCAAGTGGATCCAGTGCTTCAACGATGTGACTGCCATCATCTTCGTGGTGACAGCAGCG
ATTACAAC*CGCCTGCAGGAGGCTCTGAACGACTTCAAGAGCATCTGGAACAACAGATGGCTGCGCACCATCTCT
GTGATCCTGTTCCTCAACAAGCAAGATCTGCTCGCTGAGAAAGTCCTTGCTGGGAAATCGAAGATTGAGGACTAC
TTTCCAGAATTTGCTCGCTACACTACTCCTGAGGATGCTACTCCCGAGCCCGGAGAGGACCCACGCGTGACCCGG
GCCAAGTACTTCATTCGAGATGAGTTTCTGAGGATCAGCACTGCCAGTGGAGATGGGCGTCACTACTGCTACCCT
CATTTCACCTGCGCTGTGGACACTGAGAACATCCGCCGTGTGTTCAACGACTGCCGTGACATCATTCAGCGCATG
CACCTTCGTCAGTACGAGCTGCTCTAA

MINI-G$_s$183

SEQ ID NO 24:

MGHHHHHH*ANKKIEKQLQKDKQVYRATHRLLLLGANSGKSTIVKQMRILHGGGGG\*ETKFQVDKVNFHMFDVG
GQRDERRKWIQCFNDVTAIIFVVSSDYN*RLQEALNDFKSIWNNRWLRTISVILFLNKQDLLAEKVLAGKSKIE
DYFPEFARYTTPEDATPEPGEDPRVTRAKYFIRDEFLRISTASGDGRHYCYPHFTCAVDTENIRRVFNDCRDIIQ
RMHLRQYELL

SEQ ID NO 69:

ATGGGTCACCACCATCATCACCAT*GCCAACAAAAAGATCGAGAAGCAGCTGCAGAAGGACAAGCAGGTCTACCG

Figure 26 - 12

```
GGCCACGCACCGCCTGCTGCTGCTGGGTGCTGATAATTCTGGTAAAAGCACCATTGTGAAGCAGATGAGGATCCT
GCATGGGGGAGGTGGAGGC*GAGACCAAGTTCCAGGTGGACAAAGTCAACTTCCACATGTTTGACGTGGGTGGCC
AGCGCGATGAACGCCGCAAGTGGATCCAGTGCTTCAACGATGTGACTGCCATCATCTTCGTGGTGGACAGCAGCG
ATTACAAC*CGCCTGCAGGAGGCTCTGAACGACTTCAAGAGCATCTGGAACAACAGATGGCTGCGCACCATCTCT
GTGATCCTGTTCCTCAACAAGCAAGATCTGCTCGCTGAGAAAGTCCTTGCTGGGAAATCGAAGATTGAGGACTAC
TTTCCAGAATTTGCTCGCTACACTACTCCTGAGGATGCTACTCCCGAGCCCGGAGAGGACCCACGCGTGACCCGG
GCCAAGTACTTCATTCGAGATGAGTTTCTGAGGATCAGCACTGCCAGTGGAGATGGGCGTCACTACTGCTACCCT
CATTTCACCTGCGCTGTGGACACTGAGAACATCCGCCGTGTGTTCAACGACTGCCGTGACATCATTCAGCGCATG
CACCTTCGTCAGTACGAGCTGCTCTAA
```

MINI-G<sub>s</sub>199

SEQ ID NO 25:

```
MGHHHHHH*ANKKIEKQLQKDKQVYRATHRLLLLGADNSGKSTIVKQMRILHGGGGGGGG*TSGIFETKFQVDKV
NFHMFDVGGQRDERRKWIQCFNDVTAIIFVVSSDYN*RLQEALNDFKSIWNNRWLRTISVILFLNKQDLLAEKV
LAGKSKIEDYFPEFARYTTPEDATPEPGEDPRVTRAKYFIRDEFLRISTASGDGRHYCYPHFTCAVDTENIRRVF
NDCRDIIQRMHLRQYELL
```

SEQ ID NO 70:

```
ATGGGTCACCACCATCATCACCAT*GCCAACAAAAGATCGAGAAGCAGCTGCAGAAGGACAAGCAGGTCTACCG
GGCCACGCACCGCCTGCTGCTGCTGGGTGCTGATAATTCTGGTAAAAGCACCATTGTGAAGCAGATGAGGATCCT
GCATGGTGGGGGAGGCGGGGGCGGAGGT*ACTTCTGGAATCTTTGAGACCAAGTTCCAGGTGGACAAAGTCAACT
TCCACATGTTTGACGTGGGTGGCCAGCGCGATGAACGCCGCAAGTGGATCCAGTGCTTCAACGATGTGACTGCCA
TCATCTTCGTGGTGGACAGCAGCGATTACAAC*CGCCTGCAGGAGGCTCTGAACGACTTCAAGAGCATCTGGAAC
AACAGATGGCTGCGCACCATCTCTGTGATCCTGTTCCTCAACAAGCAAGATCTGCTCGCTGAGAAAGTCCTTGCT
GGGAAATCGAAGATTGAGGACTACTTTCCAGAATTTGCTCGCTACACTACTCCTGAGGATGCTACTCCCGAGCCC
GGAGAGGACCCACGCGTGACCCGGGCCAAGTACTTCATTCGAGATGAGTTTCTGAGGATCAGCACTGCCAGTGGA
GATGGGCGTCACTACTGCTACCCTCATTTCACCTGCGCTGTGGACACTGAGAACATCCGCCGTGTGTTCAACGAC
TGCCGTGACATCATTCAGCGCATGCACCTTCGTCAGTACGAGCTGCTCTAA
```

MINI-G<sub>s</sub>254

SEQ ID NO 26:

```
MGHHHHHH*ANKKIEKQLQKDKQVYRATHRLLLLGADNSGKSTIVKQARILHGGGGGGGG*TSGIFETKFQVDKV
NFHMFDVGGQRDERRKWIQCFNDVTAIIFVVSSDYN*RLQEALNDFKSIWNNRWLRTISVILFLNKQDLLAEKV
LAGKSKIEDYFPEFARYTTPEDATPEPGEDPRVTRAKYFIRDEFLRISTASGDGRHYCYPHFTCAVDTENIRRVF
NDCRDIIQRMHLRQYELL
```

SEQ ID NO 71:

```
ATGGGTCACCACCATCATCACCAT*GCCAACAAAAGATCGAGAAGCAGCTGCAGAAGGACAAGCAGGTCTACCG
GGCCACGCACCGCCTGCTGCTGCTGGGTGCTGATAATTCTGGTAAAAGCACCATTGTGAAGCAGGCGAGGATCCT
GCATGGTGGGGGAGGCGGGGGCGGAGGT*ACTTCTGGAATCTTTGAGACCAAGTTCCAGGTGGACAAAGTCAACT
TCCACATGTTTGACGTGGGTGGCCAGCGCGATGAACGCCGCAAGTGGATCCAGTGCTTCAACGATGTGACTGCCA
TCATCTTCGTGGTGGACAGCAGCGATTACAAC*CGCCTGCAGGAGGCTCTGAACGACTTCAAGAGCATCTGGAAC
AACAGATGGCTGCGCACCATCTCTGTGATCCTGTTCCTCAACAAGCAAGATCTGCTCGCTGAGAAAGTCCTTGCT
GGGAAATCGAAGATTGAGGACTACTTTCCAGAATTTGCTCGCTACACTACTCCTGAGGATGCTACTCCCGAGCCC
GGAGAGGACCCACGCGTGACCCGGGCCAAGTACTTCATTCGAGATGAGTTTCTGAGGATCAGCACTGCCAGTGGA
```

Figure 26 - 13

```
GATGGGCGTCACTACTGCTACCCTCATTTCACCTGCGCTGTGGACACTGAGAACATCCGCCGTGTGTTCAACGAC
TGCCGTGACATCATTCAGCGCATGCACCTTCGTCAGTACGAGCTGCTCTAA
```

MINI-G<sub>s</sub>350

SEQ ID NO 27:

```
MGHHHHHH*ANKKIEKQLQKDKQVYRATHRLLLLGADNSGKSTIVKQMRIHGGGGGGG*TSGIFETKFQVDKV
NFHMFDVGGQRDERRKWIQCFNDVTAIIFVVDSSDYN*RLQEALNDFKSIWNNRWLRTISVILFLNKQDLLAEKV
LAGKSKIEDYFPEFARYTTPEDATPEPGEDPRVTRAKYFIRDEFLRISTASGDGRHYCYPHFTCAVDTENIRRVF
NDCRDIIQRMHLRQYELL
```

SEQ ID NO 72:

```
ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGATAATTCTGGTAAAAGCACCATTGTGAAGCAGATGAGGATCAA
CCATGGTGGGGGAGGCGGGGGCGGAGGT*ACTTCTGGAATCTTTGAGACCAAGTTCCAGGTGGACAAAGTCAACT
TCCACATGTTTGACGTGGGTGGCCAGCGCGATGAACGCCGCAAGTGGATCCAGTGCTTCAACGATGTGACTGCCA
TCATCTTCGTGGTGGACAGCAGCGATTACAAC*CGCCTGCAGGAGGCTCTGAACGACTTCAAGAGCATCTGGAAC
AACAGATGGCTGCGCACCATCTCTGTGATCCTGTTCCTCAACAAGCAAGATCTGCTCGCTGAGAAAGTCCTTGCT
GGGAAATCGAAGATTGAGGACTACTTTCCAGAATTTGCTCGCTACACTACTCCTGAGGATGCTACTCCCGAGCCC
GGAGAGGACCCACGCGTGACCCGGGCCAAGTACTTCATTCGAGATGAGTTTCTGAGGATCAGCACTGCCAGTGGA
GATGGGCGTCACTACTGCTACCCTCATTTCACCTGCGCTGTGGACACTGAGAACATCCGCCGTGTGTTCAACGAC
TGCCGTGACATCATTCAGCGCATGCACCTTCGTCAGTACGAGCTGCTCTAA
```

MINI-Gs340

SEQ ID NO 28:

```
MGHHHHHH*ANKKIEKQLQKDKQVYRATHRLLLLGADNSGKSTIVKQMRILHGGGGGGG*TSGIFETKFQVDKV
NFHMFDVGGQRDERRKWIQCFNDVTAIIFVVDSSDYN*RLQEALNDFKSIWNNRWLRTISVILFLNKQDLLAEKV
LAGKSKIEDYFPEFARYTTPEDATPEPGEDPRVTRAKYFIRDEFLRISTASGDGRHYCYPHFTCAVDTENARRVF
NDCRDIIQRMHLRQYELL
```

SEQ ID NO 73:

```
ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGATAATTCTGGTAAAAGCACCATTGTGAAGCAGATGAGGATCCT
GCATGGTGGGGGAGGCGGGGGCGGAGGT*ACTTCTGGAATCTTTGAGACCAAGTTCCAGGTGGACAAAGTCAACT
TCCACATGTTTGACGTGGGTGGCCAGCGCGATGAACGCCGCAAGTGGATCCAGTGCTTCAACGATGTGACTGCCA
TCATCTTCGTGGTGGACAGCAGCGATTACAAC*CGCCTGCAGGAGGCTCTGAACGACTTCAAGAGCATCTGGAAC
AACAGATGGCTGCGCACCATCTCTGTGATCCTGTTCCTCAACAAGCAAGATCTGCTCGCTGAGAAAGTCCTTGCT
GGGAAATCGAAGATTGAGGACTACTTTCCAGAATTTGCTCGCTACACTACTCCTGAGGATGCTACTCCCGAGCCC
GGAGAGGACCCACGCGTGACCCGGGCCAAGTACTTCATTCGAGATGAGTTTCTGAGGATCAGCACTGCCAGTGGA
GATGGGCGTCACTACTGCTACCCTCATTTCACCTGCGCTGTGGACACTGAGAACGCCCGCCGTGTGTTCAACGAC
TGCCGTGACATCATTCAGCGCATGCACCTTCGTCAGTACGAGCTGCTCTAA
```

MINI-G<sub>s</sub>303

Figure 26 - 14

SEQ ID NO 29:

MGHHHHHH*ANKKIEKQLQKDKQVYRATHRLLLLGADNSGKSTIVKQMRILHGGGGGGGG*TSGIFETKFQVDKV
NFHMFDVGGQRDERRKWIQCFNDVTAIIFVVASSDYN*RLQEALNDFKSIWNNRWLRTISVILFLNKQDLLAEKV
LAGKSKIEDYFPEFARYTTPEDATPEPGEDPRVTRAKYFIRDEFLRISTASGDGRHYCYPHFTCAVDTENIRRVF
NDCRDIIQRMHLRQYELL

SEQ ID NO 74:

ATGGGT<u>CACCACCATCATCACCAT</u>*GCCAACAAAAAGATCGAGAAGCAGCTGCAGAAGGACAAGCAGGTCTACCG
GGCCACGCACCGCCTGCTGCTGCTGGGTGCTGATAATTCTGGTAAAAGCACCATTGTGAAGCAGATGAGGATCCT
GCATGGTGGGGGAGGCGGGGGCGGAGGT\*ACTTCTGGAATCTTTGAGACCAAGTTCCAGGTGGACAAAGTCAACT
TCCACATGTTTGACGTGGGTGGCCAGCGCGATGAACGCCGAAGTGGATCCAGTGCTTCAACGATGTGACTGCCA
TCATCTTCGTGGTGGACAGCAGCGATTACAAC*CGCCTGCAGGAGGCTCTGAACGACTTCAAGAGCATCTGGAAC
AACAGATGGCTGCGCACCATCTCTGTGATCCTGTTCCTCAACAAGCAAGATCTGCTCGCTGAGAAAGTCCTTGCT
GGGAAATCGAAGATTGAGGACTACTTTCCAGAATTTGCTCGCTACACTACTCCTGAGGATGCTACTCCCGAGCCC
GGAGAGGACCCACGCGTGACCCGGGCCAAGTACTTCATTCGAGATGAGTTTCTGAGGATCAGCACTGCCAGTGGA
GATGGGCGTCACTACTGCTACCCTCATTTCACCTGCGCTGTGGACACTGAGAACGCCCGCCGTGTGTTCAACGAC
TGCCGTGACATCATTCAGCGCATGCACCTTCGTCAGTACGAGCTGCTCTAA

<u>Mini-G<sub>s</sub>352</u>

SEQ ID NO 30:

MGHHHHHH*ANKKIEKQLQKDKQVYRATHRLLLLGADNSGKSTIVKQMRIYHGGGGGGGG\*TSGIFETKFQVDKV
NFHMFDVGGQRDERRKWIQCFNDVTAIIFVVASSDYN*RLQEALNDFKSIWNNRWLRTISVILFLNKQDLLAEKV
LAGKSKIEDYFPEFARYTTPEDATPEPGEDPRVTRAKYFIRDEFLRISTASGDGRHYCYPHFTCAVDTENARRVF
NDCRDIIQRMHLRQYELL

SEQ ID NO 75:

ATGGGT<u>CACCACCATCATCACCAT</u>*GCCAACAAAAAGATCGAGAAGCAGCTGCAGAAGGACAAGCAGGTCTACCG
GGCCACGCACCGCCTGCTGCTGCTGGGTGCTGATAATTCTGGTAAAAGCACCATTGTGAAGCAGATGAGGATCTA
CCATGGTGGGGGAGGCGGGGGCGGAGGT\*ACTTCTGGAATCTTTGAGACCAAGTTCCAGGTGGACAAAGTCAACT
TCCACATGTTTGACGTGGGTGGCCAGCGCGATGAACGCCGAAGTGGATCCAGTGCTTCAACGATGTGACTGCCA
TCATCTTCGTGGTGGACAGCAGCGATTACAAC*CGCCTGCAGGAGGCTCTGAACGACTTCAAGAGCATCTGGAAC
AACAGATGGCTGCGCACCATCTCTGTGATCCTGTTCCTCAACAAGCAAGATCTGCTCGCTGAGAAAGTCCTTGCT
GGGAAATCGAAGATTGAGGACTACTTTCCAGAATTTGCTCGCTACACTACTCCTGAGGATGCTACTCCCGAGCCC
GGAGAGGACCCACGCGTGACCCGGGCCAAGTACTTCATTCGAGATGAGTTTCTGAGGATCAGCACTGCCAGTGGA
GATGGGCGTCACTACTGCTACCCTCATTTCACCTGCGCTGTGGACACTGAGAACGCCCGCCGTGTGTTCAACGAC
TGCCGTGACATCATTCAGCGCATGCACCTTCGTCAGTACGAGCTGCTCTAA

<u>Mini-G<sub>s</sub>345</u>

SEQ ID NO 31:

MGHHHHHH*ANKKIEKQLQKDKQVYRATHRLLLLGADNSGKSTIVKQMRILHGGGGGGGG*TSGIFETKFQVDKV
NFHMFDVGGQRDERRKWIQCFNDVTAIIFVVASSDYN*RLQEALNDFKSIWNNRWLRTISVILFLNKQDLLAEKV
LAGKSKIEDYFPEFARYTTPEDATPEPGEDPRVTRAKYFIRDEFLRISTASGDGRHYCYPHFTCAVDTENARRVF

Figure 26 - 15

NDCRDIIQRMHLRQYELL

SEQ ID NO 76:

ATGGGTCACCACCATCATCACCAT*GCCAACAAAAAGATCGAGAAGCAGCTGCAGAAGGACAAGCAGGTCTACCG
GGCCACGCACCGCCTGCTGCTGCTGGGTGCTGATAATTCTGGTAAAAGCACCATTGTGAAGCAGATGAGGATCCT
GCATGGTGGGGGAGGCGGGGGCGGAGGT*ACTTCTGGAATCTTTGAGACCAAGTTCCAGGTGGACAAAGTCAACT
TCCACATGTTTGACGTGGGTGGCCAGCGCGATAACGCCGCAAGTGGATCCAGTGCTTCAACGATGTGACTGCCA
TCATCTTCGTGGTGGACAGCAGCGATTACAAC*CGCCTGCAGGAGGCTCTGAACGACTTCAAGAGCATCTGGAAC
AACAGATGGCTGCGCACCATCTCTGTGATCCTGTTCCTCAACAAGCAAGATCTGCTCGCTGAGAAAGTCCTTGCT
GGGAAATCGAAGATTGAGGACTACTTTCCAGAATTTGCTCGCTACACTACTCCTGAGGATGCTACTCCCGAGCCC
GGAGAGGACCCACGCGTGACCCGGGCCAAGTACTTCATTCGAGATGAGTTTCTGAGGATCAGCACTGCCAGTGGA
GATGGGCGTCACTACTGCTACCCTCATTTCACCTGCGCTGTGGACACTGAGAACCCCGCCGTATCTTCAACGAC
TGCCGTGACATCATTCAGCGCATGCACCTTCGTCAGTACGAGCTGCTCTAA

<u>MINI-G<sub>s</sub>389</u>

SEQ ID NO 32:

MGHHHHHH*ENLYFQGIEKQLQKDKQVYRATHRLLLLGADNSGKSTIVKQARILHGGSGGSGG***TSGIFETKFQV
DKVNFHMFDVGGQRDERRKWIQCFNDVTAIIFVVDSSDYN*RLQEALNDFKSIWNNRWLRTISVILFLNKQDLLA
EKVLAGKSKIEDYFPEFARYTTPEDATPEPGEDPRVTRAKYFIRDEFLRISTASGDGRHYCYPHFTCAVDTENIR
RVFNDCRDIIQRMHLRQYELL

SEQ ID NO 77:

ATGGGTCACCACCATCATCACCAT*GAAAATCTTTATTTCCAGGGT**ATCGAGAAGCAGCTGCAGAAGGACAAGCA
GGTCTACCGGGCCACGCACCGCCTGCTGCTGCTGGGTGCTGATAATTCTGGTAAAAGCACCATTGTGAAGCAGAT
GAGGATCCTGCATGGTGGGAGTGGCGGGAGCGGAGGT*ACTTCTGGAATCTTTGAGACCAAGTTCCAGGTGGACA
AAGTCAACTTCCACATGTTTGACGTGGGTGGCCAGCGCGATAACGCCGCAAGTGGATCCAGTGCTTCAACGATG
TGACTGCCATCATCTTCGTGGTGGACAGCAGCGATTACAAC*CGCCTGCAGGAGGCTCTGAACGACTTCAAGAGC
ATCTGGAACAACAGATGGCTGCGCACCATCTCTGTGATCCTGTTCCTCAACAAGCAAGATCTGCTCGCTGAGAAA
GTCCTTGCTGGGAAATCGAAGATTGAGGACTACTTTCCAGAATTTGCTCGCTACACTACTCCTGAGGATGCTACT
CCCGAGCCCGGAGAGGACCCACGCGTGACCCGGGCCAAGTACTTCATTCGAGATGAGTTTCTGAGGATCAGCACT
GCCAGTGGAGATGGGCGTCACTACTGCTACCCTCATTTCACCTGCGCTGTGGACACTGAGAACATCCGCCGTATC
TTCAACGACTGCCGTGACATCATTCAGCGCATGCACCTTCGTCAGTACGAGCTGCTCTAA

<u>MINI-G<sub>s</sub>391</u>

SEQ ID NO 33:

MGHHHHHH*ENLYFQGIEKQLQKDKQVYRATHRLLLLGADNSGKSTIVKQMRILHGGSGGSGG***TSGIFETKFQV
DKVNFHMFDVGGQRDERRKWIQCFNDVTAIIFVVDSSDYN*RLQEALNDFKSIWNNRWLRTISVILFLNKQDLLA
EKVLAGKSKIEDYFPEFARYTTPEDATPEPGEDPRVTRAKYFIRDEFLRISTASGDGRHYCYPHFTCAVDTENAR
RVFNDCRDIIQRMHLRQYELL

SEQ ID NO 78:

ATGGGTCACCACCATCATCACCAT*GAAAATCTTTATTTCCAGGGT**ATCGAGAAGCAGCTGCAGAAGGACAAGCA
GGTCTACCGGGCCACGCACCGCCTGCTGCTGCTGGGTGCTGATAATTCTGGTAAAAGCACCATTGTGAAGCAGAT

Figure 26 - 16

```
GAGGATCCTGCATGGTGGGAGTGGCGGGAGCGGAGGT*ACTTCTGGAATCTTTGAGACCAAGTTCCAGGTGGACA
AAGTCAACTTCCACATGTTTGACGTGGGTGGCCAGCGCGATGAACGCCGCAAGTGGATCCAGTGCTTCAACGATG
TGACTGCCATCATCTTCGTGGTGACAGCAGCGATTACAAC*CGCCTGCAGGAGGCTCTGAACGACTTCAAGAGC
ATCTGGAACAACAGATGGCTGCGCACCATCTCTGTGATCCTGTTCCTCAACAAGCAAGATCTGCTCGCTGAGAAA
GTCCTTGCTGGGAAATCGAAGATTGAGGACTACTTTCCAGAATTTGCTCGCTACACTACTCCTGAGGATGCTACT
CCCGAGCCCGGAGAGGACCCACGCGTGACCCGGGCCAAGTACTTCATTCGAGATGAGTTTCTGAGGATCAGCACT
GCCAGTGGAGATGGGCGTCACTACTGCTACCCTCATTTCACCTGCGCTGTGGACACTGAGAACGCCCGCCGTGTG
TTCAACGACTGCCGTGACATCATTCAGCGCATGCACCTTCGTCAGTACGAGCTGCTCTAA
```

MINI-G$_s$393

SEQ ID NO 34:

MGHHHHHH*ENLYFQG*\*IEKQLQKDKQVYRATHRLLLLGADNSGKSTIVKQMRILHGGSGGSGG\*TSGIFETKFQV
DKVNFHMFDVGGQRDERRKWIQCFNDVTAIIFVVDSSDYN\*RLQEALNDFKSIWNNRWLRTISVILFLNKQDLLA
EKVLAGKSKIEDYFPEFARYTTPEDATPEPGEDPRVTRAKYFIRDEFLRISTASGDGRHYCYPHFTCAVDTENAR
RDFNDCRDIIQRMHLRQYELL

SEQ ID NO 79:

```
ATGGGTCACCACCATCATCACCATGAAAATCTTTATTTCCAGGGT*ATCGAGAAGCAGCTGCAGAAGGACAAGCA
GGTCTACCGGGCCACGCACCGCCTGCTGCTGCTGGGTGCTGATAATTCTGGTAAAAGCACCATTGTGAAGCAGAT
GAGGATCCTGCATGGTGGGAGTGGCGGGAGCGGAGGT*ACTTCTGGAATCTTTGAGACCAAGTTCCAGGTGGACA
AAGTCAACTTCCACATGTTTGACGTGGGTGGCCAGCGCGATGAACGCCGCAAGTGGATCCAGTGCTTCAACGATG
TGACTGCCATCATCTTCGTGGTGACAGCAGCGATTACAAC*CGCCTGCAGGAGGCTCTGAACGACTTCAAGAGC
ATCTGGAACAACAGATGGCTGCGCACCATCTCTGTGATCCTGTTCCTCAACAAGCAAGATCTGCTCGCTGAGAAA
GTCCTTGCTGGGAAATCGAAGATTGAGGACTACTTTCCAGAATTTGCTCGCTACACTACTCCTGAGGATGCTACT
CCCGAGCCCGGAGAGGACCCACGCGTGACCCGGGCCAAGTACTTCATTCGAGATGAGTTTCTGAGGATCAGCACT
GCCAGTGGAGATGGGCGTCACTACTGCTACCCTCATTTCACCTGCGCTGTGGACACTGAGAACGCCCGCCGTATC
TTCAACGACTGCCGTGACATCATTCAGCGCATGCACCTTCGTCAGTACGAGCTGCTCTAA
```

MINI-G$_s$395

SEQ ID NO 35:

MGHHHHHH*ENLYFQG*\*NSKTEDQRNEEKAQREANKKIEKQLQKDKQVYRATHRLLLLGADNSGKSTIVKQARILH
GGSGGSGG\*TSGIFETKFQVDKVNFHMFDVGGQRDERRKWIQCFNDVTAIIFVVDSSDYN\*RLQEALNLFKSIWN
NRWLRTISVILFLNKQDLLAEKVLAGKSKIEDYFPEFARYTTPEDATPEPGEDPRVTRAKYFIRDEFLRISTASG
DGRHYCYPHFTCAVDTENIRRDFNDCRDIIQRMHLRQYELL

SEQ ID NO 80:

```
ATGGGTCACCACCATCATCACCATGAAAATCTTTATTTCCAGGGT*AACAGTAAGACCGAGGACCAGCGCAACGA
GGAGAAGGCGCAGCGTGAGGCCAACAAAAAGATCGAGAAGCAGCTGCAGAAGGACAAGCAGGTCTACCGGGCCAC
GCACCGCCTGCTGCTGCTGGGTGCTGATAATTCTGGTAAAAGCACCATTGTGAAGCAGGCGAGGATCCTGCATGG
TGGGAGTGGCGGGAGCGGAGGT*ACTTCTGGAATCTTTGAGACCAAGTTCCAGGTGGACAAAGTCAACTTCCACA
TGTTTGACGTGGGTGGCCAGCGCGATGAACGCCGCAAGTGGATCCAGTGCTTCAACGATGTGACTGCCATCATCT
TCGTGGTGACAGCAGCGATTACAAC*CGCCTGCAGGAGGCTCTGAACCTCTTCAAGAGCATCTGGAACAACAGA
TGGCTGCGCACCATCTCTGTGATCCTGTTCCTCAACAAGCAAGATCTGCTCGCTGAGAAAGTCCTTGCTGGGAAA
TCGAAGATTGAGGACTACTTTCCAGAATTTGCTCGCTACACTACTCCTGAGGATGCTACTCCCGAGCCCGGAGAG
GACCCACGCGTGACCCGGGCCAAGTACTTCATTCGAGATGAGTTTCTGAGGATCAGCACTGCCAGTGGAGATGGG
```

Figure 26 - 17

CGTCACTACTGCTACCCTCATTTCACCTGCGCTGTGGACACTGAGAACATCCGCCGTATCTTCAACGACTGCCGT
GACATCATTCAGCGCATGCACCTTCGTCAGTACGAGCTGCTCTAA

MINI-G<sub>s</sub>397

SEQ ID NO 36:

MGHHHHHH*ENLYFQG*\*NSKTEDQRNEEKAQREANKKIEKQLQKDKQVYRATHRLLLLGADNSGKSTIVKQMRILH
GGSGGSGG\*TSGIFETKFQVDKVNFHMFDVGGQRDERRKWIQCFNDVTAIIFVVDSSDYN\*RLQEALNLFKSIWN
NRWLRTISVILFLNKQDLLAEKVLAGKSKIEDYFPEFARYTTPEDATPEPGEDPRVTRAKYFIRDEFLRISTASG
DGRHYCYPHFTCAVDTENARRVFNDCRDIIQRMHLRQYELL

SEQ ID NO 81:

ATGGGTCACCACCATCATCACCAT*GAAAATCTTTATTTCCAGGGT*\*AACAGTAAGACCGAGGACCAGCGCAACGA
GGAGAAGGCGCAGCGTGAGGCCAACAAAAAGATCGAGAAGCAGCTGCAGAAGGACAAGCAGGTCTACCGGGCCAC
GCACCGCCTGCTGCTGCTGGGTGCTGATAATTCTGGTAAAAGCACCATTGTGAAGCAGATGAGGATCCTGCATGG
TGGGAGTGGCGGGAGCGGAGGT\*ACTTCTGGAATCTTTGAGACCAAGTTCCAGGTGGACAAAGTCAACTTCCACA
TGTTTGACGTGGGTGGCCAGCGCGATGAACGCCGCAAGTGGATCCAGTGCTTCAACGATGTGACTGCCATCATCT
TCGTGGTGGACAGCAGCGATTACAAC\*CGCCTGCAGGAGGCTCTGAACCTCTTCAAGAGCATCTGGAACAACAGA
TGGCTGCGCACCATCTCTGTGATCCTGTTCCTCAACAAGCAAGATCTGCTCGCTGAGAAAGTCCTTGCTGGGAAA
TCGAAGATTGAGGACTACTTTCCAGAATTTGCTCGCTACACTACTCCTGAGGATGCTACTCCCGAGCCCGGAGAG
GACCCACGCGTGACCCGGGCCAAGTACTTCATTCGAGATGAGTTTCTGAGGATCAGCACTGCCAGTGGAGATGGG
CGTCACTACTGCTACCCTCATTTCACCTGCGCTGTGGACACTGAGAACGCCCGCCGTGTGTTCAACGACTGCCGT
GACATCATTCAGCGCATGCACCTTCGTCAGTACGAGCTGCTCTAA

MINI-G<sub>s</sub>399

SEQ ID NO 37:

MGHHHHHH*ENLYFQG*\*NSKTEDQRNEEKAQREANKKIEKQLQKDKQVYRATHRLLLLGADNSGKSTIVKQMRILH
GGSGGSGG\*TSGIFETKFQVDKVNFHMFDVGGQRDERRKWIQCFNDVTAIIFVVDSSDYN\*RLQEALNLFKSIWN
NRWLRTISVILFLNKQDLLAEKVLAGKSKIEDYFPEFARYTTPEDATPEPGEDPRVTRAKYFIRDEFLRISTASG
DGRHYCYPHFTCAVDTENARRFNDCRDIIQRMHLRQYELL

SEQ ID NO 82:

ATGGGTCACCACCATCATCACCAT*GAAAATCTTTATTTCCAGGGT*\*AACAGTAAGACCGAGGACCAGCGCAACGA
GGAGAAGGCGCAGCGTGAGGCCAACAAAAAGATCGAGAAGCAGCTGCAGAAGGACAAGCAGGTCTACCGGGCCAC
GCACCGCCTGCTGCTGCTGGGTGCTGATAATTCTGGTAAAAGCACCATTGTGAAGCAGATGAGGATCCTGCATGG
TGGGAGTGGCGGGAGCGGAGGT\*ACTTCTGGAATCTTTGAGACCAAGTTCCAGGTGGACAAAGTCAACTTCCACA
TGTTTGACGTGGGTGGCCAGCGCGATGAACGCCGCAAGTGGATCCAGTGCTTCAACGATGTGACTGCCATCATCT
TCGTGGTGGACAGCAGCGATTACAAC\*CGCCTGCAGGAGGCTCTGAACCTCTTCAAGAGCATCTGGAACAACAGA
TGGCTGCGCACCATCTCTGTGATCCTGTTCCTCAACAAGCAAGATCTGCTCGCTGAGAAAGTCCTTGCTGGGAAA
TCGAAGATTGAGGACTACTTTCCAGAATTTGCTCGCTACACTACTCCTGAGGATGCTACTCCCGAGCCCGGAGAG
GACCCACGCGTGACCCGGGCCAAGTACTTCATTCGAGATGAGTTTCTGAGGATCAGCACTGCCAGTGGAGATGGG
CGTCACTACTGCTACCCTCATTTCACCTGCGCTGTGGACACTGAGAACGCCCGCCGTATCTTCAACGACTGCCGT
GACATCATTCAGCGCATGCACCTTCGTCAGTACGAGCTGCTCTAA

Figure 26 - 18

Mini-G$_s$404

SEQ ID NO 38:

MGHHHHHH*ENLYFQG*\*IEKQLQKDKQVYRATHRLLLLGADNSGKSTIVKQMRILHGGSGGSGG\*TSGIFETKFQV
DKVNFHMFDVGGQRDERRKWIQCFNDVTAIIFVVASSDYN\*RLQEALNDFKSIWNNRWLRTISVILFLNKQDLLA
EKVLAGKSKIEDYFPEFARYTTPEDATPEPGEDPRVTRAKYFIRDEFLRISTASGDGRHYCYPHFTCAVDTENIR
RVFNDCRDIIQRMHLRQYELL

SEQ ID NO 83:

ATGGGT<u>CACCACCATCATCACCAT</u>*GAAAATCTTTATTTCCAGGGT*\*ATCGAGAAGCAGCTGCAGAAGGACAAGCA
GGTCTACCGGGCCACGCACCGCCTGCTGCTGCTGGGTGCTGATAATTCTGGTAAAAGCACCATTGTGAAGCAGAT
GAGGATCCTGCATGGTGGGAGTGGCGGGAGCGGAGGT\*ACTTCTGGAATCTTTGAGACCAAGTTCCAGGTGGACA
AAGTCAACTTCCACATGTTTGACGTGGGTGGCCAGCGCGATGAACGCCGCAAGTGGATCCAGTGCTTCAACGATG
TGACTGCCATCATCTTCGTGGTGGACAGCAGCGATTACAAC\*CGCCTGCAGGAGGCTCTGAACGACTTCAAGAGC
ATCTGGAACAACAGATGGCTGCGCACCATCTCTGTGATCCTGTTCCTCAACAAGCAAGATCTGCTCGCTGAGAAA
GTCCTTGCTGGGAAATCGAAGATTGAGGACTACTTTCCAGAATTTGCTCGCTACACTACTCCTGAGGATGCTACT
CCCGAGCCCGGAGAGGACCCACGCGTGACCCGGGCCAAGTACTTCATTCGAGATGAGTTTCTGAGGATCAGCACT
GCCAGTGGAGATGGGCGTCACTACTGCTACCCTCATTTCACCTGCGCTGTGGACACTGAGAACATCCGCCGTGTG
TTCAACGACTGCCGTGACATCATTCAGCGCATGCACCTTCGTCAGTACGAGCTGCTCTAA

Mini-G$_s$406

SEQ ID NO 39:

MGHHHHHH*ENLYFQG*\*NSKTEDQRNEEKAQREANKKIEKQLQKDKQVYRATHRLLLLGADNSGKSTIVKQMRILH
GGSGGSGG\*TSGIFETKFQVDKVNFHMFDVGGQRDERRKWIQCFNDVTAIIFVVASSDYN\*RLQEALNLFKSIWN
NRWLRTISVILFLNKQDLLAEKVLAGKSKIEDYFPEFARYTTPEDATPEPGEDPRVTRAKYFIRDEFLRISTASG
DGRHYCYPHFTCAVDTENIRRVFNDCRDIIQRMHLRQYELL

SEQ ID NO 84:

ATGGGT<u>CACCACCATCATCACCAT</u>*GAAAATCTTTATTTCCAGGGT*\*AACAGTAAGACCGAGGACCAGCGCAACGA
GGAGAAGGCGCAGCGTGAGGCCAACAAAAAGATCGAGAAGCAGCTGCAGAAGGACAAGCAGGTCTACCGGGCCAC
GCACCGCCTGCTGCTGCTGGGTGCTGATAATTCTGGTAAAAGCACCATTGTGAAGCAGATGAGGATCCTGCAT**GG
TGGGAGTGGCGGGAGCGGAGGT**\*ACTTCTGGAATCTTTGAGACCAAGTTCCAGGTGGACAAAGTCAACTTCCACA
TGTTTGACGTGGGTGGCCAGCGCGATGAACGCCGCAAGTGGATCCAGTGCTTCAACGATGTGACTGCCATCATCT
TCGTGGTGGACAGCAGCGATTACAAC\*CGCCTGCAGGAGGCTCTGAACCTCTTCAAGAGCATCTGGAACAACAGA
TGGCTGCGCACCATCTCTGTGATCCTGTTCCTCAACAAGCAAGATCTGCTCGCTGAGAAAGTCCTTGCTGGGAAA
TCGAAGATTGAGGACTACTTTCCAGAATTTGCTCGCTACACTACTCCTGAGGATGCTACTCCCGAGCCCGGAGAG
GACCCACGCGTGACCCGGGCCAAGTACTTCATTCGAGATGAGTTTCTGAGGATCAGCACTGCCAGTGGAGATGGG
CGTCACTACTGCTACCCTCATTTCACCTGCGCTGTGGACACTGAGAACATCCGCCGTGTGTTCAACGACTGCCGT
GACATCATTCAGCGCATGCACCTTCGTCAGTACGAGCTGCTCTAA

Mini-G$_s$410

SEQ ID NO 40:

MGHHHHHH*ENLYFQG*\*IEKQLQKDKQVYRATHRLLLLGADNSGKSTIVKQMRIRHGGSGGSGG\*TSGIFETKFQV

Figure 26 - 19

DKVNFHMFDVGGQRDERRKWIQCFNDVTAIIFVVSSDYN*RLQEALNDFKSIWNNRWLRTISVILFLNKQDLLA
EKVLAGKSKIEDYFPEFARYTTPEDATPEPGEDPRVTRAKYFIRDEFLRISTASGDGRHYCYPHFTCAVDTENAR
RIFNDCRDIIQRMHLRQYELL

SEQ ID NO 85:

ATGGGT<u>CACCACCATCATCACCAT</u><i>GAAAATCTTTATTTCCAGGGT</i>*ATCGAGAAGCAGCTGCAGAAGGACAAGCA
GGTCTACCGGGCCACGCACCGCCTGCTGCTGCTGGGTGCTGATAATTCTGGTAAAAGCACCATTGTGAAGCAGAT
GAGGATCCGCCATGGTGGGAGTGGCGGGAGCGGAGGT*ACTTCTGGAATCTTTGAGACCAAGTTCCAGGTGGACA
AAGTCAACTTCCACATGTTTGACGTGGGTGGCCAGCGCGATGAACGCCGAAGTGGATCCAGTGCTTCAACGATG
TGACTGCCATCATCTTCGTGGTGACAGCAGCGATTACAAC*CGCCTGCAGGAGGCTCTGAACGACTTCAAGAGC
ATCTGGAACAACAGATGGCTGCGCACCATCTCTGTGATCCTGTTCCTCAACAAGCAAGATCTGCTCGCTGAGAAA
GTCCTTGCTGGGAAATCGAAGATTGAGGACTACTTTCCAGAATTTGCTCGCTACACTACTCCTGAGGATGCTACT
CCCGAGCCCGGAGAGGACCCACGCGTGACCCGGGCCAAGTACTTCATTCGAGATGAGTTTCTGAGGATCAGCACT
GCCAGTGGAGATGGGCGTCACTACTGCTACCCTCATTTCACCTGCGCTGTGGACACTGAGAACGCCCGCCGTATC
TTCAACGACTGCCGTGACATCATTCAGCGCATGCACCTTCGTCAGTACGAGCTGCTCTAA

<u>Mini-G<sub>s</sub>414</u>

SEQ ID NO 41:

MGHHHHHH<i>ENLYFQG</i>*IEKQLQKDKQVYRATHRLLLLGADNSGKSTIVKQMRIYHGGSGGSGG*TSGIFETKFQV
DKVNFHMFDVGGQRDERRKWIQCFNDVTAIIFVVSSDYN*RLQEALNDFKSIWNNRWLRTISVILFLNKQDLLA
EKVLAGKSKIEDYFPEFARYTTPEDATPEPGEDPRVTRAKYFIRDEFLRISTASGDGRHYCYPHFTCAVDTENAR
RIFNDCRDIIQRMHLRQYELL

SEQ ID NO 86:

ATGGGT<u>CACCACCATCATCACCAT</u><i>GAAAATCTTTATTTCCAGGGT</i>*ATCGAGAAGCAGCTGCAGAAGGACAAGCA
GGTCTACCGGGCCACGCACCGCCTGCTGCTGCTGGGTGCTGATAATTCTGGTAAAAGCACCATTGTGAAGCAGAT
GAGGATCTACCATGGTGGGAGTGGCGGGAGCGGAGGT*ACTTCTGGAATCTTTGAGACCAAGTTCCAGGTGGACA
AAGTCAACTTCCACATGTTTGACGTGGGTGGCCAGCGCGATGAACGCCGAAGTGGATCCAGTGCTTCAACGATG
TGACTGCCATCATCTTCGTGGTGACAGCAGCGATTACAAC*CGCCTGCAGGAGGCTCTGAACGACTTCAAGAGC
ATCTGGAACAACAGATGGCTGCGCACCATCTCTGTGATCCTGTTCCTCAACAAGCAAGATCTGCTCGCTGAGAAA
GTCCTTGCTGGGAAATCGAAGATTGAGGACTACTTTCCAGAATTTGCTCGCTACACTACTCCTGAGGATGCTACT
CCCGAGCCCGGAGAGGACCCACGCGTGACCCGGGCCAAGTACTTCATTCGAGATGAGTTTCTGAGGATCAGCACT
GCCAGTGGAGATGGGCGTCACTACTGCTACCCTCATTTCACCTGCGCTGTGGACACTGAGAACGCCCGCCGTATC
TTCAACGACTGCCGTGACATCATTCAGCGCATGCACCTTCGTCAGTACGAGCTGCTCTAA

<u>Mini-G<sub>s</sub>418</u>

SEQ ID NO 42:

MGHHHHHH<i>ENLYFQG</i>*NSKTEDQRNEEKAQREANKKIEKQLQKDKQVYRATHRLLLLGADNSGKSTIVKQMRIYH
GGSGGSGG*TSGIFETKFQVDKVNFHMFDVGGQRDERRKWIQCFNDVTAIIFVVSSDYN*RLQEALNLFKSIWN
NRWLRTISVILFLNKQDLLAEKVLAGKSKIEDYFPEFARYTTPEDATPEPGEDPRVTRAKYFIRDEFLRISTASG
DGRHYCYPHFTCAVDTENARRIFNDCRDIIQRMHLRQYELL

Figure 26 - 20

SEQ ID NO 87:

ATGGGTCACCACCATCATCACCAT*GAAAATCTTTATTTCCAGGGT*\*AACAGTAAGACCGAGGACCAGCGCAACGA
GGAGAAGGCGCAGCGTGAGGCCAACAAAAGATCGAGAAGCAGCTGCAGAAGGACAAGCAGGTCTACCGGGCCAC
GCACCGCCTGCTGCTGCTGGGTGCTGATAATTCTGGTAAAAGCACCATTGTGAAGCAGATGAGGATCTACCATGG
TGGGAGTGGCGGGAGCGGAGGT\*ACTTCTGGAATCTTTGAGACCAAGTTCCAGGTGGACAAAGTCAACTTCCACA
TGTTTGACGTGGGTGGCCAGCGCGATGAACGCCGCAAGTGGATCCAGTGCTTCAACGATGTGACTGCCATCATCT
TCGTGGTGGACAGCAGCGATTACAAC\*CGCCTGCAGGAGGCTCTGAACCTCTTCAAGAGCATCTGGAACAACAGA
TGGCTGCGCACCATCTCTGTGATCCTGTTCCTCAACAAGCAAGATCTGCTCGCTGAGAAAGTCCTTGCTGGGAAA
TCGAAGATTGAGGACTACTTTCCAGAATTTGCTCGCTACACTACTCCTGAGGATGCTACTCCCGAGCCCGGAGAG
GACCCACGCGTGACCCGGGCCAAGTACTTCATTCGAGATGAGTTTCTGAGGATCAGCACTGCCAGTGGAGATGGG
CGTCACTACTGCTACCCTCATTTCACCTGCGCTGTGGACACTGAGAACGCCCGCCGTATCTTCAACGACTGCCGT
GACATCATTCAGCGCATGCACCTTCGTCAGTACGAGCTGCTCTAA

MINI-G₃431

SEQ ID NO 43:

MGHHHHHH*ENLYFQG*\*ATHRLLLLGADNSGKSTIVKQMRILHGGSGGSGG\*TSGIFETKFQVDKVNFHMFDVGGQ
RDERRKWIQCFNDVTAIIFVVDSSYN\*RLQEALNDFKSIWNNRWLRTISVILFLNKQDLLAEKVLAGKSKIEDY
FPEFARYTTPEDATPEPGEDPRVTRAKYFIRDEFLRISTASGDGRHYCYPHFTCAVDTENARRFNDCRDIIQRM
HLRQYELL

SEQ ID NO 88:

ATGGGTCACCACCATCATCACCAT*GAAAATCTTTATTTCCAGGGT*\*GCCACGCACCGCCTGCTGCTGCTGGGTGC
TGATAATTCTGGTAAAAGCACCATTGTGAAGCAGATGAGGATCCTGCATGGTGGGAGTGGCGGGAGCGGAGGT\*A
CTTCTGGAATCTTTGAGACCAAGTTCCAGGTGGACAAAGTCAACTTCCACATGTTTGACGTGGGTGGCCAGCGCG
ATGAACGCCGCAAGTGGATCCAGTGCTTCAACGATGTGACTGCCATCATCTTCGTGGTGGACAGCAGCGATTACA
AC\*CGCCTGCAGGAGGCTCTGAACGACTTCAAGAGCATCTGGAACAACAGATGGCTGCGCACCATCTCTGTGATC
CTGTTCCTCAACAAGCAAGATCTGCTCGCTGAGAAAGTCCTTGCTGGGAAATCGAAGATTGAGGACTACTTTCCA
GAATTTGCTCGCTACACTACTCCTGAGGATGCTACTCCCGAGCCCGGAGAGGACCCACGCGTGACCCGGGCCAAG
TACTTCATTCGAGATGAGTTTCTGAGGATCAGCACTGCCAGTGGAGATGGGCGTCACTACTGCTACCCTCATTTC
ACCTGCGCTGTGGACACTGAGAACGCCCGCCGTATCTTCAACGACTGCCGTGACATCATTCAGCGCATGCACCTT
CGTCAGTACGAGCTGCTCTAA

MINI-G₅432

SEQ ID NO 44:

MGHHHHHH*ENLYFQG*\*IEKQLQKDKQVYRATHRLLLLGADNSGKSTIVKQMRILHGGGGGG\*ETKFQVDKVNFHM
FDVGGQRDERRKWIQCFNDVTAIIFVVDSSYN\*RLQEALNDFKSIWNNRWLRTISVILFLNKQDLLAEKVLAGK
SKIEDYFPEFARYTTPEDATPEPGEDPRVTRAKYFIRDEFLRISTASGDGRHYCYPHFTCAVDTENARRFNDCR
DIIQRMHLRQYELL

SEQ ID NO 89:

ATGGGTCACCACCATCATCACCAT*GAAAATCTTTATTTCCAGGGT*\*ATCGAGAAGCAGCTGCAGAAGGACAAGCA
GGTCTACCGGGCCACGCACCGCCTGCTGCTGCTGGGTGCTGATAATTCTGGTAAAAGCACCATTGTGAAGCAGAT
GAGGATCCTGCATGGTGGGGGTGGCGGGGGC\*GAGACCAAGTTCCAGGTGGACAAAGTCAACTTCCACATGTTTG
ACGTGGGTGGCCAGCGCGATGAACGCCGCAAGTGGATCCAGTGCTTCAACGATGTGACTGCCATCATCTTCGTGG

Figure 26 - 21

```
TGGACAGCAGCGATTACAAC*CGCCTGCAGGAGGCTCTGAACGACTTCAAGAGCATCTGGAACAACAGATGGCTG
CGCACCATCTCTGTGATCCTGTTCCTCAACAAGCAAGATCTGCTCGCTGAGAAAGTCCTTGCTGGGAAATCGAAG
ATTGAGGACTACTTTCCAGAATTTGCTCGCTACACTACTCCTGAGGATGCTACTCCCGAGCCCGGAGAGGACCCA
CGCGTGACCCGGGCCAAGTACTTCATTCGAGATGAGTTTCTGAGGATCAGCACTGCCAGTGGAGATGGGCGTCAC
TACTGCTACCCTCATTTCACCTGCGCTGTGGACACTGAGAACGCCCGCCGTATCTTCAACGACTGCCGTGACATC
ATTCAGCGCATGCACCTTCGTCAGTACGAGCTGCTCTAA
```

MINI-G<sub>s</sub>433

SEQ ID NO 45:

```
MGHHHHHHENLYFQG*ATHRLLLLGADNSGKSTIVKQMRILHGGGGGG*ETKFQVDKVNFHMFDVGGQRDERRKW
IQCFNDVTAIIFVVDSSDYN*RLQEALNDFKSIWNNRWLRTISVILFLNKQDLLAEKVLAGKSKIEDYFPEFARY
TTPEDATPEPGEDPRVTRAKYFIRDEFLRISTASGDGRHYCYPHFTCAVDTENARRIFNDCRDIIQRMHLRQYEL
L
```

SEQ ID NO 90:

```
ATGGGTCACCACCATCATCACCATGAAAATCTTTATTTCCAGGGT*GCCACGCACCGCCTGCTGCTGCTGGGTGC
TGATAATTCTGGTAAAAGCACCATTGTGAAGCAGATGAGGATCCTGCATGGTGGGGGTGGCGGGGGC*GAGACCA
AGTTCCAGGTGGACAAAGTCAACTTCCACATGTTTGACGTGGGTGGCCAGCGCGATGAACGCCGCAAGTGGATCC
AGTGCTTCAACGATGTGACTGCCATCATCTTCGTGGTGGACAGCAGCGATTACAAC*CGCCTGCAGGAGGCTCTG
AACGACTTCAAGAGCATCTGGAACAACAGATGGCTGCGCACCATCTCTGTGATCCTGTTCCTCAACAAGCAAGAT
CTGCTCGCTGAGAAAGTCCTTGCTGGGAAATCGAAGATTGAGGACTACTTTCCAGAATTTGCTCGCTACACTACT
CCTGAGGATGCTACTCCCGAGCCCGGAGAGGACCCACGCGTGACCCGGGCCAAGTACTTCATTCGAGATGAGTTT
CTGAGGATCAGCACTGCCAGTGGAGATGGGCGTCACTACTGCTACCCTCATTTCACCTGCGCTGTGGACACTGAG
AACGCCCGCCGTATCTTCAACGACTGCCGTGACATCATTCAGCGCATGCACCTTCGTCAGTACGAGCTGCTCTAA
```

Figure 27

```
MGAGASAEEKHSRELEKKLKEDAEKDARTVKLLLLGAGESGKSTIVKQMKIIHQDGYSLEECLEFIAIIYGNTLQ
SILAIVRAMTTLNIQYGDSARQDDARKLMHMADTIEEGTMPKEMSDIIQRLWKDSGIQACFDRASEYQLNDSAGY
YLSDLERLVTPGYVPTEQDVLRSRVKTTGIIETQFSFKDLNFRMFDVGGQRSERKKWIHCFEGVTAIIFCVALSD
YDLVLAEDEEMNRMHESMKLFDSICNNKWFTDTSIILFLNKKDLFEEKIKKSPLTICYPEYAGSNTYEEAGNYIK
VQFLELNMRRDVKEIYSHMTCATDTQNVKFVFDAVTDIIIKENLKDCGLF
```

Figure 29

```
                         10        20        30        40
αs       ----------------MGCLGNSKTEDQRNEEKAQREANKKIEKQLQKDKQVYRATHRL
αolf     ---------------MGCLGGNSKTTEDQGVDEKERREANKKIEKQLQKERLAYKATHRL
αi1      ------------------MGCTLSAEDKAAVERSKMIDRNLREDGEKAAREVKL
αo1      ---------------------MGCTLSAEERAALERSKAIEKNLKEDGISAAKDVKL
αt1      ------------------------MGAGASAEEKHSRELEKKLKEDAEKDARTVKL
αz       -------------------MGCRQSSEEKEAARRSRRIDRHLRSESQRQRREIKL
α12      MSGVVRTLSRCLLPAEAGGARERRAGSGARDAEREARRRSRDIDALLARERRAVRRLVKI
αq       ---------------MTLESIMACCLSEEAKEARRINDEIERQLRRDKRDARRELKL
α16      ---------------MARSLTWRCCPWCLTEDEKAAARVDQEINRILLEQKKQDRGELKL
                                           . . ::  *  :           ::
         12345678901234567890123456789012345678901234567890123    1234
         HN       1         2         3         4         5  |    S1

50        60  64       204       210       220       230
αs       LLLGAGESGKSTIVKQMRILHGGSGGSGGTSGIFETKFQVDKVNFHMFDVGGQRDERRKW
αolf     LLLGAGESGKSTIVKQMRILHGGSGGSGGTSGIFETRFQVDKVNFHMFDVGGQRDERRKW
αi1      LLLGAGESGKSTIVKQMKIIHGGGGGGGGTTGIVETHFTFKDLHFKMFDVGGQRSERKKW
αo1      LLLGAGESGKSTIVKQMKIIHGGSGGSGGTTGIVETHFTFKNLHFRLFDVGGQRSERKKW
αt1      LLLGAGESGKSTIVKQMKIIHGGSGGSGGTTGIIETQFSFKDLNFRMFDVGGQRSERKKW
αz       LLLGTSNSGKSTIVKQMKIIHGGGGGGGGTTGIVENKFTFKELTFKMVDVGGQRSERKKW
α12      LLLGAGESGKSTFLKQMRIIHGGSGGSGGTKGIVEHDFVIKKIPFKMVDVGGQRSQRQKW
αq       LLLGTGESGKSTFIKQMRIIHGGGGGGGGTTGIIEYPFDLQSVIFRMVDVGGQRSERRKW
α16      LLLGPGESGKSTFIKQMRIIHGGGGGGGGTTGINEYCFSVQKTNLRIVDVGGQKSERKKW
         ****  .:******::***:*:***.**.***.**  *   *  ...  :::.*****::.*:**
         567      1234567               12345678  12345678   1234567
         |         H1     |              S2    |   S3    |    H2

240       250       260       270       280       290
αs       IQCFNDVTAIIFVVASSSYNMVIREDNQTNRLQEALNLFKSIWNNRWLRTISVILFLNKQ
αolf     IQCFNDVTAIIYVAACSSYNMVIREDNNTNRLRESLDLFESIWNNRWLRTISIILFLNKQ
αi1      IHCFEGVAAIIFCVALSDYDLVLAEDEEMNRMHESMKLFDSICNNKWFTDTSIILFLNKK
αo1      IHCFEDVTAIIFCVALSGYDQVLHEDETTNRMHESLMLFDSICNNKFFIDTSIILFLNKK
αt1      IHCFEGVTCIIFIAALSAYDMVLVEDDEVNRMHESLHLFNSICNHRYFATTSIVLFLNKK
αz       IHCFEGVTAIIFCVELSGYDLKLYEDNQTSRMAESLRLFDSICNNNWFINTSLILFLNKK
α12      FQCFDGITSILFMVSSSEYDQVLMEDRRTNRLVESMNIFETIVNNKLFFNVSIILFLNKM
αq       IHCFENVTSIMFLVALSEYDQVLVESDNENRMEESKALFRTIITYPWFQNSSVILFLNKK
α16      IHCFENVIALIYLASLSEYDQCLEENNQENRMKESLALFGTILELPWFKSTSVILFLNKT
         ::**:  :  .:::  .    *  *:   : *.     .*: *:   :* :*      :    *::*****
         890      1234567              1234567890123456 78    1234567 1
         |        S4     |              H3        1      |    S5    | HG 300       310       320       330       340       350
αs       DLLAEKVLAGKSKIEDYFPEFARYTTPEDATPEPGEDPRVTRAKYFIRDEFLRISTAS--
αolf     DMLAEKVLAGKSKIEDYFPEYANYTVPEDATPDAGEDPKVTRAKFFIRDLFLRISTAT--
αi1      DLFEEKIK--KSPLTICYPEYAGSNTYEE-----------A-AAYIQCQFEDLN-----
αo1      DLFGEKIK--KSPLTICFPEYTGPNTYED-----------A-AAYIQAQFESKN-----
αt1      DVFFEKIK--KAHLSICFPDYDGPNTYED-----------A-GNYIKVQFLELN-----
αz       DLLAEKIR--RIPLTICFPEYKGQNTYEE-----------A-AVYIQRQFEDLN-----
α12      DLLVEKVK--TVSIKKHFPDFRGDPHRLE-----------DVQRYLVQCFDRK------
αq       DLLEEKIM--YSHLVDYFPEYDGPQRDAQ-----------AAREFILKMFVDLN-----
α16      DILEEKIP--TSHLATYFPSFQGPKQDAE-----------AAKRFILDMYTRMYTGCVD
         *::  **:     :   :*.:              :                 ::   :
         2345678901234567         12345678901234567890123 4567
         HG       1           |      H4        1          2     |

360       370       380       390  394
αs       -------GDGRHYCYPHFTCAVDTENIRRVFNDCRDIIQRMHLRQYELL
αolf     -------GDGKHYCYPHFTCAVDTENIRRVFNDCRDIIQRMHLKQYELL
αi1      ------KRKDTKEIYTHFTCATDTKNVQFVFDAVTDVIIKNNLKDCGLF
αo1      ------R-SPNKEIYCHMTCATDTNNIQVVFDAVTDIIIANNLRGCGLY
αt1      ------MRRDVKEIYSHMTCATDTQNVKFVFDAVTDIIIKENLKDCGLF
αz       ------RNKETKEIYSHFTCATDTSNIQFVFDAVTDVIIQNNLKYIGLC
α12      ------RRNRSKPLFHHFTTAIDTENVRFVFHAVKDTILQENLKDIMLQ
αq       ------P-DSDKIIYSHFTCATDTENIRFVFAAVKDTILQLNLKEYNLV
α16      GPEGSKKGARSRRLFSHYTCATDTQNIRKVFKDVRDSVLARYLDEINLL
                :  :  *  *  **.*:: **     *  :     *     *
               12345      1234567890123456789012345 6
               S6         H5        1         2     2
```

Figure 35

>Mini-G$_s$393
MGHHHHHHENLYFQGIEKQLQKDKQVYRATHRLLLLGADNSGKSTIVKQMRILH*GGSGGSGG*TSGIFETKFQVDKV
NFHMFDVGGQRDERRKWIQCFNDVTAIIFVVDSSDYNRLQEALNDFKSIWNNRWLRTISVILFLNKQDLLAEKVLA
GKSKIEDYFPEFARYTTPEDATPEPGEDPRVTRAKYFIRDEFLRISTASGDGRHYCYPHFTCAVDTENARRIFNDC
RDIIQRMHLRQYELL >Mini-G$_{olf}$6
MGHHHHHHENLYFQGIEKQLQKERLAYKATHRLLLLGADNSGKSTIVKQMRILH*GGSGGSGG*TSGIFETRFQVDKV
NFHMFDVGGQRDERRKWIQCFNDVTAIIYVADCSDYNRLRESLDDFESIWNNRWLRTISIILFLNKQDMLAEKVLA
GKSKIEDYFPEYANYTVPEDATPDAGEDPKVTRAKFFIRDLFLRISTATGDGKHYCYPHFTCAVDTENARRIFNDC
RDIIQRMHLKQYELL >Mini-G$_{s/q}$57
MGHHHHHHENLYFQGIEKQLQKDKQVYRATHRLLLLGADNSGKSTIVKQMRILH*GGSGGSGG*TSGIFETKFQVDKV
NFHMFDVGGQRDERRKWIQCFNDVTAIIFVVDSSDYNRLQEALNDFKSIWNNRWLRTISVILFLNKQDLLAEKVLA
GKSKIEDYFPEFARYTTPEDATPEPGEDPRVTRAKYFIRDEFLRISTASGDGRHYCYPHFTCAVDTENARRIFNDC
RDIIQRMHLREYNLV

>Mini-G$_{s/q}$58
MGHHHHHHENLYFQGIEKQLQKDKQVYRATHRLLLLGADNSGKSTIVKQMRILH*GGSGGSGG*TSGIFETKFQVDKV
NFHMFDVGGQRDERRKWIQCFNDVTAIIFVVDSSDYNRLQEALNDFKSIWNNRWLRTISVILFLNKQDLLAEKVLA
GKSKIEDYFPEFARYTTPEDATPEPGEDPRVTRAKYFIRDEFLRISTASGDGRHYCYPHFTCAVDTENARRIF**AAV
KDTILQLNLKEYNLV**

>Mini-G$_{s/q}$70
MGHHHHHHENLYFQGIEKQLQKDKQVYRATHRLLLLGADNSGKSTIVKQMRILH*GGSGGSGG*TSGIFETKFQVDKV
NFHMFDVGGQRDERRKWIQCFNDVTAIIFVVDSSDYNRLQEALNDFKSIWNNRWLRTISVILFLNKQDLLAEKVLA
GKSKIEDYFPEFARYTTPEDATPEPGEDPRVTRAKYFIRDEFLRISTASGDGRHYCYPHFTCAVDTENARRIFNDC
KDIILQMNLREYNLV

>Mini-G$_{s/q}$71
MGHHHHHHENLYFQGIEKQLQKDKQVYRRTLRLLLLGADNSGKSTIVKQMRILH*GGSGGSGG*TSGIFETKFQVDKV
NFHMFDVGGQRDERRKWIQCFNDVTAIIFVVDSSDYNRLQEALNDFKSIWNNRWLRTISVILFLNKQDLLAEKVLA
GKSKIEDYFPEFARYTTPEDATPEPGEDPRVTRAKYFIRKEFVDISTASGDGRHICYPHFTCAVDTENARRIFNDC
KDIILQMNLREYNLV

>Mini-G$_{i1}$46
MGHHHHHHENLYFQGTLSAEDKAAVERSKMIDRNLREDGEKAAREVKLLLLGADNSGKSTIVKQMKIIH*GGGGGGG
GTTG*IVETHFTFKDLHFKMFDVGGQRSERKKWIHCFEDVAAIIFCVDLSDYNRMHESMKLFDSICNNKWFTDTSII
LFLNKKDLFEEKIKKSPLTICYQEYAGSNTYEEAAAYIQCQFEDLNKRKDTKEIYTHFTCATDTKNAQFIFDAVTD
VIIKNNLKDCGLF >Mini-G$_{s/i1}$43
MGHHHHHHENLYFQGIEKQLQKDKQVYRATHRLLLLGADNSGKSTIVKQMRILH*GGSGGSGG*TSGIFETKFQVDKV
NFHMFDVGGQRDERRKWIQCFNDVTAIIFVVDSSDYNRLQEALNDFKSIWNNRWLRTISVILFLNKQDLLAEKVLA
GKSKIEDYFPEFARYTTPEDATPEPGEDPRVTRAKYFIRDEFLRISTASGDGRHYCYPHFTCAVDTENARRIFND**V
TDIIIKMNLRDCGLF**

>Mini-G$_{s/i1}$48
MGHHHHHHENLYFQGNSKTEDQRNEEKAQREANKKIEKQLQKDKQVYRATHRLLLLGADNSGKSTIVKQMRILH*GG
SGGSGG*TSGIFETKFQVDKVNFHMFDVGGQRDERRKWIQCFNDVTAIIFVVDSSDYNRLQEALNLFKSIWNNRWLR
TISVILFLNKQDLLAEKVLAGKSKIEDYFPEFARYTTPEDATPEPGEDPRVTRAKYFIRDEFLRISTASGDGRHYC
YPHFTCAVDTENARRIFNDVTDIIIKMNLRDCGLF

>Mini-G$_{o1}$12
MGHHHHHHENLYFQGIEKNLKEDGISAAKDVKLLLLGADNSGKSTIVKQMKIIH*GGSGGSGG*TTGIVETHFTFKNL
HFRLFDVGGQRSERKKWIHCFEDVTAIIFCVDLSDYNRMHESLMDFDSICNNKFFIDTSIILFLNKKDLFGEKIKK
SPLTICFPEYTGPNTYEDAAAYIQAQFESKNRSPNKEIYCHMTCATDTNNAQVIFDAVTDIIIANNLRGCGLY >Mini-G$_{12}$8
MGHHHHHHENLYFQGIDALLARERRAVRRLVKILLLGADNSGKSTFLKQMRIIH*GGSGGSGG*TKGIVEHDFVIKKI
PFKMVDVGGQRSQRQKWFQCFDGITSILFMVDSSDYNRLVESMNDFETIVNNKLFFNVSIILFLNKMDLLVEKVKT
VSIKKHFPDFRGDPHRLEDVQRYLVQCFDRKRRNSKPLFHHFTTAIDTENARFIFHAVKDTILQENLKDIMLQ

Figure 36

>Mini-G<sub>t1</sub>

CCATGGGTCACCACCATCACCATCATGAAAATCTTTATTTCCAGGGTCTGGAAAAGAAGCTGAAAGAGGACGCTGAG
AAGGATGCTCGAACCGTGAAGCTGCTGCTTCTGGGTGCCGATAATTCCGGGAAGAGCACCATCGTCAAGCAGATGA
AGATTATCCACGGTGGGAGTGGCGGGAGCGGAGGTACCACTGGCATCATCGAGACGCAGTTCTCCTTCAAGGATC
TCAACTTCCGGATGTTCGATGTGGGCGGGCAGCGCTCGGAGCGCAAGAAGTGGATCCACTGCTTCGAGGGCGTGA
CCTGCATCATCTTCATCGCGGACCTGAGCGATTACAACCGCATGCACGAGAGCCTGCACGATTTCAACAGCATCTG
CAACCACCGCTACTTCGCCACGACGTCCATCGTGCTCTTCCTTAACAAGAAGGACGTCTTCTTCGAGAAGATCAAGA
AGGCGCACCTCAGCATCTGTTTCCCGGACTACGATGGACCCAACACCTACGAGGACGCCGGCAACTACATCAAGGT
GCAGTTCCTCGAGCTCAACATGCGGCGCGACGTGAAGGAGATCTATTCCCACATGACGTGCGCCACCGACACGCA
GAACGCCAAATTTATCTTCGACGCTGTCACCGACATCATCATCAAGGAGAACCTCAAAGACTGTGGCCTCTTCTAAT
AGCTCGAG

MGHHHHHHENLYFQGLEKKLKEDAEKDARTVKLLLLGADNSGKSTIVKQMKIIH*GGSGGSGG*TTGIIETQFSFKDLNFRM
FDVGGQRSERKKWIHCFEGVTCIIFIADLSDYNRMHESLHDFNSICNHRYFATTSIVLFLNKKDVFFEKIKKAHLSICFPDYD
GPNTYEDAGNYIKVQFLELNMRRDVKEIYSHMTCATDTQNAKFIFDAVTDIIIKENLKDCGLF

>Mini-G<sub>z</sub>

CCATGGGTCACCACCATCACCATCATATTGACCGCCACCTGCGCTCAGAGAGCCAGCGGCAACGCCGCGAAATCAA
GCTGCTCCTGCTGGGCACCGACAACTCAGGCAAGAGCACCATCGTCAAACAGATGAAGATCATCCACGGAGGGGG
CGGAGGCGGGGGAGGGACCACGGGCATTGTGGAGAACAAGTTCACCTTCAAGGAGCTCACCTTCAAGATGGTGGA
CGTGGGGGGGCAGAGGTCAGAGCGCAAAAAGTGGATCCACTGCTTCGAGGGCGTCACAGCCATCATCTTCTGTGT
GGACCTCAGCGACTACAGTCGGATGGCAGAGAGCTTGCGCGACTTTGACTCCATCTGCAACAACAACTGGTTCATC
AACACCCTCACTCATCCTCCTGAACAAGAAGGACCTGCTGGCAGAGAAGATCCGCCGCATCCCGCTCACCATCT
GCTTTCCCGAGTACAAGGGCCAGAACACGTACGAGGAGCCCGCTGTCTACATCCAGCGGCAGTTTGAAGACCTGA
ACCGCAACAAGGAGACCAAGGAGATCTACTCCCACTTCACCTGCGCCACCGACACCAGTAACGCGCAGTTTATCTT
CGACGCGGTGACAGACGTCATCATACAGAACAATCTCAAGTACATTGGCCTTTGCTGATAACTCGAG

MGHHHHHHIDRHLRSESQRQRREIKLLLLGTDNSGKSTIVKQMKIIH*GGGGGGGG*TTGIVENKFTFKELTFKMVDVGGQR
SERKKWIHCFEGVTAIIFCVDLSDYSRMAESLRDFDSICNNNWFINTSLILFLNKKDLLAEKIRRIPLTICFPEYKGQNTYEEA
AVYIQRQFEDLNRNKETKEIYSHFTCATDTSNAQFIFDAVTDVIIQNNLKYIGLC

>Mini-G<sub>q</sub>

CCATGGGTCACCACCATCACCATCATATCGAGCGGCAGCTCCGCAGGGACAAGCGGGACGCCCGCCGGGAGCTC
AAGCTGCTGCTGCTCGGGACAGACAACAGTGGCAAGAGTACGTTTATCAAGCAGATGAGAATCATCCACGGAGGG
GGCGGAGGCGGGGGAGGGACCACAGGGATCATCGAATACCCCTTTGACTTACAAAGTGTCATTTTCAGAATGGTCG
ATGTAGGGGGCCAAAGGTCAGAGAGAAGAAAATGGATACACTGCTTTGAAAATGTCACCTCTATCATGTTTCTAGTA
GACCTTAGTGACTATAACCGAATGGAGGAAAGCAAGGCTGACTTTAGAACAATTATCACATACCCCTGGTTCCAGAA
CTCCTCGGTTATTCTGTTCTTAAACAAGAAAGATCTTCTAGAGGAGAAAATCATGTATTCCCATCTAGTCGACTACTT
CCCAGAATATGATGGACCCCAGAGAGATGCCCAGGCAGCCCGAGAATTCATTCTGAAGATGTTCGTGGACCTGAAC
CCAGACAGTGACAAAATTATCTACTCCCACTTCACGTGCGCCACAGACACCGAGAATGCCCGCTTTATCTTTGCTGC
CGTCAAGGACACCATCCTCCAGTTGAACCTGAAGGAGTACAATCTGGTCTAATAGCTCGAG

MGHHHHHHIERQLRRDKRDARRELKLLLLGTDNSGKSTFIKQMRIIH*GGGGGGGG*TTGIIEYPFDLQSVIFRMVDVGGQR
SERRKWIHCFENVTSIMFLVDLSDYNRMEESKADFRTIITYPWFQNSSVILFLNKKDLLEEKIMYSHLVDYFPEYDGPQRDA
QAAREFILKMFVDLNPDSDKIIYSHFTCATDTENARFIFAAVKDTILQLNLKEYNLV

>Mini-G<sub>16</sub>

CCATGGGTCACCACCATCACCATCATATCAACAGGATCCTCTTGGAGCAGAAGAAGCAGGACCGCGGGGAGCTGAA
GCTGCTGCTTTTGGGCCCAGACAACAGCGGGAAGAGCACCTTCATCAAGCAGATGCGGATCATCCACGGAGGGGG
CGGAGGCGGGGGAGGGACCACTGGCATCAACGAGTACTGCTTCTCCGTGCAGAAAACCAACCTGCGGATCGTGGA
CGTCGGGGGCCAGAAGTCAGAGCGTAAGAAATGGATCCATTGTTTCGAGAACGTGATCGCCCTCATCTACCTGGCC
GACCTGAGTGACTACAACCGCATGAAGGAGAGCCTCGCAGACTTTGGGACTATCCTGGAACTACCCTGGTTCAAAA
GCACATCCGTCATCCTCTTTCTCAACAAAACCGACATCCTGGAGGAGAAAATCCCCACCTCCCACCTGGCTACCTAT
TTCCCCAGTTTCCAGGGCCCTAAGCAGGATGCTGAGGCAGCCAAGAGGTTCATCCTGGACATGTACACGAGGATGT
ACACCGGGTGCGTGGACGGCCCCGAGGGCAGCAAGAAGGGCGCACGATCCCGACGCCTCTTCAGCCACTACACA
TGTGCCACAGACACACAGAACGCGCGCAAGATCTTCAAGGACGTGCGGGACTCGGTGCTCGCCCGCTACCTGGAC
GAGATCAACCTGCTGTAATAGCTCGAG

MGHHHHHHINRILLEQKKQDRGELKLLLLGPDNSGKSTFIKQMRIIH*GGGGGGG*TTGINEYCFSVQKTNLRIVDVGGQK
SERKKWIHCFENVIALIYLADLSDYNRMKESLADFGTILELPWFKSTSVILFLNKTDILEEKIPTSHLATYFPSFQGPKQDAEA
AKRFILDMYTRMYTGCVDGPEGSKKGARSRRLFSHYTCATDTQNARKIFKDVRDSVLARYLDEINLL

Figure 37

\>GFP-mini-G$_s$393
MGHHHHHHENLYFQGVSKGEELFTGVVPILVELDGDVNGHKFSVSGEGEGDATYGKLTLKF
ICTTGKLPVPWPTLVTTLTYGVQCFSRYPDHMKQHDFFKSAMPEGYVQERTIFFKDDGNYK
TRAEVKFEGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAAGITLGM
DELYKGGGGSIEKQLQKDKQVYRATHRLLLLGADNSGKSTIVKQMRILHGGSGGSGGTSGIF
ETKFQVDKVNFHMFDVGGQRDERRKWIQCFNDVTAIIFVVDSSDYNRLQEALNDFKSIWNN
RWLRTISVILFLNKQDLLAEKVLAGKSKIEDYFPEFARYTTPEDATPEPGEDPRVTRAKYFIRD
EFLRISTASGDGRHYCYPHFTCAVDTENARRIFNDCRDIIQRMHLRQYELL \>GFP-mini-G$_{i1}$46
MGHHHHHHENLYFQGVSKGEELFTGVVPILVELDGDVNGHKFSVSGEGEGDATYGKLTLKF
ICTTGKLPVPWPTLVTTLTYGVQCFSRYPDHMKQHDFFKSAMPEGYVQERTIFFKDDGNYK
TRAEVKFEGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAAGITLGM
DELYKGGGGSTLSAEDKAAVERSKMIDRNLREDGEKAAREVKLLLLGADNSGKSTIVKQMKII
HGGGGGGGGTTGIVETHFTFKDLHFKMFDVGGQRSERKKWIHCFEDVAAIIFCVDLSDYNR
MHESMKLFDSICNNKWFTDTSIILFLNKKDLFEEKIKKSPLTICYQEYAGSNTYEEAAAYIQCQ
FEDLNKRKDTKEIYTHFTCATDTKNAQFIFDAVTDVIIKNNLKDCGLF \>GFP-mini-G$_{s/i1}$43
MGHHHHHHENLYFQGVSKGEELFTGVVPILVELDGDVNGHKFSVSGEGEGDATYGKLTLKF
ICTTGKLPVPWPTLVTTLTYGVQCFSRYPDHMKQHDFFKSAMPEGYVQERTIFFKDDGNYK
TRAEVKFEGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAAGITLGM
DELYKGGGGSIEKQLQKDKQVYRATHRLLLLGADNSGKSTIVKQMRILHGGSGGSGGTSGIF
ETKFQVDKVNFHMFDVGGQRDERRKWIQCFNDVTAIIFVVDSSDYNRLQEALNDFKSIWNN
RWLRTISVILFLNKQDLLAEKVLAGKSKIEDYFPEFARYTTPEDATPEPGEDPRVTRAKYFIRD
EFLRISTASGDGRHYCYPHFTCAVDTENARRIFNDVTDIIKMNLRDCGLF \>GFP-mini-G$_{o1}$12
MGHHHHHHENLYFQGVSKGEELFTGVVPILVELDGDVNGHKFSVSGEGEGDATYGKLTLKF
ICTTGKLPVPWPTLVTTLTYGVQCFSRYPDHMKQHDFFKSAMPEGYVQERTIFFKDDGNYK
TRAEVKFEGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAAGITLGM
DELYKGGGGSIEKNLKEDGISAAKDVKLLLLGADNSGKSTIVKQMKIIHGGSGGSGGTTGIVE
THFTFKNLHFRLFDVGGQRSERKKWIHCFEDVTAIIFCVDLSDYNRMHESLMDFDSICNNKFF
IDTSIILFLNKKDLFGEKIKKSPLTICFPEYTGPNTYEDAAAYIQAQFESKNRSPNKEIYCHMTC
ATDTNNAQVIFDAVTDIIIANNLRGCGLY \>GFP-mini-G$_{12}$8
MGHHHHHHENLYFQGVSKGEELFTGVVPILVELDGDVNGHKFSVSGEGEGDATYGKLTLKF
ICTTGKLPVPWPTLVTTLTYGVQCFSRYPDHMKQHDFFKSAMPEGYVQERTIFFKDDGNYK
TRAEVKFEGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAAGITLGM
DELYKGGGGSIDALLARERRAVRRLVKILLLGADNSGKSTFLKQMRIIHGGSGGSGGTKGIVE
HDFVIKKIPFKMVDVGGQRSQRQKWFQCFDGITSILFMVDSSDYNRLVESMNDFETIVNNKL
FFNVSIILFLNKMDLLVEKVKTVSIKKHFPDFRGDPHRLEDVQRYLVQCFDRKRRNRSKPLFH
HFTTAIDTENARFIFHAVKDTILQENLKDIMLQ

Figure 38

```
2A con                                                 ◊
β2 con                                              o◊ ◊
mini-Gq     1 MGHHHHHHENLYFQGIERQLRRDKEDARRELKLLLLGTDNSGKSTFIKQMRIIHGGGGGG 60
mini-Gs     1 MGHHHHHHENLYFQGIEKQLQKDKQVYRATHRLLLLGADNSGKSTIVKQMRILHGGSGGS 60
mini-Gs/q57 1 MGHHHHHHENLYFQGIEKQLQKDKQVYRATHRLLLLGADNSGKSTIVKQMRILHGGSGGS 60
mini-Gs/q58 1 MGHHHHHHENLYFQGIEKQLQKDKQVYRATHRLLLLGADNSGKSTIVKQMRILHGGSGGS 60
mini-Gs/q70 1 MGHHHHHHENLYFQGIEKQLQKDKQVYRATHRLLLLGADNSGKSTIVKQMRILHGGSGGS 60
mini-Gs/q71 1 MGHHHHHHENLYFQGIEKQLQKDKQVYRRTLRLLLLGADNSGKSTIVKQMRILHGGSGGS 60
              ****************.**..**.  *  .****.*******.*****.*** **
                               34567890123    1234567       1234567
                    HN4          5  |  S1   |   H1    |

2A con                 o ◊
β2 con                   ◊
mini-Gq    61 GGTTGIIEYPFDLQSVIFPMVDVGGQRSERRKWIHCFENVTSIMFLVDLSDYNRMEESKA 120
mini-Gs    61 GGTSGIFETKFQVDKVNFHMFDVGGQRDERRKWIQCFNDVTAIIFVVDSSDYNRLQEALN 120
mini-Gs/q57 61 GGTSGIFETKFQVDKVNFHMFDVGGQRDERRKWIQCFNDVTAIIFVVDSSDYNRLQEALN 120
mini-Gs/q58 61 GGTSGIFETKFQVDKVNFHMFDVGGQRDERRKWIQCFNDVTAIIFVVDSSDYNRLQEALN 120
mini-Gs/q70 61 GGTSGIFETKFQVDKVNFHMFDVGGQRDERRKWIQCFNDVTAIIFVVDSSDYNRLQEALN 120
mini-Gs/q71 61 GGTSGIFETKFQVDKVNFHMFDVGGQRDERRKWIQCFNDVTAIIFVVDSSDYNRLQEALN 120
              ***.** * * . * *.* ****** ******.**  **.*.*.** *****..*.
               12345678  12345678  1234567890    1234567    1234567
                 S2    |    S3   |    H2    1      S4    |    H3

2A con                                                            ◊
β2 con
mini-Gq   121 DFRTIITYPWFQNSSVILFLNKKDLLEEKIMY--SHLVDYFPEYD-----------GFQ 166
mini-Gs   121 DFKSIWNNRWLRTISVILFLNKQDLLAEKVLAGKSKIEDYFPEFARYTTPEDATPEPGED 180
mini-Gs/q57 121 DFKSIWNNRWLRTISVILFLNKQDLLAEKVLAGKSKIEDYFPEFARYTTPEDATPEPGED 180
mini-Gs/q58 121 DFKSIWNNRWLRTISVILFLNKQDLLAEKVLAGKSKIEDYFPEFARYTTPEDATPEPGED 180
mini-Gs/q70 121 DFKSIWNNRWLRTISVILFLNKQDLLAEKVLAGKSKIEDYFPEFARYTTPEDATPEPGED 180
mini-Gs/q71 121 DFKSIWNNRWLRTISVILFLNKQDLLAEKVLAGKSKIEDYFPEFARYTTPEDATPEPGED 180
              **..*  .  *  .. *******.*** **..    *.. *****.             *
               89012345678    1234567 12345678901234567       12345678901
                  1       |     S5  |    HG     1       |      H4      1

2A con                                               ◊ o◊◊ ◊◊◊ ◊◊ o◊
β2 con                    o ◊◊ ◊        ◊              ◊  ◊◊ ◊◊◊ ◊◊  ◊
mini-Gq   167 RDAQAAREFILKMFVDLNPDSD---KIIYSHFTCATDTENARFIFAAVKDTILQRNLKEY 223
mini-Gs   181 PRVTRAKYFIRDEFLRISTASGDGRHYCYPHFTCAVDTENARRIFNDCRDIIQRMHLRQY 240
mini-Gs/q57 181 PRVTRAKYFIRDEFLRISTASGDGRHYCYPHFTCAVDTENARRIFNDCRDIIQRMHLREY 240
mini-Gs/q58 181 PRVTRAKYFIRDEFLRISTASGDGRHYCYPHFTCAVDTENARRIFAAVKDTILQLNLKEY 240
mini-Gs/q70 181 PRVTRAKYFIRDEFLRISTASGDGRHYCYPHFTCAVDTENARRIFNDCKDIILQMNLREY 240
mini-Gs/q71 181 PRVTRAKEFVDISTASGDGRHICYPHFTCAVDTENARRIFNDCKDIILQMNLREY 240
              . **   *.      *   . *  ****** ** .* *  ...*..*
               2345678901234567      12345    12345678901234567890123
                    H4       2  |      S6       H5     1         2

2A con            ◊◊o
β2 con            ◊◊◊
mini-Gq   224 NLV 226
mini-Gs   241 ELL 243
mini-Gs/q57 241 NLV 243
mini-Gs/q58 241 NLV 243
mini-Gs/q70 241 NLV 243
mini-Gs/q71 241 NLV 243
                *.
                456
                H5  2
```

Figure 40

```
miniGs_393    1 MGHHHHHHENLYFQG--------------------IEKQLQKDKQVYRATHRLLLLGADN  40
miniGi1_46    1 MGHHHHHHENLYFQGTLSAED-----KAAVERSKMIDRNLREDGEKAAREVKLLLLGADN  55
miniGs/i1_43  1 MGHHHHHHENLYFQG--------------------IEKQLQKDKQVYRATHRLLLLGADN  40
mniGs/i1_48   1 MGHHHHHHENLYFQGNSKTEDQRNEEKAQREANKKIEKQLQKDKQVYRATHRLLLLGADN  60
miniGo1_12    1 MGHHHHHHENLYFQG--------------------IEKNLKEDGISAAKDVKLLLLGADN  40
miniGs/o_16   1 MGHHHHHHENLYFQGNSKTEDQRNEEKAQREANKKIEKQLQKDKQVYRATHRLLLLGADN  60
                **************                     *...*. *        .*******
                                    3456789012345678901234567890123    1234567
                                    HN2          3         4         5    |   S1   | miniGs_393   41 SGKSTIVKQMRILHGGSGGSGGTSGIFETKFQVDKVNFHMFDVGGQRDERRKWIQCFNDV 100
miniGi1_46   56 SGKSTIVKQMKIIHGGGGGGGGTTGIVETHFTFKDLHFKMFDVGGQRSERKKWIHCFEDV 115
miniGs/i1_43 41 SGKSTIVKQMRILHGGSGGSGGTSGIFETKFQVDKVNFHMFDVGGQRDERRKWIQCFNDV 100
mniGs/i1_48  61 SGKSTIVKQMRILHGGSGGSGGTSGIFETKFQVDKVNFHMFDVGGQRDERRKWIQCFNDV 120
miniGo1_12   41 SGKSTIVKQMKIIHGGSGGSGGTTGIVETHFTFKNLHFRLFDVGGQRSERKKWIHCFEDV 100
miniGs/o_16  61 SGKSTIVKQMRILHGGSGGSGGTSGIFETKFQVDKVNFHMFDVGGQRDERRKWIQCFNDV 120
                **********.*.*** ** ***.** **.*    ..*..******* **.***.** **
                  1234567                12345678  12345678   1234567890
                  H1    |                S2     |  S3    |   H2     1 miniGs_393  101 TAIIFVVDSSDYNRLQEALNDFKSIWNNRWLRTISVILFLNKQDLLAEKVLAGKSKIEDY 160
miniGi1_46  116 AAIIFCVDLSDYNRMHESMKLFDSICNNKWFTDTSIILFLNKKDLFEEKIK--KSPLTIC 173
miniGs/i1_43 101 TAIIFVVDSSDYNRLQEALNDFKSIWNNRWLRTISVILFLNKQDLLAEKVLAGKSKIEDY 160
mniGs/i1_48 121 TAIIFVVDSSDYNRLQEALNLFKSIWNNRWLRTISVILFLNKQDLLAEKVLAGKSKIEDY 180
miniGo1_12  101 TAIIFCVDLSDYNRMHESLMDFDSICNNKFFIDTSIILFLNKKDLFGEKIK--KSPLTIC 158
miniGs/o_16 121 TAIIFVVDSSDYNRLQEALNLFKSIWNNRWLRTISVILFLNKQDLLAEKVLAGKSKIEDY 180
                .****.** *****..*..  * **.**.      *.******.** **.    **  .
                   1234567        123456789012345678    1234567  12345678901234567
                   S4    |          H3        1       |    S5   |   HG      1        | miniGs_393  161 FPEFARYTTPEDATPEPGEDPRVTRAKYFIRDEFLRISTASGDGRHYCYPHFTCAVDTEN 220
miniGi1_46  174 YQEYAGSNTYEEAAA-------------YIQCQFEDLNKRKDTKEIYT--HFTCATDTKN 218
miniGs/i1_43 161 FPEFARYTTPEDATPEPGEDPRVTRAKYFIRDEFLRISTASGDGRHYCYPHFTCAVDTEN 220
mniGs/i1_48 181 FPEFARYTTPEDATPEPGEDPRVTRAKYFIRDEFLRISTASGDGRHYCYPHFTCAVDTEN 240
miniGo1_12  159 FPEYTGPNTYEDAAA-------------YIQAQFESKN-RSPNKEIYC--HMTCATDTNN 202
miniGs/o_16 181 FPEFARYTTPEDATPEPGEDPRVTRAKYFIRDEFLRISTASGDGRHYCYPHFTCAVDTEN 240
                . *..    .*.*.*.             .*..*        *.  * ***  ** *
                       12345678901234567890123456   7              12345     123
                       H4        1          2         |                S6    |    H5 miniGs_393  221 ARRIFNDCRDIIQRMHLRQYELL 243
miniGi1_46  219 AQFIFDAVTDVIIKNNLKDCGLF 241
miniGs/i1_43 221 ARRIFNDVTDIIIKMNLRDCGLF 243
mniGs/i1_48 241 ARRIFNDVTDIIIKMNLRDCGLF 263
miniGo1_12  203 AQVIFDAVTDIIIANNLRGCGLY 225
miniGs/o_16 241 ARRIFNDVTDIIIAMNLRGCGLY 263
                *. **    *.*   .*.    *
                   45678901234567890123456
                   H5        1         2
```

G PROTEINS

This application is a continuation application of U.S. application Ser. No. 15/549,246, filed Aug. 7, 2017, which is a U.S. National Stage Application of International Application No. PCT/GB2017/050221, filed Jan. 27, 2017, which was published in English on Aug. 3, 2017, as International Publication No. WO 2017/129998 A1. International Application No. PCT/GB2017/050221 claims priority to British Application No. 1601690.9 filed Jan. 29, 2016. A certified copy of British Application No. 1601690.9 filed Jan. 29, 2016, was provided in, and is available in PAIR, in U.S. patent application Ser. No. 15/549,246.

SEQUENCE LISTING

This application contains a Sequence Listing electronically submitted via EFS-Web to the United States Patent and Trademark Office as an ASCII text file entitled "P62760US—Sequence listing—17JUN19.txt" having a size of 322 kilobytes and created on Jun. 17, 2019. The information contained in the Sequence Listing is incorporated by reference herein.

The present invention relates to mutant G proteins, and particularly to mutant alpha subunits of a heterotrimeric G protein. It also relates to products comprising such mutants, uses of the mutants, and methods involving such mutants.

G proteins bind guanine nucleotides and act as molecular switches in a number of signalling pathways by interconverting between a GDP-bound inactive and a GTP-bound active state. They consist of two major classes: monomeric small G proteins and heterotrimeric G proteins. While small G proteins and the alpha subunit (Gα) of heterotrimeric G proteins both contain a GTPase domain (G-domain), Gα contains an additional helical domain (H-domain) and also forms a complex with G beta (Gβ) and G gamma (Gγ) subunits. Although they undergo a similar signalling cycle, their activation differs in one important aspect. The guanine nucleotide exchange factors (GEFs) of small G proteins are largely cytosolic proteins, whereas the GEFs of Gα subunits are usually membrane-bound G protein coupled receptors (GPCRs). While GEFS of small G proteins interact directly with the GDP binding region, GPCRs bind to Gα at a site almost 30 Å away from the GDP binding region and allosterically trigger GDP release to activate them.

GPCRs constitute a very large family of proteins that control many physiological processes and are the targets of many effective drugs. Thus, they are of considerable pharmacological importance. Reference is made particularly to Overington et al (2006) *Nature Rev. Drug Discovery* 5, 993-996 which indicates that over a quarter of present drugs have a GPCR as a target. A list of GPCRs is given in Foord et al (2005) *Pharmacol Rev.* 57, 279-288, which is incorporated herein by reference.

Three decades of biochemical and biophysical research have produced a model of G protein activation by GPCRs. Agonist binding to a GPCR induces subtle changes in the receptor structure[1-4], allowing a productive interaction to occur with the G protein. This process is likely to comprise at least two stages: an initial docking interaction, possibly involving the G protein βγ subunits or lipid moieties, induces a conformational change in the extreme C-terminus of the α subunit[5,6]. The C-terminus, which is the major receptor-binding region[7] and determinant of receptor specificity[8,9], is then able to fully engage the receptor. This interaction triggers mutually induced conformational changes in both the G protein and receptor[10]. In the G protein these changes are propagated to the nucleotide-binding pocket, resulting in the release of GDP[10,11]. In the receptor the conformational changes feedback to the ligand-binding pocket, reducing the dissociation rate of the ligand, which results in significantly increased agonist binding affinity[12,13]. The mechanism of this affinity shift is likely to result from either subtle reorganisation of the ligand-binding pocket, or transition of the complex to a lower energy state due to the conformational stabilisation imparted by G protein binding. In this ternary complex the receptor acts as a chaperone, protecting the thermally labile nucleotide-free G protein from denaturation[14,15]. In the absence of guanine nucleotides this complex is stable; however in vivo, GTP is rapidly bound due to its high cellular concentration[12,14]. This triggers a conformational change, which causes dissociation of the G protein from the receptor[16,17], and separation of the Gα and βγ subunits[14,16]. The activated α-GTP and βγ subunits are then able stimulate their respective downstream signalling pathways.

Atomic resolution mapping of the ligand-binding pocket is of significant importance for the design of drugs to modulate GPCR activity. Thus, methodology to crystallise receptors in their high-affinity agonist-bound conformation is a key prerequisite for efficient structure-based design of agonist compounds. To date, three approaches have accomplished this: first, the C-terminal peptide of transducin was crystallised in complex with both opsin[36] and metarhodopsin II[37]; second, a camelid antibody (Nb80), which induces the high-affinity agonist-bound state, has been crystallized in complex with β$_2$AR[38]; third, heterotrimeric Gs has been crystallised in complex with β$_2$AR[10]. Despite the valuable insight into GPCR activation provided by these structures, they have several major disadvantages for wider structure-based drug design applications. The opsin and metarhodopsin II complexes were solved at 3.2 Å and 2.85 Å respectively, and in both cases electron density around the chromaphore-binding pocket was strong[36,37]. However, the use of G protein C-terminal peptides to stabilise the active conformation of other GPCRs has been unsuccessful[10]. Furthermore, the conformational changes induced by the transducin peptide are much smaller than those observed in the β$_2$AR-Gs complex[10], indicating that these structures represent an intermediate conformation along the activation pathway. The Nb80-β$_2$AR complex was solved at 3.5 Å resolution, and also exhibited good electron density around the ligand-binding pocket[38]. However, the conformational changes induced by Nb80 are smaller than those observed in the β$_2$AR-Gs complex[10], suggesting that this structure may also represent an intermediate conformation. Furthermore, although Nb80 was derived specifically to bind β$_2$AR and is therefore likely to efficiently couple to other closely related GPCRs (eg β$_1$AR), new nanobodies likely need to be raised against more distantly related receptors. The β$_2$AR-Gs complex was solved at 3.2 Å resolution, however, in this structure electron density around the ligand-binding pocket was very poor. Furthermore, the complexity of crystallising G protein-GPCR complexes means this strategy is of limited use for wider structure-based drug design applications. All of the aforementioned complexes were solved at medium-high resolution, however, they provided insufficient detail around the ligand-binding pocket to accurately define the structural changes associated with the high-affinity agonist-bound conformation. Therefore, in order to accurately define these changes, and to allow optimal structure-based drug design, there is a strong requirement to solve the structures of G protein-GPCR complexes at greater than 2 Å resolution.

The separate GTPase and helical domains of the stimulatory G protein (Gαs) have been previously transfected into COS-7 cells[41]. However, individually, neither protein increased cellular cAMP production. Also, there was no investigation of the ability of the GTPase to bind a GPCR.

Gα subunits have also been shown to interact with GPCRs in a βγ-independent manner, and to undergo nucleotide exchange in the presence of a large excess of receptor, albeit with far slower kinetics than the holoenzyme[43, 45, 46]. However, all of the constructs contained an intact helical domain.

The listing or discussion of an apparently prior-published document in this specification should not necessarily be taken as an acknowledgement that the document is part of the state of the art or is common general knowledge.

Herein, we describe the design of Minimal, Engineered, G protein Alpha (MEGA) domains, which couple to GPCRs and can induce the core pharmacological and conformational changes associated with the high-affinity agonist-bound state. MEGA domains can be considered to be minimal versions of the Gα subunit, lacking part or all of the helical domain, which can couple to GPCRs even in the absence of the βγ dimer. We have identified mutations that improve both the expression and stability of the MEGA domains, while retaining the basic guanine nucleotide binding properties and functionality of the protein. The mutations that we have discovered are well conserved amongst the heterotrimeric G proteins, and are believed to transfer to members of all four classes of α subunits. Hence, this approach can be used to produce a repertoire of GTPase domains capable of coupling to different GPCRs. An alternative description of MEGA domains is mini G proteins, and both definitions can be used to describe the mutant G proteins of the invention.

Accordingly, a first aspect of the invention provides a mutant of a parent heterotrimeric G protein alpha (Gα) subunit, which mutant (i) lacks at least one helix of the helical domain of the parent Gα subunit; (ii) is capable of binding to a GPCR in the absence of a heterotrimeric G protein beta (Gβ) subunit and a heterotrimeric G protein gamma (Gγ) subunit; and (iii) has an amino acid sequence that contains one or more mutations compared to the amino acid sequence of the parent heterotrimeric Gα subunit, which mutations are selected from a deletion, a substitution and an insertion.

By a heterotrimeric G protein, we include the meaning of a protein that is made of three subunits, a guanyl-nucleotide binding alpha subunit (Gα), a beta subunit (Gβ) and a gamma subunit (Gγ). Such heterotrimeric proteins transduce signals from a GPCR to a downstream effector as described above. Gα subunits of any heterotrimeric G protein may be used in the practice of the present invention. Typically, Gα subunits are between 350 and 400 amino acids in length and have molecular weights in the range 40-45 kDa. There are four families of Gα subunit grouped on the basis of both sequence similarity and function, containing a total of seventeen Gα subunits, any of which may be used to practice the present invention:

$G\alpha_s$: $G\alpha_s$, $G\alpha_{olf}$ (olfactory)

$G\alpha_{i/o}$: $G\alpha_{i1}$, $G\alpha_{i2}$, $G\alpha_{i3}$, $G\alpha_{o1}$, $G\alpha_{o2}$, $G\alpha_z$, $G\alpha_{t1}$, $G\alpha_{t2}$, $G\alpha_{t3}$ (gustducin)

$G\alpha_{q/11}$: $G\alpha_q$, $G\alpha_{11}$, $G\alpha_{14}$, $G\alpha_{15}$ (sometimes called 16)

$G\alpha_{12/13}$: $G\alpha_{12}$, $G\alpha_{13}$

The $G_s$ and $G_i$ families regulate adenylyl cyclase activity, while $G_q$ activates phospholipase Cβ and $G_{12/13}$ can activate small GTPase families.

There are also fungal and plant classes of alpha subunits. For example, yeast are known to use the GPCR/G protein pathway; mating factor signal transduction in *Saccharomyces cerevisiae* is mediated by G protein alpha 1 subunit (GP-1). Urano et al also review G protein signalling in plants studied mainly in two model organisms *Arabidopsis thaliana* and rice (*Oryza sativa*) (Urano et al Open Biol. 2013 March; 3(3): 120186). All such Gα subunits are included in the scope of the invention. Further details of suitable Gα subunits and their classification are well known in the art, and can be found online (e.g., at the InterPro website; EMBL-EBI, Hixton, Cambridgeshire, United Kingdom), and in Flock et al 2015 (Nature 524: 173) and Anantharanman et al, 2011 (Gene 475: 63-78). Information on which Gα subunit a given GPCR couples to can also be found by consulting the scientific literature and available online databases (e.g., IUPHAR/BPS GUIDE TO PHARMACOLGY; International Union of Basic and Clinical Pharmacology (IUPHAR); British Pharmacological Society (BPS)) (see also Alexander et al, (2015) The Concise Guide to PHARMACOLOGY 2015/16: G protein-coupled receptors. *Br J Pharmacol.* 172: 5744-5869). Further details of which GPCR the mutant Gα subunit of the invention may bind to, including examples of particular GPCRs, are provided below in relation to the fourth aspect of the invention.

The amino acid sequences (and the nucleotide sequences of the cDNAs which encode them) of many Gα subunits are readily available, for example by reference to GenBank or UniProt. In particular, Flock et al, 2015 (Nature 524: 173) gives the human gene IDs for all human Gα paralogues from UniProt. It should be noted, also, that because the sequence of an increasing number of genomes are complete, the amino acid sequences of Gα subunits can be deduced therefrom.

Although the Gα may be derived from any source, it is particularly preferred if it is from a eukaryotic source. It is particularly preferred if it is derived from an animal (eg vertebrate) source such as a mammal or a bird. It is particularly preferred if the Gα subunit is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell subsequently. Thus, it will be plain that a eukaryotic Gα (such as an avian or mammalian Gα) may be expressed in a prokaryotic host cell, such as *E. coli*, but be considered to be avian- or mammalian-derived, as the case may be.

Gα subunits comprise two domains: a GTP-binding domain and a helical domain. The GTP-binding domain is homologous to Ras-like small GTPases, and includes switch regions I and II, which change conformation during activation. The switch regions are loops of alpha-helices with conformations sensitive to guanine nucleotides.

By the helical domain of a Gα subunit, we include the meaning of the helical insertion domain that is inserted into the GTP-binding domain before switch region I and is unique to heterotrimeric G proteins. This helical domain functions to sequester the guanine nucleotide at the interface with the GTP-binding domain and must be displaced to enable nucleotide dissociation. Flock et al (2015) have performed a structural and sequence alignment of Gα subunits from diverse organisms and have demonstrated that the helical domain of a Gα subunit comprises six alpha helices, denoted Helix A, Helix B, Helix C, Helix D, Helix E and Helix F. Thus, the helical domain may be regarded as the region between the first amino acid residue of Helix A and the final amino acid residue of Helix F within the amino acid sequence of a Gα subunit. However, it will be understood that the helical domain may also be considered to extend beyond these alpha helices to encompass the surrounding loop regions, ie the loop before Helix A and the loop after Helix F, such that the boundaries of the helical domain are not absolute.

In one embodiment, the mutant Gα subunit lacks at least one of alpha helices A, B, C, D, E or F of the parent heterotrimeric Gα subunit, such as at least two, three, four, five or all six of alpha helices A, B, C, D, E or F. When the mutant Gα subunit lacks more than one of alpha helices A, B, C, D, E or F, the mutant Gα subunit typically also lacks the intervening loops. Thus, if the mutant Gα subunit lacks Helix A and Helix B, the mutant Gα would also typically lack the loop connecting Helix A to Helix B, and so on.

In a preferred embodiment, the mutant Gα subunit lacks alpha helices A, B, C, D and E of the helical domain of the parent Gα subunit, and the intervening loop regions.

In another preferred embodiment, the mutant Gα subunit lacks alpha helices A, B, C, D, E and F of the helical domain of the parent Gα subunit, and the intervening loop regions.

Figure 25:
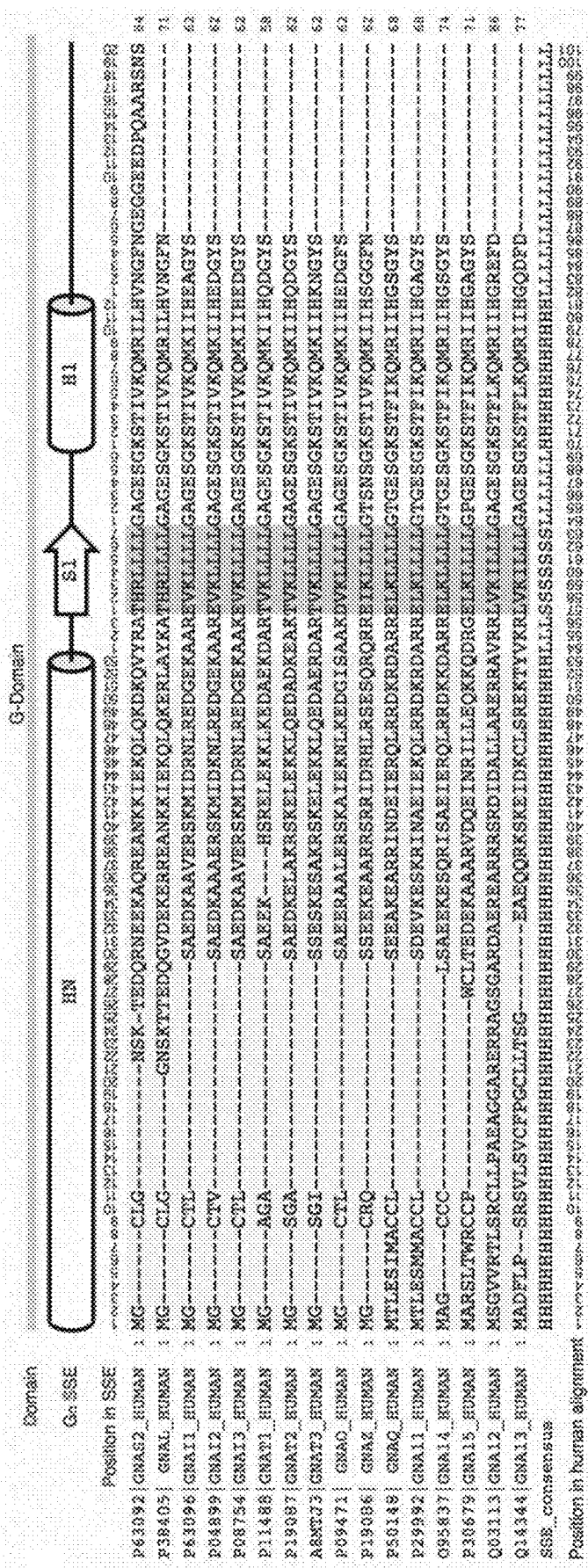
Figure 25:
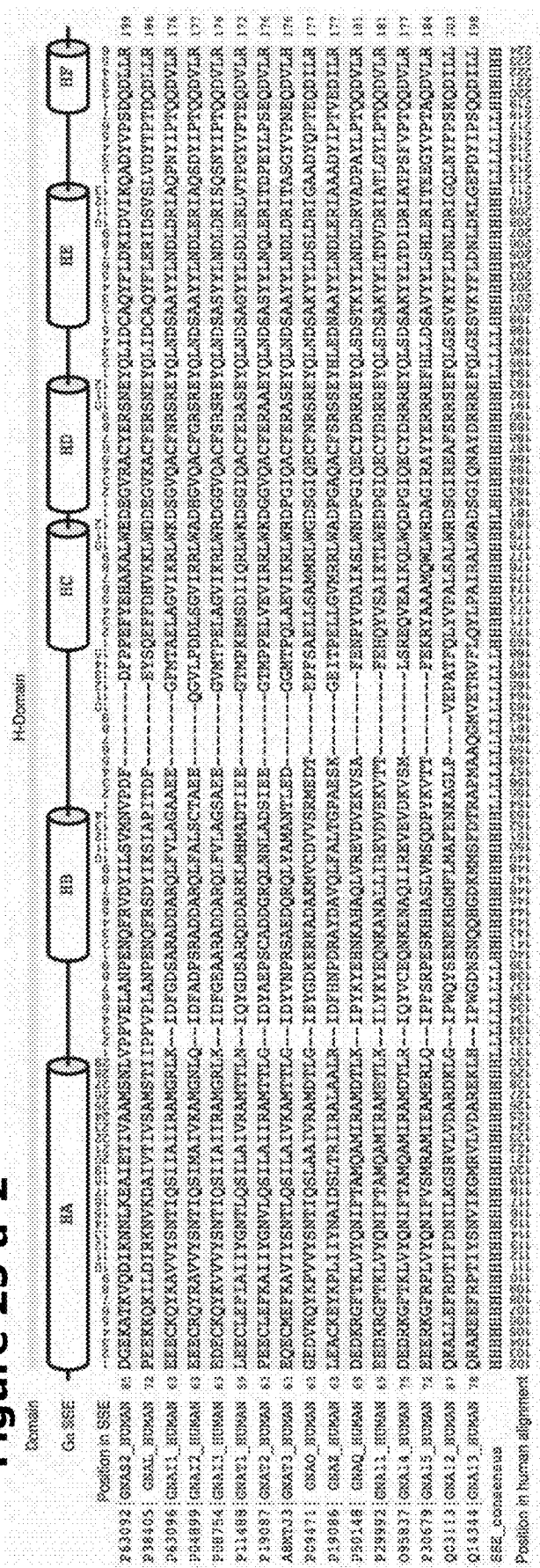
Figure 25:
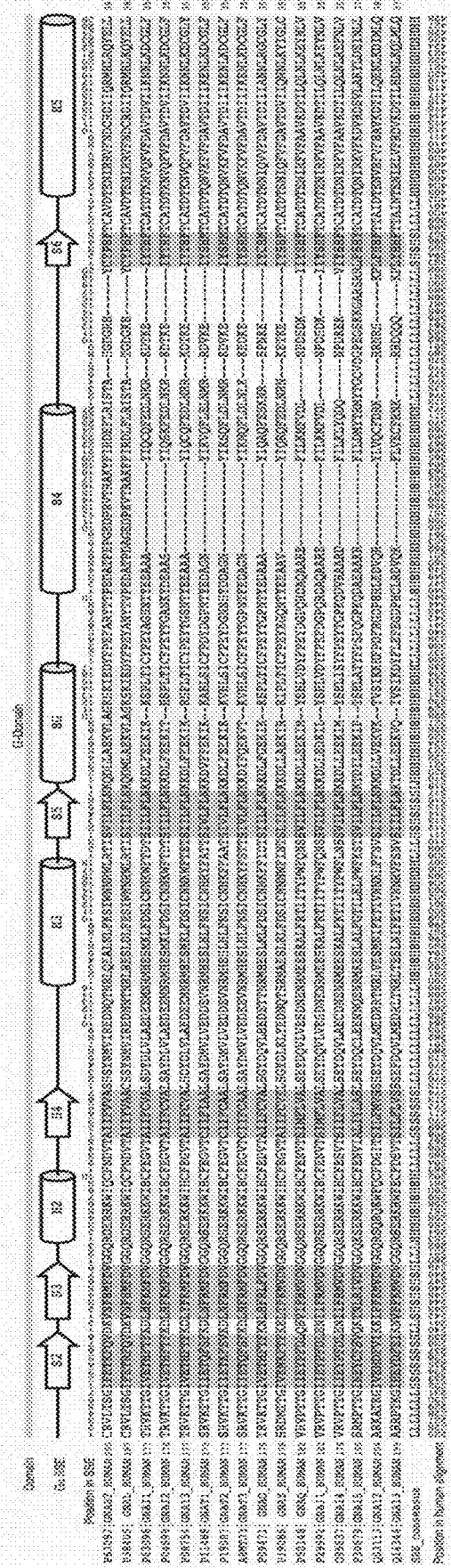

The positioning of alpha Helices A to F relative to the amino acid sequences of the seventeen human Gα paralogues is illustrated in FIG. 25 (which corresponds to Extended Date, FIG. 1 of Flock et al 2015 (Nature 524: 173), and it will be appreciated that the skilled person can readily determine their location within other Gα proteins, for instance by protein alignment and/or making use of computer algorithms that predict secondary structure (see, for example, Flock et al, 2015). For instance, Helix A in a second Gα protein would be the alpha helix that is analogous to Helix A in one of the human Gα paralogues listed in FIG. 25. An analogous helix in the second Gα subunit can be identified by searching for a similar amino acid sequence that defines Helix A in the sequence of one of the human Gα subunit paralogues, for example, by sequence alignment. Moreover, computer based algorithms are widely available in the art that can be used to predict the presence of protein motifs based on an amino acid sequence. Based upon the relative position of a particular alpha helix within the amino acid sequence and its position relative to other motifs and alpha helices, an analogous helix can readily be identified.

To enable the comparison of any amino acid residue/position between different Gα proteins, Flock et al, 2015 (Nature 524: 173) have devised a common Gα numbering (CGN) system. The CGN provides an 'address' for every residue in the DSP format, referring to: (1) the domain (D); (2) the consensus secondary sequence (S); and (3) the position (P) within the secondary structure element. For instance, phenylalanine 336 in Gα$_{i1}$ is denoted as Phe376$^{G.H5.8}$ as it is the eighth amino acid residue within the consensus helix H5 of the G-domain. The corresponding position in Gα$_{s2}$ is Phe376$^{G.H5.8}$. Loops are labelled in lowercase letters of their flanking secondary structure elements (SSE); for example, s6h5 refers to the loop connecting strand S6 with helix H5 (see FIG. 25). A CGN mapping webserver is available online.

It will be appreciated that the CGN can be used to identify the boundaries of each of Helices A-F in any Gα subunit. For example, the first residue of Helix A (H.HA) in Gαs is Asp85$^{H.HA.1}$ and the final residue of Helix F (H.HF) in Gαs is Arg199$^{H.HF.6}$. Thus, the mutant Gα subunit may lack the helical domain of the parent Gα subunit corresponding to the region defined by amino acid residue Asp85 to amino acid residue Arg199 of the long isoform of human Gαs as set out in FIG. 1 and FIG. 25.

By "corresponding region", we include the meaning of the region in the amino acid sequence of a second Gα subunit which aligns to the region in a first Gα subunit (eg the region defined by amino acid Asp85 to amino acid residue Arg199 of the long isoform of human Gαs), when the first and second Gα subunits are compared by alignment, for example by using MacVector and Clustal W. For example, FIG. 25 shows an alignment of all of the human Gα subunits, from which the region corresponding to the region defined by amino acid Asp85 to amino acid residue Arg199 of the long isoform of human Gαs, in other human Gα subunits can be identified. It will be appreciated that regions in other human Gα subunits corresponding to different regions in the long isoform of human Gα subunit may also be identified.

In a specific embodiment, the mutant Gα subunit lacks a region of the helical domain of the parent heterotrimeric Gα subunit corresponding to amino acid residues 70 to 193, 71 to 193, 85 to 193, or 85 to 199 according to the numbering of the long isoform of human Gα-s subunit as set out in FIG. 1.

It will be understood that when the mutant Gα subunit lacks the entire helical domain, the mutant Gα subunit of the invention may be considered to be an isolated GTPase domain or a Gα subunit without its helical domain.

Whether or not a given mutant Gα subunit lacks at least one helix of the helical domain of the parent Gα subunit can be determined by the skilled person, for example by aligning the amino acid sequence of the mutant Gα subunit with the amino acid sequence of the parent Gα subunit and assessing whether or not the amino acid sequence corresponding to the at least one helix of the helical domain of the parent Gα subunit is present in the amino acid sequence of the mutant Gα subunit. A similar analysis may be performed at the nucleotide sequence level.

By is capable of binding to a GPCR in the absence of a heterotrimeric G protein beta (Gβ) subunit and a heterotrimeric G protein gamma (Gγ) subunit, we include the meaning that the Gα subunit does not require the presence of a Gβ subunit and a Gγ subunit in order to bind to a GPCR. In other words, the mutant Gα subunit of the invention is able to bind to a GPCR in a βγ independent manner. Preferably, the mutant Gα subunit of the invention should bind to a GPCR with a similar affinity (that is to say typically within 1-3 fold) as the parent Gα subunit binds to the same GPCR when the parent Gα subunit binds in combination with the βγ subunit. In other words, the mutant Gα subunit should bind to a GPCR with a similar affinity as the parent heterotrimeric G protein binds to the same GPCR. By binds to a GPCR, we include the meaning of binding to a GPCR when bound by its agonist.

Various methods may be used to determine binding between a GPCR and a test compound including, for example, size exclusion chromatography, enzyme linked immunosorbent assays (ELISA), surface plasmon resonance assays, chip-based assays, immunocytofluorescence, yeast two-hybrid technology and phage display which are common practice in the art and are described, for example, in Plant et al (1995) *Analyt Biochem,* 226(2), 342-348 and Sambrook et al (2001) Molecular Cloning A Laboratory Manual. Third Edition. Cold Spring Harbor Laboratory Press, Cold Spring Harbor, N.Y. Other methods of detecting binding between a test compound and the GPCR include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other. Yet further methods are described in WO2009/081136.

In one embodiment, the mutant Gα subunit is capable of functionally binding to a GPCR in the absence of a Gβ subunit and a Gγ subunit. By "functional binding", we include the meaning that the mutant Gα subunit is able to bind to a GPCR expressed on the surface of a cell such that it can transduce a signal from the GPCR (eg having bound to a modulator, such as a ligand of the receptor) into the cell via components of a signalling pathway of the cell. Another term for such functional binding is coupling. As explained above, heterotrimeric G proteins couple with GPCRs and effectively transduce a signal from the GPCR to downstream effectors. Specifically, binding of ligands such as hormones and neurotransmitters to a GPCR activates the receptor by causing a conformational change, which in turn activates the bound G protein on the intracellular-side of the membrane. The activated receptor promotes the exchange of bound GDP for GTP on the Gα subunit. GTP binding changes the conformation of switch regions within the Gα, which allows the bound trimeric G protein (inactive) to be released from the receptor, and to dissociate into active Gα subunit (GTP-bound) and a βγ dimer. The Gα subunit and the βγ dimer go on to activate distinct downstream effectors, such as adenylyl cyclase, phosphodiesterases, phospholipase C, and ion channels. These effectors in turn regulate the intracellular concentrations of secondary messengers, such as cAMP, cGMP, diacylglycerol, sodium or calcium cations, which ultimately lead to a physiological response, usually via the downstream regulation of gene transcription. The cycle is completed by the hydrolysis of alpha subunit-bound GTP to GDP, resulting in the re-association of the alpha and beta/gamma subunits and their binding to the receptor, which terminates the signal.

Functional binding between the mutant Gα subunit and a GPCR can be seen to result in activation of the Gα subunit such that it can produce a Gα protein signal in a cell. Accordingly, in one embodiment, the mutant Gα subunit is capable of binding to a GPCR in the absence of a Gβ subunit and a Gγ subunit, such that the Gα subunit can be activated by the GPCR, for example as manifest by the generation of, or an increase in the basal level of, a Gα protein signal. By a Gα protein signal we include the meaning of any downstream signal that is normally associated with signal transduction via the particular Gα subunit in question, and so can be used as a marker for activation of the Gα subunit. The signal may be any of the signals described herein and may be assayed using any suitable technique in the art.

Functional binding may be assessed in a cellular assay, wherein a GPCR that is capable of a transducing a signal into the cell is contacted with the mutant Gα subunit, and following stimulation of the GPCR (eg with a ligand), the Gα protein signal assessed. Preferably, the cell co-expresses the mutant Gα subunit and GPCR so as to enhance the signal, and even more preferably, expression of GPCRs or the mutant Gα subunit is controlled by an inducible promoter, numerous examples of which have been described in the art and are generally available. However, any assay format that allows a Gα protein signal to be measured following the binding of Gα to its GPCR, and once the GPCR has been stimulated, can be used. Preferably, the signal is detectable. The signal may correspond to the guanyl-nucleotide binding status of the Gα subunit (eg GDP-bound or GTP-bound) which may be assessed biochemically on purified protein or enriched protein fractions, for example where the amount of radiolabelled GTPγS is detected. The signal may correspond to the GTPase activity of the Gα subunit, or it may correspond to levels of secondary messengers, or it may reflect the status of downstream effectors (eg phosphorylation status or activity of cellular proteins). Alternatively, the use of a reporter gene can provide a readout, wherein expression of the reporter gene is controlled by the signal transduced through the Gα subunit. Yet another method is to measure the affinity of the GPCR for its ligand. Still another method if to measure a phenotype of the cell known to be regulated by signalling through the Gα subunit (eg cell growth or morphology). Further details are given below.

Typically, the mutant Gα subunit functionally binds to its GPCR in a βγ independent manner with a similar or greater potency than it does in the presence of the βγ dimer. Typically, the Gα protein signal generated when the Gα subunit binds to the GPCR in the presence and absence of a βγ dimer are within 5-10 fold of each other, such as within 2-3 fold. Typically, the Gα protein signal generated when the Gα subunit binds to the GPCR in the absence of a βγ dimer would be not more than 5 times weaker than the Gα protein signal generated when the Gα subunit binds to the GPCR in the presence of a βγ dimer.

It will be appreciated that the particular Gα protein signal generated from functional binding between the Gα and the GPCR (eg activation of Gα) will often depend upon the type of Gα subunit in question. For example, Gα subunits of the Gαs type mediate signal transduction to effectors that stimulate the production of cyclic AMP (cAMP) within the cell. Conversely, Gα subunits of the Gαi type mediate signal transduction to effectors that inhibit the production of cyclic AMP within the cell. Another class of Gα subunit, of the Gαq type, activates a phospholipase C (PLC) pathway resulting in the hydrolysis of phosphoinositides to generate two classes of different second messengers, namely diacylglycerol (DAG) and inositol phosphates. Diacylglycerol activates certain protein kinase Cs (PKCs) and certain inositol phosphates stimulate the mobilisation of calcium from intracellular stores. A wide variety of intracellular effectors have been identified as being under the control of Gα subunits including cAMP, cGMP, phosphodiesterases, phospholipase C and phospholipase A2. In addition, Gα activation is able to modulate a range of ion channels and is able to inhibit certain voltage sensitive calcium transients, as well as stimulating cardiac potassium channels. The skilled person will be able to select an appropriate assay for a given Gα subunit (see, for example, Neves et al (2002) *Science* 296: 1636-1639; and Cabrera-Vera et al (2013) *Endocrine Reviews* 24: 765-781).

When Gα subunits that modulate cAMP are tested, standard techniques for detecting cAMP may be used to assess functional binding, such as competitive assays which quantitate [3H]cAMP in the presence of unlabelled cAMP.

The GTPase enzymatic activity by Gα subunits can be measured, for example in plasma membrane preparations, by determining the breakdown of γ32P GTP using techniques that are well known in the art (eg see Signal Transduction: A Practical Approach: G Milligan, Ed. Oxford University Press, Oxford, England).

When Gα subunits that modulate phospholipase C are tested, inositol lipids can be extracted and analysed using standard lipid extraction techniques. DAG can also be measured using thin-layer chromatography. Water soluble derivatives of all three inositol lipids (IP1, IP2, IP3) can also be quantified using radiolabelling techniques or HPLC. DAG can also be produced from phosphatidyl choline. The breakdown of this phospholipid in response to Gα activation can also be measured using radiolabelling techniques.

The mobilisation of intracellular calcium or the influx from calcium from outside of the cell can be measured using standard techniques. The choice of the appropriate calcium indicator, fluorescent, bioluminescent, metallochromic or calcium sensitive microelectrodes depends on the cell type and the magnitude and time constant of the event under study (Borle (1990) *Environ Health Perspect* 84: 45-56). As an exemplary method of calcium detection, cells could be loaded with the calcium sensitive fluorescent dye fura-2 or indo-1, using standard methods, and any change in calcium measured using a fluorometer.

Further examples of suitable assays include: calcium mobilisation (Gonzalez J E, Maher M P. Cellular fluorescent indicators and voltage/ion probe reader (VIPR) tools for ion channel and receptor drug discovery. Receptors Channels. 2002; 8(5-6):283-95, Dupriez V J, Maes K, Le Poul E, Burgeon E, Detheux M. Aequorin-based functional assays for G-protein-coupled receptors, ion channels, and tyrosine kinase receptors. Receptors Channels. 2002; 8(5-6):319-30), changes in cAMP levels (Weber M, Ferrer M, Zheng W, Inglese J, Strulovici B, Kunapuli P. A 1536-well cAMP assay for Gs- and Gi-coupled receptors using enzyme fragmentation complementation. Assay Drug Dev Technol. 2004 February; 2(1):39-49.), activation of kinase pathways (Leroy D, Missotten M, Waltzinger C, Martin T, Scheer A. G protein-coupled receptor-mediated ERK1/2 phosphorylation: towards a generic sensor of GPCR activation. J Recept Signal Transduct Res. 2007; 27(1):83-97), regulation of gene transcription for example via the use of a reporter gene (Liu B, Wu D. Analysis of the coupling of G12/13 to G protein-coupled receptors using a luciferase reporter assay. Methods Mol Biol. 2004; 237:145-9, Kent T C, Thompson K S, Naylor L H. Development of a generic dual-reporter gene assay for screening G-protein-coupled receptors J Biomol Screen. 2005 August; 10(5):437-46), recruitment of β-arrestin (Hudson C C, Oakley R H, Sjaastad M D, Loomis C R. High-content screening of known G protein-coupled receptors by arrestin translocation Methods Enzymol. 2006; 414:63-78), activation of G proteins such as measuring GTPase activity (Jameson E E, Roof R A, Whorton M R, Mosberg H I, Sunahara R K, Neubig R R, Kennedy R T. Real-time detection of basal and stimulated G protein GTPase activity using fluorescent GTP analogues. J Biol Chem. 2005 Mar. 4; 280(9):7712-9) or measuring [35S]GTPgamma(γ)S binding (Rodgers G, Hubert C, McKinzie J, Suter T, Statnick M, Emmerson P, Stancato L. Development of displacement binding and GTPgammaS scintillation proximity assays for the identification of antagonists of the micro-opioid receptor. Assay Drug Dev Technol. 2003 October; 1(5):627-36).

Generally, binding of a G protein to a GPCR has been shown to increase the affinity of the GPCR for its agonist (see, for example, Leff (1995) *TiPS* 16: 89), and so, in addition to assessing activation of the mutant Gα subunit, for example by assessing a Gα protein signal, a preferred way of assessing functional binding between a mutant Gα subunit and a GPCR is by measuring the affinity of the GPCR for its ligand. In this way, functional binding can be characterised by an increase in the affinity of a GPCR for its agonist when the GPCR is bound to the Gα subunit compared to the affinity of the GPCR for its agonist when the GPCR is not bound to the Gα subunit. Such an increase in affinity can be measured using any suitable technique in the art, including competitive binding assays, optionally where one or both of the competing ligands are detectably labelled.

An example of such an assay is described in the Examples, which measures competition between the antagonist 3H-dihydroalprenolol (3H-DHA) and the agonist isoprenaline for binding to a beta adrenergic receptor in the presence and absence of Gαs. To increase the sensitivity of such assays, it may be desirable to also expose the GPCR and/or Gα subunit to an agent that is known to stabilise the Gα subunit or the agonist conformation. Examples of such agents include antibodies (eg nanobodies) or other proteins whose function mimics that of the natural agonist. Specific examples are Nanobody 35 (Ref 40) and Nanobody 80 (Ref 38), and further examples are provided in WO2012007593, WO2015121092, and WO2014122183. It will be appreciated that other such antibodies/nanobodies can be selected, for example by injecting purified GPCRs or GPCRs overexpressed in whole cells into mice or llamas, selecting antibodies/nanobodies that bind to the GPCR, and selecting those antibodies/nanobodies that activate the GPCR in whole cells (eg by screening for increased production of a downstream effect of the GPCR activated signalling pathway).

When binding of a G protein to a GPCR is known to increase the affinity of the GPCR for an agonist, typically, binding of the mutant Gα subunit in the absence of a Gβ subunit and a Gγ subunit, to a GPCR increases the affinity of the GPCR for the agonist by at least 1-fold, 2-fold, 3-fold, 4-fold or 5-fold. Preferably, the binding of the mutant Gα subunit in the absence of a Gβ subunit and a Gγ subunit, to a GPCR increases the affinity of the GPCR for the agonist by at least 10-fold, 50-fold or 100-fold.

It will be appreciated that some G proteins may decrease the affinity of GPCRs for their antagonists, in which case functional binding between a mutant Gα subunit and a GPCR may be assessed by measuring this decrease in affinity. Similar assays to those described above for measuring an increase in affinity for agonist may be used to measure a decrease in affinity for antagonists. When binding of a G protein to a GPCR is known to decrease the affinity of the GPCR for an antagonist, typically, binding of the mutant Gα subunit in the absence of a Gβ subunit and a Gγ subunit, to a GPCR decreases the affinity of the GPCR for the antagonist by at least 1-fold, 2-fold, 3-fold, 4-fold or 5-fold. Preferably, binding of the mutant Gα subunit in the absence of a Gβ subunit and a Gγ subunit, to a GPCR decreases the affinity of the GPCR for the antagonist by at least 10-fold, 50-fold, 100-fold or 150-fold.

As outlined above, the interaction between a GPCR and a heterotrimeric G protein induces conformational changes in both the G protein and receptor. In particular, there is a movement of the cytoplasmic end of transmembrane helix 6 of the GPCR by 10 Å or more away from the core of the receptor. Thus, functional binding of the mutant Gα subunit in the absence of a Gβ subunit and a Gγ subunit, to a GPCR, would be expected to induce one or more of these conformational changes that are evident when the parent Gα subunit binds to the GPCR together with the Gβ and Gγ subunits. To put it another way, binding of the mutant Gα subunit is expected to make the GPCR adopt its G protein-bound conformation. In one embodiment, therefore, binding of the mutant Gα subunit in the absence of a Gβ subunit and a Gγ subunit, to a GPCR, results in the movement of the cytoplasmic end of transmembrane helix 6 of the GPCR by 10 Å or more away from the core of the receptor, such as by at least 11 Å, 12 Å, 13 Å, 14 Å, 15 Å or 16 Å away from the core of the receptor. It will be appreciated, therefore, that this provides yet another way of determining whether the Gα subunit functionally binds to or couples to a GPCR.

Various methods to probe protein structure are known in the art and any suitable method may be used. For example any structural biology technique such as x-ray crystallography may be used. Other methods include electron microscopy, NMR, direct measurement by epr spectroscopy or FRET.

Yet another way of assessing functional binding or coupling between a mutant Gα subunit and a GPCR is to assess the stability of the GPCR/agonist/mutant Gα subunit complex under denaturing conditions and compare it to the stability of the GPCR/agonist complex under denaturing conditions. If the stability (eg thermostability) of the GPCR/agonist/mutant Gα subunit complex is greater than the stability of the GPCR/agonist complex, this would be indicative of functional binding. It will be appreciated that when the thermostability of a GPCR/G protein complex is measured, the temperature of the experiment should be performed within the temperature range tolerated by the mutant Gα subunit (eg to ensure that it is possible to detect ligand binding). Typically, this means performing the experiment below 35° C. but for some particularly unstable Gα subunits, it may be necessary to keep the temperature very low (eg below 10° C.). Of course it will also be appreciated that the stability measurements may be performed in the presence of the βγ subunits. Any suitable method of measuring stability may be used, for example as described below and in the Examples (see also FIGS. 10, 11 and 17).

Examples of assays that may be used to assess whether a mutant Gα subunit functionally binds to or couples to a GPCR are also described in Example 5, and include (i) an agonist affinity shift assay, (ii) a thermostability assay, (iii) fluorescence-detection size exclusion chromatography (FSEC), (iv) fluorescence-based saturation binding analysis, and (v) size exclusion chromatography (SEC). Thus, it will be appreciated that any one or more of these assays, either alone or in combination with one of the assays described above, may be used to determine functional binding or coupling between a mutant Gα subunit and a GPCR.

In a preferred embodiment, the mutant Gα subunit has increased stability under denaturing conditions compared to its parent Gα subunit and/or is expressed at a higher level than its parent Gα subunit, when expressed in a cell. Thus, it will be appreciated that when compared to its parent Gα subunit, the mutant Gα subunit contains one or more mutations that increases the stability of the mutant Gα subunit under denaturing conditions and/or increases the expression level of the mutant Gα subunit, when expressed in a cell, compared to its parent Gα subunit.

The mutant Gα subunit may be one which has increased stability to any denaturant or denaturing condition such as to any one or more of heat, a detergent, a chaotropic agent or an extreme of pH. Thus, it is appreciated that the mutant Gα may have an extended lifetime, relative to its parent, under destabilising conditions.

In relation to an increased stability to heat (ie thermostability), this can readily be determined by measuring binding to a known binding partner (eg GPCR) or by using spectroscopic methods such as fluorescence, CD or light scattering at a particular temperature. Typically, when the Gα subunit binds to a binding partner (eg GPCR), the ability of the Gα subunit to bind that binding partner (eg GPCR) at a particular temperature may be used to determine thermostability of the mutant. It may be convenient to determine a "quasi $T_m$" ie the temperature at which 50% of the Gα subunit is inactivated under stated conditions after incubation for a given period of time (eg 30 minutes). Mutant Gα subunits of higher thermostability have an increased quasi Tm compared to their parents. Alternatively, thermostability can be assessed by measuring stability at a given temperature as a function of time. For example, the length of time at a given temperature by which the level of binding partner (eg GPCR) binding falls to 50% of the level of binding partner (eg GPCR) binding at time zero may be determined (Shibata et al, 2009 *J Mol Biol*). In either case however, it is appreciated that temperature is the denaturant.

In relation to an increased stability to a detergent or to a chaotrope, typically the Gα subunit is incubated for a defined time in the presence of a test detergent or a test chaotropic agent and the stability is determined using, for example, binding partner binding or a spectroscopic method as discussed above.

In relation to an extreme of pH, a typical test pH would be chosen (eg in the range 4.5 to 5.5 (low pH) or in the range 8.5 to 9.5 (high pH)).

Because relatively harsh detergents are used during crystallisation procedures, it is preferred that the mutant Gα subunits are stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the mutant Gα subunit is more stable to any of $C_9$ maltoside or glucoside, $C_8$ maltoside or glucoside, LDAO and SDS, and so it is preferred that these detergents are used for stability testing.

Because of its ease of determination, it is preferred that the mutant Gα has increased thermostability compared to its parent protein. It will be appreciated that heat is acting as the denaturant, and this can readily be removed by cooling the sample, for example by placing on ice. It is believed that thermostability may also be a guide to the stability to other denaturants or denaturing conditions. Thus, increased thermostability is likely to translate into stability in denaturing detergents, especially those that are more denaturing than DDM, eg those detergents with a smaller head group and a shorter alkyl chain and/or with a charged head group.

When an extreme of pH is used as the denaturing condition, it will be appreciated that this can be removed quickly by adding a neutralising agent. Similarly, when a chaotrope is used as a denaturant, the denaturing effect can be removed by diluting the sample below the concentration in which the chaotrope exerts its chaotropic effect.

The mutant Gα subunit may be one that is expressed at a higher level in a cell than its parent Gα subunit. Preferably, the mutant Gα subunit is expressed in a cell at a level than is at least 1-fold greater than the level of its parent Gα subunit when expressed in the cell under the same conditions, such as at least 2-fold, 3-fold, 4-fold or 5-fold greater, and more preferably at least 10-fold or 50-fold greater. Suitable expression systems are described in further detail below and in the Examples, and include constitutive or inducible expression systems in bacteria or yeasts, virus expression systems such as baculovirus, semliki forest virus and lentiviruses, or transient transfection in insect or mammalian cells. Methods for assessing protein expression are well known in the art and include techniques such as ELISA, SDS-PAGE analysis, western blotting, gel filtration and HPLC.

It is appreciated that some mutant Gα subunits of the first aspect of the invention may be expressed at a lower level in a cell and/or be less stable under denaturing conditions than their parent Gα subunits, but such mutant Gα subunits may form complexes with a GPCR, which are more stable under denaturing conditions than complexes formed between their parent Gα subunits and a GPCR.

GPCRs are thought to exist in multiple distinct conformations which are associated with different pharmacological classes of ligand such as agonists and antagonists, and to cycle between these conformations in order to function (Kenakin T. (1997) *Ann N Y Acad Sci* 812, 116-125). Switching between conformations contributes to the difficulty in obtaining crystal structures of receptors. Therefore, the ability to stabilise a particular conformation is highly desirable for crystallisation studies. As discussed in the Examples, the inventors have found that the mutant Gα subunits described herein increase the thermostability of GPCRs in their agonist bound form. Hence, in a further embodiment, the mutant Gα subunit of the first aspect of the invention is able to stabilise a particular conformation of the GPCR upon binding to the GPCR. By stabilise a particular conformation, we include the meaning that the conformation is stabilised under denaturing conditions. In other words, the conformation has an extended lifetime as manifest by retention of ligand binding ability under denaturing conditions. Preferably, the particular conformation is an agonist conformation. Methods for assessing stability under denaturing conditions include those outlined above and are well known in the art (see, for example, WO2008/114020). Briefly, they may include subjecting the GPCR to denaturing conditions, either in the absence or presence of ligand, and then measuring retention of ligand binding. When the GPCR is subjected to the denaturing conditions in the absence of ligand, the GPCR is then contacted with ligand to assess to what extent the GPCR can still bind to ligand. To measure the stability of a particular conformation it is necessary to use a ligand of that conformational class in the stability experiments (eg agonist for agonist conformation, and so on). Since the conformation that is being stabilised is typically an agonist conformation, the ligand used for measuring stability is typically an agonist although it will be appreciated that partial agonists may also be used.

Typically, the mutant Gα subunits of the first aspect of the invention should retain the ability to bind to nucleotides (eg guanine nucleotides such as GDP, GTP or nucleotide derivatives such as GTPγS or GppNp) as do their parent Gα subunits. Similarly, the mutant Gα subunits should retain the ability to bind to Gβ and/or Gγ subunits as do their parent Gα subunits. Binding to nucleotides may stabilise the mutant Gα subunit, and so the retention of these abilities is particularly desirable for structural analysis of G protein-GPCR complexes (eg by cryo-electron microscopy) as described further below.

For the avoidance of doubt, however, mutant Gα subunits that do not retain one or both of these activities are still encompassed by the mutant Gα subunits of the invention.

The switch I region of the Gα subunit is composed of the loop between the helical domain and the beta strand 2 of the GTPase domain (CGN: G.hfs2), but also overlaps with Helix F from the helical domain. Switch I can be defined using the CGN system as the region located between the first amino acid residue of Helix F (H.HF) and the first amino acid residue of beta strand 2 (G.S2) (eg in human Gα$_s$, this would be D194$^{H.HF.1}$-I207$^{G.S2.1}$ including the two specified amino acid residues).

In one embodiment, the mutant Gα subunit retains the switch I region of its parent Gα subunit, eg the region corresponding to amino acid residues Asp 194 to Ile 207 according to the numbering of the long isoform of human Gαs as set out in FIG. 1. It will be understood that this embodiment may correspond to the embodiment where the region corresponding to Helices A-E of the helical domain of the parent Gα subunit is deleted. The inventors have found that in the absence of other mutations that increase stability and/or expression levels of the mutant Gα subunit compared to its parent Gα subunit, the switch I region is important for achieving expression. However, in the presence of one or more mutations that increase stability and/or expression levels of the mutant Gα subunit compared to its parent Gα subunit, the switch I region may be truncated or deleted entirely. Thus, in another embodiment, the mutant Gα subunit is one where the switch I region (eg the region corresponding to amino acid residues Asp 194 to Ile 207 according to the numbering of the long isoform of human Gαs as set out in FIG. 1) or part thereof of the parent Gα subunit is deleted. By part thereof, we include the meaning of at least 1, 2, 3, 4, 5, 6, 7, 8, 9, 10, 11, 12, or 13 amino acid residues of the region corresponding to amino acid residues Asp 194 to Ile 207 according to the numbering of the long isoform of human Gαs as set out in FIG. 1. Preferably the part of the switch I region that is deleted comprises a stretch of consecutive amino acid residues that has been deleted.

In yet another embodiment, the switch I region of the parent heterotrimeric G protein alpha subunit is replaced by a switch I region of a small GTPase. Switch I regions from small GTPases can be readily identified, for example by structural and sequence alignment as described herein.

In a particularly preferred embodiment of the mutant Gα subunit of the first aspect of the invention, the helical domain, switch I region and the linker 1 region that links the GTPase domain to the N terminus of the helical domain, of the parent Gα domain are all deleted. The linker 1 region (CGN: G.s1h1) varies in length between different Gα subunits but can be defined using the CGN system as the region between the first and last residues of the helix 1/Helix A loop (G.h1ha), for example human Gαs V65$^{G.h1ha.1}$-S84$^{G.h1ha.20}$ (including the two specified residues). Alternatively, it can be defined as the region located between the final residue of helix 1 (G.H1) and the first residue of the helix A (H.HA), for example human Gαs H64$^{G.H1.12}$-D85$^{H.HA.1}$ (excluding the two specified residues).

Accordingly, the mutant Gα subunit may be one in which the region of the parent Gα subunit that corresponds to amino acid residues 65 to 207 according to the numbering of the long isoform of human Gα-s subunit as set out in FIG. 1, is deleted.

However, it will be appreciated that it may be desirable to retain one or more amino acid residues (eg 2, 3, 4 or 5) at either or both ends of this region. For example, the mutant Gα subunit may be one in which the region of the parent Gα subunit that corresponds to amino acid residues 66 to 207, 67 to 207, 68 to 207, 69 to 207, 70 to 207, 65 to 206, 65 to 205, 65 to 204, 65 to 203, or 65 to 202 according to the numbering of the long isoform of human Gα-s subunit as set out in FIG. 1, is deleted.

In particularly preferred embodiment of the mutant Gα subunit of the first aspect of the invention, the mutant Gα subunit is one in which the region of the parent Gα subunit that corresponds to amino acid residues 65 to 203 according to the numbering of the long isoform of human Gα-s subunit as set out in FIG. 1, is deleted. Alternatively, this region may be defined as the region between the final residue of helix 1 (G.H1) and the amino acid residue three residues N-terminal to the first amino acid residue of beta sheet (G.S2), for example human GαS H64$^{G.H1.12}$-T204$^{G.hfs2.5}$ (including the two specified residues). It is especially preferred if this region is replaced with an amino acid linker as described further below. Preferred examples include linkers of eight amino acids in length such as GGSGGSGG (SEQ ID NO:93) or GGGGGGGG (SEQ ID NO:94).

It will also be appreciated that it may be desirable to delete one or more additional amino acid residues (eg 2, 3, 4, or 5) at either or both ends of this region. For example, the mutant Gα subunit may be one in which the region of the parent Gα subunit that corresponds to amino acid residues 60 to 207, 61 to 207, 62 to 207, 63 to 207, 64 to 207, 65 to 208, 65 to 209, 65 to 210, 65 to 211 or 65 to 212 according to the numbering of the long isoform of human Gα-s subunit as set out in FIG. 1, is deleted.

In another embodiment of the mutant Gα subunit of the first aspect of the invention, the helical domain and the linker 1 region that links the GTPase domain to the N terminus of the helical domain, of the parent Gα subunit, are deleted, but the switch I region of the parent Gα subunit is deleted or else replaced with a switch I region from a small GTPase.

To facilitate crystallisation, expression and/or purification of mutant Gα subunits, it may be desirable to delete one or more amino acids from the N terminus of the parent Gα subunit. Thus, in one embodiment, the mutant Gα subunit of the first aspect of the invention has an N-terminally truncated amino acid sequence when compared to the parent Gα subunit. For example, up to 10 amino acids may be deleted from the N-terminus, such as up to 9, 8, 7, 6, 5, 4, 3, or 2 amino acids, or 1 amino acid, may be deleted from the N-terminus. In another example, up to 15, 20, 25, 30, 35 or 40 amino acids may be deleted from the N-terminus. Typically, the deletion from the N-terminus is between 5 and 20 amino acids. Deletion of the N-terminus is believed to be particularly favourable for crystallisation purposes, and so if the mutant Gα subunit is to be crystallised it may be desirable to delete up to 40 amino acids from the N-terminus of its parent Gα subunit. In contrast, in the case where binding to a βγ dimer is desirable, the N-terminus should not be deleted, or only up to the 5 N-terminal residues be deleted (eg the N-terminal 1, 2, 3, 4 or 5 residues). In particularly preferred embodiments, the N-terminal 5 amino acids of the parent Gα subunit are deleted, or the N-terminal 20 amino acids of the parent Gα subunit are deleted or the N-terminal 21 amino acids from the parent Gα subunit are deleted or the N-terminal 25 amino acids from the parent Gα subunit are deleted.

In a further preferred embodiment, the mutant Gα subunit is one where all of the amino acid residues N-terminal of the amino acid residue Ile/Leu$^{HN43}$, as shown in FIG. 29, are deleted. For example, when the mutant Gα subunit is a mutant Gαs subunit, this corresponds to deleting the first 25 amino acids corresponding to the first 25 amino acids of human Gαs according to the numbering of human Gαs as shown in FIG. 29.

It will be appreciated that the mutant Gα subunit may comprise any of the N-terminal truncations defined herein in combination with any of the deletions of the helical domain, linker 1 region and switch I region mentioned above. For example, the mutant Gα subunit may comprise any of the N-terminal truncations defined herein and be a mutant Gα subunit in which the region of the parent Gα subunit that corresponds to amino acid residues 65 to 203 according to the numbering of the long isoform of human Gα-s subunit as set out in FIG. 1, is deleted.

In those embodiments of the first aspect of the invention where the switch I region, or part thereof, of the parent Gα subunit is maintained, the inventors have found that individual replacement of the following amino acid residues in the parent Gα subunit lead to an increase in expression: Leu 197 and Cys 200 of the long isoform of human Gαs as shown in FIG. 1. Thus, in one embodiment, the mutant Gα subunit is one which, when compared to the parent Gα subunit, contains one or more mutations in the switch I region, and in a more specific embodiment, the mutant Gα subunit is one which, when compared to the parent Gα subunit, has a different amino acid at a position which corresponds to any one or more of the following positions according to the numbering of the long isoform of human Gα-s subunit as set out in FIG. 1: Leu 197 and Cys 200. Using the CGN system, these amino acid residues are identified as L197$^{H.HF.4}$ and C200$^{G.hfs2.1}$. When the amino acid residue at position L197$^{H.HF.4}$ is a leucine, it is preferably substituted for an alanine residue, and when the amino acid residue at position C200$^{G.hfs2.1}$ is a cysteine, it is preferably substituted for a serine residue.

In another embodiment, the mutant Gα subunit is one wherein the switch III region of the parent heterotrimeric G protein alpha subunit, or part thereof, is deleted. The switch III region can be defined using the CGN system as the region located between the last residue of beta sheet 4 (G.S4) and the first residue of helix 3 (G.H3), for example human Gαs Ala249$^{G.S4.7}$ to Arg265$^{G.H3.1}$ (excluding the two specified residues). Thus, the mutant Gα subunit may be one in which the region of the parent Gα subunit that corresponds to amino acid residues Ser 250 to Asn 264 according to the numbering of the long isoform of human Gα-s subunit as set out in FIG. 1, or part thereof, is deleted. By part thereof, we include the meaning of at least 1, 2, 3, 4, 5, 6, 7, 8, 9, 10, 11, 12, 13, 14 or 15 amino acid residues of the region corresponding to amino acid residues Ser 250 to Asn 264 according to the numbering of the long isoform of human Gαs as set out in FIG. 1. Preferably the part of the switch III region that is deleted comprises a stretch of consecutive amino acid residues that has been deleted. For example, the inventors have found that deleting the stretch of amino acids corresponding to Asn254$^{G.s4h3.5}$ to Thr263$^{G.s4h3.14}$ provides a mutant Gα subunit with particularly good properties (eg in terms of coupling to a GPCR and improved stability/expression levels), and so in a specific embodiment, the mutant Gα subunit is one in which the region of the parent Gα subunit that corresponds to amino acid residues 254 to 263 according to the numbering of the long isoform of human Gα-s subunit as set out in FIG. 1, is deleted. However, it will be appreciated that it may be desirable to retain one or more amino acid residues (eg 2, 3, 4 or 5) at either or both ends of this region. For example, the mutant Gα subunit may be one in which the region of the parent Gα subunit that corresponds to amino acid residues 255 to 263, 256 to 263, 257 to 263, 258 to 263, 259 to 263, 254 to 262, 254 to 261, 254 to 260, 254 to 259, or 254 to 258 according to the numbering of the long isoform of human Gα-s subunit as set out in FIG. 1, is deleted. Similarly, it will be appreciated that it may be desirable to delete one or more additional amino acid residues (eg 2, 3, 4, or 5) at either or both ends of this region. For example, the mutant Gα subunit may be one in which the region of the parent Gα subunit that corresponds to amino acid residues 253 to 263, 252 to 263, 251 to 263, 250 to 263, 249 to 263, 254 to 264, 254 to 265, 254 to 266, 254 to 267, or 254 to 268 according to the numbering of the long isoform of human Gα-s subunit as set out in FIG. 1, is deleted.

It will be appreciated that the mutant Gα subunit may be one wherein the switch III region of the parent Gα subunit, or part thereof, is deleted as defined above, and may comprise any of the N-terminal truncations defined herein, and any of the deletions of the helical domain, linker 1 region and switch I region mentioned above. For example, the mutant Gα subunit may comprise any of the N-terminal truncations defined herein, and be a mutant Gα subunit in which the regions of the parent Gα subunit that correspond to amino acid residues 65 to 203, and amino acids 254 to 263, according to the numbering of the long isoform of human Gα-s subunit as set out in FIG. 1, are deleted.

In another embodiment, the mutant Gα subunit is one wherein the switch II region of the parent heterotrimeric G protein alpha subunit, or part thereof, is deleted. The switch II region can be defined using the CGN system as the region between the last amino acid residue of beta sheet 3 (G.S3) and the first amino acid residue of beta sheet 4 (G.S4), for example Gαs Val224$^{G.S3.8}$ to Ala243$^{G.S4.1}$ (excluding the two specified residues). Thus, the mutant Gα subunit may be one in which the region of the parent Gα subunit that corresponds to amino acid residues Gly 225 to Thr 242 according to the numbering of the long isoform of human Gα-s subunit as set out in FIG. 1, or part thereof, is deleted. By part thereof, we include the meaning of at least 1, 2, 3, 4, 5, 6, 7, 8, 9, 10, 11, 12, 13, 14, 15, 16, or 17 amino acid residues of the region corresponding to amino acid residues Gly 225 to Thr 242 according to the numbering of the long isoform of human Gαs as set out in FIG. 1. Preferably the part of the switch II region that is deleted comprises a stretch of consecutive amino acid residues that has been deleted. In a preferred embodiment, the mutant Gα subunit is one in which the region of the parent Gα subunit that corresponds to amino acid residues 227 to 230 according to the numbering of the long isoform of human Gα-s subunit as set out in FIG. 1, is deleted. Preferably, the switch II region or part thereof (eg the region that corresponds to amino acid residues 227 to 230 according to the numbering of the long isoform of the human Gα-s subunit as set out in FIG. 1) is replaced by a linker sequence as described further below; however, such a linker is not essential.

It will be appreciated that it may be desirable to retain one or more amino acid residues (eg 2, 3, 4 or 5) at either or both ends of the switch II region. For example, the mutant Gα subunit may be one in which the region of the parent Gα subunit that corresponds to amino acid residues 226 to 242, 227 to 242, 228 to 242, 229 to 242, 230 to 242, 225 to 241, 225 to 240, 225 to 239, 225 to 238, or 225 to 237 according to the numbering of the long isoform of human Gα-s subunit as set out in FIG. 1, is deleted. Similarly, it will be appreciated that it may be desirable to delete one or more additional amino acid residues (eg 2, 3, 4, or 5) at either or both ends of this region. For example, the mutant Gα subunit may be one in which the region of the parent Gα subunit that corresponds to amino acid residues 224 to 242, 223 to 242, 222 to 242, 221 to 242, 220 to 242, 225 to 243, 225 to 244, 225 to 245, 225 to 246 or 225 to 247 according to the numbering of the long isoform of human Gα-s subunit as set out in FIG. 1, is deleted.

It will be understood that the mutant Gα subunit may be one wherein the switch II region of the parent Gα subunit, or part thereof, is deleted as defined above, and may comprise any of the N-terminal truncations defined herein, and any of the deletions of the helical domain, linker 1 region, switch I region, and switch III region mentioned above. For example, the mutant Gα subunit may comprise any of the N-terminal truncations defined herein, and be a mutant Gα subunit in which the regions of the parent Gα subunit that correspond to amino acid residues 65 to 203, and amino acids 227 to 230, according to the numbering of the long isoform of human Gα-s subunit as set out in FIG. 1, are deleted, optionally wherein the region of the parent Gα subunit that corresponds to amino acid residues 254 to 263 is also deleted.

It will be appreciated that when any part of the parent Gα subunit is deleted (eg at least one helix of the helical domain, or any of the switch I, switch II or switch III regions or parts thereof), the remaining portions of the Gα subunit (ie the portion to the N terminus of the deletion and the portion to the C terminus of the deletion) may be joined together by a linker sequence. By 'linker sequence' we include the meaning of any chemical moiety that attaches the two portions created by a deletion, together. Preferably, the linker is a peptide. Suitable linker peptides are those that typically adopt a random coil conformation, for example the peptide may contain glycine or serine or a mixture of glycine plus serine residues. Preferably, the linker contains between 2 and 50 amino acid residues, more preferably between 2 and 30, and still more preferably between 3 and 20 such as between 3 and 8. Examples of suitable linkers are provided in Table 2 below. It is preferred if any of the helical domain, switch I and switch II regions are replaced by a linker. The requirement for a linker may depend upon the size of the deletion. For example, small deletions such as in the region of ten amino acids or less may not require a linker and the two portions created by the deletion may be joined together directly. However, larger deletions such as in the region of more than ten amino acids will generally require a linker.

As demonstrated in the Examples, the inventors have identified various mutations that increase the stability of the mutant Gα subunit under denaturing conditions and/or increase the expression of the mutant Gα subunit, when expressed in a cell, compared to its parent Gα subunit, and so it is preferred if the mutant Gα subunit of the first aspect of the invention comprises one or more mutations that increase such stability and/or expression. Examples of such mutations are listed in Tables 2-5 below, and so the mutant Gα subunit may comprise any one or more of the mutations listed in Tables 2-5 below.

In one embodiment, the mutant Gα subunit is one which, when compared to the parent Gα subunit, has a different amino acid at a position which corresponds to any one or more of (eg 2, 3, 4, 5, 6, 7, 8, 9, 10, 11, 12, 13, 14, 15, 16 or 17 of) the following positions according to the numbering of the long isoform of human Gα-s subunit as set out in FIG. 1: Val 36, His 41, Ala 48, Gly 49, Glu 50, Met 60, Leu 63, Leu 197, Lys 200, Arg 201, Phe 208, Asn 218, Gly 226, Glu 230, Ala 249, Ser 252, Leu 272, Ile 372, Val 375. Preferably, each of the amino acids is replaced by the particular amino acid residue indicated in Tables 2-5. For example, the valine at position 36 is replaced by an aspartate, the histidine at position 41 is replaced by a isoleucine or a valine, and so on. However, it will be appreciated that they may be replaced by any other amino acid provided that the mutant Gα subunit is capable of binding to a GPCR in the absence of a Gβ and a Gγ subunit.

In any aspect of the invention, although the amino acid used to replace the given amino acid at a particular position is typically a naturally occurring amino acid, typically an "encodeable" amino acid, it may be a non-natural amino acid (in which case the protein is typically made by chemical synthesis or by use of non-natural amino-acyl tRNAs). An "encodeable" amino acid is one which is incorporated into a polypeptide by translation of mRNA. It is also possible to create non-natural amino acids or introduce non-peptide linkages at a given position by covalent chemical modification, for example by post-translational treatment of the protein or semisynthesis. These post-translational modifications may be natural, such as phosphorylation, glycosylation or palmitoylation, or synthetic or biosynthetic.

In a specific embodiment, the mutant Gα subunit is a mutant Gαs subunit with an amino acid sequence which, when compared to the amino acid sequence of the parent Gα subunit, has one or more of the following mutations according to the numbering of the long isoform of human Gα-s subunit as set out in FIG. 1: V36D, H41I or H41V, A48L, G49D, E50N, M60A or M60C, L63Y or L63R or L63K, L297A, C200S, R201A, F208N, N218K, G226A, E230A, A249D or A249E, S252D or S252E, L272D or L272E, I372A or I372C, and V375I.

In a specific embodiment, the mutant Gα subunit is one which, when compared to the parent Gα subunit, has an N-terminal truncation of 5-20 or 5-25 amino acid residues in length, a deletion of the switch III region, and has a different amino acid at a position which corresponds to one or more of (eg 2, 3, 4, or 5 of) the following positions according to the numbering of the long isoform of human Gα-s subunit as set out in FIG. 1: His 41, Leu 197, Cys 200, Ala 249, and Leu 272.

In a further specific embodiment, the mutant Gα subunit is one which, when compared to the parent Gα subunit, has an N-terminal truncation of 5-20 or 5-25 amino acid residues in length, a deletion of the switch III region, and has a different amino acid at a position which corresponds to any one or more of (eg at least 2, 3, 4, 5, 6, 7 or 8 of) the following positions according to the numbering of the long isoform of human Gα-s subunit as set out in FIG. 1: Gly 49, Glu 50, Leu 63, Ala 249, Ser 252, Leu 272, Ile 372 and Val 375.

In still another specific embodiment, the mutant Gα subunit is one which, when compared to the parent Gα subunit, has a different amino acid at a position which corresponds to one or more of the following positions according to the numbering of the long isoform of human Gα-s subunit as set out in FIG. 1: Gly 49, Glu 50, Gly 226 and Ser 252.

In yet another specific embodiment, the mutant Gα subunit is one which, when compared to the parent Gα subunit, has (i) a deletion of all amino acid residues N-terminal of Ile/Leu$^{HN43}$; (ii) a deletion of the region between the final residue of helix 1 (G.H1) and the amino acid residue three residues N-terminal to the first amino acid residue of beta sheet 2 (G. S2), optionally wherein the region is replaced by an amino acid linker (eg an 8 amino acid linker such as GGSGGSGG (SEQ ID NO:93) or GGGGGGGG (SEQ ID NO:94); (iii) a deletion of ten amino acid residues between Tyr$^{S4H3.4}$ and Asn/Ser$^{S4H3.15}$; and (iv) a different amino acid at a position which corresponds to any one or more of (eg at least 1, 2, 3, 4, 5, 6 or 7 of) the following positions Gly49$^{SIH1.3}$, Glu50$^{SIH1.4}$, Ala249$^{S4.7}$, Ser252$^{S4H3.3}$, Leu272$^{H3.8}$, Ile372$^{H5.4}$ and Val375$^{H5.7}$, optionally where the residues are mutated to D49$^{SIH1.3}$, N50$^{SIH1.4}$, D249$^{S4.7}$, D252$^{S4H3.3}$, D272$^{H3.8}$, A372$^{H5.4}$ and I375$^{H5.7}$ respectively.

Typically, the mutant Gα subunit of the first aspect of the invention has at least 20% sequence identity to the amino acid sequence of the long isoform of human Gα-s subunit as set out in FIG. 1 (SEQ ID NO: 91), such at least 30%, 40%, 50%, 60% or 70% sequence identity, and more typically at least 75%, 80%, 85%, 90%, 95%, 96%, 97%, 98% or 99% sequence identity.

In a further specific embodiment, the mutant Gα subunit is one that has at least 20% sequence identity to any of the amino acid sequences in FIG. 26, corresponding to SEQ ID Nos: 1-45, for example at least 30%, 40%, 50%, 60% or 70% sequence identity, and more preferably at least 75%, 80%, 85%, 90%, 91%, 92%, 93%, 94%, 95%, 96%, 97%, 98%, or 99% sequence identity. Preferably, the mutant Gα subunit is one that comprises any of the amino acid sequences in FIG. 26, corresponding to SEQ ID Nos: 1-45.

In a further specific embodiment, the mutant Gα subunit is one that has at least 20% sequence identity to any of the amino acid sequences in any of FIGS. 29, 35, 36, 37, 38 and 40 for example at least 30%, 40%, 50%, 60% or 70% sequence identity and more preferably at least 75%, 80%, 85%, 90%, 91%, 92%, 93%, 94%, 95%, 96%, 97%, 98% or 99% sequence identity. Preferably, the mutant Gα subunit is one that comprises any one of the amino acid sequence in any of FIGS. 29, 35, 36, 37, 38 and 40.

The percent sequence identity between two polypeptides may be determined using any suitable computer program, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994 Nucleic Acids Res. 22(22): 4673-80). The parameters used may be as follows: Fast pairwise alignment parameters: K-tuple(word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

A large number of dominant negative mutations have been reported for both the heterotrimeric G proteins (reviewed by Barren & Artemyev[49]) and small G proteins (reviewed by Feig[50]). Dominant negative mutants can inhibit G protein signalling by sequestering: βγ subunits, activated GPCRs (eg GPCRs that are capable of binding to a G protein), or downstream binding partners[49, 50]. Those mutants that sequester the GPCR are particularly desirable for the design of MEGA domains since they may help to prevent dissociation of the ternary complex (ie between the Gα subunit, GPCR and βγ subunit). Thus, in one embodiment, the mutant Gα subunit of the first aspect of the invention is one which when compared to the parent Gα subunit, comprises one or more dominant negative mutations. Any such dominant negative mutation known in the art may be incorporated into the mutant Gα subunit of the invention, and some specific examples are included below.

The S17N mutation was one of the first dominant negative mutations described for ras[51] and the corresponding mutations has been characterised in Gαs (S54N)[52-54] and Gαt (S43N)[55,56]. Hence, in one embodiment, the mutant Gα subunit is one which, when compared to the parent Gα subunit, has a different amino acid at a position which corresponds Ser 54 according to the numbering of the long isoform of human Gα-s subunit as set out in FIG. 1. When the mutant Gα subunit is a Gα$_s$ subunit, the mutant preferably comprises the mutation S54N, and when the mutant Gα subunit is a Gαt subunit, the mutant preferably comprises the mutation S43N.

The N338D mutation located within the NKXD motif was identified as a dominant negative mutant in the yeast G protein Gpa1[58]. Analogous to Ras S17N, the Gpa1 N338D mutant appeared to form an irreversible empty binding pocket complex with the receptor, which was resistant to dissociation by guanine nucleotides[58]. The authors noted that the mutant protein was thermally labile and that receptor binding provided protection against denaturation[58]. Simon and colleagues reported that the D273N mutation, also located within the NKXD motif resulted in nucleotide-depleted Gαo, Gα11 and Gα12 subunits that exhibit a receptor-sequestering dominant negative phenotype (βγ independent)[62-64]. Thus, in another embodiment, the mutant Gα subunit is one which, when compared to the parent Gα subunit, has one or more different amino acids within the NKXD motif, optionally wherein Asn of the NKXD motif is replaced with Asp and/or wherein Asp of the NKXD motif is replaced with Asn. The NKXD motif belongs to a group of G-box motifs that are highly conserved in all G proteins, and are described in detail in the scientific literature. The CGN code for the NKXD motif in Gαs is N292$^{G.S5.7}$, K293$^{Gshg.1}$, Q294$^{G.HG.1}$ and D295$^{G.HG.2}$. When the mutant Gα subunit is a yeast Gpa1, the mutant preferably comprises the mutation N338D, and when the mutant Gα subunit is any of Gαo, Gα11 or Gα12, the mutant preferably comprises the mutation D273N.

Simon and colleagues also found that the addition of a second mutation Q205L in Gαo switched the nucleotide specificity of the Gα subunit from guanosine to xanthine nucleotides[62-64]. These double mutant Gα subunits (D273N/Q205L) also acted as receptor-sequestering dominant negative mutants under physiological conditions, where xanthine nucleotides are essentially absent. However, when supplemented with xanthine nucleotides, they regained their full biological function, making them useful tools for studying G protein signalling pathways in vivo. Further, both the D273N and D273N/Q205L mutants retained their receptor coupling selectivity. D273 in Gαo corresponds to Q227$^{G.s3h2.3}$ in Gαs. Therefore, in a further embodiment, the mutant Gα subunit of the first aspect of the invention is one which, when compared to the parent Gα subunit, has a different amino acid at a position which corresponds to Gln 227 according to the numbering of Gαs as set out in FIG. 1, and optionally has a different amino acid at a position which corresponds to Asp 295 according to the numbering of Gαs as set out in FIG. 1. When the mutant Gα subunit is a Gαo, the mutant preferably comprises the mutation Q205L, and optionally also comprises the mutation D273N.

Bourne and colleagues designed a triple mutant that exhibited a dominant negative phenotype[65]. A combination of G226A, E268A and A366S mutations produced a Gαs subunit, which efficiently sequestered both the receptor and βγ subunits in a stable nucleotide-free ternary complex[65]. Hence, in one embodiment, the mutant Gα subunit is one which, when compared to the parent Gα subunit, has one or more different amino acids at a position which corresponds to one or more, or all of, the following positions according to the numbering of the long isoform of human Gα-s subunit as set out in FIG. 1: Gly 226, Glu 268 and Ala 366. When the mutant Gα subunit is a mutant Gα subunit, the mutant preferably comprises one or more, or all of, the mutations G226A, E268A and A366S.

Pereira & Cerione reported a mutation in the switch III region, which produced a receptor-sequestering dominant negative phenotype[59]. The R238E mutation of Gαt (chimera 6[44]) was found to exist in a nucleotide deficient state. The mutant was also reported to be less thermally labile than other nucleotide deficient Gα mutants, possibly because it adopted a partially active conformation[59]. However, the same mutation in Gαs also failed to produce a dominant negative phenotype. Hence, in one embodiment, the mutant Gα subunit is a mutant Gαt subunit (chimera 6) which, when compared to the parent Gα subunit, has a different amino acid at a position which corresponds to Arg 238 according to the numbering of the Gαt subunit (chimera 6) as set out in FIG. 27.

Like most nucleotide-free Gα subunits[24,25,66,67], this triple mutant was thermally unstable[65]. Therefore two of these mutations (G226A and A366S) were combined with additional mutations in order to produce a more stable dominant negative mutant[68]. Here, the α3/β5 loop of Gαs was replaced with the corresponding region from Gαi2[48], as described in the previous section. This construct, containing a total of seven mutations, was reported to have significantly improved thermal stability[48].

In addition to dominant negative mutations, other mutations that may be desirable to incorporate into the mutant Gα subunits of the first aspect of the invention include mutations that are known to increase the affinity of a Gα subunit for a GPCR. Hence, it will be appreciated that the mutant Gα subunit may be one which, when compared to the parent Gα subunit, comprises one or more mutations known to increase the affinity of a Gα subunit for a GPCR. Any such affinity-increasing mutation known in the art may be incorporated into the mutant Gα subunit of the invention, and some specific examples are included below.

Iverson and colleagues designed two Gαi1 constructs[30], in an attempt to mimic a rotation and translocation of the α5 helix, predicted to be induced by receptor binding[29]: first, a disulphide bond was engineered between residues 156 and Q333 (mutated to cysteines), in order to induce a shift in the α5 helix; second, a positive charge was introduced at the N-terminus of the α5 helix (D328R), in order to perturb the local electrostatic distribution around the nucleotide. The crystal structure of the disulphide engineered protein was solved, confirming the presence of the disulphide bond and a shift in the position of the α5 helix[30]. Both mutants displayed increased levels of nucleotide exchange, and both were able to interact with rhodopsin, however the receptor was unable to further accelerate the rate of nucleotide exchange[30]. The D328R mutant also displayed enhanced interaction with rhodopsin compared to wild-type Gαi1[30]. Thus, in one embodiment, the mutant Gα subunit is one which, when compared to the parent Gα subunit, has a cysteine residue at each of the positions corresponding to Ile 56 and Gln 333 according to the numbering of the Gαi1 subunit as set out in FIG. 25. Additionally or alternatively, the mutant Gα subunit is one which, when compared to the parent Gα subunit, has a different amino acid at a position which corresponds to Asp 328 according to the numbering of the Gαi1 subunit as set out in FIG. 25. When the mutant Gα subunit is a Gαi subunit, preferably the mutant comprises the mutation D328R.

Grishina and Berlot have identified the α3/β5 loop (ie the loop between helix 3 and beta strand 5) of Gαs as a potential receptor contact site[48]. Replacement of this region with the corresponding loop from Gαi2 was reported to increase affinity for the β₂AR, and reduce the rate of receptor catalysed nucleotide exchange[48]. Hence, in yet a further embodiment, the mutant Gα subunit may be a mutant Gαs subunit wherein the α3/β5 loop of the parent Gαs subunit is replaced with the α3/β5 loop of a Gαi2 subunit. By the α3/β5 loop we include the meaning of the region defined by the amino acid sequence N271$^{G.H3.8}$ to I285$^{G.h3s5.3}$ of Gαs, which corresponds to K249$^{G.H3.7}$ to T263$^{G.h3s5.3}$ of Gαi2. Replacement of this loop in Gαs corresponds to the following mutations: N271K, K274D, R280K, T284D, and I285T, and so it will be appreciated that the mutant Gα subunit may be one which, when compared to the parent Gα subunit, has a different amino acid at a position which corresponds to any one or more of Asn 271, Lys 274, Arg 280, Thr 284 and Ile 285 according to the numbering of the long isoform of the human Gαs subunit as set out in FIG. 1. When the mutant Gα subunit is a Gαs subunit, preferably the mutant comprises one or more of the mutations N271K, K274D, R280K, T284D, and I285T.

Moller and colleagues reported that modification of Cys-347 within the C-terminal region of transducin prevented dissociation of the rhodopsin-transducin complex[47]. Interestingly the type of modifying reagent used appeared to determine the nucleotide binding state of the complex: iodoacetic acid (IAA) carboxymethylation of Cys-347 trapped the rhodopsin-transducin empty pocket complex, and imparted resistance to guanine nucleotide mediated dissociation[47]; 2-nitro 5-thiocyanobenzoic acid (NTCBA) treatment trapped the rhodopsin-transducin complex in the GDP bound state[47]. This may be important in the design of MEGA domains, because a nucleotide bound ternary complex may be more stable than the nucleotide depleted complex. Thus, in yet another embodiment, the mutant Gα subunit may be one wherein the amino acid residue at a position which corresponds to Cys 347 according to the numbering of the Gαt subunit as set out in FIG. 25, is chemically modified, optionally wherein said amino acid residue is carboxymethylated (eg has been treated with IAA) or cyanylated (eg has been treated with NTCBA).

The mutants of the parent Gα subunit may be produced in any suitable way and provided in any suitable form. Conventional site-directed mutagenesis may be employed, or polymerase chain reaction-based procedures well known in the art may be used.

The mutants of the parent Gα subunit are ones whose amino acid sequence comprises one or more of a deletion, an amino acid substitution and/or an insertion compared to the amino acid sequence of the parent Gα subunit. The deletion may be a deletion within the amino acid sequence of the parent Gα subunit (ie not at the termini of the sequence), but it will be appreciated that the deletion may be at one or both of the N-terminus and C-terminus of the amino acid sequence of the parent Gα subunit. Similarly, the insertion may be an insertion of one or more (eg 2, 3, 4, or 5 or more) amino acids within the amino acid sequence of the parent Gα subunit (ie not at the termini of the sequence), but also included are insertions at one or both of the N-terminus and C-terminus of the amino acid sequence of the parent Gα subunit, eg fusions.

For the avoidance of doubt, the mutant Gα subunits of the invention may also be chimeras made up of one or more parts of a first Gα subunit and one or more parts of a second Gα subunit. Chimeras may be useful for converting a Gα subunit of one class (eg Gαs) to behave more like another class (eg Gq or Gi). For example, replacement of the last 18 amino acids of the C-terminus of Gs to those from Gq allows the Gα subunit to bind to a receptor that only couples to Gq. Recent in vivo FRET studies also suggest that residues within the alpha five helix but distal to the five C-terminal residues, strongly influence specificity (see also Example 5). As explained in more detail in Example 5, the inventors have found that where transfer of mutations identified in Gs to other G protein types, alone, was not successful in generating mini G proteins of those other G protein types, another approach is to make chimeras by converting the specificity of mini-Gs to the specificity of the desired G protein. Thus, once a mutant Gα subunit of the first aspect of the invention has been developed that is capable of binding to a GPCR in the absence of a Gβ subunit and a Gγ subunit, where that mutant Gα subunit is a mutant of a particular family or type of Gα subunit (eg Gαs), it may be desirable to mutate the mutant Gα subunit further to convert the specificity of the mutant Gα subunit to that of a different family or type (eg Gαq). Examples of such chimeras are provided in Example 5 and the accompanying figures and are included in the scope of the invention. It will be appreciated that any of the mutations that confer a change in specificity from Gs to Gq identified in Example 5 may be made in relation to any of the mini Gαs proteins described herein.

Generally, the mutant Gα subunit has at least one mutation (ie a deletion, substitution or insertion) compared to its parent Gα subunit, such as at least 2, 3, 4, 5, 6, 7, 8, 9, 10, 11, 12, 13, 14, 15, 16, 17, 18, 19 or 20 mutations. Typically, the mutant Gα subunit has no more than 25 mutations, such as no more than 24, 23, 22, 21, 20, 19, 18, 17, 16, or 15 mutations. Most typically, the mutant Gα has between 5 and 15 mutations, such as between 5 and 10 mutations (eg between 5 and 9 mutations or between 5 and 8 mutations).

In an embodiment, the mutant Gα subunit comprises 1 or 2 deletions, and at least 1, 2, 3, 4, 5, 6, 7, 8, 9 or 10 amino acid substitutions. Typically, the mutant Gα subunit does not comprise more than 10 amino acid substitutions.

Preferably, the mutant Gα subunit contains 3 deletions (eg an N-terminal deletion, a deletion in the helical domain and a switch III region deletion), although it will be appreciated that fewer or more deletions may be made (eg only one deletion in switch III region in addition to a deletion of at least one helix in the helical domain).

The parent Gα subunit need not be the naturally occurring protein. Conveniently, it may be an engineered version which is capable of expression in a suitable host organism, such as *Escherichia coli*. For example, the parent Gα subunit may be a truncated form of the naturally occurring protein (truncated at either or both ends), or it may be a fusion, either to the naturally occurring protein or to a fragment thereof. Alternatively or additionally, the parent Gα, compared to a naturally-occurring Gα, may be modified in order to improve, for example, solubility, proteolytic stability (eg by truncation, deletion of loops, mutation of glycosylation sites or mutation of reactive amino acid side chains such as cysteine). In any event, the parent Gα is a protein that is able to bind to one or more GPCRs which are known to bind to the naturally occurring Gα. Thus, both the mutant Gα subunit and the parent Gα subunit should bind to the same GPCR(s). Where the parent Gα subunit is known to bind to more than one GPCR, it is preferred if the mutant Gα subunit is able to bind to the plurality of GPCRs with a comparable spread and/or rank order of affinity as the parent Gα subunit. Preferably, the mutant Gα subunit should also bind to the same β subunit(s) and γ subunit(s) as the parent Gα subunit. It is also preferred if the mutant Gα subunit binds to the same downstream effector(s) as the parent Gα subunit. However, it is appreciated that the mutant Gα subunit may bind to a different GPCR than its parent Gα subunit in the situation of chimeras as discussed above (eg where the specificity of the parent Gα subunit has been converted to the specificity of a desired G protein). Similarly, the mutant Gα protein may bind to different downstream effectors as the parent Gα subunit.

Conveniently, the mutant Gα subunit is encoded by a suitable nucleic acid molecule and expressed in a suitable host cell. Suitable nucleic acid molecules encoding the mutant Gα subunit may be made using standard cloning techniques, site-directed mutagenesis and PCR as is well known in the art. Suitable expression systems include constitutive or inducible expression systems in bacteria or yeasts, virus expression systems such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris, Spodoptera frugiperda* and *Trichoplusiani* cells. Suitable animal host cells include HEK 293, COS, S2, CHO, NS0, DT40 and so on.

It is known that some Gα subunits require specific lipids to function. In that case, it is desirable to select a host cell which performs the lipidation reaction. Additionally or alternatively the reaction could be performed using purified components during isolation and purification of the mutant Gα subunit. Thus, it will be appreciated that the mutant Gα subunits of the first aspect of the invention may be lipidated. For example, Gα is known to be covalently linked to a palmitoyl group on Gly2 and Cys3, and so the mutant Gα subunit may be lipidated by a palmitoyl group. This may be desirable for crystallisation in liquid crystal phase, or when the Gα subunit is to be studied in whole cell assays. However, in other embodiments the mutant Gα subunits of the first aspect of the invention are not lipidated, which may be preferable for structural studies in detergent solution, drug screening, binding studies (eg surface plamon resonance) etc.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

Conveniently, the mutant Gα subunit of the invention comprises a detectable moiety, such as an affinity tag (eg histidine tag, maltose-binding protein tag, GST tag, HA tag, FLAG tag); or a directly detectable label (such as a fluorophore, a radioisotope, a contrast agent, or a luminescent label); or an indirectly detectable label (such as an enzyme, an enzyme substrate, an antibody, an antibody fragment, an antigen, a hapten, a ligand, an affinity molecule, a chromogenic substrate, a protein, a peptide, a nucleic acid, a carbohydrate and a lipid). Examples of a detectable label include Green Fluorescent Protein (GFP) and so it will be appreciated that the invention includes fusion proteins between GFP and a mutant Gα subunit of the invention. Examples of such fusion proteins are described in Example 5 and FIG. 36. It will be appreciated that the mutant Gα subunit may also comprise a cleavage site, for example to enable removal of a detectable moiety during purification. Any suitable cleavage site known in the art may be used. An example is the tobacco etch virus (TEV) cleavage site.

A second aspect of the invention provides a mutant of a parent heterotrimeric G protein alpha (Gα) subunit, which mutant (i) is capable of binding to a GPCR in the absence of a heterotrimeric G protein beta (Gβ) subunit and a heterotrimeric G protein gamma (Gγ) subunit; and (ii) has a different amino acid at a position which corresponds to any one or more of (eg 2, 3, 4, 5, 6, 7, 8, 9, 10, 11, 12, 13, 14, 15, 16 or 17 of) the following positions according to the numbering of the long isoform of human Gα-s subunit as set out in FIG. 1: Val 36, His 41, Ala 48, Gly 49, Glu 50, Met 60, Leu 63, Leu 197, Cys 200, Arg 201, Phe 208, Asn 218, Gly 226, Glu 230, Ala 249, Ser 252, Leu 272, Ile 372, and Val 375.

Preferences for additional mutations that may be present in the mutant Gα subunit of the second aspect of the invention include those described above in relation to the first aspect of the invention.

Thus, the mutant Gα subunit may further comprise one or more deletions of the helical domain, switch I region, switch II region and switch III region as described above in relation to the first aspect of the invention.

Preferences for the number of mutations (eg deletions, insertions and substitutions) are also as defined above in relation to the first aspect of the invention. The mutant Gα subunit may contain only one deletion (eg in the switch III region).

For example the mutant Gα subunit may have an N-terminally truncation of 5-20 or 5-25 amino acid residues in length, a deletion of the switch III region, and a different amino acid at a position which corresponds to any one or more of (eg at least 2, 3, 4, or 5 of) the following positions according to the numbering of the long isoform of human Gα-s subunit as set out in FIG. 1: His 41, Leu 197, Cys 200, Ala 249, and Leu 272, optionally wherein at least one helix of the helical domain of the parent Gα subunit is also deleted.

A particularly preferred N-terminal truncation of the mutant Gα subunit is one where all of the amino acid residues N-terminal of the amino acid residue Ile/Leu$^{HN43}$ as shown in FIG. 29 are deleted. For example, when the mutant Gα subunit is a mutant Gαs subunit, this corresponds to deleting the first 25 amino acids corresponding to the first 25 amino acids of human Gαs according to the numbering of human Gαs as shown in FIG. 29.

In another example, the mutant Gα subunit may have an N-terminally truncation of 5-20 or 5-25 amino acid residues in length, a deletion of the switch III region, and a different amino acid at a position which corresponds to any one or more of (eg at least 2, 3, 4, 5, 6, 7 or 8 of) the following positions according to the numbering of the long isoform of human Gα-s subunit as set out in FIG. 1: Gly 49, Glu 50, Leu 63, Ala 249, Ser 252, Leu 272, lie 372 and Val 375, optionally wherein at least one helix of the helical domain of the parent Gα subunit is also deleted. For example, the mutant Gα subunit may have a different amino acid at any of the following positions according to the numbering of the long isoform of human Gα s as set out in FIG. 1, Gly 49, Glu 50, Ala 249, Ser 252, Leu 272, Ile 372 and Val 375.

The mutant Gα subunit of the second aspect of the invention may also comprise one or more dominant negative mutations and/or one or more mutations known to increase the affinity between a Gα protein and a GPCR, as described above in relation to the first aspect of the invention.

As shown in the Examples, the inventors have identified mutant Gα subunits that have increased stability under denaturing conditions compared to their parent Gα subunit. Accordingly, it is also appreciated that the invention allows for the production of compositions comprising mutant Gα subunits of the first or second aspect of the invention, characterised in that the mutant Gα is exposed to a destabilising condition. Such compositions have various applications, for example in crystallisation, drug screening, bioassay and biosensor applications. Thus, the invention also provides a composition comprising a mutant Gα subunit of the first or second aspect of the invention, characterised in that the mutant Gα is exposed to a destabilising condition effective to destabilise a parent Gα to a greater extent than the mutant Gα subunit.

By "destabilising condition" we include any condition which is capable of shifting the equilibrium of a population of Gα proteins from the folded native state in a cell the unfolded state. In this way, the proportion of Gα proteins existing in the unfolded state is increased and the proportion existing in the folded native state in a cell is decreased. This change in structure from a folded to an unfolded state leads to a detectable change in the structure of the Gα protein population. Moreover, this change in structure may lead to a detectable decrease in a biological activity of the Gα protein population. Accordingly in one embodiment, the destabilising condition is one that is effective to bring about a significant perturbation in the structure of a Gα protein population compared to the structure of that population in the absence of the destabilising condition.

By a "significant perturbation in the structure of a Gα subunit population", we mean a perturbation which, when assessed relative to the statistical variation of the measurements used to detect the perturbation, would arise by chance in less than 1 in 10 measurements, more preferably 1 in 20 measurements and even more preferably 1 in 50 or 1 in 100 measurements.

Various methods to probe protein structure are known in the art and any suitable method may be used. For example, structural perturbations may be assayed by probing conformation directly eg with covalently attached fluorescent labels or esr spin labels, or by measuring the accessibility of native or deliberately introduced amino acid side chains within a protein (Hubbell, W. L. et al., Adv. Protein. Chem. 63, 243-290 (2003); Baneres, J. L. et. al., J. Biol. Chem. 280, 20253-20260 (2005); Kobilka, B. K. and Deupi, X. Trends. Pharmacol. Sci. 28, 397-406 (2007)). Proteolytic stability, deuterium/hydrogen exchange measured by mass spectrometry or nuclear magnetic resonance spectroscopy, blue native gels, capillary zone electrophoresis, circular dichroism (CD) or linear dichroism (LD) spectra and light scattering may also be used to measure conformational changes in secondary and tertiary structures. Similarly, any suitable method for assessing Gα activity may be used as is descried above in relation to the first aspect of the invention.

A third aspect of the invention provides a polynucleotide that encodes a mutant Gα subunit according to the first or second aspect of the invention. The polynucleotide may be DNA or it may be RNA. Typically, it is comprised in a vector, such as a vector which can be used to express the said mutant Gα subunit. Suitable vectors are ones which propagate in and/or allow the expression in bacterial or mammalian or insect cells. The invention also includes cells, such as host cells, such as bacterial or eukaryotic cells, which contain a polynucleotide which encodes the mutant Gα subunit. Suitable cells include $E.\ coli$ cells, yeast cells, mammalian cells and insect cells.

Examples of polynucleotides that encode a mutant Gα subunit of the invention are provided in FIG. 26, and have the polynucleotides sequences listed in SEQ ID Nos: 46-90. Thus, in one embodiment, the polynucleotide of the third aspect of the invention has at least 20% sequence identity to the polynucleotide sequence of any of SEQ ID Nos: 46-90, such as at least 30%, 40%, 50%, 60%, 70%, 75%, 80%, 85%, 86%, 87%, 88%, 89%, 90%, 91%, 92%, 93%, 94%, 95%, 96%, 97%, 98% or 99% sequence identity. Preferably, the polynucleotide comprises the polynucleotide sequence of any of SEQ ID Nos: 46-90.

A fourth aspect of the invention provides a complex comprising (i) a mutant Gα subunit according to the first or second aspect of the invention, or a portion thereof capable of binding to a GPCR, and (ii) a GPCR or a portion thereof capable of binding to a mutant Gα subunit of the first or second aspect of the invention.

Preferences for the mutant Gα subunit include those described above for the first and second aspects of the invention. It is preferred if the mutant Gα subunit is one that has at least 20% sequence identity to the amino acid sequence of any of SEQ ID Nos: 1-45, such as at least 30%, 40%, 50%, 60% or 70% sequence identity, and more preferably at least 75%, 80%, 85%, 90%, 91%, 92%, 93%, 94%, 95%, 96%, 97%, 98%, or 99% sequence identity. Preferably, the mutant Gα subunit is one that comprises any of the amino acid sequences in FIG. 26, corresponding to SEQ ID Nos: 1-45. It is preferred if the mutant Gα subunit is one that has at least 20% sequence identity to any of the amino acid sequences in any of FIGS. 29, 35, 36, 37, 38 and 40, for example at least 30%, 40%, 50%, 60% or 70% sequence identity, and more preferably at least 75%, 80%, 85%, 90%, 91%, 92%, 93%, 94%, 95%, 96%, 97%, 98% or 99% sequence identity. Preferably, the mutant Gα subunit is one that comprises any one of the amino acid sequences in any of FIGS. 29, 35, 36, 37, 38 and 40.

It is appreciated that the complex may comprise a portion of the mutant Gα subunit that is capable of binding to a GPCR, such as one that is capable of functionally binding to a GPCR as described above. The assessment of binding between Gα subunits and GPCRs is standard practice in the art, and includes those methods described above. Generally, the portion is at least 100, 150, 200, 250 or 300 amino acids in length.

By GPCRs we include all 7-TMRs within the GPCR superfamily. Suitable GPCRs for use in the practice of the invention include, but are not limited to adenosine receptor, in particular adenosine $A_{2A}$ receptor (gene name: ADORA2A), muscarinic receptor, serotonin receptor (eg $5HT_{2C}$; gene name HTR2C), β-adrenergic receptor (e.g. βAR-1; gene name: ADRB1), neurotensin receptor ($NTS_1$; gene name: NTSR1), and orexin receptor (e.g. $OX_2$; gene name: HTR2C). In addition, the International Union of Pharmacology produces a list of GPCRs (Foord et al (2005) *Pharmacol. Rev.* 57, 279-288, incorporated herein by reference and this list is periodically updated at the IUPHAR database (International Union of Basic and Clinical Pharmacology). It will be noted that there are over 800 GPCRs in humans are divided into different classes, principally based on their amino acid sequence similarities, for example Classes A, B, C, D, E and F, for instance the rhodopsin-like receptors (Class A), the secretin receptors (Class B), the metabotropic glutamate/pheromone receptors (Class C) and the frizzled/smoothened receptors (Class F) (Fredriksson et al (2003) *Mol Pharmacol* 63: 1256-1272). GPCRs are also divided into families by reference to the natural ligands to which they bind. All GPCRs, and in particular ones which are known to couple to G proteins, are included in the scope of the invention. Thus, the GPCR may be any of a adenosine receptor, a β-adrenergic receptor, a neurotensin receptor, a muscarinic acid receptor, a 5-hydroxytryptamine receptor, a adrenoceptor, anaphylatoxin receptor, a angiotensin receptor, a apelin receptor, a bombesin receptor, a bradykinin receptor, a cannabinoid receptor, a chemokine receptor, a cholecystokinin receptor, a dopamine receptor, a endothelin receptor a free fatty acid receptor, a bile acid receptor, a galanin receptor, a motilin receptor, a ghrelin receptor, a glycoprotein hormone receptor, a GnRH receptor, a histamine receptor, a KiSS1-derived peptide receptor, a leukotriene and lipoxin receptor, a lysophospholipid receptor, a melanin-concentrating hormone receptor, a melanocortin receptor, a melatonin receptor, a neuromedin U receptor, a neuropeptide receptor, a N-formylpeptide family receptor, a nicotinic acid receptor, a opiod receptor, a opsin-like receptor, a orexin receptor, a P2Y It is appreciated that the complex may comprise a portion of the GPCR that is capable of binding to a mutant Gα subunit, such as one that is capable of functionally binding to a Gα subunit as described above. The portion may comprise only a transmembrane moiety of the GPCR. Generally, the portion is at least 100, 150, 200, 250 or 300 amino acids in length.

The amino acid sequences (and the nucleotide sequences of the cDNAs which encode them) of many GPCRs are readily available, for example by reference to GenBank. In particular, Foord et al supra gives the human gene symbols and human, mouse and rat gene IDs from Entrez Gene. It should be noted, also, that because the sequence of the human genome is substantially complete, the amino acid sequences of human GPCRs can be deduced therefrom.

Although the GPCR may be derived from any source, it is particularly preferred if it is from a eukaryotic source. It is particularly preferred if it is derived from a vertebrate source such as a mammal or a bird. It is particularly preferred if the GPCR is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell subsequently. Thus, it will be plain that a eukaryotic GPCR (such as an avian or mammalian GPCR) may be expressed in a prokaryotic host cell, such as E. coli, but be considered to be avian- or mammalian-derived, as the case may be.

In some instances, the GPCR may be composed of more than one different subunit. For example, the calcitonin gene-related peptide receptor requires the binding of a single transmembrane helix protein (RAMP1) to acquire its physiological ligand binding characteristics. Effector, accessory, auxiliary or GPCR-interacting proteins which combine with the GPCR to form or modulate a functional complex are well known in the art and include, for example, receptor kinases, G-proteins and arrestins (Bockaert et al (2004) Curr Opinion Drug Discov and Dev 7, 649-657).

As outlined above, GPCRs are thought to exist in multiple distinct conformations which are associated with different pharmacological classes of ligand such as agonists and antagonists, and to cycle between these conformations in order to function (Kenakin T. (1997) Ann N Y Acad Sci 812, 116-125). Thus, in one embodiment, the GPCR is one resides in a particular conformational state, such as an agonist conformation or an antagonist conformation. For example, the GPCR may be a mutant GPCR that has increased stability in a particular conformation (eg agonist or antagonist conformation) under denaturing conditions compared to the stability of its parent GPCR in the same particular conformation under denaturing conditions. Examples of such stabilised mutant GPCRs, and methods for making them, are well known in the art and reference is made to WO 2008/114020, WO 2009/071914, WO 2009/081136 and WO 2010/149964. Additionally or alternatively, to facilitate formation of a complex between a mutant Gα subunit and a GPCR in a particular conformation, the GPCR may be exposed to an agent known to stabilise that conformation. Examples of such agents that stabilise the agonist conformation include those described above in relation to the first aspect of the invention, such as nanobodies.

It will be appreciated that once the mutant Gα subunit of the first or second aspect of the invention forms a complex with a GPCR, the GPCR will adopt its G protein-bound state, that is one in which the cytoplasmic end of transmembrane helix 6 of the GPCR is moved away from the core of the receptor by 10 Å or more, such as by at least 11 Å, 12 Å, 13 Å, 14 Å, 15 Å or 16 Å.

It will be appreciated that it may be convenient to detectably label one or other of the mutant Gα subunit or GPCR, or the portion thereof, so as to facilitate detection of their binding. Examples of suitable labels include a peptide label, a nucleic acid label (Kerr et al (1993) JACS vol. 115, p. 2529-2531; and Brenner & Lerner (1992) Proc. Nat. Acad. Sci. USA vol. 89, p. 5381-5383), a chemical label (Ohlmeyer et al (1993) Proc. Natl. Acad. Sci. USA vol. 90, p. 109222-10926; and Maclean et al (1997) Proc. Natl. Acad. Sci. USA vol. 94, p. 2805-2810); a fluorescent label (Yamashita & Weinstock (SmithKline Beecham Corporation), WO95/32425 (1995); and Sebestyen et al (1993) Pept. Proc. Eur. Pept. Symp. 22nd 1992, p. 63-64), or a radio frequency tag (Nicolaou et al (1995) Angew. Chem. Int. Ed. Engl. vol. 34, p. 2289-2291; and Moran et al (1995) JACS vol. 117, p. 10787-10788). Any of the detectable moieties described above in relation to the first aspect of the invention may also be used.

Given that mapping of the ligand-binding pocket is of significant importance for the design of drugs to modulate GPCR activity, it may be desirable for the complex to further comprise a GPCR ligand. Including a ligand will also help to stabilise a particular conformation of the GPCR such as an agonist conformation or an antagonist conformation.

Typically, the ligand is a full agonist and is able to bind to the GPCR and is capable of eliciting a full (100%) biological response, measured for example by G-protein coupling, downstream signalling events or a physiological output such as vasodilation. The ligand may also be a partial agonist and is able to bind to the GPCR and is capable of eliciting a partial (<100%) biological response.

The ligand may also be an inverse agonist, which is a molecule which binds to a receptor and reduces its basal (ie unstimulated by agonist) activity sometimes even to zero.

The ligand may also be an antagonist, which is a molecule which binds to a receptor and blocks binding of an agonist, so preventing a biological response. Inverse agonists and partial agonists may under certain assay conditions be antagonists.

The above ligands may be orthosteric, by which we include the meaning that they combine with the same site as the endogenous agonist; or they may be allosteric or allotopic, by which we include the meaning that they combine with a site distinct from the orthosteric site. The above ligands may be syntopic, by which we include the meaning that they interact with other ligand(s) at the same or an overlapping site. They may be reversible or irreversible.

Ligands for use in the invention may also be allosteric modulators such as positive allosteric modulators, potentiators, negative allosteric modulators and inhibitors. They may have activity as agonists or inverse agonists in their own right or they may only have activity in the presence of an agonist or inverse agonist in which case they are used in combination with such molecules in order to bind to the GPCR.

Neubig et al (2003) Pharmacol. Rev. 55, 597-606, incorporated herein by reference, describes various classes of ligands.

The ligand may be any of a small molecule, a protein, a peptide, a protein scaffold, a nucleic acid, an ion, a carbohydrate, or an antibody.

Preferably, the ligand is a small organic or inorganic moiety, but it may be a peptide or polypeptide. Typically, when the ligand is a small organic or organic moiety, it has a $M_r$ of from 50 to 2000, such as from 100 to 1000, for example from 100 to 500.

Typically, the ligand binds to the GPCR with a $K_d$ of from mM to pM, such as in the range of from μM (micromolar) to nM. Generally, the ligands with the lowest Kd are preferred.

Small organic molecule ligands are well known in the art, for example see the Examples below. Other small molecule ligands include 5HT which is a full agonist at the 5HT1A receptor; eltoprazine which is a partial agonist at the 5HT1A receptor (see Newman-Tancredi et al (1997) *Neurophamacology* 36, 451-459); (+)-butaclamol and spiperone are dopamine D2 receptor inverse agonists (see Roberts & Strange (2005) *Br. J. Pharmacol.* 145, 34-42); and WIN55212-3 is a neutral antagonist of CB2 (Savinainen et al (2005) *Br. J. Pharmacol.* 145, 636-645).

The ligand may be a peptidomimetic, a nucleic acid, a peptide nucleic acid (PNA) or an aptamer. It may be an ion such as $Na^+$ or $Zn^{2+}$, a lipid such as oleamide, or a carbohydrate such as heparin.

The ligand may be a polypeptide which binds to the GPCR. Such polypeptides (by which we include oligopeptides) are typically from $M_r$ 500 to $M_r$ 50,000, but may be larger. The polypeptide may be a naturally occurring GPCR-interacting protein or other protein which interacts with the GPCR, or a derivative or fragment thereof, provided that it binds selectively to the GPCR in a particular conformation. GPCR-interacting proteins include those associated with signalling and those associated with trafficking, which often act via PDZ domains in the C terminal portion of the GPCR.

Polypeptides which are known to bind certain GPCRs include any of a G protein, an arrestin, a RGS protein, G protein receptor kinase, a RAMP, a 14-3-3 protein, a NSF, a periplakin, a spinophilin, a GPCR kinase, a receptor tyrosine kinase, an ion channel or subunit thereof, an ankyrin and a Shanks or Homer protein. Other polypeptides include NMDA receptor subunits NR1 or NR2a, calcyon, or a fibronectin domain framework. The polypeptide may be one which binds to an extracellular domain of a GPCR, such as fibulin-1. The polypeptide may be another GPCR, which binds to the selected GPCR in a hetero-oligomer. A review of protein-protein interactions at GPCRs is found in Milligan & White (2001) *Trends Pharmacol. Sci.* 22, 513-518, or in Bockaert et al (2004) *Curr. Opinion Drug Discov. Dev.* 7, 649-657 incorporated herein by reference.

The polypeptide ligand may conveniently be an antibody which binds to the GPCR. By the term "antibody" we include naturally-occurring antibodies, monoclonal antibodies and fragments thereof. We also include engineered antibodies and molecules which are antibody-like in their binding characteristics, including single chain Fv (scFv) molecules and domain antibodies (dAbs). Mention is also made of camelid antibodies and engineered camelid antibodies. Such molecules which bind GPCRs are known in the art and in any event can be made using well known technology. Suitable antibodies include ones presently used in radioimmunoassay (RIAs) for GPCRs since they tend to recognise conformational epitopes.

The polypeptide may also be a binding protein based on a modular framework, such as ankyrin repeat proteins, armadillo repeat proteins, leucine rich proteins, tetratriopeptide repeat proteins or Designed Ankyrin Repeat Proteins (DARPins) or proteins based on lipocalin or fibronectin domains or Affilin scaffolds based on either human gamma crystalline or human ubiquitin.

In one embodiment of the invention, the ligand is covalently joined to the GPCR, such as a G-protein or arrestin fusion protein. Some GPCRs (for example thrombin receptor) are cleaved N-terminally by a protease and the new N-terminus binds to the agonist site. Thus, such GPCRs are natural GPCR-ligand fusions.

It will be appreciated that the use of antibodies, or other "universal" binding polypeptides (such as G-proteins which are known to couple with many different GPCRs) may be particularly advantageous for "orphan" GPCRs for which the natural ligand, and small molecule ligands, are not known.

In an embodiment of the fourth aspect of the invention, the complex further comprises a G protein β subunit or a G protein γ subunit or a G protein βγ subunit. There are five β subunits ($G\beta_1$, $G\beta_2$, $G\beta_3$, $G\beta_4$, $G\beta_5$) and 12γ subunits ($G\gamma_1$, $G\gamma_2$, $G\gamma_3$, $G\gamma_4$, $G\gamma_5$, $G\gamma_7$, $G\gamma_8$, $G\gamma_9$, $G\gamma_{10}$, $G\gamma_{11}$, $G\gamma_{12}$, $G\gamma_{13}$), which can potentially dimerise in any combination of one Gβ subunit and one Gγ subunit, and any of these dimers could potentially bind any Gα subunit.

There are many reports in the literature about favoured combinations, particularly with regard to binding different GPCRs (for example, $G\alpha_s\beta_1\gamma_2$ favourably binds $\beta_2AR$, $G\alpha_s\beta_2\gamma_7$ or $G\alpha_s\beta_4\gamma_5$ favourably bind $A_{2A}$), and so for a given Gα or GPCR, the skilled person would be able to identify preferred β and/or γ subunit binding partners. Binding between G protein α, β and γ subunits is often regulated by other factors, such as tissue specific expression or membrane localisation. In vivo any combination is possible. The amino acid sequences (and the nucleotide sequences of the cDNAs which encode them) of many Gβ subunits and Gγ subunits are readily available, for example by reference to GenBank.

In an embodiment, the complex further comprises a nucleotide. For example, the complex may comprise a guanine nucleotide such as GDP or GTP, or a xanthine nucleotide. The nucleotide may be a derivative of a naturally occurring or synthetic nucleotide, such as GTPγS or GppNp. Thus, it will be appreciated that the complex may comprise a nucleotide and a ligand. It is well known that magnesium ions can be important for nucleotide binding, and so in a further embodiment, the complex further comprises a magnesium ion. For example, it may comprise a magnesium ion and a nucleotide.

Conveniently, the complex is produced by expressing the mutant Gα subunit or the portion thereof, and the GPCR or the portion thereof separately, and adding the two proteins together after expression under conditions appropriate for complex formation. Alternatively, a cell may be engineered to express or overexpress the mutant Gα subunit and the GPCR using standard molecular biology techniques, such that the GPCR/mutant Gα subunit can be recovered from the cell. Thus, it will be appreciated that the invention also provides a polynucleotide or expression vector capable of encoding a (i) a mutant Gα subunit according to the first or second aspect of the invention, or a portion thereof capable of binding to a GPCR, and (ii) a GPCR or a portion thereof capable of binding to a mutant Gα subunit according to the first or second aspect of the invention. The polynucleotide or expression vector may express (i) and (ii) as separate polypeptides, or (i) and (ii) may be part of the same polypeptide chain, ie (i) and (ii) may be expressed as a fusion polypeptide.

Preferably, the GPCR/mutant Gα subunit complex is soluble. Typically, the proteins are manufactured in *E. coli* or in insect cells and purified by tagging them, for example with 6×His tags and using nickel beads to isolate the recombinant proteins. For instance, typically, the mutant Gα subunits are expressed in *E. coli* and the GPCRs are expressed in insect cells using the baculovirus expression system. Similarly, differently epitope tagged versions of the proteins, can be expressed in and purified from cells. Typically, any of the nucleotide, ligand and/or magnesium ion are added to the isolated or purified complex and incubated under conditions that allow binding of the nucleotide, ligand and/or magnesium to the complex.

As is evident from the Examples, the complex of the fourth aspect of the invention is amenable to crystallisation, and so it will be appreciated that the invention also provides the complex of the fourth aspect of the invention in a crystalline form. In particular, Example 4 describes the structure of a G protein (miniG 414)—bound adenosine A2a receptor in its agonist (NECA) bound form, and so in a preferred embodiment, the complex is a crystalline complex that comprises adenosine A2a and the mutant Gα subunit, miniG 414.

The mutant Gα subunits and compositions disclosed herein are useful for crystallisation studies and are useful in drug discovery programmes. They may be used in biophysical measurements of receptor/ligand kinetic and thermodynamic parameters eg by surface plasmon resonance or fluorescence based techniques. They may be used in ligand binding screens, and may be coupled to solid surfaces for use in high throughput screens or as biosensor chips. Biosensor chips containing the mutant Gα subunits or complexes may be used to detect molecules, especially biomolecules. Further details of such methods and uses are provided below.

The invention provides a mutant Gα subunit of the first or second aspect of the invention or a complex according to the fourth aspect of the invention, which is in a solubilised form (eg after aqueous solubilisation with a detergent) and/or which is substantially free of other proteins. Preferably, the mutant Gα subunit or complex remain in their native folded state when solubilised, or the proportion of a population of mutant Gα subunits or complexes containing said mutant Gα subunits, existing in the native folded state is greater than the proportion of a population of parent Gα subunits or complexes containing said parent Gα subunits. Preferably, the mutant Gα subunit or the complex comprising a mutant Gαsubunit/GPCR maintains its structural integrity and is in a functional form (eg it is able to bind ligand or its natural binding partner (eg G protein or GPCR))

The invention provides a mutant Gα subunit of the first or second aspect of the invention or a complex according to the fourth aspect of the invention, which is immobilized to a solid support. Similarly, the invention provides a solid support to which is immobilized one or more mutant Gα subunits according to the first or second aspects of the invention or a complex according to the fourth aspect of the invention. For example, the solid support may comprise an array of (eg 2 or more, such as 5 or more, 10 or more, 50 or more, 96 or more, or 100 or more) mutant Gα subunits, or mutant Gα/GPCR complexes. The identity of the mutant Gα subunits and/or GPCRs within the array may be the same or different. Such solid supports are useful in binding screens and as biosensors.

The invention provides the use of a mutant Gα subunit of the first or second aspect of the invention or a complex according to the fourth aspect of the invention, for crystallisation.

The invention provides the use of a mutant Gα subunit of the first or second aspect of the invention or a complex according to the fourth aspect of the invention, in drug discovery.

The invention provides the use of a mutant Gα subunit of the first or second aspect of the invention or a complex according to the fourth aspect of the invention in a ligand binding screen or in assay development.

The invention provides the use of a mutant Gα subunit of the first or second aspect of the invention or a complex according to the fourth aspect of the invention, as a biosensor. In a preferred embodiment, the biosensor is one that can be used to measure ligand levels in vivo.

A fifth aspect of the invention provides a method of producing a crystal of a GPCR-Gα subunit complex, the method comprising:

(i) providing a mutant Gα subunit according to the first or second aspect of the invention, a GPCR, and optionally a GPCR ligand;

(ii) forming a complex of the mutant Gα subunit, the GPCR, and optionally the GPCR ligand; and (iii) crystallising the complex to form a crystal.

Preferences for the mutant Gα subunit and GPCR include described above in relation to the first, second and fourth aspects of the invention. It will be appreciated that steps (i) and (ii) may comprise providing a complex according to the fourth aspect of the invention.

Any suitable crystallisation method may be used to crystallise the fusion protein, such as any of those reviewed in "Crystallisation of Biological Macromolecules" (Alexander McPherson; ISBN: 0-87969-617-6), which is incorporated herein by reference. Preferably, crystallisation is carried out using the vapour diffusion method as outlined in the Examples.

Conveniently, the GPCR is crystallised in complex with the mutant Gα subunit in a particular conformation (eg agonist conformation), and so it will be appreciated that the method may further comprise contacting the GPCR with an agent known to stabilise the desired conformation, such as an appropriate ligand (agonist or antagonist) or other agent as described above (eg nanobody). The crystal can be used to solve the structure of the complex, for example using X ray crystallography, as described below.

A sixth aspect of the invention provides a method of determining the structure of a GPCR in a particular conformation (eg agonist conformation), the method comprising providing a complex of the fourth aspect of the invention, and determining the structure of the complex.

The structure of a protein, includes the primary, secondary, tertiary and, if applicable, quaternary structure of the protein. Determining the structure as used herein includes the meaning of determining the arrangement of atoms or the atomic coordinates of a protein, and is often done by a biophysical method, such as X-ray crystallography.

In an embodiment, the GPCR-Gα subunit complex is provided in crystalline form and the crystal structure of the complex is determined, for example by a biophysical method such as X ray crystallography. X ray crystallography is well known in the art. Briefly described, X-ray diffraction patterns can be obtained by diffracting X-rays off a crystal. The diffraction data are used to calculate an electron density map of the unit cell comprising the crystal; the maps are used to establish the positions of the atoms (i.e., the atomic coordinates) within the unit cell. Hence, the method may further comprise obtaining the atomic coordinates from the crystal. In an alternative embodiment, the NMR structure of the complex is determined. In yet an alternative embodiment, the structure is determined by cryo-electron microscopy.

A seventh aspect of the invention provides a method for selecting a mutant of a parent heterotrimeric Gα subunit, which mutant is capable of coupling to a GPCR in the absence of the beta and gamma subunits of the parent heterotrimeric G protein, the method comprising:

(a) providing one or more mutants of a parent heterotrimeric Gα subunit in the absence of the beta and gamma subunits of the parent heterotrimeric G protein;

(b) providing a GPCR; and (c) determining whether the or each mutant Gα subunit is able to bind to the GPCR, and selecting those mutants that are able to bind to the GPCR.

Preferences for the mutant Gα subunits, how to make them, and GPCRs include those described above in relation to the first aspect of the invention. Thus, the mutant is one that comprises one or more mutations selected from a deletion, insertion and substitution. Typically, the mutant Gα subunit lacks at least one helix of the helical domain. Conveniently, the GPCR is one that has increased stability in a particular conformation under denaturing conditions compared to the stability of its parent GPCR in the same particular conformation under denaturing conditions.

Methods for assessing binding of mutant Gα subunits to a GPCR are also described above in relation to the first aspect of the invention.

It is preferred if step (c) comprises determining whether the or each Gα subunit is able to functionally bind to (or 'couple') the GPCR and selecting those mutants that are able to bind to the GPCR.

Conveniently, step (c) comprises determining whether the or each mutant Gα subunit increases the affinity of the GPCR for agonist, upon binding to the GPCR, or determining whether the or each Gα subunit is activated upon binding to the GPCR. Alternatively, step (c) may comprise determining whether the or each mutant Gα subunit decreases the affinity of the GPCR for antagonist, upon binding to the GPCR, or determining whether the or each Gα subunit is activated upon binding to the GPCR.

It will be appreciated that step (c) may comprise any one or more of the assays for assessing whether a mutant Gα subunit functionally binds to or couples to a GPCR, described above in relation to the first aspect of the invention, namely (i) an agonist affinity shift assay, (ii) a thermostability assay, (iii) fluorescence-detection size exclusion chromatography (FSEC), (iv) fluorescence-based saturation binding analysis, and (v) size exclusion chromatography (SEC).

The inventors have found that some mutant Gα subunits of the invention stabilise a GPCR in a particular conformation, and it will be appreciated that it may be desirable to select for such mutants. Therefore, the method of the fifth aspect of the invention may further comprise determining whether the or each mutant Gα subunit is able to stabilise a particular conformation of the GPCR upon binding to the GPCR (eg an agonist conformation), and selecting such mutants that are so able. Suitable methods for testing stability in a particular conformation are well known in the art, and include those described above and in WO2008/114020. Briefly, the complex of the mutant Gα subunit and GPCR may be subjected to denaturing conditions (in the presence or absence of ligand), and the extent to which the GPCR in the complex is able to bind to ligand after being subjected to denaturing conditions assessed.

In an embodiment, prior to step (c), the GPCR is exposed to an agent capable of stabilising a particular conformation. Suitable agents are known in the art, and include a ligand (eg agonist) or other agent as described above (eg antibody, nanobody or other agent whose function mimics that of the natural agonist).

The mutant Gα subunit and/or GPCR are conveniently provided in solubilised form in which they maintain structural integrity and are in a functional form (eg are able to bind their respective binding partners, such as a GPCR for Gα, or a ligand or G protein for GPCR). An appropriate solubilising system, such as a suitable detergent (or other amphipathic agent) and buffer system is used, which may be chosen by the person skilled in the art to be effective for the particular protein. Typical detergents which may be used include, for example, dodecylmaltoside (DDM) or CHAPS or octylglucoside (OG) or many others. It may be convenient to include other compounds such as cholesterol hemisuccinate or cholesterol itself or heptane-1,2,3-triol. The presence of glycerol or proline or betaine may be useful.

Typically, the mutant Gα subunit and/or GPCR are provided in a crude extract (eg of the membrane fraction from the host cell in which they have been expressed, such as E. coli or mammalian cells). They may be provided in a form which typically comprises at least 75%, more typically at least 80% or 85% or 90% or 95% or 98% or 99% of the protein present in the sample. Of course, they are typically solubilised as discussed above, and so they are usually associated with detergent molecules and/or lipid molecules.

In one embodiment, the method of the seventh aspect of the invention further comprises determining whether the mutant Gα subunit has increased stability under denaturing conditions compared to its parent Gα subunit and/or determining whether the mutant Gα subunit is expressed at a higher level than its parent Gα subunit, when expressed in a cell. Such mutant Gα subunits are more experimentally tractable and so it is preferred if the method selects for such mutants. Suitable methods for assessing stability and expression levels are as described above and in the Examples. It is noted that some mutant Gα subunits may be expressed at a lower level and/or are less stable under denaturing conditions than their parent Gα subunits; however, when they are complexed to a GPCR, the complex is more stable under denaturing conditions than a corresponding complex comprising the parent Gα subunit. Therefore, it will be appreciated that the step of determining whether the mutant Gα subunit has increased stability under denaturing conditions compared to its parent Gα subunit, may comprising determining said stability when the mutant Gα subunit is in a complex with a GPCR.

An eighth aspect of the invention provides a method for producing a mutant of a parent heterotrimeric Gα subunit, which mutant is capable of coupling to a GPCR in the absence of the beta and gamma subunits of the parent heterotrimeric G protein, the method comprising:

(a) carrying out the method of the seventh aspect of the invention, (b) identifying the position or positions of the mutations (eg deletion, insertion and/or substitution) in the mutant Gα subunit or subunits which has been selected for increased stability, and (c) synthesising a mutant Gα subunit which contains a mutation (eg deletion, insertion and/or substitution) at one or more of the positions identified.

The invention provides a mutant Gα subunit obtainable by the method of the eighth aspect of the invention.

As shown in the Examples, the inventors have found that the mutant Gα subunits of the invention can stabilise a particular conformation of a GPCR when the Gα subunit is bound to the GPCR. Thus, a ninth aspect of the invention provides a method of stabilising a GPCR in a particular conformation, the method comprising:

(a) providing a mutant Gα subunit according to the first or second aspect of the invention, and a target GPCR, and (b) forming a complex of the mutant Gα subunit and the GPCR, wherein the GPCR is stabilised in a particular conformation.

Preferences for the mutant Gα subunit include those described above in relation to the first or second aspects of the invention. The target GPCR may be any suitable GPCR, and preferably one of the same GPCR class or family as the GPCR that is known to bind to the Gα subunit, and most preferably one that is known to bind to the Gα subunit. Examples of appropriate GPCRs are as mentioned above.

Conveniently, the mutant Gα subunit is immobilised on a solid support.

Typically, the target GPCR is provided as a solution containing the GPCR in a plurality of conformational states. Thus, the method may comprise the steps of (i) applying a solution containing a GPCR in a plurality of conformational states to a solid support comprising one or more immobilised mutant Gα subunits, (ii) forming a complex of the one or more mutant Gα subunits and the GPCR, and (iii) removing weakly bound or unbound molecules, wherein a GPCR is captured in a particular conformation. In this way, it will be appreciated that the method of the ninth aspect of the invention can be considered to be a method of capturing a GPCR in a particular conformational state.

In an embodiment, the method further comprises purifying the complex.

A tenth aspect of the invention provides a method for selecting a GPCR with increased stability, the method comprising (a) providing one or more mutants of a parent GPCR, and a mutant Gα subunit according to the first or second aspects of the invention, (b) selecting a ligand, the ligand being one which binds to the parent GPCR when the GPCR is residing in a particular conformation, (c) determining whether the or each mutant GPCR has increased stability with respect to binding the selected ligand or with respect to binding the mutant Gα subunit, compared to the stability of the parent GPCR with respect to binding that ligand or with respect to binding the mutant Gα subunit, and (d) selecting those mutants that have an increased stability compared to the parent GPCR with respect to binding the selected ligand or with respect to binding the mutant Gα subunit, wherein the particular conformation in which the GPCR resides in step (c) corresponds to the class of ligand selected in step (b).

The mutants of the parent GPCR may be produced in any suitable way and provided in any suitable form. Thus, for example, a series of specific mutants of the parent protein may be made in which each amino acid residue in all or a part of the parent protein is independently changed to another amino acid residue. For example, it may be convenient to make mutations in those parts of the protein which are predicted to be membrane spanning. Thus, conveniently, parts of the GPCR to mutate may be based on modelling. Similarly, computer programs are available which model transmembrane regions of GPCRs based on hydrophobicity (Kyle & Dolittle (1982) *J. Mol. Biol.* 157, 105-132), and use can be made of such models when selecting parts of the protein to mutate. Conventional site-directed mutagenesis may be employed, or polymerase chain reaction-based procedures well known in the art may be used. It is possible, but less desirable, to use ribosome display methods in the selection of the mutant protein.

Typically, each selected amino acid is replaced by Ala (ie Ala-scanning mutagenesis), although it may be replaced by any other amino acid. If the selected amino acid is Ala, it may conveniently be replaced by Leu. Alternatively, the amino acid may be replaced by Gly (ie Gly-scanning mutagenesis), which may allow a closer packing of neighbouring helices that may lock the protein in a particular conformation. If the selected amino acid is Gly, it may conveniently be replaced by Ala.

Alternatively, the mutants may be produced by a random mutagenesis procedure, which may be of the whole protein or of a selected portion thereof. Random mutagenesis procedures are well known in the art.

Conveniently, the mutant GPCR has one replaced amino acid compared to the parent protein (ie it is mutated at one amino acid position). In this way, the contribution to stability of a single amino acid replacement may be assessed. However, the mutant GPCR assayed for stability may have more than one replaced amino acid compared to the parent protein, such as at least 2 or 3 or 4 or 5 or 6 or 7 or 8 or 9 or 10 or 11 or 12 replacements.

The parent GPCR need not be the naturally occurring protein. Conveniently, it may be an engineered version which is capable of expression in a suitable host organism, such as *Escherichia coli*. The parent GPCR may be a truncated form of the naturally occurring protein (truncated at either or both ends), or it may be a fusion, either to the naturally occurring protein or to a fragment thereof. Alternatively or additionally, the parent GPCR, compared to a naturally-occurring GPCR, may be modified in order to improve, for example, solubility, proteolytic stability (eg by truncation, deletion of loops, mutation of glycosylation sites or mutation of reactive amino acid side chains such as cysteine). In any event, the parent GPCR is a protein that is able to bind to the selected ligand which ligand is one which is known to bind the naturally occurring GPCR. Conveniently, the parent GPCR is one which, on addition of an appropriate ligand, can affect any one or more of the downstream activities which are commonly known to be affected by G-protein activation. However, it will be appreciated that the stability of the mutant is to be compared to a parent in order to be able to assess an increase in stability.

Typically, the particular conformation is the agonist conformation and so the selected ligand is an agonist. Examples of agonist ligands for given GPCRs are known in the art and include those described above and in the Examples.

Given that the GPCR is stabilised when bound to a mutant Gα subunit, it will be appreciated that the particular conformation (eg agonist conformation) will be the particular conformation (eg agonist conformation) that has a conformation characteristic of G protein binding. For example, the conformation may be one in which the cytoplasmic end of transmembrane helix 6 of the GPCR is moved away from the core of the receptor by 10 Å or more, such as by at least 11 Å, 12 Å, 13 Å, 14 Å, 15 Å or 16 Å.

The mutant Gα subunit and/or mutant GPCR are conveniently provided in a solubilised form in which they maintain structural integrity and are in a functional form, as described above, for example in relation to the seventh aspect of the invention. However, it will be appreciated that the mutant GPCR may be provided in a membrane containing composition (ie residing in a lipid membrane), contacted with the selected ligand and the mutant Gα subunit, and then the membrane solublised, for example with a detergent.

Once the ligand has been selected, it is then determined whether the or each mutant GPCR has increased stability with respect to binding the selected ligand or with respect to binding the mutant Gα subunit compared to the parent GPCR with respect to binding that ligand or mutant Gα subunit. It will be appreciated that this step (c) is one in which it is determined whether the or each mutant GPCR has an increased stability (compared to its parent) for the particular conformation which is determined by the selected ligand. Thus, the mutant GPCR has increased stability with respect to binding the selected ligand as measured by ligand binding or whilst binding the selected ligand, or has increased stability with respect to binding the mutant Gα subunit as measured by mutant Gα subunit binding or whilst binding the mutant Gα subunit. As is discussed below, it is particularly preferred if the increased stability is assessed whilst binding the selected ligand.

The increased stability is conveniently measured by an extended lifetime of the mutant under the imposed conditions which may lead to instability (such as heat, harsh detergent conditions, chaotropic agents and so on). Destabilisation under the imposed condition is typically determined by measuring denaturation or loss of structure. As is discussed below, this may manifest itself by loss of ligand binding ability or loss of Gα subunit binding ability or loss of secondary or tertiary structure indicators.

When binding to the selected ligand is using to determine increased stability, there are different assay formats which may be used to determine stability of the mutant GPCR.

In one embodiment the mutant GPCR may be brought into contact with a ligand before being subjected to a procedure in which the stability of the mutant is determined (the mutant GPCR and ligand remaining in contact during the test period). Thus, for example, when the method is being used to select for mutant GPCRs which in one conformation bind to a ligand and which have improved thermostablity, the receptor is contacted with the ligand before being heated, and then the amount of ligand bound to the receptor following heating may be used to express thermostability compared to the parent receptor. This provides a measure of the amount of the GPCR which retains ligand binding capacity following exposure to the denaturing conditions (eg heat), which in turn is an indicator of stability.

In an alternative (but less preferred) embodiment, the mutant GPCR is subjected to a procedure in which the stability of the mutant is determined before being contacted with the ligand. Thus, for example, when the method is being used to select for mutant membrane receptors which in one conformation bind to a ligand and which have improved thermostability, the receptor is heated first, before being contacted with the ligand, and then the amount of ligand bound to the receptor may be used to express thermostability. Again, this provides a measure of the amount of the GPCR which retains ligand binding capacity following exposure to the denaturing conditions.

When binding to the mutant Gα subunit is using to determine increased stability, it will be appreciated that the mutant GPCR and mutant Gα subunit may be brought into contact with a ligand before being subjected to a procedure in which the stability of the mutant is determined (the mutant GPCR and ligand remaining in contact during the test period)

In all embodiments, it will be appreciated that the comparison of stability of the mutant is made by reference to the parent molecule under the same conditions.

It will be appreciated that in all of these embodiments, the mutants that are selected are ones which have increased stability when residing in the particular conformation compared to the parent protein. An example of the method of the method of the tenth aspect of the invention is given in Example 4.

Preferably, a mutant GPCR is selected which has increased stability under denaturing conditions such as any one or more of heat, a detergent, a chaotropic agent and an extreme of pH.

Methods for assessing stability under denaturing conditions include those mentioned above in relation to the first aspect of the invention and are also described in WO2008/114020.

Conveniently, when the ligand or mutant Gα subunit binding is used to assay the GPCR (ie used to determine if it is in a non-denatured state), the ligand or mutant Gα subunit is detectably labelled, eg radiolabelled or fluorescently labelled.

From the above, it will be appreciated that the invention includes a method for selecting a mutant GPCR with increased thermostability, the method comprising (a) providing one or more mutants of a parent GPCR, wherein the one or more mutants reside in a membrane-containing composition (b) contacting the one or more mutants with a selected ligand (eg agonist) which binds the parent GPCR, and with a mutant Gα subunit according to the first or second aspect of the invention, (c) solubilising the membrane-containing composition; (d) determining whether the or each mutant of a parent GPCR has increased thermostability when in the presence of the said ligand (eg agonist) by measuring the ability of the mutant GPCR to bind the selected said ligand (eg agonist), or to the mutant Gα subunit, at a particular temperature and after a particular time compared to the parent GPCR and (d) selecting those mutant GPCRs that bind more of the selected said ligand (eg agonist) at the particular temperature and after the particular time than the parent GPCR under the same conditions. In step (d), a fixed period of time at the particular temperature is typically used in measuring the ability of the mutant GPCR to bind the selected said ligand (eg agonist) or mutant Gα subunit. In step (d), typically a temperature and a time is chosen at which binding of the selected ligand (eg agonist) or mutant Gα subunit, by the parent GPCR is reduced by 50% during the fixed period of time at that temperature (which is indicative that 50% of the receptor is inactivated; "quasi" Tm).

It will be appreciated that it may be desirable to identify further agents that stabilise a GPCR/Gα subunit complex according to the fourth aspect of the invention. Thus, the method also provides a method of identifying one or more agents that increase the stability of a complex according to the fourth aspect of the invention, under denaturing conditions, the method comprising providing a complex according to the fourth aspect of the invention, contacting the complex with a candidate agent, and determining the effect of the candidate agent on the stability of the complex according to the fourth aspect of the invention, under denaturing conditions. The candidate agent may include a nucleotide, a phosphate analogue or a magnesium ion.

An eleventh aspect of the invention provides a method for preparing a mutant GPCR, the method comprising (a) carrying out the method of the tenth aspect of the invention;

(b) identifying the position or positions of the mutated amino acid residue or residues in the mutant GPCR or GPCRs which has been selected for increased stability, and (c) synthesising a mutant GPCR which contains a replacement amino acid at one or more of the positions identified.

The invention provides a mutant GPCR obtainable by the method of the eleventh aspect of the invention.

MEGA domains may also be a valuable tool for fragment library screening using both structural and non-structural methods. Accordingly, a twelfth aspect of the invention provides a method of identifying a binding partner of a GPCR, the method comprising:

a) providing a complex according to the fourth aspect of the invention;

b) providing one or more test compounds;

c) determining whether the or each test compound binds to the complex; and d) isolating one or more test compounds that bind to the complex.

Preferences for the complex according to the fourth aspect of the invention include those described above.

There is strong evidence to suggest that once a ternary G protein-GPCR complex is formed the ligand can be removed from the binding pocket without causing dissociation of the complex: hydroxylamine treatment of the nucleotide-free rhodopsin-transducin complex causes hydrolysis of the Schiff base bond between rhodopsin and retinal, resulting in the release of retinaloxime[14]. Hence, in an embodiment, the complex provided in step (a) does not contain a GPCR ligand. However, it will be appreciated that in other embodiments it may be useful to have the ligand bound, for example for identifying other binding partners than modulate ligand binding.

In one embodiment, the complex may be provided in a whole cell preparation, a cell membrane fragment, solubilised in detergent or it may be incorporated into a lipid monolayer, a lipid bilayer, a bead-linked lipid particle, another solid-supported lipid layer or a proteoliposome.

The inventors recognise that high throughput membrane-complex screening is facilitated by immobilising membranes on beads or on surfaces that can be arrayed or otherwise multiplexed. Typically, membrane complexes are deposited on a surface together with lipid in the form of proteoliposomes. The detergent solubilised form of the complex may be a partly pure or highly pure preparation. Purification, enabled by the improved stability and optimisation of solubilisation conditions, confers the advantage of removal of extraneous "sticky" antigens and lipids and other cell surface material such as carbohydrate to which, for example, phage may stick to.

It will be appreciated that the GPCR and/or mutant Gα subunit of the complex may be engineered to include a molecular tag at the C terminus or N-terminus as is well known in the art. The tag may be any of a FLAG tag, a His tag, a c-Myc tag, a DDDDK tag, an HSV tag, a Halo tag or a biotin tag. Such tags can be used to facilitate phage-based selection protocols in solution and may also be used to confer binding to a solid support.

The increased stability of the mutant Gα subunits and/or mutant GPCRs in a range of detergents and solubilisation buffers and additives lends them particularly well to being immobilised onto solid surfaces. Thus, in one embodiment the complex is immobilised onto a solid support. Various supports are known in the art and include, for example, beads, columns, slides, chips or plates. Immobilisation may be via covalent or non-covalent interaction.

Various formats for screening for binding partners of GPCRs are provided in WO 2009/081136, which is incorporated herein by reference, and any such format may be used.

The test compound may be provided as a biological sample. In particular, the sample could be any suitable sample taken from an individual. For example, the sample may be a fluid sample such as blood, serum, plasma or spinal fluid. Alternatively, the sample could be a tissue or cell extract.

In one embodiment, the one or more test compounds is a polypeptide. For example, the test compound may be a particular type of polypeptide which is known to bind to certain GPCRs or Gα subunits but where the identification of a conformation-specific polypeptide is desired. Alternatively, the polypeptide may be a candidate therapeutic molecule, for example an anticalin (Skerra *J Biotechnol* (2001) 74(4):257-75).

In one embodiment, the one or more test compounds is a peptide.

In one embodiment, the one or more test compounds is an affibody, a peptidomimetic, a nucleic acid, a peptide nucleic acid (PNA) or an aptamer, or a lipid or a carbohydrate.

In one embodiment, the one or more test compounds is a binding protein based on a modular framework, such as ankyrin repeat proteins, armadillo repeat proteins, leucine rich proteins, tetrariopeptide repeat proteins or Designed Ankyrin Repeat Proteins (DARPins) or proteins based on lipocalin or fibronectin domains or Affilin scaffolds based on either human gamma crystalline or human ubiquitin.

In one embodiment, the one or more test compounds is a small molecule, for example a molecule less than 5000 daltons, or the one or more test compounds is a natural product.

In one embodiment, the one or more test compounds is an antibody. For example, the test compound may be an antibody that has been raised against a mutant Gα subunit, a GPCR or a mutant Gα subunit/GPCR complex.

As used herein, the term "antibody" includes but is not limited to polyclonal, monoclonal, chimaeric, single chain, Fab fragments and fragments produced by a Fab expression library. Such fragments include fragments of whole antibodies which retain their binding activity for a target substance, Fv, F(ab') and F(ab')2 fragments, as well as genetically engineering derivatives of antibodies such as single chain antibodies (scFv), fusion proteins, domain antibodies (dAbs) and diabodies. For example, it will be appreciated that recombinant DNA technology may be used to produce further antibodies or chimeric molecules which retain the binding specificity of an original antibody. Such technology may involve fusing the DNA encoding the immunoglobulin variable region, or the complementarity determining regions (CDRs), of an antibody to the constant regions, or constant regions plus framework regions of a different immunoglobulin, as described, for example, in EP-A-184187, GB 2188638A or EP-A-239400. Moreover, a hybridoma or other cell producing an antibody may be subject to genetic mutation or other changes which may or may not alter the binding specificity of antibodies produced. Thus, since antibodies can be modified in a number of ways, the term "antibody" is to be construed as covering any specific binding member or substance having a binding domain with the required specificity. The term therefore includes antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent fused to another polypeptide are therefore included. Furthermore, antibodies and fragments thereof may be human or humanised antibodies, as is well known in the art.

Various procedures known within the art may be used to raise antibodies against mutant Gα subunits, GPCRs or mutant Gα subunit/GPCR complexes, or against fragments or fusions thereof. For example, both in vivo and in vitro immunisation are included.

It is appreciated that in some instances high throughput screening of test compounds is preferred and that the method may be used as a "library screening" method, a term well known to those skilled in the art. Thus, the test compound may be a library of test compounds. For example, the library may be a peptide or protein library produced, for example, by ribosome display or an antibody library prepared either in vivo, ex vivo or in vitro. Methodologies for preparing and screening such libraries are known in the art. Conveniently, the method is used in fragment library screening, for example using biophysical methods or crystal soaking techniques.

The invention includes screening methods to identify drugs or lead compounds of use in treating a disease or condition. It is appreciated that screening assays which are capable of high throughput operation are particularly preferred.

It is appreciated that in the methods described herein, which may be drug screening methods, a term well known to those skilled in the art, the test compound may be a drug-like compound or lead compound for the development of a drug-like compound. Thus in one embodiment, the method further comprises modifying a test compound which has been shown to bind to the complex, and determining whether the modified test compound binds to the complex.

Various methods may be used to determine binding between a mutant Gα subunit/GPCR complex and a test compound including, for example, enzyme linked immunosorbent assays (ELISA), surface plasmon resonance assays, chip-based assays, immunocytofluorescence, yeast two-hybrid technology and phage display. Other methods of detecting binding between a test compound and the complex include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other. Further methods are described in WO 2009/081136, incorporated herein by reference.

The ability to generate high affinity specific binding partners to mutant Gα/GPCR complexes will facilitate the production of therapeutic binding partners. Thus, it will be appreciated that in addition to establishing binding to the complex, it will also be desirable to determine the functional effect of a binding partner on the complex. Accordingly, in an embodiment of the method, the method further comprises determining if the binding partner affects the function of the complex to which it binds and isolating a test compound that affects the function of the complex.

For example, in one embodiment, it is determined whether the binding partner alters the binding of the GPCR in the complex to its ligand. For instance, the binding partner may be a positive or negative allosteric modulator.

In another embodiment, it is determined whether the binding partner modulates activation of a GPCR or mutant Gα subunit. For example, the binding partners may be a GPCR ligand that is a positive or negative allosteric modulator. In this assay, the complex is expressed in a whole cell, for example, in mammalian or insect cells where the complex is allowed to couple to well-known GPCR signal transduction pathways (Eglen R. M. Functional G protein-coupled receptor assays for primary and secondary screening. Comb Chem High Throughput Screen. 2005 June; 8(4):311-8), and signalling through such pathways assessed. Further details of such assays are provided above in relation to the first aspect of the invention.

In one embodiment, the method further comprises
(i) determining whether the or each test compound binds to a different complex according to the fourth aspect of the invention; and
(ii) isolating the or each test compound that does not bind to the different complex according to the fourth aspect of the invention.

In this way, it will be appreciated that the method may be used to identify binding partners that modulate the activity of a specific GPCR-Gα subunit pair, but which do not modulate both the receptor and Gα subunit in other signalling cascades. By different complex, we include the meaning of a complex that contains a different Gα subunit (eg of a different class or isoform) and/or a different GPCR to that comprised within the complex provided in step (a) of the method. For example, the different complex may comprise a Gα subunit of a different class to that of the Gα subunit in the complex of step (a) of the method of the twelfth aspect of the invention and/or a GPCR that is different to the GPCR in the complex of step (a) of the method of the twelfth aspect of the invention.

An example of a specific interface which the binding partner may bind to comprises Arg102(3.50), Ala105(3.53), Ile106(3.54), Arg107(3.55), Pro109, Leu110, Arg 111, Tyr112, Ile200(5.61), Ala203(5.64), Q207(5.67), Leu208 (5.68), Q210(5.70), Lys227(6.29), Ala231(6.33), Leu235 (6.37), Arg291(7.56), Ile 292(loop between H7 and H8), Arg293(H8) and Arg296(H8) of the human adenosine A2a receptor (Ballesteros-Weinstein numbers in parentheses) and His41 (s1.2), Asp215(s2s3.1), Val217(s3.1), Phe376 (h5.8), Cys379(h5.11), Arg380(h5.12), Asp381(h513), Ile383(h5.15), Gln384(h5.16), Arg385(h5.17), His387 (h5.19), Leu388(h5.20), Gln390(h5.22), Tyr391(h5.23), Glu392(h5.24), Leu393(h5.25), Leu394(h5.26) of human Gs. Using the B-W and CGN systems, the corresponding residues in other GPCRs and Gα subunits can be determined.

A thirteenth aspect of the invention provides a method of identifying a binding partner of a Gα subunit, the method comprising:
a) providing a mutant Gα subunit according to the first or second aspects of the invention;
b) providing one or more test compounds;
c) determining whether the or each test compound binds to the mutant Gα subunit; and
d) isolating one or more test compounds that bind to the mutant Gα subunit.

Preferences for the mutant Gα subunit include those mentioned above in relation to the first aspect of the invention, and preferences for the test compound and assay format/steps of the method include those described above in relation to the twelfth aspect of the invention.

A fourteenth aspect of the invention provides an antibody that selectively binds to a mutant Gα subunit according to the first or second aspect of the invention or to the complex according to the fourth aspect of the invention. Also included, are polynucleotides that encode such antibodies.

Examples of antibodies include those described above in relation to the twelfth aspect of the invention. The antibody may be a monoclonal antibody or a polyclonal antibody. The antibody may be an antibody fragment such as a ScFv or any of those described above. Methods of making antibodies are well known in the art. For example, for the production of polyclonal antibodies, various suitable host animals (e.g., rabbit, goat, chicken, mouse or other mammal) may be immunized by one or more injections with the immunogen. The polyclonal antibody molecules directed against the immunogenic protein can be isolated from the mammal (e.g., from the serum or egg yolk) and further purified by well known techniques, such as affinity chromatography using protein A or protein G, which provide primarily the IgG fraction of immune serum. Monoclonal antibodies can be prepared using hybridoma methods, such as those described by Kohler and Milstein, *Nature*, 256:495 (1975).

In a hybridoma method, a mouse, hamster, or other appropriate host animal, is typically immunized with an immunizing agent to elicit lymphocytes that produce or are capable of producing antibodies that will specifically bind to the immunizing agent.

It will be appreciated that antibodies to the complex may help to stabilise the complex under denaturing conditions. Also, antibodies to the complex may have therapeutic value since they are more likely to activate the receptor than antibodies raised to GPCR/ligand complexes alone.

A fifteenth aspect of the invention provides a method of assessing binding between a G protein and a GPCR, the method comprising providing a mutant Gα subunit according to the first or second aspect of the invention, and a GPCR, and assessing binding between the mutant Gα subunit and the GPCR.

Preferences for the mutant Gα subunit include those described above in relation to the first or second aspect of the invention. Any suitable GPCR may be used as described above.

Methods to assess binding between the mutant Gα subunit and GPCR are well known in the art and include those described above, for example methods for assessing protein binding as described in the first and twelfth aspects of the invention.

In an embodiment, the method comprises assessing functional binding or coupling between the mutant Gα subunit and GPCR. Again, suitable methods for doing so are described above.

Conveniently, one or both of the mutant Gα and GPCR are detectably labelled, such as fluorescently labelled. FRET may be used.

In one embodiment, the mutant Gα subunit and the GPCR are provided within a cell, optionally wherein the method is carried out in vivo or in vitro.

A sixteenth aspect of the invention provides a method of assessing the effect of an agent on binding between a G protein and a GPCR, the method comprising providing a mutant Gα subunit according to the first or second aspect of the invention, and assessing the effect of the agent on coupling between the mutant Gα subunit and the GPCR.

Preferences for the assay include those mentioned above in relation to the fifteenth aspect of the invention. As with the fifteenth aspect of the invention, the binding that is assessed may be functional binding or coupling. It will be appreciated that this method may be useful to identify agents that have a positive or negative effect on the interaction or coupling between a Gα subunit and a GPCR. For example, a decrease in the signal generated from the assay would be indicative an agent that inhibits complex formation. Generally, the method will be carried out in the presence and absence of the agent so that the effect of the agent on the interaction can be assessed.

A seventeenth aspect of the invention provides a method for selecting or designing one or more binding partners of a GPCR, a G protein, or a GPCR-G protein complex, the method comprising:

(a) providing a three dimensional structural representation of a mutant Gα subunit according to the first or second aspect of the invention, or a complex according to the four aspect of the invention, (b) using molecular modelling means to select or design one or more binding partners of the GPCR, G protein or GPCR-G protein complex, wherein the three dimensional structural representation of at least part of the mutant Gα subunit or complex is compared with a three-dimensional structural representation of one or more candidate binding partners, and one or more binding partners that are predicted to interact with the GPCR, G protein or GPCR-G protein complex are selected.

By a 'three dimensional structural representation' we include a computer generated representation or a physical representation. Typically, the representation is computer generated. Computer representations can be generated or displayed by commercially available software programs. Examples of software programs include but are not limited to QUANTA (Accelrys.COPYRIGHT.2001, 2002), O (Jones et al., Acta Crystallogr. A47, pp. 110-119 (1991)) and RIBBONS (Carson, J. Appl. Crystallogr., 24, pp. 9589-961 (1991)), which are incorporated herein by reference.

By "binding partner" we mean any molecule that binds to a GPCR, G protein or GPCR-G protein complex. Preferably, the molecule binds selectively to the GPCR, G protein or GPCR-G protein complex. For example, it is preferred if the binding partner has a $K_d$ value (dissociation constant) which is at least five or ten times lower (i.e. higher affinity) than for at least one other GPCR, G protein or GPCR-G protein complex, and preferably more than 100 or 500 times lower The binding partner may be any of a small molecule (eg with a molecule weight less than 5000 daltons, for example less than 4000, 3000, 2000, 1000 or 500 daltons); polypeptide; an anticalin; a peptide; an antibody; a chimeric antibody; a single chain antibody; an aptamer; a darpin; a Fab, $F(ab')_2$, Fv, ScFv or dAb antibody fragment; a small molecule; a natural product; an affibody; a peptidomimetic; a nucleic acid; a peptide nucleic acid molecule; a lipid; a carbohydrate; a protein based on a modular framework including ankyrin repeat proteins, armadillo repeat proteins, leucine rich proteins, tetrariopeptide repeat proteins or Designed Ankyrin Repeat Proteins (DARPins); a protein based on lipocalin or fibronectin domains or Affilin scaffolds based on either human gamma crystalline or human ubiquitin; a G protein; an RGS protein; an arrestin; a GPCR kinase; a receptor tyrosine kinase; a RAMP; a NSF; a GPCR; an NMDA receptor subunit NR1 or NR2a; calcyon; or a fragment or derivative thereof that binds to a GPCR, G protein or GPCR-G protein complex.

Methods for selecting or designing binding partners, and for using molecular modelling, are well known in the art, and are described, for example in WO2008/068534. For instance, molecular modelling techniques that may be employed in accordance with this invention include e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994).

Designing of binding partners can generally be achieved in two ways, either by the step wise assembly of a binding partner or by the de novo synthesis of a binding partner. In addition, other computer-based methods are available to select for binding partners. Thus, it will be appreciated that the method may be used in fragment screening, biophysical methods of screening and screening of DNA-encoded libraries.

An eighteenth aspect of the invention provides a method for the analysis of the interaction of one or more binding partners with a GPCR, a G protein, or a GPCR-G protein complex, the method comprising:

(a) providing a three dimensional structural representation of a mutant Gα subunit according to the first or second aspect of the invention, or a complex according to the fourth aspect of the invention, (b) providing a three dimensional structural representation of one or more binding partners to be fitted to the structure of the mutant Gα subunit or complex, or part of said structure; and (c) fitting the one of more binding partners to said structure.

By "fitting", is meant determining by automatic, or semi-automatic means, interactions between one or more atoms of a candidate binding partner and at least one atom of the GPCR, a G protein, or a GPCR-G protein complex structure of the invention, and calculating the extent to which such interactions are stable. Interactions include attraction and repulsion, brought about by charge, steric, lipophilic, considerations and the like. Charge and steric interactions of this type can be modelled computationally. An example of such computation would be via a force field such as Amber (Cornell et al. A Second Generation Force Field for the Simulation of Proteins, Nucleic Acids, and Organic Molecules, Journal of the American Chemical Society, (1995), 117(19), 5179-97) which would assign partial charges to atoms on the protein and binding partner and evaluate the electrostatic interaction energy between a protein and binding partner atom using the Coulomb potential. The Amber force field would also assign van der Waals energy terms to assess the attractive and repulsive steric interactions between two atoms. Lipophilic interactions can be modeled using a variety of means. Other methods of assessing the hydrophobic contributions to ligand binding are available and these would be known to one skilled in the art. Other methods of assessing interactions are available and would be known to one skilled in the art of designing molecules as described above. Various computer-based methods for fitting are known in the art and are described in WO 2008/068534.

In an embodiment of the seventeenth or eighteenth aspects of the invention, the three dimensional structural representation of a mutant Gα subunit according to the first or second aspect of the invention, or a complex according to the fourth aspect of the invention, is obtained by providing a mutant Gα subunit according to the first or second aspect of the invention, or a complex according to the fourth aspect of the invention, and determining the three-dimensional structure of the mutant Gα subunit or complex.

In an embodiment of the seventeenth or eighteenth aspects of the invention, the method may further comprise modifying the structural representation of the one or more binding partners so as to increase or decrease their interaction with a GPCR, a G protein, or a GPCR-G protein complex.

A nineteenth aspect of the invention provides a pharmaceutical composition comprising a mutant Gα subunit according to the first or second aspect of the invention, a complex according to the fourth aspect of the invention, or an antibody according to the fourteenth aspect of the invention.

The invention also provides a mutant Gα subunit according to the first or second aspect of the invention, a complex according to the fourth aspect of the invention, or an antibody according to the fourteenth aspect of the invention, for use in medicine.

It will be appreciated that any of the mutant Gα subunit according to the first or second aspect of the invention, a complex according to the fourth aspect of the invention, or an antibody according to the fourteenth aspect of the invention, may have therapeutic value in combating a disease or condition associated with aberrant G-protein signalling (eg upregulated G protein signalling). By a disease or condition associated aberrant G-protein signalling (eg upregulated G protein signalling), we include the meaning of any biological or medical condition or disorder in which at least part of the pathology is mediated by aberrant G-protein signalling (eg upregulated G protein signalling). The condition may be caused by the presence of the unwanted cells or else the presence of the unwanted cells may be an effect of the condition. Such diseases are well known in the art and can be identified by consulting the scientific literature. An example of such a condition is cancer. By combating a disease or condition we include the meaning of reducing or alleviating symptoms in a patient (i.e. palliative use), preventing symptoms from worsening or progressing, treating the disorder (e.g. by inhibition or elimination of the causative agent), or prevention of the condition or disorder in a subject who is free therefrom.

Accordingly, the invention also provides a mutant Gα subunit according to the first or second aspect of the invention, a complex according to the fourth aspect of the invention, or an antibody according to the fourteenth aspect of the invention, for use in combating a disease or condition associated with aberrant G-protein signalling (eg upregulated G protein signalling). Preferably, the disease or condition is cancer.

In relation to the complex according to the fourth aspect of the invention, it will be appreciated that this may potentially be used as a high affinity decoy receptor to mop up excess ligand, and so it may be useful to downregulate an inappropriately high G-protein response.

Whilst it is possible for the mutant Gα subunit, complex or antibody of the invention to be administered alone, it is preferable to present it as a pharmaceutical formulation, together with one or more acceptable carriers. The carrier(s) must be "acceptable" in the sense of being compatible with the therapeutic agent and not deleterious to the recipients thereof. Typically, the carriers will be water or saline which will be sterile and pyrogen free.

Where appropriate, the formulations may conveniently be presented in unit dosage form and may be prepared by any of the methods well known in the art of pharmacy. Such methods include the step of bringing into association the active ingredient (agent for treating or preventing a condition characterised by unwanted cells) with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The amount of the mutant Gα subunit, complex or antibody of the invention which is administered to the individual is an amount effective to combat the particular individual's condition. The amount may be determined by the physician.

Preferably, in the context of any medical use described herein, the subject to be treated is a human. Alternatively, the subject may be an animal, for example a domesticated animal (for example a dog or cat), laboratory animal (for example laboratory rodent, for example mouse, rat or rabbit) or an animal important in agriculture (i.e. livestock), for example horses, cattle, sheep or goats.

A twentieth aspect of the invention provides a kit of parts comprising (i) a mutant Gα subunit according to the first or second aspects of the invention and (ii) a GPCR or a portion thereof capable of binding to a mutant Gα subunit according to the first or second aspect of the invention. It will be appreciated that the invention also includes a kit of parts comprising (i) a polynucleotide encoding a mutant Gα subunit according to the first or second aspects of the invention and (ii) a polynucleotide encoding a GPCR or a portion thereof capable of binding to a mutant Gα subunit according to the first or second aspect of the invention.

Preferences for the mutant Gα subunit, GPCR and polynucleotides encoding them, include those outlined above in relation to the first, second, third and fourth aspects of the invention.

Conveniently, one or both of (i) and (ii) in the kit of parts are detectably labelled.

In an embodiment, the kit further comprises a GPCR ligand, suitable examples of which include any of those mentioned above. For example, the GPCR ligand may be any of a small molecule, a protein, a peptide, a protein scaffold, a nucleic acid, an ion, a carbohydrate, or an antibody.

In a further embodiment, the kit of parts further comprise a G protein β and/or G protein γ subunit. Again, suitable examples of G protein βγ subunits are described above. For example, the kit may comprise any of the five β subunits and/or any of the 12γ subunits. In a specific example, the kit may comprise β1 and/or γ2.

In yet a further embodiment, the kit of parts further comprises a nucleotide, optionally wherein the nucleotide is a guanine nucleotide such as GDP or GTP, or optionally wherein the nucleotide is a xanthine nucleotide. Other possible nucleotides include those mentioned above in relation to other aspects of the invention (eg GTPγS or GppNp)

The invention will now be described by reference to the following figures and examples.

FIG. 1. Alignment of the mini-Gs amino acid sequence (SEQ ID NO:91) with the human G alpha sequence SEQ ID NO:92). Amino acid deletions and substitutions highlighted in grey were critical for the development of a minimal GTPase domain that could function in the absence of beta and gamma subunits. The N-terminal deletion was required for crystallisation as was the deletion of the helical domain. For clarity, all numbering uses the numbers for the complete human GNASL sequence (1-394), although the mini-Gs contains only 229 amino acid residues.

FIG. 2. Saturation binding data for $β_1AR$ constructs. (a) The dissociation constant ($K_d$) of $^3H$-dihydroalprenolot ($^3H$-DHA) binding to $β_1AR$-WT was 5.0±0.6 nM. (b) The Kd of $^3H$-DHA binding to $β_1AR$-84 was 20±3 nM. Data represent mean±SEM of three independent experiments. Curves shown are from a representative experiment performed in duplicate.

Figure 3:
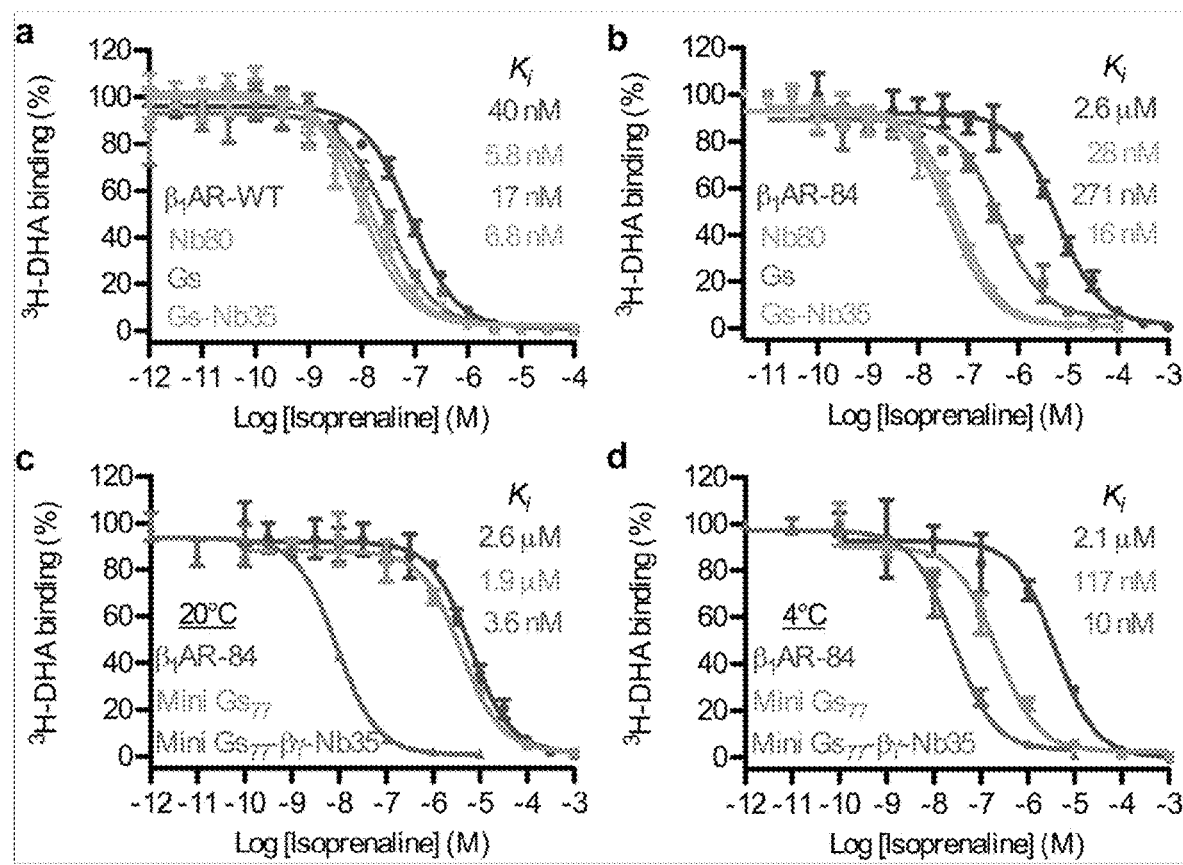

FIG. 3. Measuring G protein coupling to membrane-embedded $β_1AR$ using a competitive binding assay.

(a) For clarity, curves representing the binding reactions are described in order from the left hand side of the graph to the right hand side of the graph (Ki for isoprenaline binding is shown in parentheses, with number of independent experiments (n) also indicated): (i) $β_1AR$-WT+Nb80 (Ki 5.8±0.8 nM, n=2); (ii) $β_1AR$-WT+Gs-Nb35 (Ki 6.8±0.6 nM, n=2); (iii) $β_1AR$-WT+Gs (Ki 17±2 nM, n=2); (iv) $β_1AR$-WT (40±0 nM, n=2).

(b) For clarity, curves representing the binding reactions are described in order from the left hand side of the graph to the right hand side of the graph (Ki for isoprenaline binding is shown in parentheses, with number of independent experiments (n) also indicated): (i) $β_1AR$-84+Gs-Nb35 (Ki 16±4 nM, n=3); (ii) $β_1AR$-84+Nb80 (Ki 28±1 nM, n=2); (iii) $β_1AR$-84+Gs (Ki 271±54 nM, n=2); (iv) $β_1AR$-84 (2.6±0.3 μM, n=2).

(c) Experiments performed at 20° C. For clarity, curves representing the binding reactions are described in order from the left hand side of the graph to the right hand side of the graph (Ki for isoprenaline binding is shown in parentheses, with number of independent experiments (n) also indicated): (i) $β_1AR$-84+Mini $Gs_{77}$-βγ-Nb35 (Ki 3.6±0.8 nM, n=2); (ii) $β_1AR$-84+Mini $Gs_{77}$ (Ki 1.9±0.2 μM, n=3); (iii) $β_1AR$-84 (Ki 2.6±0.3 μM, n=15).

(d) Experiments performed at 4° C. For clarity, curves representing the binding reactions are described in order from the left hand side of the graph to the right hand side of the graph (Ki for isoprenaline binding is shown in parentheses, with number of independent experiments (n) also indicated): (i) $β_1AR$-84+Mini $Gs_{77}$-βγ-Nb35 (Ki 10 nM, n=2); (ii) $β_1AR$-84+Mini $Gs_{77}$ (Ki 117 nM, n=2); (iii) $β_1AR$-84 (Ki 2.1±0.2 μM, n=12).

Figure 4:
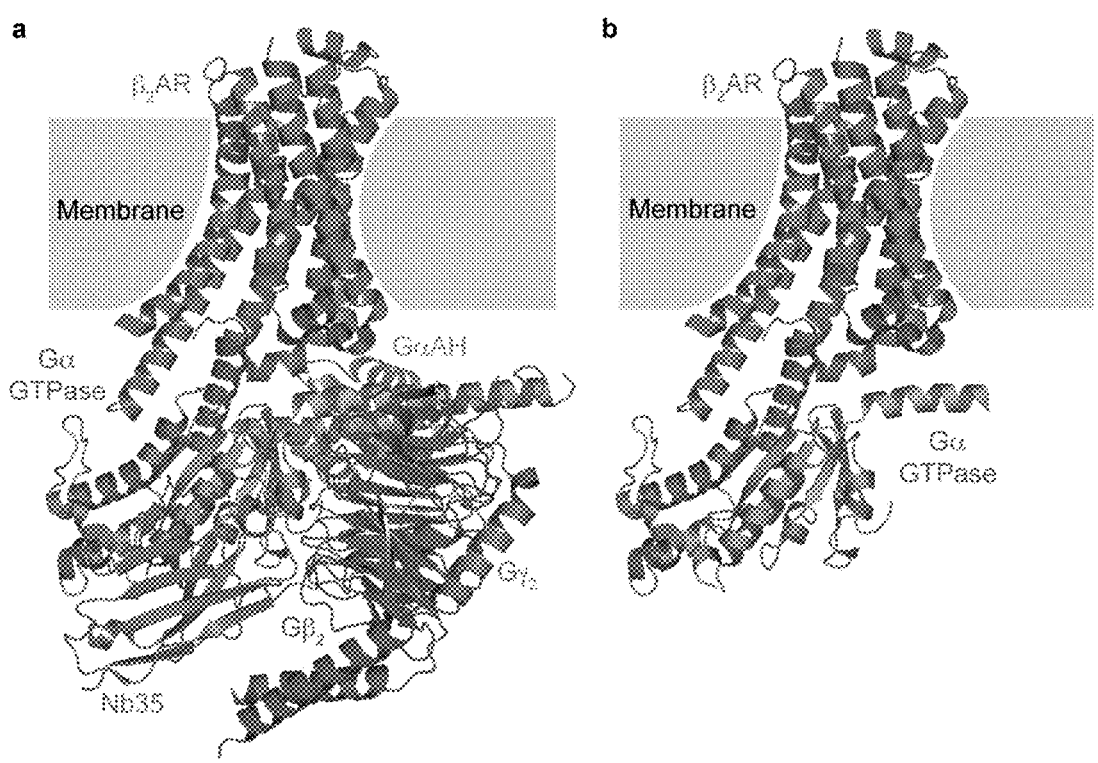

FIG. 4. Crystal structure of the $β_2AR$-WT-Gs complex[10]. (a) Heterotrimeric Gs is composed of α, β and γ subunits and is stabilised in the GPCR-bound conformation by Nb35. (b) Only the 25 KDa GαGTPase domain from Gs forms significant interactions with $β_1AR$-WT.

Figure 5:
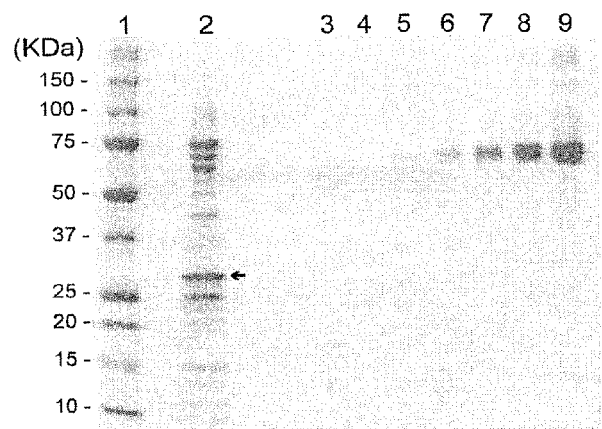

FIG. 5. Sodium dodecyl sulphate-polyacrylamide gel electrophoresis (SDS-PAGE) analysis of mini $Gs_{77}$ purification. (1) molecular weight marker, (2) mini $Gs_{77}$, (3) 25 ng BSA, (4) 50 ng BSA, (5) 100 ng BSA, (6) 250 ng BSA, (7) 500 ng BSA, (8) 1 μg BSA, (9) 2.5 μg BSA. Mini $Gs_{77}$ (indicate by the arrow) could be partially purified with a yield of approximately 200 μg per litre of *E. coli* culture, and purity of approximately 10-20 percent.

Figure 6:
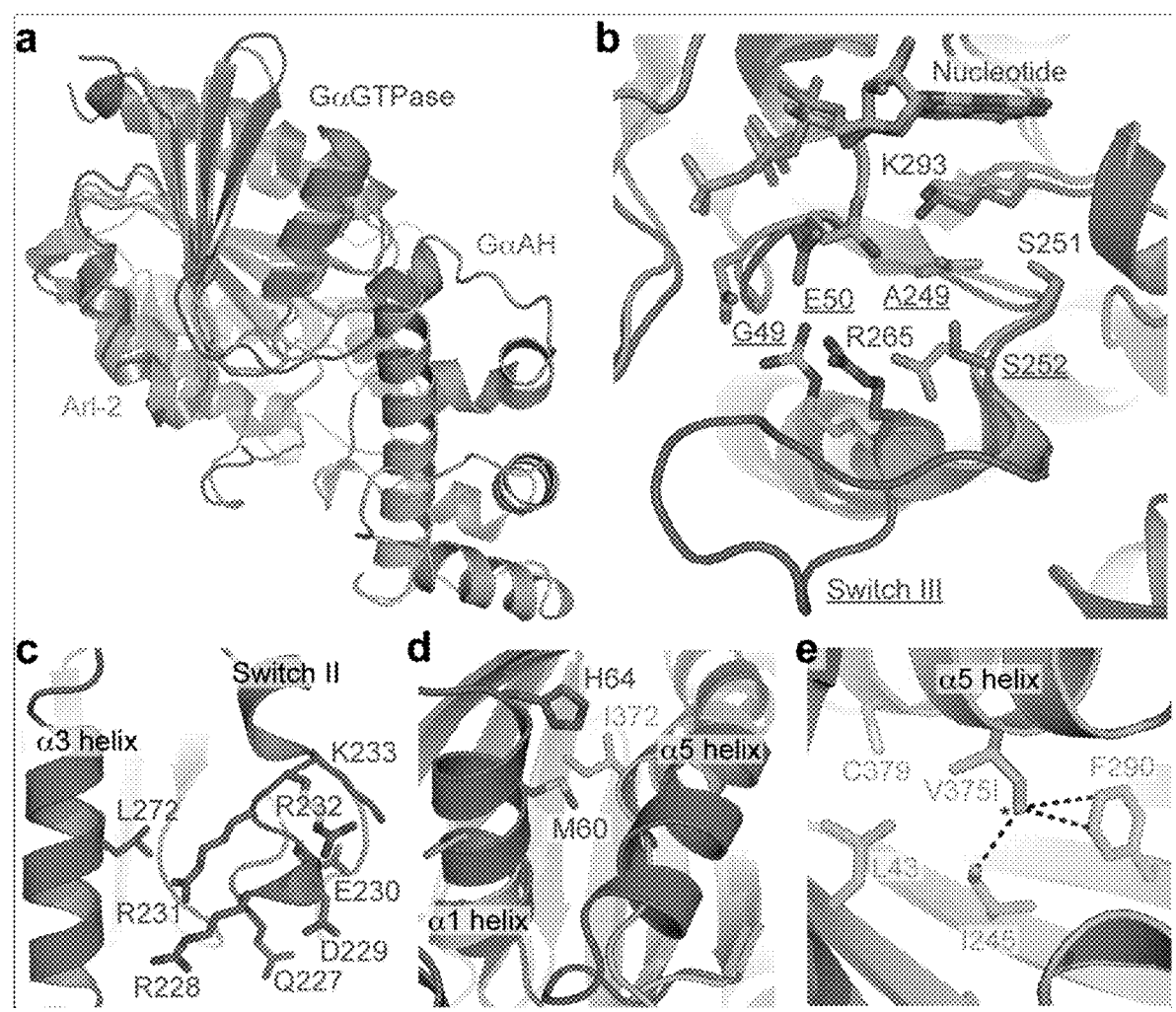

FIG. 6. Design of mutations to stabilise mini Gs. (a) Structural alignment of Gαs[81] (dark grey) and Arl-2[98] (light grey). The Gαs GTPase domain aligns to Arl-2 with an RMSD of 1.9 Å, despite sharing sequence identity of only 25 percent (determined using the Dali server[19]). (b) Alignment between the nucleotide-binding pocket of Gαs (dark grey) and Arl-2 (light grey). Mini Gs residues that were mutated to match the corresponding residue in Arl-2 (G49D, E50N, A249D, and S252D) are shown as sticks and underlined. Residues with which the mutations potentially interact are shown as sticks. (c) Mutation of Leu-272, which is located within the α3 helix, to aspartic acid allows potential interactions with a cluster of charged and polar residues (227-233) in the N-terminal region of switch II. (d) Alignment of Gαs in its GTP-bound (dark grey) and GPCR-bound (light grey) conformations. In the GPCR-bound conformation Ile-372 (α5 helix) sterically clashes with Met-60 and His-64 (α1 helix), preventing close packing of the α1 helix against the core of the GαGTPase domain. (e) The V375I mutation (modelled using the mutate function of PyMol) was designed to increase hydrophobic contacts between the core of the GαGTPase domain and the α5 helix in its GPCR-bound conformation. Residues that interact with Val-375 are shown as sticks, additional contacts (less than 4.2 Å) that are predicted to be formed by the δ-carbon (*) of the isoleucine mutation are displayed as dashed lines. Figures were prepared using PyMOL (The PyMOL Molecular Graphics System, Version 1.7.4 Schrödinger, LLC).

Figure 7:
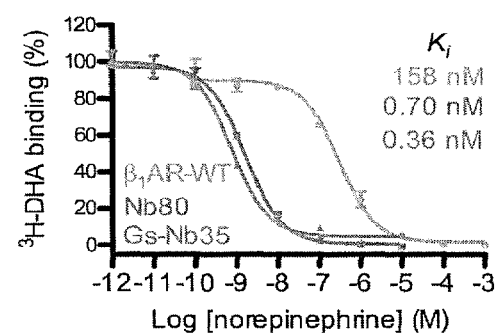

FIG. 7. $\beta_1$AR-WT competitive binding assay using the agonist norepinephrine. The assay was performed under identical buffer conditions used for the thermostability assay. For clarity, curves representing the binding reactions are described in order from the left hand side of the graph to the right hand side of the graph (Ki for isoprenaline binding is shown in parentheses, with number of independent experiments (n) also indicated): (i) $\beta_1$AR-WT+Gs-Nb35 (Ki 0.36±0.02 nM, n=2); (ii) $\beta_1$AR-WT+Nb80 (Ki 0.70±0.11 nM, n=2); (iii) $\beta_1$AR-WT (Ki 158±6 nM, n=2).

FIG. 8. Mini $Gs_{393}$ amino acid (SEQ ID NO: 34) and nucleic acid (SEQ ID NO:158) sequences. The histidine tag (HHHHHH (SEQ ID NO:167) encoded by CACCACCAT-CATCACCAT (SEQ ID NO:168)) is highlighted in dark grey, the TEV protease cleavage site is highlighted in light grey (ENLYFQG (SEQ ID NO:169) encoded by GAAAATCTTTATTTCCAGGGT (SEQ ID NO:170)), and the linker used to replace the GαAH domain is highlighted in grey (GGSGGSGG (SEQ ID NO:93) encoded by GGTGGGAGTGGCGGGAGCGGAGGT (SEQ ID NO:171)). Mutations are shown in bold type and underlined. This construct was cloned into the pET15b vector using NcoI (CCATGG) and XhoI (CTCGAG) restriction sites for $E.$ $coli$ expression. Stop codons are also highlighted (TAATAG).

Figure 9:
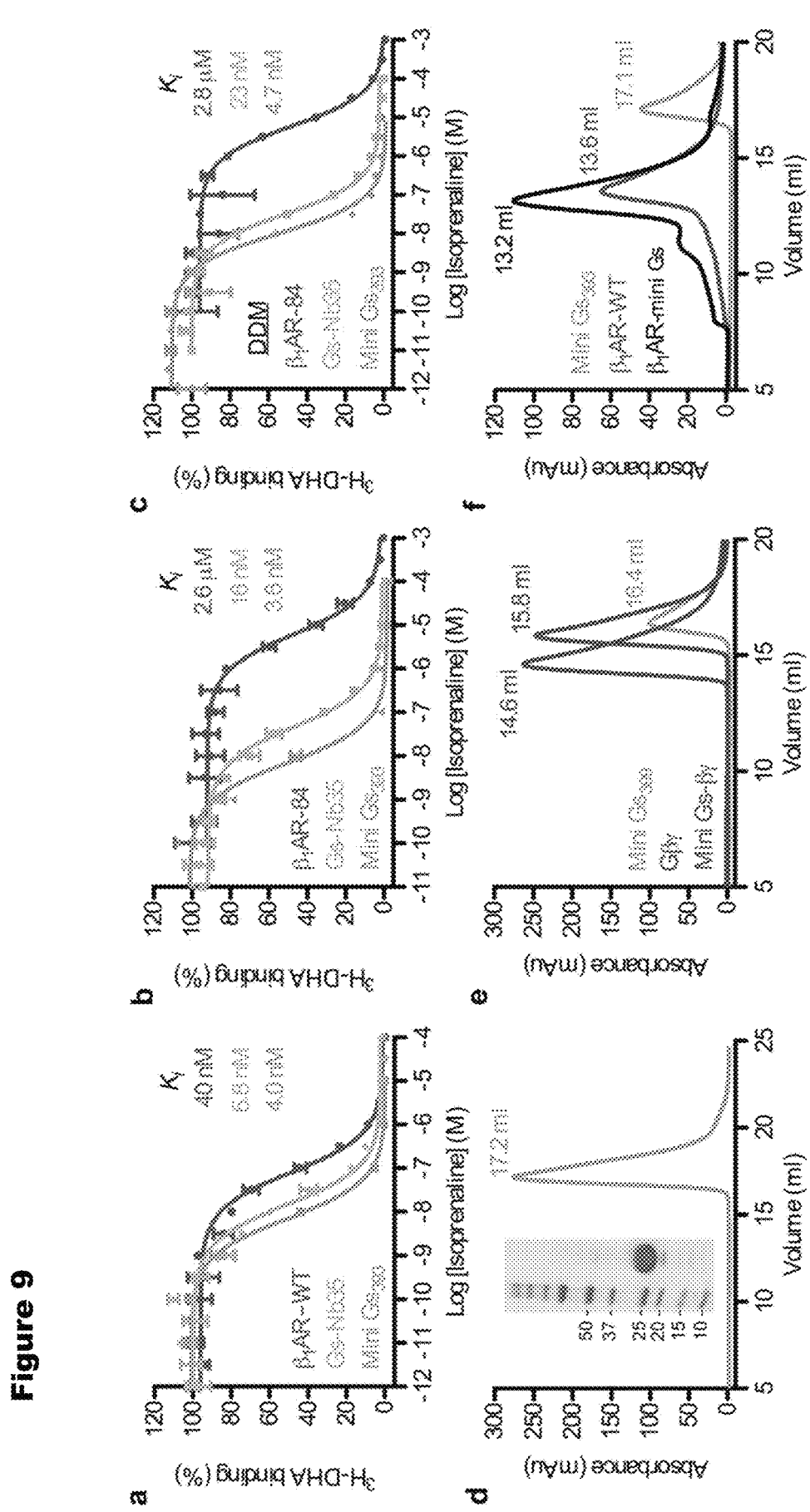

FIG. 9. Validation of mini Gs: $\beta_1$AR pharmacology and mini Gs complexes. (a-c) Measuring G protein binding to $\beta_1$AR using a competitive binding assay. (a) Receptor in membranes. For clarity, curves representing the binding reactions are described in order from the left hand side of the graph to the right hand side of the graph (Ki for isoprenaline binding is shown in parentheses, with number of independent experiments (n) also indicated): (i) $\beta_1$AR-WT+mini $Gs_{393}$ (Ki 4.1±1.1 nM, n=2); (ii) $\beta_1$AR-WT+Gs-Nb35 (Ki 6.8±0.6 nM, n=2); (iii) $\beta_1$AR-WT (Ki 40±0 nM, n=2).

(b) Receptor in membranes. For clarity, curves representing the binding reactions are described in order from the left hand side of the graph to the right hand side of the graph (Ki for isoprenaline binding is shown in parentheses, with number of independent experiments (n) also indicated): (i) $\beta_1$AR-84+mini $Gs_{393}$ (Ki 3.6±0.0 nM, n=2); (ii) $\beta_1$AR-84+Gs-Nb35 (Ki 16±4 nM, n=2); (iii) $\beta_1$AR-84 (Ki 2.6±0.3 μM, n=15).

(c) Receptor solubilised in DDM. For clarity, curves representing the binding reactions are described in order from the left hand side of the graph to the right hand side of the graph (Ki for isoprenaline binding is shown in parentheses, with number of independent experiments (n) also indicated): (i) $\beta_1$AR-84+mini $Gs_{393}$ (Ki 4.7±0.4 nM, n=2); (ii) $\beta_1$AR-84+Gs-Nb35 (Ki 23±7 nM, n=2); (iii) $\beta_1$AR-84 (Ki 2.8±0.2 μM, n=2).

(d-f) Analytical gel filtration analysis of mini Gs complexes. (d) Mini $Gs_{393}$ was purified with a yield of 100 mg per litre $E.$ $coli$ culture (inset), and resolved as a single peak with a retention volume of 17.2 ml by gel filtration. (e) Mini $Gs_{399}$, a construct in which N-terminal residues 6-25 were replaced and the L272D mutation reversed retained its ability to bind $G\beta_1\gamma_2$. An equimolar mixture of mini $Gs_{399}$ and $G\beta_1\gamma_2$ resolved as a single peak with a retention volume of 14.6 ml, compared with retention volumes of 15.8 ml or 16.4 ml for $G\beta_1\gamma_2$ or mini $Gs_{399}$, respectively. (f) Mini $Gs_{393}$ was able to bind purified $\beta_1$AR-WT in LMNG detergent. An equimolar mixture of mini $Gs_{393}$ and $\beta_1$AR-WT resolved as a predominant peak with a retention volume of 13.2 ml, compared with retention volumes of 13.6 ml or 17.1 ml for $\beta_1$AR-WT or mini $Gs_{393}$, respectively.

Figure 10:
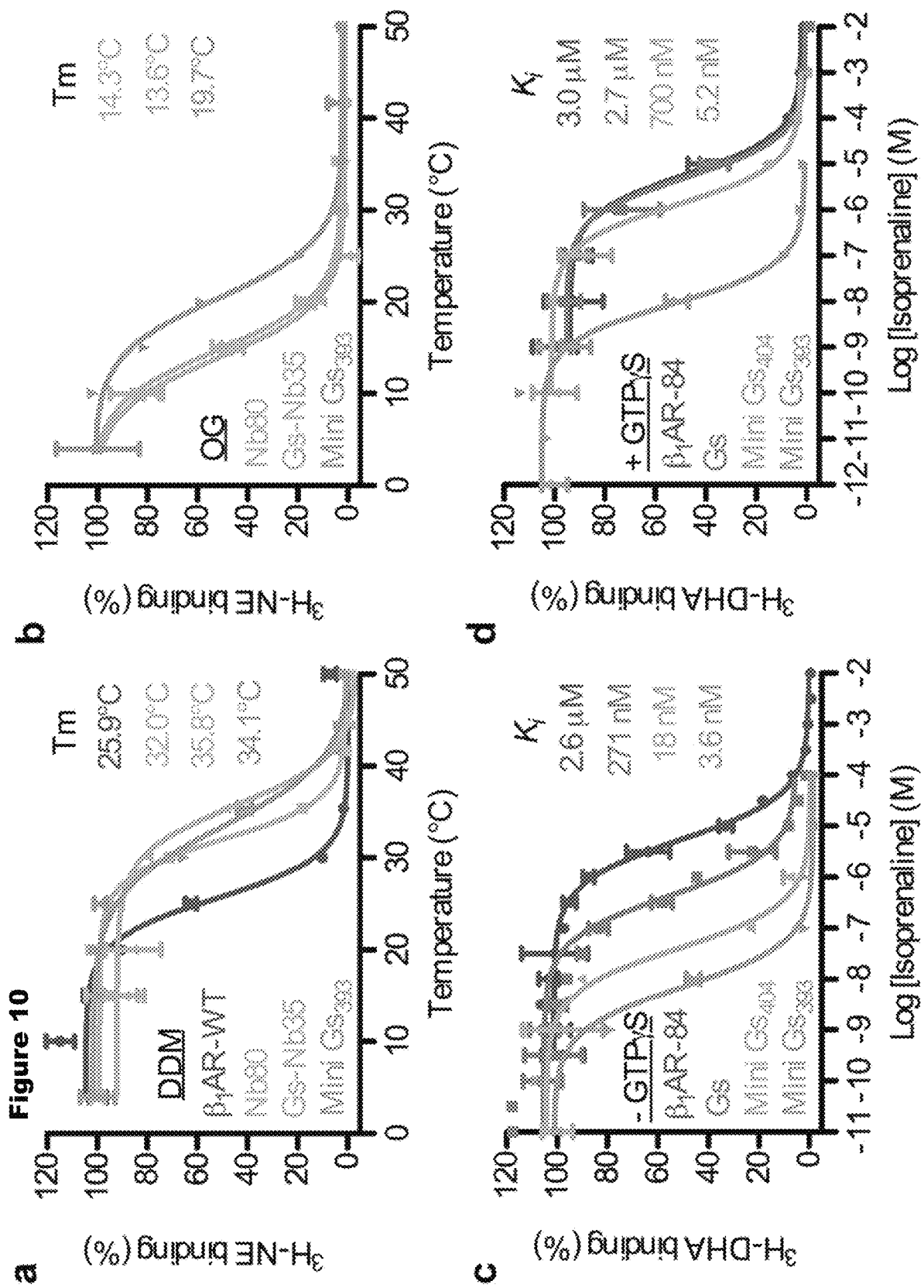

FIG. 10. Validation of mini Gs: thermostability and GTP responsiveness (a-b) Thermostability of $\beta_1$AR-WT complexes. (a) Thermostability in dodecylmaltoside. For clarity, thermostability curves are described in order from the left hand side of the graph to the right hand side of the graph (apparent Tm is shown in parentheses, with number of independent experiments (n) also indicated): (i) $\beta_1$AR-WT (Tm 25.9±0.0° C., n=3); (ii) $\beta_1$AR-WT+Nb80 (Tm 32.0±0.0° C., n=3); (iii) $\beta_1$AR-WT+mini $Gs_{393}$ (Tm 34.1±0.5° C., n=3); (iv) $\beta_1$AR-WT+Gs-Nb35 (Tm 35.8±0.1° C., n=3).

(b) Thermostability in octylglucoside; uncoupled $\beta_1$AR-WT did not survive solubilisation in OG detergent. For clarity, thermostability curves are described in order from the left hand side of the graph to the right hand side of the graph (apparent Tm is shown in parentheses, with number of independent experiments (n) also indicated): (i) $\beta_1$AR-WT+Gs-Nb35 (Tm 13.6±0.2° C., n=3); (ii) $\beta_1$AR-WT+Nb80 (Tm 14.3±0.2° C., n=3); (iii) $\beta_1$AR-WT+mini $Gs_{393}$ (Tm 19.7±0.5° C., n=3).

(c-d) GTP-mediated dissociation of $\beta_1$AR-84 complexes, measured by competitive binding assay in membranes. Mini $Gs_{404}$, is an identical construct to mini $Gs_{393}$, except the I372A and V375I mutations were reversed.

(c) No GTPγS present in the assay. For clarity, curves representing the binding reactions are described in order from the left hand side of the graph to the right hand side of the graph (Ki for isoprenaline binding is shown in parentheses, with number of independent experiments (n) also indicated): (i) $\beta_1$AR-84+mini $Gs_{393}$ (Ki 3.6±0.0 nM, n=3); (ii) $\beta_1$AR-84+mini $Gs_{404}$ (Ki 18±2 nM, n=2); (iii) $\beta_1$AR-84+Gs (Ki 271±54 nM, n=2); (iv) $\beta_1$AR-84 (Ki 2.6±0.3 μM; n=15).

(d) In the presence of 0.25 mM GTPγS in the assay. For clarity, curves representing the binding reactions are described in order from the left hand side of the graph to the right hand side of the graph (Ki for isoprenaline binding is shown in parentheses, with number of independent experiments (n) also indicated): (i) $\beta_1$AR-84+mini $Gs_{393}$ (Ki 5.2±0.7 nM, n=2); (ii) $\beta_1$AR-84+mini $Gs_{404}$ (Ki 700±60 nM, n=2); (iii) $\beta_1$AR-84+Gs (Ki 2.7±0.1 μM, n=2); (iv) $\beta_1$AR-84 (Ki 3.0±0.1 μM; n=2).

There was no statistical difference in the isoprenaline affinity of the $\beta_1$AR-WT-mini $Gs_{393}$ in the presence or absence of GTPγS. Curves shown are from a representative experiment performed in duplicate.

Figure 11:
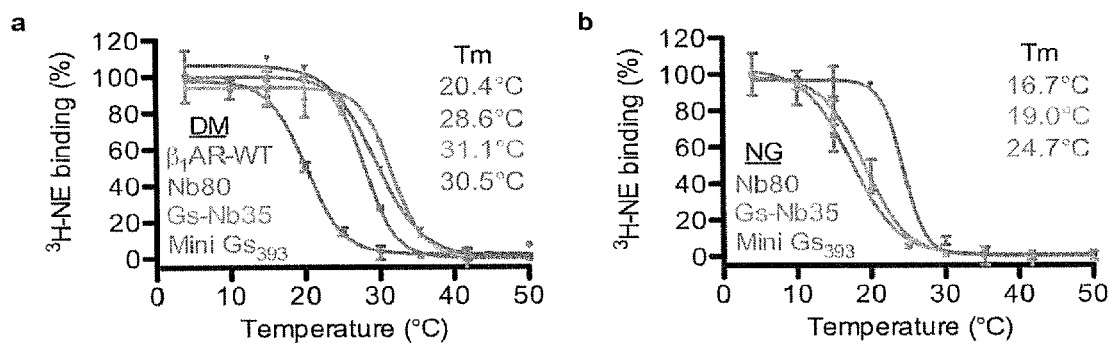

FIG. 11. Thermostability (apparent Tm) of $\beta_1$AR-WT complexes in DM or NG detergents. (a) Thermostability in decylmaltoside. For clarity, thermostability curves are described in order from the left hand side of the graph to the right hand side of the graph (apparent Tm is shown in parentheses, with number of independent experiments (n) also indicated): (i) $\beta_1$AR-WT (Tm 20.4±0.4° C., n=3); (ii) $\beta_1$AR-WT+Nb80 (Tm 28.6±0.3° C., n=3); (iii) $\beta_1$AR-WT+mini $Gs_{393}$ (Tm 30.5±0.4° C., n=3); (iv) $\beta_1$AR-WT+Gs-Nb35 (Tm 31.1±0.4° C., n=3).

(b) Thermostability in nonylglucoside; uncoupled β₁AR-WT did not survive solubilisation in NG detergent. For clarity, thermostability curves are described in order from the left hand side of the graph to the right hand side of the graph (apparent Tm is shown in parentheses, with number of independent experiments (n) also indicated): (i) β₁AR-WT+Nb80 (Tm 16.7±0.7° C., n=2); (ii) β₁AR-WT+Gs-Nb35 (Tm 19.0±0.2° C., n=2); (iii) β₁AR-WT+mini Gs₃₉₃ (Tm 24.7±0.4° C., n=2). Data represent mean±SEM of the number of independent experiments (n) indicated in the legend. Curves shown are from a representative experiment performed in duplicate.

Figure 12:
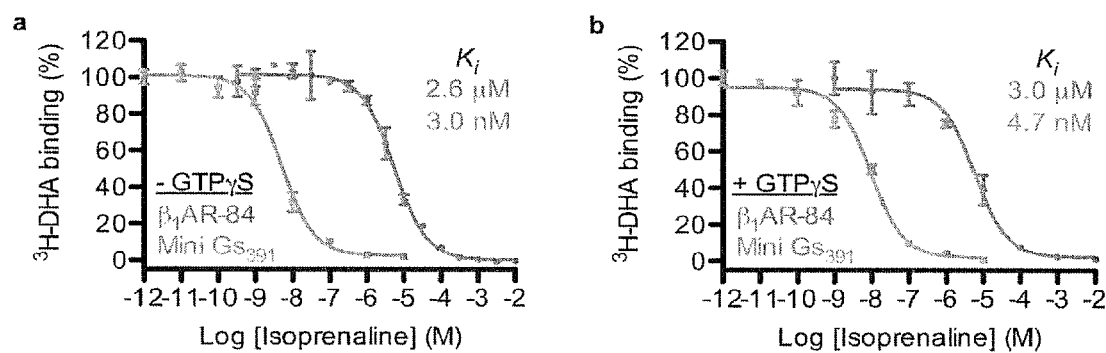

FIG. 12. GTP-mediated dissociation of the β₁AR-84-mini Gs₃₉₁ complex in the membrane, measured by competitive binding assay. Mini Gs₃₉₁ is an identical construct to mini Gs₃₉₃, except the V375I mutation was reversed.

(a) Absence of GTPγS. For clarity, curves representing the binding reactions are described in order from the left hand side of the graph to the right hand side of the graph (Ki for isoprenaline binding is shown in parentheses, with number of independent experiments (n) also indicated): (i) β₁AR-84+mini Gs₃₉₁(Ki 3.0±0.4 nM, n=2); (ii) β₁AR-84 (Ki 2.6±0.3 μM, n=15).

(b) In the presence of GTPγS (0.25 mM). For clarity, curves representing the binding reactions are described in order from the left hand side of the graph to the right hand side of the graph (Ki for isoprenaline binding is shown in parentheses, with number of independent experiments (n) also indicated): (i) β₁AR-84+mini Gs₃₉₁ (Ki 4.7±0.1 nM, n=2); (ii) β₁AR-84 (Ki 3.0±0.1 μM, n=2).

There was no statistical difference in the isoprenaline affinity of the β₁AR-WT-mini Gs₃₉₁ in the presence or absence of GTPγS. Curves shown are from a representative experiment performed in duplicate.

Figure 13:
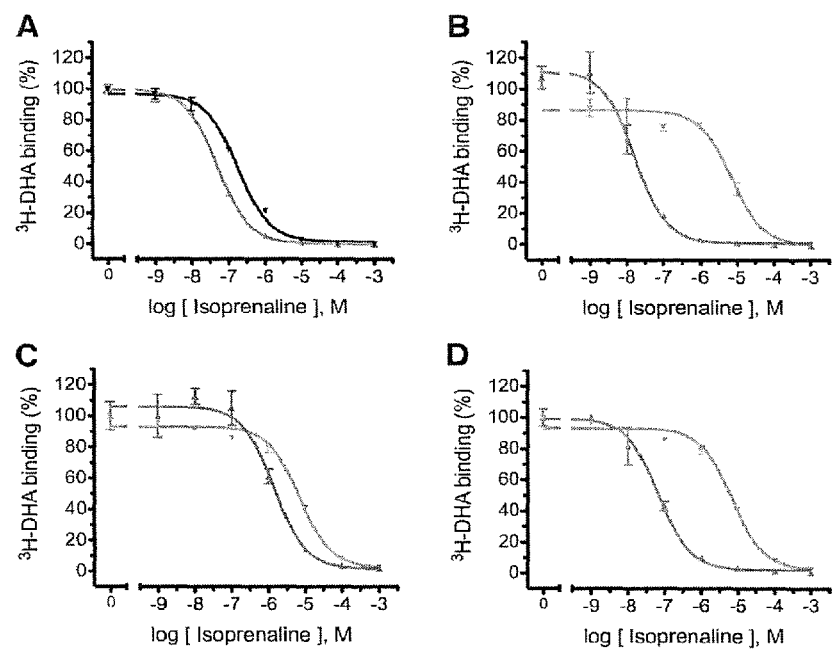

FIG. 13. β₁AR competitive binding curves in the presence of Nb80 or Gs. The affinity (IC50) of isoprenaline binding to different β₁AR constructs was measured in the presence of Nb80 and Gs. (A) A near wild type β₁AR construct (β6) displayed a high isoprenaline affinity (180 nM) in the absence of an intracellular binding partner (right hand curve). In the presence of Nb80 (left hand curve) the isoprenaline affinity only increased to 51 nM. (B) A minimally thermostabilised receptor construct (β84) displayed a lower isoprenaline affinity (7.1 μM) in the absence of an intracellular binding partner (right hand curve). In the presence of Nb80 (left hand curve) the isoprenaline affinity shifted dramatically to 16 nM. (C) In the presence of non-lipidated Gs the isoprenaline affinity of β84 only increased from 6.9 μM (right hand curve) to 1.4 μM (left hand curve). (D) In the presence of non-lipidated Gs and Nb35 the isoprenaline affinity of β84 shifted dramatically from 6.9 μM (right hand curve) to 68 nM (left hand curve). Data shown are from a single representative experiment, and error bars represent the standard error between duplicate measurements.

Figure 14:
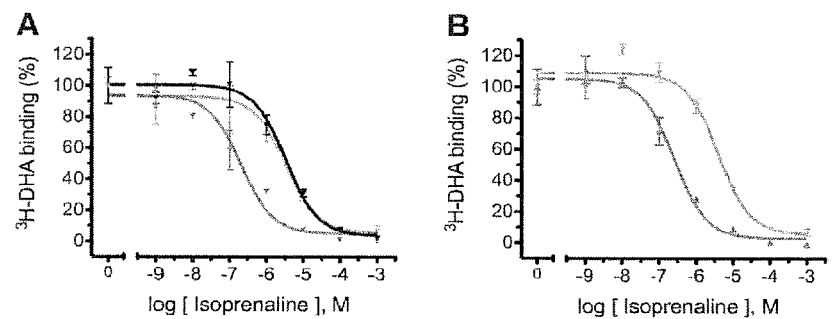

FIG. 14. β₁AR competitive binding curves in the presence of the GTPase domain. The affinity (IC50) of isoprenaline binding to the β1AR was measured in the presence of the Gαs GTPase domain. (A), At 20° C. the isoprenaline affinity of β84 (middle curve) was 3.3 μM, and did not increase (3.4 μM) in the presence of the GTPase domain (right hand upper curve). However, a combination of the GTPase domain, βγ-dimer and Nb35 induced a shift in isoprenaline affinity to 206 nM (left hand curve). (B), At 4° C. the isoprenaline affinity of β84 (right hand curve) was 3.9 μM, in presence of the GTPase domain (green) the affinity increased to 253 nM (left hand curve). Data shown are from a single representative experiment, and error bars represent the standard error between duplicate measurements.

Figure 15:
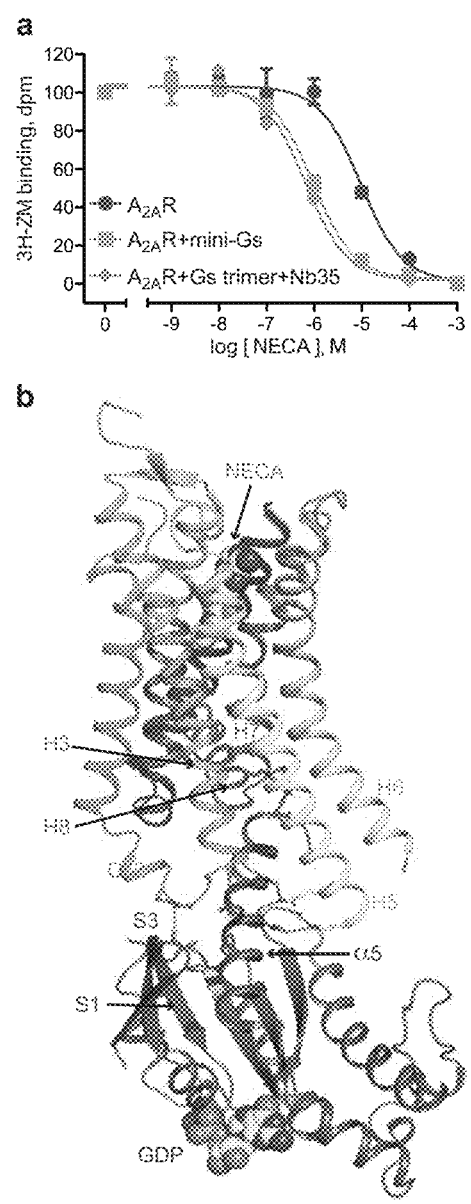

FIG. 15. Ligand binding and overall structure of mini-Gs-bound A₂ₐR. a, Mini-Gₛ increases the affinity of agonist binding to A₂ₐR similar to that observed by a heterotrimeric G protein. Competition binding curves were performed by measuring the displacement of the inverse agonist ³H-ZM241385 with increasing concentrations of the agonist NECA in triplicate (Kᵢ values in parentheses, see FIG. 16 for full data). For clarity, curves are described from the left hand side of the graph to the right hand side of the graph: (i) A₂ₐR and heterotrimeric G protein with nanobody Nb35 (Kᵢ 340±70 nM); (ii) A₂ₐR and mini-Gₛ (Kᵢ 430±80 nM); (iii), A₂ₐR (Kᵢ 4.6±0.3 μM). G proteins were all added to membranes containing A₂ₐR to give a final concentration of 25 μM and the final concentration of NaCl was 100 mM. b, The structure of A₂ₐR is depicted as a cartoon in light grey with mini-Gₛ in dark grey. The agonist NECA bound to A₂ₐR and GDP bound to mini-Gs are depicted as space-filling models. Relevant secondary structural features are labelled.

Figure 16:
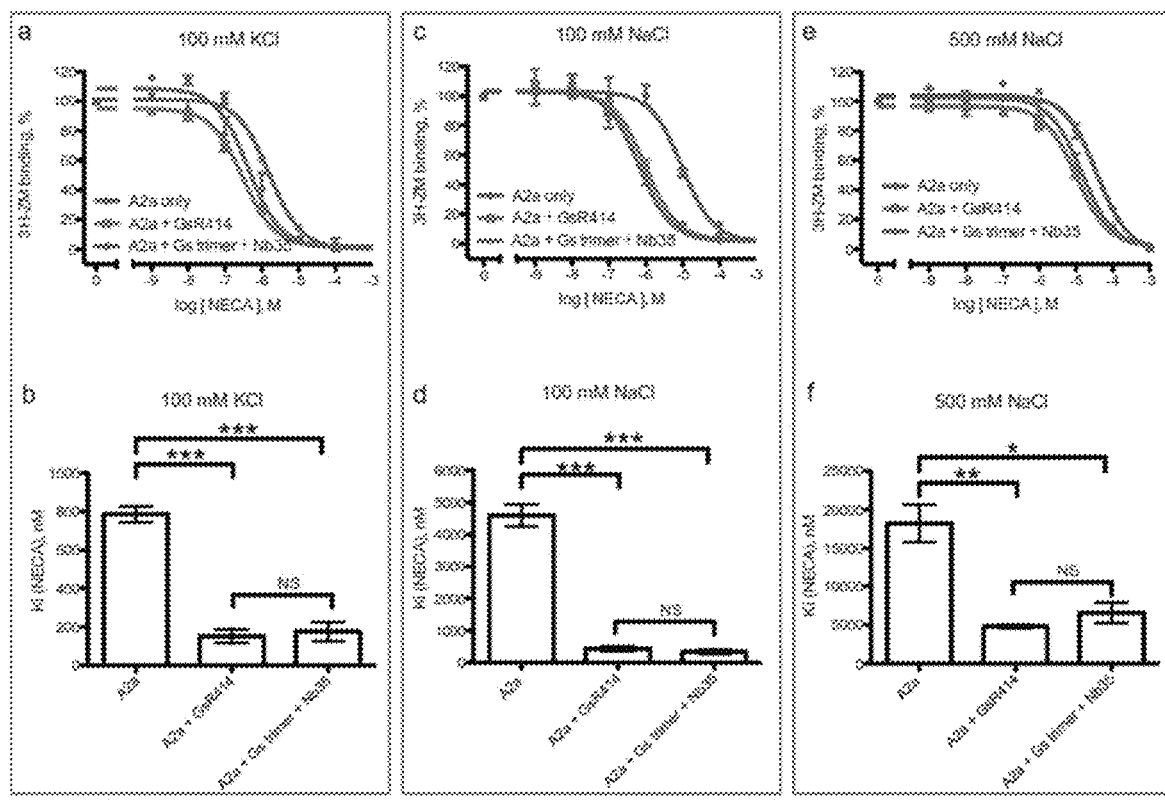

FIG. 16. Competition assays were performed on A₂ₐR expressed in HEK293 cell membranes with the agonist NECA competing for the binding of radiolabelled inverse agonist ³H-ZM241385. Experiments performed in the presence of either 100 mM KCl (a,b), 100 mM NaCl (c, d) or 500 mM NaCl (e, f) to confirm the similar behaviour of mini-Gs with heterotrimeric Gs with nanobody Nb35 for stabilisation of the complex. Results are summarised in the Table (g). Data from at least 3 independent experiments were analysed with an unpaired t-test for statistical significance.

FIG. 19. Alignment of mini-Gs (chains C (SEQ ID NO:161) & D (SEQ ID NO:162)) against bovine GNAS2 (P04896 (SEQ ID NO:160)) used in the β₂AR-Gs structure, with the CGN system for reference. Residues that are within 3.9 Å of either β2AR in the Gs-β2AR complex or A2AR in the mini-Gs-A2AR complex are highlighted in grey.

Figure 18:
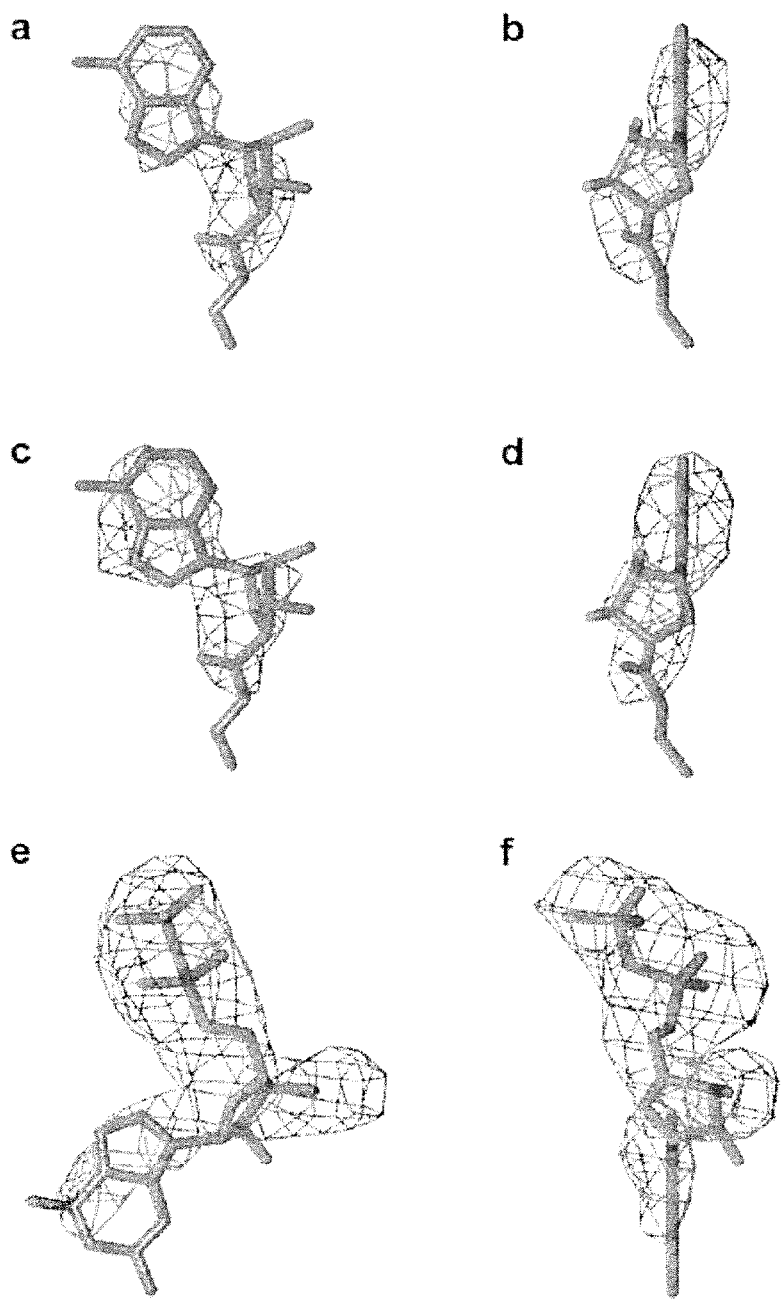

FIG. 18. Orthogonal views of omit map difference density for NECA in A₂ₐR chain A (a and b), NECA in A₂ₐR chain B (c and d) and GDP in mini-Gs chain C (e and f). The contour level is 2.5 sigma in panels a-d and 3.0 sigma in panels e and f.

FIG. 19. Alignment of mini-Gs (chains C (SEQ ID NO:161) & D (SEQ ID NO:162)) against bovine GNAS2 (P04896(SEQ ID NO:160)) used in the β₂AR-Gs structure, with the CGN system for reference. Residues that are within 3.9 Å of either β2AR in the Gs-β2AR complex or A2AR in the mini-Gs-A2AR complex are highlighted in grey.

Figure 20:
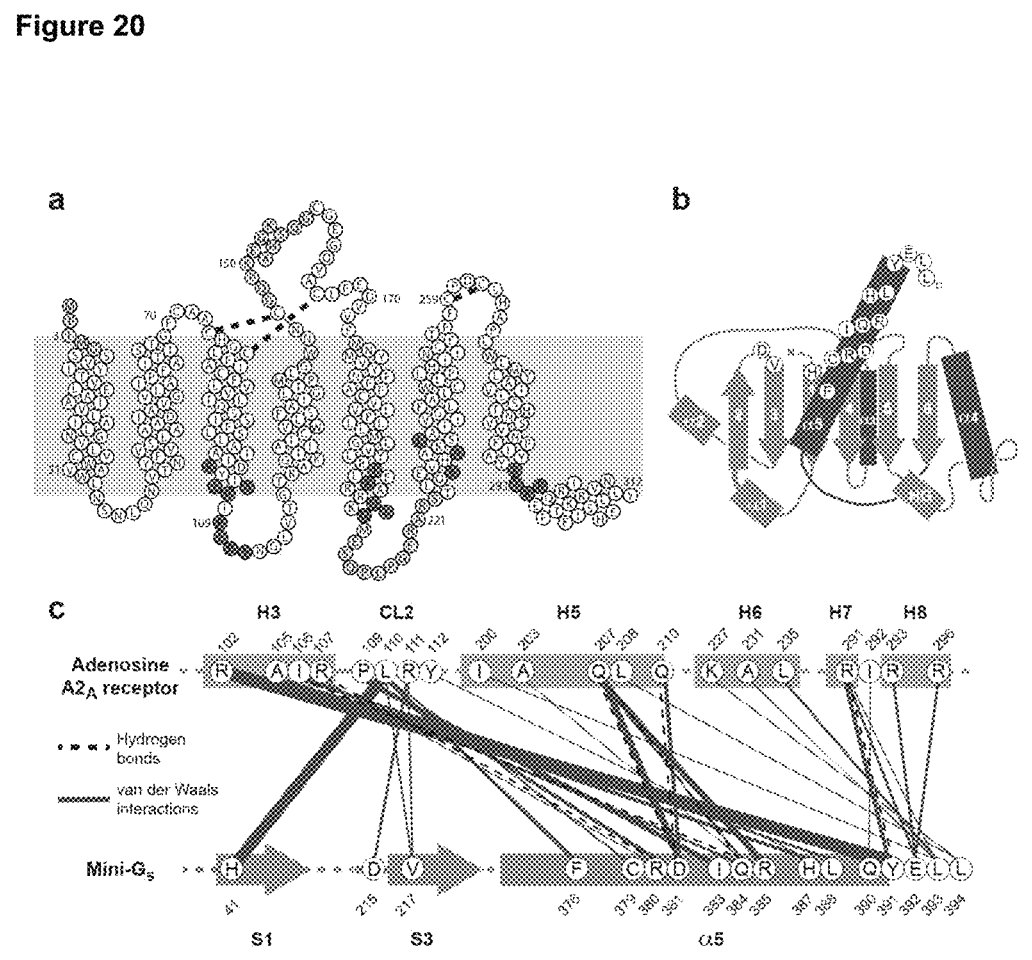

FIG. 20. Packing interactions between A₂ₐR and mini-Gₛ. a, Diagram of A₂ₐR depicting its secondary structure in the A₂ₐR-mini-Gₛ structure. Residues shaded in light grey are disordered in either chain A and/or chain B. Disulphide bonds are depicted as black dashed lines. b, cartoon of the mini-Gₛ topology. c, Diagram of contacts between mini-Gₛ and A₂ₐR, with line thickness representing the relative number of interactions between amino acid residues.

FIG. 21. Alignment of the human β2-adrenergic receptor (adrb2_human; SEQ ID NO:163), human adenosine A2A receptor (AA2AR_human; SEQ ID NO:164) with Chain A (SEQ ID NO:165) and Chain B (SEQ ID NO:166) of the crystallised A2AR-mini-Gs structure. Key Ballesteros-Weinstein numbers are shown above the sequences and mutations in the crystallised A2AR to facilitate purification and crystallization are underlined. Light grey bars indicate the positions of alpha-helices in the β2AR-Gs structure, whereas dark grey bars represent these regions in the A2AR-mini Gs structure.

Figure 22:
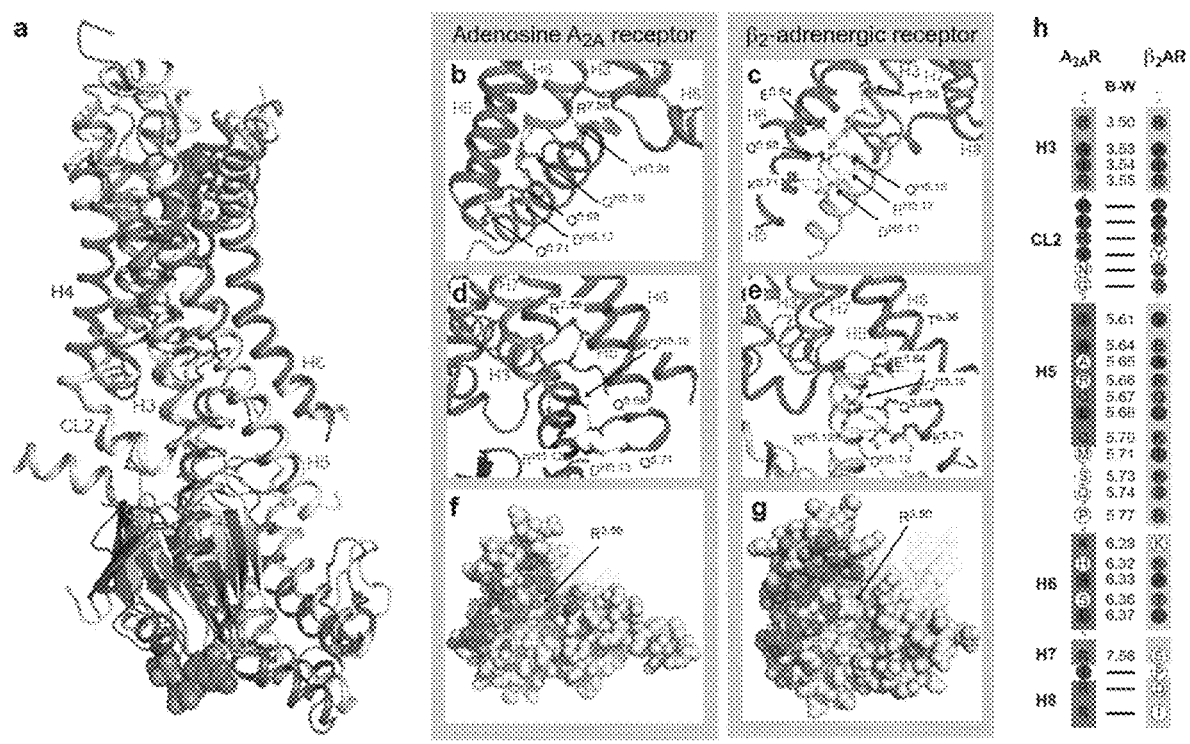

FIG. 22. Comparison of mini-$G_s$-bound $A_{2A}R$ and heterotrimeric $G_s$-bound $\beta_2AR$. a, Structural alignment of $\beta_2AR$-Gs (PDB ID: 3SN6)[10] and $A_{2A}R$-mini-$G_s$ was performed by aligning the receptors alone; $A_{2A}R$, dark grey; $\beta_2AR$, light grey. The resultant relative dispositions of $G\alpha_s$ (light grey) bound to $\beta_2AR$ and mini-$G_s$ bound to $A_{2A}R$ (dark grey) are depicted. NECA and GDP are depicted as space-filling models. The α-helical domain of $G\alpha_s$ has been omitted for clarity, along with $G\alpha_s$-bound Nb35 and $G\beta\gamma$. b-e, detailed comparisons of hydrogen bonds (dashed lines) between the respective G proteins and receptors; receptors are in the upper parts of the panels with helices labelled H3, H5, H6, H7 and H8, with mini-$G_s$ and $G\alpha_s$ in the bottom part of the panels with residues labelled using the CGN system. Labelling of amino acid residues shows the Ballesteros-Weinstein (B-W) numbers for the receptors and the CGN notation for G proteins. f and g, Views of the cytoplasmic surface of $A_{2A}R$ and $\beta_2AR$, respectively, as space-filling models with atoms making contacts with their respective G proteins in dark grey. h, Comparison of residues making contacts to G proteins in the mini-$G_s$-$A_{2A}R$ complex and the $G_s$-$\beta_2AR$ complex. Amino acid residues in the receptors that make contacts are in dark grey. Residues in white are those that do not make contact to the respective G protein, but the equivalent residue in the other receptor does. B-W numbers are given for residues in transmembrane α-helices, with a dash for residues in loops or H8. Amino acid residues 5.71-5.77 are disordered in the mini-$G_s$-$A_{2A}R$ structure.

Figure 23:
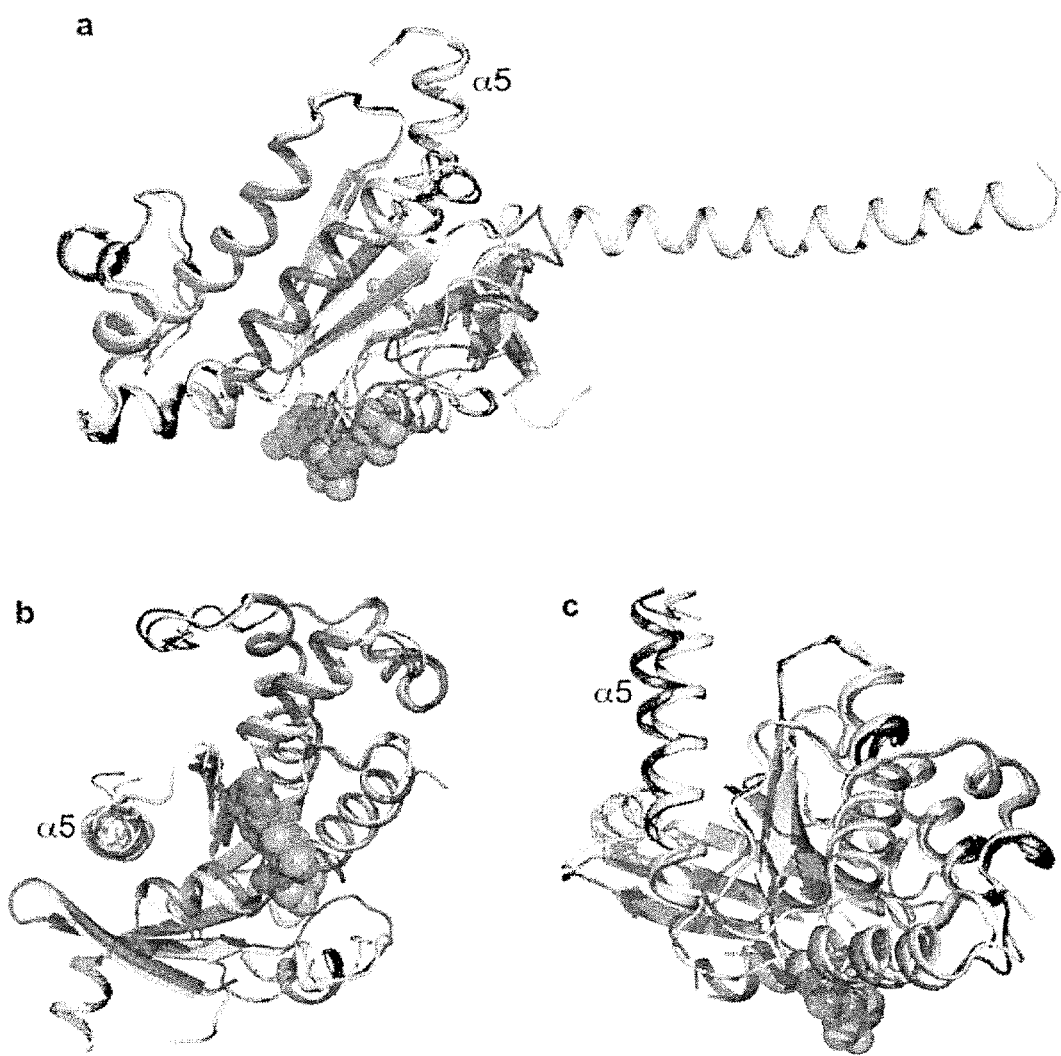

FIG. 23. Alignment of mini-Gs (chain c, dark grey) bound to A2AR with the GTPase domain of $G\alpha s$ (light grey) bound to $\beta$2AR. GDP bound to mini-Gs is depicted as a space filling model. The α5 helix that interacts with the receptors is labelled.

Figure 24:
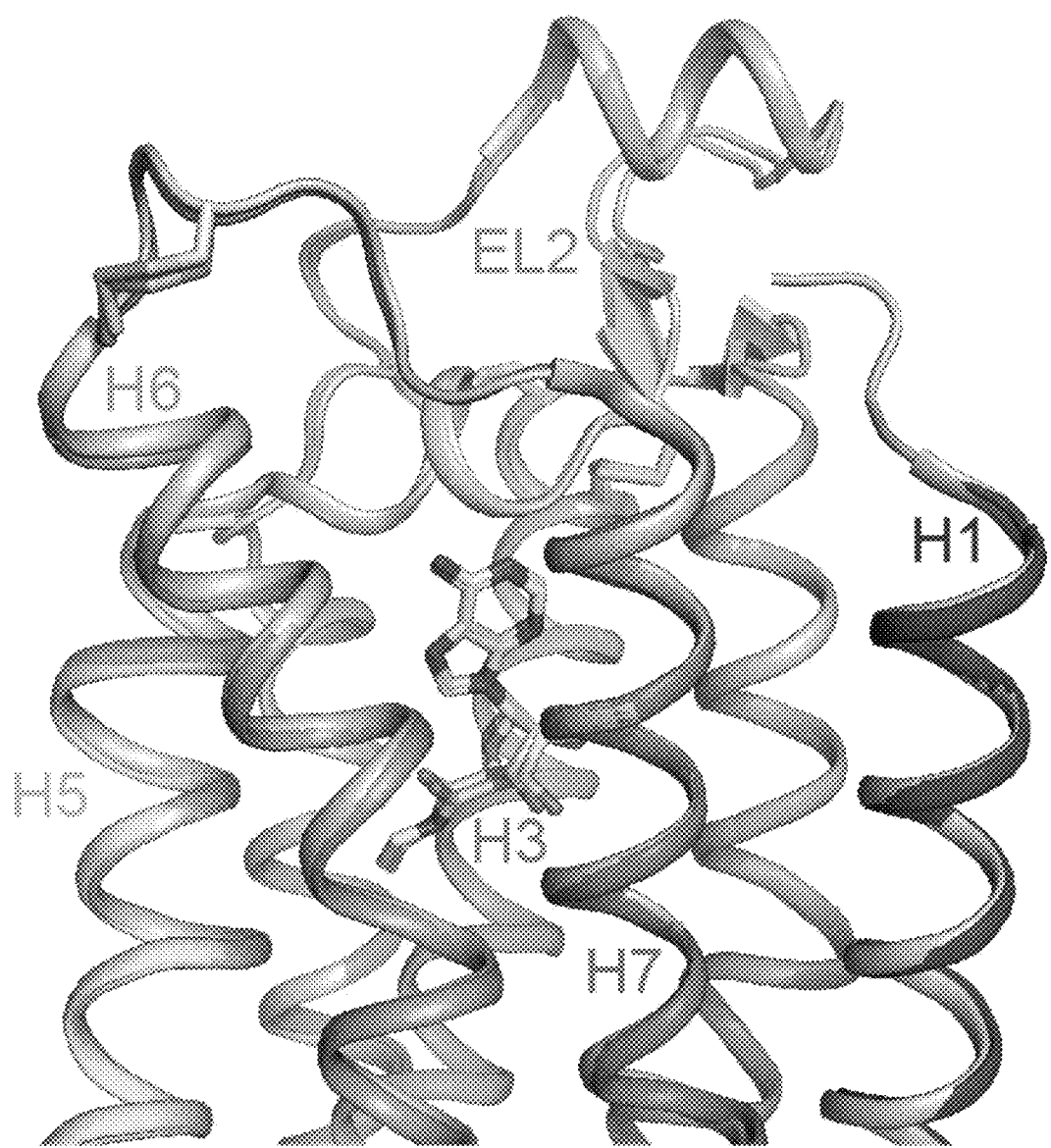
Figure 24:
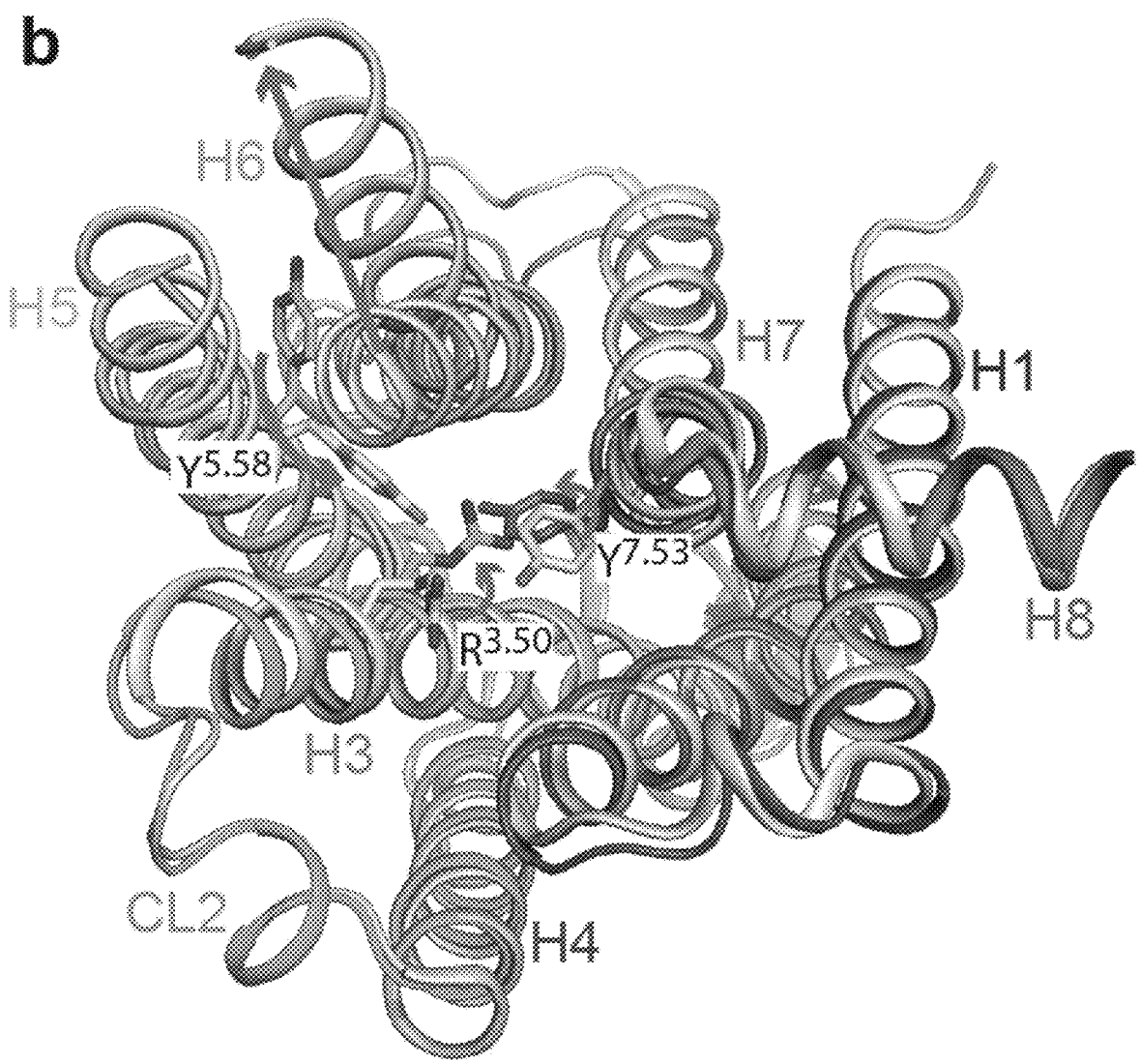
Figure 24:
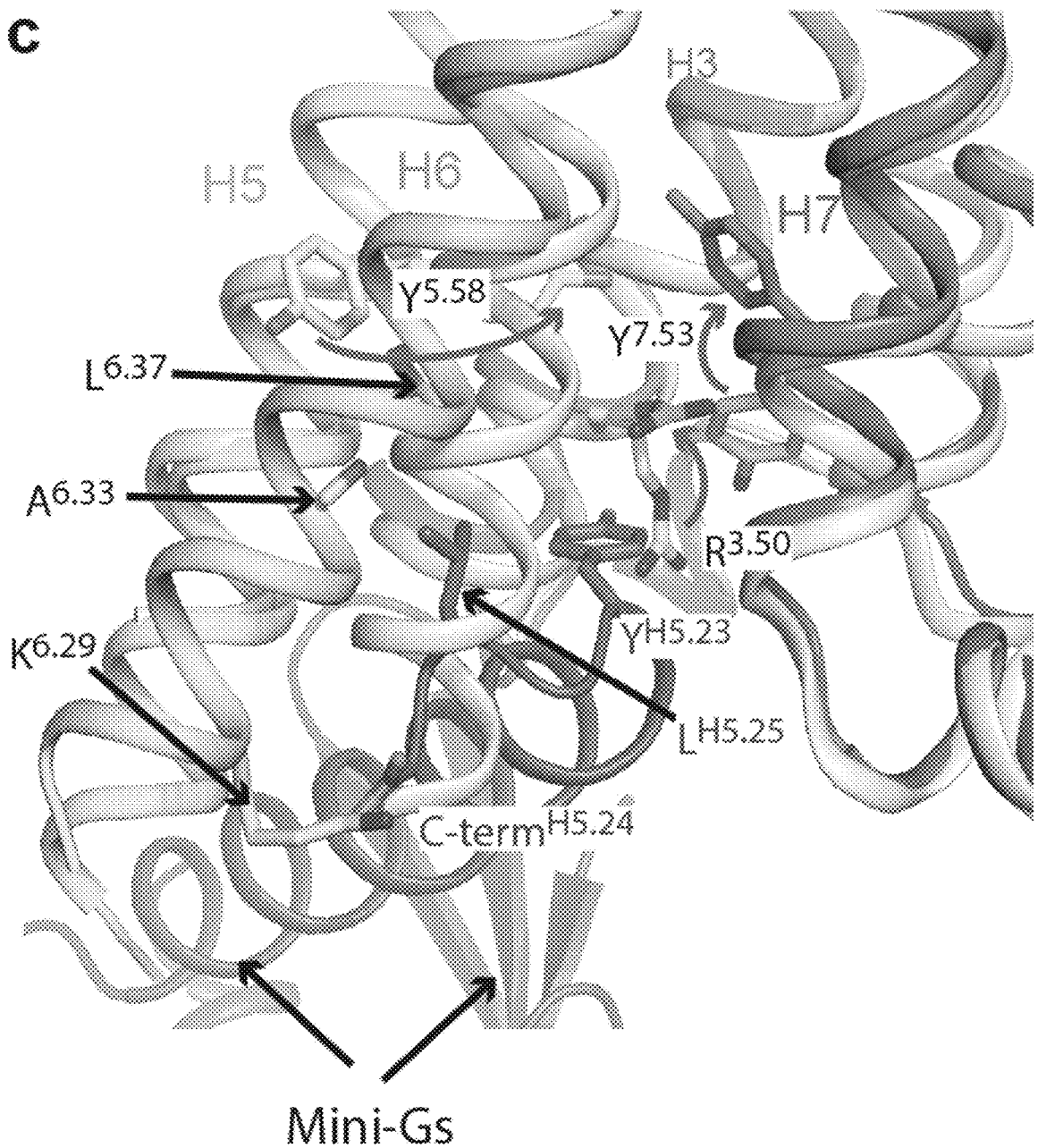

FIG. 24. Conformational changes in $A_{2A}R$ upon G protein binding. $A_{2A}R$ (dark grey) bound to mini-$G_s$ was aligned with $A_{2A}R$ in the active-intermediate conformation (light grey) bound to either NECA (PDB code 2YDV)[1] or UK432097 (PDB code 3QAK)[4] to highlight structural changes upon G protein binding. Neither structure was used for both comparisons because the large extensions of the ligand UK432097 compared to NECA distorts the extracellular surface in comparison to the NECA-bound structure and the NECA-bound structure contains a thermostabilising mutation in the intracellular half of the receptor. a, Alignment with 2YDV and the extracellular half of the receptor is viewed parallel to the membrane plane, b, Alignment with 3QAK and viewed from the cytoplasmic surface with mini-$G_s$ removed for clarity. c, Alignment with 3QAK viewed parallel to the membrane. Transmembrane α-helices in $A_{2A}R$ are labelled H3, H5, H6, H7 and the mini-Gs is labelled. Residues are labelled with their Ballesteros-Weinstein numbers and arrows depict the direction of movement upon mini-Gs binding. Conversion of B-W and CGN numbers to amino acid residues in $A_{2A}R$ and mini-$G_s$, respectively, are as follows: $R^{3.50}$, Arg102; $Y^{5.58}$, Tyr97; $K^{6.29}$, Lys227; $A^{3.33}$, Ala231 carbonyl; $L^{6.37}$, Leu235; $Y^{7.53}$, Tyr288; $Y^{H5.23}$, Tyr391; $L^{H5.25}$, Leu393; C-term$^{H5.24}$, C-terminus of mini-$G_s$ (Leu394).

FIG. 25. Human paralogue reference alignment for common $G\alpha$ numbering system[103]. a, Reference alignment of all canonical human $G\alpha$ paralogues: P63092 (SEQ ID NO:141), P38405 (SEQ ID NO:142), P63096 (SEQ ID NO:143), P04899 (SEQ ID NO:144), P08754 (SEQ ID NO:145), P11488 (SEQ ID NO:146), P19087 (SEQ ID NO:147), A8MTJ3 (SEQ ID NO:148), P09471 (SEQ ID NO:149), P19086 (SEQ ID NO:150), P50148 (SEQ ID NO:151), P29992 (SEQ ID NO:152), O95837 (SEQ ID NO:153), P30679 (SEQ ID NO:154), Q03113 (SEQ ID NO:155), and Q14344 (SEQ ID NO:156). The domain (D), consensus secondary structure (S) and position in the SSE of the human reference alignment (P) are shown on top of the alignment. b, Reference table of the definitions of SSEs used in the CGN nomenclature.

FIG. 26. Mini Gs amino acid and nucleotide sequences. Amino acid sequences are listed as SEQ ID Nos: 1-45, and nucleotide sequences are listed as SEQ ID NOs: 46-90.

FIG. 27. Amino acid sequence of Galphat subunit (Chimera 6; SEQ ID NO:140). This is a chimeric protein where residues 216-294 of bovine $G\alpha_{t1}$ have been replaced with residues 220-298 of rat $G\alpha_{i1}$. It has been crystallised in complex with $\beta\gamma$ subunits (1GOT).

Figure 28:
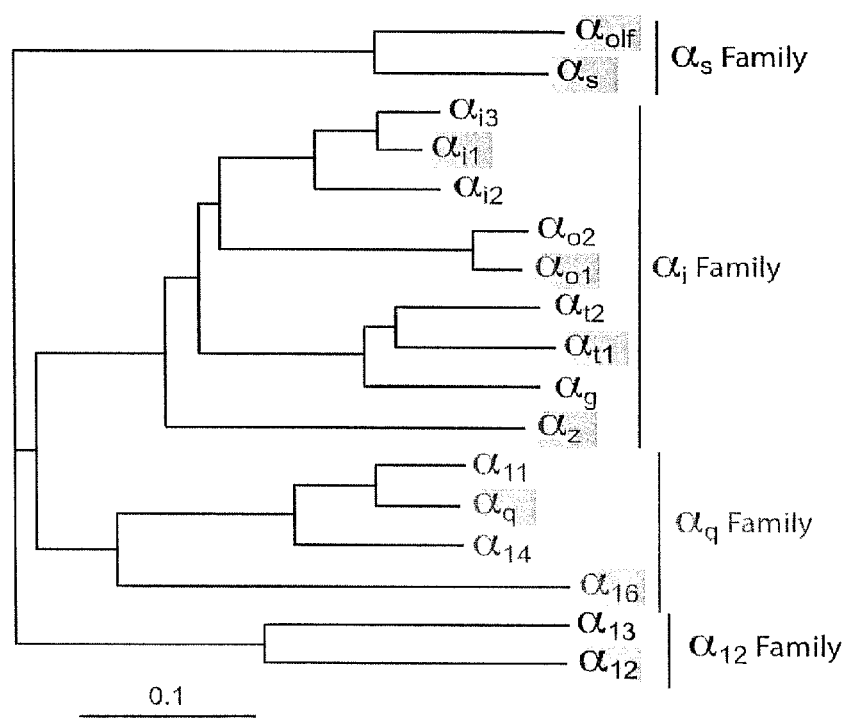

FIG. 28. Phylogenetic relationship of human $G\alpha$ subunits. All the $G\alpha$ subunits that have been highlighted in the family-specific colours were attempted to be converted into mini-G proteins. The phylogenetic relationships were determined using TreeDyn.

FIG. 29. Alignment of $G\alpha$ GTPase domain protein sequences: $\alpha$s (SEQ ID NO:95), $\alpha$o1f (SEQ ID NO:96), $\alpha$i1 (SEQ ID NO:97), $\alpha$o1 (SEQ ID NO:98), $\alpha$t1 (SEQ ID NO:99), $\alpha$z (SEQ ID NO:100), $\alpha$12 (SEQ ID NO:101), $\alpha$q (SEQ ID NO:102), and $\alpha$16 (SEQ ID NO:103). The amino acid sequences aligned are of the wild type GTPase domains of the $G\alpha$ subunits used in this study to create the initial mini-G proteins. The $G\alpha$AH domain (not shown) was deleted and replaced by a linker (GGGGGGGG (SEQ ID NO:94) or GGSGGSGG (SEQ ID NO:93) in italics). To construct mini-G proteins, the residues highlighted in grey were deleted and residues in bold were mutated to the following ($G\alpha$s residue number and the CGN in superscript: $D49^{S1H1.3}$, $N50^{S1H1.4}$, $D249^{S4.7}$, $D252^{s4H3.3}$, $D272^{H3.8}$, $A372^{H5.4}$, $I375^{H5.7}$. The glycine mutation (G217D; underlined) was incorporated into $G_{i1}$ only, to improve expression (see Results and Discussion). Numbering above the sequences is for $G\alpha_s$ and the CGN system below the sequence is used for reference.

Figure 30:
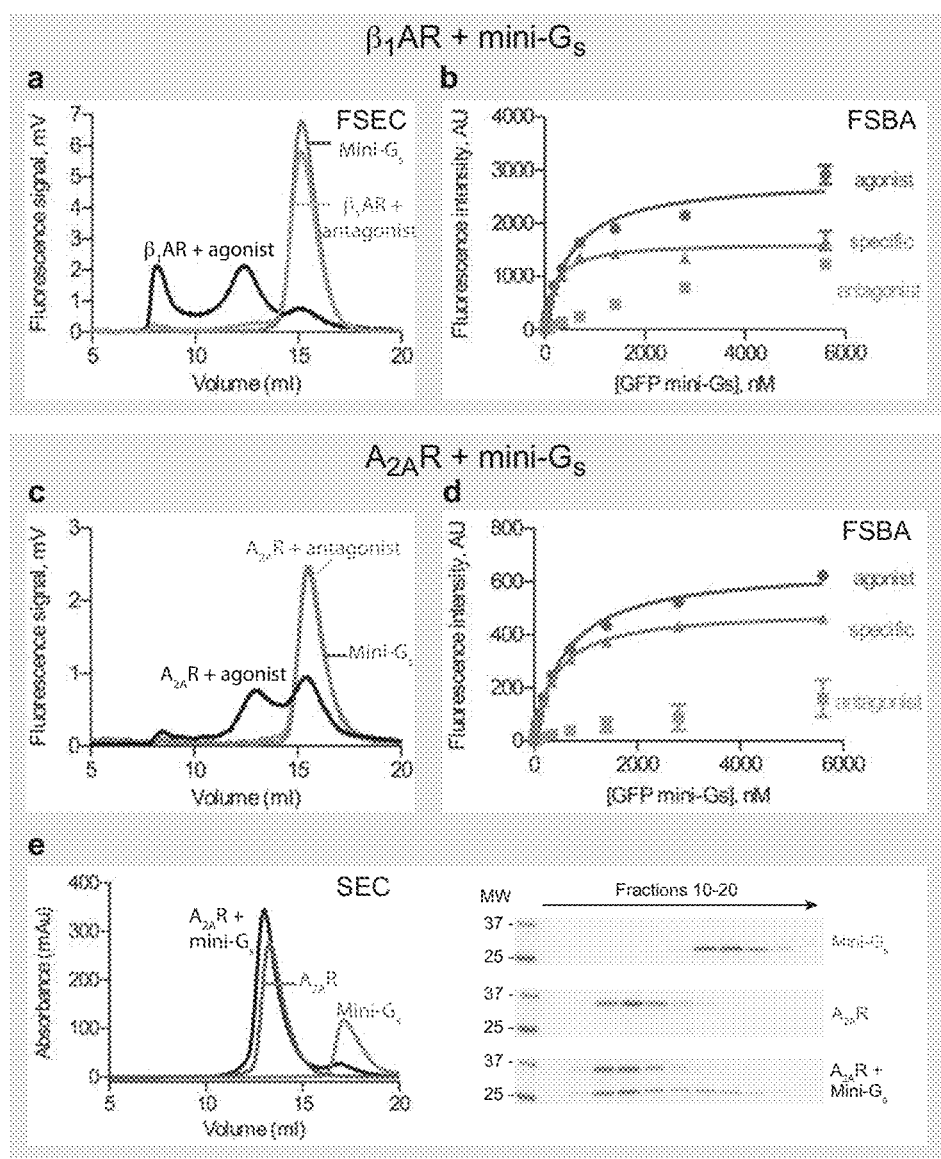

FIG. 30. The $\beta_1AR$-mini-$G_s$ and $A_{2A}R$-mini-$G_s$ complexes. (a) FSEC traces of GFP-mini-Gs with $\beta_1AR$ (retention volumes are given in parentheses): GFP-mini-$G_s$ (15.1 ml); GFP-mini-$G_s$ with $\beta_1AR$ bound to the inverse agonist ICI118551 (15.1 ml); GFP-mini-$G_s$ with $\beta_1AR$ bound to the agonist isoprenaline (8 ml, 12.1 ml and 15.1 ml). Representative chromatograms from at least two independent experiments are shown. (b) Measurement of GFP-mini-$G_s$ affinity to DDM-solubilized $\beta_1AR$ using a fluorescent saturation binding assay (FSBA); circles, $\beta_1AR$ bound to the agonist isoprenaline (total binding); squares, $\beta_1AR$ bound to the inverse agonist ICI118551 (non-specific binding); triangles, specific binding, with an apparent $K_D$ of 201±1 nM (mean±SEM, n=2). Curves shown are from a representative experiment. (c) FSEC traces of GFP-mini-$G_s$ with DDM-solubilised $A_{2A}R$ (retention volumes are given in parentheses): GFP-mini-$G_s$ (15.1 ml); GFP-mini-$G_s$ with $A_{2A}R$ bound to the inverse agonist ZM241385 (15.1 ml); GFP-mini-$G_s$ with $A_{2A}R$ bound to the agonist NECA (12.5 ml and 15.1 ml). Representative chromatograms from at least two independent experiments are shown. (d) Measurement of mini-$G_s$ affinity to DDM-solubilized $A_{2A}R$ using FSBA: circles, $A_{2A}R$ bound to the agonist NECA (total binding); squares, $A_{2A}R$ bound to the inverse agonist ZM241385 (non-specific binding); triangles, specific binding, with an apparent $K_D$ of 428±24 nM (mean±SEM, n=2). (e) Analytical size exclusion chromatography (SEC) of mini-$G_s$ bound to purified $A_{2A}R$ (retention volumes are given in parentheses): $A_{2A}R$-mini-$G_s$ complex, 153 kDa (13 ml); $A_{2A}R$, 133 kDa (13.3 ml); mini-$G_s$, 22 kDa (17.2 ml). Three panels to the right of the SEC traces are coomassie blue-stained SDS-PAGE gels of fractions from 3 separate SEC experiments: top panel, mini-$G_s$; middle panel, $A_{2A}R$; bottom panel, mini-$G_s$ mixed with NECA-bound $A_{2A}R$ (1.2:1 molar ratio).

Figure 31:
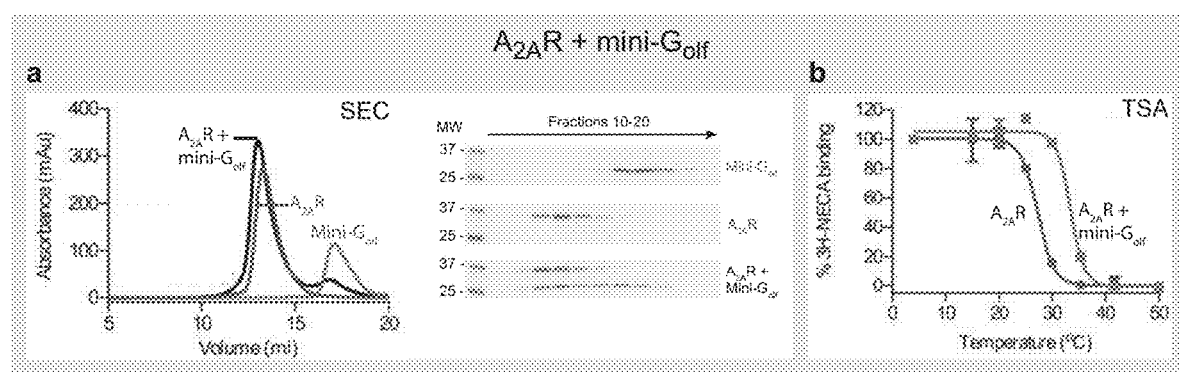

FIG. 31. The $A_{2A}R$-mini-$G_{olf}$ complex. (a) Analytical SEC of mini-$G_{olf}$ bound to purified $A_{2A}R$ (retention volumes are given in parentheses): $A_{2A}R$-mini-$G_{olf}$ complex, 153 kDa (13 ml); $A_{2A}R$, 133 kDa (13.3 ml); mini-$G_{olf}$, 23 kDa (17.1 ml). Three panels to the right of the SEC traces are coomassie blue-stained SDS-PAGE gels of fractions from 3 separate SEC experiments: top panel, mini-$G_{olf}$; middle panel, $A_{2A}R$; bottom panel, mini-$G_{olf}$ mixed with NECA-bound $A_{2A}R$ (1.2:1 molar ratio). (b) Thermostability of unpurified DM-solubilized, $^3$H-NECA-bound $A_{2A}R$. Data were analysed by nonlinear regression and apparent $T_m$ values were determined from analysis of the sigmoidal dose-response curves fitted. $T_m$ values represent mean±SEM of two independent experiments, each performed in duplicate: circles, no mini-$G_{olf}$(26.9±0.3° C.); squares, mini-Golf (32.5±1° C.). Curves shown are from a representative experiment.

Figure 32:
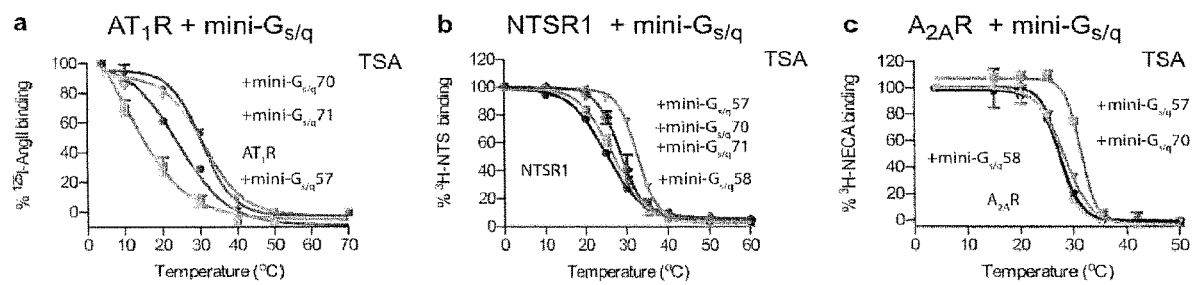

FIG. 32. Thermostability assays of various complexes between mini-$G_{s/q}$ chimeras and GPCRs. (a) Thermostability of unpurified digitonin-solubilized, $^{125}$I-AngII-bound $AT_1R$ ($T_m$ values in parentheses): circles, no mini-$G_{s/q}$ (22.6±0.4° C.); squares, mini-$G_{s/q}$57; inverted triangles, mini-$G_{s/q}$70 (30.7±1° C.); triangles, mini-$G_{s/q}$71 (30.2±0.8° C.). (b) Thermostability of unpurified DDM-solubilized, $^3$H-NTS-bound NTSR1: circles, no mini-$G_{s/q}$ (24.9±0.4° C.); squares, mini-$G_{s/q}$/57 (26.7±0.7° C.); hexagons, mini-$G_{s/q}$58 (25.1±0.4° C.); inverted triangles, mini-$G_{s/q}$70 (32.5±0.3° C.); diamonds, mini-$G_{s/q}$71 (28.6±1.1° C.). (c) Thermostability of unpurified DM-solubilized, $^3$H-NECA-bound $A_{2A}R$: circles, no mini-$G_{s/q}$ (26.9±0.3° C.); squares, mini-$G_{s/q}$57 (30.6±0.3° C.); hexagons, mini-$G_{s/q}$58 (26.9±0.5° C.); inverted triangles, mini-$G_{s/q}$70 (27.5±0.2° C.). In all panels, data (n=3) were analysed by nonlinear regression and apparent $T_m$ values were determined from analysis of the sigmoidal dose-response curves fitted with values shown as mean±SEM. Curves shown are from a representative experiment.

Figure 33:
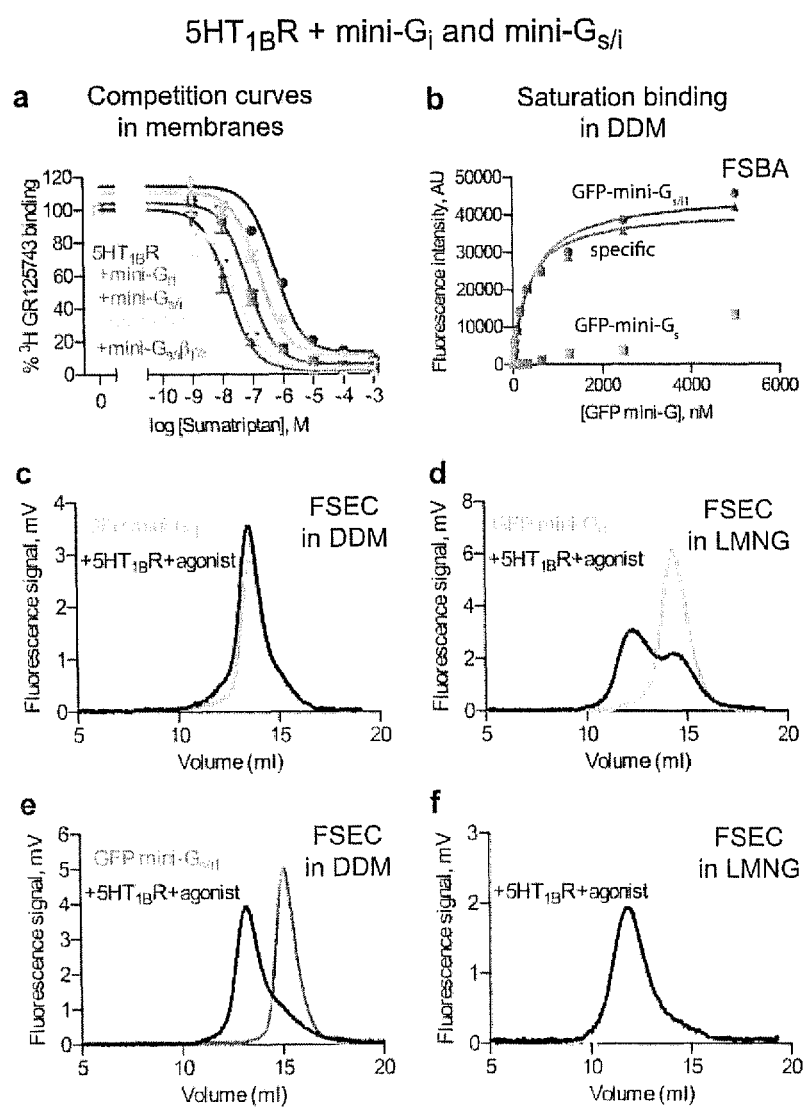

FIG. 33. The $5HT_{1B}R$-mini-$G_{i1}$ complexes. (a) Mini-$G_{i1}$ coupling increases agonist affinity to $5HT_{1B}R$. Competition binding curves were performed in duplicate (n=2) by measuring the displacement of the antagonist $^3$H-GR125743 with increasing concentration of the agonist sumatriptan ($K_i$ values representing mean±SEM in parentheses): circles, $5HT_{1B}R$ ($K_i$ 276±10 nM); hexagons, $5HT_{1B}R$ and mini-$G_{i1}$ ($K_i$ 80±13 nM); squares, $5HT_{1B}R$ and mini-$G_{s/i1}$ ($K_i$ 36±2 nM); triangles, $5HT_{1B}R$ and mini-$G_{i1}\beta_1\gamma_2$($K_i$ 15±1 nM); diamonds, $5HT_{1B}R$ and mini-$G_{s/i1}\beta_1\gamma_2$ ($K_i$ 7.2±0.8 nM). Error bars represent the SEM. (b) Measurement of mini-$G_{s/i1}$ chimera affinity to the DDM-solubilized, donitriptan-bound $5HT_{1B}R$ using FSBA: circles, $5HT_{1B}R$ and GFP-mini-$G_{s/i1}$ (total binding); squares, $5HT_{1B}R$ and GFP-mini-$G_s$ (non-specific binding); triangles, specific binding. The apparent $K_D$ of 386±47 nM represents the mean±SEM of two independent experiments. Curves shown are from a representative experiment. (c) FSEC traces of GFP-mini-$G_{i1}$ with $5HT_{1B}R$ in DDM: GFP-mini-$G_{i1}$ and donitriptan-bound $5HT_{1B}R$ purified in DDM (13.5 ml); GFP-mini-$G_{i1}$ (13.5 ml). (d) FSEC traces of GFP-mini-$G_1$ with $5HT_{1B}R$ in LMNG: GFP-mini-$G_{i1}$ and donitriptan-bound $5HT_{1B}R$ purified in LMNG (12.2 ml and 14.3 ml); GFP-mini-$G_{i1}$ (14.3 ml). (e) FSEC traces of GFP-mini-$G_{s/i1}$ with $5HT_{1B}R$: GFP-mini-$G_{s/i1}$ and donitriptan-bound $5HT_{1B}R$ purified in DDM (13.2 ml); GFP-mini-$G_{s/i1}$ (15.1 ml). (f) FSEC traces of GFP-mini-$G_{i1}\beta_1\gamma_2$ with $5HT_{1B}R$: GFP-mini-$G_{i1}\beta_1\gamma_2$ and donitriptan-bound $5HT_{1B}R$ purified in LMNG (11.8 ml); GFP-mini-$G_{i1}\beta_1\gamma_2$ (14.3 ml). In panels c-f, retention volumes are given in parentheses.

Figure 34:
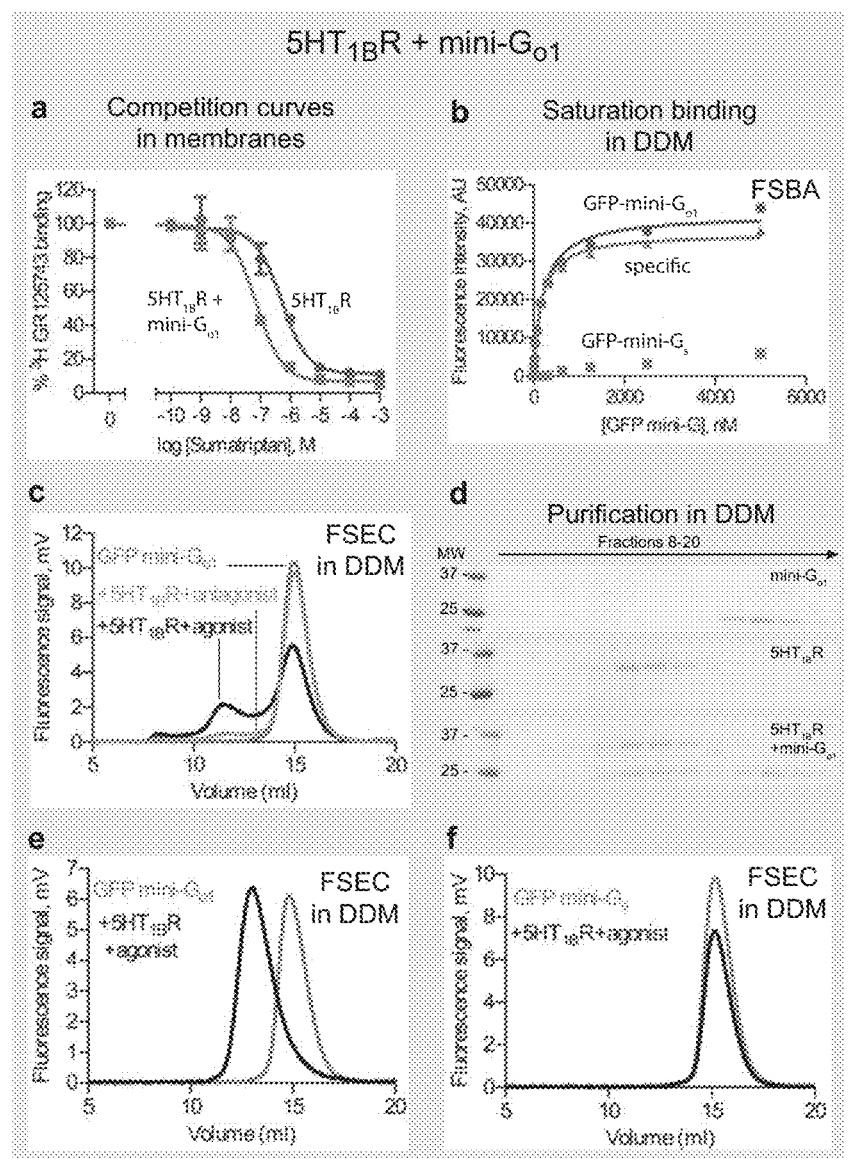

FIG. 34. The $5HT_{1B}R$-mini-$G_{o1}$ complex. (a) Competition binding curves were performed on membranes in duplicate (n=2) by measuring the displacement of the antagonist $^3$H-GR125743 with increasing concentration of the agonist sumatriptan (apparent $K_i$ values representing mean±SEM are in parentheses): circles, $5HT_{1B}R$ ($K_i$ 276±10 nM); squares, $5HT_{1B}R$ and mini-$G_{o1}$ ($K_i$ 32±3 nM). Error bars represent SEM. (b) Measurement of GFP-mini-$G_{o1}$ affinity to DDM-solubilized, donitriptan-bound $5HT_{1B}R$ using the FSBA: circles, $5HT_{1B}R$ and GFP-mini-$G_{o1}$ (total binding); squares, $5HT_{1B}R$ and GFP-mini-$G_s$ (non-specific binding); triangles, specific binding. The apparent $K_D$ value (184±24 nM) represents mean±SEM of two independent experiments. Curves shown are from a representative experiment. (c) FSEC traces of GFP-mini-$G_{o1}$ with DDM-solubilized unpurified $5HT_{1B}R$ bound to the following (retention volumes are shown in parentheses): the antagonist SB224289 (14.9 ml); the agonist donitriptan (11.3 ml and 14.9 ml). Free GFP-mini-$G_{o1}$ resolved as a predominant peak with a retention volume of 14.9 ml. (d) Mini-$G_{o1}$ forms a complex with purified $5HT_{1B}R$. The three panels are coomassie blue-stained SDS-PAGE gels of fractions from 3 separate SEC experiments: top panel, mini-$G_{o1}$; middle panel, $5HT_{1B}R$; bottom panel, mini-$G_{o1}$ mixed with donitriptan-bound $5HT_{1B}R$ (1:1 molar ratio). (e) FSEC traces of GFP-mini-$G_{o1}$ with purified $5HT_{1B}R$: GFP-mini-$G_{o1}$ with $5HT_{1B}R$ purified in DDM (13 ml); GFP-mini-$G_{o1}$ (14.8 ml). (f) FSEC traces of GFP-mini-$G_s$ with purified $5HT_{1B}R$: GFP-mini-$G_s$ with $5HT_{1B}R$ purified in DDM (negative control; 15.1 ml); GFP-mini-$G_s$ (15.1 ml). Retention volumes are shown in parentheses.

FIG. 35. Sequence of mini-G proteins used in this study: Mini-$G_s$393 (SEQ ID NO:104), Mini-$G_{olf}$6 (SEQ ID NO:105), Mini-$G_{s/q}$57 (SEQ ID NO:106), Mini-$G_{s/q}$58 (SEQ ID NO:107), Mini-$G_{s/q}$70 (SEQ ID NO:108), Mini-$G_{s/q}$71 (SEQ ID NO:109), Mini-$G_{i1}$46 (SEQ ID NO:110), Mini-$G_{s/i1}$43 (SEQ ID NO:111), Mini-$G_{s/i1}$48 (SEQ ID NO:112), Mini-$G_{o1}$12 (SEQ ID NO:113), and Mini-$G_{12}$8 (SEQ ID NO:114). The poly-histidine tag is underlined with a dotted line, the TEV protease cleavage site is highlighted in grey, and the linker used to replace the GαAH domain is in italics. Mutations are shown in bold type and underlined.

FIG. 36. Sequence of mini-G proteins that were not successfully expressed in E. coli: Mini-$G_{i1}$ (nucleic acid: SEQ ID NO:115, amino acid: SEQ ID NO:116), Mini-$G_z$ (nucleic acid: SEQ ID NO:117, amino acid: SEQ ID NO:118), Mini-$G_q$ (nucleic acid: SEQ ID NO:119, amino acid: SEQ ID NO:120), and Mini-$G_{16}$ (nucleic acid: SEQ ID NO:121, amino acid: SEQ ID NO:122). The poly-histidine tag is underlined with dotted line, the TEV site is highlighted in grey and the linker used to replace the GαAH domain is in italics. Mutations are shown in bold type and underlined. The constructs were cloned into plasmid pET15b for E. coli expression using NcoI and XhoI restriction sites.

FIG. 37. Sequence of GFP-mini-G proteins used in this study: GFP-mini-$G_s$393 (SEQ ID NO:123), GFP-mini-$G_i$146 (SEQ ID NO:124), GFP-mini-$G_{s/i}$143 (SEQ ID NO:125), GFP-mini-$G_{o1}$ (SEQ ID NO:126), and GFP-mini-$G_{12}$8 (SEQ ID NO:127). GFP (double underlined) was fused to the N-terminus of the mini-G proteins with a GGGGS linker (italics). The poly-histidine tag is underlined with a dotted line, the TEV cleavage site highlighted in grey and the linker used to replace the GαAH domain is in italics (GGSGGSGG or GGGGGGGG).

FIG. 38. Sequence alignment of selected mini-$G_{s/q}$ chimeras used in this study: mini-$G_q$ (SEQ ID NO:128), mini-$G_s$ (SEQ ID NO:129), mini-$G_{s/q}$57 (SEQ ID NO:130), mini-$G_{s/q}$58 (SEQ ID NO:131), mini-$G_{s/q}$70 (SEQ ID NO:132), and mini-$G_{s/q}$71 (SEQ ID NO:133). Residues in bold are the signature mutations of a mini-G protein. Residues in grey are those found in $G_q$. Diamonds above the sequences identify the amino acid residues in Gαs where the side chains that make atomic contacts to residues in either $β_2AR$ (β2 con) or $A_{2A}R$ (2A con). Ovals above the sequences identify the amino acid residues in Gαs where only the main chain atoms make contacts to the receptor.

Figure 39:
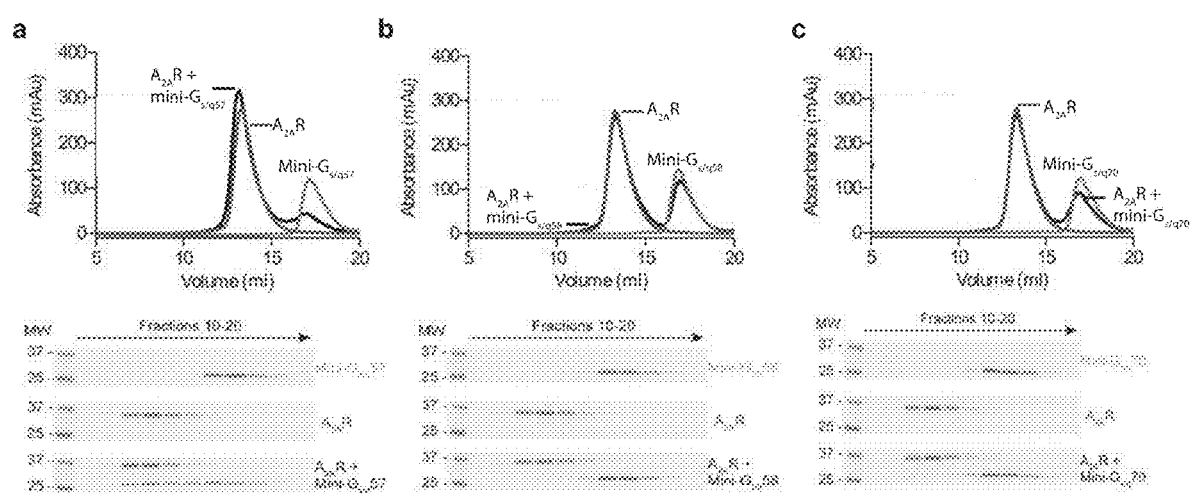

FIG. 39. Analytical SEC and SDS-PAGE analyses of purified A2AR with mini-Gs/q chimeras. Analytical SEC of mini-$G_{s/q}$57 (a), mini-$G_{s/q}$58 (b) and mini-$G_{s/q}$70 (c) bound to purified $A_{2A}R$: $A_{2A}R$-mini-$G_{s/q}$ complex; $A_{2A}R$; mini-$G_{s/q}$. Three panels below the SEC traces are coomassie blue-stained SDS-PAGE gels of fractions from 3 separate SEC experiments: top panel, mini-$G_{s/q}$; middle panel, $A_{2A}R$; bottom panel, NECA-bound $A_{2A}R$ mixed with mini-$G_{s/q}$ (1:1.2 molar ratio).

FIG. 40. Sequence alignment of the different mini-$G_{i1}$ and mini-$G_{o1}$ proteins used in this study: mini-Gs_393 (SEQ ID NO:134), mini-Gi1_46 (SEQ ID NO:135), mini-Gs/i1_43 (SEQ ID NO:136), mini-Gs/i1_48 (SEQ ID NO:137), mini-Go1_12 (SEQ ID NO:138), and mini-Gs/o_16 (SEQ ID NO:139). Residues in bold are the signature mutations of a mini-G protein. Note the additional G217D mutation (bold; residue 114 in the mini-G protein) in mini-$G_{i1}$ to improve expression. Residues in mini-$G_s$ were mutated to their equivalent in mini-$G_{i1}$ or mini-$G_{o1}$ (single underline or double underline, respectively) to make the mini-$G_{s/i1}$ or mini-$G_{s/o1}$ chimeras. Note the re-insertion of the N-terminus (highlighted in grey) in the constructs that were used to form a heterotrimer with $β_1γ_2$ (i.e. mini-$G_{i1}$_46; mini-$G_{s/i1}$_43 and mini-$G_{s/o1}$_16).

Figure 41:
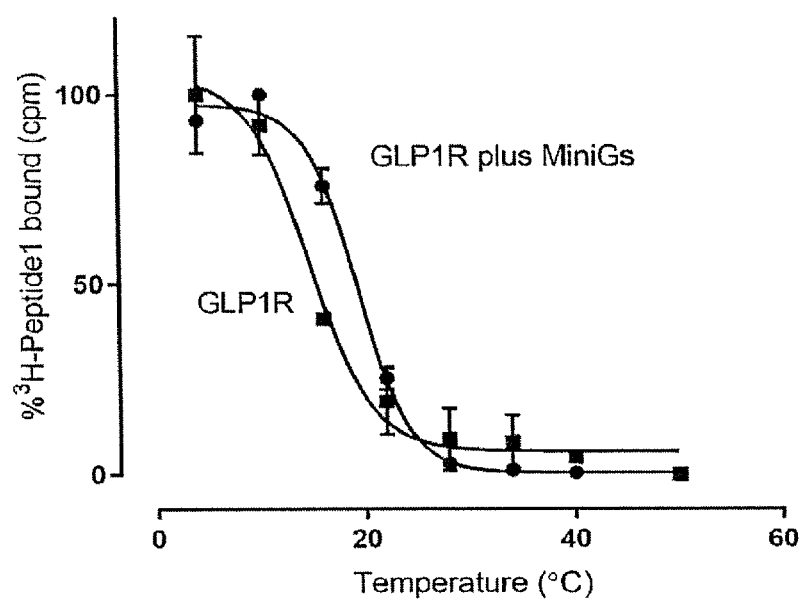

FIG. 41. Stability of GLP1R in agonist conformation in the presence of mini-Gs. Mini-Gs increase the stability of GLP1R in the presence of mini-Gs. GLP1R Tm is 14.7° C., GLP1R plus mini-Gs Tm is 19.3° C.

EXAMPLE 1: ENGINEERING A MINIMAL G PROTEIN TO FACILITATE CRYSTALLISATION OF G PROTEIN COUPLED RECEPTORS IN THEIR ACTIVE CONFORMATION

Introduction

G protein coupled receptors (GPCRs) modulate cytoplasmic signalling pathways in response to stimuli such as hormones and neurotransmitters. Structure determination of GPCRs in all activation states is vital to elucidate the precise mechanism of signal transduction. However, due to their inherent instability, crystallisation of GPCR-G protein complexes has proved particularly challenging. Here, we describe the design of a minimal G protein, which is composed solely of the GTPase domain from the adenylate cyclase stimulating G protein (Gs). Mini Gs is a small, soluble protein, which efficiently couples GPCRs in the absence of Gβγ subunits. We engineered mini Gs to form a stable complex with the β1 adrenergic receptor (β1AR), even when solubilised in short chain detergents. Mini G proteins induce similar pharmacological and structural changes in GPCRs as heterotrimeric G proteins. They are therefore novel tools, which will facilitate high throughput structure determination of GPCRs in their active conformation.

Results

Developing a Sensitive Assay to Detect Gs Coupling to β1AR

We developed a sensitive competitive binding assay, which could detect the interaction of different binding partners with $β_1AR$, by measuring the response in agonist binding affinity. The binding partners used during this work were: Nb80[38], a Nanobody that binds $β_2AR$ and induces a comparable shift in agonist affinity to lipidated Gs; Nb35[40], a Nanobody that stabilises Gs in its GPCR-bound conformation; non-lipidated Gs (Gα$sβ_1γ_2$); and non-lipidated Gβγ (G$β_1γ_2$). The concentration of binding proteins used in the assays was standardised to 25 μM, which is approximately 30-fold above the equilibrium dissociation constant ($K_D$) for Nb80 binding to $β_1AR$[96]. No affinity data was available for Gs, however we anticipated this concentration to be at least 10-fold above $K_D$.

A heterologous competitive binding assay was used to measure competition between the antagonist $^3$H-dihydroalprenolol ($^3$H-DHA) and the agonist isoprenaline. Inhibition constant ($K_i$) values were calculated using the dissociation constant ($K_d$) of $^3$H-DHA derived from saturation binding experiments (see FIG. 2). First, a wild type-like turkey $β_1AR$ construct[97] ($β_1AR$-WT) was assayed (see Table 1). This construct had an isoprenaline $K_i$ of 40±0 nM in the absence of binding partner. The $K_i$ shifted to: 5.8±0.8 nM (6.9-fold), 17±2 nM (2.4-fold), or 6.8±0.6 nM (5.9-fold) in response to Nb80, Gs, or Gs-Nb35, respectively (FIG. 3a). The shift in agonist affinity was relatively small for $β_1AR$-WT, therefore, we next tested a minimally thermostabilised construct ($β_1AR$-84), which contained some of the previously described mutations[3,96] (see Table 1). This construct had a significantly lower isoprenaline $K_i$ in its uncoupled state (2.6±0.3 μM), but produced a larger shift than $β_1AR$-WT in response to binding partners. Coupling to Nb80, Gs, or Gs-Nb35 shifted the $K_i$ to 28±1 nM (93-fold), 271±54 nM (9.6-fold), or 16±4 nM (163-fold), respectively (FIG. 3b). The competitive binding curves fitted best to single-site binding parameters. Therefore, the partial shift in agonist affinity observed for some binding partners (such as Gs) most likely reflects incomplete stabilisation of the high-affinity agonist-bound state, rather than indicating partial coupling or mixed receptor populations. These results demonstrated that non-lipidated Gs was able to couple $β_1AR$, but that Nb35 was required to stabilise the complex and elucidate an equal response in agonist binding affinity to Nb80. The competitive binding assay using $β_1AR$-84 was more sensitive than $β_1AR$-WT, and thus useful to distinguish small differences in the ability of different binding partners to stabilise the high-affinity agonist-bound state.

Isolation of the Gαs GαGTPase Domain and Measuring Binding to $β_1AR$-84

The structure of the $β_2AR$-Gs complex[10] revealed that only the GαGTPase domain from Gs forms significant interactions with the receptor (see FIG. 4). We isolated the GTPase domain at the genetic level by replacing the sequence corresponding to GαAH with a short glycine linker (see Table 2). This construct, which we named mini Gs$_{77}$, was poorly expressed in E. coli and could not be purified to homogeneity, indicating that it was very unstable. Nonetheless, a small amount of protein (approximately 200 μg/L culture) could be prepared at approximately 10-20 percent purity (see FIG. 5). The GαGTPase and GαAH domains from Gαs have previously been expressed as independent proteins in order to determine their role in guanine nucleotide binding and hydrolysis[41], but their ability to couple GPCRs has never been investigated. We tested the ability of mini $Gs_{77}$ to couple $\beta_1AR$-84 in our competitive binding assay at 20° C., in either the presence or absence of Gβγ-Nb35. No significant shift in the agonist binding affinity of $\beta_1AR$-84 (2.6±0.3 μM) was observed in the presence of mini $Gs_{77}$ (1.9±0.2 μM), but mini $Gs_{77}$-Gβγ-Nb35 induced a shift to 3.6±0.8 nM (718-fold) (FIG. 3c). This demonstrated that the partially purified GαGTPase domain was functional, but also suggested that it was unable to couple $\beta_1AR$-84 in the absence of Gβ3γ subunits. However, when we repeated the assay at 4° C., we observed a significant shift in agonist $K_i$ from 2.1±0.2 μM for the uncoupled receptor (at 4° C.) to 99±12 nM (21-fold) in response to mini $Gs_{77}$ (FIG. 3d). This was a critical result because it demonstrated that the isolated GαGTPase domain could bind $\beta_1AR$-84 in the absence of Gβγ subunits. It also suggested that thermostability was the limiting factor in its ability to stabilise the high-affinity agonist-bound state of the receptor.

Thermostabilisation of the $\beta_1AR$-Mini Gs Complex

We thermostabilised mini Gs in complex with $\beta_1AR$. Mutants were screened using our competitive binding assay at both 4° C. and 20° C. Due to the low, and variable expression level of the mutants, it was impossible to standardize the concentration used in the assays. Instead, the total mini Gs purified from 1 L of E. coli culture was used per competition curve (Table 3). Approximately 100 mutants were tested during the initial screen. Mutations that shifted the agonist affinity of $\beta_1AR$-84 more than 2-fold compared to the parental mini Gs construct (mini $Gs_{77}$) at either temperature were classed as positive. A total of 14 positive mutations, covering 11 unique positions were identified (Table 3).

A new parental construct (mini $Gs_{161}$), which contained a modified N-terminus and linker region (see Table 2), was used to combine mutations. Positive mutations were combined with one of the best mutations from the first round of screening (A249D), and their stability in complex with $\beta_1AR$-WT was tested using a thermostability assay in n-dodecyl-β-D-maltopyranoside (DDM) detergent. The agonist $^3$H-norepinephrine ($^3$H-NE) was used in the Tm assay, however due to the high background signal associated with this ligand, a maximum concentration of 200 nM could be used in the assay. This was approximately equal to the $K_i$ of uncoupled $\beta_1AR$-WT, but approximately 250-fold above $K_i$ of $\beta_1AR$-WT complexed with Nb80 or Gs-Nb35 (see FIG. 7). Therefore, Tm values quoted for uncoupled $\beta_1AR$-WT are under non-saturating agonist conditions, but $\beta_1AR$-WT complexes, which have higher agonist affinity, are under agonist saturating conditions.

The A249D mutant (mini $Gs_{162}$) had an apparent Tm of 25.1° C. (Table 4), which was lower than that of uncoupled of $\beta_1AR$-WT (25.9° C.). A double mutant (mini $Gs_{164}$), containing the A249D mutation and switch III deletion, increased the apparent Tm of the complex to 28.6° C. Addition of G49D, E50N, S252D and L272D mutations produced similar apparent Tm values (within 0.2° C. of the double mutant). These six mutations were utilised in the final construct, because of their positive individual effect on the agonist affinity of membrane-embedded $\beta_1AR$-84 (Table 3). None of the other positive mutations from the first round of screening further increased the Tm of the complex and so were rejected. All of the combinations, except L272D, also increased the Tm of the basal GDP-bound state (Table 4), as assessed by differential scanning fluorimetry (DSF).

Five of the six mutations, which were successfully combined, were clustered around the nucleotide-binding pocket and phosphate-binding loop (P-loop) (FIG. 6b). The A249D mutation was designed to interact with Lys-293 and S251, in order to stabilise the base of the nucleotide-binding pocket. Deletion of switch III, which is disordered in the GPCR-bound conformation, was intended to stabilise mini Gs by replacing this flexible loop with the defined secondary structure elements (α helix, $3_{10}$ helix and beta turn) found in Arl-2[98]. The S252D mutation was also designed to stabilise the region around switch III, through potential interactions with Arg-265. The G49D and E50N mutations, which are located in the P-loop, were designed to reduce flexibility and conformationally constrain this region, through potentially interactions with Arg-265 and Lys-293, respectively. The sixth mutation (L272D) was designed to conformationally constrain switch II, through potential interactions with a cluster of charged and polar residues (227-233) within its N-terminal region (FIG. 6c).

Screening Mutations that Stabilise the $\beta_1AR$-WT-Mini Gs Complex in Detergent Mini $Gs_{183}$, which contained the six stabilising mutations from the first round of screening, was unable to fully stabilise detergent-solubilised $\beta_1AR$-WT. Complexes of Nb80 or Gs-Nb35 had apparent Tm values 3.3° C. or 7.1° C. higher than mini $Gs_{183}$, respectively (Table 4). Therefore, a second panel of approximately 150 mutants were designed based on the structure of Gs in its receptor-bound conformation[10], using mutagenesis. These mutations were screened in a parental construct, which had a modified linker region (see Table 2). We identified four additional mutations that increased the stability of the complex in detergent (Table 4). The best mutant (I372A) increased the apparent Tm of the complex from 29.2° C. to 34.00° C. and combined additively with V375I giving a final apparent Tm of 35.0° C. This was 3.0° C. higher than Nb80 and only 0.8° C. lower than Gs-Nb35. All of the detergent stabilising mutations decreased the stability of mini Gs in the GDP-bound conformation (Table 4).

The detergent stabilising mutations were located around the α1-α5 helix interface. Alignment of Gαs in the GPCR-bound conformation[10] with the GTP-bound structure[81] revealed a steric clash between Ile-372 (in the α5 helix) and residues Met-60 and His-64 (in the α1 helix) (FIG. 6d). This clash appears to prevent close packing of the C-terminal region of the α1 helix against the core of the GaGTPase domain, exposing the core of the protein to the solvent. The I372A mutation was designed to eliminate this clash, and facilitate better packing in this region. The V375I mutation was designed to improve packing between the α5 helix and the core of the protein in the GPCR-bound conformation (FIG. 6e). During the course of this work the I372A mutation was also independently reported to stabilise the rhodopsin—$G_{i1}$ complex[92].

Validation of Mini Gs

The detergent stabilised construct (mini $Gs_{345}$) was modified for crystallography applications by changing the linker and shortening the N-terminus (see Table 2). The final stabilised construct was named mini $Gs_{393}$ (see FIG. 8). This construct was able to elucidate a equal or greater shift in agonist affinity than either Nb80 or Gs-Nb35 (FIG. 9a-c) for: membrane-embedded $\beta_1AR$-WT (4.1±1.1 nM compared to 5.8±0.8 nM, or 6.8±0.6 nM, respectively) membrane-embedded $\beta_1AR$-84 (3.6±0.0 nM compared to 28±1 nM, or 16±4 nM, respectively); and DDM solubilised $\beta_1AR$-84 (4.7±0.4 nM compared to 83±2 nM, or 23±7 nM, respectively). These data demonstrate that mini Gs was able to stabilise the high-affinity agonist-bound state of $\beta_1AR$ as well as, or better that either Nb80 or Gs-Nb35. Furthermore, there was no significant difference between the agonist binding affinity of membrane-embedded or detergent-solubilised $\beta_1AR$-84 coupled to mini $Gs_{393}$. This demonstrates that the pharmacological response of the receptor is identical in either a lipid or detergent environment.

Mini $Gs_{393}$ was highly expressed in *E. coli*: it could be purified with a yield of 100 mg per litre culture, and concentrated to over 100 mg/ml (FIG. 9*d*). Analytical gel filtration was used to demonstrate that mini $Gs_{393}$ could bind purified $\beta_1AR$-WT in lauryl maltose neopentyl glycol (LMNG) detergent. A 1:1 stochiometric mixture of mini $Gs_{393}$ and $\beta_1AR$-WT resolved as a predominant peak with a retention volume of 13.2 ml compared to 13.6 ml or 17.1 ml for $\beta_1AR$-WT or mini $Gs_{393}$, respectively (FIG. 9*e*). This result clearly demonstrated that the binding assays correlated with the formation of a stable complex between the purified protein in detergent. Furthermore, mini $Gs_{399}$, a construct in which N-terminal residues 6-25 were replaced and the L272D mutation reversed (see Table 2), retained its ability to form a heterotrimer with $G\beta\gamma$. A 1:1 stochiometric mixture of mini $Gs_{399}$ and $G\beta_1\gamma_2$ resolved as a single peak with a retention volume of 14.6 ml compared to 15.8 ml or 16.4 ml for $G\beta\gamma$ or mini $Gs_{399}$, respectively (FIG. 9*f*). This property may be useful for applications where the larger mini Gs heterotrimer is favourable (cryo-electron microscopy), or to study the role of $G\beta\gamma$ in G protein activation.

The stability of the $\beta_1AR$-WT-mini $Gs_{393}$ complex was tested in a number of different detergents. In longer chain detergents such as DDM the $\beta_1AR$-WT-mini $Gs_{393}$ complex had an apparent Tm of 34.1° C., which was 8.2° C. higher than uncoupled $\beta_1AR$-WT. In DDM mini $Gs_{393}$ was slightly less stabilising (1.7° C.) than Gs-Nb35, but slightly more stabilising (2.1° C.) than Nb80 (FIG. 10*a*). A similar pattern was observed in n-decyl-β-D-maltopyranoside (DM), where the $\beta_1AR$-WT-mini $Gs_{393}$ complex had an apparent Tm of 30.5° C., which was 10.1° C. higher than uncoupled $\beta_1AR$-WT. In Dm mini $Gs_{393}$ was slightly less stabilising than Gs-Nb35 (0.6° C.), but slightly more stabilising than Nb80 (1.9° C.) (see FIG. 11*a*). In short-chain detergents, such as n-octyl-β-D-glucopyranoside (OG), the $\beta_1AR$-WT-mini $Gs_{393}$ complex had an apparent Tm of 19.7° C., which was more stabilising than either Gs-Nb35 (6.1° C.) or Nb80 (5.4° C.) (FIG. 10*b*). A similar pattern was observed in n-nonyl-β-D-glucopyranoside (NG), where the $\beta_1AR$-WT-mini $Gs_{393}$ complex had an apparent Tm of 24.7° C., which was more stabilising than either Gs-Nb35 (5.7° C.) or Nb80 (8.0° C.) (see FIG. 11*b*). Uncoupled $\beta_1AR$-WT was completely inactivated after solubilisation in either NG or OG, demonstrating the considerable degree of thermostability imparted to the receptor by mini $Gs_{393}$ coupling. NG and OG are both suitable detergents for vapour diffusion crystallisation, highlighting this a viable approach for structure determination of GPCR-mini Gs complexes.

The nucleotide binding properties of the mutants were not extensively studied in this work, but one interesting observation was made: $\beta_1AR$-84 complexes involving mini $Gs_{393}$ were completely resistant to GTP-mediated dissociation (FIGS. 10*c* and 10*d*). GTPγS was added to the competitive binding assay (after complex formation) at a concentration of 0.25 mM, which is within the physiological range of GTP in normal human cells[99]. Uncoupled $\beta_1AR$-84 had an isoprenaline $K_i$ of 3.0±0.1 μM in the presence of GTPγS.

Treatment of the complex with GTPγS fully reversed the shift in agonist binding affinity induced by Gs from 271±54 nM to 2.7±0.1 μM (FIG. 10*c*). The shift in agonist binding affinity induced by mini $Gs_{404}$ (an identical construct to mini $Gs_{393}$, except that the I372A and V375I mutations were reversed) (see Table 2) was almost fully reversed by GTPγS (from 18±2 nM to 700±60 nM). However, there was no significant difference in the agonist binding affinity of the $\beta_1AR$-WT-mini $Gs_{393}$ complex in either the presence or absence of GTPγS (3.6±0.0 nM compared to 5.2±+0.7 nM). This unresponsiveness to GTPγS was traced to the I372A mutation, with mini $Gs_{389}$ (an identical construct to mini $Gs_{393}$, except that the V375I mutation was reversed) (see Table 2), behaving in almost identical fashion to mini $Gs_{393}$ (see FIG. 12). Therefore, the I372A mutation appears to uncouple occupancy of the nucleotide-binding pocket from GPCR binding (see discussion). This is an interesting finding, because it may allow the formation of stable GPCR-mini Gs complexes in living cells. Combined with the thermostabilising effect of mini $Gs_{393}$ coupling on GPCRs, this may allow solubilisation and purification of GPCRs that are too unstable to purify using traditional techniques.

Discussion

Several novel approaches have been developed to stabilise and crystallise GPCRs in active-like conformations, these include complexation with: G protein-derived peptides[36,37], G protein-mimicking nanobodies[38,100,101], and nanobody-stabilised heterotrimeric G proteins[10]. However, these approaches are not ideal: the G protein-derived peptides do not appear to induce the same conformational changes in the receptor as the heterotrimeric G protein; the G protein-mimicking nanobodies cannot recreate the native GPCR-G protein interface; and the heterotrimeric G protein complexes are large, dynamic, and unstable in detergent, making them particularly challenging targets for crystallisation. Therefore, we designed a minimal G protein, which was amenable to high throughput crystallisation of native-like GPCR-G protein complexes. Recently, we solved the structure of mini Gs in complex with the wild type human adenosine $A_{2a}$ receptor at 3.4 Å resolution (see Example 4). The molecular organisation of the $A_{2a}$ complex is remarkably similar to that of the $\beta_2AR$-Gs complex[10], strongly suggesting that it is an accurate reflection of the native signalling complex.

The G protein engineering work has also provided unique insight into the mechanism of G protein activation. We identified a steric clash between the α1 and α5 helices in the receptor-bound conformation, which appears to prevent close packing of the α1 helix against the core of the GαGTPase domain (FIG. 6*d*). It has previously been suggested that allosteric destabilisation of the α1 helix by GPCRs may be a key event in opening of the GαGTPase-GαAH domain interface and destabilisation of the nucleotide-binding pocket[89,90,92]. We demonstrated that mutation of Ile-372 to alanine, which was predicted to eliminate the steric clash between the α1 and α5 helices, almost completely inhibited GTP-mediated dissociation of complex. These data indicate that Ile-372 acts as a key relay between the GPCR-binding site and the nucleotide-binding pocket, and that its mutation effectively uncouples GPCR binding from nucleotide occupancy. The identification of Ile-372 as a key residue in signal transduction also demonstrates the versatility of mini G proteins, particularly minimally stabilised variants, for studying the mechanisms of G protein activation.

Mini G proteins are novel tool, which have many potential applications, including: characterisation of receptor pharmacology, binding kinetic studies, thermostabilisation of GPCR in their active conformation, drug discovery, and crystallisation of native-like GPCR-G protein complexes. Furthermore, all of the mutations reported here are located within conserved regions of the Gα subunit. Therefore, the concept is believed to be transferable to all classes of heterotrimeric G protein, which would allow the production of a panel of mini G proteins capable of coupling any GPCR.

Materials and Methods

Cloning

Details of all constructs used in this work are provided in Tables 1 and 2. Site directed mutagenesis was performed using the Quick Change protocol (Stratagene). Insertions and deletions were performed using a modified version of a previously described method[102].

Baculovirus Expression of G Proteins

G protein genes were cloned into the transfer vector pBacPAK8 (Clontech), and baculoviruses were prepared using the flashBAC ULTRA system (Oxford Expression Technologies). *Trichopulsia ni* cells (Expression Systems) were grown in ESF921 serum-free media (Expression Systems) in 5 L Optimum growth flasks (Thompson Instrument Company). Immediately before infection, heat inactivated foetal bovine serum (Sigma) was added to a final concentration of 5%. Cells were infected with third passage virus at a final concentration of 3%. In the case of co-infection with multiple viruses (for heterotrimeric Gs or Gβγ) each virus was added to a final concentration of 3%. The final volume of culture was 3 L per flask and the final cell density was $3\times10^6$ cells/ml. Cells were harvested 48 h post-infection by centrifugation at 5000 g for 5 mins, flash-frozen in liquid nitrogen and stored at −80° C.

Purification of Non-Lipidated Gαs

The cell pellet from 6 L of insect cell culture was resuspended to 400 ml in buffer A (30 mM TRIS, pH 8.0, 100 mM NaCl, 5 mM $MgCl_2$, 5 mM imidazole, 50 μM GDP). PMSF (1 mM), Pepstatin-A (2.5 ELM), Leupeptin (10 μM), Complete protease tablets (Roche), DNase I (50 μg/ml), and DTT (100 μM) were added. Cells were broken by sonication (10 minutes at 70% amplitude) and clarified by centrifugation (38,000 g for 1 h). The supernatant was loaded onto a 5 ml Ni Sepharose FF column (GE Healthcare) at 5 ml/min. The column was washed sequentially with 25 ml buffer A, 50 ml buffer B (20 mM TRIS, pH 8.0, 300 mM NaCl, 10 mM imidazole, 10% glycerol, 1 mM $MgCl_2$, 50 μM GDP), and 25 ml buffer C (20 mM TRIS, pH 8.0, 300 mM NaCl, 30 mM imidazole, 10% glycerol, 1 mM $MgCl_2$, 50 μM GDP) at 5 ml/min. The column was eluted with 25 ml buffer D (20 mM TRIS, pH 9.0, 50 mM NaCl, 500 mM imidazole, 10% glycerol, 1 mM $MgCl_2$, 50 μM GDP). The eluate was diluted to 250 ml in buffer E (20 mM TRIS, pH 9.0, 50 mM NaCl, 10% glycerol, 1 mM $MgCl_2$, 50 μM GDP, 1 mM DTT) and loaded onto a 5 ml Q Sepharose HP column (GE Healthcare) at 5 ml/min. The column was washed with 50 ml buffer E and eluted with a linear gradient of 50-300 mM NaCl (in buffer E). Peak fractions were pooled and TEV protease was added to give a final ratio of 1:20 w/w (TEV: Gαs). The sample was dialysed overnight against 1 L buffer F (20 mM HEPES, pH 7.5, 100 mM NaCl, 10% glycerol, 1 mM $MgCl_2$, 10 μM GDP). Imidazole (20 mM) and Ni-NTA resin (4 ml) were added to the sample and mixed for 1 h. The mixture was poured onto a disposable column containing 1 m Ni-NTA resin, and the flow-through collected. The column was washed with 10 ml buffer F and this wash was pooled with the flow-through. The pooled sample was concentrated to 1.5 ml using a 10 KDa MWCO Amicon Ultra centrifugal filter (Millipore). The sample was loaded onto a Superdex-200 26/600 gel filtration column (GE Healthcare), equilibrated with buffer G (10 mM HEPES, pH 7.5, 100 mM NaCl, 10% glycerol, 1 mM $MgCl_2$, 1 μM GDP, 0.1 mM TCEP). Peak fractions were pooled and concentrated to 50 mg/ml. The pure protein was aliquoted, flash-frozen in liquid nitrogen, and stored at −80° C. A typical yield was 6.5 mg pure Gαs per litre culture.

Purification of Non-Lipidated Gs Heterotrimer

Purification of non-lipidated heterotrimeric Gs was performed essentially as described for non-lipidated Gαs, except: the Ni Sepharose column was washed with 50 ml buffer C, instead of 25 ml; buffer D contained 300 mM imidazole, instead of 500 mM; the pH of buffers D and E was 8.5, instead of 9.0; the Q Sepharose column was eluted with a linear gradient of 50-200 mM NaCl, instead of 50-300 mM; and no TEV cleavage step was performed, instead fractions from the Q Sepharose column were concentrated and loaded on the Superdex-200 column. A typical yield was 7 mg pure Gs per litre culture.

Purification of Non-Lipidated Gβγ Dimer

Purification of non-lipidated Gβγ dimer was performed essentially as described for non-lipidated Gαs, except: GDP was omitted from all buffers; $MgCl_2$ was omitted from buffers B-G; buffers B and C contained 250 mM NaCl, instead of 300 mM; buffer D contained 25 mM NaCl, instead of 50 mM; buffer D contained 300 mM imidazole, instead of 500 mM; buffers E and F were supplemented with 1 mM EDTA; the Q Sepharose column was eluted with a linear gradient of 25-200 mM NaCl, instead of 50-300 mM; and no TEV cleavage step was performed, instead fractions from the Q Sepharose column were concentrated and loaded on the Superdex-200 column. A typical yield was 7.5 mg pure Gβγ per litre culture.

Expression and Purification of Nanobodies

Synthetic genes (Integrated DNA Technologies) for Nb80 and Nb35 were cloned into pET26b (Novagen) for periplasmic expression in *E. coli* strain BL21(DE3)RIL (Agilent Technologies). Cells were lysed by sonication (10 mins at 70% amplitude). Nb80 was purified by IMAC and gel filtration, with a typical yield of 12 mg pure protein per litre culture. Nb35 was purified by IMAC, cation exchange chromatography and gel filtration, with a typical yield of 26 mg pure protein per litre culture.

Expression and Purification of Mini G Proteins (for Screening)

Mini G protein mutants were cloned in pET15b (Novagen). Expression was performed in *E. coli* strain BL21(DE3) RIL. Cells were grown in 2TY media supplemented with glucose (0.1%). Cultures were induced with IPTG (100 μM) at 15° C. for 20 h. Cells were lysed by sonication (2 mins at 70% amplitude). Mutants were partially purified by IMAC. Imidazole was removed on a PD10 column (GE Healthcare), and samples were concentrated to 20 mg/ml. The partially pure protein was aliquoted, flash-frozen in liquid nitrogen, and stored at −80° C.

Expression and Purification of Mini G Proteins (Final Protocol)

BL21(DE3)RIL cells transformed with the mini G protein construct were grown in TB media supplemented with glucose (0.2%) and $MgSO_4$ (5 mM) and antifoam (0.01%). Cells were cultured in 2 L baffled flasks (Simax), shaking at 140 rpm. Cultures were grown at 30° C. until an $OD_{600}$ of 0.8 was reached. Expression was induced with IPTG (50 μM) and the temperature reduced to 25° C. Cells were harvested 20 h post-induction by centrifugation at 5000 g for 10 mins, flash-frozen in liquid nitrogen and stored at −80° C.

The cell pellet from 1 L of culture was resuspended to 200 ml in buffer A (40 mM HEPES, pH 7.5, 100 mM NaCl, 10% glycerol, 10 mM imidazole, 5 mM MgCl$_2$, 50 µM GDP). PMSF (1 mM), Pepstatin-A (2.5 µM), Leupeptin (10 µM), Complete protease tablets, DNase I (50 µg/ml), and DTT (100 µM) were added. Cells were broken by sonication (10 minutes at 70% amplitude) and clarified by centrifugation (38,000 g for 45 mins). The supernatant was loaded onto a 10 ml Ni Sepharose FF column at 5 ml/min. The column was washed with 100 ml buffer H (20 mM HEPES, pH 7.5, 500 mM NaCl, 40 mM imidazole, 10% glycerol, 1 mM MgCl$_2$, 50 µM GDP) at 5 ml/min. The column was eluted with 30 ml buffer I (20 mM HEPES, pH 7.5, 100 mM NaCl, 500 mM imidazole, 10% glycerol, 1 mM MgCl$_2$, 50 µM GDP). TEV protease was added to give a final ratio of 1:20 w/w (TEV:Gαs). DTT (1 mM) was added and the sample was dialysed overnight against 2 L buffer J (20 mM HEPES, pH 7.5, 100 mM NaCl, 10% glycerol, 1 mM MgCl$_2$, 10 µM GDP). Imidazole (20 mM) and Ni-NTA resin (4 ml) were added to the sample and mixed for 1 h. The mixture was poured onto a disposable column containing 1 m Ni-NTA resin, and the flow-through collected. The column was washed with 10 ml buffer F and this wash was pooled with the flow-through. The pooled sample was concentrated to 1.5 ml and loaded onto a Superdex-200 26/600 gel filtration column, equilibrated with buffer K (10 mM HEPES, pH 7.5, 100 mM NaCl, 10% glycerol, 1 mM MgCl$_2$, 1 µM GDP, 0.1 mM TCEP). Peak fractions were pooled and concentrated to 100 mg/ml. The pure protein was aliquoted, flash-frozen in liquid nitrogen, and stored at −80° C. A typical yield was 100 mg pure protein per litre culture.

Saturation Binding Assay

Insect cells expressing β$_1$AR were resuspended in 1 ml of assay buffer (20 mM HEPES, pH 7.5, 100 mM NaCl), supplemented with Complete EDTA-free protease inhibitors (Roche). Cells were broken by 10 passages through a bent 26 G needle. Cell debris was removed by centrifugation (3000 g for 5 mins at 4° C.). The supernatant was diluted and 2×0.96 ml aliquots taken for each sample. Alprenolol (120 µl) was added to the negative sample (1 mM final concentration) and assay buffer (120 µl) was added to the positive sample. Samples were aliquoted (12×108 µl) into a PCR plate. [$^3$H]-dihydroalprenolol (12 µl) was added to each well (to give final concentrations in the range: 2.5 nM-2.56 µM). Samples were mixed and incubated at 20° C. for 2 h. Samples (2×50 µl duplicates) were vacuum filtered through 96-well glass fibre filter plates (Merck Millipore), pre-soaked with PEI (0.1%). Each well was washed with assay buffer (3×200 µl). Filters were dried, punched into scintillation vials and 4 ml Ultima Gold scintillant (Perkin Elmer) was added. Radioactivity was quantified by scintillation counting (1 min per sample) using a Tri-Carb counter (Perkin Elmer). Data for negative samples were subtracted from positive samples. Data were plotted graphically (Prism) and K$_d$ values derived from one site saturation binding analysis.

Competitive Binding Assay

Insect cells expressing β$_1$AR were resuspended in 1 ml of assay buffer (25 mM HEPES, pH 7.5, 100 mM NaCl, 1 mM MgCl$_2$, 1 mM ascorbate), supplemented with Complete EDTA-free protease inhibitors (Roche). Cells were broken by 10 passages through a bent 26 G needle. Cell debris was removed by centrifugation (3000 g for 5 mins at 4° C.). The supernatant was diluted and a single 1.68 ml aliquot taken for each sample. Binding partner (240 µl) was added (25 µM final concentration). The mixture was aliquoted (17×96 µl) into a 0.2 ml PCR plate at 20° C. Isoprenaline (12 µl), prepared in buffer containing 1 U/ml apyrase (Sigma-Aldrich), was added to each well (final concentrations in the range: 1 pM-10 mM). Alprenolol (12 µl) was added to the negative sample (100 µM final concentration). Samples were mixed and incubated at 20° C. for 1.5 h. [$^3$H]-dihydroalprenolol (12 µl) was added to each well (5 nM or 20 nM final concentrations for β$_1$AR-WT or β$_1$AR-84, respectively). Samples were mixed and incubated at 20° C. for 1.5 h. Samples (2×50 µl duplicates) were vacuum filtered exactly as described in the saturation binding assay protocol. Data were plotted graphically and K$_i$ values derived from one site fit K$_i$ analysis.

Competitive binding assays using detergent-solubilised β$_1$AR-84 were performed using a similar protocol, except: all steps were performed at 4° C.; membranes were solubilised with DDM (0.1% final concentration) for 30 minutes, prior to addition of binding partner; separation of bound from free ligand (by gel filtration) was performed exactly as described in the thermostability assay protocol.

Thermostability Measurement of β$_1$AR-WT-Mini Gs Complexes

Insect cells expressing wild type β$_1$AR-WT were resuspended in 1 ml of assay buffer (25 mM HEPES, pH 7.5, 400 mM NaCl, 1 mM MgCl$_2$, 1 mM ascorbate, 0.1% BSA, 0.004% bacitracin), supplemented with Complete EDTA-free protease inhibitors (Roche). Cells were broken by 10 passages through a bent 26 G needle. Cell debris was removed by centrifugation (3000 g for 5 mins at 4° C.). The supernatant was diluted and 2×0.78 ml aliquots taken for each sample. Norepinephrine (120 µl) was added to the negative sample (200 µM final concentration) and assay buffer (120 µl) was added to the positive sample. Binding partner (120 µl) was added to both samples (25 µM final concentration). $^3$H-norepinephrine (120 µl), prepared in buffer containing 1 U/ml apyrase (Sigma-Aldrich), was added to both samples (200 nM final concentration). Samples were mixed and incubated at 4° C. for 1 h. Detergent (60 µl) was added to both samples (final concentration: DDM=0.1%; DM=0.13%; OG=0.8%). Samples were mixed and incubated on ice for 1 h. Insoluble material was removed by centrifugation (17000 g for 5 mins at 4° C.). The supernatant was aliquoted (9×120 µl) into 0.2 ml PCR tubes. Each sample was heated to the desired temperature (between 4 and 50° C.) for exactly 30 minutes, followed by quenching on ice for 30 minutes. Samples (2×50 µl duplicates) were applied to Toyopearl HW-40F resin, which was pre-equilibrated (25 mM HEPES, pH 7.5, 100 mM NaCl, 1 mM MgCl$_2$, 0.025% DDM) and packed (225 µl bed volume) in 96-well filter plates (Merck Millipore). Plates were centrifuged (1800 rpm for 5 mins at 4° C.). The filtrate was transferred to Isoplates (Perkin Elmer), and 200 µl Optiphase Supermix scintillant (Perkin Elmer) was added to each well. Radioactivity was quantified by scintillation counting (1 min per well) using a MicroBeta counter (Perkin Elmer). Data for negative samples were subtracted from positive samples. Data were plotted graphically and apparent melting temperature (Tm) values derived from sigmoidal dose-response (variable slope) analysis.

Thermostability Measurement of GDP-Bound Mini Gs Mutants by Differential Scanning Fluorimetry (DSF)

Mini Gs mutants (30 µg) were diluted to 135 µl with assay buffer (10 mM HEPES, pH 7.5, 100 mM NaCl, 1 mM MgCl$_2$, 1 mM GDP, 2 mM DTT). SYPRO-orange (15 µl) was added from a 20× stock solution to give a final concentration of 2×. Samples were mixed and 2×50 µl aliquots (duplicates) were transferred to 0.2 ml PCR tubes (Qiagen). Thermostability measurements were performed using a Rotor-Gene Q (Qiagen). Samples were equilibrated for 90 s at 25° C. before ramping from 25 to 99° C. at 4 s/° C. The melting temperature (Tm), corresponding to the inflection point of the curve, was derived from analysis using the Rotor-Gene Q software. Tm values were calculated as the mean±SEM from three independent experiments.

Gel Filtration Analysis of Mini G Protein Complexes

Mini Gs-βγ complexes were prepared using mini $Gs_{399}$: a construct in which N-terminal residues 6-25 were replaced and the L272D mutation was reversed (see Table 2). Purified mini $Gs_{399}$ was mixed with non-lipidated $G\beta_1\gamma_2$ subunits in an equimolar ratio (6.7 nmol each), diluted to 200 µl with buffer L (10 mM HEPES, pH 7.5, 100 mM NaCl, 1 mM $MgCl_2$, 1 µM GDP, 0.1 mM TCEP) and incubated on ice for 4 hours. The entire sample (200 µl) was loaded onto a Superdex-200 10/300 gel filtration column, equilibrated with buffer L.

The $\beta_1$AR-mini Gs complex was prepared using wild type $\beta_1$AR-WT purified in LMNG detergent. Purified $\beta_1$AR-WT and mini Gs were mixed in an equimolar ratio (3.3 nmol each), diluted to 200 µl with buffer M (10 mM HEPES, pH 7.5, 100 mM NaCl, 10% glycerol, 1 mM $MgCl_2$, 1 µM ascorbic acid, 1 µM isoprenaline, 0.002% LMNG) and incubated on ice for 4 hours. The entire sample (200 µl) was loaded onto a Superdex-200 10/300 gel filtration column, equilibrated with buffer M.

EXAMPLE 2: DEVELOPMENT OF AN ASSAY TO DETECT COUPLING OF NON-LIPIDATED GS TO THE $\beta_1$AR Introduction A myriad of structural and biophysical data has provided clues as to why obtaining a high-resolution structure of a G protein-GPCR complex has proved difficult: flexibility within the nucleotide-free G protein appears to be the main problem[7, 24, 42, 61]. We have engineered a minimal GPCR-binding protein that still couples to a GPCR but removes much of the flexibility that has made crystallisation of the complex so difficult. First, we developed an assay capable of detecting coupling of non-lipidated Gs to the $\beta_1$AR. Next, we expressed the isolated GTPase domain from Gαs and demonstrated that it was able to couple $\beta_1$AR even in the absence of the βγ dimer. However, production of the GTPase domain was difficult due to poor expression and severe thermal instability. Therefore, we performed mutagenic screens and identified mutations that improved both the expression and stability of the isolated GTPase domain, whilst retaining the basic guanine nucleotide binding properties and functionality of the protein. The mutations we discovered are well conserved amongst the heterotrimeric G proteins, and are anticipated to transfer to members of all four classes of α subunits. Therefore, this approach can be used to produce a repertoire of GTPase domains capable of coupling almost all GPCRs. Herein, we describe the design of Minimal, Engineered, G protein Alpha (MEGA) domains, which couple activated GPCRs and induce the core pharmacological and conformational changes associated with the high-affinity agonist-bound state.

Results

Development of an Assay to Detect Coupling of Non-Lipidated Gs to the $\beta_1$AR We have developed a competitive binding assay capable of detecting coupling of purified, non-lipidated Gs (see Experimental Procedures) to cell membranes containing the $\beta_1$AR receptor. Initially, we screened different $\beta_1$AR constructs in order to identify receptors that displayed a large increase in agonist affinity in response to Nb80[38] binding. A near wild-type $\beta_1$AR construct (β6) had a relatively high affinity for isoprenaline (approximately 180 nM), which only increased 3.5 fold in response to Nb80 binding (FIG. 13a). However, a series of minimally thermostabilised receptors displayed a much larger shift in response to Nb80 binding. One of these constructs (β84), which contained four thermostabilising mutations (see Experimental Procedures), was chosen to further characterize Nb80 and Gs coupling. β84 had a much lower affinity for isoprenaline (approximately 7.1 LM), but displayed a more significant shift upon Nb80 binding, resulting in an affinity of approximately 16 nM (FIG. 13b). However, Gs coupling resulted in only a small shift in agonist affinity, from approximately 6.9 µM to 1.4 µM (FIG. 13c). Therefore, we hypothesised that addition of Nb35, which was used to facilitate crystallisation of the $\beta_2$AR-Gs complex[7], may stabilise the complex, and produce a larger shift in agonist affinity. Here, we observed a shift in isoprenaline affinity from approximately 6.9 µM to 68 nM (FIG. 13d), similar to that obtained with Nb80.

Expression and Characterization of the Isolated GTPase Domain of Gαs

A large number of constructs were tested to find the best method of isolating the GTPase domain from Gαs. This process essentially involved deletion of the helical domain from its position within the switch I region. The strategies evaluated were: (1) deletion of the helical domain and any associated regions (residues 57-207) that were disordered in the crystal structure of the $\beta_2$AR-Gs complex[7]; (2) deletion of the helical domain (residues 70-193), and linking the resulting termini with a short glycine linker to retain a near native switch I region; (3) deletion of the helical domain and switch I (residues 65-203), and linking the resulting termini with a longer glycine linker; (4) deletion of the helical domain and switch I (residues 67-205), and insertion of the switch I region from structurally related small GTPases. A number of variations of each strategy were tested, thus residue ranges quoted are approximations. We found that strategy (1) removed regions of the GTPase domain vital for its stability in the absence of the receptor, and was therefore unsuitable. Strategies 2-4 were all successful, and resulted in expression of a small amount of isolated GTPase domain in E. coli (approximately 100 µg/L culture). The expression level between different constructs was variable, but difficult to quantify. Generally, complete removal of the helical domain and switch I (strategy 3) resulted the highest expression levels.

The isolated GTPase domain was partially purified from E. coli, and its ability to couple the $\beta_1$AR was determined using the agonist-shift assay described above. First, we tested coupling of the GTPase domain, but no increase in affinity was observed (FIG. 14a). Second, we tested the GTPase domain in the presence of βγ subunits and Nb35 (FIG. 14a), here a shift in affinity was observed (from approximately 3.3 µM to 206 nM). Finally, we tested coupling of the GTPase domain at 4° C. (FIG. 14b), here a shift in affinity was observed (from approximately 3.9 µM to 253 nM). This demonstrated that the isolated GTPase domain was active, and was able couple the receptor in the absence of βγ subunits. However, it indicated that the GTPase domain was thermally unstable, and would require engineering to produce a stable protein suitable for crystallisation applications.

Stabilization of the GTPase Domain Through Mutagenesis

An initial screen of approximately 50 modifications (mutations, deletions and chimeras) was performed. The modifications were designed to: remove superfluous sequences (compared to the small GTPases), stabilise the nucleotide-binding site, constrain the conformationally dynamic switch regions, stabilise the inactive state of the G protein, or stabilise the active conformation of the G protein. No modifications were made in regions that directly interact with the receptor. The parental construct used for mutagenesis consisted of: a 20 amino acid deletion of the N-terminus, complete deletion of the helical domain, and retention of a slightly modified switch I region (see Experimental Procedures).

Mutants were expressed in E. coli and partially purified by IMAC. In order to estimate the stabilising effect of each modification, agonist-shift assays were performed at 4 and 20° C.; a summary of the assay data is presented in Table 5. The expression levels of the mutants differed widely, thus the concentration of each mutant used in the assays could not be standardised. Instead the entire quantity of protein purified from one litre of culture was included in each assay. Importantly, the concentration of protein used in the assay does affect the magnitude of the shift in agonist affinity. Thus, the data must be interpreted as a combination of expression level and stabilising effect. Four key modifications (Δ switch III, A249D, L272D and H41I), which dramatically improved expression and/or stability of the isolated GTPase domain, were identified (Table 5). Both the A249D mutation and deletion of switch III resulted in significantly improved expression levels (approximately 1-2 mg/L culture); the L272D and H41I mutations did not significantly improve expression levels. All of the mutants induced a large shift in agonist affinity (10-60 nM final isoprenaline affinity) when assayed at 4° C. (Table 5). Furthermore, the A249D and Δ switch III mutants induced a large shift in agonist affinity (53 and 30 nM final isoprenaline affinity respectively) when assayed at 20° C. (Table 5). The L272D and H41I mutants also induced a shift in agonist affinity (464 and 589 nM final isoprenaline affinity respectively) when assayed at 20° C. (Table 5), albeit not as large as the A249D and Δ switch III mutants. However, it must be noted that the concentration of the A249D and Δ switch III mutants used in the assay was approximately 5-fold higher. Four additional mutations (G49D, E50N, G226A and S252D) that improved the stability of the GTPase domain were also identified (Table 5). However, the proximity of these mutations to the aforementioned sites indicates that their mechanism of action is likely to be similar, therefore, their additive properties must be determined empirically.

Discussion

The solution of high-resolution structures of GPCRs in their fully active conformation is of major importance for the design of novel agonist compounds. We have developed a unique strategy to engineer the isolated GTPase domain of G protein α subunits to couple and conformationally activate GPCRs.

Heterotrimeric G proteins can couple GPCRs efficiently in their lipidated, membrane associated state[5]. MEGA domains include non-lipidated mutant Gα subunits, whose mechanism of receptor binding is anticipated to be similar to that of the holoenzyme. Therefore, a prerequisite to the design of MEGA domains was the development of an assay capable of detecting coupling of non-lipidated G proteins to GPCRs. Initially, we found that non-lipidated Gs induced only a small shift in agonist affinity for a minimally thermostabilised $β_1AR$. However, addition of Nb35, which was used to facilitate crystallisation of the $β_2AR$-Gs complex[7], produced a much larger response. Nb35 appears to inhibit dissociation of the G protein heterotrimer by conformationally constraining the switch II region, and stabilising the α/β subunit interface. Nb35 is therefore likely to reduce the conformational dynamics of the GPCR-G protein ternary complex, possibly mimicking the stabilising effect of membrane anchorage, albeit through a different mechanism.

We assessed several different strategies to isolate the GTPase domain from Gs. We found that complete removal of the helical domain and switch I resulted in slightly better expression and stability. Initially, we found that the GTPase domain induced a significant shift in agonist affinity only in the presence of βγ dimer and Nb35, suggesting that βγ subunits were still required for efficient coupling. However, we hypothesised that the βγ dimer and Nb35 may simply act to stabilise the thermally labile GTPase domain[28]. Therefore, we repeated the assays at 4° C., and found that the GTPase domain was capable of efficiently coupling the receptor in a βγ-independent manner. GPCRs can catalyse low-level nucleotide exchange on Gα subunits[4], however, the βγ dimer is required to facilitate rapid exchange and thus signal amplification[56,57]. Deletion of the helical domain allows efficient coupling of the GTPase domain to the receptor, in a βγ-independent manner. This is probably due to more rapid GDP dissociation from the GTPase domain, which results in more efficient coupling the receptor. Together, these data suggests that the mechanism of interaction between the receptor and the isolated GTPase domain is similar to that of the holoenzyme. Therefore, MEGA domains are likely to induce native-like conformational changes in the receptor, and thus represent a true mimetic of G protein coupling.

We used mutagenesis to improve the stability and expression of the GTPase domain. A number of key mutations were identified that dramatically improved the expression level and/or stability of the GTPase domain, the mechanisms of which are discussed below. The A249D mutation improved both the expression and stability of the GTPase domain. In the small GTPases an aspartic acid is often found in this position, where it stabilises the lysine of the NKXD motif through a salt-bridge interaction. This lysine residue forms the base of the nucleotide-binding pocket and participates in a π-cation stacking interaction with the guanine ring[92]. This position is not exclusively occupied by an aspartic acid in the small GTPases, however within each class it is generally conserved or non-conserved, indicating that it may be inherent to the stability of certain GTPase families. In heterotrimeric G proteins this position is occupied by either an alanine or serine residue, except Gαz, where a glutamic acid residue is present. However, the lysine from the NKXD motif is stabilized through a salt-bridge interaction with an aspartic or glutamic acid from the helical domain (Asp-173 in Gαs). This interaction is broken when the domain interface separates during activation[7]. The A249D mutation is thought to stabilise the nucleotide-binding pocket and increase the GDP binding affinity, although this has not yet been tested.

Deletion of switch III improved both the expression and stability of the GTPase domain. In heterotrimeric G proteins switch III is involved in mediating the conformational changes induced by GTP uptake, and is required for effector binding[93]. In the small GTPases switch III is absent and the corresponding region consists of distinct secondary structural elements: the β4 strand terminates in a type-I turn, which connects directly to a $3_{10}$ helical segment preceding the α3 helix (secondary structure assignments were performed using the STRIDE web-server[94, 95]). The improvements in stability achieved by deletion of switch III are likely to be a result of replacing a highly flexible loop with more ordered secondary structure elements. The increase in expression level is likely to result from a combination of the improved stability and a more energetically favourable folding pathway.

The H41I mutation significantly improved the stability of the isolated GTPase domain. Histidine 41 has been reported to contribute significantly to the elevated levels of basal nucleotide exchange observed in Gαs compared with Gt[96]. It was previously reported that mutation of histidine 41 to valine, which is found in this position in Gt, halved the level of basal nucleotide exchange of Gαs[96]. We showed that the H41V mutation improved the stability of the MEGA domain (see Table 5), however, the H41I mutation was optimal in this position. This mutation improves the stability of the GTPase domain because it enhances the interactions between the α5 helix and the αN/β1 loop. Close packing in this region stabilises the α5 helix, thus reducing the rate of GDP dissociation[96].

The L272D mutation, which is located in the α2 helix (adjacent to switch II), significantly improved the stability of the isolated GTPase domain. Switch II changes structure dramatically between GDP and GTP-bound states[97]: in the GDP bound state switch II is more dynamic, and often disordered in crystal structures[98]; in the GTP-bound state switch II becomes highly ordered[30,99], and in Gs this region forms the main effector-binding site[100]. The L272D mutation is likely to directly interact with switch II, and conformationally constrain the whole region. Intriguingly, it may form a salt bridge interaction with a highly-conserved arginine residue in switch II (Arg-231), which is ideally positioned for such an interaction in the GTP-bound state[30]. This is likely to improve the stability of the GTPase domain by limiting exposure of the hydrophobic residues beneath switch II to the aqueous environment.

In summary, we have demonstrated that, despite being unstable and poorly expressed, the isolated GTPase domain from Gαs can efficiently couple the β$_1$AR in a βγ-independent manner. We have performed an extensive mutagenesis screen and identified four key mutations, which dramatically increase the expression and/or stability of the domain.

Methods and Materials

β$_1$AR Constructs

The 384 construct, which was used for G protein binding assays, contained a number of modifications: an N-terminal MBP fusion protein; N-terminal truncation (residues 1-32); intracellular loop 3 deletion (residues 244-271); C-terminal truncation at residue 367; C-terminal hexa histidine-tag; a C116L mutation; an engineered disulphide bond (M40C-L103C); and four thermostabilising mutations (M90V, D322K, F327A and F338M). The receptor was expressed using the BaculoGold baculovirus expression system (BD Bioscience) in the *Trichopulsia ni* (High Five) cell line (Life Technologies).

Gαs GTPase Domain Constructs

The parental GTPase domain used for the initial mutagenesis screens is described below (all numbering refers to the long isoform of Gαs). The construct consisted of: an N-terminal hexa histidine-tag; N-terminal deletion (residues 1-20); helical domain deletion (residues 71-193), leaving a near native switch I intact, and linking the termini with a Gly$_2$ linker; and two mutations in switch I region (L197A and C200S), to remove unfavorable surface residues exposed by removal of the helical domain.

Expression and Purification of Heterotrimeric Gs

Non-lipidated heterotrimeric Gs used in this study was composed of: human Gαs (long-form: including the variably spliced region in linker-1), which contained a four amino acid deletion of the N-terminus to remove all potential palmitoylation sites[101]; human Gβ1 (containing an N-terminal hexa histidine-tag); and human Gγ2 containing a C68S mutation to remove the prenylation site[102]. Baculovirus constructs encoding each individual subunit were constructed using the flashBAC ULTRA system (Oxford Expression Technologies). The Gs heterotrimer was expressed in *Spodoptera frugiperda* (SF9) cells grown in TNM-FH media (Sigma) containing 10% foetal calf serum (Gibco) and 1% lipids (BD Bioscience). Cells were infected using P3 virus at concentration of 2% for each subunit, in a 1:1:1 ratio. Cells were incubated for 48 hours at 27° C. Cells were harvested by centrifugation at 4000 g for 10 minutes and washed with of PBS (15% of culture volume). The cell pellet was flash frozen in liquid nitrogen and stored at −80° C.

The cell pellet from three litres of culture was resuspended in 150 ml of lysis buffer (30 mM Tris, 100 mM NaCl, 10% glycerol, 5 mM MgCl$_2$, 100 μM GDP, 0.5 mM PMSF, 2.5 μM Pepstatin-A, 10 μM Leupeptin, 50 μg/ml DNaseI, 50 μg/ml RNaseA, pH 8.0) containing Complete EDTA-free protease inhibitors, and DTT was added to a final concentration of 0.1 mM. The cells were broken by sonication, and insoluble material removed by centrifugation at 38000 g for 40 minutes. The supernatant was filtered (0.45 μM) and loaded onto a 5 ml Ni-Sepharose fast flow HisTrap column (GE Healthcare) at 5 ml/min. The column was washed with ten column volumes of lysis buffer, followed by ten column volumes of wash buffer (20 mM Tris, 250 mM NaCl, 5 mM imidazole, 10% glycerol, 1 mM MgCl$_2$, 50 μM GDP, pH 8.0) at 5 ml/min. The column was eluted with 25 ml elution buffer (20 mM Tris, 50 mM NaCl, 200 mM imidazole, 10% glycerol, 1 mM MgCl$_2$, 50 μM GDP, pH 8.3) at 2 ml/min. The eluent was diluted with 225 ml of Q buffer (20 mM Tris, 50 mM NaCl, 10% glycerol, 0.5 mM MgCl$_2$, 50 μM GDP, 1 mM DTT, pH 8.3). The mixture was loaded directly onto a 5 ml Q-Sepharose HP HiTrap column (GE Healthcare) at 5 ml/min. The column was washed with ten column volumes of Q buffer at 5 ml/min. Gs was eluted with a linear NaCl gradient from 50 mM to 250 mM (Q buffer containing 250 mM NaCl) over 40 column volumes at 2 ml/min. Fractions containing Gs were pooled and concentrated to 5-10 mg/ml using a 10 KDa cut off Amicon Ultra concentrator (Millipore). Concentrated Gs was loaded onto a Superdex-200 (16/60) gel filtration column (GE Healthcare) equilibrated with GF buffer (20 mM Tris, 100 mM NaCl, 10% glycerol, 0.2 mM MgCl$_2$, 2 μM GDP, 0.1 mM TCEP, pH 8.0) at 1 ml/min. Fractions containing pure Gs were pooled, concentrated to 10 mg/ml, flash frozen in liquid nitrogen and stored at −80° C. The typical yield was 1-2 mg of pure Gs per litre of culture.

Expression and Purification of Nb35

The Nb35[10] gene was synthesised (Integrated DNA Technologies) and cloned into the pET26b vector (Merck). Nb35 was expressed in BL21(DE3)-RIL cells (Merck). Cultures were grown in terrific broth media, supplemented with glucose (0.1%) and MgSO$_4$ (2 mM), to an OD$_{600\ nm}$ of 0.8 at 37° C. Expression was induced with IPTG (50 μM), at 28° C. for approximately 18 hours. Cells were harvested by centrifugation at 4000 g, and stored at −80° C.

The cell pellet from six litres of culture was resuspended in 200 ml of lysis buffer (40 mM Hepes, 100 mM NaCl, 5 mM imidazole, 5 mM MgCl$_2$, 1 mM PMSF, 100 μg/ml lysozyme, 50 μg/ml DNaseA, pH 7.5) containing Complete EDTA-free protease inhibitors. The cells were incubate on ice for 30 minutes, then broken by sonication, and insoluble material removed by centrifugation at 38000 g for 30 minutes. The supernatant was filtered (0.45 µM) and loaded onto a 5 ml Ni-Sepharose fast flow HisTrap column (GE Healthcare) at 5 ml/min. The column was washed with 15 column volumes of wash buffer (20 mM Hepes, 300 mM NaCl, 40 mM imidazole, pH 7.5) at 5 ml/min. The column was eluted with 25 ml elution buffer (20 mM Hepes, 500 mM imidazole, pH 7.0) at 2 ml/min. The eluent was diluted with 225 ml of SP buffer (20 mM Hepes, pH 7.0), and loaded directly onto a 5 ml SP-Sepharose HP HiTrap column (GE Healthcare) at 5 ml/min. The column was washed with ten column volumes of SP buffer at 5 ml/min. Nb35 was eluted with a linear NaCl gradient from 0 mM to 250 mM (SP buffer containing 250 mM NaCl) over 40 column volumes at 2 ml/min. Fractions containing Nb35 were pooled and dialysed against 500 ml of GF buffer (20 mM Tris, 100 mM NaCl, 10% glycerol, pH 7.5) overnight, with two external buffer changes. Nb35 was concentrated to 20 mg/ml using a 3 KDa cut off Amicon Ultra concentrator (Millipore). Concentrated Nb35 was loaded onto a Superdex-200 (16/60) gel filtration column (GE Healthcare) equilibrated with GF buffer at 1 ml/min. Fractions containing pure Nb35 were pooled, concentrated to 20 mg/ml, flash frozen in liquid nitrogen and stored at −80° C. The typical yield was 5 mg of pure Nb35 per litre of culture.

Partial Purification of Gαs GTPase Domains for Use in Agonist-Shift Assays

GTPase domains were expressed in BL21(DE3)-RIL cells. Cultures were grown in 2TY media, supplemented with glucose (0.1%), to an $OD_{600}$ nm of 0.5-0.8 at 25° C. Expression was induced with IPTG (100 µM), at 15° C. for approximately 16 hours. Cells were harvested by centrifugation at 4000 g, and stored at −80° C.

The cell pellet from two litres of culture was resuspended in 22 ml of lysis buffer (30 mM Tris, 100 mM NaCl, 10 mM imidazole, 20% glycerol, 5 mM $MgCl_2$, 3 mM ATP, 100 µM GDP, 0.5 mM PMSF, 2.5 µM Pepstatin-A, 10 µM Leupeptin, 50 µg/ml lysozyme, 20 µg/ml DNaseI, pH 7.5) containing Complete EDTA-free protease inhibitors. DTT (0.1 mM) was added and the cells were incubated on ice for 30 minutes. The cells were broken by sonication, and insoluble material removed by centrifugation at 50000 g for 40 minutes. The supernatant was filtered (0.45 µM), 1 ml Ni-Sepharose fast flow resin (GE Healthcare) was added, and the suspension was mixed at 4° C. for 1.5 hours. The mixture was poured into an empty PD10 column (GE Healthcare) and washed with 20 ml of wash buffer (20 mM Tris, 300 mM NaCl, 40 mM imidazole, 20% glycerol, 1 mM $MgCl_2$, 50 µM GDP, pH 7.5). The column was eluted with 2.5 ml elution buffer (20 mM Tris, 100 mM NaCl, 400 mM imidazole, 20% glycerol, 1 mM $MgCl_2$, 50 µM GDP, pH 7.5). The partially purified protein was desalted into GF buffer (20 mM Tris, 100 mM NaCl, 10% glycerol, 1 mM $MgCl_2$, 50 µM GDP, 0.1 mM DTT, pH 7.5) using a PD10 column (GE Healthcare). The desalted protein was concentrated to a final volume of 400 µL using a 10 KDa cut off Amicon Ultra concentrator (Millipore). The concentrated protein was flash frozen in liquid nitrogen and stored at −80° C.

Agonist-Shift Assay

The cell pellet from approximately 2 ml of High Five culture expressing the 384 receptor construct was resuspended in 1 ml of lysis buffer (20 mM Tris, 100 mM NaCl, 1 mM $MgCl_2$, 1 mM ascorbic acid, pH 7.5) containing Complete EDTA-free protease inhibitors (Roche). Cells were lysed by 10 passages through a bent 26 G needle, and insoluble material removed by centrifugation (5 mins at 3000 g). The supernatant, containing crude membrane fractions, was diluted to 8 ml in lysis buffer (0.8 ml per competition curve required). G protein, MEGA domain, Nb80 or buffer (200 µl) was added to the crude membranes (0.8 ml), and homogenised by 3 passages through a bent 26 G needle. The final concentration of G protein or Nb80 used in the assay was approximately 1 mg/ml; the final concentration of MEGA domains used depended on their expression levels. Nine aliquots (88 µl each) were transferred to a 96-well PCR plate (on ice). Isoprenaline (11 µl) was added to seven samples to give final competitive ligand concentration curve of $1\times10^{-3}$-$1\times10^{-9}$ M; isoprenaline dilutions were prepared in lysis buffer containing 1 U/ml apyrase (Sigma). Buffer (11 µl) was added to one of the remaining samples to determine total signal, and alprenolol (11 µl) was added to the final sample to determine background signal (100 µM final concentration). Samples were incubated at 4° C. for 2 hours (or at 20° C. for 1 hour). $^3$H-dihydroalprenolol (Perkin Elmer) was added to each well (11 µl) to give a final concentration of 10 nM (≤Kd of β84). Samples were incubated at 4° C. for 2 hours (or at 20° C. for 1 hour). Samples were filtered on 96-well GF/B filter plates (Millipore), pre-soaked in lysis buffer containing 0.1% PEI. Plates were washed three times (200 µl) with ice-cold wash buffer (20 mM Tris, 100 mM NaCl, 1 mM $MgCl_2$, pH 7.5). Plates were dried and filters punched out into scintillation vials. Scintillant (4 ml) was added, samples were incubated overnight and then tritium was counted in a liquid scintillation counter (Beckmann Coulter). Data were analysed using the 'one site—fit log IC50' function of Prism (GraphPad).

EXAMPLE 3: APPLICATIONS

MEGA domains have a wide range of applications in the design of therapeutics to modulate GPCR and G protein activity.

Stabilisation of GPCRs During Purification

GPCRs are conformationally dynamic, which contributes to their poor thermostability in detergent[69]. MEGA domains are likely to conformationally and thermally stabilise GPCR, and will therefore improve the efficiency of purification procedures.

Thermostabilisation of GPCRs in their Fully Active Conformation

MEGA domains are likely to significantly improve the thermostability of their bound GPCR. However, further dramatic improvements in stability may be achieved through mutagenic thermostabilisation of the receptor[88] whilst in complex with the MEGA domain. The resulting MEGA-StaR complex will be highly stable, and suitable for even the most demanding applications. Furthermore, GPCRs thermostabilised in this manner may adopt a fully active conformation even in the absence of the MEGA domain or ligand, providing a unique opportunity for drug design.

Structure Determination of GPCRs in their Fully Active Conformation

The stabilising properties of MEGA domains will permit high-resolution structure determination of the high-affinity agonist-bound state of GPCRs, using both x-ray crystallography and NMR.

Fragment Library Screening Against Activated GPCRs

MEGA domains may also be a valuable tool for fragment library screening using both structural and non-structural methods. There is strong evidence to suggest that once the ternary G protein-GPCR complex is formed the ligand can be removed from the binding pocket without causing dissociation of the complex: hydroxylamine treatment of the nucleotide-free rhodopsin-transducin complex causes hydrolysis of the Schiff base bond between rhodopsin and retinal, resulting in the release of retinaloxime[14]. However, this causes neither dissociation of the complex, or decay of the Meta-II photochemical state into inactive opsin, furthermore the chromaphore site appears to remain in its open conformation[14]. Therefore it may be possible to produce a ligand-free MEGA-GPCR complex in which the empty ligand-binding pocket maintains the high-affinity agonist-bound conformation. Ligand-free complexes represent an ideal substrate for fragment library screening using biophysical methods or crystal soaking techniques. These complexes will also be of significant importance for the design of agonists to target orphan receptors.

Screening Compounds that Block Specific G Protein-GPCR Interfaces

The ligand-binding pocket and extracellular surface of GPCRs are the main targets exploited in drug design, however, downstream signalling proteins also have significant therapeutic potential. Several peptides and small molecules that modulate G protein α subunits have been reported[70-72]. Although these molecules generally target a single class of G protein, the promiscuous nature of the G protein signalling means they are unlikely to be suitable for therapeutic applications. Structures of MEGA-GPCR complexes will allow the design of small molecules that target a specific G protein-receptor interface. Thus, signalling through a specific G protein-receptor pair could be inhibited, whilst retaining the activity of both the receptor and G protein in other signalling cascades.

Development of Cell-Based Assays

Due to their monomeric nature, MEGA domains will be useful in the development of fluorescent assays to study receptor/G protein coupling in vivo.

Understanding the Molecular Mechanisms of Receptor Specificity

MEGA domains may also allow us to determine the molecular mechanisms of receptor specificity beyond the Gα-GPCR interface. MEGA domains can be reconstituted with different combinations of βγ subunits, these GPCR-MEGA-βγ complexes may be more amenable to crystallisation than the full G protein-GPCR complexes. Therefore, the interactions between C-terminus of the receptor and the βγ subunits can be studied. This may allow design of allosteric modulators that can target specific GPCR-G protein complexes, based on the βγ components of the G protein heterotrimer.

MEGA Domains as Therapeutic Agents

MEGA domains can be engineered to sequester GPCRs, βγ subunits or downstream effectors. These dominant negative mutants may themselves be valuable therapeutic agents, for example in cancer therapy.

EXAMPLE 4: STRUCTURE OF THE ADENOSINE $A_{2A}$ RECEPTOR BOUND TO AN ENGINEERED G PROTEIN

Introduction

G protein-coupled receptors (GPCRs) are essential components of the chemical intercellular signalling network throughout the body. To understand the molecular mechanism of signalling, structures are necessary of receptors in both an inactive conformation and in an active conformation coupled to a heterotrimeric G protein. Here we report the first structure of the adenosine $A_{2A}$ receptor ($A_{2A}R$) bound to a highly engineered G protein, mini-$G_s$, to 3.4 Å resolution. Mini-$G_s$ binds to $A_{2A}R$ through an extensive interface (1048 Å[105]) that is similar, but not identical, to the interface between the $β_2$-adrenergic receptor and $G_s$. The structure of $A_{2A}R$ bound to mini-$G_s$ identifies key amino acid residues involved in the transition of the receptor from an agonist-bound active-intermediate state to the fully active G protein bound state. The structure highlights both the diversity and similarity in GPCR-G protein coupling and hints at the potential complexity of the molecular basis for G protein specificity.

Adenosine is a signalling molecule that activates four different adenosine receptors in humans, $A_1$, $A_{2A}$, $A_{2B}$ and $A_3$, and has been implicated in a wide range of physiological processes including angiogenesis, immune function and sleep regulation (reviewed in[104,105]). In addition, there is strong evidence that high concentrations of extracellular adenosine is deleterious to cell health and contributes to pathological effects observed in neurodegenerative diseases, inflammatory disorders, cancer and ischaemia-reperfusion injury (reviewed in[106]). There is thus considerable interest in the development of subtype specific agonists and antagonists to the adenosine receptors. Over the last 40 years a wide range of compounds have been developed by traditional medicinal chemistry[105,107] and, more recently, structure based drug design has been implemented to develop novel antagonists of the adenosine $A_{2A}$ receptor ($A_{2A}R$) for the potential treatment of Parkinson's disease[108]. An agonist targeting $A_{2A}R$ (regadenoson) is approved by the FDA for myocardial perfusion imaging[107] and agonists specific for $A_3R$ are under development for their anti-cancer and anti-inflammatory properties[109].

Comparison of the structures of $A_{2A}R$ bound to either inverse agonists[110-112] or agonists[1,4,113] elucidated molecular determinants of subtype specificity and efficacy[114]. However, the mechanism of activation of the receptor to allow coupling to G proteins and the basis of G protein selectivity is not fully understood. Structures of $A_{2A}R$ in the inactive state have been determined bound either to the antagonists ZM241385[110-112], XAC110, caffeine[110] or 1,2,4-triazines[108], and all the structures are very similar. An intramembrane $Na^+$ ion that can act as an allosteric antagonist was identified in the highest resolution structure (1.8 Å)[115], and a homologous $Na^+$ ion has been subsequently identified in other high-resolution structures of GPCRs[96,116,117]. Four agonist-bound structures of $A_{2A}R$ have also been determined after co-crystallisation with either adenosine[1], NECA[1], CGS21680[113] or UK432097[4]. All the structures are very similar and are thought to represent an active-intermediate conformation of the receptor, but not the fully active receptor that binds a G protein[1]. Observations that support this conclusion include the presence of key rotamer changes of conserved amino acid residues associated with activation of other GPCRs, but the absence of a significant movement of the cytoplasmic end of transmembrane helix 6 (H6) away from the receptor core[114]. The G protein-coupled state of $A_{2A}R$ exhibits higher affinity binding of agonists compared to the uncoupled state[18], but it is unclear whether the agonist bound structures determined so far depict the binding pocket in a high affinity or low affinity conformation. In contrast to $A_{2A}R$, crystallisation of either $β_1AR$ or $β_2AR$ bound to agonists resulted in structures of the inactive conformation that differ only subtly from structures bound to antagonists[2,3]. It is now apparent that $β_2AR$ exists in an ensemble of conformations whether bound to antagonists, agonists or to no ligand at all, and the presence of agonists increases the probability of formation of the active state[119]. The activated state is then stabilised by the binding of a G protein[10] or by a G protein mimetic (nanobody)[38]. Therefore, in order to elucidate the structure of the activated state of $A_{2A}R$, we have determined its structure bound to an engineered G protein.

Results

Structure of G Protein-Bound $A_{2A}R$.

Figure 17:
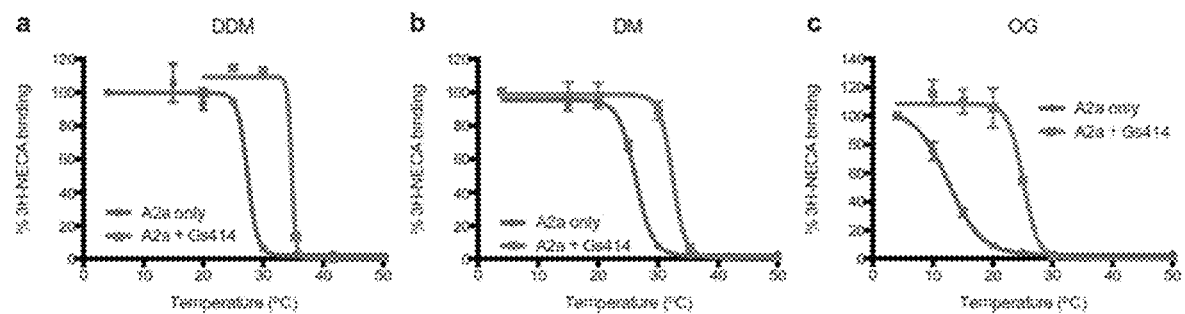

There is a single reported structure of a GPCR bound to a heterotrimeric G protein, namely $G_s$-bound $\beta_2AR$[10]. The crystallisation was a real tour de force, requiring the development of a specific nanobody, Nb35, to stabilise the $G\alpha\beta\gamma$ trimer by binding at the interface between $G\alpha$ and $G\beta$, fusion of T4-lysozyme to the N-terminus of $\beta_2AR$, the use of a novel mono-olein derivative MAG 7:7 for crystallisation in meso and a complex procedure for purification and crystallisation. The $\beta_2AR$-$G_s$ structure[10] showed that virtually all the contacts between the receptor and G protein were made to the $G\alpha$ subunit and therefore, in theory, $G\beta\gamma$ was unnecessary for complex formation. We therefore adopted an alternative approach, engineering the $G\alpha_s$ subunit to make it more amenable for the formation of well-ordered crystals, which in principle should allow the crystallisation of any $G_s$ coupled receptor in the activated state[120]. We developed a minimal G protein, mini-$G_s$, that comprised a truncated form of the GTPase domain of $G\alpha_s$, including 8 point mutations to stabilise the protein in the absence of $G\beta\gamma$ and in the presence of detergents[120]. Truncations included the switch III region, 23 amino acids from the N-terminus and the $\alpha$-helical domain, all of which would benefit crystal formation by decreasing the structural heterogeneity of the complex. Mini-$G_s$ reproduced the increase in agonist affinity that occurred upon incubation of the receptor in the presence of the heterotrimeric G protein $G_s$ and it also showed identical sensitivity to the presence of the allosteric antagonist $Na^+$ (FIGS. 15 and 16). In addition, mini-$G_s$ readily formed a complex with $A_{2A}R$ in the presence of the agonist NECA and the complex was considerably more thermostable than NECA-bound $A_{2A}R$, particularly in short chain detergents (FIG. 17). This complex was crystallised in the detergent octylthioglucoside by vapour diffusion and a data set was collected from two crystals (see further methods). The $A_{2A}R$-mini-$G_s$ structure was determined by molecular replacement using the structure of NECA-bound $A_{2A}R$ (PDB ID: 2YDV)[1] and the $G\alpha_s$ GTPase domain from the $\beta_2AR$-$G_s$ complex (PDB ID: 3SN6)[10] as search models and the structure refined to 3.4 Å (Table 6).

There are two mini-$G_s$-$A_{2A}R$ complexes per crystallographic asymmetric unit composed of either chains A and C (complex AC) or chains B and D (complex BD). The best electron density was observed for complex AC (chain A, $A_{2A}R$; chain C, mini-$G_s$), and included density for the agonist NECA bound to $A_{2A}R$ and density for a molecule of GDP bound to mini-$G_s$ (FIG. 18). Chain B ($A_{2A}R$) in complex BD also contained density for NECA, but chain D (mini-$G_s$) did not contain density corresponding to GDP. It is unclear from the structure why the two molecules of mini-$G_s$ differ in GDP occupancy, because the structures are virtually identical (rmsd 0.12 Å over 1127 atoms) and although the GDP site in chain D is in the vicinity of extracellular loop 2 of a symmetry related receptor (chain A), this loop is disordered and there is no suggestion that it would prevent nucleotide binding. The presence of GDP in the mini-$G_s$ structure is a reflection of the properties of the engineered G protein, which, after complex formation, is insensitive to GTP$\gamma$S-mediated dissociation[120]. Thus this structure can be regarded as a complex between a GPCR and a GDP-bound G protein before GDP has dissociated. The two $A_{2A}R$ molecules in the asymmetric unit are also virtually identical (rmsd 0.05 Å over 1665 atoms), but differ significantly to previously determined $A_{2A}R$ structures due to the outward movement of the cytoplasmic end of transmembrane helix 6 (H6; discussed below). Structural alignment of complex AC with complex BD showed that mini-$G_s$ was oriented slightly differently between the receptors with a rotation of the GTPase domain by 3° relative to the receptor, and results in slightly different packing between mini-$G_s$ and $A_{2A}R$ (FIG. 19). While it is possible that this is due to the presence of GDP in one complex but not the other, it seems more likely that it arises from differences in lattice contacts. Even so, this may represent a natural variation in the interface between mini-$G_s$ and $A_{2A}R$ due to the flexible nature of the activated G protein and the receptor. All subsequent analyses will be discussed in the context of complex AC, as the electron density for this complex was better defined, especially for some of the residues involved in the interactions between mini-$G_s$ and $A_{2A}R$.

The interface between $A_{2A}R$ and mini-$G_s$ in complex AC is formed between 20 amino acid residues from the receptor and 17 residues in mini-$G_s$ (FIGS. 19, 20 and 21), comprising a total buried surface area of 1048 Å[105] on the receptor. It is striking that of the 20 amino acid residues in contact with mini-$G_s$, there are 6 Arg residues, 10 hydrophobic residues and 2 Gln residues. The main areas in the receptor that contact mini-$G_s$ are found at the cytoplasmic end of H3, cytoplasmic loop 2 (CL2), the cytoplasmic end of H5, three residues in H6 and a positively charged region at the turn between H7 and H8 (FIG. 20). In mini-$G_s$, contacts are made predominantly by the $\alpha$5 helix involving 14 amino acid residues that pack against residues in H3, CL2, H5, H6, H7 and H8 of $A_{2A}R$. Additional interactions include His41$^{S1.2}$ in $\beta$-sheet S1, Val217$^{S3.1}$ in S3 and Asp215$^{S253.1}$ in the loop between S2 and S3 that make contact with residues in CL2 in $A_{2A}R$ (FIG. 22; superscripts refer to the CGN system for G proteins[103]). Amino acid residues in $A_{2A}R$ and mini-$G_s$ form complementary surfaces that pack together predominantly via van der Waals interactions (~90% of contacts) with 6 polar interactions across the interface. This complementarity is particularly evident in the packing of the sequence PLRY in CL2 of $A_{2A}R$ against residues in S1, S3, the S2-S3 loop and $\alpha$5, with Leu110 sitting in a pocket formed from His41$^{S1.2}$, Val217$^{S3.1}$, Phe376$^{H5.8}$, Cys379$^{H5.11}$ and Arg380$^{H5.12}$. Helix $\alpha$5 protrudes into the cleft within the cytoplasmic face of $A_{2A}R$ created through the outward movement of the cytoplasmic end of H6, with the apex of the $\alpha$5 helix, Tyr391$^{H5.23}$, making extensive van der Waals interactions with Arg102$^{3.50}$ (superscript refers to the Ballesteros-Weinstein numbering system for GPCRs[121]) that forms the whole upper surface of the cleft (FIG. 22). The overall orientation of the $\alpha$5 helix may also be facilitated by the favourable helix dipoles between H8 of the receptor and $\alpha$5, which form a nearly contiguous kinked helix.

Comparison of the Receptor-G Protein Interface in $\beta_2AR$-Gs and $A_{2A}R$-Mini-Gs Structures Superposition of the receptors in the $A_{2A}R$-mini-$G_s$ complex and the $\beta_2AR$-$G_s$ complex[10] shows that the receptors have very similar architectures (rmsd 1.7 Å over 1239 atoms), with the majority of the differences occurring in the extracellular region where the amino acid sequences are the most divergent (FIG. 22). In contrast, the intracellular faces of the receptors align very well, including the large outward shift of the cytoplasmic end of H6. However, mini-$G_s$ does not superimpose exactly on the $G\alpha$ subunit of the heterotrimeric G protein bound to $\beta_2AR$ (FIG. 22), with a difference in orientation of ~15°, although the difference is smaller (~10°) for the α5 helix. This is a consequence of the different amino acid residues in $A_{2A}R$ compared to $β_2AR$ (FIGS. 18 and 22), which results in a slightly different packing of the G proteins to the receptors. However, alignment of mini-$G_s$ with $Gα_s$ bound to $β_2AR$ shows that they are essentially identical (rmsd 0.92 Å over 1158 atoms), with the most significant difference being an 8° tilt between the respective α5 helices, resulting in a 3.7 Å displacement of the Cα of Tyr391 in mini-Gs away from the core of the G protein (FIG. 23). Strikingly, the most significant difference between the mini-$G_s$-$A_{2A}R$ interface compared to the Gs-$β_2AR$ interface also occurs in this region as a result of the different amino acid sequences at the H7-H8 boundary. In $A_{2A}R$, H7 terminates with Arg291$^{7.56}$ and forms the sequence R$^{7.56}$IREFR (amino acid residues in italics do not contact mini-$G_s$), compared to the sequence S$^{7.56}$PDFRI in the equivalent position of $β_2AR$, where none of the residues make contacts with $Gα_s$. In $A_{2A}R$, Arg291$^{7.56}$ forms a hydrogen bond with the carbonyl group of Tyr 391$^{H5.23}$, with van der Waals contacts also being made by Arg291$^{7.56}$, Ile292 and Arg293 to helix α5 in mini-$G_s$. Another region of the receptors that differs in the presence/absence of contacts to their respective G proteins is at the end of H5. In $β_2AR$, H5 extends an additional turn compared to $A_{2A}R$ where this region is disordered in the structure, perhaps because the CL3 loop in $A_{2A}R$ is 18 amino acid residues shorter than in $β_2AR$. Therefore, in $β_2AR$, additional contacts are made between the receptor (Ile233$^{5.72}$, Lys235$^{5.74}$, Ser236$^{5.75}$ and Arg239$^{5.78}$) and Gαs (Asp323$^{H4.3}$, Asp343$^{H4.23}$, Leu346$^{H4.26}$, Arg347$^{H4.27}$, T350$^{H4.S6.3}$ and Y358$^{H4.S6.11}$) that are not present in the $A_{2A}R$-mini-Gs structure (FIGS. 17 and 18).

Although there are significant differences in receptor-G protein contacts, there are also many similarities (FIG. 3). For example, at the cytoplasmic end of H3 the carbonyl groups of Ile$^{3.54}$ and Arg$^{3.55}$ (Thr$^{3.55}$ in $β_2AR$) in both $A_{2A}R$ and $β_2AR$ form the hydrogen bonds Ile$^{3.54}$-Gln$^{H5.16}$ and Arg$^{3.55}$-Arg$^{H5.12}$, although in the $β_2AR$-Gs complex Gln$^{H5.16}$ makes an additional hydrogen bond to the side chain of Glu$^{5.64}$, which is Ala in $A_{2A}R$. In both receptors, Gln$^{5.68}$ makes two hydrogen bonds to the G protein, but in $β_2AR$ these are to Gln$^{H5.16}$ and Arg$^{H5.17}$, whereas in $A_{2A}R$ the interaction to Gln$^{H5.16}$ is identical but the second hydrogen bond is to the backbone carbonyl group of Asp$^{H5.13}$. In another example, Asp$^{H5.13}$ forms hydrogen bonds to both receptors, but this consists of a salt bridge to Lys$^{5.71}$ in $β_2AR$ compared to a single hydrogen bond to Gln$^{5.71}$ in $A_{2A}R$. From these examples it is clear that although a very few contacts are identical, the majority are similar, differing in the specifics of the amino acid side chains involved, their conformation at the interface and the nature of the interaction.

Conformational Changes in $A_{2A}R$ Upon Mini-$G_s$ Binding

Previously reported structures of $A_{2A}R$ bound to agonists are in an active-intermediate conformation[1,4,113]. This assignment is based on the similarities of rotamer changes in the receptor core and the movement of transmembrane helices that are also observed in the structures of the active state of $β_2AR$ bound to a nanobody[36] and rhodopsin in an active state[36,122]. However, as the extent of H6 movement in agonist-bound $A_{2A}R$ is less than one half of that observed in the other receptors, there would be insufficient room in the cytoplasmic cleft to accommodate the C-terminal peptide of a G protein[1]. Comparison of the active-intermediate state of UK432097-bound $A_{2A}R$[12] with the structure of $A_{2A}R$ bound to mini-$G_s$ identified major re-arrangements in the cytoplasmic half of the receptor core to accommodate G protein binding (FIG. 24) and will be described in terms of the re-arrangements required to transition from the active-intermediate state to the G protein-bound conformation. Firstly, the cytoplasmic end of H6 moves away from the receptor core by 14 Å as measured between the Cα atoms of Thr224$^{6.26}$. This movement is achieved through H6 bending outwards with little discernible rotation around the helix axis. The extent of H6 movement is dictated by van der Waals interactions between Lys227$^{6.29}$, Ala231$^{6.33}$ and Leu235$^{6.37}$ in $A_{2A}R$ and Leu393$^{H5.25}$ and the carboxy terminus of mini-$G_s$. The movement of H6 requires significant changes in the packing of the cytoplasmic end of H6 with helices H5 and H7. In particular, the side chains of highly conserved Tyr197$^{5.58}$ and Tyr288$^{7.53}$ both adopt new rotamers to fill the space previously occupied by the side chains of Leu235$^{6.37}$ (whose Cα moves by 3.7 Å) and Ile238$^{6.40}$ (Cα moves by 2.2 Å) respectively. The shift in Tyr288$^{7.53}$ allows Arg102$^{3.50}$ of the conserved DRY motif to adopt a fully extended conformation, packing against the side chain of Tyr391$^{H5.23}$ in the α5 helix of mini-$G_s$.

In contrast to the considerable re-arrangements of the cytoplasmic half of the receptor to allow mini-$G_s$ binding, there are no significant changes in the extracellular half of the receptor when the NECA-bound $A_{2A}R$-mini-$G_s$ structure is compared to NECA-bound $A_{2A}R$ (FIG. 24). Thus the disposition of the ligand binding pocket described in the active-intermediate state does indeed describe the high-affinity state of NECA-bound to $A_{2A}R$. Clearly, however, the structures are not informative of any potential changes in dynamics within the receptor that could also contribute to the change in ligand affinity.

Conclusions $A_{2A}R$ is the first GPCR where both an active-intermediate and a fully active conformation have been defined structurally. However, the structure of the neurotensin receptor bound to the agonist peptide neurotensin[1,4,110-114] shows very similar characteristics to adenosine-bound $A_{2A}R$ and therefore probably also represents an active-intermediate state[23,124]. Recently, it has been proposed based on extensive EPR data that $β_2AR$ also exists in two distinct states in the active conformation, although the structure of the second state has not yet been elucidated[119]. However, it is clear from this work that there can be distinct conformations with or without G protein bound that lie on the activation pathway of agonist bound receptors. Given the highly conserved nature of the mechanism of GPCR activation, it is likely that the active-intermediate of $A_{2A}R$ may represent a common intermediate for many Class A GPCRs, although it may exist only transiently depending on the energy landscape of the receptor.

The similarities and differences between the G protein interfaces of $β_2AR$ and $A_{2A}R$ are a consequence of the different amino acid sequences of the receptors and result in a slightly different position and orientation of the G protein with respect to the receptor. Thus it is to be expected that $G_s$ will also interact slightly differently with other $G_s$-coupled receptors and that other G proteins, such as $G_i$ and $G_q$, will also show differences in the details of their interactions with receptors, due both to different amino acid sequences and the flexible nature of both receptors and G proteins. Thus the relatively 'loose' nature of the G protein binding interface may allow significant variations in G protein orientation. However, one of the beauties of the conserved mechanism of G protein activation by GPCRs[103] is provided that helix α5 is displaced away from the nucleotide binding pocket, causing the order-to-disorder transition of α1 and nucleotide release, the exact mode of interaction with the receptor is largely superfluous.

Methods and Materials

Expression and Purification.

Mini-$G_s$ (construct 414) was expressed in *E. coli* and purified by immobilised metal affinity chromatography (IMAC) and gel filtration chromatography (see further methods). The wild type human $A_{2A}R$ (residues 1-308), which contained the N154A mutation to remove a potential N-linked glycosylation site, was expressed in insect cells utilising the baculovirus expression system. $A_{2A}R$ was purified in the presence of the agonist NECA, in n-decyl-β-D-maltopyranoside (DM) detergent by IMAC and gel filtration chromatography (see further methods).

Complexation and Crystallisation.

Agonist-bound, purified $A_{2A}R$ (in DM) was mixed with a 1.2-fold molar excess of mini-$G_s$, apyrase was added and the sample was incubated overnight on ice. The complex was exchanged into n-octyl-β-D-thioglucopyranoside (OTG) detergent, purified by gel filtration, and crystallised by vapour diffusion (see further methods).

Data Collection, Structure Solution and Refinement.

Diffraction data were collected from two cryo-cooled crystals (100K), using either standard or helical collection modes, at beamline ID23-2 (European Synchrotron Radiation Facility). The structure was solved by molecular replacement using thermostabilised $A_{2A}R$ (PDB code 2YDV) and the $G\alpha_s$ GTPase domain from the $\beta_2AR$-Gs complex (3SN6) as search models (see further methods).

Further Methods

Expression and Purification of Mini-$G_s$

Mini-$G_s$414, which incorporated an N-terminal histidine tag ($His_{10}$) and TEV protease cleavage site was expressed in *E. coli* strain BL21(DE3)RIL. Expression was induced with IPTG (50 μM) for 20 h at 25° C. Cells were harvested by centrifugation and lysed by sonication in lysis buffer (40 mM HEPES pH 7.5, 100 mM NaCl, 10% glycerol, 10 mM imidazole, 5 mM $MgCl_2$, 50 μM GDP, 1 mM PMSF, 2.5 μM Pepstatin-A, 10 μM Leupeptin, 50 μg/ml DNase I, 100 μg/ml lysozyme, 100 μM DTT), supplemented with Complete™ protease inhibitors (Roche). The lysate was clarified by centrifugation and loaded onto a 10 ml $Ni^{2+}$ Sepharose FF column. The column was washed with wash buffer (20 mM HEPES pH 7.5, 500 mM NaCl, 40 mM imidazole, 10% glycerol, 1 mM $MgCl_2$, 50 μM GDP) and eluted with elution buffer (20 mM HEPES pH 7.5, 100 mM NaCl, 500 mM imidazole, 10% glycerol, 1 mM $MgCl_2$, 50 μM GDP). TEV protease was added and the sample was dialysed overnight against dialysis buffer (20 mM HEPES pH 7.5, 100 mM NaCl, 10% glycerol, 1 mM $MgCl_2$, 10 μLM GDP). TEV protease was removed by negative purification on $Ni^{2+}$-NTA resin (Qiagen). The sample was concentrated to 1.5 ml and loaded onto a Superdex-200 26/600 gel filtration column, equilibrated with gel filtration buffer (10 mM HEPES pH 7.5, 100 mM NaCl, 10% glycerol, 1 mM $MgCl_2$, 1 μM GDP, 0.1 mM TCEP). Peak fractions were pooled and concentrated to 100 mg/ml. The pure protein was aliquoted, flash-frozen in liquid nitrogen, and stored at −80° C. A typical yield was 100 mg of pure mini-$G_s$414 per litre of culture.

Expression and Purification of Adenosine $A_{2A}R$

Wild type human adenosine $A_{2A}R$ (residues 1-308) was modified to contain a C-terminal histidine tag ($His_{10}$) and TEV protease cleavage site. The N154A mutation was introduced to remove a potential N-linked glycosylation site. Baculoviruses were prepared using the flashBAC ULTRA system (Oxford Expression Technologies). *Trichopulsia ni* cells were grown in ESF921 media (Expression Systems) to a density of $3\times10^6$ cells/ml, infected with $A_{2A}R$ baculovirus and incubated for 72 h. Cells were harvested and membranes prepared by two ultracentrifugation steps in membrane buffer (20 mM HEPES pH7.5, 1 mM EDTA, 1 mM PMSF).

NECA (100 μM), NaCl (300 mM), PMSF (1 mM) and Complete™ protease inhibitors (Roche) were added to the membranes, and the sample was mixed for 30 min at room temperature. Membranes were solubilised with 2% n-decyl-β-D-maltopyranoside (DM) on ice for 1 h. The sample was clarified by ultracentrifugation and loaded onto a 5 ml Ni-NTA column (Qiagen). The column was washed with wash buffer (20 mM HEPES pH 7.5, 500 mM NaCl, 10% glycerol, 80 mM imidazole, 100 μM NECA, 0.15% DM), and eluted with elution buffer (20 mM HEPES pH 7.5, 100 mM NaCl, 10% glycerol, 300 mM imidazole, 100 μM NECA, 0.15% DM). The eluate was concentrated using a 50 kDa cutoff Amicon unit (Millipore), and exchanged in to desalting buffer (10 mM HEPES pH 7.5, 100 mM NaCl, 10% glycerol, 100 μM NECA, 0.15% DM) using a PD10 column (GE Healthcare). TEV protease was added, and the sample was incubated on ice overnight. The sample was concentrated to 0.2 ml and loaded onto a Superdex 200 column (GE Healthcare). Peak fractions were pooled and concentrated to approximately 20 mg/ml. A typical yield was 2 mg of pure $A_{2A}R$ per litre of culture.

Complexation and Crystallisation

Purified $A_{2A}R$ was mixed with a 1.2-fold molar excess of mini-$G_s$414. $MgCl_2$ (1 mM) and apyrase (0.1 U) were added, and the mixture was incubated on ice overnight. The sample was diluted 10-fold in gel filtration buffer (10 mM HEPES pH 7.5, 100 mM NaCl, 100 μM NECA, 0.35% n-octyl-β-D-thioglucopyranoside OTG), concentrated to 0.2 ml, and loaded on to a Superdex 200 column (pre-equilibrated in the same buffer). Peak fractions, containing the $A_{2A}R$-mini-$G_s$ complex, were pooled and concentrated to 20 mg/ml. The $A_{2A}R$-mini-$G_s$ complex was crystallised by vapour diffusion in OTG either in the presence or absence of cholesterol hemisuccinate (CHS). Crystallisation plates were set up at 4° C. using 120 nl sitting drops. Crystals used for structure solution were grown in two conditions, either: 0.1 M NaOAc pH 5.5, 10% PEG 2000 (in the presence of CHS); or 0.1 M NaOAc pH 5.7, 9.5% PEG 2000 MME (in the absence of CHS). Crystals were cryo-protected in mother liquor supplemented with 30% PEG 400 and flash frozen in liquid nitrogen.

Data Collection, Processing and Refinement

Diffraction data were collected at the European Synchrotron Radiation Facility on beamline ID23-2 with a Pilatus 2M detector, using a 10 μm microfocus beam (0.8729 Å wavelength). Data were collected using either standard or helical collection modes. Data from two crystals were used for structure solution. Data were processed using MOSFLM[104] and AIMLESS[105]. The structure was solved by molecular replacement with PHASER[106] using the structures of the thermostabilised $A_{2A}R$ (PDB code 2YDV)[107] and the $G\alpha_s$ GTPase domain (residues 40-59 and 205-394) from the $\beta_2AR$-$G_s$ complex (PDB code 3SN6)[108] as search models. Model refinement and rebuilding were performed using REFMAC[109] and COOT[110].

Competition Binding Assay

FreeStyle HEK293-F cells transiently expressing wild type $A_{2A}R$ were resuspended in either assay buffer A (25 mM HEPES, pH 7.5, 100 mM KCl, 1 mM $MgCl_2$), assay buffer B (25 mM HEPES, pH 7.5, 100 mM NaCl, 1 mM $MgCl_2$), or assay buffer C (25 mM HEPES, pH 7.5, 500 mM NaCl, 1 mM MgCl$_2$), and were lysed by 10 passages through a 26 G needle. Purified binding partners were buffer-exchanged to the respective buffer before being added to the membranes at a final concentration of 25 µM. The mixture was aliquoted and NECA was added (0 to 1 mM final concentration, prepared in assay buffers containing 1 u/mL apyrase). The samples were incubated for 90 min at 22° C., $^3$H-ZM241385 was added at its apparent K$_d$ (2.5 nM), and the samples were incubated for a further 90 min at 22° C. Non-specific binding was determined in the presence of 100 µM of ZM241385. Receptor-bound and free radioligand were separated by filtration through 96-well GF/B filter plates (pre-soaked with 0.1% polyethyleneimine), and washed 3 times with the appropriate buffer. Plates were dried and radioactivity was quantified by liquid scintillation counting using a Tri-Carb 2910 TR (Perkin Elmer). Data were analyzed by nonlinear regression using GraphPad Prism software. The K$_i$ for NECA binding was derived from one-site fit Ki analysis. Data from at least three independent experiments, each performed in duplicate, were analyzed using an unpaired two-tailed t-test for statistical significance.

Thermostability Assay

Membranes from *Trichopulsia ni* cells expressing wild type human A$_{2A}$R were resuspended in Tm buffer (25 mM HEPES pH 7.5, 100 mM NaCl, 1 mM MgCl$_2$) and homogenised by 10 passages through a 26-gauge needle. Binding partner was added at a final concentration of 25 µM. $^3$H-NECA and unlabelled NECA were mixed in a ratio of 1:5 and added to the membranes to give a final concentration of 1 µM (approximately 10-fold above the apparent K$_d$). The samples were incubated at room temperature for 1 h, then chilled on ice for 30 min. DDM, DM or OG were added to a final concentration of 0.1%, 0.13% or 0.8%, respectively, and samples were incubated on ice for 1 h. Cell debris was removed by centrifugation for 5 min at 20,000×g and the supernatant was aliquoted into PCR strips. Samples were heated to the desired temperature for exactly 30 min, then quenched on ice for 30 min. Samples (50 µl) were loaded onto gel filtration resin packed into a 96-well filter plate (Millipore), which was centrifuged to separate receptor-bound from free radioligand. Non-specific binding was determined in the presence of 200 µM unlabeled NECA. Radioactivity was quantified by liquid scintillation counting using a MicroBeta TriLux scintillation counter (PerkinElmer). Data were analyzed by nonlinear regression using GraphPad Prism software. Apparent T$_m$ values were derived from sigmoidal dose-response analysis. Results represent the mean±SEM of two independent experiments, performed in duplicate.

TABLE 1

Turkey β1AR constructs used during this work. The β1AR-WT construct contained N- and C-terminal truncations, and the C116L mutation. These modifications were designed to prevent glycosylation or improve expression[15]. The β1AR-84 construct contained an additional deletion of cytoplasmic loop three. Thermostabilising mutations (M90V, D322K, F327A, and F388M)[2,3]. A disulphide link between transmembrane helices 1 and 2, facilitated by the M40C and L103C mutations. The C358A mutation, designed to prevent palmitoylation. An N-terminal MBP fusion, designed to facilitate crystallisation.

| Construct | Deleted residues | Mutations | Other modifications |
|---|---|---|---|
| β$_1$AR-WT | 1-32<br>424-483 | C116L | 6 His tag (C-terminus) |
| β$_1$AR-84 | 1-32<br>244-271<br>368-483 | M40C<br>M90V<br>L103C<br>C116L<br>D322K<br>F327A<br>C358A<br>F388M | MBP fusion<br>(N-terminus)<br>6 His tag (C-terminus) |

TABLE 2

Parental mini Gs constructs used during this work.

| Construct | Deleted residues | GαAH linker | Mutations | Other modifications |
|---|---|---|---|---|
| Mini Gs$_{77}$ | 1-21<br>67-193 | Gly$_3$ | L197A<br>C200S | N-terminal 6 His tag |
| Mini Gs$_{161}$ | 1-21<br>65-208 | Gly$_5$ | None | N-terminal 6 His tag |
| Mini Gs$_{199}$ | 1-21<br>65-203<br>254-263<br>(switch III) | Gly$_8$ | G49D<br>E50N<br>A249D<br>S252D<br>L272D | N-terminal 6 His tag |
| Mini Gs$_{391}$ | 1-25<br>65-203<br>254-263<br>(switch III) | GGSGGSGG | G49D<br>E50N<br>A249D<br>S252D<br>L272D<br>I372A | N-terminal 6 His tag<br>TEV protease site |

TABLE 2-continued

Parental mini Gs constructs used during this work.

| Construct | Deleted residues | GαAH linker | Mutations | Other modifications |
|---|---|---|---|---|
| Mini Gs$_{393}$ | 1-25<br>65-203<br>254-263<br>(switch III) | GGSGGSGG | G49D<br>E50N<br>A249D<br>S252D<br>L272D<br>I372A<br>V375I | N-terminal 6 His tag<br>TEV protease site |
| Mini Gs$_{399}$ | 1-5<br>65-203<br>254-263<br>(switch III) | GGSGGSGG | G49D<br>E50N<br>A249D<br>S252D<br>I372A<br>V375I | N-terminal 6 His tag<br>TEV protease site |
| Mini Gs$_{404}$ | 1-25<br>65-203<br>254-263<br>(switch III) | GGSGGSGG | G49D<br>E50N<br>A249D<br>S252D<br>L272D | N-terminal 6 His tag<br>TEV protease site |

TABLE 3

Competitive binding assay data showing the isoprenaline K$_i$ of β$_1$AR-84 in response to different binding partners. Data are from a single experiment performed in duplicate unless otherwise stated in the table, in these cases data represent mean ± SEM, from the number of independent experiments (n) indicated. The effect of mutations on the expression level of mini Gs was estimated from SDS-PAGE gels. Mutants that caused more than a 2-fold change in expression compared to the parental construct are shown simply as an increase (+) or decrease (−). [a] Common Gα numbering (CGN) system. [b] Not applicable. [c] Not determined. [d] Substitution of switch II residues 227-230 with two glycine residues. [e] Deletion of switch III residues 254-263.

| Binding partner | Mutation | CGN code[a] | β$_1$AR-WT Tm in complex DDM (° C.) | Mini Gs basal Tm (° C.) |
|---|---|---|---|---|
| None | n.a.[b] | n.a. | 25.9 ± 0.0 (n = 3) | n.a. |
| Nb80 | n.a. | n.a. | 32.0 ± 0.0 (n = 3) | n.a. |
| Gs-Nb35 | n.a. | n.a. | 35.8 ± 0.1 (n = 3) | n.a. |
| Gαs | n.a. | n.a. | n.d.[c] | 50.1 ± 0.1 (n = 3) |
| Mini Gs$_{162}$ | A249D | | 25.1 (n = 1) | 60.6 ± 0.1 (n = 3) |
| Mini Gs$_{164}$ | A249D-SIII[d] | | 28.6 (n = 1) | 66.5 ± 0.0 (n = 3) |
| Mini Gs$_{165}$ | A249D-S252D-SIII | | 28.5 ± 0.2 (n = 2) | 68.7 ± 0.0 (n = 3) |
| Mini Gs$_{169}$ | A249D-S252D-SIII- | | 28.8 (n = 1) | 67.1 ± 0.0 (n = 3) |
| Mini Gs$_{183}$ | G49D-E50N-A249D-<br>S252D-SIII-L272D | | 28.7 ± 0.2 (n = 4) | 72.5 ± 0.0 (n = 3) |
| Mini Gs$_{199}$[e] | G49D-E50N-A249D-<br>S252D-SIII-L272D | | 29.2 ± 0.2 (n = 17) | 72.5 ± 0.0 (n = 3) |
| Mini Gs$_{254}$ | M60A | 60$^{G.H1.8}$ | 31.5 ± 0.3 (n = 5) | 70.3 ± 0.0 (n = 3) |
| Mini Gs$_{350}$ | L63Y | 63$^{G.11.1}$ | 30.9 ± 0.4 (n = 2) | 70.7 ± 0.0 (n = 3) |
| Mini Gs$_{340}$ | I372A | 372$^{G.H5.4}$ | 34.0 (n = 1) | 66.6 ± 0.1 (n = 3) |
| Mini GS$_{303}$ | V375I | 375$^{G.H5.7}$ | 31.5 ± 0.6 (n = 3) | 70.3 ± 0.0 (n = 3) |
| Mini Gs$_{352}$ | L63Y-I372A | | 34.5 (n = 1) | 64.7 ± 0.1 (n = 3) |
| Mini Gs$_{345}$ | I372A-V375I | | 35.0 (n = 1) | 65.4 ± 0.1 (n = 3) |

TABLE 4

Thermostability (Tm) measurements for either β₁AR-WT complexes or mini Gs mutants in the basal GDP-bound state. Tm values represent the mean ± SEM from the number of independent experiments (n) indicated in the table. Some Tm values were determined from a single experiments performed in duplicate, with an assumed error of ± 0.5° C. Tm values for mini Gs in the GDP-bound state were determined by differential scanning fluorimetry.[a] Common Gα numbering (CGN) system.[b] Not applicable.[c] Not determined.[d] Deletion of switch III residues 254-263 is referred to as SIII.[e] Mini Gs$_{199}$ contains the same mutations as mini GS$_{183}$, but has a redesigned linker region (see Table 2), and was used as the parental construct for screening detergent stabilising mutations.

| Binding partner | Mutation | CGN code[a] | β₁AR-84 isoprenaline Ki (nM) 4° C. | 20° C. | Effect on expression |
|---|---|---|---|---|---|
| None | n.a.[b] | n.a. | 2080 ± 181 (n = 12) | 2615 ± 273 (n = 15) | n.a. |
| Nb80 | n.a. | n.a. | n.d.[c] | 28 ± 1 (n = 2) | n.a. |
| Gs | n.a. | n.a. | 419 ± 80 (n = 2) | 271 ± 54 (n = 2) | n.a. |
| Gs-Nb35 | n.a. | n.a. | n.d. | 16 ± 4 (n = 3) | n.a. |
| Mini Gs$_{77}$ | Parental | n.a. | 99 ± 12 (n = 4) | 1867 ± 228 (n = 3) | n.a. |
| Mini Gs$_{81}$ | H41I | 41$^{G.S1.2}$ | 32 | 393 | |
| Mini Gs$_{84}$ | H41V | 41$^{G.S1.2}$ | 51 | 491 | |
| Mini Gs$_{186}$ | A48L | 48$^{G.s1h1.2}$ | 43 | 174 | |
| Mini Gs$_{130}$ | G49D | 49$^{G.s1h1.3}$ | 25 | 285 | |
| Mini Gs$_{116}$ | E50N | 50$^{G.s1h1.4}$ | 37 | 724 | |
| Mini Gs$_{134}$ | R201A | 201$^{G.hfa2.2}$ | 31 | 1479 | − |
| Mini Gs$_{98}$ | 227-230 sub[d] | 227$^{G.s3h2.3}$ | 23 | 533 | |
| Mini Gs$_{175}$ | E230A | 230$^{G.h2.3}$ | 51 | 545 | |
| Mini Gs$_{92}$ | A249D | 249$^{G.S4.7}$ | 10 | 35 | + |
| Mini Gs$_{104}$ | A249E | 249$^{G.S4.7}$ | 70 | 388 | |
| Mini Gs$_{117}$ | S252D | 252$^{G.sh4.3}$ | 14 | 94 | + |
| Mini Gs$_{118}$ | S252E | 252$^{G.s4h3.3}$ | 38 | 383 | + |
| Mini Gs$_{105}$ | 254-263 del[e] | 254$^{G.s4h3.5}$ | 21 | 20 | + |
| Mini Gs$_{94}$ | L272D | 272$^{G.H3.8}$ | 7 | 310 | |

TABLE 5

Agonist-shift assay data for GTPase domain mutants. Assays were performed using membranes containing the 61AR reconstituted with partially purified GTPase domain mutants (total amount purified from 1 litre of E. coli culture). Assays were performed at 4 and 20° C. for each mutant. The table shows the final isoprenaline affinity of the receptor under each condition. The starting isoprenaline affinity of the receptor was 3.03 ± 0.81 μM (n = 16), with values in the range of 1.5-4.4 μM. Therefore, a shift in agonist affinity less than threefold cannot be considered significant. Quantification of expression levels was not possible due to the use of partially purified material. Therefore, a simplified scale was used to indicate the relative expression level compared to the parental construct. Note: some mutants that did not induce a shift in agonist affinity at 4° C. were not tested at 20° C. (denoted by n.d. in the table).

| Modification/mutation | Approximate isoprenaline IC50 (nM) At 4° C. | At 20° C. | Approximate expression level |
|---|---|---|---|
| Parental construct | 136 | 2100 | |
| V36D/N218K | 115 | 2100 | − |
| V36D/N218K/T40A | 551 | 2400 | −− |
| V36D/N218K/T40D | 427 | 3200 | = |
| Y37D | 81 | 2000 | = |
| Y37R/R42D | 2300 | n.d. | −−− |
| H41I | 58 | 589 | = |
| H41L | 285 | 3900 | − |
| H41M | 307 | 1800 | = |
| H41V | 77 | 737 | = |
| A48D | 185 | 1800 | −−− |
| G49D | 37 | 428 | = |
| E50N | 55 | 1100 | = |
| G49D/E50N | 44 | 364 | = |
| S54N | 462 | 2100 | −−− |
| R199K | 108 | 1900 | + |
| R199D | 109 | 1800 | = |
| R201A | 46 | 2200 | = |
| F208N | 250 | 1300 | = |
| G226A | 127 | 1200 | = |
| Δ227-230/GG linker | 34 | 799 | = |
| W234A/F238A | 584 | 4000 | − |
| C237E | 93 | 1900 | = |
| D240G | 510 | 4400 | − |
| A249S | 146 | 1600 | − |
| A249D | 15 | 53 | ++ |

TABLE 5-continued

Agonist-shift assay data for GTPase domain mutants. Assays were performed using membranes containing the β1AR reconstituted with partially purified GTPase domain mutants (total amount purified from 1 litre of E. coli culture). Assays were performed at 4 and 20° C. for each mutant. The table shows the final isoprenaline affinity of the receptor under each condition. The starting isoprenaline affinity of the receptor was 3.03 ± 0.81 μM (n = 16), with values in the range of 1.5-4.4 μM. Therefore, a shift in agonist affinity less than threefold cannot be considered significant. Quantification of expression levels was not possible due to the use of partially purified material. Therefore, a simplified scale was used to indicate the relative expression level compared to the parental construct. Note: some mutants that did not induce a shift in agonist affinity at 4° C. were not tested at 20° C. (denoted by n.d. in the table).

| Modification/mutation | Approximate isoprenaline IC50 (nM) At 4° C. | Approximate isoprenaline IC50 (nM) At 20° C. | Approximate expression level |
|---|---|---|---|
| A249E | 104 | 582 | + |
| S252D | 21 | 142 | + |
| S252E | 57 | 575 | + |
| L270N/I348N | 4300 | n.d. | --- |
| L272D | 10 | 464 | + |
| L272E | 42 | 110 | = |
| S275D | 136 | 2000 | = |
| N279E/I235K | 1200 | 2800 | --- |
| N279D/Q235K | 102 | 2000 | --- |
| S286C/I382C | 4200 | 7000 | --- |
| D295N | 2400 | n.d. | --- |
| R356S | 229 | 2800 | = |
| R356D | 161 | 3300 | = |
| Δ255-262/G linker | 1300 | n.d. | -- |
| Δ254-263 | 31 | 30 | ++ |
| Δ254-263/Y253P | 23 | 142 | ++ |
| Δ266-340/Gαi1 chimera | 4400 | n.d. | --- |
| Δ266-341/ras chimera | 2200 | n.d. | --- |

TABLE 6

Data collection and refinement statistics

Data collection

| | |
|---|---|
| Space group | P $2_1 2_1 2_1$ |
| Cell dimensions a, b, c (Å) | 90.6, 111.8, 161.3 |
| Resolution (Å) | 40.3-3.4 (3.49-3.40) |
| $R_{merge}$ | 0.173 (0.747) |
| I/σI | 3.6 (1.2) |
| Completeness (cY0) | 90.6 (78.5) |
| Redundancy | 2.6 (2.4) |

Refinement

| | |
|---|---|
| Resolution (Å) | 40.3-3.4 |
| No. reflections | 19788 |
| $R_{work}/R_{free}$ (%) | 28.4/31.5 |
| No. atoms | 7359 |
| Protein | 7248 |
| Ligand/detergent/nucleotide | 44/40/27 |
| Water | 0 |

B-factors (Å$^2$)

| | |
|---|---|
| Protein | 79.9 |
| Ligand/detergent/nucleotide | 67.9/98.6/69.0 |

R.M.S.D.

| | |
|---|---|
| Bond lengths (Å) | 0.008 |
| Bond angles (°) | 1.15 |

REFERENCES

1. Lebon, G., et al. (2011). Agonist-bound adenosine A2A receptor structures; reveal common features; of GPCR activation. Nature; 474(7352): 521-5.
2. Rosenbaum, D. M., et al. Lyons et al. (2011). Structure and function of an irreversible agonist-β(2) adrenoceptor complex. Nature; 469(7329): 236-40.
3. Warne, T., et al. (2011). The structural basis for agonist and partial agonist action on a β(1)-adrenergic receptor. Nature; 469(7329): 241-4.
4. Xu, F., et al. (2011). Structure of an agonist-bound human A2A adenosine receptor. Science; 332(6027): 322-7.
5. Herrmann, R., et al. (2004). Sequence of interactions in receptor-G protein coupling. J Biol Chem; 279(23): 24283-24290.
6. Herrmann, R., et al. (2006). Rhodopsin-transducin coupling: role of the Galpha C-terminus in nucleotide exchange catalysis. Vision Res; 46(27): 4582-4593.
7. Hamm, H. E., et al. (1988). Site of G protein binding to rhodopsin mapped with synthetic peptides from the alpha subunit. Science; 241(4867): 832-5.
8. Conklin, B. R., et al. (1993). Substitution of three amino acids switches receptor specificity of Gq alpha to that of Gi alpha. Nature; 363(6426): 274-276.
9. Conklin, B. R., et al. (1996). Carboxyl-terminal mutations of Gq alpha and Gs alpha that alter the fidelity of receptor activation. Mol Pharmacol; 50(4): 885-890.
10. Rasmussen, S. G., et al. (2011). Crystal structure of the β2 adrenergic receptor-Gs protein complex. Nature; 477 (7366): 549-55.
11. Chung, K. Y., et al. (2011). Conformational changes in the G protein Gs induced by the beta2 adrenergic receptor. Nature; 477(7366): 611-615.
12. Chabre, M., et al. (1989). Molecular mechanism of visual transduction. Eur J Biochem; 179(2): 255-266.
13. Delean, A., et al. (1980). A Ternary Complex Model Explains the Agonist-Specific Binding-Properties of the Adenylate Cyclase-Coupled Beta-Adrenergic-Receptor. J Biol Chem; 255(15): 7108-17.

14. Bornancin, F., et al. (1989). The transitory complex between photoexcited rhodopsin and transducin. Reciprocal interaction between the retinal site in rhodopsin and the nucleotide site in transducin. Eur J Biochem; 184(3): 687-98.
15. Sprang, S. R. (1997). G protein mechanisms: insights from structural analysis. Annu Rev Biochem; 66: 639-78.
16. Fung, B. K. (1983). Characterization of transducin from bovine retinal rod outer segments. I. Separation and reconstitution of the subunits. J Biol Chem; 258(17): 10495-10502.
17. Fung, B. K., et al. (1983). Characterization of transducin from bovine retinal rod outer segments. II. Evidence for distinct binding sites and conformational changes revealed by limited proteolysis with trypsin. J Biol Chem; 258(17): 10503-10510.
18. Wittinghofer, A., et al. (2011). Structure-function relationships of the G domain, a canonical switch motif. Annu Rev Biochem; 80: 943-971.
19. Holm L., et al. (2010). Dali server: conservation mapping in 3D. Nucleic Acids Res; 38 (Web Server issue): W545-9.
20. Hall, A., et al. (1986). The effect of Mg2+ on the guanine nucleotide exchange rate of p21N-ras. J Biol Chem; 261(24): 10963-10965.
21. Higashijima, T., et al. (1987). Effects of Mg2+ and the beta gamma-subunit complex on the interactions of guanine nucleotides with G proteins. J Biol Chem; 262(2): 762-6.
22. Jones, J. C., et al. (2011). The crystal structure of a self-activating G protein alpha subunit reveals its distinct mechanism of Signal; initiation. Sci Signal; 4(159): ra8.
23. Majumdar, S., et al. (2004). Perturbing the linker regions of the alpha-subunit of transducin: a new class of constitutively active GTP-binding proteins. J Biol Chem; 279 (38): 40137-40145.
24. Ferguson, K. M., et al. (1986). The influence of bound GDP on the kinetics of guanine nucleotide binding to G proteins. J Biol Chem; 261(16): 7393-7399.
25. Posner, B. A., et al. (1998). The A326S mutant of Gialpha1 as an approximation of the receptor-bound state. J Biol Chem; 273(34): 21752-21758.
26. Vetter, I. R., et al. (2001). The guanine nucleotide-binding switch in three dimensions. Science 294(5545): 1299-1304.
27. Kapoor, N., et al. (2009). Structural evidence for a sequential release mechanism for activation of heterotrimeric G proteins. J Mol Biol 393(4): 882-897.
28. Natochin, M., et al. (2001). Probing the mechanism of rhodopsin-catalyzed transducin activation. J Neurochem; 77(1): 202-210.
29. Oldham, W. M., et al. (2006). Mechanism of the receptor-catalyzed activation of heterotrimeric G proteins. Nat Struct Mol Biol; 13(9): 772-7.
30. Preininger, A. M., et al. (2009). Helix dipole movement and conformational variability contribute to allosteric GDP release in Galphai subunits. Biochemistry; 48(12): 2630-2642.
31. Abdulaev, N. G., et al. (2005). Heterotrimeric G-protein alpha-subunit adopts a "preactivated" conformation when associated with betagamma-subunits. J Biol Chem; 280 (45): 38071-38080.
32. Weiss, E. R., et al. (1988). Receptor activation of G proteins. FASEB J; 2(13): 2841-2848.
33. Hou, Y., et al. (2000). Selective role of G protein gamma subunits in receptor interaction. J Biol Chem; 275(50): 38961-38964.
34. McIntire, W. E., et al. (2001). The G protein beta subunit is a determinant in the coupling of Gs to the beta 1-adrenergic and A2a adenosine receptors. J Biol Chem; 276(19): 15801-15809.
35. Richardson, M., et al. (1999). The alpha2A-adrenergic receptor discriminates between Gi heterotrimers of different betagamma subunit composition in Sf9 insect cell membranes. J Biol Chem; 274(19): 13525-13533.
36. Scheerer, P., et al. Hildebrand et al. (2008). Crystal structure of opsin in its G-protein-interacting conformation. Nature; 455(7212): 497-502.
37. Choe, H. W., et al. (2011). Crystal structure of metarhodopsin II. Nature; 471(7340): 651-5.
38. Rasmussen S. G., et al. (2011). Structure of a nanobody-stabilized active state of the 3(2) adrenoceptor. Nature; 469(7329): 175-80.
39. Abdulaev, N. G., et al. (2006). The receptor-bound "empty pocket" state of the heterotrimeric G-protein alpha-subunit is conformationally dynamic. Biochemistry; 45(43): 12986-12997.
40. Westfield, G. H., et al. (2011). Structural flexibility of the G alpha s alpha-helical domain in the beta2-adrenoceptor Gs complex. Proc Natl Acad Sci USA; 108(38): 16086-91.
41. Markby D. W. et al. (1993). Separate GTP binding and GTPase activating domains of a G alpha subunit. Science; 262(5141): 1895-901.
42. Dohlman, H. G., et al. (2012). Signal; activation and inactivation by the Galpha helical domain: a long-neglected partner in G protein signaling. Sci Signal; 5(226): re2.
43. Phillips, W. J., et al. (1992). Rhodopsin/transducin interactions. II. Influence of the transducin-beta gamma subunit complex on the coupling of the transducin-alpha subunit to rhodopsin. J Biol Chem; 267(24): 17040-6.
44. Skiba, N., et al. (1996). Mapping of effector binding sites of transducin alpha-subunit using G alpha t/G alpha ii chimeras. J Biol Chem; 271(1): 413-424.
45. Singh, G., et al. (2012). A constitutively active Galpha subunit provides insights into the mechanism of G protein activation. Biochemistry; 51(15): 3232-3240.
46. Herrmann, R., et al. (2006). Signal transfer from GPCRs to G proteins: role of the G alpha N-terminal region in rhodopsin-transducin coupling. J Biol Chem; 281(40): 30234-30241.
47. Bubis, J., et al. (2001). Chemical modification of transducin with iodoacetic acid: transducin-alpha carboxymethylated at Cys(347) allows transducin binding to Light-activated rhodopsin but prevents its release in the presence of GTP. Arch Biochem; Biophys 395(2): 146-157.
48. Grishina, G., et al. (2000). A surface-exposed region of G(salpha) in which substitutions decrease receptor-mediated activation and increase receptor affinity. Mol Pharmacol; 57(6): 1081-1092.
49. Barren, B., et al. (2007). Mechanisms of dominant negative G-protein alpha subunits. J Neurosci Res; 85(16): 3505-3514.
50. Feig, L. A., et al. (1999). Tools of the trade: use of dominant-inhibitory mutants of Ras-family GTPases. Nat Cell Biol 1(2): E25-27.
51. Feig, L. A., et al. (1988). Inhibition of NIH 3T3 cell proliferation by a mutant ras protein with preferential affinity for GDP. Mol Cell Biol 8(8): 3235-3243.
52. Cleator, J. H., et al. (1999). The N54 mutant of Galphas has a conditional dominant negative phenotype which 53. Cleator, J. H., et al. (2004). A dominant negative Galphas mutant that prevents thyroid-stimulating hormone receptor activation of cAMP production and inositol 1,4,5-trisphosphate turnover: competition by different G proteins for activation by a common receptor. J Biol Chem; 279(35): 36601-36607.
54. Hildebrandt, J. D., et al. (1991). A mutation in the putative Mg(2+)-binding site of Gs alpha prevents its activation by receptors. Mol Cell Biol 11(10): 4830-4838
55. Natochin, M., et al. (2006). Dominant negative mutants of transducin-alpha that block activated receptor. Biochemistry; 45(20): 6488-6494.
56. Ramachandran, S., et al. (2011). A dominant-negative Galpha mutant that traps a stable rhodopsin-Galpha-GTP-betagamma complex. J Biol Chem; 286(14): 12702-12711.
57. Slepak, V. Z., et al. (1995). Functional analysis of a dominant negative mutant of G alpha i2. J Biol Chem; 270(8): 4037-4041.
58. Wu, Y. L., et al. (2004). Dominant-negative inhibition of pheromone receptor signaling by a single point mutation in the G protein alpha subunit. J Biol Chem; 279(34): 35287-35297.
59. Pereira, R., et al. (2005). Δ switch 3 point mutation in the alpha subunit of transducin yields a unique dominant-negative inhibitor. J Biol Chem; 280(42): 35696-35703.
60. Barren, B., et al. (2006). Mutation R238E in transducin-alpha yields a GTPase and effector-deficient, but not dominant-negative, G-protein alpha-subunit. Mol Vis 12: 492-498.
61. Zurita, A. R., et al. (2008). The same mutation in Gsalpha and transducin alpha reveals behavioral differences between these highly homologous G protein alpha-subunits. Proc Natl Acad Sci USA 105(7): 2363-2368.
62. Yu, B., et al. (2000). Inhibition of subsets of G protein-coupled receptors by empty mutants of G protein alpha subunits in g(o): G(11): and G(16). J Biol Chem; 275(1): 71-76.
63. Yu, B., et al. (1998). Interaction of the xanthine nucleotide binding Goalpha mutant with G protein-coupled receptors. J Biol Chem; 273(46): 30183-30188.
64. Yu, B., et al. (1997). Characterization of a Goalpha mutant that binds xanthine nucleotides. J Biol Chem; 272(29): 18015-18019.
65. Iiri, T., et al. (1999). Gsalpha mutant designed to inhibit receptor signaling through Gs.
Proc Natl Acad Sci USA; 96(2): 499-504.
66. Iiri, T., et al. (1994). Rapid GDP release from Gs alpha in patients with gain and loss of endocrine function. Nature; 371(6493): 164-168.
67. Warner, D. R., et al. (1998). A novel mutation in the switch 3 region of Gsalpha in a patient with Albright hereditary osteodystrophy impairs GDP binding and receptor activation. J Biol Chem; 273(37): 23976-23983.
68. Berlot, C. H., et al. (2002). A highly effective dominant negative alpha s construct containing mutations that affect distinct functions inhibits multiple Gs-coupled receptor signaling pathways. J Biol Chem; 277(23): 21080-21085.
69. Serrano-Vega, M. J., et al. (2008). Conformational thermostabilization of the beta1-adrenergic receptor in a detergent-resistant form. Proc Natl Acad Sci USA 105(3): 877-882.
70. Johnston, C. A., et al. (2005). Structure of Galpha(i1) bound to a GDP-selective peptide provides insight into guanine nucleotide exchange. Structure 13(7): 1069-1080.
71. Kimple, R. J., et al. (2002). Structural determinants for GoLoco-induced inhibition of nucleotide release by Galpha subunits. Nature; 416(6883): 878-881.
72. Nishimura, A., et al. (2010). Structural basis for the specific inhibition of heterotrimeric Gq protein by a small molecule. Proc Natl Acad Sci USA 107(31): 13666-13671.
73. Umezawa, Y., et al. (1998). CH/pi interactions as demonstrated in the crystal structure of guanine-nucleotide binding proteins, Src homology-2 domains and human growth hormone in complex with their specific ligands. Bioorg Med Chem; 6(4): 493-504.
74. Li, Q., et al. (1997). Communication between switch II and switch III of the transducin alpha subunit is essential for target activation. J Biol Chem; 272(35): 21673-21676
75. Frishman, D., et al. et al. Knowledge-based protein secondary structure assignment.
Proteins 23(4): 566-579.
76. Heinig, M., et al. (2004). STRIDE: a web server for secondary structure assignment from known atomic coordinates of proteins. Nucleic Acids Res; 32 (Web Server issue): W500-502.
77. Muradov, K. G., et al. (2000). Coupling between the N- and C-terminal domains influences transducin-alpha intrinsic GDP/GTP exchange. Biochemistry; 39(14): 3937-3942.
78. Lambright, D. G. et al. (1994). Structural determinants for activation of the alpha-subunit of a heterotrimeric G protein. Nature; 369(6482): 621-628.
79. Coleman, D. E et al. (1998). Crystal structures; of the G protein Gi alpha 1 complexed with GDP and Mg2+: a crystallographic titration experiment. Biochemistry; 37(41): 14376-14385.
80. Noel, J. P., et al. (1993). The 2.2 A crystal structure of transducin-alpha complexed with GTP gamma S. Nature; 366(6456): 654-663.
81. Sunahara, R. K., et al. (1997). Crystal structure of the adenylyl cyclase activator Gsalpha. Science; 278(5345): 1943-7.
82. Tesmer, J. J., et al. (1997). Crystal structure of the catalytic domains of adenylyl cyclase in a complex with Gsalpha.GTPgammaS. Science 278(5345): 1907-1916.
83. Kleuss, C., et al. (2003). Galpha(s) is palmitoylated at the N-terminal glycine. EMBO J 22(4): 826-832.
84. Simonds, W. F., et al. (1991). G-protein beta gamma dimers. Membrane targeting requiRes; subunit coexpression and intact gamma C-A-A-X domain. J Biol Chem; 266(9): 5363-5366.
85. Spiegel, A. M., et al. (1991). The G protein connection: molecular basis of membrane association. Trends Biochem Sci; 16(9): 338-41.
86. Herrmann, R., et al. (2006). Signal; transfer from GPCRs to G proteins: role of the G alpha N-terminal region in rhodopsin-transducin coupling. J Biol Chem; 281(40): 30234-41.
87. Alexander, N. S., et al. (2014). Energetic analysis of the rhodopsin-G-protein complex links the α5 helix to GDP release. Nat Struct Mol Biol; 21(1): 56-63.
88. Dror, R. O., et al. (2015). SIGNAL; TRANSDUCTION. Structural basis for nucleotide exchange in heterotrimeric G proteins. Science; 348(6241): 1361-5.
89. Flock, T., et al. (2015). Universal allosteric mechanism for Gα activation by GPCRs.

90. Kaya, A. I., et al. (2014). A conserved phenylalanine as a relay between the α5 helix and the GDP binding region of heterotrimeric Gi protein α subunit. J Biol Chem; 289(35): 24475-87.
91. Van Eps, N., et al. (2011). Interaction of a G protein with an activated receptor opens the interdomain interface in the alpha subunit. Proc Natl Acad Sci USA; 108(23): 9420-4.
92. Sun, D., et al. (2015). Probing Gαi1 protein activation at single-amino acid resolution. Nat Struct Mol Biol; 22(9): 686-94.
93. Vuong T. M., et al. (1984). Millisecond activation of transducin in the cyclic nucleotide cascade of vision. Nature; 311(5987): 659-61.
94. Kuhn, H. 1981. Interactions of rod cell proteins with the disc membrane: influence of light, ionic strength, and nucleotides. Curr Top Membr Transp; 15: 171-201.
95. Fung, B. K., et al. (1981). Flow of information in the light-triggered cyclic nucleotide cascade of vision. Proc Natl Acad Sci; USA 78(1): 152-6.
96. Miller-Gallacher, R. et al., (2014). The 2.1 Å Resolution Structure of Cyanopindolol-Bound β1-Adrenoceptor Identifies an Intramembrane Na+ Ion that Stabilises the Ligand-Free Receptor. PLoS One 9 (3): e92727.
97. Warne, T., et al, (2003). Expression and purification of truncated, non-glycosylated turkey beta-adrenergic receptors for crystallization. Biochim Biophys Acta; 1610(1): 133-40.
98. Hanzal-Bayer, M., et al. (2002). The complex of Arl2-GTP and PDE delta: from structure to function. EMBO J; 21(9): 2095-106.
99. Traut, T. W. (1994). Physiological concentrations of purines and pyrimidines. Mol Cell Biochem; 140(1): 1-22.
100. Ring A. M., et al. (2013). Adrenaline-activated structure of 32-adrenoceptor stabilized by an engineered nanobody. Nature; 502(7472): 575-9.
101. Weichert D., et al. (2014). Covalent agonists for studying G protein-coupled receptor activation. Proc Natl Acad Sci USA; 111(29): 10744-8.
102. Hansson K, M. D., et al. (2008). PCR-mediated deletion of plasmid DNA. Anal Biochem; 375(2): 373-5.
103. Flock, T., et al. (2015). Universal allosteric mechanism for Gα activation by GPCRs. Nature; 524(7564): 173-9.
104. Fredholm, B. B., et al. (2001). International Union of Pharmacology. XXV. Nomenclature and classification of adenosine receptors. Pharmacol Rev; 53(4): 527-552.
105. Fredholm, B. B., et al. (2011). International Union of Basic and Clinical Pharmacology. LXXXI. Nomenclature and classification of adenosine receptors—an update. Pharmacol Rev; 63(1): 1-34.
106. Chen, J. F., et al. (2013). Adenosine receptors as drug targets-what are the challenges? Nat Rev Drug Discov; 12(4): 265-286.
107. Muller, C. E., et al. (2011). Recent developments in adenosine receptor ligands and their potential as novel drugs. Biochim Biophys Acta; 1808(5): 1290-1308.
108. Congreve, M., et al. (2012). Discovery of 1,2,4-triazine derivatives as adenosine A(2A) antagonists using structure based drug design. Journal of medicinal chemistry; 55(5): 1898-1903.
109. Fishman, P., et al. (2012). Pharmacological and therapeutic effects of A3 adenosine receptor agonists. Drug Discov Today; 17(7-8): 359-366.
110. Dore, A. S., et al. (2011). Structure of the adenosine A(2A) receptor in complex with ZM241385 and the xanthines XAC and caffeine. Structure; 19(9): 1283-1293.
111. Hino, T., et al. (2012). G-protein-coupled receptor inactivation by an allosteric inverse-agonist antibody. Nature; 482(7384): 237-240.
112. Jaakola, V. P., et al. (2008). The 2.6 angstrom crystal structure of a human A2A adenosine receptor bound to an antagonist. Science; 322(5905): 1211-1217.
113. Lebon, G., et al. (2015). Molecular Determinants of CGS21680 Binding to the Human Adenosine A2A Receptor. Mol Pharmacol; 87(6): 907-915.
114. Lebon, G., et al. (2012). Agonist-bound structures of G protein-coupled receptors. Current opinion in structural biology; 22(4): 482-90.
115. Liu, W., et al. (2012). Structural basis for allosteric regulation of GPCRs by sodium ions. Science; 337(6091): 232-236.
116. Fenalti, G., et al. (2014). Molecular control of delta-opioid receptor signalling. Nature; 506(7487): 191-196.
117. Zhang, C., et al. (2012). High-resolution crystal structure of human protease-activated receptor 1. Nature; 492 (7429): 387-392.
118. Murphree, L. J., et al. (2002). Human A(2A) adenosine receptors: high-affinity agonist binding to receptor-G protein complexes containing Gbeta(4). Mol Pharmacol; 61(2): 455-462.
119. Manglik, A., et al. (2015). Structural Insights into the Dynamic Process of beta2-Adrenergic Receptor Signaling. Cell; 161(5): 1101-1111.
120. Carpenter, B., et al. (2016). Engineering a minimal G Protein to facilitate crystallisation of G protein coupled receptors in their active conformation. Submitted.
121. Ballesteros, J. A., et al. (1995). Integrated methods for the construction of three dimensional models and computational probing of structure function relations in G protein-coupled receptors. Methods in Neurosciences; 25: 366-428.
122. Park, J. H., et al. (2008). Crystal structure of the ligand-free G-protein-coupled receptor opsin. Nature; 454 (7201): 183-187.
123. Krumm, B. E., et al. (2015). Structural prerequisites for G-protein activation by the neurotensin receptor. Nat Commun; 6: 7895.
124. White, J. F. et al. (2012). Structure of the agonist-bound neurotensin receptor. Nature; 490(7421): 508-513.
125. Leslie, A. G. (2006). The integration of macromolecular diffraction data. Acta Crystallogr D Biol Crystallogr; 62(Pt 1): 48-57.
126. Evans, P. R., et al. (2013). How good are my data and what is the resolution? Acta Cryst. D Biol Crystallogr; 69(Pt 7): 1204-1214.
127. McCoy, A. J., et al. (2007). Phaser crystallographic software. J Appl Crystallogr; 40(Pt 4): 658-674.
128. Murshudov, G. N, et al. (2011). REFMAC5 for the refinement of macromolecular crystal structures. Acta Crystallogr D Biol Crystallogr; 67(Pt 4): 355-367.
129. Emsley, P., et al. (2010). Features and development of Coot. Acta Crystallogr D Biol Crystallogr; 66(Pt 4): 486-501.

EXAMPLE 5: FURTHER MINI-G PROTEINS

Summary

The first mini-G protein developed was mini-$G_s$. Here we extend the family of mini-G proteins to include mini-$G_{olf}$, mini-$G_{i1}$, mini-$G_{o1}$ and the chimeras mini-$G_{s/q}$ and mini-$G_{s/i}$. The mini-G proteins were shown to couple to relevant GPCRs and to form stable complexes with purified receptors that could be purified by size exclusion chromatography. Agonist-bound GPCRs coupled to a mini-G protein showed higher thermal stability compared to the agonist-bound receptor alone. Fusion of GFP at the N-terminus of mini-G proteins allowed receptor coupling to be monitored by fluorescence-detection size exclusion chromatography (FSEC) and, in a separate assay, the affinity of mini-G protein binding to detergent-solubilised receptors was determined. This work provides the foundation for the development of any mini-G protein and, ultimately, for the structure determination of any GPCR in a fully active state.

Introduction

The concept of mini-G proteins shows great promise for accelerating the rate of structure determination of GPCRs in their active states. However, there are four families of Gα subunits (FIG. 28; $G\alpha_s$, $G\alpha_i$, $G\alpha_q$, and $G\alpha_{12}$) that show different specificities for various GPCRs [24]. Thus to be truly useful as tools in structural biology, at least one member from each family needs to be converted into a mini-G protein. Here we report the development of mini-G proteins for all the major Gα families. We also describe five different assays that can be used to characterize the binding of the mini-G proteins to GPCRs and show in three cases that the complexes can be purified by size exclusion chromatography. The two different methodologies for generating the mini-G proteins can be applied easily to any other Gα subunit, opening the doorway to studies on potentially any GPCR from any species.

Materials and Methods

Ligands

The $\beta_1$-adrenergic receptor ($\beta_1$AR) agonist isoproterenol hydrochloride and inverse agonist ICI118551 hydrochloride were from Sigma-Aldrich. The adenosine $A_{2A}$ receptor ($A_{2A}R$) agonist NECA and antagonist ZM241385 were also from Sigma Aldrich. Serotonin $5HT_{1B}$ receptor ($5HT_{1B}R$) agonist donitriptan hydrochloride and selective antagonist SB224289 hydrochloride were from Santa Cruz Biotechnology; the agonist sumatriptan succinate was from Cayman chemical. Angiotensin II receptor ($AT_1R$) agonist angiotensin II was from Tocris. All radioactive ligands were from PerkinElmer.

GPCR Constructs, Expression and Purification

Human adenosine $A_{2A}$ receptor ($A_{2A}R$)

Two different $A_{2A}R$ constructs were used during this work. For SEC experiments using purified receptor, an $A_{2A}R$ construct was used that contained an N-terminal thioredoxin fusion protein to increase the molecular weight of the receptor. Without this fusion protein, $A_{2A}R$ and the mini-G protein had identical mobility on SDS-PAGE, thus making it difficult to visualise the separate components when analyzing a complex. The thioredoxin-$A_{2A}R$ fusion protein consisted of an N-terminal cleavable leader sequence (gp67), His10 tag and TEV protease cleavage site, followed by thioredoxin, which was connected to wild-type human $A_{2A}R$ (residues 6-316) through an EAAAKA linker. $A_{2A}R$ contained the N154A mutation to remove a potential N-linked glycosylation site. For all other experiments, a C-terminally truncated human $A_{2A}R$ construct was used (residues 1-317), which contained a C-terminal His10 tag and TEV protease cleavage site and the N154A mutation to remove the potential N-linked glycosylation site. Both constructs were expressed using the baculovirus expression system as described previously [19] (see Example 4). Cells were harvested by centrifugation 72 hours post infection, resuspended in hypotonic buffer (20 mM HEPES pH7.5, 1 mM EDTA, 1 mM PMSF), flash-frozen in liquid nitrogen and stored at −80° C. until use. Purification of the receptor was performed in DDM using $Ni^{2+}$-affinity chromatography followed by SEC essentially as described previously [19].

Turkey $\beta_1$-Adrenergic Receptor ($\beta_1$AR)

A truncated version of wild type turkey $\beta_1$AR (construct βAR6; [25]) contained truncations at the N-terminus and the C-terminus and a C-terminal His6 tag for purification [25], and was expressed using the baculovirus expression system at 27° C. as described previously [26]. Cells were harvested by centrifugation 48 hours post infection, resuspended in hypotonic buffer (20 mM Tris HCl pH8, 1 mM EDTA, 1 mM PMSF), flash-frozen in liquid nitrogen and stored at −80° C. until use.

Human Angiotensin Type II Receptor 1 ($AT_1R$)

Wild type $AT_1R$ (residues 1-359) had a C-terminal factor X cleavage site followed by GFP and a His10 tag for purification, and was expressed using the tetracycline-inducible mammalian expression system as a stable cell line in HEK293 cells [27]. Cells were grown in DMEM containing 5% tetracycline-free FBS until they were 80% confluent and then tetracycline was added to a final concentration of 1 µg/ml. Cells were grown for 24 hours and then harvested, and resuspended in PBS, flash frozen in liquid nitrogen and stored at −80° C. until use.

Rat Neurotensin Receptor (NTSR1)

NTSR1 was expressed as described previously [13]. The baculovirus construct NTSR1 consisted of the hemagglutinin signal peptide and the Flag tag, followed by the wild-type rat NTSR1 (residues 43-396) and a C-terminal His10 tag. Recombinant baculovirus was generated using a modified pFastBac1 transfer plasmid (Invitrogen). *Trichoplusia ni* cells were infected with recombinant virus, and the temperature was lowered from 27° C. to 21° C. Cells were harvested by centrifugation 48 hours post infection, resuspended in hypotonic buffer (10 mM HEPES pH 7.5, 10 mM $MgCl_2$, 20 mM KCl), flash-frozen in liquid nitrogen and stored at −80° C. until use.

Human Serotonin $5HT_{1B}$ Receptor ($5HT_{1B}R$)

Wild-type $5HT_{1B}R$ (residues 34-390) was modified to contain a C-terminal TEV cleavage site and a His10 tag, cloned into plasmid pBacPAK8 and recombinant baculoviruses were prepared using the FlashBAC ULTRA system (Oxford Expression Technologies). *Trichoplusia ni* cells were grown in ESF921 media (Expression Systems) to a density of $3\times10^6$ cells/ml, infected with $5HT_{1B}R$ baculovirus and incubated for 48 h at 27° C. for expression. Purification of the receptor was performed in either DDM or LMNG using $Ni^{2+}$-affinity chromatography followed by SEC.

Expression, Purification and Stability of G Protein Subunits

For constructs see FIGS. 29 and 35-37. Expression, purification and stability measurements by differential scanning fluorimetry (DSF) of the mini-G proteins as well as the non-lipidated $G\beta_1\gamma_2$ dimer, were performed following the protocols described in Example 1. The stability of mini-G proteins was also determined in detergent using native DSF (NanoTemper Prometheus). Mini-G proteins (2 mg/ml) in 50 mM HEPES pH 7.5 (KOH), 20 mM MgCl2, 50 mM NaCl, 1 µM GDP were mixed with either no detergent (control), 0.1% LMNG or 0.1% DDM. Samples were incubated on ice (minimum 30 min) prior to heating on the Prometheus (20% excitation, 15° C.-85° C., rate of 2.0° C./min) and the onset of scattering determined.

SEC of the $A_{2A}$R-Mini-Gs Complex

The thioredoxin fusion construct of $A_{2A}$R was purified in DDM, mini-G protein was added in excess at a 1:1.2 molar ratio, incubated overnight on ice and then loaded onto a Superdex S200 10/300 size exclusion column (10 mM HEPES pH 7.5, 100 mM NaCl, 1 mM $MgCl_2$, 100 μM NECA, 0.02% DDM; 4° C., 0.5 ml/min). Peak fractions were analysed by SDS-PAGE.

FSEC Assays (1) $A_{2A}$R

Insect cell membranes containing a total of 20 μg (560 pmol) wild-type $A_{2A}$R ($20 \times 10^6$ cells) were solubilized for 30 min on ice in 40 mM HEPES pH7.5, 500 mM NaCl, 2 mM $MgCl_2$, 2 U/mL apyrase (Sigma-Aldrich), and 0.5% (v/v) DDM in a final volume of 2 ml. Insoluble material was removed by ultracentrifugation (30 min, 4° C., 135,000×g). The supernatant was divided into aliquots for the subsequent assay. To 500 μl of the supernatant was added either the agonist NECA or the inverse agonist ZM241385 (negative control), both at a final concentration of 60 μM. GFP-mini-$G_s$ (6 μg; 110 pmol) was then added and allowed to bind for 90 min on ice before loading 200 μl onto a Superdex S200 10/300 size exclusion column (buffer 20 mM HEPES 7.5, 100 mM NaCl, 10 mM $MgCl_2$, 1 μM NECA or ZM241385, 0.03% DDM, 4° C., flow rate 0.45 ml/min). The control sample contained 6 μg GFP-mini-$G_s$ only in 500 μl assay buffer. GFP fluorescence was detected by a Hitachi fluorometer (mV) set to an excitation of 488 nm and an emission of 525 nm.

(2) $β_1$AR

Insect cell membranes containing a total of 8 μg (178 pmol) wild-type $β_1$AR ($30 \times 10^6$ cells) were solubilized for 30 min on ice in 20 mM Tris-HCl pH8, 500 mM NaCl, 5 mM $MgCl_2$, 2 U/mL apyrase and 0.5% (v/v) DDM. Insoluble material was removed by ultracentrifugation (30 min, 4° C., 135,000×g). The supernatant was divided into aliquots for the subsequent assay. Isoprenaline (100 μM final concentration) or ICI118551 (10 μM final concentration) were added to 500 μl of the supernatant. GFP-mini-$G_s$ (6 μg) was then added and allowed to bind for 90 min on ice before loading 200 μl onto a Superdex S200 10/300 size exclusion column (buffer 20 mM HEPES pH 7.5, 100 mM NaCl, 10 mM $MgCl_2$, 1 μM isoprenaline or ICI118551, 0.03% DDM, 4° C., flow rate 0.45 ml/min). The control sample contained 6 μg GFP-mini-G only in 500 μl assay buffer.

(3) $5HT_{1B}$R

When detergent-solubilized unpurified receptor was used, insect cells expressing 610 pmol $5HT_{1B}$R ($40 \times 10^6$ cells) were resuspended in 20 mM HEPES pH 7.5, 100 mM NaCl, 10 mM $MgCl_2$ to a final cell density of $20 \times 10^6$ cells/ml and solubilized with 0.5% DDM (45 min, 4° C.). Insoluble material was removed by ultracentrifugation (30 min, 4° C., 135,000×g). The supernatant was divided into 900 μl aliquots for the subsequent assay. GFP-mini-$G_{o1}$ (5 μg) was added with either donitriptan or SB224289, each to a final concentration of 100 μM, and allowed to bind for 90 min on ice before loading 500 μl onto a Superdex S200 10/300 size exclusion column. The control sample contained 5 μg GFP-mini-$G_{o1}$ in 500 μl assay buffer.

In some FSEC experiments, purified $5HT_{1B}$R was used. Donitriptan-bound, purified receptor (120 μg; 3 nmol) in either LMNG or DDM was incubated for 90 min on ice with 4 μg (60-80 pmol) either of GFP-mini-$G_{i1}$, GFP-mini-$G_{o1}$ or GFP-mini-$G_s$ (negative control) in a final volume of 450 μl. Samples (200 μl) were then loaded onto Superdex S200 10/300 size exclusion column (buffer 20 mM HEPES pH 7.5, 100 mM NaCl, 10 mM $MgCl_2$, 1 μM 0.03% DDM or 0.001% LMNG buffer, 4° C., flow rate 0.45 ml/min).

Fluorescent Saturation Binding Assay (FSBA)

(1) $β_1$AR

Membranes prepared from insect cells expressing $β_1$AR ($50 \times 10^6$ cells) were solubilized in 20 mM Tris-HCl pH8, 500 mM NaCl, 3 mM imidazole, 0.5% DDM (1 hour, 4° C., final volume 8 ml). Insoluble material was removed by ultracentrifugation (30 min, 4° C., 135,000×g) and the supernatant was divided into two aliquots. The agonist isoprenaline was added to one sample (final concentration 10 μM) and the inverse agonist ICI118551 was added to the other (final concentration 1 μM). Samples were then aliquoted 200 μl per well into a black $Ni^{2+}$-coated 96-well plate (Pierce; Thermo Fisher). The receptor was allowed to bind via its His tag for 1 h on ice. The supernatant was then aspirated and 200 μl GFP-mini-$G_s$ at varying concentrations (0 to 2.8 μM) were added and incubated for a further 90 min on ice. The supernatant was then removed by aspiration and each well washed 4 times with buffer A (10 μM isoprenaline (agonist), 20 mM Tris-HCl pH8, 100 mM NaCl, 1 mM $MgCl_2$, 1 mg/mL BSA, 30 mM imidazole, 0.03% DDM,) or buffer B (1 μM ICI118551 (inverse agonist), 20 mM Tris-HCl pH8, 100 mM NaCl, 1 mM $MgCl_2$, 1 mg/mL BSA, 30 mM imidazole, 0.03% DDM). Elution of the receptor-GFP-mini-$G_s$ complex from the sides of the well to make a homogeneous solution was performed with 200 μl of the respective wash buffers that contained 300 mM imidazole. Fluorescence was then measured using a Pherastar plate reader (BMG Labtech, Inc.) with excitation at 485 nm and emission at 520 nm. ΔF data (fluorescence agonist condition minus fluorescence antagonist condition) corresponding to specific binding were analysed by non-linear regression using GraphPad Prism version 5.0 (GraphPad Software, San Diego, Calif.) and apparent $K_D$ values derived from one site-specific binding analysis.

(2) $A_{2a}$R

The assay was performed essentially as described above for $β_1$AR, but the buffer conditions were different. Solubilisation of insect cell membranes ($40 \times 10^6$ cells) was performed in 10 ml of 20 mM Tris-HCl pH8, 500 mM NaCl, 10 mM imidazole and 0.5% DDM. After ultracentrifugation, the agonist NECA (10 μM final concentration) was added to one supernatant sample and the inverse agonist ZM241385 (10 μM final concentration) to the other. Washing buffers for $A_{2a}$R were buffer C (10 uM NECA, 20 mM Tris-HCl pH8, 100 mM NaCl, 1 mM MgCl2, 1 mg/mL BSA, 50 mM imidazole, 0.03% DDM) or buffer D (10 μM ZM241385, 20 mM Tris-HCl pH8, 100 mM NaCl, 1 mM MgCl2, 1 mg/mL BSA, 50 mM imidazole, 0.03% DDM).

(3) $5HT_{1B}$R

Insect cells expressing $5HT_{1B}$R ($50 \times 10^6$ cells) were solubilized with buffer containing 10 μM Donitriptan, 20 mM Tris-HCl pH8; 500 mM NaCl; 10 mM imidazole, 0.5% DDM (1 h, 4° C., final volume 6 ml). Insoluble material was removed by ultracentrifugation (30 min, 4° C., 135,000×g) and 200 μl of supernatant was then aliquoted per well into a black $Ni^{2+}$-coated 96-well plate. The receptor was allowed to bind via its His tag for 1 h on ice. The supernatant was then aspirated and 200 μl either of GFP-mini-$G_{o1}$, GFP-mini-$G_{s/i1}$ or GFP-mini-$G_s$ (negative control) at varying concentrations (from 0 to 5 μM) were added and incubated for a further 90 min on ice. The supernatant was then removed by aspiration and each well washed 4 times with buffer E (1 μM Donitriptan, 20 mM Tris-HCl pH8, 100 mM NaCl, 1 mM $MgCl_2$, 1 mg/mL BSA, 50 mM imidazole, 0.03% DDM). Elution was carried out with 200 μL of buffer E containing 300 mM imidazole. ΔF data (fluorescence $G_{o1}$ condition minus fluorescence $G_s$ condition) corresponding to specific binding were analysed by non-linear regression using GraphPad Prism version 5.0 (GraphPad Software, San Diego, Calif.) and apparent $K_D$ values derived from one site-specific binding analysis.

Competition Binding Assay

Insect cells expressing $5HT_{1B}R$ were resuspended in 1 ml of assay buffer (20 mM HEPES pH7.5, 100 mM NaCl, 1 mM $MgCl_2$, 1 mM ascorbate, 20 μM pargyline) at a final concentration of $2\times10^6$ cells/ml. Cells were sheared by 10 passages through a bent 26G needle. The supernatant was diluted 10-fold in assay buffer and aliquots (900 μl) taken for each sample. Mini-G protein (100 μl, 25 μM final concentration) or buffer (negative control) was added. The mixture was aliquoted into a 0.2 ml PCR plate, 96 μl per well. Sumatriptan (12 μl), prepared in assay buffer also containing 2 U/ml apyrase, was added to each well (final concentrations in the range of 100 μM to 1 mM). Non-specific binding was determined in the presence of 100 μM donitriptan. Samples were mixed and incubated at 4° C. for 2 h. [$^3$H]-GR125743 (12 μl) was added at its apparent $K_D$ (10 nM) concentration. Samples were mixed and incubated at 4° C. for 2 h before filtering through 96-well glass fibre GF/B filter plate (Merck Millipore) and washing with ice-cold assay buffer. Filters were dried, punched into scintillation vials and 4 ml Ultima Gold scintillant (Perkin Elmer) were added. Radioactivity was quantified by scintillation counting (1 min per sample) using a Tri-Carb counter (Perkin Elmer), and $K_i$ values were determined using GraphPad Prism version 5.0 (GraphPad Software, San Diego, Calif.).

Thermostability Assay (1) $A_{2A}R$

Membranes from *Trichoplusia ni* cells expressing wild-type human $A_{2A}R$ were resuspended in $T_m$ buffer (25 mM HEPES pH 7.5, 100 mM NaCl, 1 mM $MgCl_2$) and homogenized by ten passages through a 26G needle. Mini-G protein was added at a final concentration of 25 μM. $^3$H-NECA and unlabeled NECA were mixed in a molar ratio of 1:5 and added to the membranes to give a final concentration of 1 μM (approximately ten-fold above the apparent $K_D$). The samples were incubated at room temperature for 1 h, then chilled on ice for 30 min. Decylmaltoside (DM) was added to a final concentration of 0.13%, and samples were incubated on ice for 1 h. Cell debris and insoluble material were removed by centrifugation (5 min, 20,000×g, 4° C.) and the supernatant was aliquoted (120 μl) into PCR strips. Samples were heated to the desired temperature for exactly 30 min, then quenched on ice for 30 min. Samples (50 μl) were loaded onto gel-filtration resin (Toyopearl HW-40F) packed into a 96-well filter plate (Millipore), which was centrifuged to separate receptor-bound from free radioligand [28]. Nonspecific binding was determined in the presence of 200 μM unlabelled NECA. Radioactivity was quantified by liquid scintillation counting using a MicroBeta TriLux scintillation counter (PerkinElmer). Data were analysed by non-linear regression using GraphPad Prism software. Apparent $T_m$ values were derived from sigmoidal dose-response analysis performed by non-liner regression. Results represent the mean±SEM of two independent experiments, performed in duplicate.

(2) NTSR1

Cell pellets from 10 ml of insect cell cultures were resuspended in 1.8 ml buffer containing DDM to give a final buffer composition of 50 mM TrisHCl pH 7.4, 100 mM NaCl, 1 mM MgCl2, 1% (w/v) DDM. The samples were placed on a rotating mixer at 4° C. for 1 hour. Cell debris and non-solubilized material were removed by ultracentrifugation (152,800×g, 4° C., 30 min), and the supernatant containing detergent-solubilized NTSR1 was used to test for thermal stability in the presence of NTS and mini-G proteins. For thermal denaturation curves, the supernatants were diluted 6.67-fold into assay buffer (50 mM TrisHCl pH 7.4, 100 mM NaCl, 1 mM $MgCl_2$) containing 22.5 μM mini-G protein and 10 nM $^3$H-NTS and incubated for 1 hour on ice. After addition of apyrase (0.25 units/ml, NEB), the sample was placed on ice for an additional 30 min. Samples (120 μl aliquots) were exposed to different temperatures between 0° C. and 60° C. for 30 min and placed on ice. Separation of receptor-ligand-mini-G protein complex from free $^3$H-NTS (100 μl) was achieved by centrifugation-assisted gel filtration (spin assay) using Bio-Spin 30 Tris columns (BioRad), equilibrated with RDB buffer [50 mM TrisHCl pH7.4, 1 mM EDTA, 0.1% (w/v) DDM, 0.2% (w/v) CHAPS, 0.04% (w/v) CHS], essentially as described previously [29]. Control reactions on ice were recorded at the start and at the end of each denaturation experiment. The percentage of activity remaining after heat exposure was determined with respect to the unheated control. Data were analyzed by nonlinear regression using a Boltzmann sigmoidal equation in the Prism software (GraphPad).

(3) $AT_1R$

HEK 293 cells expressing wild type $AT_1R$ were resuspended in a radioligand binding assay buffer (50 mM HEPES pH 7.4, 150 mM NaCl, 1 mM EDTA, 0.1% BSA, 40 μg/ml bacitracin) and homogenized by sonication (4 sec pulse). Mini-G protein and apyrase were added at a final concentration of 25 μM and 0.1 units/ml, respectively. $^{125}$I-Ang II and unlabeled Ang II were added at a concentration of 0.5 nM and 25 nM respectively (approximately 50 times the apparent $K_D$ value). The sample was incubated at room temperature (20° C.) for an hour, chilled on ice for 10 minutes and then digitonin was added to a final concentration of 1% and incubated on ice for an hour. Insoluble material was removed by centrifugation (2 min, 20,000×g, 4° C.). The reaction mix was split into a number of 115 μl aliquots and each was incubated at various temperatures for exactly 30 minutes. The reactions were then quenched on ice for 5 minutes. $^{125}$I-Ang II bound to $AT_1R$ was separated from unbound $^{125}$I-Ang II using centrifugation-assisted gel filtration column, essentially as described previously [27]. Non-specific binding was determined using a 500-fold excess of cold ligand. Radioactivity was measured using liquid scintillation counting. Data was analysed by non-linear regression using GraphPad prism software and apparent $T_m$ values were derived by non-linear regression of the sigmoidal dose-response curve.

Results and Discussion

Initial Development of New Mini-G Proteins

The recently designed minimal G protein, mini-$G_s$ [23], comprises only the GαGTPase domain from $G_s$ and 3 deletions and 7 mutations to thermostabilise it (FIG. 29). Mini-$G_s$ coupled to both the $\beta_1$-adrenergic receptor ($\beta_1AR$) and the adenosine $A_{2A}$ receptor ($A_{2A}R$), and resulted in the same increase in agonist affinity as observed for heterotrimeric $G_s$ coupling [19, 23 and Examples 1 and 4]. However, there are 4 families of Gα subunits (FIG. 28) and GPCRs couple to distinct G proteins depending upon their physiological function [24]. Therefore, to provide tools for the structure determination of any GPCR in its fully active state, it was necessary to develop versions of mini-G proteins for at least one member from each of the other families. All of the mutations and deletions used to create mini-$G_s$ are located within conserved regions of the Gα subunit (FIG.

29). Therefore, in theory, these mutations were potentially transferable to the other Gα families, allowing the production of a panel of mini-G proteins capable of coupling to any GPCR.

Archetypical members from each Gα family were selected and include the following: $G_{olf}$ from the $G_s$ family, $G_{i1}$, $G_{o1}$, $G_z$ and $G_t$ from the $G_i$ family, $G_q$ and $G_{16}$ from the $G_{q/11}$ family, and $G_{12}$ from the $G_{12/13}$ family. The mutations required to convert $G\alpha_s$ into mini-$G_s$ were transferred en bloc to the selected Gα proteins to produce a mini-G protein version of each (FIG. 29). These mutations were the following: (i) deletion of all amino acid residues N-terminal of Ile/Leu$^{HN43}$; (ii) deletion of the α-helical domain between residues H$^{H1S2.12}$ and the Thr, three residues N-terminal to Ile$^{S2-1}$, and replacement with an 8 amino acid residue linker; (iii) deletion of 10 amino acid residues of switch III between Tyr$^{S4H3.4}$ and Asn/Ser$^{S4H3.15}$; (iv) mutating 7 residues to D49$^{S1H1.3}$, N50$^{S1H1.4}$, D249$^{S4.7}$, D252$^{S4H3.3}$, D272$^{H3.8}$, A372$^{H5.4}$, I375$^{H5.7}$. Residue numbers are for $G\alpha_s$ and superscripts refer to the CGN system for comparing residues in G proteins [6]. Initial characterization of each mini-G protein was performed by assessing expression in *Escherichia coli* and purification by Ni$^{2+}$-affinity chromatography and size exclusion chromatography (SEC). Four out of the eight engineered mini-G proteins (mini-$G_{olf}$, mini-$G_{i1}$, mini-$G_{o1}$ and mini-$G_{12}$) fulfilled these initial criteria i.e. they were all stable enough in their basal conformation to allow high-yield expression and purification. The yield of purified mini-G protein per litre of culture and their stability as measured by differential scanning fluorimetry (in parentheses) are as follows: mini-$G_s$, 100 mg/L (65° C.); mini-$G_{olf}$, 80 mg/L (65° C.); mini-$G_{o1}$ 100 mg/L (64° C.); mini-$G_{12}$ 25 mg/L (73° C.). The worst expressed of the four new mini-G proteins was mini-$G_{i1}$, so an additional mutation G217D was incorporated and the truncation at the N-terminus shortened, which increased the yield of pure protein to 12 mg/L, although the stability was only 48° C. Thus, mini-$G_{olf}$, mini $G_{i1}$, mini-$G_{o1}$ and mini-$G_{12}$ were all of sufficient stability to be used to test their ability to couple to relevant GPCRs. The amino acid sequences of the mini-G proteins are given in FIG. 35.

Four mini-G proteins were not expressed in *E. coli*, namely mini-$G_z$, mini-$G_t$, mini-$G_{16}$ and mini-$G_q$ (amino acid sequences are given in FIG. 36). The failure of the en bloc transfer of the deletions and mutations from mini-$G_s$, despite the high conservation of G protein structures, highlights our lack of understanding of the folding of these proteins. Indeed, it is well known that an accessory factor, Ric8, is required for the efficient folding of $G_q$ in mammalian cells [30], and other unknown factors may also be required. For the purpose of this study, we therefore did not perform any further development of mini-$G_{t1}$ and mini-$G_z$, given that two other members of the $G_i$ family, mini-$G_{i1}$ and mini-$G_{o1}$, already gave stable mini-G proteins. In contrast, as neither member of the $G_q$ family tested produced a stable mini-G protein, we decided to develop alternative strategies to make a usable version of mini-$G_q$, whilst further work on mini-$G_{16}$ was terminated. The successful engineering of a version of mini-$G_q$ chimera will be discussed later.

Assay Development and Validation Using the Mini-$G_s$ System

The ultimate goal of developing mini-G proteins is the structure determination of GPCRs in the fully active state bound to an agonist and a mini-G protein. In the simplest format, this necessitates the purification of the GPCR in detergents and forming the G protein-GPCR complex from the purified components in vitro. It was therefore essential to devise some simple assays that could assess whether a mini-G protein had coupled to a GPCR in detergent solution. This turned out to be not as straightforward as originally anticipated due to the potential instability of either the GPCR and/or mini-G protein in either their inactive and/or active conformations. These issues were not obvious when the original work on the development of mini-$G_s$ was performed, because mini-$G_s$ is one of the most stable mini-G proteins developed and also the thermostabilised $β_1$-adrenergic receptor ($β_1$AR) and the wild type adenosine $A_{2A}$ receptor ($A_{2A}$R) were both much more stable than other GPCRs. We therefore developed five separate assays for assessing whether a mini-G protein coupled to a GPCR and/or formed a stable complex in detergent. These were all first tested using mini-$G_s$ coupling to $β_1$AR and $A_{2A}$R. Each assay has its own limitations, which are often apparent in the subsequent sections where they were used on less stable receptors and the newly developed mini-G proteins, and these are discussed below. The five different assays that were used are the following: (i) agonist affinity shift assay; (ii) thermostability assay (TSA); (iii) fluorescence-based saturation binding analysis (FSBA) of GFP-mini-G protein binding; (iv) fluorescence-detection size exclusion chromatography (FSEC); (v) size exclusion chromatography (SEC) of purified complex. A brief rationale for the use of each assay with their advantages and disadvantages are given below.

(i) Agonist Affinity Shift Assay

The development of mini-$G_s$ relied on the agonist affinity shift assay to identify those mutants that coupled to $β_1$AR [23]. It is generally considered that the defining feature of G protein coupling is an increase in the affinity of an agonist for the G protein-GPCR complex compared to the GPCR alone. For example, wild type $β_2$AR binds an agonist 100-fold more tightly when coupled to a G protein than the receptor alone [31]. However, the shift in agonist affinity in other receptors is often considerably smaller than that observed for $β_2$AR, such as the 10-fold shift in agonist affinity observed in $β_1$AR [31] and may be entirely absent eg NTSR1. However, the advantage of this assay is that it can be performed using standard pharmacological procedures in high-throughput, using receptors in either membrane preparations or solubilized in detergent. Assays may use either a radiolabelled agonist in saturation binding experiments or, more usually, a radiolabelled antagonist in competition binding experiments [19, 23 and Examples 1 and 4] (and see experiments below on the serotonin 5HT$_{1B}$ receptor). The advantage of this assay is that it is very sensitive and can be performed on membrane-bound receptors i.e. in a format where the receptor is most stable in all conformations. The disadvantage of this assay is that some receptors may not show a shift in agonist affinity when coupled to a G protein.

(ii) Thermostability Assay

The thermostability of a detergent-solubilised GPCR depends upon the type of detergent used and whether the receptor is either ligand-free, agonist-bound or antagonist-bound [32, 33]. In addition, the receptor stability tends to be increased by an increase in affinity and/or decrease in the off-rate of the ligand [34]. Often, the agonist bound state is one of the least stable conformations of a receptor, presumably because agonists increase the probability of transitions to a fully active state. In the inactive state there is close packing of the intracellular surface of the transmembrane α-helices. Upon activation, the outward movement of helices 5 and 6 disrupts this close packed structure and creates a crevice where the C-terminus of the G protein binds, thus allowing G protein coupling [35]. The structures of nonrhodopsin GPCRs in the fully active state have been determined only when they have been stabilized through binding of a heterotrimeric G protein [2], a conformation-specific nanobody [14, 17, 18] or a mini-G protein [19]. The interface between a GPCR and a G protein is over 1000 Å$^2$ [2, 19], and is therefore predicted to increase the thermostability of the agonist-bound GPCR-G protein complex compared to the agonist-bound GPCR. This was observed for both $β_1AR$ and $A_{2A}R$, which were consistently more stable in the agonist-bound state when coupled to mini-$G_s$ in a variety of different detergents compared to when mini-$G_s$ was absent [19, 23 and Examples 1 and 4].

A typical thermostability assay measures how much of a radiolabelled agonist remains bound to a detergent-solubilised receptor after heating at different temperatures for 30 minutes [33]. The advantage of this assay is that it is fast and high-throughput and can be performed in any detergent of choice. Another advantage is that the agonist-GPCR-mini-G protein complex can be pre-formed in membranes, which may stabilise the receptor upon detergent solubilisation, allowing the assay to be performed. If there is a shift in thermostability in the presence of a mini-G protein, then this is strongly suggestive of binding or coupling.

(iii) Fluorescence-Detection Size Exclusion Chromatography (FSEC)

FSEC is a rapid methodology for assessing whether a membrane protein fused to GFP is stable in detergent by performing SEC on an unpurified detergent solubilisate and monitoring GFP fluorescence in the eluate [36]. A membrane protein stable in detergent gives a symmetrical peak at a size consistent with the molecular weight of the membrane protein plus the mass of specifically bound detergent and lipid. By fusing GFP to the N-terminus of mini-G proteins (FIG. 37), it was possible to use FSEC to monitor whether a stable complex was formed between the mini-G protein and a GPCR. The GFP-mini-$G_s$ fusion protein has a molecular weight of 54 kDa and migrated with a retention volume of 15.1 ml on FSEC. When this was mixed with either DDM-solubilised $β_1AR$ or $A_{2A}R$ in the presence of an agonist, then an additional peak was observed at 12.1-12.5 ml (FIG. 30a,c), which was consistent with the molecular weight of the detergent-solubilised receptor bound to GFP-mini-$G_s$ (~180 kDa). This additional peak was not observed if the receptors were bound to an inverse agonist. An additional peak was sometimes observed at a retention volume of 8 ml, which corresponds to the void volume of the SEC column and was due presumably to aggregates of GFP-mini-$G_s$.

The advantage of this assay is that it is a quick assessment of whether a GPCR forms a complex with a mini-G protein, because the receptor does not need to be purified and the SEC experiment takes under an hour. However, the major limitation is that only small amounts of GFP-mini-$G_s$ can be used per experiment to avoid saturation of the detector and producing a very broad peak that would obscure the presence of the complex between the GPCR and GFP-mini-G protein. Thus the concentration of the mini-G protein is below its $K_D$ for association with a receptor and therefore the assay is not quantitative. In addition, the receptor-mini-G protein complex must be detergent-stable for a peak to be observed. Many GPCR-G protein complexes are too unstable to be observed in DDM and therefore it is essential to assess milder detergents such as LMNG (see section on the serotonin $5HT_{1B}$ receptor).

(iv) Fluorescence-Based Saturation Binding Analysis of Mini-G Protein Binding

To determine the affinity of mini-G protein binding to a receptor, the fluorescence-based saturation binding assay (FSBA) was developed. In this assay, the amount of the GFP-mini-G protein specifically bound to an immobilized receptor was determined using a fluorescent plate reader. As proof of principle, DDM-solubilised $β_1AR$ or $A_{2A}R$ were immobilized onto $Ni^{2+}$-coated wells of a 96-well plate via their C-terminal poly-histidine tag, in the presence of either an agonist or inverse agonist. GFP-mini-$G_s$ was then added at increasing concentrations. After washing to remove any non-specifically bound GFP-mini-$G_s$, the amount of GFP-mini-$G_s$ fluorescence was measured (FIG. 30b,d). GFP-mini-$G_s$ showed a specific saturated binding to the receptor with apparent $K_D$ values of 201±1 nM (n=2) and 428±24 nM (n=2) for GFP-mini-$G_s$ binding to $β_1AR$ and $A_{2A}R$, respectively.

The FSBA is a simple assay for determining the affinity of mini-G protein binding to a receptor in vitro. However, it must be appreciated that the apparent affinity determined may be specific only for the conditions in the assay. In particular, the type of detergent used may have a profound effect on the affinity, especially if it slightly destabilizes the active state of the receptor. The agonist may also affect the apparent affinity of the mini-G protein, depending on how effective the agonist is in stabilizing the active state of the receptor. However, the FSBA remains a useful tool for biophysical analyses of mini-G protein binding to a receptor.

(v) Size Exclusion Chromatography (SEC)

The ultimate biochemical assay for observing coupling of mini-G proteins to a receptor is combining the purified components in vitro and then observing the co-elution of the relevant proteins on SEC [23 and Example 1]. Purified $A_{2A}R$ and purified mini-$G_s$ were mixed at a molar ratio of 1:1.2 in the presence of the agonist NECA, the complex allowed to form and then separation was performed by SEC. The $A_{2A}R$-mini-$G_s$ complex resolved as a predominant peak with an apparent molecular weight of 153 kDa compared with 133 kDa for the receptor alone and 22 kDa for mini-$G_s$ alone. SDS-PAGE analysis confirmed the presence of both $A_{2A}R$ and mini-$G_s$ in fractions from the 153 kDa complex (FIG. 30e).

The advantage of using purified components and SEC for analyzing complex formation is that complex formation is observed unambiguously. The conditions for complex formation can be refined and the stability of the complex can be assessed readily after a period of days by repeating the SEC. These data are essential for successful determination of the structure of a GPCR-mini-G protein complex. The disadvantage of this assay is that sufficient quantities of purified receptor are required and this may be limiting in the initial stages of a project.

Characterisation of Mini-G Proteins

Mini-$G_{olf}$ Couples and Stabilizes $A_{2A}R$

The GTPase domains of $G_{olf}$ and $G_s$ share 87% sequence identity (80% for the full length α subunits) and both G proteins couple to $A_{2A}R$ [37]. Of the 17 amino acid residues in mini-$G_s$ that make direct contact to residues in $A_{2A}R$ in the crystal structure of the $A_{2A}R$-mini-$G_s$ complex [19 and Example 4], all of these residues are identical except that two Arg residues in $G_s$ are replaced with two Lys residues in $G_{olf}$. Despite the high degree of sequence homology between these two isoforms, $Gα_{olf}$ is far more difficult to overexpress than $Gα_s$, in fact, the only method reported to produce functional $Gα_{olf}$ is co-expression with the molecular chaperone RIC8B in insect cells [38]. Therefore, we constructed mini-$G_{olf}$ to investigate whether the mini-G protein version would be better expressed that native α subunit. Mini-$G_{olf}$ was constructed by transferring the 7 point mutations and 3 deletions from mini-$G_s$ (FIG. 29) and mini-$G_{olf}$ was highly expressed in *E. coli* and as stable as mini-$G_s$. The coupling of mini-$G_{olf}$ to $A_{2A}R$ was assessed by SEC of the complex assembled in vitro from purified proteins and a thermostability assay [19, 23 and Examples 1 and 4]. Purified NECA-bound $A_{2A}R$ was mixed with mini-$G_{olf}$ and analysed by SEC and SDS-PAGE (FIG. 31a). The apparent molecular weight of mini-$G_{olf}$ was 23 kDa (17.1 ml; theoretical molecular weight 26 kDa) and the apparent molecular weight of purified $A_{2A}R$ in DM was 133 kDa (13.3 ml). The complex $A_{2A}R$-mini-$G_{olf}$ resolved as a predominant peak with an apparent molecular weight of 153 kDa (13 ml) and contained both $A_{2A}R$ and mini-$G_{olf}$. Mini-$G_{olf}$ also stabilized agonist-bound DM-solubilised $A_{2A}R$, with mini-$G_{olf}$-coupled $A_{2A}R$ showing an apparent $T_m$ of 32.5±1° C. in comparison with 26.9±0.3° C. for the receptor alone (FIG. 31b). This stability was similar to that obtained with mini-$G_s$ (32.9° C.) under the same conditions [19 and Example 4].

The results with mini-$G_{olf}$ were very encouraging in terms of both the transferability of the mutations, the expression and stability of the mini-$G_{olf}$ and the stability of the $A_{2A}R$-mini-$G_{olf}$ complex. Thus where there is a high degree of homology between G proteins, then there is good transferability of the mutations, as was previously observed for the transfer of thermostabilising mutations between GPCRs [39]. These data also suggested that even if the native α subunit is poorly expressed the mini-G protein version may be highly expressed and very stable.

Development of Chimeric Mini-$G_{s/g}$ to Study $G_q$-Coupled Receptors

The expression of mini-$G_q$ in *E. coli* was unsuccessful. One possibility to explain this is that efficient folding of $G_q$ in vivo is dependent on the molecular chaperone Ric8 [30] and that mini-$G_q$ had a similar requirement. Indeed, co-expression of Ric8 with mini-$G_q$ in the baculovirus expression system led to the overproduction of mini-$G_q$. However, upon purification of mini-$G_q$ it was not possible to dissociate Ric8 (results not shown), suggesting that the mini-$G_q$ was perhaps not correctly folded and/or was very unstable. Given the lack of success in transferring the mini-G protein mutations from $G_s$ to $G_q$, another strategy was developed.

The second strategy used to try and develop mini-$G_q$ was to transfer the specificity determinants of $G_q$ onto mini-$G_s$. It is well established that the C-terminal region of a Gα subunit forms the main receptor binding site [40] and is one of the main determinants of coupling specificity [41, 42]. Mutating as few as 3-5 amino acids at the C-terminus of the G alpha subunit has been shown to switch the specificity of coupling to some GPCRs [41, 42]. However, the two GPCR-G protein structures published to date [2, 19] revealed an extensive interface between the receptors and Gα, suggesting that other regions of the G protein may also play a role in specificity. Recent in vivo FRET studies suggest that residues within the α5 helix, but distal to the five C-terminal residues, strongly influence specificity [43].

Mini-$G_s$ did not couple to any of the $G_q$-coupled receptors tested (results not shown). We then evaluated a number of mini-$G_{s/q}$ chimeras (FIG. 38) for both gain of binding to $G_q$-coupled receptors (FIG. 32a,b) and loss of binding to the cognate $G_s$-coupled receptor $A_{2A}R$, predominantly using thermostability assays (FIG. 32c) and SEC (FIG. 39). First, the chimera mini-$G_{s/q}$57 was constructed in which the five C-terminal amino acids of mini-$G_s$ ($Q^{H5.22}YELL^{H5.26}$) were changed to those found in Gα$_q$, which required three mutations ($Q390E^{H5.22}$, $E392N^{H5.24}$ and $L394V^{H5.26}$). We did not observe any detectable interaction between this construct and any of the $G_q$ receptors tested (FIG. 32a,b). Furthermore, a complex between mini-$G_{s/q}$57 and $A_{2A}R$ was still observed (FIG. 32c and FIG. 39), suggesting that the mutations were insufficient to change the specificity of $G_s$ to $G_q$. Next, the chimera mini-$G_{s/q}$58 was constructed in which the final 19 amino acid residues in the α5 helix of mini-$G_s$ ($Phe376^{H5.8}$-$Leu394^{H5.26}$) were changed to those in Gα$_q$; this required 13 mutations ($N377A^{H5-9}$, $D378A^{H5.10}$, $C379V^{H5.11}$, $R380K^{H5.12}$, $I382T^{H5.14}$, $Q384L^{H5.16}$, $R385Q^{H5.17}$, $M386L^{H5.18}$, $H387N^{H5.19}$, $R389K^{H5.21}$, $Q390E^{H5.22}$, $E392N^{H5.24}$ and $L394V^{H5.26}$). Mini-$G_{s/q}$58 did not couple to $A_{2A}R$ (FIG. 32c and FIG. 39), demonstrating that residues in the α5 helix beyond the C-terminal 5 amino acids are important in G protein specificity. However, there was no significant shift in the thermostability of the $G_q$-coupled receptor NTSR1 in the presence of mini-$G_{s/q}$58 (FIG. 32b). We reasoned that this may be because the stability of mini-$G_{s/q}$58 was impaired, because mutating the last 19 amino acid residues in mini-Gs would have also changed residues buried in the core of the G protein, thus affecting the stability of the mini-$G_s$ backbone. Therefore, a refined version of this chimera, mini-$G_{s/q}$70, was constructed in which residues in the α5 helix whose side chains formed direct contacts (3.9 Å cut-off) with either β$_2$AR [2] or $A_{2A}R$ [19] in the G protein-bound structures were mutated to match those in Gα$_q$ ($R380K^{H5.12}$, $Q384L^{H5.16}$, $R385Q^{H5.17}$, $H387N^{H5.19}$, $E392N^{H5.24}$ and $L394V^{H5.26}$; FIG. 38). In addition, the mutation $Q390E^{H5.22}$ was included, despite only making contact to $A_{2A}R$ via its backbone, as it is buried in the receptor-G protein interface and may be important for binding to $G_q$-coupled receptors. Mini-$G_{s/q}$70 gave better binding to both $G_q$-coupled receptors tested, NTSR1 and $AT_1R$, and showed no binding to $A_{2A}R$ (FIG. 32 and FIG. 39).

Two other chimeras were also constructed to try and improve on mini-$G_{s/q}$70. Mini-$G_{s/q}$72 contained the additional mutation $C379V^{H5.11}$ compared to mini-$G_{s/q}$70 and, although the $C379^{H5.11}$ side chain does not form direct contacts with either $A_{2A}R$ or β$_2$AR, its mutation to Val is predicted to introduce a direct interaction between the Val γ2 carbon and Leu110 from $A_{2A}R$. However, the $AT_1R$-mini-$G_{s/q}$72 complex did not have a higher thermostability than $AT_1R$-mini-$G_{s/q}$70 (results not shown). Finally, the chimera mini-$G_{s/q}$71 was constructed in which residues from other regions of Gα that form direct contacts with either β$_2$AR [2] or $A_{2A}R$ [19] were mutated to match those in Gα$_q$. This included the seven mutations in mini-$G_{s/q}$70 ($R380K^{H5.12}$, $Q384L^{H5.16}$, $R385Q^{H5.17}$, $H387N^{H5.19}$, $Q390E^{H5.22}$, $E392N^{H5.24}$ and $L394V^{H5.26}$) and six additional mutations ($A39R^{HNS1.3}$, $H41L^{S1.2}$, $D343K^{H4.23}$, $L346V^{H4.26}$, $R347D^{H4.27}$ and $Y358I^{H4S6.11}$). $D343^{H4.23}$ was the only amino acid residue whose side chain did not interact with either $A_{2A}R$ or β$_2$AR, but the mutation to Lys was included because the longer side chain could potentially interact with a receptor and the charge reversal may be important for specificity. Conversely, $Thr350^{H4S6.3}$ was not mutated to Pro in mini-$G_{s/q}$71 even though its side chain forms direct contacts with β$_2$AR. Alignment of Gα$_s$ with two independently solved structures of Gα$_q$ [44, 45] showed that this region of the G proteins differ significantly and thus, in Gα$_q$, this residue is unlikely to interact with the receptor. However, after all these considerations to make an improved version of mini-$G_{s/q}$70, mini-$G_{s/q}$71 did not improve the thermostability of agonist-bound $G_q$-coupled receptors compared to mini-$G_{s/q}$70 (FIG. 32a,b).

Mini-$G_{i1}$: Tackling Stability Issues

Transfer of the 7 point mutations and 3 deletions from mini-$G_s$ into $G\alpha_{i1}$ to make mini-$G_{i1}$ was not successful, as the resultant protein was very poorly expressed and had low stability (results not shown). Whilst the work on developing chimeras of mini-$G_{s/q}$ was underway, we decided to first study the reasons why mini-$G_{i1}$ appeared to be so unstable. Therefore, to improve expression, stability and to allow binding of the mini-$G_{i1}$ to the βγ subunits, the N-terminus (residues 4-18) was re-inserted, Asp249$^{H3.8}$ was mutated back to Leu, and the G217D$^{H2.S4.3}$ mutation introduced based on a sequence comparison between $G_{i1}$ (poorly expressed) and $G_s/G_o$ (highly expressed) (FIG. 29 and FIG. 35). The resultant mini-$G_{i1}$ (construct 46) yielded only 12 mg of purified protein per litre of culture and was 17° C. less stable than mini-$G_s$, but was suitable for initial studies in GPCR coupling.

The serotonin 5-HT$_{1B}$ receptor (5HT$_{1B}$R) was used as a model $G_i$-coupled receptor for developing mini-$G_{i1}$ because it could be expressed and purified in DDM using the baculovirus expression system and its structure determined in the inactive state [10]. Initially, GFP-mini-$G_{i1}$ was tested using FSEC for binding to purified 5HT$_{1B}$R (in DDM) and bound to the agonist donitriptan. However, the GFP-mini-$G_{i1}$ (FIG. 37) migrated at 13.5 ml in the absence of receptor or in the presence of donitriptan-bound 5HT$_{1B}$R, indicating that no coupling occurred (FIG. 33c). However, when the LMNG-purified 5HT$_{1B}$R was used, the FSEC showed two peaks, one corresponding to free GFP-mini-$G_{i1}$ with a retention volume of 14.3 ml and the other corresponding to GFP-mini-$G_{i1}$ bound to donitriptan-activated 5HT$_{1B}$R, with a retention volume of 12.2 ml (FIG. 33d). As donitriptan-bound 5HT$_{1B}$R has been crystallised, this suggested that the receptor is reasonably stable in detergent, which in turn suggested that the instability of the GFP-mini-$G_{i1}$-5HT$_{1B}$R-donitriptan complex was probably due to the mini-G protein rather than the receptor. This was tested by forming a heterotrimer between GFP-mini-$G_{i1}$46 (FIG. 37) and $\beta_1\gamma_2$, making a mini-trimer complex with donitriptan-bound 5HT$_{1B}$R in LMNG and performing FSEC. The GFP-mini-trimer in complex with the LMNG-purified 5HT$_{1B}$R resolved as a single peak with a retention volume of 11.8 ml compared to 14.3 ml for the free GFP-mini-$G_{i1}\beta_1\gamma_2$ trimer (FIG. 33f). Thus the $\beta_1\gamma_2$ subunits restored the stability of mini-$G_{i1}$.

Although the mini-$G_{i1}\beta_1\gamma_2$ trimer coupled successfully to LMNG-solubilised 5HT$_{1B}$R, this is not as desirable for crystallography as a mini-G protein coupled receptor due to the large size of the heterotrimeric G protein. Therefore, following the successful strategy of changing the coupling of mini-$G_s$ to that of $G_q$ by making a mini-$G_{s/q}$ chimera, the same strategy was applied to engineer a mini-$G_{s/i1}$ chimera (FIG. 35 and FIG. 40). Therefore 9 mutations (C379V$^{H5.11}$, R380T$^{H5.12}$, Q384I$^{H5.16}$, R385K$^{H5.17}$, H387N$^{H5.19}$, Q390D$^{H5.22}$, Y391C$^{H5.23}$, E392G$^{H5.24}$ and L394F$^{H5.26}$) were introduced into the α5 helix of mini-$G_s$ to change its coupling specificity to that of $G_{i1}$. A complex between GFP-mini-$G_{s/i1}$43 (FIG. 37) with donitriptan-bound DDM-purified 5HT$_{1B}$R resolved as a single peak with a retention volume of 13.2 ml compared to 15.1 ml for the free GFP-mini-$G_{s/i1}$ (FIG. 33e). Thus mini-$G_{s/i1}$ was indeed more stable than mini-$G_{i1}$. The specificity of mini-$G_s$ compared to mini-$G_{s/i1}$ for donitriptan-bound, DDM-solubilised 5HT$_{1B}$R was confirmed using FSBA (FIG. 33b). No specific coupling of GFP-mini-$G_s$ to 5HT$_{1B}$R was observed, although specific coupling to GFP-mini-$G_{s/i1}$ (apparent $K_D$ 386 nM; FIG. 33b) was confirmed.

In order to compare all the mini-$G_{i1}$ constructs and the role of $\beta_1\gamma_2$, agonist affinity shift assays were performed on 5HT$_{1B}$R. The uncoupled receptor showed a $K_i$ for the agonist sumatriptan in this assay of 276±10 nM, which was shifted by mini-$G_{i1}$46 and mini-$G_{s/i1}$43 to 80±13 nM and 36±2 nM, respectively (FIG. 33a). However, addition of $\beta_1\gamma_2$ to the mini-G proteins resulted in a further increase in agonist affinity to 15±1 nM and 7.2±0.8 nM for mini-$G_{i1}$46-$\beta_1\gamma_2$ and mini-$G_{s/i1}$43-$\beta_1\gamma_2$, respectively. Thus despite the successful generation of both mini-$G_{i1}$ and mini-$G_{s/i1}$, their stability is still not perfect as binding of $\beta_1\gamma_2$ stabilises the mini-G proteins and elicits a greater increase in agonist affinity upon coupling of the mini-trimers.

Coupling of Mini-$G_{o1}$ to 5HT$_{1B}$R

The GTPase domain of $G_{o1}$ and $G_{i1}$ are highly conserved (80% identity), but the mini-G proteins derived from them behaved very differently. Unlike the unstable mini-$G_{i1}$, mini-$G_{o1}$ expressed well (100 mg/L), had high stability comparable to mini-$G_s$ and it was largely insensitive to the presence of mild detergents. Since 5HT$_{1B}$R couples to both $G_o$ and $G_i$ family members [46], we tested mini-$G_{o1}$ coupling to 5HT$_{1B}$R and compared the results to coupling with mini-$G_{i1}$ (see above). On FSEC, GFP-mini-$G_{o1}$12 (FIG. 37) partially coupled to donitriptan-bound, DDM-solubilised 5HT$_{1B}$R (unpurified), with the higher molecular weight species (retention volume 13 ml) reduced when the receptor was bound to an antagonist (FIG. 34c). This was in contrast to the results with mini-$G_{i1}$ under the same conditions where no binding was observed (FIG. 33c). The partial coupling probably resulted from the low concentration of 5HT$_{1B}$R and GFP-mini-$G_{o1}$ used in the assay, because when the experiment was repeated using purified 5HT$_{1B}$R and GFP-mini-$G_{o1}$, all of the GFP-mini-$G_{o1}$ bound to the receptor (FIG. 34e). In addition, the complex was purified by SEC and SDS-PAGE indicated co-elution of 5HT$_{1B}$R and mini-$G_{o1}$ in a 1:1.2 molar ratio (FIG. 34d). GFP-mini-$G_{o1}$ bound to DDM-solubilised 5HT$_{1B}$R in the presence of donitriptan with an apparent $K_D$ of 184±24 nM (FIG. 34b). In membranes, mini-$G_{o1}$12 shifted the agonist affinity for 5HT$_{1B}$R from 276±10 nM to 32±3 nM (FIG. 34a).

The properties of mini-$G_{o1}$ make this an ideal choice for structural studies of $G_o/G_i$ coupled receptors, rather than using mini-$G_{s/i}$, as it is more highly expressed and more tolerant of detergents.

Conclusions

The aim of the work presented here was to generate a range of mini-G proteins that could be used as a basis for the structure determination of GPCRs in their fully active state. The original work in developing mini-G proteins was performed on $G_s$ [23], which turned out to be one of the best expressed and most stable of the mini-G proteins. Transfer of the relevant mutations to other G proteins was successful in deriving mini-$G_{olf}$, mini-$G_{o1}$ and mini-$G_{12}$. Both mini-$G_{olf}$ and mini-$G_{o1}$ coupled to relevant receptors only in the presence of an agonist and formed stable complexes that could be purified by SEC. Currently, we have not been able to demonstrate binding of mini-$G_{12}$ to any receptor (results not shown), even though it is highly expressed in E. coli and has high thermal stability, suggesting that the protein is in a folded state. In contrast, initial trials to generate mini-$G_{t1}$, mini-$G_z$, mini-$G_q$ and mini-$G_{16}$ were unsuccessful due to no expression in E. coli. Mini-$G_{i1}$ expressed very poorly, but was improved upon further mutagenesis, but was still not as stable as mini-$G_s$ and required binding of βγ subunits to attain a full agonist affinity shift in the 5HT$_{1B}$R.

The second approach to generate mini-G proteins for those that did not work initially was to make chimeras by converting the specificity of mini-$G_s$ to the specificity of the desired G protein. This was developed initially for $G_q$ by mutating in mini-$G_s$ only those residues in the α5 helix whose side chains make contact to either $β_2AR$ or $A_{2A}R$ in the crystal structures of the relevant complexes [2, 19], to match the equivalent residues in $G_q$. The final mini-$G_{s/q}$ chimera was stable, overexpressed in E. coli and coupled to $G_q$-coupled receptors but not to $G_s$-coupled receptors. The process was also successful in generating a mini-$G_{s/i1}$ amd mini-$G_{s/o}$ chimera. The α5 helix provides ~70% of the buried surface area between the GTPase domain and the receptor in the two G protein-GPCR complexes crystallised to date. The work here shows that changing these contacts is sufficient to alter the specificity of coupling. However, this is not to say that the remaining 30% of the interface is not important, merely that a range of amino acid residues can be accommodated in this interface and therefore it plays a less important role in defining both specificity and the affinity of G protein binding.

The mini-G proteins and their properties are shown in Table 7. On the whole, the expression levels are satisfactory in E. coli and the stability of the mini-G proteins in the absence of detergent is also good. However, their stability decreases in detergent, particularly in high concentrations, with the greatest decrease in stability observed at high detergent concentrations (greater than 0.5% w/v) and with detergents that are regarded as harsh for membrane protein purification [47]. Thus care must be exercised in the initial choice of detergent for forming receptor-mini-G protein complexes.

In conclusion, the range of mini-G proteins developed here will lead to further knowledge on the active structures of receptors through the crystallisation of receptor-mini-G protein complexes. This will expand our understanding of the signaling of GPCRs as well as having useful applications for drug discovery.

TABLE 7

Mutants of mini-G proteins and their characteristics.

| Mini-G protein | Construct | Yield of pure protein per L of E. coli (mg) | Stability measured by DSF (° C) | Stability in detergent measured by native DSF (° C) | | |
|---|---|---|---|---|---|---|
| | | | | No detergent | 0.1% LMNG | 0.1% DDM |
| $G_s$ | 393 | 100 | 65.3 ± 0.0 | 47.7 ± 0.2 | 44.9 ± 0.2 | 39.1 ± 0.0 |
| $G_{olf}$ | 6 | 80 | 64.8 ± 0.4 | 44.3 ± 0.1 | 41.9 ± 0.0 | 37.4 ± 0.2 |
| $G_{s/q}$ | 70 | 50 | 67.2 ± 0.4 | 47.2 ± 0.3 | 44.2 ± 0.2 | 36.2 ± 0.1 |
| $G_{s/i1}$ | 43 | 40 | 69.0 ± 0.1 | 44.8 ± 0.0 | 41.1 ± 0.1 | 35.9 ± 0.1 |
| $G_{o1}$ | 12 | 100 | 63.8 ± 0.1 | 43.6 ± 0.2 | 40.7 ± 0.1 | 32.6 ± 0.2 |
| $G_{t2}$ | 8 | 25 | 72.6 ± 0.3 | 50.3 ± 0.1 | 46.0 ± 0.1 | 41.2 ± 0.2 |

| Mini-G protein that bind βγ | Construct | Yield of pure protein per L of E. coli (mg) | Stability measured by DSF (° C) |
|---|---|---|---|
| $G_s$ | 399 | 100 | 71.6 ± 0.0 |
| $G_{olf}$ | 9 | 144 | 66.1 ± 0.1 |
| $G_{i1}$ | 76 | 30 | 70.7 ± 0.1 |
| $G_{s/i1}$ | 46 | 12 | 47.8 ± 0.3 |
| $G_{s/i1}$ | 48 | 10 | 72.1 ± 0.1 |
| $G_{s/o1}$ | 16 | 15 | 69.0 ± 0.1 |

REFERENCES FOR EXAMPLE 5

1. Rosenbaum D M, Rasmussen S G, Kobilka B K. The structure and function of G-protein-coupled receptors. Nature. 2009; 459(7245):356-63. doi: 10.1038/nature08144. PubMed PMID: 19458711; PubMed Central PMCID: PMCPMC3967846.
2. Rasmussen S G, DeVree B T, Zou Y, Kruse A C, Chung K Y, Kobilka T S, et al. Crystal structure of the beta2 adrenergic receptor-Gs protein complex. Nature. 2011; 477(7366):549-55. Epub 2011 Jul. 21. doi: 10.1038/nature10361. PubMed PMID: 21772288; PubMed Central PMCID: PMC3184188.
3. Tate C G, Schertler G F. Engineering G protein-coupled receptors to facilitate their structure determination. Curr Opin Struct Biol. 2009; 19(4):386-95. Epub 2009 Aug. 18. doi: 10.1016/j.sbi.2009.07.004. PubMed PMID: 19682887.
4. Venkatakrishnan A J, Deupi X, Lebon G, Tate C G, Schertler G F, Babu M M. Molecular signatures of G-protein-coupled receptors. Nature. 2013; 494(7436):185-94. Epub 2013 Feb. 15. doi: 10.1038/nature11896. PubMed PMID: 23407534.
5. Venkatakrishnan A J, Deupi X, Lebon G, Heydenreich F M, Flock T, Miljus T, et al. Diverse activation pathways in class A GPCRs converge near the G-protein-coupling region. Nature. 2016; 536(7617):484-7. doi: 10.1038/nature19107. PubMed PMID: 27525504.
6. Flock T, Ravarani C N, Sun D, Venkatakrishnan A J, Kayikci M, Tate C G, et al. Universal allosteric mechanism for Galpha activation by GPCRs. Nature. 2015; 524(7564):173-9. Epub 2015 Jul. 7. doi: 10.1038/nature14663. PubMed PMID: 26147082; PubMed Central PMCID: PMC4866443.
7. Warne T, Moukhametzianov R, Baker J G, Nehme R, Edwards P C, Leslie A G, et al. The structural basis for agonist and partial agonist action on a beta(1)-adrenergic receptor. Nature. 2011; 469(7329):241-4. Epub 2011 Jan. 14. doi: 10.1038/nature09746. PubMed PMID: 21228877; PubMed Central PMCID: PMC3023143.
8. Rosenbaum D M, Zhang C, Lyons J A, Holl R, Aragao D, Arlow D H, et al. Structure and function of an irreversible agonist-beta(2) adrenoceptor complex. Nature. 2011; 469 (7329):236-40. Epub 2011 Jan. 14. doi: 10.1038/nature09665. PubMed PMID: 21228876; PubMed Central PMCID: PMC3074335.
9. Zhang J, Zhang K, Gao Z G, Paoletta S, Zhang D, Han G W, et al. Agonist-bound structure of the human P2Y12 receptor. Nature. 2014; 509(7498):119-22. doi: 10.1038/nature13288. PubMed PMID: 24784220; PubMed Central PMCID: PMCPMC4128917.
10. Wang C, Jiang Y, Ma J, Wu H, Wacker D, Katritch V, et al. Structural basis for molecular recognition at serotonin receptors. Science. 2013; 340(6132):610-4. doi: 10.1126/science.1232807. PubMed PMID: 23519210; PubMed Central PMCID: PMCPMC3644373.
11. Lebon G, Warne T, Edwards P C, Bennett K, Langmead C J, Leslie A G, et al. Agonist-bound adenosine A2A receptor structures reveal common features of GPCR activation. Nature. 2011; 474(7352):521-5. Epub 2011 May 20. doi: 10.1038/nature10136. PubMed PMID: 21593763; PubMed Central PMCID: PMC3146096.
12. Xu F, Wu H, Katritch V, Han G W, Jacobson K A, Gao Z G, et al. Structure of an agonist-bound human A2A adenosine receptor. Science. 2011; 332(6027):322-7. Epub 2011 Mar. 12. doi: 10.1126/science.1202793. PubMed PMID: 21393508; PubMed Central PMCID: PMC3086811.
13. White J F, Noinaj N, Shibata Y, Love J, Kloss B, Xu F, et al. Structure of the agonist-bound neurotensin receptor. Nature. 2012; 490(7421):508-13. Epub 2012 Oct. 12. doi:

14. Rasmussen S G, Choi H J, Fung J J, Pardon E, Casarosa P, Chae P S, et al. Structure of a nanobody-stabilized active state of the beta(2) adrenoceptor. Nature. 2011; 469(7329):175-80. Epub 2011 Jan. 14. doi: 10.1038/nature09648. PubMed PMID: 21228869; PubMed Central PMCID: PMC3058308.
15. Choe H W, Kim Y J, Park J H, Morizumi T, Pai E F, Krauss N, et al. Crystal structure of metarhodopsin II. Nature. 2011; 471(7340):651-5. doi: nature09789 [pii] 10.1038/nature09789. PubMed PMID: 21389988.
16. Standfuss J, Edwards P C, D'Antona A, Fransen M, Xie G, Oprian D D, et al. The structural basis of agonist-induced activation in constitutively active rhodopsin. Nature. 2011; 471(7340):656-60. doi: nature09795 [pii] 10.1038/nature09795. PubMed PMID: 21389983.
17. Kruse A C, Ring A M, Manglik A, Hu J, Hu K, Eitel K, et al. Activation and allosteric modulation of a muscarinic acetylcholine receptor. Nature. 2013; 504(7478):101-6. doi: 10.1038/nature12735. PubMed PMID: 24256733; PubMed Central PMCID: PMCPMC4020789.
18. Sounier R, Mas C, Steyaert J, Laeremans T, Manglik A, Huang W, et al. Propagation of conformational changes during mu-opioid receptor activation. Nature. 2015; 524 (7565):375-8. doi: 10.1038/nature14680. PubMed PMID: 26245377; PubMed Central PMCID: PMCPMC4820006.
19. Carpenter B, Nehme R, Warne T, Leslie A G, Tate C G. Structure of the adenosine A(2A) receptor bound to an engineered G protein. Nature. 2016; 536(7614):104-7. Epub 2016 Jul. 28. doi: 10.1038/nature18966. PubMed PMID: 27462812; PubMed Central PMCID: PMC4979997.
20. Park J H, Scheerer P, Hofmann K P, Choe H W, Ernst O P. Crystal structure of the ligand-free G-protein-coupled receptor opsin. Nature. 2008; 454(7201):183-7. Epub 2008 Jun. 20. doi: nature07063 [pii] 10.1038/nature07063. PubMed PMID: 18563085.
21. Scheerer P, Park J H, Hildebrand P W, Kim Y J, Krauss N, Choe H W, et al. Crystal structure of opsin in its G-protein-interacting conformation. Nature. 2008; 455 (7212):497-502. Epub 2008 Sep. 27. doi: nature07330 [pii]10.1038/nature07330. PubMed PMID: 18818650.
22. Pardon E, Laeremans T, Triest S, Rasmussen S G, Wohlkonig A, Ruf A, et al. A general protocol for the generation of Nanobodies for structural biology. Nat Protoc. 2014; 9(3):674-93. doi: 10.1038/nprot.2014.039. PubMed PMID: 24577359; PubMed Central PMCID: PMCPMC4297639.
23. Carpenter B, Tate C G. Engineering a minimal G protein to facilitate crystallisation of G protein-coupled receptors in their active conformation. Protein engineering, design & selection: PEDS. 2016; 29(12):583-94. Epub 2016 Sep. 28. doi: 10.1093/protein/gzw049. PubMed PMID: 27672048.
24. Syrovatkina V, Alegre K O, Dey R, Huang X Y. Regulation, Signaling, and Physiological Functions of G-Proteins. Journal of molecular biology. 2016; 428(19): 3850-68. Epub 2016 Aug. 16. doi: 10.1016/j.jmb.2016.08.002. PubMed PMID: 27515397; PubMed Central PMCID: PMC5023507.
25. Warne T, Chirnside J, Schertler G F. Expression and purification of truncated, non-glycosylated turkey beta-adrenergic receptors for crystallization. Biochim Biophys Acta. 2003; 1610(1):133-40. PubMed PMID: 12586387.
26. Warne T, Serrano-Vega M J, Baker J G, Moukhametzianov R, Edwards P C, Henderson R, et al. Structure of a beta1-adrenergic G-protein-coupled receptor. Nature. 2008; 454(7203):486-91. Epub 2008 Jul. 3. doi: nature07101 [pii]10.1038/nature07101. PubMed PMID: 18594507.
27. Thomas J, Tate C G. Quality control in eukaryotic membrane protein overproduction. J Mol Biol. 2014; 426(24):4139-54. doi: 10.1016/j.jmb.2014.10.012. PubMed PMID: 25454020; PubMed Central PMCID: PMCPMC4271737.
28. Lebon G, Bennett K, Jazayeri A, Tate C G. Thermostabilisation of an agonist-bound conformation of the human adenosine A(2A) receptor. J Mol Biol. 2011; 409(3):298-310. doi: S0022-2836(11)00378-0 [pii] 10.1016/j.jmb.2011.03.075. PubMed PMID: 21501622.
29. Shibata Y, White J F, Serrano-Vega M J, Magnani F, Aloia A L, Grisshammer R, et al. Thermostabilization of the neurotensin receptor NTS1. J Mol Biol. 2009; 390(2): 262-77. Epub 2009 May 9. doi: S0022-2836(09)00535-X [pii] 10.1016/j.jmb.2009.04.068. PubMed PMID: 19422831.
30. Chan P, Thomas C J, Sprang S R, Tall G G. Molecular chaperoning function of Ric-8 is to fold nascent heterotrimeric G protein alpha subunits. Proc Natl Acad Sci USA. 2013; 110(10):3794-9. doi: 10.1073/pnas.1220943110. PubMed PMID: 23431197; PubMed Central PMCID: PMCPMC3593926.
31. Green S A, Holt B D, Liggett S B. Beta 1- and beta 2-adrenergic receptors display subtype-selective coupling to Gs. Mol Pharmacol. 1992; 41(5):889-93. PubMed PMID: 1350321.
32. Tate C G. A crystal clear solution for determining G-protein-coupled receptor structures. Trends in biochemical sciences. 2012; 37(9):343-52. doi: 10.1016/j.tibs.2012.06.003. PubMed PMID: 22784935.
33. Magnani F, Serrano-Vega M J, Shibata Y, Abdul-Hussein S, Lebon G, Miller-Gallacher J, et al. A mutagenesis and screening strategy to generate optimally thermostabilized membrane proteins for structural studies. Nat Protoc. 2016; 11(8):1554-71. doi: 10.1038/nprot.2016.088. PubMed PMID: 27466713.
34. Zhang X, Stevens R C, Xu F. The importance of ligands for G protein-coupled receptor stability. Trends in biochemical sciences. 2015; 40(2):79-87. doi: 10.1016/j.tibs.2014.12.005. PubMed PMID: 25601764.
35. Lebon G, Warne T, Tate C G. Agonist-bound structures of G protein-coupled receptors. Curr Opin Struct Biol. 2012. Epub 2012 Apr. 7. doi: 10.1016/j.sbi.2012.03.007. PubMed PMID: 22480933.
36. Kawate T, Gouaux E. Fluorescence-detection size-exclusion chromatography for precrystallization screening of integral membrane proteins. Structure. 2006; 14(4): 673-81. doi: 10.1016/j.str.2006.01.013. PubMed PMID: 16615909.
37. Kull B, Svenningsson P, Fredholm B B. Adenosine A(2A) receptors are colocalized with and activate g(olf) in rat striatum. Molecular pharmacology. 2000; 58(4): 771-7. Epub 2000 Sep. 22. PubMed PMID: 10999947.
38. Chan P, Gabay M, Wright F A, Kan W, Oner S S, Lanier S M, et al. Purification of heterotrimeric G protein alpha subunits by GST-Ric-8 association: primary characterization of purified G alpha(olf). J Biol Chem. 2011; 286(4): 2625-35. doi: 10.1074/jbc.M110.178897. PubMed PMID: 21115479; PubMed Central PMCID: PMCPMC3024758.
39. Serrano-Vega M J, Tate C G. Transferability of thermostabilizing mutations between beta-adrenergic receptors.

Mol Membr Biol. 2009; 26(8):385-96. Epub 2009 Nov. 4. doi: 10.3109/09687680903208239. PubMed PMID: 19883298.
40. Hamm H E, Deretic D, Arendt A, Hargrave P A, Koenig B, Hofmann K P. Site of G protein binding to rhodopsin mapped with synthetic peptides from the alpha subunit. Science. 1988; 241(4867):832-5. Epub 1988 Aug. 12. PubMed PMID: 3136547.
41. Conklin B R, Farfel Z, Lustig K D, Julius D, Bourne H R. Substitution of three amino acids switches receptor specificity of Gq alpha to that of Gi alpha. Nature. 1993; 363(6426):274-6. Epub 1993 May 20. doi: 10.1038/363274a0. PubMed PMID: 8387644.
42. Conklin B R, Herzmark P, Ishida S, Voyno-Yasenetskaya T A, Sun Y, Farfel Z, et al. Carboxyl-terminal mutations of Gq alpha and Gs alpha that alter the fidelity of receptor activation. Mol Pharmacol. 1996; 50(4):885-90. Epub 1996 Oct. 1. PubMed PMID: 8863834.
43. Semack A, Sandhu M, Malik R U, Vaidehi N, Sivaramakrishnan S. Structural Elements in the Galphas and Galphaq C Termini That Mediate Selective G Protein-coupled Receptor (GPCR) Signaling. J Biol Chem. 2016; 291(34):17929-40. doi: 10.1074/jbc.M116.735720. PubMed PMID: 27330078; PubMed Central PMCID: PMCPMC5016181.
44. Nishimura A, Kitano K, Takasaki J, Taniguchi M, Mizuno N, Tago K, et al. Structural basis for the specific inhibition of heterotrimeric Gq protein by a small molecule. Proc Natl Acad Sci USA. 2010; 107(31):13666-71. doi: 10.1073/pnas.1003553107. PubMed PMID: 20639466; PubMed Central PMCID: PMCPMC2922266.
45. Tesmer V M, Kawano T, Shankaranarayanan A, Kozasa T, Tesmer J J. Snapshot of activated G proteins at the membrane: the Galphaq-GRK2-Gbetagamma complex. Science. 2005; 310(5754):1686-90. doi: 10.1126/science.1118890. PubMed PMID: 16339447.
46. Clawges H M, Depree K M, Parker E M, Graber S G. Human 5-HT1 receptor subtypes exhibit distinct G protein coupling behaviors in membranes from Sf9 cells. Biochemistry. 1997; 36(42):12930-8. Epub 1997 Oct. 23. doi: 10.1021/bi970112b. PubMed PMID: 9335552.
47. Tate C G. Practical considerations of membrane protein instability during purification and crystallisation. Methods Mol Biol. 2010; 601:187-203. doi: 10.1007/978-1-60761-344-2 12. PubMed PMID: 20099147.

EXAMPLE 6: EFFECT OF MINI-Gs ON GLP1R

To assess the effect of mini-Gs on receptor stability we measured GLP1R stability following detergent solubilisation. To this end, prior to solubilisation cells expressing human GLP1R receptor were incubated with tritiated peptide agonist and mini-Gs. The mixture was allowed to reach equilibrium at room temperature for 1 hour before solubilisation at 4° C. for 1 hour. Aliquots of the receptor/ligand/mini-Gs were incubated at different temperatures for 30 minutes. Following separation of excess unbound ligand from the receptor bound molecules, the levels of retained radioactivity were measured for each temperature which was plotted against temperature points. The results was compared with the control arm of the experiment with was identical but lacked mini-Gs. Presence of the mini-Gs significantly increased the stability of the agonist bound conformation (FIG. 41).

The invention claimed is:

1. A mutant of a human parent heterotrimeric G protein alpha (Gα) subunit, which mutant:
  lacks the amino acid sequence of at least one of helix A, helix B, helix C, helix D, helix E, or helix F of the helical domain of the naturally-occurring parent Gα subunit, corresponding to amino acid residues 85-113, 123-136, 144-154, 157-168, 174-186 and 194-199, respectively, according to the numbering of the long isoform of human Gα-s subunit of SEQ ID NO:92;
  is capable of binding to a GPCR in the absence of a heterotrimeric G protein beta (Gβ) subunit and a heterotrimeric G protein gamma (Gγ) subunit; and
  has an amino acid sequence that contains one or more mutations compared to the amino acid sequence of the parent heterotrimeric Gα subunit, which mutations are selected from a deletion, a substitution and an insertion.

2. The mutant Gα subunit according to claim 1, wherein the mutant lacks a region of the helical domain of the parent heterotrimeric Gα subunit corresponding to amino acid residues 70-193, 71-193, 85-193, or 85-199 according to the numbering of the long isoform of human Gα-s subunit as set out in SEQ ID NO:92.

3. The mutant Gα subunit according to claim 1 wherein binding of the mutant Gα subunit to a GPCR increases the affinity of the GPCR for an agonist.

4. The mutant Gα subunit according to claim 1, wherein binding of the mutant Gα subunit to a GPCR activates the Gα subunit.

5. The mutant Gα subunit according to claim 4, wherein activation of the Gα subunit generates a Gα protein signal in a cell.

6. The mutant Gα subunit according to claim 1, wherein the mutant Gα subunit has increased stability under denaturing conditions compared to its parent Gα subunit or is expressed at a higher level than its parent Gα subunit, when expressed in a cell.

7. The mutant Gα subunit according to claim 1, wherein the mutant Gα subunit is able to stabilize a particular conformation of the GPCR upon binding to the GPCR.

8. The mutant Gα subunit according to claim 1, wherein the mutant Gα subunit is capable of binding to a nucleotide, such as a guanine nucleotide, or wherein the mutant Gα subunit is capable of binding to a Gβ and/or Gγ subunit of a heterotrimeric G protein.

9. The mutant Gα subunit according to claim 1, wherein the Gα subunit is any one of a $Gα_s$, $Gα_{i/o}$, $Gα_{q/11}$, or $Gα_{12/13}$ subunit.

10. The mutant Gα subunit according to claim 1, wherein the switch I region of the parent heterotrimeric G protein alpha subunit is not deleted, or wherein the switch I region of the parent heterotrimeric G protein alpha subunit is deleted or replaced by a switch I region of a small GTPase, or wherein the switch I region of the parent heterotrimeric G protein alpha subunit corresponds to amino acid residues 194-207 according to the numbering of the long isoform of human Gα-s subunit as set out in SEQ ID NO:92.

11. The mutant Gα subunit according to claim 1, wherein the helical domain or part thereof and/or the switch I region or part thereof, of the parent heterotrimeric G protein alpha subunit is replaced by a linker sequence, or wherein the region of the parent heterotrimeric Gα subunit that corresponds to amino acid residues 65 to 203 according to the numbering of the long isoform of human Gα-s subunit as set out in SEQ ID NO:92, is deleted or replaced by a linker sequence.

12. The mutant Gα subunit according to claim 1, which, when compared to the parent Gα subunit, has an N-terminally truncated amino acid sequence, or contains one or more mutations in the switch I region.

13. The mutant Gα subunit according to claim 1, wherein the switch III region of the parent heterotrimeric G protein alpha subunit is deleted.

14. The mutant Gα subunit according to claim 1, wherein the switch II region, or part thereof, of the parent heterotrimeric Gα subunit, is replaced by a linker sequence.

15. The mutant Gα subunit according to claim 1, which, when compared to the parent Gα subunit, has a different amino acid at a position which corresponds to any one or more of the following positions according to the numbering of the long isoform of human Gα-s subunit as set out in SEQ ID NO:92: Val 36, His 41, Ala 48, Gly 49, Glu 50, Met 60, Leu 63, Leu 197, Cys 200, Arg 201, Phe 208, Asn 218, Gly 226, Glu 230, Ala 249, Ser 252, Leu 272, Ile 372, Val 375.

16. The mutant Gα subunit according to claim 1, wherein the mutant Gα subunit has at least 20% sequence identity to the amino acid sequence of the long isoform of human Gα-s subunit as set out in SEQ ID NO:92, or to any of the amino acid sequences as set out in SEQ ID NO:95-140.

17. The mutant Gα subunit according to claim 1, which, when compared to the parent Gα subunit, comprises one or more dominant negative mutations.

18. The mutant Gα subunit according to claim 1, which, when compared to the parent Gα subunit, has one or more different amino acids within the NKXD motif.

19. The mutant Gα subunit according to claim 1, wherein the mutant lacks helices A to E or lacks helices A to F of the helical domain of the parent Gα subunit.

20. The mutant Gα subunit according to claim 1, which is a mutant Gαt subunit wherein the amino acid residue at a position that corresponds to Cys 347 according to the numbering of the Gαt subunit as set out in any one of SEQ ID NO:141-156, is chemically modified.

21. The mutant Gα subunit according to claim 1, wherein the mutant Gα subunit has increased stability under denaturing conditions compared to its parent Gα subunit and is expressed at a higher level than its parent Gα subunit, when expressed in a cell.

22. The mutant Gα subunit according to claim 1, wherein the mutant Gα subunit is capable of binding to a nucleotide, such as a guanine nucleotide, and wherein the mutant Gα subunit is capable of binding to a Gβ and/or Gγ subunit of a heterotrimeric G protein.

* * * * *

SEQUENCE LISTING

```
<160> NUMBER OF SEQ ID NOS: 171

<210> SEQ ID NO 1
<211> LENGTH: 288
<212> TYPE: PRT
<213> ORGANISM: Artificial Sequence
<220> FEATURE:
<223> OTHER INFORMATION: MINI GS55

<400> SEQUENCE: 1

Met Gly His His His His His His His His Glu Asn Leu Tyr
1               5                   10                  15

Phe Gln Ser Gly Cys Leu Gly Asn Ser Lys Thr Glu Asp Gln Arg Asn
                20                  25                  30

Glu Glu Lys Ala Gln Arg Glu Ala Asn Lys Lys Ile Glu Lys Gln Leu
            35                  40                  45

Gln Lys Asp Lys Gln Val Tyr Arg Ala Thr His Arg Leu Leu Leu Leu
        50                  55                  60

Gly Ala Gly Glu Ser Gly Lys Ser Thr Ile Val Lys Gln Met Arg Ile
    65                  70                  75                  80

Leu His Val Asn Gly Gly Asp Gln Asp Leu Leu Arg Cys Arg Val
                    85                  90                  95

Leu Thr Ser Gly Ile Phe Glu Thr Lys Phe Gln Val Asp Lys Val Asn
                100                 105                 110

Phe His Met Phe Asp Val Gly Gly Gln Arg Asp Glu Arg Arg Lys Trp
            115                 120                 125

Ile Gln Cys Phe Asn Asp Val Thr Ala Ile Ile Phe Val Val Ala Ser
        130                 135                 140
```

```
Ser Ser Tyr Asn Met Val Ile Arg Glu Asp Asn Gln Thr Asn Arg Leu
145                 150                 155                 160

Gln Glu Ala Leu Asn Leu Phe Lys Ser Ile Trp Asn Asn Arg Trp Leu
                165                 170                 175

Arg Thr Ile Ser Val Ile Leu Phe Leu Asn Lys Gln Asp Leu Leu Ala
            180                 185                 190

Glu Lys Val Leu Ala Gly Lys Ser Lys Ile Glu Asp Tyr Phe Pro Glu
        195                 200                 205

Phe Ala Arg Tyr Thr Thr Pro Glu Asp Ala Thr Pro Glu Pro Gly Glu
    210                 215                 220

Asp Pro Arg Val Thr Arg Ala Lys Tyr Phe Ile Arg Asp Glu Phe Leu
225                 230                 235                 240

Arg Ile Ser Thr Ala Ser Gly Asp Gly Arg His Tyr Cys Tyr Pro His
                245                 250                 255

Phe Thr Cys Ala Val Asp Thr Glu Asn Ile Arg Arg Val Phe Asn Asp
                260                 265                 270

Cys Arg Asp Ile Ile Gln Arg Met His Leu Arg Gln Tyr Glu Leu Leu
                275                 280                 285

<210> SEQ ID NO 2
<211> LENGTH: 257
<212> TYPE: PRT
<213> ORGANISM: Artificial Sequence
<220> FEATURE:
<223> OTHER INFORMATION: MINI GS77

<400> SEQUENCE: 2

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
            100                 105                 110

Ser Ser Tyr Asn Met Val Ile Arg Glu Asp Asn Gln Thr Asn Arg
        115                 120                 125

Leu Gln Glu Ala Leu Asn Leu Phe Lys Ser Ile Trp Asn Asn Arg Trp
    130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
                180                 185                 190

Glu Asp Pro Arg Val Thr Arg Ala Lys Tyr Phe Ile Arg Asp Glu Phe
                195                 200                 205

Leu Arg Ile Ser Thr Ala Ser Gly Asp Gly Arg His Tyr Cys Tyr Pro
    210                 215                 220
```

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
            245                 250                 255

Leu

<210> SEQ ID NO 3
<211> LENGTH: 257
<212> TYPE: PRT
<213> ORGANISM: Artificial Sequence
<220> FEATURE:
<223> OTHER INFORMATION: MINI GS81

<400> SEQUENCE: 3

Met Gly His His His His His Ala Asn Lys Lys Ile Glu Lys Gln
1               5                   10                  15

Leu Gln Lys Asp Lys Gln Val Tyr Arg Ala Thr Ile Arg Leu Leu
                20                  25                  30

Leu Gly Ala Gly Glu Ser Gly Lys Ser Thr Ile Val Lys Gln Met Arg
            35                  40                  45

Ile Leu His Val Asn Gly Gly Asp Gln Asp Ala Leu Arg Ser Arg
        50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Lys
                85                  90                  95

Trp Ile Gln Cys Phe Asn Asp Val Thr Ala Ile Ile Phe Val Val Ala
                100                 105                 110

Ser Ser Ser Tyr Asn Met Val Ile Arg Glu Asp Asn Gln Thr Asn Arg
            115                 120                 125

Leu Gln Glu Ala Leu Asn Leu Phe Lys Ser Ile Trp Asn Asn Arg Trp
130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
        195                 200                 205

Leu Arg Ile Ser Thr Ala Ser Gly Asp Gly Arg His Tyr Cys Tyr Pro
210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
            245                 250                 255

Leu

<210> SEQ ID NO 4
<211> LENGTH: 257
<212> TYPE: PRT
<213> ORGANISM: Artificial Sequence
<220> FEATURE:
<223> OTHER INFORMATION: MINI GS84

<400> SEQUENCE: 4

Met Gly His His His His His Ala Asn Lys Lys Ile Glu Lys Gln
1               5                   10                  15

Leu Gln Lys Asp Lys Gln Val Tyr Arg Ala Thr Val Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
            100                 105                 110

Ser Ser Ser Tyr Asn Met Val Ile Arg Glu Asp Asn Gln Thr Asn Arg
            115                 120                 125

Leu Gln Glu Ala Leu Asn Leu Phe Lys Ser Ile Trp Asn Asn Arg Trp
    130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
        195                 200                 205

Leu Arg Ile Ser Thr Ala Ser Gly Asp Gly Arg His Tyr Cys Tyr Pro
    210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 5
<211> LENGTH: 257
<212> TYPE: PRT
<213> ORGANISM: Artificial Sequence
<220> FEATURE:
<223> OTHER INFORMATION: MINI GS186

<400> SEQUENCE: 5

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Leu Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala

```
                100                 105                 110
Ser Ser Ser Tyr Asn Met Val Ile Arg Glu Asp Asn Gln Thr Asn Arg
            115                 120                 125
Leu Gln Glu Ala Leu Asn Leu Phe Lys Ser Ile Trp Asn Asn Arg Trp
            130                 135                 140
Leu Arg Thr Ile Ser Val Ile Leu Phe Leu Asn Lys Gln Asp Leu Leu
145                 150                 155                 160
Ala Glu Lys Val Leu Ala Gly Lys Ser Lys Ile Glu Asp Tyr Phe Pro
                165                 170                 175
Glu Phe Ala Arg Tyr Thr Thr Pro Glu Asp Ala Thr Pro Glu Pro Gly
                180                 185                 190
Glu Asp Pro Arg Val Thr Arg Ala Lys Tyr Phe Ile Arg Asp Glu Phe
            195                 200                 205
Leu Arg Ile Ser Thr Ala Ser Gly Asp Gly Arg His Tyr Cys Tyr Pro
            210                 215                 220
His Phe Thr Cys Ala Val Asp Thr Glu Asn Ile Arg Arg Val Phe Asn
225                 230                 235                 240
Asp Cys Arg Asp Ile Ile Gln Arg Met His Leu Arg Gln Tyr Glu Leu
                245                 250                 255
Leu

<210> SEQ ID NO 6
<211> LENGTH: 257
<212> TYPE: PRT
<213> ORGANISM: Artificial Sequence
<220> FEATURE:
<223> OTHER INFORMATION: MINI GS130

<400> SEQUENCE: 6

Met Gly His His His His His His Ala Asn Lys Lys Ile Glu Lys Gln
1               5                   10                  15
Leu Gln Lys Asp Lys Gln Val Tyr Arg Ala Thr His Arg Leu Leu Leu
            20                  25                  30
Leu Gly Ala Asp Glu Ser Gly Lys Ser Thr Ile Val Lys Gln Met Arg
        35                  40                  45
Ile Leu His Val Asn Gly Gly Asp Gln Asp Ala Leu Arg Ser Arg
    50                  55                  60
Val Leu Thr Ser Gly Ile Phe Glu Thr Lys Phe Gln Val Asp Lys Val
65                  70                  75                  80
Asn Phe His Met Phe Asp Val Gly Gly Gln Arg Asp Glu Arg Arg Lys
                85                  90                  95
Trp Ile Gln Cys Phe Asn Asp Val Thr Ala Ile Ile Phe Val Val Ala
            100                 105                 110
Ser Ser Ser Tyr Asn Met Val Ile Arg Glu Asp Asn Gln Thr Asn Arg
            115                 120                 125
Leu Gln Glu Ala Leu Asn Leu Phe Lys Ser Ile Trp Asn Asn Arg Trp
            130                 135                 140
Leu Arg Thr Ile Ser Val Ile Leu Phe Leu Asn Lys Gln Asp Leu Leu
145                 150                 155                 160
Ala Glu Lys Val Leu Ala Gly Lys Ser Lys Ile Glu Asp Tyr Phe Pro
                165                 170                 175
Glu Phe Ala Arg Tyr Thr Thr Pro Glu Asp Ala Thr Pro Glu Pro Gly
                180                 185                 190
Glu Asp Pro Arg Val Thr Arg Ala Lys Tyr Phe Ile Arg Asp Glu Phe
            195                 200                 205
```

```
Leu Arg Ile Ser Thr Ala Ser Gly Asp Gly Arg His Tyr Cys Tyr Pro
        210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 7
<211> LENGTH: 257
<212> TYPE: PRT
<213> ORGANISM: Artificial Sequence
<220> FEATURE:
<223> OTHER INFORMATION: MINI GS116

<400> SEQUENCE: 7

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
                20                  25                  30

Leu Gly Ala Gly Asn Ser Gly Lys Ser Thr Ile Val Lys Gln Met Arg
            35                  40                  45

Ile Leu His Val Asn Gly Gly Asp Gln Asp Ala Leu Arg Ser Arg
50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
                100                 105                 110

Ser Ser Ser Tyr Asn Met Val Ile Arg Glu Asp Asn Gln Thr Asn Arg
            115                 120                 125

Leu Gln Glu Ala Leu Asn Leu Phe Lys Ser Ile Trp Asn Asn Arg Trp
        130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
        195                 200                 205

Leu Arg Ile Ser Thr Ala Ser Gly Asp Gly Arg His Tyr Cys Tyr Pro
        210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 8
<211> LENGTH: 257
<212> TYPE: PRT
<213> ORGANISM: Artificial Sequence
<220> FEATURE:
<223> OTHER INFORMATION: MINI GS134
```

<400> SEQUENCE: 8

```
Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Ala
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
                100                 105                 110

Ser Ser Ser Tyr Asn Met Val Ile Arg Glu Asp Asn Gln Thr Asn Arg
            115                 120                 125

Leu Gln Glu Ala Leu Asn Leu Phe Lys Ser Ile Trp Asn Asn Arg Trp
        130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
        195                 200                 205

Leu Arg Ile Ser Thr Ala Ser Gly Asp Gly Arg His Tyr Cys Tyr Pro
    210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu
```

<210> SEQ ID NO 9
<211> LENGTH: 257
<212> TYPE: PRT
<213> ORGANISM: Artificial Sequence
<220> FEATURE:
<223> OTHER INFORMATION: MINI GS111

<400> SEQUENCE: 9

```
Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Ala Gln Arg Asp Glu Arg Arg Lys
```

```
            85                  90                  95
Trp Ile Gln Cys Phe Asn Asp Val Thr Ala Ile Ile Phe Val Val Ala
            100                 105                 110

Ser Ser Ser Tyr Asn Met Val Ile Arg Glu Asp Asn Gln Thr Asn Arg
            115                 120                 125

Leu Gln Glu Ala Leu Asn Leu Phe Lys Ser Ile Trp Asn Asn Arg Trp
        130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
            195                 200                 205

Leu Arg Ile Ser Thr Ala Ser Gly Asp Gly Arg His Tyr Cys Tyr Pro
        210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 10
<211> LENGTH: 255
<212> TYPE: PRT
<213> ORGANISM: Artificial Sequence
<220> FEATURE:
<223> OTHER INFORMATION: MINI GS98

<400> SEQUENCE: 10

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gly Arg Arg Lys Trp Ile
                85                  90                  95

Gln Cys Phe Asn Asp Val Thr Ala Ile Ile Phe Val Val Ala Ser Ser
            100                 105                 110

Ser Tyr Asn Met Val Ile Arg Glu Asp Asn Gln Thr Asn Arg Leu Gln
            115                 120                 125

Glu Ala Leu Asn Leu Phe Lys Ser Ile Trp Asn Asn Arg Trp Leu Arg
        130                 135                 140

Thr Ile Ser Val Ile Leu Phe Leu Asn Lys Gln Asp Leu Leu Ala Glu
145                 150                 155                 160

Lys Val Leu Ala Gly Lys Ser Lys Ile Glu Asp Tyr Phe Pro Glu Phe
                165                 170                 175

Ala Arg Tyr Thr Thr Pro Glu Asp Ala Thr Pro Glu Pro Gly Glu Asp
            180                 185                 190
```

```
Pro Arg Val Thr Arg Ala Lys Tyr Phe Ile Arg Asp Glu Phe Leu Arg
        195                 200                 205

Ile Ser Thr Ala Ser Gly Asp Gly Arg His Tyr Cys Tyr Pro His Phe
210                 215                 220

Thr Cys Ala Val Asp Thr Glu Asn Ile Arg Arg Val Phe Asn Asp Cys
225                 230                 235                 240

Arg Asp Ile Ile Gln Arg Met His Leu Arg Gln Tyr Glu Leu Leu
            245                 250                 255

<210> SEQ ID NO 11
<211> LENGTH: 257
<212> TYPE: PRT
<213> ORGANISM: Artificial Sequence
<220> FEATURE:
<223> OTHER INFORMATION: MINI GS175

<400> SEQUENCE: 11

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Ala Arg Arg Lys
                85                  90                  95

Trp Ile Gln Cys Phe Asn Asp Val Thr Ala Ile Ile Phe Val Val Ala
            100                 105                 110

Ser Ser Ser Tyr Asn Met Val Ile Arg Glu Asp Asn Gln Thr Asn Arg
        115                 120                 125

Leu Gln Glu Ala Leu Asn Leu Phe Lys Ser Ile Trp Asn Asn Arg Trp
    130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
    195                 200                 205

Leu Arg Ile Ser Thr Ala Ser Gly Asp Gly Arg His Tyr Cys Tyr Pro
210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 12
<211> LENGTH: 257
<212> TYPE: PRT
<213> ORGANISM: Artificial Sequence
<220> FEATURE:
```

<223> OTHER INFORMATION: MINI GS92

<400> SEQUENCE: 12

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Asp
            100                 105                 110

Ser Ser Ser Tyr Asn Met Val Ile Arg Glu Asp Asn Gln Thr Asn Arg
        115                 120                 125

Leu Gln Glu Ala Leu Asn Leu Phe Lys Ser Ile Trp Asn Asn Arg Trp
    130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
        195                 200                 205

Leu Arg Ile Ser Thr Ala Ser Gly Asp Gly Arg His Tyr Cys Tyr Pro
    210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 13
<211> LENGTH: 257
<212> TYPE: PRT
<213> ORGANISM: Artificial Sequence
<220> FEATURE:
<223> OTHER INFORMATION: MINI GS104

<400> SEQUENCE: 13

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                    85                  90                  95

Trp Ile Gln Cys Phe Asn Asp Val Thr Ala Ile Ile Phe Val Val Glu
                100                 105                 110

Ser Ser Ser Tyr Asn Met Val Ile Arg Glu Asp Asn Gln Thr Asn Arg
            115                 120                 125

Leu Gln Glu Ala Leu Asn Leu Phe Lys Ser Ile Trp Asn Asn Arg Trp
        130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
                180                 185                 190

Glu Asp Pro Arg Val Thr Arg Ala Lys Tyr Phe Ile Arg Asp Glu Phe
            195                 200                 205

Leu Arg Ile Ser Thr Ala Ser Gly Asp Gly Arg His Tyr Cys Tyr Pro
        210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 14
<211> LENGTH: 257
<212> TYPE: PRT
<213> ORGANISM: Artificial Sequence
<220> FEATURE:
<223> OTHER INFORMATION: MINI GS117

<400> SEQUENCE: 14

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
                100                 105                 110

Ser Ser Asp Tyr Asn Met Val Ile Arg Glu Asp Asn Gln Thr Asn Arg
            115                 120                 125

Leu Gln Glu Ala Leu Asn Leu Phe Lys Ser Ile Trp Asn Asn Arg Trp
        130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly

```
                    180                 185                 190
Glu Asp Pro Arg Val Thr Arg Ala Lys Tyr Phe Ile Arg Asp Glu Phe
            195                 200                 205

Leu Arg Ile Ser Thr Ala Ser Gly Asp Gly Arg His Tyr Cys Tyr Pro
            210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
            245                 250                 255

Leu

<210> SEQ ID NO 15
<211> LENGTH: 257
<212> TYPE: PRT
<213> ORGANISM: Artificial Sequence
<220> FEATURE:
<223> OTHER INFORMATION: MINI GS118

<400> SEQUENCE: 15

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
            100                 105                 110

Ser Ser Glu Tyr Asn Met Val Ile Arg Glu Asp Asn Gln Thr Asn Arg
        115                 120                 125

Leu Gln Glu Ala Leu Asn Leu Phe Lys Ser Ile Trp Asn Asn Arg Trp
    130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
            195                 200                 205

Leu Arg Ile Ser Thr Ala Ser Gly Asp Gly Arg His Tyr Cys Tyr Pro
            210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
            245                 250                 255

Leu

<210> SEQ ID NO 16
<211> LENGTH: 247
```

-continued

```
<212> TYPE: PRT
<213> ORGANISM: Artificial Sequence
<220> FEATURE:
<223> OTHER INFORMATION: MINI GS105

<400> SEQUENCE: 16

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
                20                  25                  30

Leu Gly Ala Gly Glu Ser Gly Lys Ser Thr Ile Val Lys Gln Met Arg
            35                  40                  45

Ile Leu His Val Asn Gly Gly Asp Gln Asp Ala Leu Arg Ser Arg
        50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
                100                 105                 110

Ser Ser Ser Tyr Asn Arg Leu Gln Glu Ala Leu Asn Leu Phe Lys Ser
            115                 120                 125

Ile Trp Asn Asn Arg Trp Leu Arg Thr Ile Ser Val Ile Leu Phe Leu
        130                 135                 140

Asn Lys Gln Asp Leu Leu Ala Glu Lys Val Leu Ala Gly Lys Ser Lys
145                 150                 155                 160

Ile Glu Asp Tyr Phe Pro Glu Phe Ala Arg Tyr Thr Thr Pro Glu Asp
                165                 170                 175

Ala Thr Pro Glu Pro Gly Glu Asp Pro Arg Val Thr Arg Ala Lys Tyr
            180                 185                 190

Phe Ile Arg Asp Glu Phe Leu Arg Ile Ser Thr Ala Ser Gly Asp Gly
        195                 200                 205

Arg His Tyr Cys Tyr Pro His Phe Thr Cys Ala Val Asp Thr Glu Asn
    210                 215                 220

Ile Arg Arg Val Phe Asn Asp Cys Arg Asp Ile Ile Gln Arg Met His
225                 230                 235                 240

Leu Arg Gln Tyr Glu Leu Leu
                245

<210> SEQ ID NO 17
<211> LENGTH: 257
<212> TYPE: PRT
<213> ORGANISM: Artificial Sequence
<220> FEATURE:
<223> OTHER INFORMATION: MINI GS94

<400> SEQUENCE: 17

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
                20                  25                  30

Leu Gly Ala Gly Glu Ser Gly Lys Ser Thr Ile Val Lys Gln Met Arg
            35                  40                  45

Ile Leu His Val Asn Gly Gly Asp Gln Asp Ala Leu Arg Ser Arg
        50                  55                  60

Val Leu Thr Ser Gly Ile Phe Glu Thr Lys Phe Gln Val Asp Lys Val
65                  70                  75                  80
```

-continued

```
Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
            100                 105                 110

Ser Ser Ser Tyr Asn Met Val Ile Arg Glu Asp Asn Gln Thr Asn Arg
        115                 120                 125

Leu Gln Glu Ala Leu Asn Asp Phe Lys Ser Ile Trp Asn Asn Arg Trp
    130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175

Glu Phe Ala Arg Tyr Thr Thr Pro Glu Asp Ala Thr Pro Glu Pro Gly
            180                 185                 190

Glu Asp Pro Arg Val Thr Arg Ala Lys Tyr Phe Ile Arg Asp Glu Phe
        195                 200                 205

Leu Arg Ile Ser Thr Ala Ser Gly Asp Gly Arg His Tyr Cys Tyr Pro
    210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 18
<211> LENGTH: 257
<212> TYPE: PRT
<213> ORGANISM: Artificial Sequence
<220> FEATURE:
<223> OTHER INFORMATION: MINI GS113

<400> SEQUENCE: 18

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Val Asn Gly Gly Asp Gln Asp Ala Leu Arg Ser Arg
    50                  55                  60

Val Leu Thr Ser Gly Ile Phe Glu Thr Lys Phe Gln Val Asp Lys Val
65                  70                  75                  80

Asn Phe His Met Phe Asp Val Gly Gly Gln Arg Asp Glu Arg Arg Lys
                85                  90                  95

Trp Ile Gln Cys Phe Asn Asp Val Thr Ala Ile Ile Phe Val Val Ala
            100                 105                 110

Ser Ser Ser Tyr Asn Met Val Ile Arg Glu Asp Asn Gln Thr Asn Arg
        115                 120                 125

Leu Gln Glu Ala Leu Asn Glu Phe Lys Ser Ile Trp Asn Asn Arg Trp
    130                 135                 140

Leu Arg Thr Ile Ser Val Ile Leu Phe Leu Asn Lys Gln Asp Leu Leu
145                 150                 155                 160

Ala Glu Lys Val Leu Ala Gly Lys Ser Lys Ile Glu Asp Tyr Phe Pro
                165                 170                 175
```

```
Glu Phe Ala Arg Tyr Thr Thr Pro Glu Asp Ala Thr Pro Glu Pro Gly
                180                 185                 190

Glu Asp Pro Arg Val Thr Arg Ala Lys Tyr Phe Ile Arg Asp Glu Phe
            195                 200                 205

Leu Arg Ile Ser Thr Ala Ser Gly Asp Gly Arg His Tyr Cys Tyr Pro
        210                 215                 220

His Phe Thr Cys Ala Val Asp Thr Glu Asn Ile Arg Arg Val Phe Asn
225                 230                 235                 240

Asp Cys Arg Asp Ile Ile Gln Arg Met His Leu Arg Gln Tyr Glu Leu
                245                 250                 255

Leu

<210> SEQ ID NO 19
<211> LENGTH: 242
<212> TYPE: PRT
<213> ORGANISM: Artificial Sequence
<220> FEATURE:
<223> OTHER INFORMATION: MINI GS161

<400> SEQUENCE: 19

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Gly Glu Ser Gly Lys Ser Thr Ile Val Lys Gln Met Arg
        35                  40                  45

Ile Leu His Gly Gly Gly Gly Glu Thr Lys Phe Gln Val Asp Lys
50                  55                  60

Val Asn Phe His Met Phe Asp Val Gly Gly Gln Arg Asp Glu Arg Arg
65                  70                  75                  80

Lys Trp Ile Gln Cys Phe Asn Asp Val Thr Ala Ile Ile Phe Val Val
                85                  90                  95

Ala Ser Ser Ser Tyr Asn Met Val Ile Arg Glu Asp Asn Gln Thr Asn
                100                 105                 110

Arg Leu Gln Glu Ala Leu Asn Leu Phe Lys Ser Ile Trp Asn Asn Arg
            115                 120                 125

Trp Leu Arg Thr Ile Ser Val Ile Leu Phe Leu Asn Lys Gln Asp Leu
130                 135                 140

Leu Ala Glu Lys Val Leu Ala Gly Lys Ser Lys Ile Glu Asp Tyr Phe
145                 150                 155                 160

Pro Glu Phe Ala Arg Tyr Thr Thr Pro Glu Asp Ala Thr Pro Glu Pro
                165                 170                 175

Gly Glu Asp Pro Arg Val Thr Arg Ala Lys Tyr Phe Ile Arg Asp Glu
            180                 185                 190

Phe Leu Arg Ile Ser Thr Ala Ser Gly Asp Gly Arg His Tyr Cys Tyr
        195                 200                 205

Pro His Phe Thr Cys Ala Val Asp Thr Glu Asn Ile Arg Arg Val Phe
    210                 215                 220

Asn Asp Cys Arg Asp Ile Ile Gln Arg Met His Leu Arg Gln Tyr Glu
225                 230                 235                 240

Leu Leu

<210> SEQ ID NO 20
<211> LENGTH: 242
<212> TYPE: PRT
<213> ORGANISM: Artificial Sequence
```

<220> FEATURE:
<223> OTHER INFORMATION: MINI GS162

<400> SEQUENCE: 20

Met Gly His His His His His Ala Asn Lys Lys Ile Glu Lys Gln
1               5                   10                  15

Leu Gln Lys Asp Lys Gln Val Tyr Arg Ala Thr His Arg Leu Leu
                20                  25                  30

Leu Gly Ala Gly Glu Ser Gly Lys Ser Thr Ile Val Lys Gln Met Arg
            35                  40                  45

Ile Leu His Gly Gly Gly Gly Glu Thr Lys Phe Gln Val Asp Lys
        50                  55                  60

Val Asn Phe His Met Phe Asp Val Gly Gly Gln Arg Asp Glu Arg Arg
65                  70                  75                  80

Lys Trp Ile Gln Cys Phe Asn Asp Val Thr Ala Ile Ile Phe Val Val
                85                  90                  95

Asp Ser Ser Ser Tyr Asn Met Val Ile Arg Glu Asp Asn Gln Thr Asn
                100                 105                 110

Arg Leu Gln Glu Ala Leu Asn Leu Phe Lys Ser Ile Trp Asn Asn Arg
            115                 120                 125

Trp Leu Arg Thr Ile Ser Val Ile Leu Phe Leu Asn Lys Gln Asp Leu
        130                 135                 140

Leu Ala Glu Lys Val Leu Ala Gly Lys Ser Lys Ile Glu Asp Tyr Phe
145                 150                 155                 160

Pro Glu Phe Ala Arg Tyr Thr Thr Pro Glu Asp Ala Thr Pro Glu Pro
                165                 170                 175

Gly Glu Asp Pro Arg Val Thr Arg Ala Lys Tyr Phe Ile Arg Asp Glu
            180                 185                 190

Phe Leu Arg Ile Ser Thr Ala Ser Gly Asp Gly Arg His Tyr Cys Tyr
        195                 200                 205

Pro His Phe Thr Cys Ala Val Asp Thr Glu Asn Ile Arg Arg Val Phe
        210                 215                 220

Asn Asp Cys Arg Asp Ile Ile Gln Arg Met His Leu Arg Gln Tyr Glu
225                 230                 235                 240

Leu Leu

<210> SEQ ID NO 21
<211> LENGTH: 232
<212> TYPE: PRT
<213> ORGANISM: Artificial Sequence
<220> FEATURE:
<223> OTHER INFORMATION: MINI GS164

<400> SEQUENCE: 21

Met Gly His His His His His Ala Asn Lys Lys Ile Glu Lys Gln
1               5                   10                  15

Leu Gln Lys Asp Lys Gln Val Tyr Arg Ala Thr His Arg Leu Leu
                20                  25                  30

Leu Gly Ala Gly Glu Ser Gly Lys Ser Thr Ile Val Lys Gln Met Arg
            35                  40                  45

Ile Leu His Gly Gly Gly Gly Glu Thr Lys Phe Gln Val Asp Lys
        50                  55                  60

Val Asn Phe His Met Phe Asp Val Gly Gly Gln Arg Asp Glu Arg Arg
65                  70                  75                  80

Lys Trp Ile Gln Cys Phe Asn Asp Val Thr Ala Ile Ile Phe Val Val
                85                  90                  95

```
Asp Ser Ser Ser Tyr Asn Arg Leu Gln Glu Ala Leu Asn Leu Phe Lys
            100                 105                 110

Ser Ile Trp Asn Asn Arg Trp Leu Arg Thr Ile Ser Val Ile Leu Phe
        115                 120                 125

Leu Asn Lys Gln Asp Leu Leu Ala Glu Lys Val Leu Ala Gly Lys Ser
    130                 135                 140

Lys Ile Glu Asp Tyr Phe Pro Glu Phe Ala Arg Tyr Thr Thr Pro Glu
145                 150                 155                 160

Asp Ala Thr Pro Glu Pro Gly Glu Asp Pro Arg Val Thr Arg Ala Lys
                165                 170                 175

Tyr Phe Ile Arg Asp Glu Phe Leu Arg Ile Ser Thr Ala Ser Gly Asp
                180                 185                 190

Gly Arg His Tyr Cys Tyr Pro His Phe Thr Cys Ala Val Asp Thr Glu
            195                 200                 205

Asn Ile Arg Arg Val Phe Asn Asp Cys Arg Asp Ile Ile Gln Arg Met
    210                 215                 220

His Leu Arg Gln Tyr Glu Leu Leu
225                 230

<210> SEQ ID NO 22
<211> LENGTH: 232
<212> TYPE: PRT
<213> ORGANISM: Artificial Sequence
<220> FEATURE:
<223> OTHER INFORMATION: MINI GS165

<400> SEQUENCE: 22

Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
                20                  25                  30

Leu Gly Ala Gly Glu Ser Gly Lys Ser Thr Ile Val Lys Gln Met Arg
            35                  40                  45

Ile Leu His Gly Gly Gly Gly Glu Thr Lys Phe Gln Val Asp Lys
    50                  55                  60

Val Asn Phe His Met Phe Asp Val Gly Gly Gln Arg Asp Glu Arg Arg
65                  70                  75                  80

Lys Trp Ile Gln Cys Phe Asn Asp Val Thr Ala Ile Ile Phe Val Val
                85                  90                  95

Asp Ser Ser Asp Tyr Asn Arg Leu Gln Glu Ala Leu Asn Leu Phe Lys
            100                 105                 110

Ser Ile Trp Asn Asn Arg Trp Leu Arg Thr Ile Ser Val Ile Leu Phe
        115                 120                 125

Leu Asn Lys Gln Asp Leu Leu Ala Glu Lys Val Leu Ala Gly Lys Ser
    130                 135                 140

Lys Ile Glu Asp Tyr Phe Pro Glu Phe Ala Arg Tyr Thr Thr Pro Glu
145                 150                 155                 160

Asp Ala Thr Pro Glu Pro Gly Glu Asp Pro Arg Val Thr Arg Ala Lys
                165                 170                 175

Tyr Phe Ile Arg Asp Glu Phe Leu Arg Ile Ser Thr Ala Ser Gly Asp
                180                 185                 190

Gly Arg His Tyr Cys Tyr Pro His Phe Thr Cys Ala Val Asp Thr Glu
            195                 200                 205

Asn Ile Arg Arg Val Phe Asn Asp Cys Arg Asp Ile Ile Gln Arg Met
    210                 215                 220
```

```
His Leu Arg Gln Tyr Glu Leu Leu
225                 230

<210> SEQ ID NO 23
<211> LENGTH: 232
<212> TYPE: PRT
<213> ORGANISM: Artificial Sequence
<220> FEATURE:
<223> OTHER INFORMATION: MINI GS169

<400> SEQUENCE: 23

Met Gly His His His His His Ala Asn Lys Lys Ile Glu Lys Gln
1               5                   10                  15

Leu Gln Lys Asp Lys Gln Val Tyr Arg Ala Thr His Arg Leu Leu
            20                  25                  30

Leu Gly Ala Gly Glu Ser Gly Lys Ser Thr Ile Val Lys Gln Met Arg
        35                  40                  45

Ile Leu His Gly Gly Gly Gly Glu Thr Lys Phe Gln Val Asp Lys
    50                  55                  60

Val Asn Phe His Met Phe Asp Val Gly Gly Gln Arg Asp Glu Arg Arg
65              70                  75                  80

Lys Trp Ile Gln Cys Phe Asn Asp Val Thr Ala Ile Ile Phe Val Val
                85                  90                  95

Asp Ser Ser Asp Tyr Asn Arg Leu Gln Glu Ala Leu Asn Asp Phe Lys
                100                 105                 110

Ser Ile Trp Asn Asn Arg Trp Leu Arg Thr Ile Ser Val Ile Leu Phe
            115                 120                 125

Leu Asn Lys Gln Asp Leu Leu Ala Glu Lys Val Leu Ala Gly Lys Ser
    130                 135                 140

Lys Ile Glu Asp Tyr Phe Pro Glu Phe Ala Arg Tyr Thr Thr Pro Glu
145                 150                 155                 160

Asp Ala Thr Pro Glu Pro Gly Glu Asp Pro Arg Val Thr Arg Ala Lys
                165                 170                 175

Tyr Phe Ile Arg Asp Glu Phe Leu Arg Ile Ser Thr Ala Ser Gly Asp
            180                 185                 190

Gly Arg His Tyr Cys Tyr Pro His Phe Thr Cys Ala Val Asp Thr Glu
        195                 200                 205

Asn Ile Arg Arg Val Phe Asn Asp Cys Arg Asp Ile Ile Gln Arg Met
    210                 215                 220

His Leu Arg Gln Tyr Glu Leu Leu
225                 230

<210> SEQ ID NO 24
<211> LENGTH: 232
<212> TYPE: PRT
<213> ORGANISM: Artificial Sequence
<220> FEATURE:
<223> OTHER INFORMATION: MINI GS183

<400> SEQUENCE: 24

Met Gly His His His His His Ala Asn Lys Lys Ile Glu Lys Gln
1               5                   10                  15

Leu Gln Lys Asp Lys Gln Val Tyr Arg Ala Thr His Arg Leu Leu
            20                  25                  30

Leu Gly Ala Asp Asn Ser Gly Lys Ser Thr Ile Val Lys Gln Met Arg
        35                  40                  45

Ile Leu His Gly Gly Gly Gly Gly Glu Thr Lys Phe Gln Val Asp Lys
```

Val Asn Phe His Met Phe Asp Val Gly Gly Gln Arg Asp Glu Arg Arg
65                  70                  75                  80

Lys Trp Ile Gln Cys Phe Asn Asp Val Thr Ala Ile Ile Phe Val Val
                85                  90                  95

Asp Ser Ser Asp Tyr Asn Arg Leu Gln Glu Ala Leu Asn Asp Phe Lys
            100                 105                 110

Ser Ile Trp Asn Asn Arg Trp Leu Arg Thr Ile Ser Val Ile Leu Phe
        115                 120                 125

Leu Asn Lys Gln Asp Leu Leu Ala Glu Lys Val Leu Ala Gly Lys Ser
130                 135                 140

Lys Ile Glu Asp Tyr Phe Pro Glu Phe Ala Arg Tyr Thr Thr Pro Glu
145                 150                 155                 160

Asp Ala Thr Pro Glu Pro Gly Glu Asp Pro Arg Val Thr Arg Ala Lys
                165                 170                 175

Tyr Phe Ile Arg Asp Glu Phe Leu Arg Ile Ser Thr Ala Ser Gly Asp
            180                 185                 190

Gly Arg His Tyr Cys Tyr Pro His Phe Thr Cys Ala Val Asp Thr Glu
        195                 200                 205

Asn Ile Arg Arg Val Phe Asn Asp Cys Arg Asp Ile Ile Gln Arg Met
210                 215                 220

His Leu Arg Gln Tyr Glu Leu Leu
225                 230

<210> SEQ ID NO 25
<211> LENGTH: 240
<212> TYPE: PRT
<213> ORGANISM: Artificial Sequence
<220> FEATURE:
<223> OTHER INFORMATION: MINI GS199

<400> SEQUENCE: 25

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Asp Asn Ser Gly Lys Ser Thr Ile Val Lys Gln Met Arg
        35                  40                  45

Ile Leu His Gly Gly Gly Gly Gly Gly Thr Ser Gly Ile Phe
    50                  55                  60

Glu Thr Lys Phe Gln Val Asp Lys Val Asn Phe His Met Phe Asp Val
65                  70                  75                  80

Gly Gly Gln Arg Asp Glu Arg Arg Lys Trp Ile Gln Cys Phe Asn Asp
                85                  90                  95

Val Thr Ala Ile Ile Phe Val Val Asp Ser Ser Asp Tyr Asn Arg Leu
            100                 105                 110

Gln Glu Ala Leu Asn Asp Phe Lys Ser Ile Trp Asn Asn Arg Trp Leu
        115                 120                 125

Arg Thr Ile Ser Val Ile Leu Phe Leu Asn Lys Gln Asp Leu Leu Ala
130                 135                 140

Glu Lys Val Leu Ala Gly Lys Ser Lys Ile Glu Asp Tyr Phe Pro Glu
145                 150                 155                 160

Phe Ala Arg Tyr Thr Thr Pro Glu Asp Ala Thr Pro Glu Pro Gly Glu
                165                 170                 175

Asp Pro Arg Val Thr Arg Ala Lys Tyr Phe Ile Arg Asp Glu Phe Leu

```
                180                 185                 190
Arg Ile Ser Thr Ala Ser Gly Asp Gly Arg His Tyr Cys Tyr Pro His
            195                 200                 205

Phe Thr Cys Ala Val Asp Thr Glu Asn Ile Arg Arg Val Phe Asn Asp
            210                 215                 220

Cys Arg Asp Ile Ile Gln Arg Met His Leu Arg Gln Tyr Glu Leu Leu
225                 230                 235                 240

<210> SEQ ID NO 26
<211> LENGTH: 240
<212> TYPE: PRT
<213> ORGANISM: Artificial Sequence
<220> FEATURE:
<223> OTHER INFORMATION: MINI GS254

<400> SEQUENCE: 26

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Asp Asn Ser Gly Lys Ser Thr Ile Val Lys Gln Ala Arg
        35                  40                  45

Ile Leu His Gly Gly Gly Gly Gly Gly Thr Ser Gly Ile Phe
    50                  55                  60

Glu Thr Lys Phe Gln Val Asp Lys Val Asn Phe His Met Phe Asp Val
65                  70                  75                  80

Gly Gly Gln Arg Asp Glu Arg Arg Lys Trp Ile Gln Cys Phe Asn Asp
                85                  90                  95

Val Thr Ala Ile Ile Phe Val Val Asp Ser Ser Asp Tyr Asn Arg Leu
            100                 105                 110

Gln Glu Ala Leu Asn Asp Phe Lys Ser Ile Trp Asn Asn Arg Trp Leu
        115                 120                 125

Arg Thr Ile Ser Val Ile Leu Phe Leu Asn Lys Gln Asp Leu Leu Ala
    130                 135                 140

Glu Lys Val Leu Ala Gly Lys Ser Lys Ile Glu Asp Tyr Phe Pro Glu
145                 150                 155                 160

Phe Ala Arg Tyr Thr Thr Pro Glu Asp Ala Thr Pro Glu Pro Gly Glu
                165                 170                 175

Asp Pro Arg Val Thr Arg Ala Lys Tyr Phe Ile Arg Asp Glu Phe Leu
            180                 185                 190

Arg Ile Ser Thr Ala Ser Gly Asp Gly Arg His Tyr Cys Tyr Pro His
        195                 200                 205

Phe Thr Cys Ala Val Asp Thr Glu Asn Ile Arg Arg Val Phe Asn Asp
    210                 215                 220

Cys Arg Asp Ile Ile Gln Arg Met His Leu Arg Gln Tyr Glu Leu Leu
225                 230                 235                 240

<210> SEQ ID NO 27
<211> LENGTH: 240
<212> TYPE: PRT
<213> ORGANISM: Artificial Sequence
<220> FEATURE:
<223> OTHER INFORMATION: MINI GS350

<400> SEQUENCE: 27

Met Gly His His His His His His Ala Asn Lys Lys Ile Glu Lys Gln
1               5                   10                  15
```

-continued

Leu Gln Lys Asp Lys Gln Val Tyr Arg Ala Thr His Arg Leu Leu Leu
            20                  25                  30

Leu Gly Ala Asp Asn Ser Gly Lys Ser Thr Ile Val Lys Gln Met Arg
            35                  40                  45

Ile Tyr His Gly Gly Gly Gly Gly Gly Thr Ser Gly Ile Phe
50                      55                      60

Glu Thr Lys Phe Gln Val Asp Lys Val Asn Phe His Met Phe Asp Val
65                  70                      75                  80

Gly Gly Gln Arg Asp Glu Arg Arg Lys Trp Ile Gln Cys Phe Asn Asp
            85                      90                      95

Val Thr Ala Ile Ile Phe Val Val Asp Ser Ser Asp Tyr Asn Arg Leu
                100                     105                     110

Gln Glu Ala Leu Asn Asp Phe Lys Ser Ile Trp Asn Asn Arg Trp Leu
            115                     120                     125

Arg Thr Ile Ser Val Ile Leu Phe Leu Asn Lys Gln Asp Leu Leu Ala
        130                     135                     140

Glu Lys Val Leu Ala Gly Lys Ser Lys Ile Glu Asp Tyr Phe Pro Glu
145                     150                     155                     160

Phe Ala Arg Tyr Thr Thr Pro Glu Asp Ala Thr Pro Glu Pro Gly Glu
                165                     170                     175

Asp Pro Arg Val Thr Arg Ala Lys Tyr Phe Ile Arg Asp Glu Phe Leu
            180                     185                     190

Arg Ile Ser Thr Ala Ser Gly Asp Gly Arg His Tyr Cys Tyr Pro His
        195                     200                     205

Phe Thr Cys Ala Val Asp Thr Glu Asn Ile Arg Arg Val Phe Asn Asp
210                     215                     220

Cys Arg Asp Ile Ile Gln Arg Met His Leu Arg Gln Tyr Glu Leu Leu
225                     230                     235                     240

<210> SEQ ID NO 28
<211> LENGTH: 240
<212> TYPE: PRT
<213> ORGANISM: Artificial Sequence
<220> FEATURE:
<223> OTHER INFORMATION: MINI GS340

<400> SEQUENCE: 28

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Asp Asn Ser Gly Lys Ser Thr Ile Val Lys Gln Met Arg
            35                  40                  45

Ile Leu His Gly Gly Gly Gly Gly Gly Thr Ser Gly Ile Phe
50                      55                      60

Glu Thr Lys Phe Gln Val Asp Lys Val Asn Phe His Met Phe Asp Val
65                  70                      75                  80

Gly Gly Gln Arg Asp Glu Arg Arg Lys Trp Ile Gln Cys Phe Asn Asp
            85                      90                      95

Val Thr Ala Ile Ile Phe Val Val Asp Ser Ser Asp Tyr Asn Arg Leu
                100                     105                     110

Gln Glu Ala Leu Asn Asp Phe Lys Ser Ile Trp Asn Asn Arg Trp Leu
            115                     120                     125

Arg Thr Ile Ser Val Ile Leu Phe Leu Asn Lys Gln Asp Leu Leu Ala
        130                     135                     140

```
Glu Lys Val Leu Ala Gly Lys Ser Lys Ile Glu Asp Tyr Phe Pro Glu
145                 150                 155                 160

Phe Ala Arg Tyr Thr Thr Pro Glu Asp Ala Thr Pro Glu Pro Gly Glu
                165                 170                 175

Asp Pro Arg Val Thr Arg Ala Lys Tyr Phe Ile Arg Asp Glu Phe Leu
                180                 185                 190

Arg Ile Ser Thr Ala Ser Gly Asp Gly Arg His Tyr Cys Tyr Pro His
            195                 200                 205

Phe Thr Cys Ala Val Asp Thr Glu Asn Ala Arg Arg Val Phe Asn Asp
                210                 215                 220

Cys Arg Asp Ile Ile Gln Arg Met His Leu Arg Gln Tyr Glu Leu Leu
225                 230                 235                 240

<210> SEQ ID NO 29
<211> LENGTH: 240
<212> TYPE: PRT
<213> ORGANISM: Artificial Sequence
<220> FEATURE:
<223> OTHER INFORMATION: MINI GS303

<400> SEQUENCE: 29

Met Gly His His His His His His Ala Asn Lys Lys Ile Glu Lys Gln
1               5                   10                  15

Leu Gln Lys Asp Lys Gln Val Tyr Arg Ala Thr His Arg Leu Leu Leu
                20                  25                  30

Leu Gly Ala Asp Asn Ser Gly Lys Ser Thr Ile Val Lys Gln Met Arg
            35                  40                  45

Ile Leu His Gly Gly Gly Gly Gly Gly Gly Thr Ser Gly Ile Phe
        50                  55                  60

Glu Thr Lys Phe Gln Val Asp Lys Val Asn Phe His Met Phe Asp Val
65                  70                  75                  80

Gly Gly Gln Arg Asp Glu Arg Arg Lys Trp Ile Gln Cys Phe Asn Asp
                85                  90                  95

Val Thr Ala Ile Ile Phe Val Val Asp Ser Ser Asp Tyr Asn Arg Leu
                100                 105                 110

Gln Glu Ala Leu Asn Asp Phe Lys Ser Ile Trp Asn Asn Arg Trp Leu
            115                 120                 125

Arg Thr Ile Ser Val Ile Leu Phe Leu Asn Lys Gln Asp Leu Leu Ala
        130                 135                 140

Glu Lys Val Leu Ala Gly Lys Ser Lys Ile Glu Asp Tyr Phe Pro Glu
145                 150                 155                 160

Phe Ala Arg Tyr Thr Thr Pro Glu Asp Ala Thr Pro Glu Pro Gly Glu
                165                 170                 175

Asp Pro Arg Val Thr Arg Ala Lys Tyr Phe Ile Arg Asp Glu Phe Leu
                180                 185                 190

Arg Ile Ser Thr Ala Ser Gly Asp Gly Arg His Tyr Cys Tyr Pro His
            195                 200                 205

Phe Thr Cys Ala Val Asp Thr Glu Asn Ile Arg Arg Ile Phe Asn Asp
                210                 215                 220

Cys Arg Asp Ile Ile Gln Arg Met His Leu Arg Gln Tyr Glu Leu Leu
225                 230                 235                 240

<210> SEQ ID NO 30
<211> LENGTH: 240
<212> TYPE: PRT
<213> ORGANISM: Artificial Sequence
<220> FEATURE:
```

<223> OTHER INFORMATION: MINI GS352

<400> SEQUENCE: 30

```
Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Asp Asn Ser Gly Lys Ser Thr Ile Val Lys Gln Met Arg
        35                  40                  45

Ile Tyr His Gly Gly Gly Gly Gly Gly Thr Ser Gly Ile Phe
    50                  55                  60

Glu Thr Lys Phe Gln Val Asp Lys Val Asn Phe His Met Phe Asp Val
65                  70                  75                  80

Gly Gly Gln Arg Asp Glu Arg Arg Lys Trp Ile Gln Cys Phe Asn Asp
                85                  90                  95

Val Thr Ala Ile Ile Phe Val Val Asp Ser Ser Asp Tyr Asn Arg Leu
                100                 105                 110

Gln Glu Ala Leu Asn Asp Phe Lys Ser Ile Trp Asn Asn Arg Trp Leu
            115                 120                 125

Arg Thr Ile Ser Val Ile Leu Phe Leu Asn Lys Gln Asp Leu Leu Ala
130                 135                 140

Glu Lys Val Leu Ala Gly Lys Ser Lys Ile Glu Asp Tyr Phe Pro Glu
145                 150                 155                 160

Phe Ala Arg Tyr Thr Thr Pro Glu Asp Ala Thr Pro Glu Pro Gly Glu
                165                 170                 175

Asp Pro Arg Val Thr Arg Ala Lys Tyr Phe Ile Arg Asp Glu Phe Leu
            180                 185                 190

Arg Ile Ser Thr Ala Ser Gly Asp Gly Arg His Tyr Cys Tyr Pro His
        195                 200                 205

Phe Thr Cys Ala Val Asp Thr Glu Asn Ala Arg Arg Val Phe Asn Asp
    210                 215                 220

Cys Arg Asp Ile Ile Gln Arg Met His Leu Arg Gln Tyr Glu Leu Leu
225                 230                 235                 240
```

<210> SEQ ID NO 31
<211> LENGTH: 240
<212> TYPE: PRT
<213> ORGANISM: Artificial Sequence
<220> FEATURE:
<223> OTHER INFORMATION: MINI GS345

<400> SEQUENCE: 31

```
Met Gly His His His His His Ala Asn Lys Lys Ile Glu Lys Gln
1               5                   10                  15

Leu Gln Lys Asp Lys Gln Val Tyr Arg Ala Thr His Arg Leu Leu Leu
            20                  25                  30

Leu Gly Ala Asp Asn Ser Gly Lys Ser Thr Ile Val Lys Gln Met Arg
        35                  40                  45

Ile Leu His Gly Gly Gly Gly Gly Gly Thr Ser Gly Ile Phe
    50                  55                  60

Glu Thr Lys Phe Gln Val Asp Lys Val Asn Phe His Met Phe Asp Val
65                  70                  75                  80

Gly Gly Gln Arg Asp Glu Arg Arg Lys Trp Ile Gln Cys Phe Asn Asp
                85                  90                  95

Val Thr Ala Ile Ile Phe Val Val Asp Ser Ser Asp Tyr Asn Arg Leu
                100                 105                 110
```

```
Gln Glu Ala Leu Asn Asp Phe Lys Ser Ile Trp Asn Arg Trp Leu
        115                 120                 125

Arg Thr Ile Ser Val Ile Leu Phe Leu Asn Lys Gln Asp Leu Leu Ala
130                 135                 140

Glu Lys Val Leu Ala Gly Lys Ser Lys Ile Glu Asp Tyr Phe Pro Glu
145                 150                 155                 160

Phe Ala Arg Tyr Thr Thr Pro Glu Asp Ala Thr Pro Glu Pro Gly Glu
                165                 170                 175

Asp Pro Arg Val Thr Arg Ala Lys Tyr Phe Ile Arg Asp Glu Phe Leu
                180                 185                 190

Arg Ile Ser Thr Ala Ser Gly Asp Gly Arg His Tyr Cys Tyr Pro His
            195                 200                 205

Phe Thr Cys Ala Val Asp Thr Glu Asn Ala Arg Arg Ile Phe Asn Asp
            210                 215                 220

Cys Arg Asp Ile Ile Gln Arg Met His Leu Arg Gln Tyr Glu Leu Leu
225                 230                 235                 240

<210> SEQ ID NO 32
<211> LENGTH: 243
<212> TYPE: PRT
<213> ORGANISM: Artificial Sequence
<220> FEATURE:
<223> OTHER INFORMATION: MINI GS389

<400> SEQUENCE: 32

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg
                20                  25                  30

Leu Leu Leu Leu Gly Ala Asp Asn Ser Gly Lys Ser Thr Ile Val Lys
            35                  40                  45

Gln Ala Arg Ile Leu His Gly Gly Ser Gly Gly Ser Gly Gly Thr Ser
        50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
                180                 185                 190

Glu Phe Leu Arg Ile Ser Thr Ala Ser Gly Asp Gly Arg His Tyr Cys
            195                 200                 205

Tyr Pro His Phe Thr Cys Ala Val Asp Thr Glu Asn Ile Arg Arg Ile
        210                 215                 220

Phe Asn Asp Cys Arg Asp Ile Ile Gln Arg Met His Leu Arg Gln Tyr
225                 230                 235                 240
```

Glu Leu Leu

<210> SEQ ID NO 33
<211> LENGTH: 243
<212> TYPE: PRT
<213> ORGANISM: Artificial Sequence
<220> FEATURE:
<223> OTHER INFORMATION: MINI GS391

<400> SEQUENCE: 33

```
Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
            35                  40                  45

Gln Met Arg Ile Leu His Gly Gly Ser Gly Gly Ser Gly Gly Thr Ser
    50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
            115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
            195                 200                 205

Tyr Pro His Phe Thr Cys Ala Val Asp Thr Glu Asn Ala Arg Arg Val
    210                 215                 220

Phe Asn Asp Cys Arg Asp Ile Ile Gln Arg Met His Leu Arg Gln Tyr
225                 230                 235                 240

Glu Leu Leu
```

<210> SEQ ID NO 34
<211> LENGTH: 243
<212> TYPE: PRT
<213> ORGANISM: Artificial Sequence
<220> FEATURE:
<223> OTHER INFORMATION: MINI GS393

<400> SEQUENCE: 34

```
Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
            35                  40                  45
```

Gln Met Arg Ile Leu His Gly Gly Ser Gly Gly Ser Gly Gly Thr Ser
    50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
            115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
            195                 200                 205

Tyr Pro His Phe Thr Cys Ala Val Asp Thr Glu Asn Ala Arg Arg Ile
    210                 215                 220

Phe Asn Asp Cys Arg Asp Ile Ile Gln Arg Met His Leu Arg Gln Tyr
225                 230                 235                 240

Glu Leu Leu

<210> SEQ ID NO 35
<211> LENGTH: 263
<212> TYPE: PRT
<213> ORGANISM: Artificial Sequence
<220> FEATURE:
<223> OTHER INFORMATION: MINI GS395

<400> SEQUENCE: 35

Met Gly His His His His His His Glu Asn Leu Tyr Phe Gln Gly Asn
1               5                   10                  15

Ser Lys Thr Glu Asp Gln Arg Asn Glu Glu Lys Ala Gln Arg Glu Ala
            20                  25                  30

Asn Lys Lys Ile Glu Lys Gln Leu Gln Lys Asp Lys Gln Val Tyr Arg
        35                  40                  45

Ala Thr His Arg Leu Leu Leu Leu Gly Ala Asp Asn Ser Gly Lys Ser
    50                  55                  60

Thr Ile Val Lys Gln Ala Arg Ile Leu His Gly Gly Ser Gly Gly Ser
65                  70                  75                  80

Gly Gly Thr Ser Gly Ile Phe Glu Thr Lys Phe Gln Val Asp Lys Val
                85                  90                  95

Asn Phe His Met Phe Asp Val Gly Gly Gln Arg Asp Glu Arg Arg Lys
            100                 105                 110

Trp Ile Gln Cys Phe Asn Asp Val Thr Ala Ile Ile Phe Val Val Asp
        115                 120                 125

Ser Ser Asp Tyr Asn Arg Leu Gln Glu Ala Leu Asn Leu Phe Lys Ser
    130                 135                 140

Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys

```
                165                 170                 175
Ile Glu Asp Tyr Phe Pro Glu Phe Ala Arg Tyr Thr Thr Pro Glu Asp
            180                 185                 190

Ala Thr Pro Glu Pro Gly Glu Asp Pro Arg Val Thr Arg Ala Lys Tyr
        195                 200                 205

Phe Ile Arg Asp Glu Phe Leu Arg Ile Ser Thr Ala Ser Gly Asp Gly
    210                 215                 220

Arg His Tyr Cys Tyr Pro His Phe Thr Cys Ala Val Asp Thr Glu Asn
225                 230                 235                 240

Ile Arg Arg Ile Phe Asn Asp Cys Arg Asp Ile Ile Gln Arg Met His
                245                 250                 255

Leu Arg Gln Tyr Glu Leu Leu
            260

<210> SEQ ID NO 36
<211> LENGTH: 263
<212> TYPE: PRT
<213> ORGANISM: Artificial Sequence
<220> FEATURE:
<223> OTHER INFORMATION: MINI GS397

<400> SEQUENCE: 36

Met Gly His His His His His His Glu Asn Leu Tyr Phe Gln Gly Asn
1               5                   10                  15

Ser Lys Thr Glu Asp Gln Arg Asn Glu Glu Lys Ala Gln Arg Glu Ala
            20                  25                  30

Asn Lys Lys Ile Glu Lys Gln Leu Gln Lys Asp Lys Gln Val Tyr Arg
        35                  40                  45

Ala Thr His Arg Leu Leu Leu Leu Gly Ala Asp Asn Ser Gly Lys Ser
    50                  55                  60

Thr Ile Val Lys Gln Met Arg Ile Leu His Gly Gly Ser Gly Gly Ser
65                  70                  75                  80

Gly Gly Thr Ser Gly Ile Phe Glu Thr Lys Phe Gln Val Asp Lys Val
                85                  90                  95

Asn Phe His Met Phe Asp Val Gly Gly Gln Arg Asp Glu Arg Arg Lys
            100                 105                 110

Trp Ile Gln Cys Phe Asn Asp Val Thr Ala Ile Ile Phe Val Val Asp
        115                 120                 125

Ser Ser Asp Tyr Asn Arg Leu Gln Glu Ala Leu Asn Leu Phe Lys Ser
    130                 135                 140

Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys
                165                 170                 175

Ile Glu Asp Tyr Phe Pro Glu Phe Ala Arg Tyr Thr Thr Pro Glu Asp
            180                 185                 190

Ala Thr Pro Glu Pro Gly Glu Asp Pro Arg Val Thr Arg Ala Lys Tyr
        195                 200                 205

Phe Ile Arg Asp Glu Phe Leu Arg Ile Ser Thr Ala Ser Gly Asp Gly
    210                 215                 220

Arg His Tyr Cys Tyr Pro His Phe Thr Cys Ala Val Asp Thr Glu Asn
225                 230                 235                 240

Ala Arg Arg Val Phe Asn Asp Cys Arg Asp Ile Ile Gln Arg Met His
                245                 250                 255

Leu Arg Gln Tyr Glu Leu Leu
            260
```

<210> SEQ ID NO 37
<211> LENGTH: 263
<212> TYPE: PRT
<213> ORGANISM: Artificial Sequence
<220> FEATURE:
<223> OTHER INFORMATION: MINI GS399

<400> SEQUENCE: 37

Met Gly His His His His His Glu Asn Leu Tyr Phe Gln Gly Asn
1               5                   10                  15

Ser Lys Thr Glu Asp Gln Arg Asn Glu Lys Ala Gln Arg Glu Ala
            20                  25                  30

Asn Lys Lys Ile Glu Lys Gln Leu Gln Lys Asp Lys Gln Val Tyr Arg
        35                  40                  45

Ala Thr His Arg Leu Leu Leu Gly Ala Asp Asn Ser Gly Lys Ser
    50                  55                  60

Thr Ile Val Lys Gln Met Arg Ile Leu His Gly Gly Ser Gly Ser
65                  70                  75                  80

Gly Gly Thr Ser Gly Ile Phe Glu Thr Lys Phe Gln Val Asp Lys Val
                85                  90                  95

Asn Phe His Met Phe Asp Val Gly Gly Gln Arg Asp Glu Arg Arg Lys
            100                 105                 110

Trp Ile Gln Cys Phe Asn Asp Val Thr Ala Ile Ile Phe Val Val Asp
        115                 120                 125

Ser Ser Asp Tyr Asn Arg Leu Gln Glu Ala Leu Asn Leu Phe Lys Ser
130                 135                 140

Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys
                165                 170                 175

Ile Glu Asp Tyr Phe Pro Glu Phe Ala Arg Tyr Thr Thr Pro Glu Asp
            180                 185                 190

Ala Thr Pro Glu Pro Gly Glu Asp Pro Arg Val Thr Arg Ala Lys Tyr
        195                 200                 205

Phe Ile Arg Asp Glu Phe Leu Arg Ile Ser Thr Ala Ser Gly Asp Gly
    210                 215                 220

Arg His Tyr Cys Tyr Pro His Phe Thr Cys Ala Val Asp Thr Glu Asn
225                 230                 235                 240

Ala Arg Arg Ile Phe Asn Asp Cys Arg Asp Ile Ile Gln Arg Met His
                245                 250                 255

Leu Arg Gln Tyr Glu Leu Leu
            260

<210> SEQ ID NO 38
<211> LENGTH: 243
<212> TYPE: PRT
<213> ORGANISM: Artificial Sequence
<220> FEATURE:
<223> OTHER INFORMATION: MINI GS404

<400> SEQUENCE: 38

Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

```
Leu Leu Leu Gly Ala Asp Asn Ser Gly Lys Ser Thr Ile Val Lys
         35                  40                  45

Gln Met Arg Ile Leu His Gly Ser Gly Ser Gly Gly Thr Ser
 50                  55                  60

Gly Ile Phe Glu Thr Lys Phe Gln Val Asp Lys Val Asn Phe His Met
 65                  70                  75                  80

Phe Asp Val Gly Gly Gln Arg Asp Glu Arg Arg Lys Trp Ile Gln Cys
                 85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ile Arg Arg Val
    210                 215                 220

Phe Asn Asp Cys Arg Asp Ile Ile Gln Arg Met His Leu Arg Gln Tyr
225                 230                 235                 240

Glu Leu Leu

<210> SEQ ID NO 39
<211> LENGTH: 263
<212> TYPE: PRT
<213> ORGANISM: Artificial Sequence
<220> FEATURE:
<223> OTHER INFORMATION: MINI GS406

<400> SEQUENCE: 39

Met Gly His His His His His His Glu Asn Leu Tyr Phe Gln Gly Asn
 1               5                  10                  15

Ser Lys Thr Glu Asp Gln Arg Asn Glu Glu Lys Ala Gln Arg Glu Ala
             20                  25                  30

Asn Lys Lys Ile Glu Lys Gln Leu Gln Lys Asp Lys Gln Val Tyr Arg
         35                  40                  45

Ala Thr His Arg Leu Leu Leu Leu Gly Ala Asp Asn Ser Gly Lys Ser
     50                  55                  60

Thr Ile Val Lys Gln Met Arg Ile Leu His Gly Ser Gly Gly Ser
 65                  70                  75                  80

Gly Gly Thr Ser Gly Ile Phe Glu Thr Lys Phe Gln Val Asp Lys Val
                 85                  90                  95

Asn Phe His Met Phe Asp Val Gly Gly Gln Arg Asp Glu Arg Arg Lys
            100                 105                 110

Trp Ile Gln Cys Phe Asn Asp Val Thr Ala Ile Ile Phe Val Val Asp
        115                 120                 125

Ser Ser Asp Tyr Asn Arg Leu Gln Glu Ala Leu Asn Leu Phe Lys Ser
    130                 135                 140

Ile Trp Asn Asn Arg Trp Leu Arg Thr Ile Ser Val Ile Leu Phe Leu
```

```
                145                 150                 155                 160
Asn Lys Gln Asp Leu Leu Ala Glu Lys Val Leu Ala Gly Lys Ser Lys
                    165                 170                 175

Ile Glu Asp Tyr Phe Pro Glu Phe Ala Arg Tyr Thr Thr Pro Glu Asp
                    180                 185                 190

Ala Thr Pro Glu Pro Gly Asp Pro Arg Val Thr Arg Ala Lys Tyr
                    195                 200                 205

Phe Ile Arg Asp Glu Phe Leu Arg Ile Ser Thr Ala Ser Gly Asp Gly
                    210                 215                 220

Arg His Tyr Cys Tyr Pro His Phe Thr Cys Ala Val Asp Thr Glu Asn
225                 230                 235                 240

Ile Arg Arg Val Phe Asn Asp Cys Arg Asp Ile Ile Gln Arg Met His
                    245                 250                 255

Leu Arg Gln Tyr Glu Leu Leu
                    260

<210> SEQ ID NO 40
<211> LENGTH: 243
<212> TYPE: PRT
<213> ORGANISM: Artificial Sequence
<220> FEATURE:
<223> OTHER INFORMATION: MINI GS410

<400> SEQUENCE: 40

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg
                20                  25                  30

Leu Leu Leu Leu Gly Ala Asp Asn Ser Gly Lys Ser Thr Ile Val Lys
                35                  40                  45

Gln Met Arg Ile Arg His Gly Gly Ser Gly Gly Ser Gly Gly Thr Ser
        50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
                100                 105                 110

Asn Arg Leu Gln Glu Ala Leu Asn Asp Phe Lys Ser Ile Trp Asn Asn
                115                 120                 125

Arg Trp Leu Arg Thr Ile Ser Val Ile Leu Phe Leu Asn Lys Gln Asp
        130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
                180                 185                 190

Glu Phe Leu Arg Ile Ser Thr Ala Ser Gly Asp Gly Arg His Tyr Cys
                195                 200                 205

Tyr Pro His Phe Thr Cys Ala Val Asp Thr Glu Asn Ala Arg Arg Ile
                210                 215                 220

Phe Asn Asp Cys Arg Asp Ile Ile Gln Arg Met His Leu Arg Gln Tyr
225                 230                 235                 240

Glu Leu Leu
```

<210> SEQ ID NO 41
<211> LENGTH: 243
<212> TYPE: PRT
<213> ORGANISM: Artificial Sequence
<220> FEATURE:
<223> OTHER INFORMATION: MINI GS414

<400> SEQUENCE: 41

```
Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Tyr His Gly Gly Ser Gly Gly Ser Gly Gly Thr Ser
50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
    210                 215                 220

Phe Asn Asp Cys Arg Asp Ile Ile Gln Arg Met His Leu Arg Gln Tyr
225                 230                 235                 240

Glu Leu Leu
```

<210> SEQ ID NO 42
<211> LENGTH: 263
<212> TYPE: PRT
<213> ORGANISM: Artificial Sequence
<220> FEATURE:
<223> OTHER INFORMATION: MINI GS418

<400> SEQUENCE: 42

```
Met Gly His His His His His Glu Asn Leu Tyr Phe Gln Gly Asn
1               5                   10                  15

Ser Lys Thr Glu Asp Gln Arg Asn Glu Glu Lys Ala Gln Arg Glu Ala
            20                  25                  30

Asn Lys Lys Ile Glu Lys Gln Leu Gln Lys Asp Lys Gln Val Tyr Arg
        35                  40                  45

Ala Thr His Arg Leu Leu Leu Leu Gly Ala Asp Asn Ser Gly Lys Ser
50                  55                  60
```

```
Thr Ile Val Lys Gln Met Arg Ile Tyr His Gly Gly Ser Gly Gly Ser
 65                  70                  75                  80

Gly Gly Thr Ser Gly Ile Phe Glu Thr Lys Phe Gln Val Asp Lys Val
             85                  90                  95

Asn Phe His Met Phe Asp Val Gly Gly Gln Arg Asp Glu Arg Arg Lys
            100                 105                 110

Trp Ile Gln Cys Phe Asn Asp Val Thr Ala Ile Ile Phe Val Val Asp
            115                 120                 125

Ser Ser Asp Tyr Asn Arg Leu Gln Glu Ala Leu Asn Leu Phe Lys Ser
130                 135                 140

Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys
                165                 170                 175

Ile Glu Asp Tyr Phe Pro Glu Phe Ala Arg Tyr Thr Thr Pro Glu Asp
            180                 185                 190

Ala Thr Pro Glu Pro Gly Glu Asp Pro Arg Val Thr Arg Ala Lys Tyr
            195                 200                 205

Phe Ile Arg Asp Glu Phe Leu Arg Ile Ser Thr Ala Ser Gly Asp Gly
210                 215                 220

Arg His Tyr Cys Tyr Pro His Phe Thr Cys Ala Val Asp Thr Glu Asn
225                 230                 235                 240

Ala Arg Arg Ile Phe Asn Asp Cys Arg Asp Ile Ile Gln Arg Met His
                245                 250                 255

Leu Arg Gln Tyr Glu Leu Leu
            260

<210> SEQ ID NO 43
<211> LENGTH: 230
<212> TYPE: PRT
<213> ORGANISM: Artificial Sequence
<220> FEATURE:
<223> OTHER INFORMATION: MINI GS431

<400> SEQUENCE: 43

Met Gly His His His His His His Glu Asn Leu Tyr Phe Gln Gly Ala
 1               5                  10                  15

Thr His Arg Leu Leu Leu Leu Gly Ala Asp Asn Ser Gly Lys Ser Thr
             20                  25                  30

Ile Val Lys Gln Met Arg Ile Leu His Gly Gly Ser Gly Gly Ser Gly
         35                  40                  45

Gly Thr Ser Gly Ile Phe Glu Thr Lys Phe Gln Val Asp Lys Val Asn
 50                  55                  60

Phe His Met Phe Asp Val Gly Gly Gln Arg Asp Glu Arg Arg Lys Trp
 65                  70                  75                  80

Ile Gln Cys Phe Asn Asp Val Thr Ala Ile Ile Phe Val Val Asp Ser
                 85                  90                  95

Ser Asp Tyr Asn Arg Leu Gln Glu Ala Leu Asn Asp Phe Lys Ser Ile
            100                 105                 110

Trp Asn Asn Arg Trp Leu Arg Thr Ile Ser Val Ile Leu Phe Leu Asn
        115                 120                 125

Lys Gln Asp Leu Leu Ala Glu Lys Val Leu Ala Gly Lys Ser Lys Ile
130                 135                 140

Glu Asp Tyr Phe Pro Glu Phe Ala Arg Tyr Thr Thr Pro Glu Asp Ala
145                 150                 155                 160
```

```
Thr Pro Glu Pro Gly Glu Asp Pro Arg Val Thr Arg Ala Lys Tyr Phe
            165                 170                 175

Ile Arg Asp Glu Phe Leu Arg Ile Ser Thr Ala Ser Gly Asp Gly Arg
            180                 185                 190

His Tyr Cys Tyr Pro His Phe Thr Cys Ala Val Asp Thr Glu Asn Ala
            195                 200                 205

Arg Arg Ile Phe Asn Asp Cys Arg Asp Ile Ile Gln Arg Met His Leu
            210                 215                 220

Arg Gln Tyr Glu Leu Leu
225                 230

<210> SEQ ID NO 44
<211> LENGTH: 236
<212> TYPE: PRT
<213> ORGANISM: Artificial Sequence
<220> FEATURE:
<223> OTHER INFORMATION: MINI GS432

<400> SEQUENCE: 44

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Gly Gly Glu Thr Lys Phe
    50                  55                  60

Gln Val Asp Lys Val Asn Phe His Met Phe Asp Val Gly Gly Gln Arg
65                  70                  75                  80

Asp Glu Arg Arg Lys Trp Ile Gln Cys Phe Asn Asp Val Thr Ala Ile
                85                  90                  95

Ile Phe Val Val Asp Ser Ser Asp Tyr Asn Arg Leu Gln Glu Ala Leu
            100                 105                 110

Asn Asp Phe Lys Ser Ile Trp Asn Asn Arg Trp Leu Arg Thr Ile Ser
        115                 120                 125

Val Ile Leu Phe Leu Asn Lys Gln Asp Leu Leu Ala Glu Lys Val Leu
130                 135                 140

Ala Gly Lys Ser Lys Ile Glu Asp Tyr Phe Pro Glu Phe Ala Arg Tyr
145                 150                 155                 160

Thr Thr Pro Glu Asp Ala Thr Pro Glu Pro Gly Glu Asp Pro Arg Val
            165                 170                 175

Thr Arg Ala Lys Tyr Phe Ile Arg Asp Glu Phe Leu Arg Ile Ser Thr
            180                 185                 190

Ala Ser Gly Asp Gly Arg His Tyr Cys Tyr Pro His Phe Thr Cys Ala
        195                 200                 205

Val Asp Thr Glu Asn Ala Arg Arg Ile Phe Asn Asp Cys Arg Asp Ile
210                 215                 220

Ile Gln Arg Met His Leu Arg Gln Tyr Glu Leu Leu
225                 230                 235

<210> SEQ ID NO 45
<211> LENGTH: 223
<212> TYPE: PRT
<213> ORGANISM: Artificial Sequence
<220> FEATURE:
<223> OTHER INFORMATION: MINI GS433
```

<400> SEQUENCE: 45

Met Gly His His His His His Glu Asn Leu Tyr Phe Gln Gly Ala
1               5                   10                  15

Thr His Arg Leu Leu Leu Gly Ala Asp Asn Ser Gly Lys Ser Thr
            20                  25                  30

Ile Val Lys Gln Met Arg Ile Leu His Gly Gly Gly Gly Gly Glu
        35                  40                  45

Thr Lys Phe Gln Val Asp Lys Val Asn Phe His Met Phe Asp Val Gly
    50                  55                  60

Gly Gln Arg Asp Glu Arg Arg Lys Trp Ile Gln Cys Phe Asn Asp Val
65              70                  75                  80

Thr Ala Ile Ile Phe Val Val Asp Ser Ser Asp Tyr Asn Arg Leu Gln
                85                  90                  95

Glu Ala Leu Asn Asp Phe Lys Ser Ile Trp Asn Asn Arg Trp Leu Arg
            100                 105                 110

Thr Ile Ser Val Ile Leu Phe Leu Asn Lys Gln Asp Leu Leu Ala Glu
        115                 120                 125

Lys Val Leu Ala Gly Lys Ser Lys Ile Glu Asp Tyr Phe Pro Glu Phe
    130                 135                 140

Ala Arg Tyr Thr Thr Pro Glu Asp Ala Thr Pro Glu Pro Gly Glu Asp
145                 150                 155                 160

Pro Arg Val Thr Arg Ala Lys Tyr Phe Ile Arg Asp Glu Phe Leu Arg
                165                 170                 175

Ile Ser Thr Ala Ser Gly Asp Gly Arg His Tyr Cys Tyr Pro His Phe
            180                 185                 190

Thr Cys Ala Val Asp Thr Glu Asn Ala Arg Arg Ile Phe Asn Asp Cys
        195                 200                 205

Arg Asp Ile Ile Gln Arg Met His Leu Arg Gln Tyr Glu Leu Leu
    210                 215                 220

<210> SEQ ID NO 46
<211> LENGTH: 867
<212> TYPE: DNA
<213> ORGANISM: Artificial Sequence
<220> FEATURE:
<223> OTHER INFORMATION: MINI GS55

<400> SEQUENCE: 46

```
atgggtcacc accatcatca ccatcatcac caccatgaaa atctttattt ccagtctggc        60
tgcctcggga acagtaagac cgaggaccag cgcaacgagg agaaggcgca gcgtgaggcc       120
aacaaaaaga tcgagaagca gctgcagaag acaagcagg tctaccgggc cacgcaccgc       180
ctgctgctgc tgggtgctgg agaatctggt aaaagcacca ttgtgaagca gatgaggatc       240
ctgcatgtta atggcggagg tgatcaggac ctgcttcgct gccgtgtcct gacttctgga       300
atctttgaga ccaagttcca ggtcgacaaa gtcaacttcc acatgtttga cgtgggtggc       360
cagcgcgatg aacgccgcaa gtggatccag tgcttcaacg atgtgactgc catcatcttc       420
gtggtggcca gcagcagcta caacatggtc atccgggagg acaaccagac caaccgcctg       480
caggaggctc tgaacctctt caagagcatc tggaacaaca atggctgcg caccatctct       540
gtgatcctgt tcctcaacaa gcaagatctg ctcgctgaga aagtccttgc tgggaaatcg       600
aagattgagg actactttcc agaatttgct cgctacacta ctcctgagga tgctactccc       660
gagcccggag aggaccccacg cgtgacccgg gccaagtact tcattcgaga tgagtttctg       720
aggatcagca ctgccagtgg agatgggcgt cactactgct accctcattt cacctgcgct       780
```

```
gtggacactg agaacatccg ccgtgtgttc aacgactgcc gtgacatcat tcagcgcatg    840
caccttcgtc agtacgagct gctctaa                                       867
```

<210> SEQ ID NO 47
<211> LENGTH: 774
<212> TYPE: DNA
<213> ORGANISM: Artificial Sequence
<220> FEATURE:
<223> OTHER INFORMATION: MINI GS77

<400> SEQUENCE: 47

```
atgggtcacc accatcatca ccatgccaac aaaaagatcg agaagcagct gcagaaggac     60
aagcaggtct accgggccac gcaccgcctg ctgctgctgg gtgctggaga atctggtaaa    120
agcaccattg tgaagcagat gaggatcctg catgttaatg cggaggtga tcaggacgcg     180 cttcgctccc gtgtcctgac ttctggaatc tttgagacca gttccaggt cgacaaagtc    240 aacttccaca tgtttgacgt gggtggccag cgcgatgaac gccgcaagtg gatccagtgc    300
ttcaacgatg tgactgccat catcttcgtg gtggccagca gcagctacaa catggtcatc    360
cgggaggaca accagaccaa ccgcctgcag gaggctctga acctcttcaa gagcatctgg    420
aacaacagat ggctgcgcac catctctgtg atcctgttcc tcaacaagca agatctgctc    480
gctgagaaag tccttgctgg gaaatcgaag attgaggact actttccaga atttgctcgc    540
tacactactc ctgaggatgc tactcccgag cccggagagg acccacgcgt gacccgggcc    600
aagtacttca ttcgagatga gtttctgagg atcagcactg ccagtggaga tgggcgtcac    660
tactgctacc ctcatttcac ctgcgctgtg gacactgaga acatccgccg tgtgttcaac    720
gactgccgtg acatcattca gcgcatgcac cttcgtcagt acgagctgct ctaa          774
```

<210> SEQ ID NO 48
<211> LENGTH: 774
<212> TYPE: DNA
<213> ORGANISM: Artificial Sequence
<220> FEATURE:
<223> OTHER INFORMATION: MINI GS81

<400> SEQUENCE: 48

```
atgggtcacc accatcatca ccatgccaac aaaaagatcg agaagcagct gcagaaggac     60
aagcaggtct accgggccac gatccgcctg ctgctgctgg gtgctggaga atctggtaaa    120
agcaccattg tgaagcagat gaggatcctg catgttaatg cggaggtga tcaggacgcg     180 cttcgctccc gtgtcctgac ttctggaatc tttgagacca gttccaggt cgacaaagtc    240 aacttccaca tgtttgacgt gggtggccag cgcgatgaac gccgcaagtg gatccagtgc    300
ttcaacgatg tgactgccat catcttcgtg gtggccagca gcagctacaa catggtcatc    360
cgggaggaca accagaccaa ccgcctgcag gaggctctga acctcttcaa gagcatctgg    420
aacaacagat ggctgcgcac catctctgtg atcctgttcc tcaacaagca agatctgctc    480
gctgagaaag tccttgctgg gaaatcgaag attgaggact actttccaga atttgctcgc    540
tacactactc ctgaggatgc tactcccgag cccggagagg acccacgcgt gacccgggcc    600
aagtacttca ttcgagatga gtttctgagg atcagcactg ccagtggaga tgggcgtcac    660
tactgctacc ctcatttcac ctgcgctgtg gacactgaga acatccgccg tgtgttcaac    720
gactgccgtg acatcattca gcgcatgcac cttcgtcagt acgagctgct ctaa          774
```

<210> SEQ ID NO 49

<211> LENGTH: 774
<212> TYPE: DNA
<213> ORGANISM: Artificial Sequence
<220> FEATURE:
<223> OTHER INFORMATION: MINI GS84

<400> SEQUENCE: 49

```
atgggtcacc accatcatca ccatgccaac aaaaagatcg agaagcagct gcagaaggac      60
aagcaggtct accgggccac ggtccgcctg ctgctgctgg gtgctggaga atctggtaaa     120
agcaccattg tgaagcagat gaggatcctg catgttaatg gcggaggtga tcaggacgcg     180
cttcgctccc gtgtcctgac ttctggaatc tttgagacca gttccaggt cgacaaagtc      240
aacttccaca tgtttgacgt gggtggccag cgcgatgaac gccgcaagtg gatccagtgc     300
ttcaacgatg tgactgccat catcttcgtg gtggccagca gcagctacaa catggtcatc     360
cgggaggaca accagaccaa ccgcctgcag gaggctctga acctcttcaa gagcatctgg     420
aacaacagat ggctgcgcac catctctgtg atcctgttcc tcaacaagca agatctgctc     480
gctgagaaag tccttgctgg gaaatcgaag attgaggact actttccaga atttgctcgc     540
tacactactc ctgaggatgc tactcccgag cccggagagg acccacgcgt gacccgggcc     600
aagtacttca ttcgagatga gtttctgagg atcagcactg ccagtggaga tgggcgtcac     660
tactgctacc ctcatttcac ctgcgctgtg gacactgaga acatccgccg tgtgttcaac     720
gactgccgtg acatcattca gcgcatgcac cttcgtcagt acgagctgct ctaa            774
```

<210> SEQ ID NO 50
<211> LENGTH: 774
<212> TYPE: DNA
<213> ORGANISM: Artificial Sequence
<220> FEATURE:
<223> OTHER INFORMATION: MINI GS186

<400> SEQUENCE: 50

```
atgggtcacc accatcatca ccatgccaac aaaaagatcg agaagcagct gcagaaggac      60
aagcaggtct accgggccac gcaccgcctg ctgctgctgg gtcttggaga atctggtaaa     120
agcaccattg tgaagcagat gaggatcctg catgttaatg gcggaggtga tcaggacgcg     180
cttcgctccc gtgtcctgac ttctggaatc tttgagacca gttccaggt cgacaaagtc      240
aacttccaca tgtttgacgt gggtggccag cgcgatgaac gccgcaagtg gatccagtgc     300
ttcaacgatg tgactgccat catcttcgtg gtggccagca gcagctacaa catggtcatc     360
cgggaggaca accagaccaa ccgcctgcag gaggctctga acctcttcaa gagcatctgg     420
aacaacagat ggctgcgcac catctctgtg atcctgttcc tcaacaagca agatctgctc     480
gctgagaaag tccttgctgg gaaatcgaag attgaggact actttccaga atttgctcgc     540
tacactactc ctgaggatgc tactcccgag cccggagagg acccacgcgt gacccgggcc     600
aagtacttca ttcgagatga gtttctgagg atcagcactg ccagtggaga tgggcgtcac     660
tactgctacc ctcatttcac ctgcgctgtg gacactgaga acatccgccg tgtgttcaac     720
gactgccgtg acatcattca gcgcatgcac cttcgtcagt acgagctgct ctaa            774
```

<210> SEQ ID NO 51
<211> LENGTH: 774
<212> TYPE: DNA
<213> ORGANISM: Artificial Sequence
<220> FEATURE:
<223> OTHER INFORMATION: MINI GS130

<400> SEQUENCE: 51

```
atgggtcacc accatcatca ccatgccaac aaaaagatcg agaagcagct gcagaaggac    60
aagcaggtct accgggccac gcaccgcctg ctgctgctgg gtgctgatga atctggtaaa   120
agcaccattg tgaagcagat gaggatcctg catgttaatg gcggaggtga tcaggacgcg   180
cttcgctccc gtgtcctgac ttctggaatc tttgagacca gttccaggt cgacaaagtc   240 aacttccaca tgtttgacgt gggtggccag cgcgatgaac gccgcaagtg gatccagtgc   300
ttcaacgatg tgactgccat catcttcgtg gtggccagca gcagctacaa catggtcatc   360
cgggaggaca accagaccaa ccgcctgcag gaggctctga acctcttcaa gagcatctgg   420
aacaacagat ggctgcgcac catctctgtg atcctgttcc tcaacaagca agatctgctc   480
gctgagaaag tccttgctgg gaaatcgaag attgaggact actttccaga atttgctcgc   540
tacactactc ctgaggatgc tactcccgag cccggagagg acccacgcgt gacccgggcc   600
aagtacttca ttcgagatga gtttctgagg atcagcactg ccagtggaga tgggcgtcac   660
tactgctacc ctcatttcac ctgcgctgtg gacactgaga catccgccg tgtgttcaac   720 gactgccgtg acatcattca gcgcatgcac cttcgtcagt acgagctgct ctaa         774
```

<210> SEQ ID NO 52
<211> LENGTH: 774
<212> TYPE: DNA
<213> ORGANISM: Artificial Sequence
<220> FEATURE:
<223> OTHER INFORMATION: MINI GS116

<400> SEQUENCE: 52

```
atgggtcacc accatcatca ccatgccaac aaaaagatcg agaagcagct gcagaaggac    60
aagcaggtct accgggccac gcaccgcctg ctgctgctgg gtgctggaaa ttctggtaaa   120
agcaccattg tgaagcagat gaggatcctg catgttaatg gcggaggtga tcaggacgcg   180
cttcgctccc gtgtcctgac ttctggaatc tttgagacca gttccaggt cgacaaagtc   240 aacttccaca tgtttgacgt gggtggccag cgcgatgaac gccgcaagtg gatccagtgc   300
ttcaacgatg tgactgccat catcttcgtg gtggccagca gcagctacaa catggtcatc   360
cgggaggaca accagaccaa ccgcctgcag gaggctctga acctcttcaa gagcatctgg   420
aacaacagat ggctgcgcac catctctgtg atcctgttcc tcaacaagca agatctgctc   480
gctgagaaag tccttgctgg gaaatcgaag attgaggact actttccaga atttgctcgc   540
tacactactc ctgaggatgc tactcccgag cccggagagg acccacgcgt gacccgggcc   600
aagtacttca ttcgagatga gtttctgagg atcagcactg ccagtggaga tgggcgtcac   660
tactgctacc tcatttcac ctgcgctgtg gacactgaga catccgccg tgtgttcaac   720 gactgccgtg acatcattca gcgcatgcac cttcgtcagt acgagctgct ctaa         774
```

<210> SEQ ID NO 53
<211> LENGTH: 774
<212> TYPE: DNA
<213> ORGANISM: Artificial Sequence
<220> FEATURE:
<223> OTHER INFORMATION: MINI GS134

<400> SEQUENCE: 53

```
atgggtcacc accatcatca ccatgccaac aaaaagatcg agaagcagct gcagaaggac    60
aagcaggtct accgggccac gcaccgcctg ctgctgctgg gtgctggaga atctggtaaa   120
agcaccattg tgaagcagat gaggatcctg catgttaatg gcggaggtga tcaggacgcg   180
```

| | |
|---|---|
| cttcgctccg ctgtcctgac ttctggaatc tttgagacca agttccaggt cgacaaagtc | 240 |
| aacttccaca tgtttgacgt gggtggccag cgcgatgaac gccgcaagtg gatccagtgc | 300 |
| ttcaacgatg tgactgccat catcttcgtg gtggccagca gcagctacaa catggtcatc | 360 |
| cgggaggaca accagaccaa ccgcctgcag gaggctctga acctcttcaa gagcatctgg | 420 |
| aacaacagat ggctgcgcac catctctgtg atcctgttcc tcaacaagca agatctgctc | 480 |
| gctgagaaag tccttgctgg gaaatcgaag attgaggact actttccaga atttgctcgc | 540 |
| tacactactc ctgaggatgc tactcccgag cccggagagg acccacgcgt gacccgggcc | 600 |
| aagtacttca ttcgagatga gtttctgagg atcagcactg ccagtggaga tgggcgtcac | 660 |
| tactgctacc ctcatttcac ctgcgctgtg gacactgaga acatccgccg tgtgttcaac | 720 |
| gactgccgtg acatcattca gcgcatgcac cttcgtcagt acgagctgct ctaa | 774 |

<210> SEQ ID NO 54
<211> LENGTH: 774
<212> TYPE: DNA
<213> ORGANISM: Artificial Sequence
<220> FEATURE:
<223> OTHER INFORMATION: MINI GS111

<400> SEQUENCE: 54

| | |
|---|---|
| atgggtcacc accatcatca ccatgccaac aaaaagatcg agaagcagct gcagaaggac | 60 |
| aagcaggtct accgggccac gcaccgcctg ctgctgctgg gtgctggaga atctggtaaa | 120 |
| agcaccattg tgaagcagat gaggatcctg catgttaatg gcggaggtga tcaggacgcg | 180 |
| cttcgctccc gtgtcctgac ttctggaatc tttgagacca agttccaggt cgacaaagtc | 240 |
| aacttccaca tgtttgacgt gggtgcccag cgcgatgaac gccgcaagtg gatccagtgc | 300 |
| ttcaacgatg tgactgccat catcttcgtg gtggccagca gcagctacaa catggtcatc | 360 |
| cgggaggaca accagaccaa ccgcctgcag gaggctctga acctcttcaa gagcatctgg | 420 |
| aacaacagat ggctgcgcac catctctgtg atcctgttcc tcaacaagca agatctgctc | 480 |
| gctgagaaag tccttgctgg gaaatcgaag attgaggact actttccaga atttgctcgc | 540 |
| tacactactc ctgaggatgc tactcccgag cccggagagg acccacgcgt gacccgggcc | 600 |
| aagtacttca ttcgagatga gtttctgagg atcagcactg ccagtggaga tgggcgtcac | 660 |
| tactgctacc ctcatttcac ctgcgctgtg gacactgaga acatccgccg tgtgttcaac | 720 |
| gactgccgtg acatcattca gcgcatgcac cttcgtcagt acgagctgct ctaa | 774 |

<210> SEQ ID NO 55
<211> LENGTH: 768
<212> TYPE: DNA
<213> ORGANISM: Artificial Sequence
<220> FEATURE:
<223> OTHER INFORMATION: MINI GS98

<400> SEQUENCE: 55

| | |
|---|---|
| atgggtcacc accatcatca ccatgccaac aaaaagatcg agaagcagct gcagaaggac | 60 |
| aagcaggtct accgggccac gcaccgcctg ctgctgctgg gtgctggaga atctggtaaa | 120 |
| agcaccattg tgaagcagat gaggatcctg catgttaatg gcggaggtga tcaggacgcg | 180 |
| cttcgctccc gtgtcctgac ttctggaatc tttgagacca agttccaggt cgacaaagtc | 240 |
| aacttccaca tgtttgacgt gggtggcgga gggcgccgca agtggatcca gtgcttcaac | 300 |
| gatgtgactg ccatcatctt cgtggtggcc agcagcagct acaacatggt catccggag | 360 |
| gacaaccaga ccaaccgcct gcaggaggct ctgaacctct tcaagagcat ctggaacaac | 420 |

```
agatggctgc gcaccatctc tgtgatcctg ttcctcaaca agcaagatct gctcgctgag      480
aaagtccttg ctgggaaatc gaagattgag gactactttc cagaatttgc tcgctacact      540
actcctgagg atgctactcc cgagcccgga gaggacccac gcgtgacccg ggccaagtac      600
ttcattcgag atgagtttct gaggatcagc actgccagtg gagatgggcg tcactactgc      660
taccctcatt tcacctgcgc tgtggacact gagaacatcc gccgtgtgtt caacgactgc      720
cgtgacatca ttcagcgcat gcaccttcgt cagtacgagc tgctctaa                   768
```

<210> SEQ ID NO 56
<211> LENGTH: 774
<212> TYPE: DNA
<213> ORGANISM: Artificial Sequence
<220> FEATURE:
<223> OTHER INFORMATION: MINI GS175

<400> SEQUENCE: 56

```
atgggtcacc accatcatca ccatgccaac aaaaagatcg agaagcagct gcagaaggac       60
aagcaggtct accgggccac gcaccgcctg ctgctgctgg gtgctggaga atctggtaaa      120
agcaccattg tgaagcagat gaggatcctg catgttaatg gcggaggtga tcaggacgcg      180
cttcgctccc gtgtcctgac ttctggaatc tttgagacca agttccaggt cgacaaagtc      240
aacttccaca tgtttgacgt gggtggccag cgcgatgcac gccgcaagtg gatccagtgc      300
ttcaacgatg tgactgccat catcttcgtg gtggccagca gcagctacaa catggtcatc      360
cgggaggaca accagaccaa ccgcctgcag gaggctctga acctcttcaa gagcatctgg      420
aacaacagat ggctgcgcac catctctgtg atcctgttcc tcaacaagca agatctgctc      480
gctgagaaag tccttgctgg gaaatcgaag attgaggact actttccaga atttgctcgc      540
tacactactc ctgaggatgc tactcccgag cccggagagg acccacgcgt gacccgggcc      600
aagtacttca ttcgagatga gtttctgagg atcagcactg ccagtggaga tgggcgtcac      660
tactgctacc ctcatttcac ctgcgctgtg gacactgaga acatccgccg tgtgttcaac      720
gactgccgtg acatcattca gcgcatgcac cttcgtcagt acgagctgct ctaa           774
```

<210> SEQ ID NO 57
<211> LENGTH: 774
<212> TYPE: DNA
<213> ORGANISM: Artificial Sequence
<220> FEATURE:
<223> OTHER INFORMATION: MINI GS92

<400> SEQUENCE: 57

```
atgggtcacc accatcatca ccatgccaac aaaaagatcg agaagcagct gcagaaggac       60
aagcaggtct accgggccac gcaccgcctg ctgctgctgg gtgctggaga atctggtaaa      120
agcaccattg tgaagcagat gaggatcctg catgttaatg gcggaggtga tcaggacgcg      180
cttcgctccc gtgtcctgac ttctggaatc tttgagacca agttccaggt cgacaaagtc      240
aacttccaca tgtttgacgt gggtggccag cgcgatgaac gccgcaagtg gatccagtgc      300
ttcaacgatg tgactgccat catcttcgtg gtggacagca gcagctacaa catggtcatc      360
cgggaggaca accagaccaa ccgcctgcag gaggctctga acctcttcaa gagcatctgg      420
aacaacagat ggctgcgcac catctctgtg atcctgttcc tcaacaagca agatctgctc      480
gctgagaaag tccttgctgg gaaatcgaag attgaggact actttccaga atttgctcgc      540
tacactactc ctgaggatgc tactcccgag cccggagagg acccacgcgt gacccgggcc      600
```

```
aagtacttca ttcgagatga gtttctgagg atcagcactg ccagtggaga tgggcgtcac    660
tactgctacc ctcatttcac ctgcgctgtg gacactgaga acatccgccg tgtgttcaac    720
gactgccgtg acatcattca gcgcatgcac cttcgtcagt acgagctgct ctaa          774
```

<210> SEQ ID NO 58
<211> LENGTH: 774
<212> TYPE: DNA
<213> ORGANISM: Artificial Sequence
<220> FEATURE:
<223> OTHER INFORMATION: MINI GS104

<400> SEQUENCE: 58

```
atgggtcacc accatcatca ccatgccaac aaaaagatcg agaagcagct gcagaaggac     60
aagcaggtct accgggccac gcaccgcctg ctgctgctgg gtgctggaga atctggtaaa    120
agcaccattg tgaagcagat gaggatcctg catgttaatg gcggaggtga tcaggacgcg    180
cttcgctccc gtgtcctgac ttctggaatc tttgagacca agttccaggt cgacaaagtc    240
aacttccaca tgtttgacgt gggtggccag cgcgatgaac gccgcaagtg gatccagtgc    300
ttcaacgatg tgactgccat catcttcgtg gtggagagca gcagctacaa catggtcatc    360
cgggaggaca accagaccaa ccgcctgcag gaggctctga acctcttcaa gagcatctgg    420
aacaacagat ggctgcgcac catctctgtg atcctgttcc tcaacaagca agatctgctc    480
gctgagaaag tccttgctgg gaaatcgaag attgaggact actttccaga atttgctcgc    540
tacactactc ctgaggatgc tactcccgag cccggagagg acccacgcgt gacccgggcc    600
aagtacttca ttcgagatga gtttctgagg atcagcactg ccagtggaga tgggcgtcac    660
tactgctacc ctcatttcac ctgcgctgtg gacactgaga acatccgccg tgtgttcaac    720
gactgccgtg acatcattca gcgcatgcac cttcgtcagt acgagctgct ctaa          774
```

<210> SEQ ID NO 59
<211> LENGTH: 774
<212> TYPE: DNA
<213> ORGANISM: Artificial Sequence
<220> FEATURE:
<223> OTHER INFORMATION: MINI GS117

<400> SEQUENCE: 59

```
atgggtcacc accatcatca ccatgccaac aaaaagatcg agaagcagct gcagaaggac     60
aagcaggtct accgggccac gcaccgcctg ctgctgctgg gtgctggaga atctggtaaa    120
agcaccattg tgaagcagat gaggatcctg catgttaatg gcggaggtga tcaggacgcg    180
cttcgctccc gtgtcctgac ttctggaatc tttgagacca agttccaggt cgacaaagtc    240
aacttccaca tgtttgacgt gggtggccag cgcgatgaac gccgcaagtg gatccagtgc    300
ttcaacgatg tgactgccat catcttcgtg gtggccagca gcgactacaa catggtcatc    360
cgggaggaca accagaccaa ccgcctgcag gaggctctga acctcttcaa gagcatctgg    420
aacaacagat ggctgcgcac catctctgtg atcctgttcc tcaacaagca agatctgctc    480
gctgagaaag tccttgctgg gaaatcgaag attgaggact actttccaga atttgctcgc    540
tacactactc ctgaggatgc tactcccgag cccggagagg acccacgcgt gacccgggcc    600
aagtacttca ttcgagatga gtttctgagg atcagcactg ccagtggaga tgggcgtcac    660
tactgctacc ctcatttcac ctgcgctgtg gacactgaga acatccgccg tgtgttcaac    720
gactgccgtg acatcattca gcgcatgcac cttcgtcagt acgagctgct ctaa          774
```

<210> SEQ ID NO 60
<211> LENGTH: 774
<212> TYPE: DNA
<213> ORGANISM: Artificial Sequence
<220> FEATURE:
<223> OTHER INFORMATION: MINI GS118

<400> SEQUENCE: 60

| | |
|---|---|
| atgggtcacc accatcatca ccatgccaac aaaaagatcg agaagcagct gcagaaggac | 60 |
| aagcaggtct accgggccac gcaccgcctg ctgctgctgg gtgctggaga atctggtaaa | 120 |
| agcaccattg tgaagcagat gaggatcctg catgttaatg gcggaggtga tcaggacgcg | 180 |
| cttcgctccc gtgtcctgac ttctggaatc tttgagacca agttccaggt cgacaaagtc | 240 |
| aacttccaca tgtttgacgt gggtggccag cgcgatgaac gccgcaagtg gatccagtgc | 300 |
| ttcaacgatg tgactgccat catcttcgtg gtggccagca gcgagtacaa catggtcatc | 360 |
| cgggaggaca accagaccaa ccgcctgcag gaggctctga acctcttcaa gagcatctgg | 420 |
| aacaacagat ggctgcgcac catctctgtg atcctgttcc tcaacaagca agatctgctc | 480 |
| gctgagaaag tccttgctgg gaaatcgaag attgaggact actttccaga atttgctcgc | 540 |
| tacactactc ctgaggatgc tactcccgag cccggagagg acccacgcgt gacccgggcc | 600 |
| aagtacttca ttcgagatga gtttctgagg atcagcactg ccagtggaga tgggcgtcac | 660 |
| tactgctacc ctcatttcac ctgcgctgtg gacactgaga catccgccg tgtgttcaac | 720 |
| gactgccgtg acatcattca gcgcatgcac cttcgtcagt acgagctgct ctaa | 774 |

<210> SEQ ID NO 61
<211> LENGTH: 744
<212> TYPE: DNA
<213> ORGANISM: Artificial Sequence
<220> FEATURE:
<223> OTHER INFORMATION: MINI GS105

<400> SEQUENCE: 61

| | |
|---|---|
| atgggtcacc accatcatca ccatgccaac aaaaagatcg agaagcagct gcagaaggac | 60 |
| aagcaggtct accgggccac gcaccgcctg ctgctgctgg gtgctggaga atctggtaaa | 120 |
| agcaccattg tgaagcagat gaggatcctg catgttaatg gcggaggtga tcaggacgcg | 180 |
| cttcgctccc gtgtcctgac ttctggaatc tttgagacca agttccaggt cgacaaagtc | 240 |
| aacttccaca tgtttgacgt gggtggccag cgcgatgaac gccgcaagtg gatccagtgc | 300 |
| ttcaacgatg tgactgccat catcttcgtg gtggccagca gcagctacaa ccgcctgcag | 360 |
| gaggctctga acctcttcaa gagcatctgg aacaacagat ggctgcgcac catctctgtg | 420 |
| atcctgttcc tcaacaagca agatctgctc gctgagaaag tccttgctgg gaaatcgaag | 480 |
| attgaggact actttccaga atttgctcgc tacactactc ctgaggatgc tactcccgag | 540 |
| cccggagagg acccacgcgt gacccgggcc aagtacttca ttcgagatga gtttctgagg | 600 |
| atcagcactg ccagtggaga tgggcgtcac tactgctacc ctcatttcac ctgcgctgtg | 660 |
| gacactgaga catccgccg tgtgttcaac gactgccgtg acatcattca gcgcatgcac | 720 |
| cttcgtcagt acgagctgct ctaa | 744 |

<210> SEQ ID NO 62
<211> LENGTH: 774
<212> TYPE: DNA
<213> ORGANISM: Artificial Sequence
<220> FEATURE:
<223> OTHER INFORMATION: MINI GS94

<400> SEQUENCE: 62

```
atgggtcacc accatcatca ccatgccaac aaaaagatcg agaagcagct gcagaaggac    60
aagcaggtct accgggccac gcaccgcctg ctgctgctgg gtgctggaga atctggtaaa   120
agcaccattg tgaagcagat gaggatcctg catgttaatg gcggaggtga tcaggacgcg   180
cttcgctccc gtgtcctgac ttctggaatc tttgagacca agttccaggt cgacaaagtc   240
aacttccaca tgtttgacgt gggtggccag cgcgatgaac gccgcaagtg gatccagtgc   300
ttcaacgatg tgactgccat catcttcgtg gtggccagca gcagctacaa catggtcatc   360
cgggaggaca accagaccaa ccgcctgcag gaggctctga cgacttcaa gagcatctgg   420
aacaacagat ggctgcgcac catctctgtg atcctgttcc tcaacaagca agatctgctc   480
gctgagaaag tccttgctgg gaaatcgaag attgaggact actttccaga atttgctcgc   540
tacactactc ctgaggatgc tactcccgag cccggagagg acccacgcgt gacccgggcc   600
aagtacttca ttcgagatga gtttctgagg atcagcactg ccagtggaga tgggcgtcac   660
tactgctacc ctcatttcac ctgcgctgtg gacactgaga acatccgccg tgtgttcaac   720
gactgccgtg acatcattca gcgcatgcac cttcgtcagt acgagctgct ctaa          774
```

<210> SEQ ID NO 63
<211> LENGTH: 774
<212> TYPE: DNA
<213> ORGANISM: Artificial Sequence
<220> FEATURE:
<223> OTHER INFORMATION: MINI GS113

<400> SEQUENCE: 63

```
atgggtcacc accatcatca ccatgccaac aaaaagatcg agaagcagct gcagaaggac    60
aagcaggtct accgggccac gcaccgcctg ctgctgctgg gtgctggaga atctggtaaa   120
agcaccattg tgaagcagat gaggatcctg catgttaatg gcggaggtga tcaggacgcg   180
cttcgctccc gtgtcctgac ttctggaatc tttgagacca agttccaggt cgacaaagtc   240
aacttccaca tgtttgacgt gggtggccag cgcgatgaac gccgcaagtg gatccagtgc   300
ttcaacgatg tgactgccat catcttcgtg gtggccagca gcagctacaa catggtcatc   360
cgggaggaca accagaccaa ccgcctgcag gaggctctga cgagttcaa gagcatctgg   420
aacaacagat ggctgcgcac catctctgtg atcctgttcc tcaacaagca agatctgctc   480
gctgagaaag tccttgctgg gaaatcgaag attgaggact actttccaga atttgctcgc   540
tacactactc ctgaggatgc tactcccgag cccggagagg acccacgcgt gacccgggcc   600
aagtacttca ttcgagatga gtttctgagg atcagcactg ccagtggaga tgggcgtcac   660
tactgctacc ctcatttcac ctgcgctgtg gacactgaga acatccgccg tgtgttcaac   720
gactgccgtg acatcattca gcgcatgcac cttcgtcagt acgagctgct ctaa          774
```

<210> SEQ ID NO 64
<211> LENGTH: 729
<212> TYPE: DNA
<213> ORGANISM: Artificial Sequence
<220> FEATURE:
<223> OTHER INFORMATION: MINI GS161

<400> SEQUENCE: 64

```
atgggtcacc accatcatca ccatgccaac aaaaagatcg agaagcagct gcagaaggac    60
aagcaggtct accgggccac gcaccgcctg ctgctgctgg gtgctggaga atctggtaaa   120
agcaccattg tgaagcagat gaggatcctg catgggggag gtggaggcga gaccaagttc   180
```

```
caggtggaca aagtcaactt ccacatgttt gacgtgggtg ccagcgcga tgaacgccgc    240 aagtggatcc agtgcttcaa cgatgtgact gccatcatct tcgtggtggc cagcagcagc    300
tacaacatgg tcatccggga ggacaaccag accaaccgcc tgcaggaggc tctgaacctc    360
ttcaagagca tctggaacaa cagatggctg cgcaccatct ctgtgatcct gttcctcaac    420
aagcaagatc tgctcgctga aaagtccttg ctgggaaat cgaagattga ggactacttt    480
ccagaatttg ctcgctacac tactcctgag gatgctactc ccgagcccgg agaggaccca    540
cgcgtgaccc gggccaagta cttcattcga gatgagtttc tgaggatcag cactgccagt    600
ggagatgggc gtcactactg ctaccctcat ttcacctgcg ctgtggacac tgagaacatc    660
cgccgtgtgt tcaacgactg ccgtgacatc attcagcgca tgcaccttcg tcagtacgag    720
ctgctctaa                                                            729
```

<210> SEQ ID NO 65
<211> LENGTH: 729
<212> TYPE: DNA
<213> ORGANISM: Artificial Sequence
<220> FEATURE:
<223> OTHER INFORMATION: MINI GS162

<400> SEQUENCE: 65

```
atgggtcacc accatcatca ccatgccaac aaaaagatcg agaagcagct gcagaaggac     60
aagcaggtct accgggccac gcaccgcctg ctgctgctgg gtgctggaga atctggtaaa    120
agcaccattg tgaagcagat gaggatcctg catggggag gtggaggcga gaccaagttc    180
caggtggaca aagtcaactt ccacatgttt gacgtgggtg ccagcgcga tgaacgccgc    240 aagtggatcc agtgcttcaa cgatgtgact gccatcatct tcgtggtgga cagcagcagc    300
tacaacatgg tcatccggga ggacaaccag accaaccgcc tgcaggaggc tctgaacctc    360
ttcaagagca tctggaacaa cagatggctg cgcaccatct ctgtgatcct gttcctcaac    420
aagcaagatc tgctcgctga aaagtccttg ctgggaaat cgaagattga ggactacttt    480
ccagaatttg ctcgctacac tactcctgag gatgctactc ccgagcccgg agaggaccca    540
cgcgtgaccc gggccaagta cttcattcga gatgagtttc tgaggatcag cactgccagt    600
ggagatgggc gtcactactg ctaccctcat ttcacctgcg ctgtggacac tgagaacatc    660
cgccgtgtgt tcaacgactg ccgtgacatc attcagcgca tgcaccttcg tcagtacgag    720
ctgctctaa                                                            729
```

<210> SEQ ID NO 66
<211> LENGTH: 699
<212> TYPE: DNA
<213> ORGANISM: Artificial Sequence
<220> FEATURE:
<223> OTHER INFORMATION: MINI GS164

<400> SEQUENCE: 66

```
atgggtcacc accatcatca ccatgccaac aaaaagatcg agaagcagct gcagaaggac     60
aagcaggtct accgggccac gcaccgcctg ctgctgctgg gtgctggaga atctggtaaa    120
agcaccattg tgaagcagat gaggatcctg catggggag gtggaggcga gaccaagttc    180
caggtggaca aagtcaactt ccacatgttt gacgtgggtg ccagcgcga tgaacgccgc    240 aagtggatcc agtgcttcaa cgatgtgact gccatcatct tcgtggtgga cagcagcagc    300
tacaaccgcc tgcaggaggc tctgaacctc ttcaagagca tctggaacaa cagatggctg    360
```

| | |
|---|---|
| cgcaccatct ctgtgatcct gttcctcaac aagcaagatc tgctcgctga gaaagtcctt | 420 |
| gctgggaaat cgaagattga ggactacttt ccagaatttg ctcgctacac tactcctgag | 480 |
| gatgctactc ccgagcccgg agaggaccca cgcgtgaccc gggccaagta cttcattcga | 540 |
| gatgagtttc tgaggatcag cactgccagt ggagatgggc gtcactactg ctaccctcat | 600 |
| ttcacctgcg ctgtggacac tgagaacatc cgccgtgtgt tcaacgactg ccgtgacatc | 660 |
| attcagcgca tgcaccttcg tcagtacgag ctgctctaa | 699 |

<210> SEQ ID NO 67
<211> LENGTH: 699
<212> TYPE: DNA
<213> ORGANISM: Artificial Sequence
<220> FEATURE:
<223> OTHER INFORMATION: MINI GS165

<400> SEQUENCE: 67

| | |
|---|---|
| atgggtcacc accatcatca ccatgccaac aaaaagatcg agaagcagct gcagaaggac | 60 |
| aagcaggtct accgggccac gcaccgcctg ctgctgctgg gtgctggaga atctggtaaa | 120 |
| agcaccattg tgaagcagat gaggatcctg catgggggag gtggaggcga gaccaagttc | 180 |
| caggtggaca aagtcaactt ccacatgttt gacgtgggtg gccagcgcga tgaacgccgc | 240 |
| aagtggatcc agtgcttcaa cgatgtgact gccatcatct tcgtggtgga cagcagcgat | 300 |
| tacaaccgcc tgcaggaggc tctgaacctc ttcaagagca tctggaacaa cagatggctg | 360 |
| cgcaccatct ctgtgatcct gttcctcaac aagcaagatc tgctcgctga gaaagtcctt | 420 |
| gctgggaaat cgaagattga ggactacttt ccagaatttg ctcgctacac tactcctgag | 480 |
| gatgctactc ccgagcccgg agaggaccca cgcgtgaccc gggccaagta cttcattcga | 540 |
| gatgagtttc tgaggatcag cactgccagt ggagatgggc gtcactactg ctaccctcat | 600 |
| ttcacctgcg ctgtggacac tgagaacatc cgccgtgtgt tcaacgactg ccgtgacatc | 660 |
| attcagcgca tgcaccttcg tcagtacgag ctgctctaa | 699 |

<210> SEQ ID NO 68
<211> LENGTH: 699
<212> TYPE: DNA
<213> ORGANISM: Artificial Sequence
<220> FEATURE:
<223> OTHER INFORMATION: MINI GS169

<400> SEQUENCE: 68

| | |
|---|---|
| atgggtcacc accatcatca ccatgccaac aaaaagatcg agaagcagct gcagaaggac | 60 |
| aagcaggtct accgggccac gcaccgcctg ctgctgctgg gtgctggaga atctggtaaa | 120 |
| agcaccattg tgaagcagat gaggatcctg catgggggag gtggaggcga gaccaagttc | 180 |
| caggtggaca aagtcaactt ccacatgttt gacgtgggtg gccagcgcga tgaacgccgc | 240 |
| aagtggatcc agtgcttcaa cgatgtgact gccatcatct tcgtggtgga cagcagcgat | 300 |
| tacaaccgcc tgcaggaggc tctgaacgac ttcaagagca tctggaacaa cagatggctg | 360 |
| cgcaccatct ctgtgatcct gttcctcaac aagcaagatc tgctcgctga gaaagtcctt | 420 |
| gctgggaaat cgaagattga ggactacttt ccagaatttg ctcgctacac tactcctgag | 480 |
| gatgctactc ccgagcccgg agaggaccca cgcgtgaccc gggccaagta cttcattcga | 540 |
| gatgagtttc tgaggatcag cactgccagt ggagatgggc gtcactactg ctaccctcat | 600 |
| ttcacctgcg ctgtggacac tgagaacatc cgccgtgtgt tcaacgactg ccgtgacatc | 660 |
| attcagcgca tgcaccttcg tcagtacgag ctgctctaa | 699 |

<210> SEQ ID NO 69
<211> LENGTH: 699
<212> TYPE: DNA
<213> ORGANISM: Artificial Sequence
<220> FEATURE:
<223> OTHER INFORMATION: MINI GS183

<400> SEQUENCE: 69

```
atgggtcacc accatcatca ccatgccaac aaaaagatcg agaagcagct gcagaaggac      60
aagcaggtct accgggccac gcaccgcctg ctgctgctgg gtgctgataa ttctggtaaa     120
agcaccattg tgaagcagat gaggatcctg catggggggag gtggaggcga gaccaagttc    180
caggtggaca agtcaactt ccacatgttt gacgtgggtg ccagcgcga tgaacgccgc       240
aagtggatcc agtgcttcaa cgatgtgact gccatcatct cgtggtgga cagcagcgat      300
tacaaccgcc tgcaggaggc tctgaacgac ttcaagagca tctggaacaa cagatggctg     360
cgcaccatct ctgtgatcct gttcctcaac aagcaagatc tgctcgctga aaagtccttt    420
gctgggaaat cgaagattga ggactacttt ccagaatttg ctcgctacac tactcctgag    480
gatgctactc ccgagcccgg agaggaccca cgcgtgaccc gggccaagta cttcattcga    540
gatgagtttc tgaggatcag cactgccagt ggagatgggc gtcactactg ctaccctcat    600
ttcacctgcg ctgtggacac tgagaacatc cgccgtgtgt tcaacgactg ccgtgacatc    660
attcagcgca tgcaccttcg tcagtacgag ctgctctaa                           699
```

<210> SEQ ID NO 70
<211> LENGTH: 723
<212> TYPE: DNA
<213> ORGANISM: Artificial Sequence
<220> FEATURE:
<223> OTHER INFORMATION: MINI GS199

<400> SEQUENCE: 70

```
atgggtcacc accatcatca ccatgccaac aaaaagatcg agaagcagct gcagaaggac     60
aagcaggtct accgggccac gcaccgcctg ctgctgctgg gtgctgataa ttctggtaaa    120
agcaccattg tgaagcagat gaggatcctg catggtgggg gaggcggggg cggaggtact    180
tctggaatct ttgagaccaa gttccaggtg gacaaagtca acttccacat gtttgacgtg    240
ggtggccagc gcgatgaacg ccgcaagtgg atccagtgct tcaacgatgt gactgccatc    300
atcttcgtgg tggacagcag cgattacaac cgcctgcagg aggctctgaa cgacttcaag    360
agcatctgga acaacagatg gctgcgcacc atctctgtga tcctgttcct caacaagcaa    420
gatctgctcg ctgagaaagt ccttgctggg aaatcgaaga ttgaggacta ctttccagaa    480
tttgctcgct acactactcc tgaggatgct actcccgagc ccggagagga cccacgcgtg    540
acccgggcca gtacttcat cgagatgag tttctgagga tcagcactgc cagtggagat     600
gggcgtcact actgctaccc tcatttcacc tgcgctgtgg acactgagaa catccgccgt    660
gtgttcaacg actgccgtga catcattcag cgcatgcacc ttcgtcagta cgagctgctc    720
taa                                                                    723
```

<210> SEQ ID NO 71
<211> LENGTH: 723
<212> TYPE: DNA
<213> ORGANISM: Artificial Sequence
<220> FEATURE:
<223> OTHER INFORMATION: MINI GS254

<400> SEQUENCE: 71

```
atgggtcacc accatcatca ccatgccaac aaaaagatcg agaagcagct gcagaaggac    60
aagcaggtct accgggccac gcaccgcctg ctgctgctgg gtgctgataa ttctggtaaa   120
agcaccattg tgaagcaggc gaggatcctg catggtgggg aggcggggg cggaggtact   180
tctggaatct ttgagaccaa gttccaggtg acaaagtca acttccacat gtttgacgtg   240
ggtggccagc gcgatgaacg ccgcaagtgg atccagtgct caacgatgt gactgccatc   300
atcttcgtgg tggacagcag cgattacaac cgcctgcagg aggctctgaa cgacttcaag   360
agcatctgga caacagatg gctgcgcacc atctctgtga tcctgttcct caacaagcaa   420
gatctgctcg ctgagaaagt ccttgctggg aaatcgaaga ttgaggacta ctttccagaa   480
tttgctcgct acactactcc tgaggatgct actcccgagc ccggagagga cccacgcgtg   540
acccgggcca agtacttcat cgagatgag tttctgagga tcagcactgc cagtggagat   600
gggcgtcact actgctaccc tcatttcacc tgcgctgtgg acactgagaa catccgccgt   660
gtgttcaacg actgccgtga catcattcag cgcatgcacc ttcgtcagta cgagctgctc   720
taa                                                                723
```

<210> SEQ ID NO 72
<211> LENGTH: 723
<212> TYPE: DNA
<213> ORGANISM: Artificial Sequence
<220> FEATURE:
<223> OTHER INFORMATION: MINI GS350

<400> SEQUENCE: 72

```
atgggtcacc accatcatca ccatgccaac aaaaagatcg agaagcagct gcagaaggac    60
aagcaggtct accgggccac gcaccgcctg ctgctgctgg gtgctgataa ttctggtaaa   120
agcaccattg tgaagcagat gaggatctac catggtgggg aggcggggg cggaggtact   180
tctggaatct ttgagaccaa gttccaggtg acaaagtca acttccacat gtttgacgtg   240
ggtggccagc gcgatgaacg ccgcaagtgg atccagtgct caacgatgt gactgccatc   300
atcttcgtgg tggacagcag cgattacaac cgcctgcagg aggctctgaa cgacttcaag   360
agcatctgga caacagatg gctgcgcacc atctctgtga tcctgttcct caacaagcaa   420
gatctgctcg ctgagaaagt ccttgctggg aaatcgaaga ttgaggacta ctttccagaa   480
tttgctcgct acactactcc tgaggatgct actcccgagc ccggagagga cccacgcgtg   540
acccgggcca agtacttcat cgagatgag tttctgagga tcagcactgc cagtggagat   600
gggcgtcact actgctaccc tcatttcacc tgcgctgtgg acactgagaa catccgccgt   660
gtgttcaacg actgccgtga catcattcag cgcatgcacc ttcgtcagta cgagctgctc   720
taa                                                                723
```

<210> SEQ ID NO 73
<211> LENGTH: 723
<212> TYPE: DNA
<213> ORGANISM: Artificial Sequence
<220> FEATURE:
<223> OTHER INFORMATION: MINI GS340

<400> SEQUENCE: 73

```
atgggtcacc accatcatca ccatgccaac aaaaagatcg agaagcagct gcagaaggac    60
aagcaggtct accgggccac gcaccgcctg ctgctgctgg gtgctgataa ttctggtaaa   120
agcaccattg tgaagcagat gaggatcctg catggtgggg aggcggggg cggaggtact   180
```

```
tctggaatct ttgagaccaa gttccaggtg acaaagtca acttccacat gtttgacgtg      240
ggtggccagc gcgatgaacg ccgcaagtgg atccagtgct tcaacgatgt gactgccatc      300
atcttcgtgg tggacagcag cgattacaac cgcctgcagg aggctctgaa cgacttcaag      360
agcatctgga caacagatg gctgcgcacc atctctgtga tcctgttcct caacaagcaa       420
gatctgctcg ctgagaaagt ccttgctggg aaatcgaaga ttgaggacta ctttccagaa      480
tttgctcgct acactactcc tgaggatgct actcccgagc ccggagagga cccacgcgtg      540
acccgggcca agtacttcat tcgagatgag tttctgagga tcagcactgc cagtggagat      600
gggcgtcact actgctaccc tcatttcacc tgcgctgtgg acactgagaa cgcccgccgt      660
gtgttcaacg actgccgtga catcattcag cgcatgcacc ttcgtcagta cgagctgctc      720
taa                                                                    723

<210> SEQ ID NO 74
<211> LENGTH: 723
<212> TYPE: DNA
<213> ORGANISM: Artificial Sequence
<220> FEATURE:
<223> OTHER INFORMATION: MINI GS303

<400> SEQUENCE: 74
atgggtcacc accatcatca ccatgccaac aaaaagatcg agaagcagct gcagaaggac      60
aagcaggtct accgggccac gcaccgcctg ctgctgctgg gtgctgataa ttctggtaaa      120
agcaccattg tgaagcagat gaggatcctg catggtgggg gaggcggggg cggaggtact      180
tctggaatct ttgagaccaa gttccaggtg acaaagtca acttccacat gtttgacgtg       240
ggtggccagc gcgatgaacg ccgcaagtgg atccagtgct tcaacgatgt gactgccatc      300
atcttcgtgg tggacagcag cgattacaac cgcctgcagg aggctctgaa cgacttcaag      360
agcatctgga caacagatg gctgcgcacc atctctgtga tcctgttcct caacaagcaa       420
gatctgctcg ctgagaaagt ccttgctggg aaatcgaaga ttgaggacta ctttccagaa      480
tttgctcgct acactactcc tgaggatgct actcccgagc ccggagagga cccacgcgtg      540
acccgggcca agtacttcat tcgagatgag tttctgagga tcagcactgc cagtggagat      600
gggcgtcact actgctaccc tcatttcacc tgcgctgtgg acactgagaa cgcccgccgt      660
gtgttcaacg actgccgtga catcattcag cgcatgcacc ttcgtcagta cgagctgctc      720
taa                                                                    723

<210> SEQ ID NO 75
<211> LENGTH: 723
<212> TYPE: DNA
<213> ORGANISM: Artificial Sequence
<220> FEATURE:
<223> OTHER INFORMATION: MINI GS352

<400> SEQUENCE: 75
atgggtcacc accatcatca ccatgccaac aaaaagatcg agaagcagct gcagaaggac      60
aagcaggtct accgggccac gcaccgcctg ctgctgctgg gtgctgataa ttctggtaaa      120
agcaccattg tgaagcagat gaggatctac catggtgggg gaggcggggg cggaggtact      180
tctggaatct ttgagaccaa gttccaggtg acaaagtca acttccacat gtttgacgtg       240
ggtggccagc gcgatgaacg ccgcaagtgg atccagtgct tcaacgatgt gactgccatc      300
atcttcgtgg tggacagcag cgattacaac cgcctgcagg aggctctgaa cgacttcaag      360
```

| | |
|---|---|
| agcatctgga caacagatg gctgcgcacc atctctgtga tcctgttcct caacaagcaa | 420 |
| gatctgctcg ctgagaaagt ccttgctggg aaatcgaaga ttgaggacta ctttccagaa | 480 |
| tttgctcgct acactactcc tgaggatgct actcccgagc ccggagagga cccacgcgtg | 540 |
| acccgggcca agtacttcat tcgagatgag tttctgagga tcagcactgc cagtggagat | 600 |
| gggcgtcact actgctaccc tcatttcacc tgcgctgtgg acactgagaa cgcccgccgt | 660 |
| gtgttcaacg actgccgtga catcattcag cgcatgcacc ttcgtcagta cgagctgctc | 720 |
| taa | 723 |

<210> SEQ ID NO 76
<211> LENGTH: 723
<212> TYPE: DNA
<213> ORGANISM: Artificial Sequence
<220> FEATURE:
<223> OTHER INFORMATION: MINI GS345

<400> SEQUENCE: 76

| | |
|---|---|
| atgggtcacc accatcatca ccatgccaac aaaaagatcg agaagcagct gcagaaggac | 60 |
| aagcaggtct accgggccac gcaccgcctg ctgctgctgg gtgctgataa ttctggtaaa | 120 |
| agcaccattg tgaagcagat gaggatcctg catggtgggg aggcggggg cggaggtact | 180 |
| tctggaatct ttgagaccaa gttccaggtg gacaaagtca acttccacat gtttgacgtg | 240 |
| ggtggccagc gcgatgaacg ccgcaagtgg atccagtgct tcaacgatgt gactgccatc | 300 |
| atcttcgtgg tggacagcag cgattacaac cgcctgcagg aggctctgaa cgacttcaag | 360 |
| agcatctgga caacagatg gctgcgcacc atctctgtga tcctgttcct caacaagcaa | 420 |
| gatctgctcg ctgagaaagt ccttgctggg aaatcgaaga ttgaggacta ctttccagaa | 480 |
| tttgctcgct acactactcc tgaggatgct actcccgagc ccggagagga cccacgcgtg | 540 |
| acccgggcca agtacttcat tcgagatgag tttctgagga tcagcactgc cagtggagat | 600 |
| gggcgtcact actgctaccc tcatttcacc tgcgctgtgg acactgagaa cgcccgccgt | 660 |
| atcttcaacg actgccgtga catcattcag cgcatgcacc ttcgtcagta cgagctgctc | 720 |
| taa | 723 |

<210> SEQ ID NO 77
<211> LENGTH: 732
<212> TYPE: DNA
<213> ORGANISM: Artificial Sequence
<220> FEATURE:
<223> OTHER INFORMATION: MINI GS389

<400> SEQUENCE: 77

| | |
|---|---|
| atgggtcacc accatcatca ccatgaaaat ctttatttcc agggtatcga gaagcagctg | 60 |
| cagaaggaca agcaggtcta ccgggccacg caccgcctgc tgctgctggg tgctgataat | 120 |
| tctggtaaaa gcaccattgt gaagcaggcg aggatcctgc atggtgggag tggcgggagc | 180 |
| ggaggtactt ctggaatctt tgagaccaag ttccaggtga caaagtcaa cttccacatg | 240 |
| tttgacgtgg gtggccagcg cgatgaacgc cgcaagtgga tccagtgctt caacgatgtg | 300 |
| actgccatca tcttcgtggt ggacagcagc gattacaacc gcctgcagga ggctctgaac | 360 |
| gacttcaaga gcatctggaa caacagatgg ctgcgcacca tctctgtgat cctgttcctc | 420 |
| aacaagcaag atctgctcgc tgagaaagtc cttgctggga aatcgaagat tgaggactac | 480 |
| tttccagaat ttgctcgcta cactactcct gaggatgcta ctcccgagcc ggagaggac | 540 |
| ccacgcgtga cccgggccaa gtacttcatt cgagatgagt ttctgaggat cagcactgcc | 600 |

```
agtggagatg ggcgtcacta ctgctaccct catttcacct gcgctgtgga cactgagaac    660
atccgccgta tcttcaacga ctgccgtgac atcattcagc gcatgcacct tcgtcagtac    720
gagctgctct aa                                                        732
```

<210> SEQ ID NO 78
<211> LENGTH: 732
<212> TYPE: DNA
<213> ORGANISM: Artificial Sequence
<220> FEATURE:
<223> OTHER INFORMATION: MINI GS391

<400> SEQUENCE: 78

```
atgggtcacc accatcatca ccatgaaaat ctttatttcc agggtatcga gaagcagctg     60
cagaaggaca agcaggtcta ccgggccacg caccgcctgc tgctgctggg tgctgataat    120
tctggtaaaa gcaccattgt gaagcagatg aggatcctgc atggtgggag tggcgggagc    180
ggaggtactt ctggaatctt tgagaccaag ttccaggtgg acaaagtcaa cttccacatg    240
tttgacgtgg gtggccagcg cgatgaacgc cgcaagtgga tccagtgctt caacgatgtg    300
actgccatca tcttcgtggt ggacagcagc gattacaacc gcctgcagga ggctctgaac    360
gacttcaaga gcatctggaa caacagatgg ctgcgcacca tctctgtgat cctgttcctc    420
aacaagcaag atctgctcgc tgagaaagtc cttgctggga atcgaagatt gaggactac     480 tttccagaat tgctcgcta cactactcct gaggatgcta ctcccgagcc cggagaggac    540
ccacgcgtga cccgggccaa gtacttcatt cgagatgagt ttctgaggat cagcactgcc    600
agtggagatg ggcgtcacta ctgctaccct catttcacct gcgctgtgga cactgagaac    660
gcccgccgtg tgttcaacga ctgccgtgac atcattcagc gcatgcacct tcgtcagtac    720
gagctgctct aa                                                        732
```

<210> SEQ ID NO 79
<211> LENGTH: 732
<212> TYPE: DNA
<213> ORGANISM: Artificial Sequence
<220> FEATURE:
<223> OTHER INFORMATION: MINI GS393

<400> SEQUENCE: 79

```
atgggtcacc accatcatca ccatgaaaat ctttatttcc agggtatcga gaagcagctg     60
cagaaggaca agcaggtcta ccgggccacg caccgcctgc tgctgctggg tgctgataat    120
tctggtaaaa gcaccattgt gaagcagatg aggatcctgc atggtgggag tggcgggagc    180
ggaggtactt ctggaatctt tgagaccaag ttccaggtgg acaaagtcaa cttccacatg    240
tttgacgtgg gtggccagcg cgatgaacgc cgcaagtgga tccagtgctt caacgatgtg    300
actgccatca tcttcgtggt ggacagcagc gattacaacc gcctgcagga ggctctgaac    360
gacttcaaga gcatctggaa caacagatgg ctgcgcacca tctctgtgat cctgttcctc    420
aacaagcaag atctgctcgc tgagaaagtc cttgctggga atcgaagatt gaggactac     480 tttccagaat tgctcgcta cactactcct gaggatgcta ctcccgagcc cggagaggac    540
ccacgcgtga cccgggccaa gtacttcatt cgagatgagt ttctgaggat cagcactgcc    600
agtggagatg ggcgtcacta ctgctaccct catttcacct gcgctgtgga cactgagaac    660
gcccgccgta tcttcaacga ctgccgtgac atcattcagc gcatgcacct tcgtcagtac    720
gagctgctct aa                                                        732
```

<210> SEQ ID NO 80
<211> LENGTH: 792
<212> TYPE: DNA
<213> ORGANISM: Artificial Sequence
<220> FEATURE:
<223> OTHER INFORMATION: MINI GS395

<400> SEQUENCE: 80

| | | | | | |
|---|---|---|---|---|---|
| atgggtcacc | accatcatca | ccatgaaaat | ctttatttcc | agggtaacag | taagaccgag | 60 |
| gaccagcgca | acgaggagaa | ggcgcagcgt | gaggccaaca | aaaagatcga | gaagcagctg | 120 |
| cagaaggaca | agcaggtcta | ccgggccacg | caccgcctgc | tgctgctggg | tgctgataat | 180 |
| tctggtaaaa | gcaccattgt | gaagcaggcg | aggatcctgc | atggtgggag | tggcgggagc | 240 |
| ggaggtactt | ctggaatctt | tgagaccaag | ttccaggtgg | acaaagtcaa | cttccacatg | 300 |
| tttgacgtgg | gtggccagcg | cgatgaacgc | cgcaagtgga | tccagtgctt | caacgatgtg | 360 |
| actgccatca | tcttcgtggt | ggacagcagc | gattacaacc | gcctgcagga | ggctctgaac | 420 |
| ctcttcaaga | gcatctggaa | caacagatgg | ctgcgcacca | tctctgtgat | cctgttcctc | 480 |
| aacaagcaag | atctgctcgc | tgagaaagtc | cttgctggga | atcgaagatt | gaggactac | 540 |
| tttccagaat | ttgctcgcta | cactactcct | gaggatgcta | ctcccgagcc | cggagaggac | 600 |
| ccacgcgtga | cccgggccaa | gtacttcatt | cgagatgagt | ttctgaggat | cagcactgcc | 660 |
| agtggagatg | ggcgtcacta | ctgctaccct | catttcacct | gcgctgtgga | cactgagaac | 720 |
| atccgccgta | tcttcaacga | ctgccgtgac | atcattcagc | gcatgcacct | tcgtcagtac | 780 |
| gagctgctct | aa | | | | | 792 |

<210> SEQ ID NO 81
<211> LENGTH: 792
<212> TYPE: DNA
<213> ORGANISM: Artificial Sequence
<220> FEATURE:
<223> OTHER INFORMATION: MINI GS397

<400> SEQUENCE: 81

| | | | | | |
|---|---|---|---|---|---|
| atgggtcacc | accatcatca | ccatgaaaat | ctttatttcc | agggtaacag | taagaccgag | 60 |
| gaccagcgca | acgaggagaa | ggcgcagcgt | gaggccaaca | aaaagatcga | gaagcagctg | 120 |
| cagaaggaca | agcaggtcta | ccgggccacg | caccgcctgc | tgctgctggg | tgctgataat | 180 |
| tctggtaaaa | gcaccattgt | gaagcagatg | aggatcctgc | atggtgggag | tggcgggagc | 240 |
| ggaggtactt | ctggaatctt | tgagaccaag | ttccaggtgg | acaaagtcaa | cttccacatg | 300 |
| tttgacgtgg | gtggccagcg | cgatgaacgc | cgcaagtgga | tccagtgctt | caacgatgtg | 360 |
| actgccatca | tcttcgtggt | ggacagcagc | gattacaacc | gcctgcagga | ggctctgaac | 420 |
| ctcttcaaga | gcatctggaa | caacagatgg | ctgcgcacca | tctctgtgat | cctgttcctc | 480 |
| aacaagcaag | atctgctcgc | tgagaaagtc | cttgctggga | atcgaagatt | gaggactac | 540 |
| tttccagaat | ttgctcgcta | cactactcct | gaggatgcta | ctcccgagcc | cggagaggac | 600 |
| ccacgcgtga | cccgggccaa | gtacttcatt | cgagatgagt | ttctgaggat | cagcactgcc | 660 |
| agtggagatg | ggcgtcacta | ctgctaccct | catttcacct | gcgctgtgga | cactgagaac | 720 |
| gcccgccgtg | tgttcaacga | ctgccgtgac | atcattcagc | gcatgcacct | tcgtcagtac | 780 |
| gagctgctct | aa | | | | | 792 |

<210> SEQ ID NO 82
<211> LENGTH: 792

<212> TYPE: DNA
<213> ORGANISM: Artificial Sequence
<220> FEATURE:
<223> OTHER INFORMATION: MINI GS399

<400> SEQUENCE: 82

```
atgggtcacc accatcatca ccatgaaaat ctttatttcc agggtaacag taagaccgag    60
gaccagcgca acgaggagaa ggcgcagcgt gaggccaaca aaaagatcga gaagcagctg   120
cagaaggaca agcaggtcta ccgggccacg caccgcctgc tgctgctggg tgctgataat   180
tctggtaaaa gcaccattgt gaagcagatg aggatcctgc atggtgggag tggcgggagc   240
ggaggtactt ctggaatctt tgagaccaag ttccaggtgg acaaagtcaa cttccacatg   300
tttgacgtgg gtggccagcg cgatgaacgc cgcaagtgga tccagtgctt caacgatgtg   360
actgccatca tcttcgtggt ggacagcagc gattacaacc gcctgcagga ggctctgaac   420
ctcttcaaga gcatctggaa caacagatgg ctgcgcacca tctctgtgat cctgttcctc   480
aacaagcaag atctgctcgc tgagaaagtc cttgctggga atcgaagat tgaggactac    540
tttccagaat tgctcgcta cactactcct gaggatgcta ctcccgagcc cggagaggac   600
ccacgcgtga cccgggccaa gtacttcatt cgagatgagt ttctgaggat cagcactgcc   660
agtggagatg ggcgtcacta ctgctaccct catttcacct gcgctgtgga cactgagaac   720
gcccgccgta tcttcaacga ctgccgtgac atcattcagc gcatgcacct tcgtcagtac   780
gagctgctct aa                                                       792
```

<210> SEQ ID NO 83
<211> LENGTH: 732
<212> TYPE: DNA
<213> ORGANISM: Artificial Sequence
<220> FEATURE:
<223> OTHER INFORMATION: MINI GS404

<400> SEQUENCE: 83

```
atgggtcacc accatcatca ccatgaaaat ctttatttcc agggtatcga gaagcagctg    60
cagaaggaca agcaggtcta ccgggccacg caccgcctgc tgctgctggg tgctgataat   120
tctggtaaaa gcaccattgt gaagcagatg aggatcctgc atggtgggag tggcgggagc   180
ggaggtactt ctggaatctt tgagaccaag ttccaggtgg acaaagtcaa cttccacatg   240
tttgacgtgg gtggccagcg cgatgaacgc cgcaagtgga tccagtgctt caacgatgtg   300
actgccatca tcttcgtggt ggacagcagc gattacaacc gcctgcagga ggctctgaac   360
gacttcaaga gcatctggaa caacagatgg ctgcgcacca tctctgtgat cctgttcctc   420
aacaagcaag atctgctcgc tgagaaagtc cttgctggga atcgaagat tgaggactac    480
tttccagaat tgctcgcta cactactcct gaggatgcta ctcccgagcc cggagaggac   540
ccacgcgtga cccgggccaa gtacttcatt cgagatgagt ttctgaggat cagcactgcc   600
agtggagatg ggcgtcacta ctgctaccct catttcacct gcgctgtgga cactgagaac   660
atccgccgtg tgttcaacga ctgccgtgac atcattcagc gcatgcacct tcgtcagtac   720
gagctgctct aa                                                       732
```

<210> SEQ ID NO 84
<211> LENGTH: 792
<212> TYPE: DNA
<213> ORGANISM: Artificial Sequence
<220> FEATURE:
<223> OTHER INFORMATION: MINI GS406

<400> SEQUENCE: 84

```
atgggtcacc accatcatca ccatgaaaat ctttatttcc agggtaacag taagaccgag      60
gaccagcgca acgaggagaa ggcgcagcgt gaggccaaca aaaagatcga gaagcagctg     120
cagaaggaca agcaggtcta ccgggccacg caccgcctgc tgctgctggg tgctgataat     180
tctggtaaaa gcaccattgt gaagcagatg aggatcctgc atggtgggag tggcgggagc     240
ggaggtactt ctggaatctt tgagaccaag ttccaggtgg acaaagtcaa cttccacatg     300
tttgacgtgg gtggccagcg cgatgaacgc cgcaagtgga tccagtgctt caacgatgtg     360
actgccatca tcttcgtggt ggacagcagc gattacaacc gcctgcagga ggctctgaac     420
ctcttcaaga gcatctggaa caacagatgg ctgcgcacca tctctgtgat cctgttcctc     480
aacaagcaag atctgctcgc tgagaaagtc cttgctggga atcgaagat tgaggactac      540
tttccagaat ttgctcgcta cactactcct gaggatgcta ctcccgagcc cggagaggac     600
ccacgcgtga cccgggccaa gtacttcatt cgagatgagt ttctgaggat cagcactgcc     660
agtggagatg ggcgtcacta ctgctaccct catttcacct gcgctgtgga cactgagaac     720
atccgccgtg tgttcaacga ctgccgtgac atcattcagc gcatgcacct tcgtcagtac     780
gagctgctct aa                                                         792
```

<210> SEQ ID NO 85
<211> LENGTH: 732
<212> TYPE: DNA
<213> ORGANISM: Artificial Sequence
<220> FEATURE:
<223> OTHER INFORMATION: MINI GS410

<400> SEQUENCE: 85

```
atgggtcacc accatcatca ccatgaaaat ctttatttcc agggtatcga gaagcagctg      60
cagaaggaca agcaggtcta ccgggccacg caccgcctgc tgctgctggg tgctgataat     120
tctggtaaaa gcaccattgt gaagcagatg aggatccggc atggtgggag tggcgggagc     180
ggaggtactt ctggaatctt tgagaccaag ttccaggtgg acaaagtcaa cttccacatg     240
tttgacgtgg gtggccagcg cgatgaacgc cgcaagtgga tccagtgctt caacgatgtg     300
actgccatca tcttcgtggt ggacagcagc gattacaacc gcctgcagga ggctctgaac     360
gacttcaaga gcatctggaa caacagatgg ctgcgcacca tctctgtgat cctgttcctc     420
aacaagcaag atctgctcgc tgagaaagtc cttgctggga atcgaagat tgaggactac      480
tttccagaat ttgctcgcta cactactcct gaggatgcta ctcccgagcc cggagaggac     540
ccacgcgtga cccgggccaa gtacttcatt cgagatgagt ttctgaggat cagcactgcc     600
agtggagatg ggcgtcacta ctgctaccct catttcacct gcgctgtgga cactgagaac     660
gcccgccgta tcttcaacga ctgccgtgac atcattcagc gcatgcacct tcgtcagtac     720
gagctgctct aa                                                         732
```

<210> SEQ ID NO 86
<211> LENGTH: 732
<212> TYPE: DNA
<213> ORGANISM: Artificial Sequence
<220> FEATURE:
<223> OTHER INFORMATION: MINI GS414

<400> SEQUENCE: 86

```
atgggtcacc accatcatca ccatgaaaat ctttatttcc agggtatcga gaagcagctg      60
cagaaggaca agcaggtcta ccgggccacg caccgcctgc tgctgctggg tgctgataat     120
```

```
tctggtaaaa gcaccattgt gaagcagatg aggatctacc atggtgggag tggcgggagc    180
ggaggtactt ctggaatctt tgagaccaag ttccaggtgg acaaagtcaa cttccacatg    240
tttgacgtgg gtggccagcg cgatgaacgc cgcaagtgga tccagtgctt caacgatgtg    300
actgccatca tcttcgtggt ggacagcagc gattacaacc gcctgcagga ggctctgaac    360
gacttcaaga gcatctggaa caacagatgg ctgcgcacca tctctgtgat cctgttcctc    420
aacaagcaag atctgctcgc tgagaaagtc cttgctggga atcgaagat tgaggactac     480 tttccagaat tgctcgcta cactactcct gaggatgcta ctcccgagcc cggagaggac     540
ccacgcgtga cccgggccaa gtacttcatt cgagatgagt ttctgaggat cagcactgcc    600
agtggagatg ggcgtcacta ctgctaccct catttcacct gcgctgtgga cactgagaac    660
gcccgccgta tcttcaacga ctgccgtgac atcattcagc gcatgcacct tcgtcagtac    720
gagctgctct aa                                                        732
```

```
<210> SEQ ID NO 87
<211> LENGTH: 792
<212> TYPE: DNA
<213> ORGANISM: Artificial Sequence
<220> FEATURE:
<223> OTHER INFORMATION: MINI GS418

<400> SEQUENCE: 87
atgggtcacc accatcatca ccatgaaaat ctttatttcc agggtaacag taagaccgag    60
gaccagcgca acgaggagaa ggcgcagcgt gaggccaaca aaaagatcga agcagctg     120 cagaaggaca agcaggtcta ccgggccacg caccgcctgc tgctgctggg tgctgataat    180
tctggtaaaa gcaccattgt gaagcagatg aggatctacc atggtgggag tggcgggagc    240
ggaggtactt ctggaatctt tgagaccaag ttccaggtgg acaaagtcaa cttccacatg    300
tttgacgtgg gtggccagcg cgatgaacgc cgcaagtgga tccagtgctt caacgatgtg    360
actgccatca tcttcgtggt ggacagcagc gattacaacc gcctgcagga ggctctgaac    420
ctcttcaaga gcatctggaa caacagatgg ctgcgcacca tctctgtgat cctgttcctc    480
aacaagcaag atctgctcgc tgagaaagtc cttgctggga atcgaagat tgaggactac     540 tttccagaat tgctcgcta cactactcct gaggatgcta ctcccgagcc cggagaggac     600
ccacgcgtga cccgggccaa gtacttcatt cgagatgagt ttctgaggat cagcactgcc    660
agtggagatg ggcgtcacta ctgctaccct catttcacct gcgctgtgga cactgagaac    720
gcccgccgta tcttcaacga ctgccgtgac atcattcagc gcatgcacct tcgtcagtac    780
gagctgctct aa                                                        792
```

```
<210> SEQ ID NO 88
<211> LENGTH: 693
<212> TYPE: DNA
<213> ORGANISM: Artificial Sequence
<220> FEATURE:
<223> OTHER INFORMATION: MINI GS431

<400> SEQUENCE: 88
atgggtcacc accatcatca ccatgaaaat ctttatttcc agggtgccac gcaccgcctg    60
ctgctgctgg gtgctgataa ttctggtaaa agcaccattg tgaagcagat gaggatcctg   120
catggtggga gtggcgggag cggaggtact tctggaatct ttgagaccaa gttccaggtg   180
gacaaagtca acttccacat gtttgacgtg ggtggccagc gcgatgaacg ccgcaagtgg   240
```

```
atccagtgct tcaacgatgt gactgccatc atcttcgtgg tggacagcag cgattacaac    300
cgcctgcagg aggctctgaa cgacttcaag agcatctgga caacagatg gctgcgcacc     360 atctctgtga tcctgttcct caacaagcaa gatctgctcg ctgagaaagt ccttgctggg    420
aaatcgaaga ttgaggacta cttttccagaa tttgctcgct acactactcc tgaggatgct   480
actcccgagc ccggagagga cccacgcgtg acccgggcca agtacttcat tcgagatgag    540
tttctgagga tcagcactgc cagtggagat gggcgtcact actgctaccc tcatttcacc    600
tgcgctgtgg acactgagaa cgcccgccgt atcttcaacg actgccgtga catcattcag    660
cgcatgcacc ttcgtcagta cgagctgctc taa                                 693
```

<210> SEQ ID NO 89
<211> LENGTH: 711
<212> TYPE: DNA
<213> ORGANISM: Artificial Sequence
<220> FEATURE:
<223> OTHER INFORMATION: MINI GS432

<400> SEQUENCE: 89

```
atgggtcacc accatcatca ccatgaaaat ctttatttcc agggtatcga agcagctg      60 cagaaggaca agcaggtcta ccgggccacg caccgcctgc tgctgctggg tgctgataat    120
tctggtaaaa gcaccattgt gaagcagatg aggatcctgc atggtggggg tggcgggggc    180
gagaccaagt tccaggtgga caaagtcaac ttccacatgt ttgacgtggg tggccagcgc    240
gatgaacgcc gcaagtggat ccagtgcttc aacgatgtga ctgccatcat cttcgtggtg    300
gacagcagcg attacaaccg cctgcaggag gctctgaacg acttcaagag catctggaac    360
aacagatggc tgcgcaccat ctctgtgatc ctgttcctca acaagcaaga tctgctcgct    420
gagaaagtcc ttgctgggaa atcgaagatt gaggactact ttccagaatt gctcgctac    480 actactcctg aggatgctac tcccgagccc ggagaggacc cacgcgtgac ccgggccaag    540
tacttcattc gagatgagtt tctgaggatc agcactgcca gtggagatgg gcgtcactac    600
tgctaccctc atttcacctg cgctgtggac actgagaacg cccgccgtat cttcaacgac    660
tgccgtgaca tcattcagcg catgcacctt cgtcagtacg agctgctcta a             711
```

<210> SEQ ID NO 90
<211> LENGTH: 672
<212> TYPE: DNA
<213> ORGANISM: Artificial Sequence
<220> FEATURE:
<223> OTHER INFORMATION: MINI GS433

<400> SEQUENCE: 90

```
atgggtcacc accatcatca ccatgaaaat ctttatttcc agggtgccac gcaccgcctg    60
ctgctgctgg gtgctgataa ttctggtaaa agcaccattg tgaagcagat gaggatcctg    120
catggtgggg gtggcggggg cgagaccaag ttccaggtgg acaaagtcaa cttccacatg    180
tttgacgtgg gtggccagcg cgatgaacgc cgcaagtgga tccagtgctt caacgatgtg    240
actgccatca tcttcgtggt ggacagcagc gattacaacc gcctgcagga ggctctgaac    300
gacttcaaga gcatctggaa caacagatgg ctgcgcacca tctctgtgat cctgttcctc    360
aacaagcaag atctgctcgc tgagaaagtc cttgctggga atcgaagat tgaggactac    420 tttccagaat tgctcgcta cactactcct gaggatgcta ctcccgagcc cggagaggac    480
ccacgcgtga cccgggccaa gtacttcatt cgagatgagt ttctgaggat cagcactgcc    540
agtggagatg ggcgtcacta ctgctaccct catttcacct gcgctgtgga cactgagaac    600
```
gcccgccgta tcttcaacga ctgccgtgac atcattcagc gcatgcacct tcgtcagtac     660
gagctgctct aa     672

<210> SEQ ID NO 91
<211> LENGTH: 229
<212> TYPE: PRT
<213> ORGANISM: Artificial Sequence
<220> FEATURE:
<223> OTHER INFORMATION: Mini Gs v2

<400> SEQUENCE: 91

Met Ile Glu Lys Gln Leu Gln Lys Asp Lys Gln Val Tyr Arg Ala Thr
1               5                   10                  15

His Arg Leu Leu Leu Leu Gly Ala Asp Asn Ser Gly Lys Ser Thr Ile
                20                  25                  30

Val Lys Gln Met Arg Ile Leu His Gly Gly Ser Gly Gly Ser Gly Gly
            35                  40                  45

Thr Ser Gly Ile Phe Glu Thr Lys Phe Gln Val Asp Lys Val Asn Phe
        50                  55                  60

His Met Phe Asp Val Gly Gly Gln Arg Asp Glu Arg Arg Lys Trp Ile
65                  70                  75                  80

Gln Cys Phe Asn Asp Val Thr Ala Ile Ile Phe Val Val Asp Ser Ser
                85                  90                  95

Asp Tyr Asn Arg Leu Gln Glu Ala Leu Asn Asp Phe Lys Ser Ile Trp
                100                 105                 110

Asn Asn Arg Trp Leu Arg Thr Ile Ser Val Ile Leu Phe Leu Asn Lys
            115                 120                 125

Gln Asp Leu Leu Ala Glu Lys Val Leu Ala Gly Lys Ser Lys Ile Glu
        130                 135                 140

Asp Tyr Phe Pro Glu Phe Ala Arg Tyr Thr Thr Pro Glu Asp Ala Thr
145                 150                 155                 160

Pro Glu Pro Gly Glu Asp Pro Arg Val Thr Arg Ala Lys Tyr Phe Ile
                165                 170                 175

Arg Asp Glu Phe Leu Arg Ile Ser Thr Ala Ser Gly Asp Gly Arg His
            180                 185                 190

Tyr Cys Tyr Pro His Phe Thr Cys Ala Val Asp Thr Glu Asn Ala Arg
        195                 200                 205

Arg Ile Phe Asn Asp Cys Arg Asp Ile Ile Gln Arg Met His Leu Arg
    210                 215                 220

Gln Tyr Glu Leu Leu
225

<210> SEQ ID NO 92
<211> LENGTH: 394
<212> TYPE: PRT
<213> ORGANISM: Homo sapiens
<220> FEATURE:
<223> OTHER INFORMATION: Human G alpha s

<400> SEQUENCE: 92

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
 50                  55                  60

Val Asn Gly Phe Asn Gly Glu Gly Glu Asp Pro Gln Ala Ala
 65                  70                  75                  80

Arg Ser Asn Ser Asp Gly Glu Lys Ala Thr Lys Val Gln Asp Ile Lys
                 85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asp Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Ile Ile Gln
    370                 375                 380

Arg Met His Leu Arg Gln Tyr Glu Leu Leu
385                 390

<210> SEQ ID NO 93
<211> LENGTH: 8
<212> TYPE: PRT
<213> ORGANISM: Artificial Sequence
<220> FEATURE:
<223> OTHER INFORMATION: Linker

<400> SEQUENCE: 93

Gly Gly Ser Gly Gly Ser Gly Gly
1               5

```
<210> SEQ ID NO 94
<211> LENGTH: 8
<212> TYPE: PRT
<213> ORGANISM: Artificial Sequence
<220> FEATURE:
<223> OTHER INFORMATION: Linker

<400> SEQUENCE: 94

Gly Gly Gly Gly Gly Gly Gly Gly
1               5

<210> SEQ ID NO 95
<211> LENGTH: 263
<212> TYPE: PRT
<213> ORGANISM: Homo sapiens
<220> FEATURE:
<223> OTHER INFORMATION: ?s

<400> SEQUENCE: 95

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Gly Gly Ser Gly Gly Ser Gly Gly Thr Ser Gly Ile Phe Glu Thr Lys
65                  70                  75                  80

Phe Gln Val Asp Lys Val Asn Phe His Met Phe Asp Val Gly Gly Gln
                85                  90                  95

Arg Asp Glu Arg Arg Lys Trp Ile Gln Cys Phe Asn Asp Val Thr Ala
            100                 105                 110

Ile Ile Phe Val Val Ala Ser Ser Tyr Asn Met Val Ile Arg Glu
        115                 120                 125

Asp Asn Gln Thr Asn Arg Leu Gln Glu Ala Leu Asn Leu Phe Lys Ser
    130                 135                 140

Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys
                165                 170                 175

Ile Glu Asp Tyr Phe Pro Glu Phe Ala Arg Tyr Thr Thr Pro Glu Asp
            180                 185                 190

Ala Thr Pro Glu Pro Gly Glu Asp Pro Arg Val Thr Arg Ala Lys Tyr
        195                 200                 205

Phe Ile Arg Asp Glu Phe Leu Arg Ile Ser Thr Ala Ser Gly Asp Gly
    210                 215                 220

Arg His Tyr Cys Tyr Pro His Phe Thr Cys Ala Val Asp Thr Glu Asn
225                 230                 235                 240

Ile Arg Arg Val Phe Asn Asp Cys Arg Asp Ile Ile Gln Arg Met His
                245                 250                 255

Leu Arg Gln Tyr Glu Leu Leu
            260

<210> SEQ ID NO 96
<211> LENGTH: 265
<212> TYPE: PRT
<213> ORGANISM: Homo sapiens
```

<220> FEATURE:
<223> OTHER INFORMATION: ?olf

<400> SEQUENCE: 96

Met Gly Cys Leu Gly Gly Asn Ser Lys Thr Thr Glu Asp Gln Gly Val
1               5                   10                  15

Asp Glu Lys Glu Arg Arg Glu Ala Asn Lys Lys Ile Glu Lys Gln Leu
            20                  25                  30

Gln Lys Glu Arg Leu Ala Tyr Lys Ala Thr His Arg Leu Leu Leu Leu
        35                  40                  45

Gly Ala Gly Glu Ser Gly Lys Ser Thr Ile Val Lys Gln Met Arg Ile
    50                  55                  60

Leu His Gly Gly Ser Gly Gly Ser Gly Gly Thr Ser Gly Ile Phe Glu
65                  70                  75                  80

Thr Arg Phe Gln Val Asp Lys Val Asn Phe His Met Phe Asp Val Gly
                85                  90                  95

Gly Gln Arg Asp Glu Arg Arg Lys Trp Ile Gln Cys Phe Asn Asp Val
            100                 105                 110

Thr Ala Ile Ile Tyr Val Ala Ala Cys Ser Ser Tyr Asn Met Val Ile
        115                 120                 125

Arg Glu Asp Asn Asn Thr Asn Arg Leu Arg Glu Ser Leu Asp Leu Phe
    130                 135                 140

Glu Ser Ile Trp Asn Asn Arg Trp Leu Arg Thr Ile Ser Ile Ile Leu
145                 150                 155                 160

Phe Leu Asn Lys Gln Asp Met Leu Ala Glu Lys Val Leu Ala Gly Lys
                165                 170                 175

Ser Lys Ile Glu Asp Tyr Phe Pro Glu Tyr Ala Asn Tyr Thr Val Pro
            180                 185                 190

Glu Asp Ala Thr Pro Asp Ala Gly Glu Asp Pro Lys Val Thr Arg Ala
        195                 200                 205

Lys Phe Phe Ile Arg Asp Leu Phe Leu Arg Ile Ser Thr Ala Thr Gly
    210                 215                 220

Asp Gly Lys His Tyr Cys Tyr Pro His Phe Thr Cys Ala Val Asp Thr
225                 230                 235                 240

Glu Asn Ile Arg Arg Val Phe Asn Asp Cys Arg Asp Ile Ile Gln Arg
                245                 250                 255

Met His Leu Lys Gln Tyr Glu Leu Leu
            260                 265

<210> SEQ ID NO 97
<211> LENGTH: 239
<212> TYPE: PRT
<213> ORGANISM: Homo sapiens
<220> FEATURE:
<223> OTHER INFORMATION: ?i1

<400> SEQUENCE: 97

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Gly Gly Gly Gly Gly Gly Gly
    50                  55                  60

Gly Thr Thr Gly Ile Val Glu Thr His Phe Thr Phe Lys Asp Leu His

```
                65                  70                  75                  80
        Phe Lys Met Phe Asp Val Gly Gly Gln Arg Ser Glu Arg Lys Lys Trp
                            85                  90                  95
        Ile His Cys Phe Glu Gly Val Ala Ala Ile Ile Phe Cys Val Ala Leu
                            100                 105                 110
        Ser Asp Tyr Asp Leu Val Leu Ala Glu Asp Glu Met Asn Arg Met
                            115                 120                 125
        His Glu Ser Met Lys Leu Phe Asp Ser Ile Cys Asn Asn Lys Trp Phe
                            130                 135                 140
        Thr Asp Thr Ser Ile Ile Leu Phe Leu Asn Lys Lys Asp Leu Phe Glu
        145                 150                 155                 160
        Glu Lys Ile Lys Lys Ser Pro Leu Thr Ile Cys Tyr Pro Glu Tyr Ala
                            165                 170                 175
        Gly Ser Asn Thr Tyr Glu Glu Ala Ala Tyr Ile Gln Cys Gln Phe
                            180                 185                 190
        Glu Asp Leu Asn Lys Arg Lys Asp Thr Lys Glu Ile Tyr Thr His Phe
                            195                 200                 205
        Thr Cys Ala Thr Asp Thr Lys Asn Val Gln Phe Val Phe Asp Ala Val
                            210                 215                 220
        Thr Asp Val Ile Ile Lys Asn Asn Leu Lys Asp Cys Gly Leu Phe
        225                 230                 235
```

<210> SEQ ID NO 98
<211> LENGTH: 238
<212> TYPE: PRT
<213> ORGANISM: Homo sapiens
<220> FEATURE:
<223> OTHER INFORMATION: ?o1

<400> SEQUENCE: 98

```
        Met Gly Cys Thr Leu Ser Ala Glu Glu Arg Ala Ala Leu Glu Arg Ser
        1                   5                   10                  15
        Lys Ala Ile Glu Lys Asn Leu Lys Glu Asp Gly Ile Ser Ala Ala Lys
                            20                  25                  30
        Asp Val Lys Leu Leu Leu Leu Gly Ala Gly Glu Ser Gly Lys Ser Thr
                            35                  40                  45
        Ile Val Lys Gln Met Lys Ile Ile His Gly Ser Gly Gly Ser Gly
                            50                  55                  60
        Gly Thr Thr Gly Ile Val Glu Thr His Phe Thr Phe Lys Asn Leu His
        65                  70                  75                  80
        Phe Arg Leu Phe Asp Val Gly Gly Gln Arg Ser Glu Arg Lys Lys Trp
                            85                  90                  95
        Ile His Cys Phe Glu Asp Val Thr Ala Ile Ile Phe Cys Val Ala Leu
                            100                 105                 110
        Ser Gly Tyr Asp Gln Val Leu His Glu Asp Glu Thr Thr Asn Arg Met
                            115                 120                 125
        His Glu Ser Leu Met Leu Phe Asp Ser Ile Cys Asn Asn Lys Phe Phe
                            130                 135                 140
        Ile Asp Thr Ser Ile Ile Leu Phe Leu Asn Lys Lys Asp Leu Phe Gly
        145                 150                 155                 160
        Glu Lys Ile Lys Lys Ser Pro Leu Thr Ile Cys Phe Pro Glu Tyr Thr
                            165                 170                 175
        Gly Pro Asn Thr Tyr Glu Asp Ala Ala Ala Tyr Ile Gln Ala Gln Phe
                            180                 185                 190
        Glu Ser Lys Asn Arg Ser Pro Asn Lys Glu Ile Tyr Cys His Met Thr
```

195                 200                 205
Cys Ala Thr Asp Thr Asn Asn Ile Gln Val Val Phe Asp Ala Val Thr
            210                 215                 220

Asp Ile Ile Ile Ala Asn Asn Leu Arg Gly Cys Gly Leu Tyr
225                 230                 235

<210> SEQ ID NO 99
<211> LENGTH: 235
<212> TYPE: PRT
<213> ORGANISM: Homo sapiens
<220> FEATURE:
<223> OTHER INFORMATION: ?t1

<400> SEQUENCE: 99

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
            35                  40                  45

Met Lys Ile Ile His Gly Gly Ser Gly Gly Ser Gly Gly Thr Thr Gly
50                  55                  60

Ile Ile Glu Thr Gln Phe Ser Phe Lys Asp Leu Asn Phe Arg Met Phe
65                  70                  75                  80

Asp Val Gly Gly Gln Arg Ser Glu Arg Lys Lys Trp Ile His Cys Phe
                85                  90                  95

Glu Gly Val Thr Cys Ile Ile Phe Ile Ala Ala Leu Ser Ala Tyr Asp
            100                 105                 110

Met Val Leu Val Glu Asp Asp Glu Val Asn Arg Met His Glu Ser Leu
            115                 120                 125

His Leu Phe Asn Ser Ile Cys Asn His Arg Tyr Phe Ala Thr Thr Ser
130                 135                 140

Ile Val Leu Phe Leu Asn Lys Lys Asp Val Phe Phe Glu Lys Ile Lys
145                 150                 155                 160

Lys Ala His Leu Ser Ile Cys Phe Pro Asp Tyr Asp Gly Pro Asn Thr
                165                 170                 175

Tyr Glu Asp Ala Gly Asn Tyr Ile Lys Val Gln Phe Leu Glu Leu Asn
            180                 185                 190

Met Arg Arg Asp Val Lys Glu Ile Tyr Ser His Met Thr Cys Ala Thr
            195                 200                 205

Asp Thr Gln Asn Val Lys Phe Val Phe Asp Ala Val Thr Asp Ile Ile
            210                 215                 220

Ile Lys Glu Asn Leu Lys Asp Cys Gly Leu Phe
225                 230                 235

<210> SEQ ID NO 100
<211> LENGTH: 239
<212> TYPE: PRT
<213> ORGANISM: Homo sapiens
<220> FEATURE:
<223> OTHER INFORMATION: ?z

<400> SEQUENCE: 100

Met Gly Cys Arg Gln Ser Ser Glu Glu Lys Glu Ala Ala Arg Arg Ser
1               5                   10                  15

Arg Arg Ile Asp Arg His Leu Arg Ser Glu Ser Gln Arg Gln Arg Arg
            20                  25                  30

Glu Ile Lys Leu Leu Leu Gly Thr Ser Asn Ser Gly Lys Ser Thr
     35                  40                  45

Ile Val Lys Gln Met Lys Ile Ile His Gly Gly Gly Gly Gly Gly
 50                  55                  60

Gly Thr Thr Gly Ile Val Glu Asn Lys Phe Thr Phe Lys Glu Leu Thr
 65                  70                  75                  80

Phe Lys Met Val Asp Val Gly Gly Gln Arg Ser Glu Arg Lys Lys Trp
                 85                  90                  95

Ile His Cys Phe Glu Gly Val Thr Ala Ile Ile Phe Cys Val Glu Leu
             100                 105                 110

Ser Gly Tyr Asp Leu Lys Leu Tyr Glu Asp Asn Gln Thr Ser Arg Met
         115                 120                 125

Ala Glu Ser Leu Arg Leu Phe Asp Ser Ile Cys Asn Asn Asn Trp Phe
130                 135                 140

Ile Asn Thr Ser Leu Ile Leu Phe Leu Asn Lys Lys Asp Leu Leu Ala
145                 150                 155                 160

Glu Lys Ile Arg Arg Ile Pro Leu Thr Ile Cys Phe Pro Glu Tyr Lys
                165                 170                 175

Gly Gln Asn Thr Tyr Glu Glu Ala Ala Val Tyr Ile Gln Arg Gln Phe
            180                 185                 190

Glu Asp Leu Asn Arg Asn Lys Glu Thr Lys Glu Ile Tyr Ser His Phe
        195                 200                 205

Thr Cys Ala Thr Asp Thr Ser Asn Ile Gln Phe Val Phe Asp Ala Val
210                 215                 220

Thr Asp Val Ile Ile Gln Asn Asn Leu Lys Tyr Ile Gly Leu Cys
225                 230                 235

<210> SEQ ID NO 101
<211> LENGTH: 263
<212> TYPE: PRT
<213> ORGANISM: Homo sapiens
<220> FEATURE:
<223> OTHER INFORMATION: ?12

<400> SEQUENCE: 101

Met Ser Gly Val Val Arg Thr Leu Ser Arg Cys Leu Leu Pro Ala Glu
 1               5                  10                  15

Ala Gly Gly Ala Arg Glu Arg Arg Ala Gly Ser Gly Ala Arg Asp Ala
                20                  25                  30

Glu Arg Glu Ala Arg Arg Ser Arg Asp Ile Asp Ala Leu Leu Ala
             35                  40                  45

Arg Glu Arg Arg Ala Val Arg Arg Leu Val Lys Ile Leu Leu Leu Gly
 50                  55                  60

Ala Gly Glu Ser Gly Lys Ser Thr Phe Leu Lys Gln Met Arg Ile Ile
 65                  70                  75                  80

His Gly Gly Ser Gly Gly Ser Gly Gly Thr Lys Gly Ile Val Glu His
                 85                  90                  95

Asp Phe Val Ile Lys Lys Ile Pro Phe Lys Met Val Asp Val Gly Gly
             100                 105                 110

Gln Arg Ser Gln Arg Gln Lys Trp Phe Gln Cys Phe Asp Gly Ile Thr
         115                 120                 125

Ser Ile Leu Phe Met Val Ser Ser Ser Glu Tyr Asp Gln Val Leu Met
130                 135                 140

Glu Asp Arg Arg Thr Asn Arg Leu Val Glu Ser Met Asn Ile Phe Glu
145                 150                 155                 160

Thr Ile Val Asn Asn Lys Leu Phe Phe Asn Val Ser Ile Ile Leu Phe
              165                 170                 175

Leu Asn Lys Met Asp Leu Leu Val Glu Lys Val Lys Thr Val Ser Ile
          180                 185                 190

Lys Lys His Phe Pro Asp Phe Arg Gly Asp Pro His Arg Leu Glu Asp
          195                 200                 205

Val Gln Arg Tyr Leu Val Gln Cys Phe Asp Arg Lys Arg Asn Arg
    210                 215                 220

Ser Lys Pro Leu Phe His His Phe Thr Thr Ala Ile Asp Thr Glu Asn
225                 230                 235                 240

Val Arg Phe Val Phe His Ala Val Lys Asp Thr Ile Leu Gln Glu Asn
              245                 250                 255

Leu Lys Asp Ile Met Leu Gln
          260

<210> SEQ ID NO 102
<211> LENGTH: 245
<212> TYPE: PRT
<213> ORGANISM: Homo sapiens
<220> FEATURE:
<223> OTHER INFORMATION: ?q

<400> SEQUENCE: 102

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Gly Gly Gly Gly Gly Gly Thr Thr Gly Ile Ile Glu Tyr Pro Phe
65                  70                  75                  80

Asp Leu Gln Ser Val Ile Phe Arg Met Val Asp Val Gly Gly Gln Arg
                85                  90                  95

Ser Glu Arg Arg Lys Trp Ile His Cys Phe Glu Asn Val Thr Ser Ile
            100                 105                 110

Met Phe Leu Val Ala Leu Ser Glu Tyr Asp Gln Val Leu Val Glu Ser
        115                 120                 125

Asp Asn Glu Asn Arg Met Glu Glu Ser Lys Ala Leu Phe Arg Thr Ile
    130                 135                 140

Ile Thr Tyr Pro Trp Phe Gln Asn Ser Ser Val Ile Leu Phe Leu Asn
145                 150                 155                 160

Lys Lys Asp Leu Leu Glu Glu Lys Ile Met Tyr Ser His Leu Val Asp
                165                 170                 175

Tyr Phe Pro Glu Tyr Asp Gly Pro Gln Arg Asp Ala Gln Ala Ala Arg
            180                 185                 190

Glu Phe Ile Leu Lys Met Phe Val Asp Leu Asn Pro Asp Ser Asp Lys
        195                 200                 205

Ile Ile Tyr Ser His Phe Thr Cys Ala Thr Asp Thr Glu Asn Ile Arg
    210                 215                 220

Phe Val Phe Ala Ala Val Lys Asp Thr Ile Leu Gln Leu Asn Leu Lys
225                 230                 235                 240

Glu Tyr Asn Leu Val
            245

<210> SEQ ID NO 103
<211> LENGTH: 260
<212> TYPE: PRT
<213> ORGANISM: Homo sapiens
<220> FEATURE:
<223> OTHER INFORMATION: ?16

<400> SEQUENCE: 103

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
50                  55                  60

Ile His Gly Gly Gly Gly Gly Gly Thr Thr Gly Ile Asn Glu
65              70                  75                  80

Tyr Cys Phe Ser Val Gln Lys Thr Asn Leu Arg Ile Val Asp Val Gly
                85                  90                  95

Gly Gln Lys Ser Glu Arg Lys Lys Trp Ile His Cys Phe Glu Asn Val
            100                 105                 110

Ile Ala Leu Ile Tyr Leu Ala Ser Leu Ser Glu Tyr Asp Gln Cys Leu
        115                 120                 125

Glu Glu Asn Asn Gln Glu Asn Arg Met Lys Glu Ser Leu Ala Leu Phe
    130                 135                 140

Gly Thr Ile Leu Glu Leu Pro Trp Phe Lys Ser Thr Val Ile Leu
145                 150                 155                 160

Phe Leu Asn Lys Thr Asp Ile Leu Glu Glu Lys Ile Pro Thr Ser His
                165                 170                 175

Leu Ala Thr Tyr Phe Pro Ser Phe Gln Gly Pro Lys Gln Asp Ala Glu
            180                 185                 190

Ala Ala Lys Arg Phe Ile Leu Asp Met Tyr Thr Arg Met Tyr Thr Gly
        195                 200                 205

Cys Val Asp Gly Pro Glu Gly Ser Lys Lys Gly Ala Arg Ser Arg Arg
    210                 215                 220

Leu Phe Ser His Tyr Thr Cys Ala Thr Asp Thr Gln Asn Ile Arg Lys
225                 230                 235                 240

Val Phe Lys Asp Val Arg Asp Ser Val Leu Ala Arg Tyr Leu Asp Glu
                245                 250                 255

Ile Asn Leu Leu
            260

<210> SEQ ID NO 104
<211> LENGTH: 243
<212> TYPE: PRT
<213> ORGANISM: Artificial Sequence
<220> FEATURE:
<223> OTHER INFORMATION: Mini-Gs393

<400> SEQUENCE: 104

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

```
Gln Met Arg Ile Leu His Gly Gly Ser Gly Gly Thr Ser
 50                  55                  60

Gly Ile Phe Glu Thr Lys Phe Gln Val Asp Lys Val Asn Phe His Met
 65                  70                  75                  80

Phe Asp Val Gly Gly Gln Arg Asp Glu Arg Arg Lys Trp Ile Gln Cys
                 85                  90                  95

Phe Asn Asp Val Thr Ala Ile Ile Phe Val Val Asp Ser Ser Asp Tyr
                100                 105                 110

Asn Arg Leu Gln Glu Ala Leu Asn Asp Phe Lys Ser Ile Trp Asn Asn
                115                 120                 125

Arg Trp Leu Arg Thr Ile Ser Val Ile Leu Phe Leu Asn Lys Gln Asp
                130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
                180                 185                 190

Glu Phe Leu Arg Ile Ser Thr Ala Ser Gly Asp Gly Arg His Tyr Cys
                195                 200                 205

Tyr Pro His Phe Thr Cys Ala Val Asp Thr Glu Asn Ala Arg Arg Ile
210                 215                 220

Phe Asn Asp Cys Arg Asp Ile Ile Gln Arg Met His Leu Arg Gln Tyr
225                 230                 235                 240

Glu Leu Leu

<210> SEQ ID NO 105
<211> LENGTH: 243
<212> TYPE: PRT
<213> ORGANISM: Artificial Sequence
<220> FEATURE:
<223> OTHER INFORMATION: Mini-Golf6

<400> SEQUENCE: 105

Met Gly His His His His His His Glu Asn Leu Tyr Phe Gln Gly Ile
 1               5                  10                  15

Glu Lys Gln Leu Gln Lys Glu Arg Leu Ala Tyr Lys Ala Thr His Arg
                 20                  25                  30

Leu Leu Leu Leu Gly Ala Asp Asn Ser Gly Lys Ser Thr Ile Val Lys
                 35                  40                  45

Gln Met Arg Ile Leu His Gly Gly Ser Gly Gly Ser Gly Gly Thr Ser
 50                  55                  60

Gly Ile Phe Glu Thr Arg Phe Gln Val Asp Lys Val Asn Phe His Met
 65                  70                  75                  80

Phe Asp Val Gly Gly Gln Arg Asp Glu Arg Arg Lys Trp Ile Gln Cys
                 85                  90                  95

Phe Asn Asp Val Thr Ala Ile Ile Tyr Val Ala Asp Cys Ser Asp Tyr
                100                 105                 110

Asn Arg Leu Arg Glu Ser Leu Asp Asp Phe Glu Ser Ile Trp Asn Asn
                115                 120                 125

Arg Trp Leu Arg Thr Ile Ser Ile Ile Leu Phe Leu Asn Lys Gln Asp
                130                 135                 140

Met Leu Ala Glu Lys Val Leu Ala Gly Lys Ser Lys Ile Glu Asp Tyr
145                 150                 155                 160
```

```
Phe Pro Glu Tyr Ala Asn Tyr Thr Val Pro Glu Asp Ala Thr Pro Asp
                165                 170                 175

Ala Gly Glu Asp Pro Lys Val Thr Arg Ala Lys Phe Phe Ile Arg Asp
            180                 185                 190

Leu Phe Leu Arg Ile Ser Thr Ala Thr Gly Asp Gly Lys His Tyr Cys
        195                 200                 205

Tyr Pro His Phe Thr Cys Ala Val Asp Thr Glu Asn Ala Arg Arg Ile
    210                 215                 220

Phe Asn Asp Cys Arg Asp Ile Ile Gln Arg Met His Leu Lys Gln Tyr
225                 230                 235                 240

Glu Leu Leu

<210> SEQ ID NO 106
<211> LENGTH: 243
<212> TYPE: PRT
<213> ORGANISM: Artificial Sequence
<220> FEATURE:
<223> OTHER INFORMATION: Mini-Gs/q57

<400> SEQUENCE: 106

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Ser Gly Ser Gly Gly Thr Ser
    50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
    210                 215                 220

Phe Asn Asp Cys Arg Asp Ile Ile Gln Arg Met His Leu Arg Glu Tyr
225                 230                 235                 240

Asn Leu Val

<210> SEQ ID NO 107
<211> LENGTH: 243
<212> TYPE: PRT
<213> ORGANISM: Artificial Sequence
```

<220> FEATURE:
<223> OTHER INFORMATION: Mini-Gs/q58

<400> SEQUENCE: 107

Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Ser Gly Gly Ser Gly Gly Thr Ser
50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
210                 215                 220

Phe Ala Ala Val Lys Asp Thr Ile Leu Gln Leu Asn Leu Lys Glu Tyr
225                 230                 235                 240

Asn Leu Val

<210> SEQ ID NO 108
<211> LENGTH: 243
<212> TYPE: PRT
<213> ORGANISM: Artificial Sequence
<220> FEATURE:
<223> OTHER INFORMATION: Mini-Gs/q70

<400> SEQUENCE: 108

Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Ser Gly Gly Ser Gly Gly Thr Ser
50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

```
Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
    210                 215                 220

Phe Asn Asp Cys Lys Asp Ile Ile Leu Gln Met Asn Leu Arg Glu Tyr
225                 230                 235                 240

Asn Leu Val

<210> SEQ ID NO 109
<211> LENGTH: 243
<212> TYPE: PRT
<213> ORGANISM: Artificial Sequence
<220> FEATURE:
<223> OTHER INFORMATION: Mini-Gs/q71

<400> SEQUENCE: 109

Met Gly His His His His His His Glu Asn Leu Tyr Phe Gln Gly Ile
1               5                   10                  15

Glu Lys Gln Leu Gln Lys Asp Lys Gln Val Tyr Arg Arg Thr Leu Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Ser Gly Gly Ser Gly Gly Thr Ser
    50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Lys
            180                 185                 190

Glu Phe Val Asp Ile Ser Thr Ala Ser Gly Asp Gly Arg His Ile Cys
        195                 200                 205
```

Tyr Pro His Phe Thr Cys Ala Val Asp Thr Glu Asn Ala Arg Arg Ile
210                 215                 220

Phe Asn Asp Cys Lys Asp Ile Ile Leu Gln Met Asn Leu Arg Glu Tyr
225                 230                 235                 240

Asn Leu Val

<210> SEQ ID NO 110
<211> LENGTH: 241
<212> TYPE: PRT
<213> ORGANISM: Artificial Sequence
<220> FEATURE:
<223> OTHER INFORMATION: Mini-Gi146

<400> SEQUENCE: 110

Met Gly His His His His His His Glu Asn Leu Tyr Phe Gln Gly Thr
1               5                   10                  15

Leu Ser Ala Glu Asp Lys Ala Ala Val Glu Arg Ser Lys Met Ile Asp
                20                  25                  30

Arg Asn Leu Arg Glu Asp Gly Glu Lys Ala Ala Arg Glu Val Lys Leu
            35                  40                  45

Leu Leu Leu Gly Ala Asp Asn Ser Gly Lys Ser Thr Ile Val Lys Gln
50                  55                  60

Met Lys Ile Ile His Gly Gly Gly Gly Gly Gly Thr Thr Gly
65                  70                  75                  80

Ile Val Glu Thr His Phe Thr Phe Lys Asp Leu His Phe Lys Met Phe
                85                  90                  95

Asp Val Gly Gly Gln Arg Ser Glu Arg Lys Lys Trp Ile His Cys Phe
            100                 105                 110

Glu Asp Val Ala Ala Ile Ile Phe Cys Val Asp Leu Ser Asp Tyr Asn
        115                 120                 125

Arg Met His Glu Ser Met Lys Leu Phe Asp Ser Ile Cys Asn Asn Lys
130                 135                 140

Trp Phe Thr Asp Thr Ser Ile Ile Leu Phe Leu Asn Lys Lys Asp Leu
145                 150                 155                 160

Phe Glu Glu Lys Ile Lys Lys Ser Pro Leu Thr Ile Cys Tyr Gln Glu
                165                 170                 175

Tyr Ala Gly Ser Asn Thr Tyr Glu Glu Ala Ala Ala Tyr Ile Gln Cys
            180                 185                 190

Gln Phe Glu Asp Leu Asn Lys Arg Lys Asp Thr Lys Glu Ile Tyr Thr
        195                 200                 205

His Phe Thr Cys Ala Thr Asp Thr Lys Asn Ala Gln Phe Ile Phe Asp
210                 215                 220

Ala Val Thr Asp Val Ile Ile Lys Asn Asn Leu Lys Asp Cys Gly Leu
225                 230                 235                 240

Phe

<210> SEQ ID NO 111
<211> LENGTH: 243
<212> TYPE: PRT
<213> ORGANISM: Artificial Sequence
<220> FEATURE:
<223> OTHER INFORMATION: Mini-Gs/i143

<400> SEQUENCE: 111

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg

```
                    20                  25                  30
Leu Leu Leu Leu Gly Ala Asp Asn Ser Gly Lys Ser Thr Ile Val Lys
            35                  40                  45

Gln Met Arg Ile Leu His Gly Gly Ser Gly Gly Ser Gly Gly Thr Ser
 50                  55                  60

Gly Ile Phe Glu Thr Lys Phe Gln Val Asp Lys Val Asn Phe His Met
 65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
    210                 215                 220

Phe Asn Asp Val Thr Asp Ile Ile Ile Lys Met Asn Leu Arg Asp Cys
225                 230                 235                 240

Gly Leu Phe

<210> SEQ ID NO 112
<211> LENGTH: 263
<212> TYPE: PRT
<213> ORGANISM: Artificial Sequence
<220> FEATURE:
<223> OTHER INFORMATION: Mini-Gs/i148

<400> SEQUENCE: 112

Met Gly His His His His His His Glu Asn Leu Tyr Phe Gln Gly Asn
 1               5                  10                  15

Ser Lys Thr Glu Asp Gln Arg Asn Glu Glu Lys Ala Gln Arg Glu Ala
            20                  25                  30

Asn Lys Lys Ile Glu Lys Gln Leu Gln Lys Asp Lys Gln Val Tyr Arg
        35                  40                  45

Ala Thr His Arg Leu Leu Leu Leu Gly Ala Asp Asn Ser Gly Lys Ser
    50                  55                  60

Thr Ile Val Lys Gln Met Arg Ile Leu His Gly Gly Ser Gly Gly Ser
 65                  70                  75                  80

Gly Gly Thr Ser Gly Ile Phe Glu Thr Lys Phe Gln Val Asp Lys Val
                85                  90                  95

Asn Phe His Met Phe Asp Val Gly Gly Gln Arg Asp Glu Arg Arg Lys
            100                 105                 110

Trp Ile Gln Cys Phe Asn Asp Val Thr Ala Ile Ile Phe Val Val Asp
        115                 120                 125

Ser Ser Asp Tyr Asn Arg Leu Gln Glu Ala Leu Asn Leu Phe Lys Ser
    130                 135                 140
```

```
Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys
                165                 170                 175

Ile Glu Asp Tyr Phe Pro Glu Phe Ala Arg Tyr Thr Thr Pro Glu Asp
            180                 185                 190

Ala Thr Pro Glu Pro Gly Glu Asp Pro Arg Val Thr Arg Ala Lys Tyr
        195                 200                 205

Phe Ile Arg Asp Glu Phe Leu Arg Ile Ser Thr Ala Ser Gly Asp Gly
    210                 215                 220

Arg His Tyr Cys Tyr Pro His Phe Thr Cys Ala Val Asp Thr Glu Asn
225                 230                 235                 240

Ala Arg Arg Ile Phe Asn Asp Val Thr Asp Ile Ile Ile Lys Met Asn
                245                 250                 255

Leu Arg Asp Cys Gly Leu Phe
            260

<210> SEQ ID NO 113
<211> LENGTH: 225
<212> TYPE: PRT
<213> ORGANISM: Artificial Sequence
<220> FEATURE:
<223> OTHER INFORMATION: Mini-Go112

<400> SEQUENCE: 113

Met Gly His His His His His His Glu Asn Leu Tyr Phe Gln Gly Ile
1               5                   10                  15

Glu Lys Asn Leu Lys Glu Asp Gly Ile Ser Ala Ala Lys Asp Val Lys
            20                  25                  30

Leu Leu Leu Leu Gly Ala Asp Asn Ser Gly Lys Ser Thr Ile Val Lys
        35                  40                  45

Gln Met Lys Ile Ile His Gly Ser Gly Gly Ser Gly Gly Thr Thr
    50                  55                  60

Gly Ile Val Glu Thr His Phe Thr Phe Lys Asn Leu His Phe Arg Leu
65                  70                  75                  80

Phe Asp Val Gly Gly Gln Arg Ser Glu Arg Lys Lys Trp Ile His Cys
                85                  90                  95

Phe Glu Asp Val Thr Ala Ile Ile Phe Cys Val Asp Leu Ser Asp Tyr
            100                 105                 110

Asn Arg Met His Glu Ser Leu Met Asp Phe Asp Ser Ile Cys Asn Asn
        115                 120                 125

Lys Phe Phe Ile Asp Thr Ser Ile Ile Leu Phe Leu Asn Lys Lys Asp
    130                 135                 140

Leu Phe Gly Glu Lys Ile Lys Lys Ser Pro Leu Thr Ile Cys Phe Pro
145                 150                 155                 160

Glu Tyr Thr Gly Pro Asn Thr Tyr Glu Asp Ala Ala Ala Tyr Ile Gln
                165                 170                 175

Ala Gln Phe Glu Ser Lys Asn Arg Ser Pro Asn Lys Glu Ile Tyr Cys
            180                 185                 190

His Met Thr Cys Ala Thr Asp Thr Asn Asn Ala Gln Val Ile Phe Asp
        195                 200                 205

Ala Val Thr Asp Ile Ile Ile Ala Asn Asn Leu Arg Gly Cys Gly Leu
    210                 215                 220

Tyr
225
```

<210> SEQ ID NO 114
<211> LENGTH: 226
<212> TYPE: PRT
<213> ORGANISM: Artificial Sequence
<220> FEATURE:
<223> OTHER INFORMATION: Mini-G128

<400> SEQUENCE: 114

```
Met Gly His His His His His His Glu Asn Leu Tyr Phe Gln Gly Ile
1               5                   10                  15

Asp Ala Leu Leu Ala Arg Glu Arg Arg Ala Val Arg Arg Leu Val Lys
            20                  25                  30

Ile Leu Leu Leu Gly Ala Asp Asn Ser Gly Lys Ser Thr Phe Leu Lys
        35                  40                  45

Gln Met Arg Ile Ile His Gly Ser Gly Gly Ser Gly Gly Thr Lys
    50                  55                  60

Gly Ile Val Glu His Asp Phe Val Ile Lys Ile Pro Phe Lys Met
65                  70                  75                  80

Val Asp Val Gly Gly Gln Arg Ser Gln Arg Gln Lys Trp Phe Gln Cys
                85                  90                  95

Phe Asp Gly Ile Thr Ser Ile Leu Phe Met Val Asp Ser Ser Asp Tyr
            100                 105                 110

Asn Arg Leu Val Glu Ser Met Asn Asp Phe Glu Thr Ile Val Asn Asn
        115                 120                 125

Lys Leu Phe Phe Asn Val Ser Ile Ile Leu Phe Leu Asn Lys Met Asp
    130                 135                 140

Leu Leu Val Glu Lys Val Lys Thr Val Ser Ile Lys Lys His Phe Pro
145                 150                 155                 160

Asp Phe Arg Gly Asp Pro His Arg Leu Glu Asp Val Gln Arg Tyr Leu
                165                 170                 175

Val Gln Cys Phe Asp Arg Lys Arg Arg Asn Arg Ser Lys Pro Leu Phe
            180                 185                 190

His His Phe Thr Thr Ala Ile Asp Thr Glu Asn Ala Arg Phe Ile Phe
        195                 200                 205

His Ala Val Lys Asp Thr Ile Leu Gln Glu Asn Leu Lys Asp Ile Met
    210                 215                 220

Leu Gln
225
```

<210> SEQ ID NO 115
<211> LENGTH: 691
<212> TYPE: DNA
<213> ORGANISM: Artificial Sequence
<220> FEATURE:
<223> OTHER INFORMATION: Mini-Gt1

<400> SEQUENCE: 115

```
ccatgggtca ccaccatcac catcatgaaa atctttattt ccagggtctg gaaagaagc     60 tgaaagagga cgctgagaag gatgctcgaa ccgtgaagct gctgcttctg ggtgccgata    120
attccgggaa gagcaccatc gtcaagcaga tgaagattat ccacgtgggg agtggcggga    180
gcggaggtac cactggcatc atcgagacgc agttctccct caaggatctc aacttccgga    240
tgttcgatgt gggcgggcag cgctcggagc gcaagaagtg gatccactgc ttcgagggcg    300
tgacctgcat catcttcatc gcggacctga gcgattacaa ccgcatgcac gagagcctgc    360
acgatttcaa cagcatctgc aaccaccgct acttcgccac gacgtccatc gtgctcttcc    420
```

```
ttaacaagaa ggacgtcttc ttcgagaaga tcaagaaggc gcacctcagc atctgtttcc    480
cggactacga tggacccaac acctacgagg acgccggcaa ctacatcaag gtgcagttcc    540
tcgagctcaa catgcggcgc gacgtgaagg agatctattc ccacatgacg tgcgccaccg    600
acacgcagaa cgccaaattt atcttcgacg ctgtcaccga catcatcatc aaggagaacc    660
tcaaagactg tggcctcttc taatagctcg a                                   691
```

<210> SEQ ID NO 116
<211> LENGTH: 226
<212> TYPE: PRT
<213> ORGANISM: Artificial Sequence
<220> FEATURE:
<223> OTHER INFORMATION: Mini-Gt1

<400> SEQUENCE: 116

```
Met Gly His His His His His His Glu Asn Leu Tyr Phe Gln Gly Leu
1               5                   10                  15

Glu Lys Lys Leu Lys Glu Asp Ala Glu Lys Asp Ala Arg Thr Val Lys
            20                  25                  30

Leu Leu Leu Leu Gly Ala Asp Asn Ser Gly Lys Ser Thr Ile Val Lys
        35                  40                  45

Gln Met Lys Ile Ile His Gly Ser Gly Gly Ser Gly Gly Thr Thr
    50                  55                  60

Gly Ile Ile Glu Thr Gln Phe Ser Phe Lys Asp Leu Asn Phe Arg Met
65                  70                  75                  80

Phe Asp Val Gly Gly Gln Arg Ser Glu Arg Lys Lys Trp Ile His Cys
                85                  90                  95

Phe Glu Gly Val Thr Cys Ile Ile Phe Ile Ala Asp Leu Ser Asp Tyr
            100                 105                 110

Asn Arg Met His Glu Ser Leu His Asp Phe Asn Ser Ile Cys Asn His
        115                 120                 125

Arg Tyr Phe Ala Thr Thr Ser Ile Val Leu Phe Leu Asn Lys Lys Asp
    130                 135                 140

Val Phe Phe Glu Lys Ile Lys Lys Ala His Leu Ser Ile Cys Phe Pro
145                 150                 155                 160

Asp Tyr Asp Gly Pro Asn Thr Tyr Glu Asp Ala Gly Asn Tyr Ile Lys
                165                 170                 175

Val Gln Phe Leu Glu Leu Asn Met Arg Arg Asp Val Lys Glu Ile Tyr
            180                 185                 190

Ser His Met Thr Cys Ala Thr Asp Thr Gln Asn Ala Lys Phe Ile Phe
        195                 200                 205

Asp Ala Val Thr Asp Ile Ile Ile Lys Glu Asn Leu Lys Asp Cys Gly
    210                 215                 220

Leu Phe
225
```

<210> SEQ ID NO 117
<211> LENGTH: 671
<212> TYPE: DNA
<213> ORGANISM: Artificial Sequence
<220> FEATURE:
<223> OTHER INFORMATION: Mini-Gz

<400> SEQUENCE: 117

```
ccatgggtca ccaccatcac catcatattg accgccacct gcgctcagag agccagcggc    60
aacgccgcga aatcaagctg ctcctgctgg gcaccgacaa ctcaggcaag agcaccatcg   120
```

-continued

```
tcaaacagat gaagatcatc cacggagggg gcggaggcgg gggagggacc acgggcattg    180
tggagaacaa gttcaccttc aaggagctca ccttcaagat ggtggacgtg gggggggcaga   240 ggtcagagcg caaaaagtgg atccactgct tcgagggcgt cacagccatc atcttctgtg    300
tggacctcag cgactacagt cggatggcag agagcttgcg cgactttgac tccatctgca    360
acaacaactg gttcatcaac acctcactca tcctcttcct gaacaagaag acctgctgg     420 cagagaagat ccgccgcatc ccgctcacca tctgctttcc cgagtacaag ggccagaaca    480
cgtacgagga ggccgctgtc tacatccagc ggcagtttga agacctgaac cgcaacaagg    540
agaccaagga gatctactcc cacttcacct gcgccaccga caccagtaac gcgcagttta    600
tcttcgacgc ggtgacagac gtcatcatac agaacaatct caagtacatt ggcctttgct    660
gataactcga g                                                         671
```

<210> SEQ ID NO 118
<211> LENGTH: 219
<212> TYPE: PRT
<213> ORGANISM: Artificial Sequence
<220> FEATURE:
<223> OTHER INFORMATION: Mini-Gz

<400> SEQUENCE: 118

```
Met Gly His His His His His His Ile Asp Arg His Leu Arg Ser Glu
1               5                   10                  15

Ser Gln Arg Gln Arg Arg Glu Ile Lys Leu Leu Leu Leu Gly Thr Asp
            20                  25                  30

Asn Ser Gly Lys Ser Thr Ile Val Lys Gln Met Lys Ile Ile His Gly
        35                  40                  45

Gly Gly Gly Gly Gly Gly Thr Thr Gly Ile Val Glu Asn Lys Phe
    50                  55                  60

Thr Phe Lys Glu Leu Thr Phe Lys Met Val Asp Val Gly Gly Gln Arg
65                  70                  75                  80

Ser Glu Arg Lys Lys Trp Ile His Cys Phe Glu Gly Val Thr Ala Ile
                85                  90                  95

Ile Phe Cys Val Asp Leu Ser Asp Tyr Ser Arg Met Ala Glu Ser Leu
            100                 105                 110

Arg Asp Phe Asp Ser Ile Cys Asn Asn Asn Trp Phe Ile Asn Thr Ser
        115                 120                 125

Leu Ile Leu Phe Leu Asn Lys Lys Asp Leu Leu Ala Glu Lys Ile Arg
    130                 135                 140

Arg Ile Pro Leu Thr Ile Cys Phe Pro Glu Tyr Lys Gly Gln Asn Thr
145                 150                 155                 160

Tyr Glu Glu Ala Ala Val Tyr Ile Gln Arg Gln Phe Glu Asp Leu Asn
                165                 170                 175

Arg Asn Lys Glu Thr Lys Glu Ile Tyr Ser His Phe Thr Cys Ala Thr
            180                 185                 190

Asp Thr Ser Asn Ala Gln Phe Ile Phe Asp Ala Val Thr Asp Val Ile
        195                 200                 205

Ile Gln Asn Asn Leu Lys Tyr Ile Gly Leu Cys
    210                 215
```

<210> SEQ ID NO 119
<211> LENGTH: 671
<212> TYPE: DNA
<213> ORGANISM: Artificial Sequence
<220> FEATURE:

<223> OTHER INFORMATION: Mini-Gq

<400> SEQUENCE: 119

```
ccatgggtca ccaccatcac catcatatcg agcggcagct ccgcagggac aagcgggacg    60
cccgccggga gctcaagctg ctgctgctcg ggacagacaa cagtggcaag agtacgttta   120
tcaagcagat gagaatcatc cacggagggg gcggaggcgg gggagggacc acagggatca   180
tcgaataccc ctttgactta caaagtgtca ttttcagaat ggtcgatgta ggggccaaa    240
ggtcagagag aagaaaatgg atacactgct ttgaaaatgt cacctctatc atgtttctag   300
tagaccttag tgactataac cgaatggagg aaagcaaggc tgactttaga acaattatca   360
catacccctg gttccagaac tcctcggtta ttctgttctt aaacaagaaa gatcttctag   420
aggagaaaat catgtattcc catctagtcg actacttccc agaatatgat ggaccccaga   480
gagatgccca ggcagcccga gaattcattc tgaagatgtt cgtggacctg aacccagaca   540
gtgacaaaat tatctactcc cacttcacgt gcgccacaga caccgagaat gcccgcttta   600
tctttgctgc cgtcaaggac accatcctcc agttgaacct gaaggagtac aatctggtct   660
aatagctcga g                                                         671
```

<210> SEQ ID NO 120
<211> LENGTH: 218
<212> TYPE: PRT
<213> ORGANISM: Artificial Sequence
<220> FEATURE:
<223> OTHER INFORMATION: Mini-Gq

<400> SEQUENCE: 120

```
Met Gly His His His His His His Ile Glu Arg Gln Leu Arg Arg Asp
  1               5                  10                  15

Lys Arg Asp Ala Arg Arg Glu Leu Lys Leu Leu Leu Leu Gly Thr Asp
             20                  25                  30

Asn Ser Gly Lys Ser Thr Phe Ile Lys Gln Met Arg Ile Ile His Gly
         35                  40                  45

Gly Gly Gly Gly Gly Gly Gly Thr Thr Gly Ile Ile Glu Tyr Pro Phe
     50                  55                  60

Asp Leu Gln Ser Val Ile Phe Arg Met Val Asp Val Gly Gly Gln Arg
 65                  70                  75                  80

Ser Glu Arg Arg Lys Trp Ile His Cys Phe Glu Asn Val Thr Ser Ile
                 85                  90                  95

Met Phe Leu Val Asp Leu Ser Asp Tyr Asn Arg Met Glu Glu Ser Lys
            100                 105                 110

Ala Asp Phe Arg Thr Ile Ile Thr Tyr Pro Trp Phe Gln Asn Ser Ser
        115                 120                 125

Val Ile Leu Phe Leu Asn Lys Lys Asp Leu Leu Glu Glu Lys Ile Met
    130                 135                 140

Tyr Ser His Leu Val Asp Tyr Phe Pro Glu Tyr Asp Gly Pro Gln Arg
145                 150                 155                 160

Asp Ala Gln Ala Ala Arg Glu Phe Ile Leu Lys Met Phe Val Asp Leu
                165                 170                 175

Asn Pro Asp Ser Asp Lys Ile Ile Tyr Ser His Phe Thr Cys Ala Thr
            180                 185                 190

Asp Thr Glu Asn Ala Arg Phe Ile Phe Ala Ala Val Lys Asp Thr Ile
        195                 200                 205

Leu Gln Leu Asn Leu Lys Glu Tyr Asn Leu
    210                 215
```

<210> SEQ ID NO 121
<211> LENGTH: 707
<212> TYPE: DNA
<213> ORGANISM: Artificial Sequence
<220> FEATURE:
<223> OTHER INFORMATION: Mini-G16

<400> SEQUENCE: 121

```
ccatgggtca ccaccatcac catcatatca acaggatcct cttggagcag aagaagcagg      60
accgcgggga gctgaagctg ctgcttttgg gcccagacaa cagcgggaag agcaccttca     120
tcaagcagat gcggatcatc cacggagggg gcggaggcgg gggagggacc actggcatca     180
acgagtactg cttctccgtg cagaaaacca acctgcggat cgtggacgtc ggggccaga     240
agtcagagcg taagaaatgg atccattgtt tcgagaacgt gatcgccctc atctacctgg     300
ccgacctgag tgactacaac cgcatgaagg agagcctcgc agactttggg actatcctgg     360
aactaccctg gttcaaaagc acatccgtca tcctctttct caacaaaacc gacatcctgg     420
aggagaaaat ccccacctcc cacctggcta cctatttccc cagtttccag ggccctaagc     480
aggatgctga ggcagccaag aggttcatcc tggacatgta cacgaggatg tacaccgggt     540
gcgtggacgg ccccgagggc agcaagaagg gcgcacgatc ccgacgcctc ttcagccact     600
acacatgtgc cacagacaca cagaacgcgc gcaagatctt caaggacgtg cgggactcgg     660
tgctcgcccg ctacctggac gagatcaacc tgctgtaata gctcgag               707
```

<210> SEQ ID NO 122
<211> LENGTH: 231
<212> TYPE: PRT
<213> ORGANISM: Artificial Sequence
<220> FEATURE:
<223> OTHER INFORMATION: Mini-G16

<400> SEQUENCE: 122

```
Met Gly His His His His His His Ile Asn Arg Ile Leu Leu Glu Gln
1               5                   10                  15

Lys Lys Gln Asp Arg Gly Glu Leu Lys Leu Leu Leu Leu Gly Pro Asp
            20                  25                  30

Asn Ser Gly Lys Ser Thr Phe Ile Lys Gln Met Arg Ile Ile His Gly
        35                  40                  45

Gly Gly Gly Gly Gly Gly Thr Thr Gly Ile Asn Glu Tyr Cys Phe
    50                  55                  60

Ser Val Gln Lys Thr Asn Leu Arg Ile Val Asp Val Gly Gly Gln Lys
65                  70                  75                  80

Ser Glu Arg Lys Lys Trp Ile His Cys Phe Glu Asn Val Ile Ala Leu
                85                  90                  95

Ile Tyr Leu Ala Asp Leu Ser Asp Tyr Asn Arg Met Lys Glu Ser Leu
            100                 105                 110

Ala Asp Phe Gly Thr Ile Leu Glu Leu Pro Trp Phe Lys Ser Thr Ser
        115                 120                 125

Val Ile Leu Phe Leu Asn Lys Thr Asp Ile Leu Glu Glu Lys Ile Pro
    130                 135                 140

Thr Ser His Leu Ala Thr Tyr Phe Pro Ser Phe Gln Gly Pro Lys Gln
145                 150                 155                 160

Asp Ala Glu Ala Ala Lys Arg Phe Ile Leu Asp Met Tyr Thr Arg Met
                165                 170                 175

Tyr Thr Gly Cys Val Asp Gly Pro Glu Gly Ser Lys Lys Gly Ala Arg
```

```
                    180                 185                 190
Ser Arg Arg Leu Phe Ser His Tyr Thr Cys Ala Thr Asp Thr Gln Asn
                195                 200                 205

Ala Arg Lys Ile Phe Lys Asp Val Arg Asp Ser Val Leu Ala Arg Tyr
            210                 215                 220

Leu Asp Glu Ile Asn Leu Leu
225                 230

<210> SEQ ID NO 123
<211> LENGTH: 486
<212> TYPE: PRT
<213> ORGANISM: Artificial Sequence
<220> FEATURE:
<223> OTHER INFORMATION: GFP-mini-Gs393

<400> SEQUENCE: 123

Met Gly His His His His His His Glu Asn Leu Tyr Phe Gln Gly Val
1               5                   10                  15

Ser Lys Gly Glu Glu Leu Phe Thr Gly Val Val Pro Ile Leu Val Glu
            20                  25                  30

Leu Asp Gly Asp Val Asn Gly His Lys Phe Ser Val Ser Gly Glu Gly
        35                  40                  45

Glu Gly Asp Ala Thr Tyr Gly Lys Leu Thr Leu Lys Phe Ile Cys Thr
    50                  55                  60

Thr Gly Lys Leu Pro Val Pro Trp Pro Thr Leu Val Thr Thr Leu Thr
65                  70                  75                  80

Tyr Gly Val Gln Cys Phe Ser Arg Tyr Pro Asp His Met Lys Gln His
                85                  90                  95

Asp Phe Phe Lys Ser Ala Met Pro Glu Gly Tyr Val Gln Glu Arg Thr
            100                 105                 110

Ile Phe Phe Lys Asp Asp Gly Asn Tyr Lys Thr Arg Ala Glu Val Lys
        115                 120                 125

Phe Glu Gly Asp Thr Leu Val Asn Arg Ile Glu Leu Lys Gly Ile Asp
    130                 135                 140

Phe Lys Glu Asp Gly Asn Ile Leu Gly His Lys Leu Glu Tyr Asn Tyr
145                 150                 155                 160

Asn Ser His Asn Val Tyr Ile Met Ala Asp Lys Gln Lys Asn Gly Ile
                165                 170                 175

Lys Val Asn Phe Lys Ile Arg His Asn Ile Glu Asp Gly Ser Val Gln
            180                 185                 190

Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
    210                 215                 220

Asp Pro Asn Glu Lys Arg Asp His Met Val Leu Leu Glu Phe Val Thr
225                 230                 235                 240

Ala Ala Gly Ile Thr Leu Gly Met Asp Glu Leu Tyr Lys Gly Gly Gly
                245                 250                 255

Gly Ser Ile Glu Lys Gln Leu Gln Lys Asp Lys Gln Val Tyr Arg Ala
            260                 265                 270

Thr His Arg Leu Leu Leu Leu Gly Ala Asp Asn Ser Gly Lys Ser Thr
        275                 280                 285

Ile Val Lys Gln Met Arg Ile Leu His Gly Gly Ser Gly Gly Ser Gly
    290                 295                 300

Gly Thr Ser Gly Ile Phe Glu Thr Lys Phe Gln Val Asp Lys Val Asn
```

```
                305                 310                 315                 320
        Phe His Met Phe Asp Val Gly Gly Gln Arg Asp Glu Arg Arg Lys Trp
                        325                 330                 335

Ile Gln Cys Phe Asn Asp Val Thr Ala Ile Ile Phe Val Val Asp Ser
                        340                 345                 350

Ser Asp Tyr Asn Arg Leu Gln Glu Ala Leu Asn Asp Phe Lys Ser Ile
                        355                 360                 365

Trp Asn Asn Arg Trp Leu Arg Thr Ile Ser Val Ile Leu Phe Leu Asn
                        370                 375                 380

Lys Gln Asp Leu Leu Ala Glu Lys Val Leu Ala Gly Lys Ser Lys Ile
        385                 390                 395                 400

Glu Asp Tyr Phe Pro Glu Phe Ala Arg Tyr Thr Thr Pro Glu Asp Ala
                        405                 410                 415

Thr Pro Glu Pro Gly Glu Asp Pro Arg Val Thr Arg Ala Lys Tyr Phe
                        420                 425                 430

Ile Arg Asp Glu Phe Leu Arg Ile Ser Thr Ala Ser Gly Asp Gly Arg
                        435                 440                 445

His Tyr Cys Tyr Pro His Phe Thr Cys Ala Val Asp Thr Glu Asn Ala
                        450                 455                 460

Arg Arg Ile Phe Asn Asp Cys Arg Asp Ile Ile Gln Arg Met His Leu
        465                 470                 475                 480

Arg Gln Tyr Glu Leu Leu
                        485

<210> SEQ ID NO 124
<211> LENGTH: 484
<212> TYPE: PRT
<213> ORGANISM: Artificial Sequence
<220> FEATURE:
<223> OTHER INFORMATION: GFP-mini-Gi146

<400> SEQUENCE: 124

Met Gly His His His His His His Glu Asn Leu Tyr Phe Gln Gly Val
        1               5                   10                  15

Ser Lys Gly Glu Glu Leu Phe Thr Gly Val Val Pro Ile Leu Val Glu
                        20                  25                  30

Leu Asp Gly Asp Val Asn Gly His Lys Phe Ser Val Ser Gly Glu Gly
                        35                  40                  45

Glu Gly Asp Ala Thr Tyr Gly Lys Leu Thr Leu Lys Phe Ile Cys Thr
                        50                  55                  60

Thr Gly Lys Leu Pro Val Pro Trp Pro Thr Leu Val Thr Thr Leu Thr
        65                  70                  75                  80

Tyr Gly Val Gln Cys Phe Ser Arg Tyr Pro Asp His Met Lys Gln His
                        85                  90                  95

Asp Phe Phe Lys Ser Ala Met Pro Glu Gly Tyr Val Gln Glu Arg Thr
                        100                 105                 110

Ile Phe Phe Lys Asp Asp Gly Asn Tyr Lys Thr Arg Ala Glu Val Lys
                        115                 120                 125

Phe Glu Gly Asp Thr Leu Val Asn Arg Ile Glu Leu Lys Gly Ile Asp
                        130                 135                 140

Phe Lys Glu Asp Gly Asn Ile Leu Gly His Lys Leu Glu Tyr Asn Tyr
        145                 150                 155                 160

Asn Ser His Asn Val Tyr Ile Met Ala Asp Lys Gln Lys Asn Gly Ile
                        165                 170                 175

Lys Val Asn Phe Lys Ile Arg His Asn Ile Glu Asp Gly Ser Val Gln
```

180                 185                 190
Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
        210                 215                 220

Asp Pro Asn Glu Lys Arg Asp His Met Val Leu Leu Glu Phe Val Thr
225                 230                 235                 240

Ala Ala Gly Ile Thr Leu Gly Met Asp Glu Leu Tyr Lys Gly Gly Gly
                245                 250                 255

Gly Ser Thr Leu Ser Ala Glu Asp Lys Ala Ala Val Glu Arg Ser Lys
        260                 265                 270

Met Ile Asp Arg Asn Leu Arg Glu Asp Gly Glu Lys Ala Ala Arg Glu
        275                 280                 285

Val Lys Leu Leu Leu Leu Gly Ala Asp Asn Ser Gly Lys Ser Thr Ile
        290                 295                 300

Val Lys Gln Met Lys Ile Ile His Gly Gly Gly Gly Gly Gly Gly Gly
305                 310                 315                 320

Thr Thr Gly Ile Val Glu Thr His Phe Thr Phe Lys Asp Leu His Phe
                325                 330                 335

Lys Met Phe Asp Val Gly Gly Gln Arg Ser Glu Arg Lys Lys Trp Ile
                340                 345                 350

His Cys Phe Glu Asp Val Ala Ala Ile Ile Phe Cys Val Asp Leu Ser
            355                 360                 365

Asp Tyr Asn Arg Met His Glu Ser Met Lys Leu Phe Asp Ser Ile Cys
        370                 375                 380

Asn Asn Lys Trp Phe Thr Asp Thr Ser Ile Ile Leu Phe Leu Asn Lys
385                 390                 395                 400

Lys Asp Leu Phe Glu Glu Lys Ile Lys Lys Ser Pro Leu Thr Ile Cys
                405                 410                 415

Tyr Gln Glu Tyr Ala Gly Ser Asn Thr Tyr Glu Glu Ala Ala Ala Tyr
            420                 425                 430

Ile Gln Cys Gln Phe Glu Asp Leu Asn Lys Arg Lys Asp Thr Lys Glu
        435                 440                 445

Ile Tyr Thr His Phe Thr Cys Ala Thr Asp Thr Lys Asn Ala Gln Phe
        450                 455                 460

Ile Phe Asp Ala Val Thr Asp Val Ile Ile Lys Asn Asn Leu Lys Asp
465                 470                 475                 480

Cys Gly Leu Phe

<210> SEQ ID NO 125
<211> LENGTH: 486
<212> TYPE: PRT
<213> ORGANISM: Artificial Sequence
<220> FEATURE:
<223> OTHER INFORMATION: GFP-mini-Gs/i143

<400> SEQUENCE: 125

Met Gly His His His His His His Glu Asn Leu Tyr Phe Gln Gly Val
1               5                   10                  15

Ser Lys Gly Glu Glu Leu Phe Thr Gly Val Val Pro Ile Leu Val Glu
            20                  25                  30

Leu Asp Gly Asp Val Asn Gly His Lys Phe Ser Val Ser Gly Glu Gly
        35                  40                  45

Glu Gly Asp Ala Thr Tyr Gly Lys Leu Thr Leu Lys Phe Ile Cys Thr
    50                  55                  60

```
Thr Gly Lys Leu Pro Val Pro Trp Pro Thr Leu Val Thr Thr Leu Thr
 65                  70                  75                  80

Tyr Gly Val Gln Cys Phe Ser Arg Tyr Pro Asp His Met Lys Gln His
                 85                  90                  95

Asp Phe Phe Lys Ser Ala Met Pro Glu Gly Tyr Val Gln Glu Arg Thr
                100                 105                 110

Ile Phe Phe Lys Asp Asp Gly Asn Tyr Lys Thr Arg Ala Glu Val Lys
                115                 120                 125

Phe Glu Gly Asp Thr Leu Val Asn Arg Ile Glu Leu Lys Gly Ile Asp
130                 135                 140

Phe Lys Glu Asp Gly Asn Ile Leu Gly His Lys Leu Glu Tyr Asn Tyr
145                 150                 155                 160

Asn Ser His Asn Val Tyr Ile Met Ala Asp Lys Gln Lys Asn Gly Ile
                165                 170                 175

Lys Val Asn Phe Lys Ile Arg His Asn Ile Glu Asp Gly Ser Val Gln
                180                 185                 190

Leu Ala Asp His Tyr Gln Gln Asn Thr Pro Ile Gly Asp Gly Pro Val
                195                 200                 205

Leu Leu Pro Asp Asn His Tyr Leu Ser Thr Gln Ser Ala Leu Ser Lys
210                 215                 220

Asp Pro Asn Glu Lys Arg Asp His Met Val Leu Leu Glu Phe Val Thr
225                 230                 235                 240

Ala Ala Gly Ile Thr Leu Gly Met Asp Glu Leu Tyr Lys Gly Gly Gly
                245                 250                 255

Gly Ser Ile Glu Lys Gln Leu Gln Lys Asp Lys Gln Val Tyr Arg Ala
                260                 265                 270

Thr His Arg Leu Leu Leu Leu Gly Ala Asp Asn Ser Gly Lys Ser Thr
                275                 280                 285

Ile Val Lys Gln Met Arg Ile Leu His Gly Ser Gly Gly Ser Gly
                290                 295                 300

Gly Thr Ser Gly Ile Phe Glu Thr Lys Phe Gln Val Asp Lys Val Asn
305                 310                 315                 320

Phe His Met Phe Asp Val Gly Gly Gln Arg Asp Glu Arg Arg Lys Trp
                325                 330                 335

Ile Gln Cys Phe Asn Asp Val Thr Ala Ile Ile Phe Val Val Asp Ser
                340                 345                 350

Ser Asp Tyr Asn Arg Leu Gln Glu Ala Leu Asn Asp Phe Lys Ser Ile
                355                 360                 365

Trp Asn Asn Arg Trp Leu Arg Thr Ile Ser Val Ile Leu Phe Leu Asn
                370                 375                 380

Lys Gln Asp Leu Leu Ala Glu Lys Val Leu Ala Gly Lys Ser Lys Ile
385                 390                 395                 400

Glu Asp Tyr Phe Pro Glu Phe Ala Arg Tyr Thr Thr Pro Glu Asp Ala
                405                 410                 415

Thr Pro Glu Pro Gly Glu Asp Pro Arg Val Thr Arg Ala Lys Tyr Phe
                420                 425                 430

Ile Arg Asp Glu Phe Leu Arg Ile Ser Thr Ala Ser Gly Asp Gly Arg
                435                 440                 445

His Tyr Cys Tyr Pro His Phe Thr Cys Ala Val Asp Thr Glu Asn Ala
                450                 455                 460

Arg Arg Ile Phe Asn Asp Val Thr Asp Ile Ile Lys Met Asn Leu
465                 470                 475                 480
```

```
Arg Asp Cys Gly Leu Phe
                485

<210> SEQ ID NO 126
<211> LENGTH: 468
<212> TYPE: PRT
<213> ORGANISM: Artificial Sequence
<220> FEATURE:
<223> OTHER INFORMATION: GFP-mini-Go112

<400> SEQUENCE: 126

Met Gly His His His His His Glu Asn Leu Tyr Phe Gln Gly Val
1               5                   10                  15

Ser Lys Gly Glu Glu Leu Phe Thr Gly Val Val Pro Ile Leu Val Glu
            20                  25                  30

Leu Asp Gly Asp Val Asn Gly His Lys Phe Ser Val Ser Gly Glu Gly
            35                  40                  45

Glu Gly Asp Ala Thr Tyr Gly Lys Leu Thr Leu Lys Phe Ile Cys Thr
        50                  55                  60

Thr Gly Lys Leu Pro Val Pro Trp Pro Thr Leu Val Thr Thr Leu Thr
65                  70                  75                  80

Tyr Gly Val Gln Cys Phe Ser Arg Tyr Pro Asp His Met Lys Gln His
                85                  90                  95

Asp Phe Phe Lys Ser Ala Met Pro Glu Gly Tyr Val Gln Glu Arg Thr
            100                 105                 110

Ile Phe Phe Lys Asp Asp Gly Asn Tyr Lys Thr Arg Ala Glu Val Lys
        115                 120                 125

Phe Glu Gly Asp Thr Leu Val Asn Arg Ile Glu Leu Lys Gly Ile Asp
130                 135                 140

Phe Lys Glu Asp Gly Asn Ile Leu Gly His Lys Leu Glu Tyr Asn Tyr
145                 150                 155                 160

Asn Ser His Asn Val Tyr Ile Met Ala Asp Lys Gln Lys Asn Gly Ile
                165                 170                 175

Lys Val Asn Phe Lys Ile Arg His Asn Ile Glu Asp Gly Ser Val Gln
            180                 185                 190

Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
210                 215                 220

Asp Pro Asn Glu Lys Arg Asp His Met Val Leu Leu Glu Phe Val Thr
225                 230                 235                 240

Ala Ala Gly Ile Thr Leu Gly Met Asp Glu Leu Tyr Lys Gly Gly Gly
                245                 250                 255

Gly Ser Ile Glu Lys Asn Leu Lys Glu Asp Gly Ile Ser Ala Ala Lys
            260                 265                 270

Asp Val Lys Leu Leu Leu Leu Gly Ala Asp Asn Ser Gly Lys Ser Thr
        275                 280                 285

Ile Val Lys Gln Met Lys Ile Ile His Gly Ser Gly Gly Ser Gly
        290                 295                 300

Gly Thr Thr Gly Ile Val Glu Thr His Phe Thr Phe Lys Asn Leu His
305                 310                 315                 320

Phe Arg Leu Phe Asp Val Gly Gly Gln Arg Ser Glu Arg Lys Lys Trp
                325                 330                 335

Ile His Cys Phe Glu Asp Val Thr Ala Ile Ile Phe Cys Val Asp Leu
            340                 345                 350
```

```
Ser Asp Tyr Asn Arg Met His Glu Ser Leu Met Asp Phe Asp Ser Ile
            355                 360                 365

Cys Asn Asn Lys Phe Phe Ile Asp Thr Ser Ile Ile Leu Phe Leu Asn
370                 375                 380

Lys Lys Asp Leu Phe Gly Glu Lys Ile Lys Lys Ser Pro Leu Thr Ile
385                 390                 395                 400

Cys Phe Pro Glu Tyr Thr Gly Pro Asn Thr Tyr Glu Asp Ala Ala Ala
                405                 410                 415

Tyr Ile Gln Ala Gln Phe Glu Ser Lys Asn Arg Ser Pro Asn Lys Glu
            420                 425                 430

Ile Tyr Cys His Met Thr Cys Ala Thr Asp Thr Asn Asn Ala Gln Val
        435                 440                 445

Ile Phe Asp Ala Val Thr Asp Ile Ile Ile Ala Asn Asn Leu Arg Gly
450                 455                 460

Cys Gly Leu Tyr
465

<210> SEQ ID NO 127
<211> LENGTH: 469
<212> TYPE: PRT
<213> ORGANISM: Artificial Sequence
<220> FEATURE:
<223> OTHER INFORMATION: GFP-mini-G128

<400> SEQUENCE: 127

Met Gly His His His His His His Glu Asn Leu Tyr Phe Gln Gly Val
1               5                   10                  15

Ser Lys Gly Glu Glu Leu Phe Thr Gly Val Val Pro Ile Leu Val Glu
            20                  25                  30

Leu Asp Gly Asp Val Asn Gly His Lys Phe Ser Val Ser Gly Glu Gly
        35                  40                  45

Glu Gly Asp Ala Thr Tyr Gly Lys Leu Thr Leu Lys Phe Ile Cys Thr
    50                  55                  60

Thr Gly Lys Leu Pro Val Pro Trp Pro Thr Leu Val Thr Thr Leu Thr
65                  70                  75                  80

Tyr Gly Val Gln Cys Phe Ser Arg Tyr Pro Asp His Met Lys Gln His
                85                  90                  95

Asp Phe Phe Lys Ser Ala Met Pro Glu Gly Tyr Val Gln Glu Arg Thr
            100                 105                 110

Ile Phe Phe Lys Asp Asp Gly Asn Tyr Lys Thr Arg Ala Glu Val Lys
        115                 120                 125

Phe Glu Gly Asp Thr Leu Val Asn Arg Ile Glu Leu Lys Gly Ile Asp
    130                 135                 140

Phe Lys Glu Asp Gly Asn Ile Leu Gly His Lys Leu Glu Tyr Asn Tyr
145                 150                 155                 160

Asn Ser His Asn Val Tyr Ile Met Ala Asp Lys Gln Lys Asn Gly Ile
                165                 170                 175

Lys Val Asn Phe Lys Ile Arg His Asn Ile Glu Asp Gly Ser Val Gln
            180                 185                 190

Leu Ala Asp His Tyr Gln Gln Asn Thr Pro Ile Gly Asp Gly Pro Val
        195                 200                 205

Leu Leu Pro Asp Asn His Tyr Leu Ser Thr Gln Ser Ala Leu Ser Lys
    210                 215                 220

Asp Pro Asn Glu Lys Arg Asp His Met Val Leu Leu Glu Phe Val Thr
225                 230                 235                 240
```

```
Ala Ala Gly Ile Thr Leu Gly Met Asp Glu Leu Tyr Lys Gly Gly Gly
            245                 250                 255

Gly Ser Ile Asp Ala Leu Leu Ala Arg Glu Arg Ala Val Arg Arg
        260                 265                 270

Leu Val Lys Ile Leu Leu Leu Gly Ala Asp Asn Ser Gly Lys Ser Thr
        275                 280                 285

Phe Leu Lys Gln Met Arg Ile Ile His Gly Ser Gly Gly Ser Gly
        290                 295                 300

Gly Thr Lys Gly Ile Val Glu His Asp Phe Val Ile Lys Lys Ile Pro
305                 310                 315                 320

Phe Lys Met Val Asp Val Gly Gly Gln Arg Ser Gln Arg Gln Lys Trp
                325                 330                 335

Phe Gln Cys Phe Asp Gly Ile Thr Ser Ile Leu Phe Met Val Asp Ser
                340                 345                 350

Ser Asp Tyr Asn Arg Leu Val Glu Ser Met Asn Asp Phe Glu Thr Ile
            355                 360                 365

Val Asn Asn Lys Leu Phe Phe Asn Val Ser Ile Ile Leu Phe Leu Asn
        370                 375                 380

Lys Met Asp Leu Leu Val Glu Lys Val Lys Thr Val Ser Ile Lys Lys
385                 390                 395                 400

His Phe Pro Asp Phe Arg Gly Asp Pro His Arg Leu Glu Asp Val Gln
                405                 410                 415

Arg Tyr Leu Val Gln Cys Phe Asp Arg Lys Arg Arg Asn Arg Ser Lys
                420                 425                 430

Pro Leu Phe His His Phe Thr Thr Ala Ile Asp Thr Glu Asn Ala Arg
                435                 440                 445

Phe Ile Phe His Ala Val Lys Asp Thr Ile Leu Gln Glu Asn Leu Lys
        450                 455                 460

Asp Ile Met Leu Gln
465

<210> SEQ ID NO 128
<211> LENGTH: 226
<212> TYPE: PRT
<213> ORGANISM: Artificial Sequence
<220> FEATURE:
<223> OTHER INFORMATION: mini-Gq

<400> SEQUENCE: 128

Met Gly His His His His His His Glu Asn Leu Tyr Phe Gln Gly Ile
1               5                   10                  15

Glu Arg Gln Leu Arg Arg Asp Lys Arg Asp Ala Arg Arg Glu Leu Lys
            20                  25                  30

Leu Leu Leu Leu Gly Thr Asp Asn Ser Gly Lys Ser Thr Phe Ile Lys
        35                  40                  45

Gln Met Arg Ile Ile His Gly Gly Gly Gly Gly Gly Gly Thr Thr
    50                  55                  60

Gly Ile Ile Glu Tyr Pro Phe Asp Leu Gln Ser Val Ile Phe Arg Met
65                  70                  75                  80

Val Asp Val Gly Gly Gln Arg Ser Glu Arg Arg Lys Trp Ile His Cys
                85                  90                  95

Phe Glu Asn Val Thr Ser Ile Met Phe Leu Val Asp Leu Ser Asp Tyr
                100                 105                 110

Asn Arg Met Glu Glu Ser Lys Ala Asp Phe Arg Thr Ile Ile Thr Tyr
            115                 120                 125
```

```
Pro Trp Phe Gln Asn Ser Ser Val Ile Leu Phe Leu Asn Lys Lys Asp
            130                 135                 140

Leu Leu Glu Glu Lys Ile Met Tyr Ser His Leu Val Asp Tyr Phe Pro
145                 150                 155                 160

Glu Tyr Asp Gly Pro Gln Arg Asp Ala Gln Ala Ala Arg Glu Phe Ile
                165                 170                 175

Leu Lys Met Phe Val Asp Leu Asn Pro Asp Ser Asp Lys Ile Ile Tyr
            180                 185                 190

Ser His Phe Thr Cys Ala Thr Asp Thr Glu Asn Ala Arg Phe Ile Phe
                195                 200                 205

Ala Ala Val Lys Asp Thr Ile Leu Gln Leu Asn Leu Lys Glu Tyr Asn
210                 215                 220

Leu Val
225

<210> SEQ ID NO 129
<211> LENGTH: 243
<212> TYPE: PRT
<213> ORGANISM: Artificial Sequence
<220> FEATURE:
<223> OTHER INFORMATION: mini-Gs

<400> SEQUENCE: 129

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg
                20                  25                  30

Leu Leu Leu Leu Gly Ala Asp Asn Ser Gly Lys Ser Thr Ile Val Lys
            35                  40                  45

Gln Met Arg Ile Leu His Gly Gly Ser Gly Gly Ser Gly Gly Thr Ser
50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
210                 215                 220

Phe Asn Asp Cys Arg Asp Ile Ile Gln Arg Met His Leu Arg Gln Tyr
225                 230                 235                 240

Glu Leu Leu
```

```
<210> SEQ ID NO 130
<211> LENGTH: 243
<212> TYPE: PRT
<213> ORGANISM: Artificial Sequence
<220> FEATURE:
<223> OTHER INFORMATION: mini-Gs/q57

<400> SEQUENCE: 130

Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Ser Gly Gly Ser Gly Gly Thr Ser
    50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
    210                 215                 220

Phe Asn Asp Cys Arg Asp Ile Ile Gln Arg Met His Leu Arg Glu Tyr
225                 230                 235                 240

Asn Leu Val

<210> SEQ ID NO 131
<211> LENGTH: 243
<212> TYPE: PRT
<213> ORGANISM: Artificial Sequence
<220> FEATURE:
<223> OTHER INFORMATION: mini-Gs/q58

<400> SEQUENCE: 131

Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Ser Gly Gly Ser Gly Gly Thr Ser
    50                  55                  60

Gly Ile Phe Glu Thr Lys Phe Gln Val Asp Lys Val Asn Phe His Met
```

```
            65                  70                  75                  80
        Phe Asp Val Gly Gly Gln Arg Asp Glu Arg Arg Lys Trp Ile Gln Cys
                         85                  90                  95

Phe Asn Asp Val Thr Ala Ile Ile Phe Val Val Asp Ser Ser Asp Tyr
                        100                 105                 110

Asn Arg Leu Gln Glu Ala Leu Asn Asp Phe Lys Ser Ile Trp Asn Asn
                        115                 120                 125

Arg Trp Leu Arg Thr Ile Ser Val Ile Leu Phe Leu Asn Lys Gln Asp
                        130                 135                 140

Leu Leu Ala Glu Lys Val Leu Ala Gly Lys Ser Lys Ile Glu Asp Tyr
        145                 150                 155                 160

Phe Pro Glu Phe Ala Arg Tyr Thr Thr Pro Glu Asp Ala Thr Pro Glu
                        165                 170                 175

Pro Gly Glu Asp Pro Arg Val Thr Arg Ala Lys Tyr Phe Ile Arg Asp
                        180                 185                 190

Glu Phe Leu Arg Ile Ser Thr Ala Ser Gly Asp Gly Arg His Tyr Cys
                        195                 200                 205

Tyr Pro His Phe Thr Cys Ala Val Asp Thr Glu Asn Ala Arg Arg Ile
                        210                 215                 220

Phe Ala Ala Val Lys Asp Thr Ile Leu Gln Leu Asn Leu Lys Glu Tyr
        225                 230                 235                 240

Asn Leu Val

<210> SEQ ID NO 132
<211> LENGTH: 243
<212> TYPE: PRT
<213> ORGANISM: Artificial Sequence
<220> FEATURE:
<223> OTHER INFORMATION: mini-Gs/q70

<400> SEQUENCE: 132

Met Gly His His His His His Glu Asn Leu Tyr Phe Gln Gly Ile
        1               5                   10                  15

Glu Lys Gln Leu Gln Lys Asp Lys Gln Val Tyr Arg Ala Thr His Arg
                        20                  25                  30

Leu Leu Leu Leu Gly Ala Asp Asn Ser Gly Lys Ser Thr Ile Val Lys
                        35                  40                  45

Gln Met Arg Ile Leu His Gly Gly Ser Gly Gly Ser Gly Gly Thr Ser
                        50                  55                  60

Gly Ile Phe Glu Thr Lys Phe Gln Val Asp Lys Val Asn Phe His Met
        65                  70                  75                  80

Phe Asp Val Gly Gly Gln Arg Asp Glu Arg Arg Lys Trp Ile Gln Cys
                        85                  90                  95

Phe Asn Asp Val Thr Ala Ile Ile Phe Val Val Asp Ser Ser Asp Tyr
                        100                 105                 110

Asn Arg Leu Gln Glu Ala Leu Asn Asp Phe Lys Ser Ile Trp Asn Asn
                        115                 120                 125

Arg Trp Leu Arg Thr Ile Ser Val Ile Leu Phe Leu Asn Lys Gln Asp
                        130                 135                 140

Leu Leu Ala Glu Lys Val Leu Ala Gly Lys Ser Lys Ile Glu Asp Tyr
        145                 150                 155                 160

Phe Pro Glu Phe Ala Arg Tyr Thr Thr Pro Glu Asp Ala Thr Pro Glu
                        165                 170                 175

Pro Gly Glu Asp Pro Arg Val Thr Arg Ala Lys Tyr Phe Ile Arg Asp
                        180                 185                 190
```

```
Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
210                 215                 220

Phe Asn Asp Cys Lys Asp Ile Ile Leu Gln Met Asn Leu Arg Glu Tyr
225                 230                 235                 240

Asn Leu Val

<210> SEQ ID NO 133
<211> LENGTH: 243
<212> TYPE: PRT
<213> ORGANISM: Artificial Sequence
<220> FEATURE:
<223> OTHER INFORMATION: mini-Gs/q71

<400> SEQUENCE: 133

Met Gly His His His His His His Glu Asn Leu Tyr Phe Gln Gly Ile
1               5                   10                  15

Glu Lys Gln Leu Gln Lys Asp Lys Gln Val Tyr Arg Arg Thr Leu Arg
            20                  25                  30

Leu Leu Leu Leu Gly Ala Asp Asn Ser Gly Lys Ser Thr Ile Val Lys
        35                  40                  45

Gln Met Arg Ile Leu His Gly Ser Gly Gly Ser Gly Gly Thr Ser
50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Lys
            180                 185                 190

Glu Phe Val Asp Ile Ser Thr Ala Ser Gly Asp Gly Arg His Ile Cys
        195                 200                 205

Tyr Pro His Phe Thr Cys Ala Val Asp Thr Glu Asn Ala Arg Arg Ile
210                 215                 220

Phe Asn Asp Cys Lys Asp Ile Ile Leu Gln Met Asn Leu Arg Glu Tyr
225                 230                 235                 240

Asn Leu Val

<210> SEQ ID NO 134
<211> LENGTH: 243
<212> TYPE: PRT
<213> ORGANISM: Artificial Sequence
<220> FEATURE:
<223> OTHER INFORMATION: miniGs_393

<400> SEQUENCE: 134
```

```
Met Gly His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Ser Gly Gly Ser Gly Gly Thr Ser
50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
            115                 120                 125

Arg Trp Leu Arg Thr Ile Ser Val Ile Leu Phe Leu Asn Lys Gln Asp
        130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
210                 215                 220

Phe Asn Asp Cys Arg Asp Ile Ile Gln Arg Met His Leu Arg Gln Tyr
225                 230                 235                 240

Glu Leu Leu

<210> SEQ ID NO 135
<211> LENGTH: 234
<212> TYPE: PRT
<213> ORGANISM: Artificial Sequence
<220> FEATURE:
<223> OTHER INFORMATION: miniGi1_46

<400> SEQUENCE: 135

Met Gly His His His His His Glu Asn Leu Tyr Phe Gln Gly Thr
1               5                   10                  15

Leu Ser Ala Glu Asp Lys Ala Ala Val Glu Arg Ser Lys Met Ile Asp
            20                  25                  30

Arg Asn Leu Arg Glu Asp Gly Glu Lys Ala Ala Arg Glu Val Lys Leu
        35                  40                  45

Leu Leu Leu Gly Ala Asp Asn Ser Gly Lys Ser Thr Ile Val Lys Gln
        50                  55                  60

Met Lys Ile Ile His Gly Gly Gly Gly Gly Gly Thr Thr Gly
65                  70                  75                  80

Ile Val Glu Thr His Phe Thr Phe Lys Asp Leu His Phe Lys Met Phe
                85                  90                  95

Asp Val Gly Gly Gln Arg Ser Glu Arg Lys Lys Trp Ile His Cys Phe
            100                 105                 110

Glu Asp Val Ala Ala Ile Ile Phe Cys Val Asp Leu Ser Asp Tyr Asn
```

```
              115                 120                 125
Arg Met His Glu Ser Met Lys Leu Phe Asp Ser Ile Cys Asn Asn Lys
        130                 135                 140

Trp Phe Thr Asp Thr Ser Ile Ile Leu Phe Leu Asn Lys Lys Asp Leu
145                 150                 155                 160

Phe Glu Glu Lys Ile Lys Tyr Gln Glu Tyr Ala Gly Ser Asn Thr Tyr
                165                 170                 175

Glu Glu Ala Ala Ala Tyr Ile Gln Cys Gln Phe Glu Asp Leu Asn Lys
            180                 185                 190

Arg Lys Asp Thr Lys Glu Ile Tyr Thr His Phe Thr Cys Ala Thr Asp
        195                 200                 205

Thr Lys Asn Ala Gln Phe Ile Phe Asp Ala Val Thr Asp Val Ile Ile
210                 215                 220

Lys Asn Asn Leu Lys Asp Cys Gly Leu Phe
225                 230

<210> SEQ ID NO 136
<211> LENGTH: 243
<212> TYPE: PRT
<213> ORGANISM: Artificial Sequence
<220> FEATURE:
<223> OTHER INFORMATION: miniGs/i1_43

<400> SEQUENCE: 136

Met Gly His His His His His His Glu Asn Leu Tyr Phe Gln Gly Ile
1               5                   10                  15

Glu Lys Gln Leu Gln Lys Asp Lys Gln Val Tyr Arg Ala Thr His Arg
            20                  25                  30

Leu Leu Leu Leu Gly Ala Asp Asn Ser Gly Lys Ser Thr Ile Val Lys
        35                  40                  45

Gln Met Arg Ile Leu His Gly Gly Ser Gly Gly Ser Gly Gly Thr Ser
    50                  55                  60

Gly Ile Phe Glu Thr Lys Phe Gln Val Asp Lys Val Asn Phe His Met
65                  70                  75                  80

Phe Asp Val Gly Gly Gln Arg Asp Glu Arg Arg Lys Trp Ile Gln Cys
                85                  90                  95

Phe Asn Asp Val Thr Ala Ile Ile Phe Val Val Asp Ser Ser Asp Tyr
            100                 105                 110

Asn Arg Leu Gln Glu Ala Leu Asn Asp Phe Lys Ser Ile Trp Asn Asn
        115                 120                 125

Arg Trp Leu Arg Thr Ile Ser Val Ile Leu Phe Leu Asn Lys Gln Asp
    130                 135                 140

Leu Leu Ala Glu Lys Val Leu Ala Gly Lys Ser Lys Ile Glu Asp Tyr
145                 150                 155                 160

Phe Pro Glu Phe Ala Arg Tyr Thr Thr Pro Glu Asp Ala Thr Pro Glu
                165                 170                 175

Pro Gly Glu Asp Pro Arg Val Thr Arg Ala Lys Tyr Phe Ile Arg Asp
            180                 185                 190

Glu Phe Leu Arg Ile Ser Thr Ala Ser Gly Asp Gly Arg His Tyr Cys
        195                 200                 205

Tyr Pro His Phe Thr Cys Ala Val Asp Thr Glu Asn Ala Arg Arg Ile
    210                 215                 220

Phe Asn Asp Val Thr Asp Ile Ile Ile Lys Met Asn Leu Arg Asp Cys
225                 230                 235                 240

Gly Leu Phe
```

<210> SEQ ID NO 137
<211> LENGTH: 263
<212> TYPE: PRT
<213> ORGANISM: Artificial Sequence
<220> FEATURE:
<223> OTHER INFORMATION: mniGs/i1_48

<400> SEQUENCE: 137

Met Gly His His His His His Glu Asn Leu Tyr Phe Gln Gly Asn
1               5                   10                  15

Ser Lys Thr Glu Asp Gln Arg Asn Glu Glu Lys Ala Gln Arg Glu Ala
            20                  25                  30

Asn Lys Lys Ile Glu Lys Gln Leu Gln Lys Asp Lys Gln Val Tyr Arg
        35                  40                  45

Ala Thr His Arg Leu Leu Leu Leu Gly Ala Asp Asn Ser Gly Lys Ser
    50                  55                  60

Thr Ile Val Lys Gln Met Arg Ile Leu His Gly Gly Ser Gly Gly Ser
65                  70                  75                  80

Gly Gly Thr Ser Gly Ile Phe Glu Thr Lys Phe Gln Val Asp Lys Val
                85                  90                  95

Asn Phe His Met Phe Asp Val Gly Gly Gln Arg Asp Glu Arg Arg Lys
            100                 105                 110

Trp Ile Gln Cys Phe Asn Asp Val Thr Ala Ile Ile Phe Val Val Asp
        115                 120                 125

Ser Ser Asp Tyr Asn Arg Leu Gln Glu Ala Leu Asn Leu Phe Lys Ser
    130                 135                 140

Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys
                165                 170                 175

Ile Glu Asp Tyr Phe Pro Glu Phe Ala Arg Tyr Thr Thr Pro Glu Asp
            180                 185                 190

Ala Thr Pro Glu Pro Gly Glu Asp Pro Arg Val Thr Arg Ala Lys Tyr
        195                 200                 205

Phe Ile Arg Asp Glu Phe Leu Arg Ile Ser Thr Ala Ser Gly Asp Gly
    210                 215                 220

Arg His Tyr Cys Tyr Pro His Phe Thr Cys Ala Val Asp Thr Glu Asn
225                 230                 235                 240

Ala Arg Arg Ile Phe Asn Asp Val Thr Asp Ile Ile Ile Lys Met Asn
                245                 250                 255

Leu Arg Asp Cys Gly Leu Phe
            260

<210> SEQ ID NO 138
<211> LENGTH: 218
<212> TYPE: PRT
<213> ORGANISM: Artificial Sequence
<220> FEATURE:
<223> OTHER INFORMATION: miniGo1_12

<400> SEQUENCE: 138

Met Gly His His His His His Glu Asn Leu Tyr Phe Gln Gly Ile
1               5                   10                  15

Glu Lys Asn Leu Lys Glu Asp Gly Ile Ser Ala Ala Lys Asp Val Lys
            20                  25                  30

Leu Leu Leu Leu Gly Ala Asp Asn Ser Gly Lys Ser Thr Ile Val Lys

```
            35                  40                  45
Gln Met Lys Ile Ile His Gly Gly Ser Gly Gly Thr Thr
 50                  55                  60

Gly Ile Val Glu Thr His Phe Thr Phe Lys Asn Leu His Phe Arg Leu
 65                  70                  75                  80

Phe Asp Val Gly Gly Gln Arg Ser Glu Arg Lys Lys Trp Ile His Cys
                 85                  90                  95

Phe Glu Asp Val Thr Ala Ile Ile Phe Cys Val Asp Leu Ser Asp Tyr
                100                 105                 110

Asn Arg Met His Glu Ser Leu Met Asp Phe Asp Ser Ile Cys Asn Asn
                115                 120                 125

Lys Phe Phe Ile Asp Thr Ser Ile Ile Leu Phe Leu Asn Lys Lys Asp
130                 135                 140

Leu Phe Gly Glu Lys Ile Lys Phe Pro Glu Tyr Thr Gly Pro Asn Thr
145                 150                 155                 160

Tyr Glu Asp Ala Ala Ala Tyr Ile Gln Ala Gln Phe Glu Ser Lys Asn
                165                 170                 175

Arg Ser Pro Asn Lys Glu Ile Tyr Cys His Met Thr Cys Ala Thr Asp
                180                 185                 190

Thr Asn Asn Ala Gln Val Ile Phe Asp Ala Val Thr Asp Ile Ile Ile
                195                 200                 205

Ala Asn Asn Leu Arg Gly Cys Gly Leu Tyr
210                 215

<210> SEQ ID NO 139
<211> LENGTH: 263
<212> TYPE: PRT
<213> ORGANISM: Artificial Sequence
<220> FEATURE:
<223> OTHER INFORMATION: miniGs/o_16

<400> SEQUENCE: 139

Met Gly His His His His His Glu Asn Leu Tyr Phe Gln Gly Asn
 1               5                  10                  15

Ser Lys Thr Glu Asp Gln Arg Asn Glu Glu Lys Ala Gln Arg Glu Ala
                20                  25                  30

Asn Lys Lys Ile Glu Lys Gln Leu Gln Lys Asp Lys Gln Val Tyr Arg
                35                  40                  45

Ala Thr His Arg Leu Leu Leu Leu Gly Ala Asp Asn Ser Gly Lys Ser
 50                  55                  60

Thr Ile Val Lys Gln Met Arg Ile Leu His Gly Gly Ser Gly Gly Ser
 65                  70                  75                  80

Gly Gly Thr Ser Gly Ile Phe Glu Thr Lys Phe Gln Val Asp Lys Val
                 85                  90                  95

Asn Phe His Met Phe Asp Val Gly Gly Gln Arg Asp Glu Arg Arg Lys
                100                 105                 110

Trp Ile Gln Cys Phe Asn Asp Val Thr Ala Ile Ile Phe Val Val Asp
                115                 120                 125

Ser Ser Asp Tyr Asn Arg Leu Gln Glu Ala Leu Asn Leu Phe Lys Ser
130                 135                 140

Ile Trp Asn Asn Arg Trp Leu Arg Thr Ile Ser Val Ile Leu Phe Leu
145                 150                 155                 160

Asn Lys Gln Asp Leu Leu Ala Glu Lys Val Leu Ala Gly Lys Ser Lys
                165                 170                 175

Ile Glu Asp Tyr Phe Pro Glu Phe Ala Arg Tyr Thr Thr Pro Glu Asp
```

```
                180                 185                 190
Ala Thr Pro Glu Pro Gly Glu Asp Pro Arg Val Thr Arg Ala Lys Tyr
            195                 200                 205

Phe Ile Arg Asp Glu Phe Leu Arg Ile Ser Thr Ala Ser Gly Asp Gly
            210                 215                 220

Arg His Tyr Cys Tyr Pro His Phe Thr Cys Ala Val Asp Thr Glu Asn
225                 230                 235                 240

Ala Arg Arg Ile Phe Asn Asp Val Thr Asp Ile Ile Ile Ala Met Asn
            245                 250                 255

Leu Arg Gly Cys Gly Leu Tyr
            260

<210> SEQ ID NO 140
<211> LENGTH: 350
<212> TYPE: PRT
<213> ORGANISM: Artificial Sequence
<220> FEATURE:
<223> OTHER INFORMATION: G?t subunit (chimera 6)

<400> SEQUENCE: 140

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45

Met Lys Ile Ile His Gln Asp Gly Tyr Ser Leu Glu Glu Cys Leu Glu
    50                  55                  60

Phe Ile Ala Ile Ile Tyr Gly Asn Thr Leu Gln Ser Ile Leu Ala Ile
65              70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
        115                 120                 125

Asp Ser Gly Ile Gln Ala Cys Phe Asp Arg Ala Ser Glu Tyr Gln Leu
    130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Ala Ile Ile Phe Cys Val Ala Leu Ser
    210                 215                 220

Asp Tyr Asp Leu Val Leu Ala Glu Asp Glu Glu Met Asn Arg Met His
225                 230                 235                 240

Glu Ser Met Lys Leu Phe Asp Ser Ile Cys Asn Asn Lys Trp Phe Thr
                245                 250                 255

Asp Thr Ser Ile Ile Leu Phe Leu Asn Lys Lys Asp Leu Phe Glu Glu
            260                 265                 270

Lys Ile Lys Lys Ser Pro Leu Thr Ile Cys Tyr Pro Glu Tyr Ala Gly
```

```
                275                 280                 285
Ser Asn Thr Tyr Glu Glu Ala Gly Asn Tyr Ile Lys Val Gln Phe Leu
    290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Asp Ala Val Thr
                325                 330                 335

Asp Ile Ile Ile Lys Glu Asn Leu Lys Asp Cys Gly Leu Phe
                340                 345                 350

<210> SEQ ID NO 141
<211> LENGTH: 394
<212> TYPE: PRT
<213> ORGANISM: Homo sapiens
<220> FEATURE:
<223> OTHER INFORMATION: P63092

<400> SEQUENCE: 141

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asp Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
```

|       |       |       |       | 290   |       |       |       |       | 295   |       |       |       |       | 300   |       |
|-------|-------|-------|-------|-------|-------|-------|-------|-------|-------|-------|-------|-------|-------|-------|-------|

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
                340                 345                 350

Gly Asp Gly Arg His Tyr Cys Tyr Pro His Phe Thr Cys Ala Val Asp
            355                 360                 365

Thr Glu Asn Ile Arg Arg Val Phe Asn Asp Cys Arg Asp Ile Ile Gln
        370                 375                 380

Arg Met His Leu Arg Gln Tyr Glu Leu Leu
385                 390

<210> SEQ ID NO 142
<211> LENGTH: 381
<212> TYPE: PRT
<213> ORGANISM: Homo sapiens
<220> FEATURE:
<223> OTHER INFORMATION: P38405

<400> SEQUENCE: 142

Met Gly Cys Leu Gly Gly Asn Ser Lys Thr Thr Glu Asp Gln Gly Val
1               5                   10                  15

Asp Glu Lys Glu Arg Arg Glu Ala Asn Lys Lys Ile Glu Lys Gln Leu
            20                  25                  30

Gln Lys Glu Arg Leu Ala Tyr Lys Ala Thr His Arg Leu Leu Leu Leu
        35                  40                  45

Gly Ala Gly Glu Ser Gly Lys Ser Thr Ile Val Lys Gln Met Arg Ile
    50                  55                  60

Leu His Val Asn Gly Phe Asn Pro Glu Glu Lys Lys Gln Lys Ile Leu
65                  70                  75                  80

Asp Ile Arg Lys Asn Val Lys Asp Ala Ile Val Thr Ile Val Ser Ala
                85                  90                  95

Met Ser Thr Ile Ile Pro Pro Val Pro Leu Ala Asn Pro Glu Asn Gln
            100                 105                 110

Phe Arg Ser Asp Tyr Ile Lys Ser Ile Ala Pro Ile Thr Asp Phe Glu
        115                 120                 125

Tyr Ser Gln Glu Phe Phe Asp His Val Lys Lys Leu Trp Asp Asp Glu
    130                 135                 140

Gly Val Lys Ala Cys Phe Glu Arg Ser Asn Glu Tyr Gln Leu Ile Asp
145                 150                 155                 160

Cys Ala Gln Tyr Phe Leu Glu Arg Ile Asp Ser Val Ser Leu Val Asp
                165                 170                 175

Tyr Thr Pro Thr Asp Gln Asp Leu Leu Arg Cys Arg Val Leu Thr Ser
            180                 185                 190

Gly Ile Phe Glu Thr Arg Phe Gln Val Asp Lys Val Asn Phe His Met
        195                 200                 205

Phe Asp Val Gly Gly Gln Arg Asp Glu Arg Arg Lys Trp Ile Gln Cys
    210                 215                 220

Phe Asn Asp Val Thr Ala Ile Ile Tyr Val Ala Ala Cys Ser Ser Tyr
225                 230                 235                 240

Asn Met Val Ile Arg Glu Asp Asn Asn Thr Asn Arg Leu Arg Glu Ser
                245                 250                 255

Leu Asp Leu Phe Glu Ser Ile Trp Asn Asn Arg Trp Leu Arg Thr Ile

-continued

```
                260                 265                 270
Ser Ile Ile Leu Phe Leu Asn Lys Gln Asp Met Leu Ala Glu Lys Val
            275                 280                 285

Leu Ala Gly Lys Ser Lys Ile Glu Asp Tyr Phe Pro Glu Tyr Ala Asn
            290                 295                 300

Tyr Thr Val Pro Glu Asp Ala Thr Pro Asp Ala Gly Glu Asp Pro Lys
305                 310                 315                 320

Val Thr Arg Ala Lys Phe Phe Ile Arg Asp Leu Phe Leu Arg Ile Ser
            325                 330                 335

Thr Ala Thr Gly Asp Gly Lys His Tyr Cys Tyr Pro His Phe Thr Cys
            340                 345                 350

Ala Val Asp Thr Glu Asn Ile Arg Arg Val Phe Asn Asp Cys Arg Asp
            355                 360                 365

Ile Ile Gln Arg Met His Leu Lys Gln Tyr Glu Leu Leu
            370                 375                 380

<210> SEQ ID NO 143
<211> LENGTH: 354
<212> TYPE: PRT
<213> ORGANISM: Homo sapiens
<220> FEATURE:
<223> OTHER INFORMATION: P63096

<400> SEQUENCE: 143

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Ala Gly Tyr Ser Glu Glu
        50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
```

```
            245                 250                 255
Lys Trp Phe Thr Asp Thr Ser Ile Ile Leu Phe Leu Asn Lys Lys Asp
        260                 265                 270
Leu Phe Glu Glu Lys Ile Lys Lys Ser Pro Leu Thr Ile Cys Tyr Pro
        275                 280                 285
Glu Tyr Ala Gly Ser Asn Thr Tyr Glu Glu Ala Ala Ala Tyr Ile Gln
        290                 295                 300
Cys Gln Phe Glu Asp Leu Asn Lys Arg Lys Asp Thr Lys Glu Ile Tyr
305                 310                 315                 320
Thr His Phe Thr Cys Ala Thr Asp Thr Lys Asn Val Gln Phe Val Phe
                325                 330                 335
Asp Ala Val Thr Asp Val Ile Ile Lys Asn Asn Leu Lys Asp Cys Gly
                340                 345                 350
Leu Phe

<210> SEQ ID NO 144
<211> LENGTH: 355
<212> TYPE: PRT
<213> ORGANISM: Homo sapiens
<220> FEATURE:
<223> OTHER INFORMATION: P04899

<400> SEQUENCE: 144

Met Gly Cys Thr Val Ser Ala Glu Asp Lys Ala Ala Glu Arg Ser
1               5                   10                  15
Lys Met Ile Asp Lys Asn Leu Arg Glu Asp Gly Glu Lys Ala Ala Arg
            20                  25                  30
Glu Val Lys Leu Leu Leu Leu Gly Ala Gly Glu Ser Gly Lys Ser Thr
        35                  40                  45
Ile Val Lys Gln Met Lys Ile Ile His Glu Asp Gly Tyr Ser Glu Glu
    50                  55                  60
Glu Cys Arg Gln Tyr Arg Ala Val Val Tyr Ser Asn Thr Ile Gln Ser
65                  70                  75                  80
Ile Met Ala Ile Val Lys Ala Met Gly Asn Leu Gln Ile Asp Phe Ala
                85                  90                  95
Asp Pro Ser Arg Ala Asp Asp Ala Arg Gln Leu Phe Ala Leu Ser Cys
            100                 105                 110
Thr Ala Glu Glu Gln Gly Val Leu Pro Asp Asp Leu Ser Gly Val Ile
        115                 120                 125
Arg Arg Leu Trp Ala Asp His Gly Val Gln Ala Cys Phe Gly Arg Ser
    130                 135                 140
Arg Glu Tyr Gln Leu Asn Asp Ser Ala Ala Tyr Tyr Leu Asn Asp Leu
145                 150                 155                 160
Glu Arg Ile Ala Gln Ser Asp Tyr Ile Pro Thr Gln Gln Asp Val Leu
                165                 170                 175
Arg Thr Arg Val Lys Thr Thr Gly Ile Val Glu Thr His Phe Thr Phe
            180                 185                 190
Lys Asp Leu His Phe Lys Met Phe Asp Val Gly Gly Gln Arg Ser Glu
        195                 200                 205
Arg Lys Lys Trp Ile His Cys Phe Glu Gly Val Thr Ala Ile Ile Phe
    210                 215                 220
Cys Val Ala Leu Ser Ala Tyr Asp Leu Val Leu Ala Glu Asp Glu Glu
225                 230                 235                 240
Met Asn Arg Met His Glu Ser Met Lys Leu Phe Asp Ser Ile Cys Asn
                245                 250                 255
```

Asn Lys Trp Phe Thr Asp Thr Ser Ile Ile Leu Phe Leu Asn Lys Lys
              260                 265                 270

Asp Leu Phe Glu Glu Lys Ile Thr His Ser Pro Leu Thr Ile Cys Phe
              275                 280                 285

Pro Glu Tyr Thr Gly Ala Asn Lys Tyr Asp Glu Ala Ala Ser Tyr Ile
              290                 295                 300

Gln Ser Lys Phe Glu Asp Leu Asn Lys Arg Lys Asp Thr Lys Glu Ile
305                 310                 315                 320

Tyr Thr His Phe Thr Cys Ala Thr Asp Thr Lys Asn Val Gln Phe Val
              325                 330                 335

Phe Asp Ala Val Thr Asp Val Ile Ile Lys Asn Asn Leu Lys Asp Cys
              340                 345                 350

Gly Leu Phe
        355

<210> SEQ ID NO 145
<211> LENGTH: 354
<212> TYPE: PRT
<213> ORGANISM: Homo sapiens
<220> FEATURE:
<223> OTHER INFORMATION: P08754

<400> SEQUENCE: 145

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Lys
              20                  25                  30

Glu Val Lys Leu Leu Leu Leu Gly Ala Gly Glu Ser Gly Lys Ser Thr
              35                  40                  45

Ile Val Lys Gln Met Lys Ile Ile His Glu Asp Gly Tyr Ser Glu Asp
        50                  55                  60

Glu Cys Lys Gln Tyr Lys Val Val Val Tyr Ser Asn Thr Ile Gln Ser
65                  70                  75                  80

Ile Ile Ala Ile Ile Arg Ala Met Gly Arg Leu Lys Ile Asp Phe Gly
              85                  90                  95

Glu Ala Ala Arg Ala Asp Asp Ala Arg Gln Leu Phe Val Leu Ala Gly
              100                 105                 110

Ser Ala Glu Glu Gly Val Met Thr Pro Glu Leu Ala Gly Val Ile Lys
              115                 120                 125

Arg Leu Trp Arg Asp Gly Gly Val Gln Ala Cys Phe Ser Arg Ser Arg
        130                 135                 140

Glu Tyr Gln Leu Asn Asp Ser Ala Ser Tyr Tyr Leu Asn Asp Leu Asp
145                 150                 155                 160

Arg Ile Ser Gln Ser Asn Tyr Ile Pro Thr Gln Gln Asp Val Leu Arg
              165                 170                 175

Thr Arg Val Lys Thr Thr Gly Ile Val Glu Thr His Phe Thr Phe Lys
              180                 185                 190

Asp Leu Tyr Phe Lys Met Phe Asp Val Gly Gly Gln Arg Ser Glu Arg
              195                 200                 205

Lys Lys Trp Ile His Cys Phe Glu Gly Val Thr Ala Ile Ile Phe Cys
        210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
              245                 250                 255

Lys Trp Phe Thr Glu Thr Ser Ile Ile Leu Phe Leu Asn Lys Lys Asp
            260                 265                 270

Leu Phe Glu Glu Lys Ile Lys Arg Ser Pro Leu Thr Ile Cys Tyr Pro
            275                 280                 285

Glu Tyr Thr Gly Ser Asn Thr Tyr Glu Glu Ala Ala Tyr Ile Gln
            290                 295                 300

Cys Gln Phe Glu Asp Leu Asn Arg Arg Lys Asp Thr Lys Glu Ile Tyr
305                 310                 315                 320

Thr His Phe Thr Cys Ala Thr Asp Thr Lys Asn Val Gln Phe Val Phe
                    325                 330                 335

Asp Ala Val Thr Asp Val Ile Ile Lys Asn Asn Leu Lys Glu Cys Gly
                    340                 345                 350

Leu Tyr

<210> SEQ ID NO 146
<211> LENGTH: 350
<212> TYPE: PRT
<213> ORGANISM: Homo sapiens
<220> FEATURE:
<223> OTHER INFORMATION: P11488

<400> SEQUENCE: 146

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
            35                  40                  45

Met Lys Ile Ile His Gln Asp Gly Tyr Ser Leu Glu Glu Cys Leu Glu
50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                    85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
            115                 120                 125

Asp Ser Gly Ile Gln Ala Cys Phe Glu Arg Ala Ser Glu Tyr Gln Leu
130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                    165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
            195                 200                 205

His Cys Phe Glu Gly Val Thr Cys Ile Ile Phe Ile Ala Ala Leu Ser
210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                    245                 250                 255

```
Thr Thr Ser Ile Val Leu Phe Leu Asn Lys Lys Asp Val Phe Glu
            260                 265                 270

Lys Ile Lys Lys Ala His Leu Ser Ile Cys Phe Pro Asp Tyr Asp Gly
    275                 280                 285

Pro Asn Thr Tyr Glu Asp Ala Gly Asn Tyr Ile Lys Val Gln Phe Leu
    290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350

<210> SEQ ID NO 147
<211> LENGTH: 354
<212> TYPE: PRT
<213> ORGANISM: Homo sapiens
<220> FEATURE:
<223> OTHER INFORMATION: P19087

<400> SEQUENCE: 147

Met Gly Ser Gly Ala Ser Ala Glu Asp Lys Glu Leu Ala Lys Arg Ser
1               5                   10                  15

Lys Glu Leu Glu Lys Lys Leu Gln Glu Asp Ala Asp Lys Glu Ala Lys
            20                  25                  30

Thr Val Lys Leu Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
    50                  55                  60

Glu Cys Leu Glu Phe Lys Ala Ile Ile Tyr Gly Asn Val Leu Gln Ser
65                  70                  75                  80

Ile Leu Ala Ile Ile Arg Ala Met Thr Thr Leu Gly Ile Asp Tyr Ala
                85                  90                  95

Glu Pro Ser Cys Ala Asp Asp Gly Arg Gln Leu Asn Asn Leu Ala Asp
            100                 105                 110

Ser Ile Glu Glu Gly Thr Met Pro Pro Glu Leu Val Glu Val Ile Arg
        115                 120                 125

Arg Leu Trp Lys Asp Gly Gly Val Gln Ala Cys Phe Glu Arg Ala Ala
    130                 135                 140

Glu Tyr Gln Leu Asn Asp Ser Ala Ser Tyr Tyr Leu Asn Gln Leu Glu
145                 150                 155                 160

Arg Ile Thr Asp Pro Glu Tyr Leu Pro Ser Glu Gln Asp Val Leu Arg
                165                 170                 175

Ser Arg Val Lys Thr Thr Gly Ile Ile Glu Thr Lys Phe Ser Val Lys
            180                 185                 190

Asp Leu Asn Phe Arg Met Phe Asp Val Gly Gly Gln Arg Ser Glu Arg
        195                 200                 205

Lys Lys Trp Ile His Cys Phe Glu Gly Val Thr Cys Ile Ile Phe Cys
    210                 215                 220

Ala Ala Leu Ser Ala Tyr Asp Met Val Leu Val Glu Asp Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
            260                 265                 270
```

```
Leu Phe Glu Glu Lys Ile Lys Lys Val His Leu Ser Ile Cys Phe Pro
            275                 280                 285

Glu Tyr Asp Gly Asn Asn Ser Tyr Asp Asp Ala Gly Asn Tyr Ile Lys
        290                 295                 300

Ser Gln Phe Leu Asp Leu Asn Met Arg Lys Asp Val Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Ile Lys Glu Asn Leu Lys Asp Cys Gly
            340                 345                 350

Leu Phe

<210> SEQ ID NO 148
<211> LENGTH: 354
<212> TYPE: PRT
<213> ORGANISM: Homo sapiens
<220> FEATURE:
<223> OTHER INFORMATION: A8MTJ3

<400> SEQUENCE: 148

Met Gly Ser Gly Ile Ser Ser Glu Ser Lys Glu Ser Ala Lys Arg Ser
1               5                   10                  15

Lys Glu Leu Glu Lys Lys Leu Gln Glu Asp Ala Glu Arg Asp Ala Arg
            20                  25                  30

Thr Val Lys Leu Leu Leu Gly Ala Gly Glu Ser Gly Lys Ser Thr
            35                  40                  45

Ile Val Lys Gln Met Lys Ile Ile His Lys Asn Gly Tyr Ser Glu Gln
50                  55                  60

Glu Cys Met Glu Phe Lys Ala Val Ile Tyr Ser Asn Thr Leu Gln Ser
65                  70                  75                  80

Ile Leu Ala Ile Val Lys Ala Met Thr Thr Leu Gly Ile Asp Tyr Val
                85                  90                  95

Asn Pro Arg Ser Ala Glu Asp Gln Arg Gln Leu Tyr Ala Met Ala Asn
            100                 105                 110

Thr Leu Glu Asp Gly Gly Met Thr Pro Gln Leu Ala Glu Val Ile Lys
            115                 120                 125

Arg Leu Trp Arg Asp Pro Gly Ile Gln Ala Cys Phe Glu Arg Ala Ser
130                 135                 140

Glu Tyr Gln Leu Asn Asp Ser Ala Ala Tyr Tyr Leu Asn Asp Leu Asp
145                 150                 155                 160

Arg Ile Thr Ala Ser Gly Tyr Val Pro Asn Glu Gln Asp Val Leu His
                165                 170                 175

Ser Arg Val Lys Thr Thr Gly Ile Ile Glu Thr Gln Phe Ser Phe Lys
            180                 185                 190

Asp Leu His Phe Arg Met Phe Asp Val Gly Gly Gln Arg Ser Glu Arg
            195                 200                 205

Lys Lys Trp Ile His Cys Phe Glu Gly Val Thr Cys Ile Ile Phe Cys
210                 215                 220

Ala Ala Leu Ser Ala Tyr Asp Met Val Leu Val Glu Asp Glu Glu Val
225                 230                 235                 240

Asn Arg Met His Glu Ser Leu His Leu Phe Asn Ser Ile Cys Asn His
                245                 250                 255

Lys Tyr Phe Ser Thr Thr Ser Ile Val Leu Phe Leu Asn Lys Lys Asp
            260                 265                 270

Ile Phe Gln Glu Lys Val Thr Lys Val His Leu Ser Ile Cys Phe Pro
```

```
                275                 280                 285
Glu Tyr Thr Gly Pro Asn Thr Phe Glu Asp Ala Gly Asn Tyr Ile Lys
290                 295                 300

Asn Gln Phe Leu Asp Leu Asn Leu Lys Lys Glu Asp Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Ile Lys Glu Asn Leu Lys Asp Cys Gly
                340                 345                 350

Leu Phe

<210> SEQ ID NO 149
<211> LENGTH: 354
<212> TYPE: PRT
<213> ORGANISM: Homo sapiens
<220> FEATURE:
<223> OTHER INFORMATION: P09471

<400> SEQUENCE: 149

Met Gly Cys Thr Leu Ser Ala Glu Glu Arg Ala Ala Leu Glu Arg Ser
1               5                   10                  15

Lys Ala Ile Glu Lys Asn Leu Lys Glu Asp Gly Ile Ser Ala Ala Lys
                20                  25                  30

Asp Val Lys Leu Leu Leu Leu Gly Ala Gly Glu Ser Gly Lys Ser Thr
            35                  40                  45

Ile Val Lys Gln Met Lys Ile Ile His Glu Asp Gly Phe Ser Gly Glu
        50                  55                  60

Asp Val Lys Gln Tyr Lys Pro Val Val Tyr Ser Asn Thr Ile Gln Ser
65                  70                  75                  80

Leu Ala Ala Ile Val Arg Ala Met Asp Thr Leu Gly Ile Glu Tyr Gly
                85                  90                  95

Asp Lys Glu Arg Lys Ala Asp Ala Lys Met Val Cys Asp Val Val Ser
            100                 105                 110

Arg Met Glu Asp Thr Glu Pro Phe Ser Ala Glu Leu Leu Ser Ala Met
        115                 120                 125

Met Arg Leu Trp Gly Asp Ser Gly Ile Gln Glu Cys Phe Asn Arg Ser
130                 135                 140

Arg Glu Tyr Gln Leu Asn Asp Ser Ala Lys Tyr Tyr Leu Asp Ser Leu
145                 150                 155                 160

Asp Arg Ile Gly Ala Ala Asp Tyr Gln Pro Thr Glu Gln Asp Ile Leu
                165                 170                 175

Arg Thr Arg Val Lys Thr Thr Gly Ile Val Glu Thr His Phe Thr Phe
            180                 185                 190

Lys Asn Leu His Phe Arg Leu Phe Asp Val Gly Gly Gln Arg Ser Glu
        195                 200                 205

Arg Lys Lys Trp Ile His Cys Phe Glu Asp Val Thr Ala Ile Ile Phe
210                 215                 220

Cys Val Ala Leu Ser Gly Tyr Asp Gln Val Leu His Glu Asp Glu Thr
225                 230                 235                 240

Thr Asn Arg Met His Glu Ser Leu Met Leu Phe Asp Ser Ile Cys Asn
                245                 250                 255

Asn Lys Phe Phe Ile Asp Thr Ser Ile Ile Leu Phe Leu Asn Lys Lys
            260                 265                 270

Asp Leu Phe Gly Glu Lys Ile Lys Lys Ser Pro Leu Thr Ile Cys Phe
        275                 280                 285
```

-continued

```
Pro Glu Tyr Thr Gly Pro Asn Thr Tyr Glu Asp Ala Ala Tyr Ile
    290                 295                 300

Gln Ala Gln Phe Glu Ser Lys Asn Arg Ser Pro Asn Lys Glu Ile Tyr
305                 310                 315                 320

Cys His Met Thr Cys Ala Thr Asp Thr Asn Asn Ile Gln Val Val Phe
                325                 330                 335

Asp Ala Val Thr Asp Ile Ile Ile Ala Asn Asn Leu Arg Gly Cys Gly
                340                 345                 350

Leu Tyr
```

<210> SEQ ID NO 150
<211> LENGTH: 355
<212> TYPE: PRT
<213> ORGANISM: Homo sapiens
<220> FEATURE:
<223> OTHER INFORMATION: P19086

<400> SEQUENCE: 150

```
Met Gly Cys Arg Gln Ser Ser Glu Glu Lys Glu Ala Ala Arg Arg Ser
1               5                   10                  15

Arg Arg Ile Asp Arg His Leu Arg Ser Glu Ser Gln Arg Gln Arg Arg
                20                  25                  30

Glu Ile Lys Leu Leu Leu Leu Gly Thr Ser Asn Ser Gly Lys Ser Thr
            35                  40                  45

Ile Val Lys Gln Met Lys Ile Ile His Ser Gly Gly Phe Asn Leu Glu
        50                  55                  60

Ala Cys Lys Glu Tyr Lys Pro Leu Ile Ile Tyr Asn Ala Ile Asp Ser
65                  70                  75                  80

Leu Thr Arg Ile Ile Arg Ala Leu Ala Ala Leu Arg Ile Asp Phe His
                85                  90                  95

Asn Pro Asp Arg Ala Tyr Asp Ala Val Gln Leu Phe Ala Leu Thr Gly
                100                 105                 110

Pro Ala Glu Ser Lys Gly Glu Ile Thr Pro Glu Leu Leu Gly Val Met
            115                 120                 125

Arg Arg Leu Trp Ala Asp Pro Gly Ala Gln Ala Cys Phe Ser Arg Ser
    130                 135                 140

Ser Glu Tyr His Leu Glu Asp Asn Ala Ala Tyr Tyr Leu Asn Asp Leu
145                 150                 155                 160

Glu Arg Ile Ala Ala Ala Asp Tyr Ile Pro Thr Val Glu Asp Ile Leu
                165                 170                 175

Arg Ser Arg Asp Met Thr Thr Gly Ile Val Glu Asn Lys Phe Thr Phe
                180                 185                 190

Lys Glu Leu Thr Phe Lys Met Val Asp Val Gly Gly Gln Arg Ser Glu
            195                 200                 205

Arg Lys Lys Trp Ile His Cys Phe Glu Gly Val Thr Ala Ile Ile Phe
    210                 215                 220

Cys Val Glu Leu Ser Gly Tyr Asp Leu Lys Leu Tyr Glu Asp Asn Gln
225                 230                 235                 240

Thr Ser Arg Met Ala Glu Ser Leu Arg Leu Phe Asp Ser Ile Cys Asn
                245                 250                 255

Asn Asn Trp Phe Ile Asn Thr Ser Leu Ile Leu Phe Leu Asn Lys Lys
                260                 265                 270

Asp Leu Leu Ala Glu Lys Ile Arg Arg Ile Pro Leu Thr Ile Cys Phe
            275                 280                 285
```

```
Pro Glu Tyr Lys Gly Gln Asn Thr Tyr Glu Glu Ala Ala Val Tyr Ile
290                 295                 300

Gln Arg Gln Phe Glu Asp Leu Asn Arg Asn Lys Glu Thr Lys Glu Ile
305                 310                 315                 320

Tyr Ser His Phe Thr Cys Ala Thr Asp Thr Ser Asn Ile Gln Phe Val
                325                 330                 335

Phe Asp Ala Val Thr Asp Val Ile Ile Gln Asn Asn Leu Lys Tyr Ile
                340                 345                 350

Gly Leu Cys
        355

<210> SEQ ID NO 151
<211> LENGTH: 359
<212> TYPE: PRT
<213> ORGANISM: Homo sapiens
<220> FEATURE:
<223> OTHER INFORMATION: P50148

<400> SEQUENCE: 151

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Leu Gly Thr Gly
            35                  40                  45

Glu Ser Gly Lys Ser Thr Phe Ile Lys Gln Met Arg Ile Ile His Gly
50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285
```

```
Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
        355

<210> SEQ ID NO 152
<211> LENGTH: 359
<212> TYPE: PRT
<213> ORGANISM: Homo sapiens
<220> FEATURE:
<223> OTHER INFORMATION: P29992

<400> SEQUENCE: 152

Met Thr Leu Glu Ser Met Met Ala Cys Cys Leu Ser Asp Glu Val Lys
1               5                   10                  15

Glu Ser Lys Arg Ile Asn Ala Glu Ile Glu Lys Gln Leu Arg Arg Asp
                20                  25                  30

Lys Arg Asp Ala Arg Arg Glu Leu Lys Leu Leu Leu Leu Gly Thr Gly
            35                  40                  45

Glu Ser Gly Lys Ser Thr Phe Ile Lys Gln Met Arg Ile Ile His Gly
50                  55                  60

Ala Gly Tyr Ser Glu Glu Asp Lys Arg Gly Phe Thr Lys Leu Val Tyr
65                  70                  75                  80

Gln Asn Ile Phe Thr Ala Met Gln Ala Met Ile Arg Ala Met Glu Thr
                85                  90                  95

Leu Lys Ile Leu Tyr Lys Tyr Glu Gln Asn Lys Ala Asn Ala Leu Leu
            100                 105                 110

Ile Arg Glu Val Asp Val Glu Lys Val Thr Thr Phe Glu His Gln Tyr
        115                 120                 125

Val Ser Ala Ile Lys Thr Leu Trp Glu Asp Pro Gly Ile Gln Glu Cys
    130                 135                 140

Tyr Asp Arg Arg Arg Glu Tyr Gln Leu Ser Asp Ser Ala Lys Tyr Tyr
145                 150                 155                 160

Leu Thr Asp Val Asp Arg Ile Ala Thr Leu Gly Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Glu Asn Ile Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Asp Lys Ile Leu Tyr Ser His Leu
        275                 280                 285
```

Val Asp Tyr Phe Pro Glu Phe Asp Gly Pro Gln Arg Asp Ala Gln Ala
            290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
            355

<210> SEQ ID NO 153
<211> LENGTH: 355
<212> TYPE: PRT
<213> ORGANISM: Homo sapiens
<220> FEATURE:
<223> OTHER INFORMATION: O95837

<400> SEQUENCE: 153

Met Ala Gly Cys Cys Cys Leu Ser Ala Glu Glu Lys Glu Ser Gln Arg
1               5                   10                  15

Ile Ser Ala Glu Ile Glu Arg Gln Leu Arg Arg Asp Lys Lys Asp Ala
            20                  25                  30

Arg Arg Glu Leu Lys Leu Leu Leu Leu Gly Thr Gly Glu Ser Gly Lys
        35                  40                  45

Ser Thr Phe Ile Lys Gln Met Arg Ile Ile His Gly Ser Gly Tyr Ser
    50                  55                  60

Asp Glu Asp Arg Lys Gly Phe Thr Lys Leu Val Tyr Gln Asn Ile Phe
65                  70                  75                  80

Thr Ala Met Gln Ala Met Ile Arg Ala Met Asp Thr Leu Arg Ile Gln
                85                  90                  95

Tyr Val Cys Glu Gln Asn Lys Glu Asn Ala Gln Ile Ile Arg Glu Val
            100                 105                 110

Glu Val Asp Lys Val Ser Met Leu Ser Arg Glu Gln Val Glu Ala Ile
        115                 120                 125

Lys Gln Leu Trp Gln Asp Pro Gly Ile Gln Glu Cys Tyr Asp Arg Arg
    130                 135                 140

Arg Glu Tyr Gln Leu Ser Asp Ser Ala Lys Tyr Tyr Leu Thr Asp Ile
145                 150                 155                 160

Asp Arg Ile Ala Thr Pro Ser Phe Val Pro Thr Gln Gln Asp Val Leu
                165                 170                 175

Arg Val Arg Val Pro Thr Thr Gly Ile Ile Glu Tyr Pro Phe Asp Leu
            180                 185                 190

Glu Asn Ile Ile Phe Arg Met Val Asp Val Gly Gly Gln Arg Ser Glu
        195                 200                 205

Arg Arg Lys Trp Ile His Cys Phe Glu Ser Val Thr Ser Ile Ile Phe
    210                 215                 220

Leu Val Ala Leu Ser Glu Tyr Asp Gln Val Leu Ala Glu Cys Asp Asn
225                 230                 235                 240

Glu Asn Arg Met Glu Glu Ser Lys Ala Leu Phe Lys Thr Ile Ile Thr
                245                 250                 255

Tyr Pro Trp Phe Leu Asn Ser Ser Val Ile Leu Phe Leu Asn Lys Lys
            260                 265                 270

Asp Leu Leu Glu Glu Lys Ile Met Tyr Ser His Leu Ile Ser Tyr Phe
        275                 280                 285

-continued

```
Pro Glu Tyr Thr Gly Pro Lys Gln Asp Val Arg Ala Ala Arg Asp Phe
    290                 295                 300

Ile Leu Lys Leu Tyr Gln Asp Gln Asn Pro Asp Lys Glu Lys Val Ile
305                 310                 315                 320

Tyr Ser His Phe Thr Cys Ala Thr Asp Thr Asp Asn Ile Arg Phe Val
                325                 330                 335

Phe Ala Ala Val Lys Asp Thr Ile Leu Gln Leu Asn Leu Arg Glu Phe
                340                 345                 350

Asn Leu Val
        355

<210> SEQ ID NO 154
<211> LENGTH: 374
<212> TYPE: PRT
<213> ORGANISM: Homo sapiens
<220> FEATURE:
<223> OTHER INFORMATION: P30679

<400> SEQUENCE: 154

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
    130                 135                 140

Arg Ala Tyr Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
    195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
    275                 280                 285
```

Ser His Leu Ala Thr Tyr Phe Pro Ser Phe Gln Gly Pro Lys Gln Asp
290 295 300

Ala Glu Ala Ala Lys Arg Phe Ile Leu Asp Met Tyr Thr Arg Met Tyr
305 310 315 320

Thr Gly Cys Val Asp Gly Pro Glu Gly Ser Lys Lys Gly Ala Arg Ser
325 330 335

Arg Arg Leu Phe Ser His Tyr Thr Cys Ala Thr Asp Thr Gln Asn Ile
340 345 350

Arg Lys Val Phe Lys Asp Val Arg Asp Ser Val Leu Ala Arg Tyr Leu
355 360 365

Asp Glu Ile Asn Leu Leu
370

<210> SEQ ID NO 155
<211> LENGTH: 381
<212> TYPE: PRT
<213> ORGANISM: Homo sapiens
<220> FEATURE:
<223> OTHER INFORMATION: Q03113

<400> SEQUENCE: 155

Met Ser Gly Val Val Arg Thr Leu Ser Arg Cys Leu Leu Pro Ala Glu
1 5 10 15

Ala Gly Gly Ala Arg Glu Arg Arg Ala Gly Ser Gly Ala Arg Asp Ala
20 25 30

Glu Arg Glu Ala Arg Arg Arg Ser Arg Asp Ile Asp Ala Leu Leu Ala
35 40 45

Arg Glu Arg Arg Ala Val Arg Arg Leu Val Lys Ile Leu Leu Leu Gly
50 55 60

Ala Gly Glu Ser Gly Lys Ser Thr Phe Leu Lys Gln Met Arg Ile Ile
65 70 75 80

His Gly Arg Glu Phe Asp Gln Lys Ala Leu Leu Glu Phe Arg Asp Thr
85 90 95

Ile Phe Asp Asn Ile Leu Lys Gly Ser Arg Val Leu Val Asp Ala Arg
100 105 110

Asp Lys Leu Gly Ile Pro Trp Gln Tyr Ser Glu Asn Glu Lys His Gly
115 120 125

Met Phe Leu Met Ala Phe Glu Asn Lys Ala Gly Leu Pro Val Glu Pro
130 135 140

Ala Thr Phe Gln Leu Tyr Val Pro Ala Leu Ser Ala Leu Trp Arg Asp
145 150 155 160

Ser Gly Ile Arg Glu Ala Phe Ser Arg Arg Ser Glu Phe Gln Leu Gly
165 170 175

Glu Ser Val Lys Tyr Phe Leu Asp Asn Leu Asp Arg Ile Gly Gln Leu
180 185 190

Asn Tyr Phe Pro Ser Lys Gln Asp Ile Leu Leu Ala Arg Lys Ala Thr
195 200 205

Lys Gly Ile Val Glu His Asp Phe Val Ile Lys Lys Ile Pro Phe Lys
210 215 220

Met Val Asp Val Gly Gly Gln Arg Ser Gln Arg Gln Lys Trp Phe Gln
225 230 235 240

Cys Phe Asp Gly Ile Thr Ser Ile Leu Phe Met Val Ser Ser Ser Glu
245 250 255

Tyr Asp Gln Val Leu Met Glu Asp Arg Arg Thr Asn Arg Leu Val Glu
260 265 270

```
Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
        290                 295                 300

Val Lys Thr Val Ser Ile Lys Lys His Phe Pro Asp Phe Arg Gly Asp
305                 310                 315                 320

Pro His Arg Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
                340                 345                 350

Ala Ile Asp Thr Glu Asn Val Arg Phe Val Phe His Ala Val Lys Asp
        355                 360                 365

Thr Ile Leu Gln Glu Asn Leu Lys Asp Ile Met Leu Gln
        370                 375                 380

<210> SEQ ID NO 156
<211> LENGTH: 377
<212> TYPE: PRT
<213> ORGANISM: Homo sapiens
<220> FEATURE:
<223> OTHER INFORMATION: Q14344

<400> SEQUENCE: 156

Met Ala Asp Phe Leu Pro Ser Arg Ser Val Leu Ser Val Cys Phe Pro
1               5                   10                  15

Gly Cys Leu Leu Thr Ser Gly Glu Ala Glu Gln Gln Arg Lys Ser Lys
            20                  25                  30

Glu Ile Asp Lys Cys Leu Ser Arg Glu Lys Thr Tyr Val Lys Arg Leu
        35                  40                  45

Val Lys Ile Leu Leu Leu Gly Ala Gly Glu Ser Gly Lys Ser Thr Phe
    50                  55                  60

Leu Lys Gln Met Arg Ile Ile His Gly Gln Asp Phe Asp Gln Arg Ala
65                  70                  75                  80

Arg Glu Glu Phe Arg Pro Thr Ile Tyr Ser Asn Val Ile Lys Gly Met
                85                  90                  95

Arg Val Leu Val Asp Ala Arg Glu Lys Leu His Ile Pro Trp Gly Asp
            100                 105                 110

Asn Ser Asn Gln Gln His Gly Asp Lys Met Met Ser Phe Asp Thr Arg
        115                 120                 125

Ala Pro Met Ala Ala Gln Gly Met Val Glu Thr Arg Val Phe Leu Gln
    130                 135                 140

Tyr Leu Pro Ala Ile Arg Ala Leu Trp Ala Asp Ser Gly Ile Gln Asn
145                 150                 155                 160

Ala Tyr Asp Arg Arg Arg Glu Phe Gln Leu Gly Glu Ser Val Lys Tyr
                165                 170                 175

Phe Leu Asp Asn Leu Asp Lys Leu Gly Glu Pro Asp Tyr Ile Pro Ser
            180                 185                 190

Gln Gln Asp Ile Leu Leu Ala Arg Arg Pro Thr Lys Gly Ile His Glu
        195                 200                 205

Tyr Asp Phe Glu Ile Lys Asn Val Pro Phe Lys Met Val Asp Val Gly
    210                 215                 220

Gly Gln Arg Ser Glu Arg Lys Arg Trp Phe Glu Cys Phe Asp Ser Val
225                 230                 235                 240

Thr Ser Ile Leu Phe Leu Val Ser Ser Ser Glu Phe Asp Gln Val Leu
                245                 250                 255
```

```
Met Glu Asp Arg Leu Thr Asn Arg Leu Thr Glu Ser Leu Asn Ile Phe
            260                 265                 270

Glu Thr Ile Val Asn Asn Arg Val Phe Ser Asn Val Ser Ile Ile Leu
        275                 280                 285

Phe Leu Asn Lys Thr Asp Leu Leu Glu Glu Lys Val Gln Ile Val Ser
        290                 295                 300

Ile Lys Asp Tyr Phe Leu Glu Phe Glu Gly Asp Pro His Cys Leu Arg
305                 310                 315                 320

Asp Val Gln Lys Phe Leu Val Glu Cys Phe Arg Asn Lys Arg Arg Asp
                325                 330                 335

Gln Gln Gln Lys Pro Leu Tyr His His Phe Thr Thr Ala Ile Asn Thr
            340                 345                 350

Glu Asn Ile Arg Leu Val Phe Arg Asp Val Lys Asp Thr Ile Leu His
            355                 360                 365

Asp Asn Leu Lys Gln Leu Met Leu Gln
        370                 375
```

<210> SEQ ID NO 157
<211> LENGTH: 5
<212> TYPE: PRT
<213> ORGANISM: Artificial Sequence
<220> FEATURE:
<223> OTHER INFORMATION: DDDDK tag

<400> SEQUENCE: 157

```
Asp Asp Asp Asp Lys
1               5
```

<210> SEQ ID NO 158
<211> LENGTH: 742
<212> TYPE: DNA
<213> ORGANISM: Artificial Sequence
<220> FEATURE:
<223> OTHER INFORMATION: Mini Gs393 gene sequence

<400> SEQUENCE: 158

```
ccatgggtca ccaccatcat caccatgaaa tctttatttt ccagggtatc gagaagcagc     60
tgcagaagga caagcaggtc taccgggcca cgcaccgcct gctgctgctg ggtgctgata    120
attctggtaa aagcaccatt gtgaagcaga tgaggatcct gcatggtggg agtggcggga    180
gcggaggtct tctggaatct ttgagaccaa gttccaggtg acaaagtca acttccacat    240
gtttgacgtg ggtggccagc gcgatgaacg ccgcaagtgg atccagtgct caacgatgt    300
gactgccatc atcttcgtgg tggacagcag cgattacaac cgcctgcagg aggctctgaa    360
cgacttcaag agcatctgga caacagatg gctgcgcacc atctctgtga tcctgttcct    420
caacaagcaa gatctgctcg ctgagaaagt ccttgctggg aaatcgaaga ttgaggacta    480
ctttccagaa tttgctcgct acactactcc tgaggatgct actcccgagc cggagagga    540
cccacgcgtg acccgggcca agtacttcat tcgagatgag tttctgagga tcagcactgc    600
cagtggagat gggcgtcact actgctaccc tcattttcacc tgcgctgtgg acactgagaa    660
cgcccgccgt atcttcaacg actgccgtga catcattcag cgcatgcacc ttcgtcagta    720
cgagctgctc taatagctcg ag                                             742
```

<210> SEQ ID NO 159
<211> LENGTH: 243
<212> TYPE: PRT
<213> ORGANISM: Artificial Sequence
<220> FEATURE:

<223> OTHER INFORMATION: Mini Gs393 protein sequence

<400> SEQUENCE: 159

```
Met Gly His His His His His His Glu Asn Leu Tyr Phe Gln Gly Ile
1               5                   10                  15
Glu Lys Gln Leu Gln Lys Asp Lys Gln Val Tyr Arg Ala Thr His Arg
            20                  25                  30
Leu Leu Leu Leu Gly Ala Asp Asn Ser Gly Lys Ser Thr Ile Val Lys
        35                  40                  45
Gln Met Arg Ile Leu His Gly Gly Ser Gly Gly Ser Gly Gly Thr Ser
    50                  55                  60
Gly Ile Phe Glu Thr Lys Phe Gln Val Asp Lys Val Asn Phe His Met
65                  70                  75                  80
Phe Asp Val Gly Gly Gln Arg Asp Glu Arg Arg Lys Trp Ile Gln Cys
                85                  90                  95
Phe Asn Asp Val Thr Ala Ile Ile Phe Val Val Asp Ser Ser Asp Tyr
            100                 105                 110
Asn Arg Leu Gln Glu Ala Leu Asn Asp Phe Lys Ser Ile Trp Asn Asn
        115                 120                 125
Arg Trp Leu Arg Thr Ile Ser Val Ile Leu Phe Leu Asn Lys Gln Asp
    130                 135                 140
Leu Leu Ala Glu Lys Val Leu Ala Gly Lys Ser Lys Ile Glu Asp Tyr
145                 150                 155                 160
Phe Pro Glu Phe Ala Arg Tyr Thr Thr Pro Glu Asp Ala Thr Pro Glu
                165                 170                 175
Pro Gly Glu Asp Pro Arg Val Thr Arg Ala Lys Tyr Phe Ile Arg Asp
            180                 185                 190
Glu Phe Leu Arg Ile Ser Thr Ala Ser Gly Asp Gly Arg His Tyr Cys
        195                 200                 205
Tyr Pro His Phe Thr Cys Ala Val Asp Thr Glu Asn Ala Arg Arg Ile
    210                 215                 220
Phe Asn Asp Cys Arg Asp Ile Ile Gln Arg Met His Leu Arg Gln Tyr
225                 230                 235                 240
Glu Leu Leu
```

<210> SEQ ID NO 160
<211> LENGTH: 394
<212> TYPE: PRT
<213> ORGANISM: Bos taurus
<220> FEATURE:
<223> OTHER INFORMATION: spP04896

<400> SEQUENCE: 160

```
Met Gly Cys Leu Gly Asn Ser Lys Thr Glu Asp Gln Arg Asn Glu Glu
1               5                   10                  15
Lys Ala Gln Arg Glu Ala Asn Lys Lys Ile Glu Lys Gln Leu Gln Lys
            20                  25                  30
Asp Lys Gln Val Tyr Arg Ala Thr His Arg Leu Leu Leu Leu Gly Ala
        35                  40                  45
Gly Glu Ser Gly Lys Ser Thr Ile Val Lys Gln Met Arg Ile Leu His
    50                  55                  60
Val Asn Gly Phe Asn Gly Glu Gly Gly Glu Glu Asp Pro Gln Ala Ala
65                  70                  75                  80
Arg Ser Asn Ser Asp Gly Glu Lys Ala Thr Lys Val Gln Asp Ile Lys
                85                  90                  95
```

```
Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asp Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
    210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Ile Ile Gln
    370                 375                 380

Arg Met His Leu Arg Gln Tyr Glu Leu Leu
385                 390

<210> SEQ ID NO 161
<211> LENGTH: 229
<212> TYPE: PRT
<213> ORGANISM: Artificial Sequence
<220> FEATURE:
<223> OTHER INFORMATION: Mini Gs C

<400> SEQUENCE: 161

Gly Ile Glu Lys Gln Leu Gln Lys Asp Lys Gln Val Tyr Arg Ala Thr
1               5                   10                  15

His Arg Leu Leu Leu Leu Gly Ala Asp Asn Ser Gly Lys Ser Thr Ile
            20                  25                  30

Val Lys Gln Met Arg Ile Tyr His Gly Gly Ser Gly Gly Ser Gly Gly
        35                  40                  45

Thr Ser Gly Ile Phe Glu Thr Lys Phe Gln Val Asp Lys Val Asn Phe
    50                  55                  60
```

```
His Met Phe Asp Val Gly Gly Gln Arg Asp Glu Arg Arg Lys Trp Ile
 65                  70                  75                  80

Gln Cys Phe Asn Asp Val Thr Ala Ile Ile Phe Val Val Asp Ser Ser
                 85                  90                  95

Asp Tyr Asn Arg Leu Gln Glu Ala Leu Asn Asp Phe Lys Ser Ile Trp
            100                 105                 110

Asn Asn Arg Trp Leu Arg Thr Ile Ser Val Ile Leu Phe Leu Asn Lys
        115                 120                 125

Gln Asp Leu Leu Ala Glu Lys Val Leu Ala Gly Lys Ser Lys Ile Glu
130                 135                 140

Asp Tyr Phe Pro Glu Phe Ala Arg Tyr Thr Thr Pro Glu Asp Ala Thr
145                 150                 155                 160

Pro Glu Pro Gly Glu Asp Pro Arg Val Thr Arg Ala Lys Tyr Phe Ile
                165                 170                 175

Arg Asp Glu Phe Leu Arg Ile Ser Thr Ala Ser Gly Asp Gly Arg His
            180                 185                 190

Tyr Cys Tyr Pro His Phe Thr Cys Ala Val Asp Thr Glu Asn Ala Arg
        195                 200                 205

Arg Ile Phe Asn Asp Cys Arg Asp Ile Ile Gln Arg Met His Leu Arg
    210                 215                 220

Gln Tyr Glu Leu Leu
225

<210> SEQ ID NO 162
<211> LENGTH: 229
<212> TYPE: PRT
<213> ORGANISM: Artificial Sequence
<220> FEATURE:
<223> OTHER INFORMATION: Mini Gs D

<400> SEQUENCE: 162

Gly Ile Glu Lys Gln Leu Gln Lys Asp Lys Gln Val Tyr Arg Ala Thr
  1               5                  10                  15

His Arg Leu Leu Leu Leu Gly Ala Asp Asn Ser Gly Lys Ser Thr Ile
             20                  25                  30

Val Lys Gln Met Arg Ile Tyr His Gly Gly Ser Gly Gly Ser Gly Gly
         35                  40                  45

Thr Ser Gly Ile Phe Glu Thr Lys Phe Gln Val Asp Lys Val Asn Phe
 50                  55                  60

His Met Phe Asp Val Gly Gly Gln Arg Asp Glu Arg Arg Lys Trp Ile
 65                  70                  75                  80

Gln Cys Phe Asn Asp Val Thr Ala Ile Ile Phe Val Val Asp Ser Ser
                 85                  90                  95

Asp Tyr Asn Arg Leu Gln Glu Ala Leu Asn Asp Phe Lys Ser Ile Trp
            100                 105                 110

Asn Asn Arg Trp Leu Arg Thr Ile Ser Val Ile Leu Phe Leu Asn Lys
        115                 120                 125

Gln Asp Leu Leu Ala Glu Lys Val Leu Ala Gly Lys Ser Lys Ile Glu
130                 135                 140

Asp Tyr Phe Pro Glu Phe Ala Arg Tyr Thr Thr Pro Glu Asp Ala Thr
145                 150                 155                 160

Pro Glu Pro Gly Glu Asp Pro Arg Val Thr Arg Ala Lys Tyr Phe Ile
                165                 170                 175

Arg Asp Glu Phe Leu Arg Ile Ser Thr Ala Ser Gly Asp Gly Arg His
            180                 185                 190
```

Tyr Cys Tyr Pro His Phe Thr Cys Ala Val Asp Thr Glu Asn Ala Arg
            195                 200                 205

Arg Ile Phe Asn Asp Cys Arg Asp Ile Ile Gln Arg Met His Leu Arg
210                 215                 220

Gln Tyr Glu Leu Leu
225

<210> SEQ ID NO 163
<211> LENGTH: 413
<212> TYPE: PRT
<213> ORGANISM: Homo sapiens
<220> FEATURE:
<223> OTHER INFORMATION: adrb2 human

<400> SEQUENCE: 163

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
            85                  90                  95

Lys Met Trp Thr Phe Gly Asn Phe Trp Cys Glu Phe Trp Thr Ser Ile
        100                 105                 110

Asp Val Leu Cys Val Thr Ala Ser Ile Glu Thr Leu Cys Val Ile Ala
            115                 120                 125

Val Asp Arg Tyr Phe Ala Ile Thr Ser Pro Phe Lys Tyr Gln Ser Leu
130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
            165                 170                 175

Thr His Gln Glu Ala Ile Asn Cys Tyr Ala Asn Glu Thr Cys Cys Asp
        180                 185                 190

Phe Phe Thr Asn Gln Ala Tyr Ala Ile Ala Ser Ser Ile Val Ser Phe
            195                 200                 205

Tyr Val Pro Leu Val Ile Met Val Phe Val Tyr Ser Arg Val Phe Gln
210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
            245                 250                 255

Gly Leu Arg Arg Ser Ser Lys Phe Cys Leu Lys Glu His Lys Ala Leu
        260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
290                 295                 300

Lys Glu Val Tyr Ile Leu Leu Asn Trp Ile Gly Tyr Val Asn Ser Gly
305                 310                 315                 320

```
Phe Asn Pro Leu Ile Tyr Cys Arg Ser Pro Asp Phe Arg Ile Ala Phe
                325                 330                 335

Gln Glu Leu Leu Cys Leu Arg Ser Ser Leu Lys Ala Tyr Gly Asn
            340                 345                 350

Gly Tyr Ser Ser Asn Gly Asn Thr Gly Glu Gln Ser Gly Tyr His Val
                355                 360                 365

Glu Gln Glu Lys Glu Asn Lys Leu Leu Cys Glu Asp Leu Pro Gly Thr
370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410

<210> SEQ ID NO 164
<211> LENGTH: 412
<212> TYPE: PRT
<213> ORGANISM: Homo sapiens
<220> FEATURE:
<223> OTHER INFORMATION: AA2AR human

<400> SEQUENCE: 164

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270
```

Ala Ile Val Leu Ser His Thr Asn Ser Val Val Asn Pro Phe Ile Tyr
            275                 280                 285

Ala Tyr Arg Ile Arg Glu Phe Arg Gln Thr Phe Arg Lys Ile Ile Arg
        290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
    370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
            405                 410

<210> SEQ ID NO 165
<211> LENGTH: 325
<212> TYPE: PRT
<213> ORGANISM: Artificial Sequence
<220> FEATURE:
<223> OTHER INFORMATION: AA2AR human A

<400> SEQUENCE: 165

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Ala His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
            245                 250                 255

Phe Phe Cys Pro Asp Cys Ser His Ala Pro Leu Trp Leu Met Tyr Leu
        260                 265                 270

Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
    290                 295                 300

Ser His Val Leu Glu Asn Leu Tyr Phe Gln Gly His His His His
305                 310                 315                 320

His His His His His
            325

<210> SEQ ID NO 166
<211> LENGTH: 325
<212> TYPE: PRT
<213> ORGANISM: Artificial Sequence
<220> FEATURE:
<223> OTHER INFORMATION: AA2AR human B

<400> SEQUENCE: 166

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
130                 135                 140

Asn Cys Gly Gln Pro Lys Glu Gly Lys Ala His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
            245                 250                 255

```
Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
    290                 295                 300

Ser His Val Leu Glu Asn Leu Tyr Phe Gln Gly His His His His
305                 310                 315                 320

His His His His His
            325
```

<210> SEQ ID NO 167
<211> LENGTH: 6
<212> TYPE: PRT
<213> ORGANISM: Artificial Sequence
<220> FEATURE:
<223> OTHER INFORMATION: His-tag

<400> SEQUENCE: 167

```
His His His His His His
1               5
```

<210> SEQ ID NO 168
<211> LENGTH: 18
<212> TYPE: DNA
<213> ORGANISM: Artificial Sequence
<220> FEATURE:
<223> OTHER INFORMATION: His-tag

<400> SEQUENCE: 168
caccaccatc atcaccat                                                 18

<210> SEQ ID NO 169
<211> LENGTH: 7
<212> TYPE: PRT
<213> ORGANISM: Artificial Sequence
<220> FEATURE:
<223> OTHER INFORMATION: TEV protease site

<400> SEQUENCE: 169

```
Glu Asn Leu Tyr Phe Gln Gly
1               5
```

<210> SEQ ID NO 170
<211> LENGTH: 21
<212> TYPE: DNA
<213> ORGANISM: Artificial Sequence
<220> FEATURE:
<223> OTHER INFORMATION: TEV protease site

<400> SEQUENCE: 170
gaaaatcttt atttccaggg t                                             21

<210> SEQ ID NO 171
<211> LENGTH: 24
<212> TYPE: DNA
<213> ORGANISM: Artificial Sequence
<220> FEATURE:
<223> OTHER INFORMATION: GGSGGSGG linker sequence

<400> SEQUENCE: 171
ggtgggagtg gcgggagcgg aggt                                          24